US012486499B2

(12) United States Patent
Schalk et al.

(10) Patent No.: US 12,486,499 B2
(45) Date of Patent: Dec. 2, 2025

(54) BIOCATALYTIC METHOD FOR THE CONTROLLED DEGRADATION OF TERPENE COMPOUNDS

(71) Applicant: Firmenich SA, Satigny (CH)

(72) Inventors: Michel Schalk, Satigny (CH); Fabienne Deguerry, Satigny (CH); Daniel Solis Escalante, Satigny (CH); Pauline Anziani, Satigny (CH); Sabine Beccucci, Satigny (CH)

(73) Assignee: FIRMENICH SA, Satigny (CH)

( * ) Notice: Subject to any disclaimer, the term of this patent is extended or adjusted under 35 U.S.C. 154(b) by 0 days.

(21) Appl. No.: 17/596,878

(22) PCT Filed: Jul. 8, 2020

(86) PCT No.: PCT/EP2020/069217
§ 371 (c)(1),
(2) Date: Dec. 20, 2021

(87) PCT Pub. No.: WO2021/005097
PCT Pub. Date: Jan. 14, 2021

(65) Prior Publication Data

US 2023/0183761 A1 Jun. 15, 2023

(30) Foreign Application Priority Data

Jul. 10, 2019 (EP) .................................... 19000332
Nov. 13, 2019 (EP) .................................... 19208951

(51) Int. Cl.
*C12P 7/62* (2022.01)
*C12N 9/02* (2006.01)
*C12N 9/18* (2006.01)

(52) U.S. Cl.
CPC ............ *C12N 9/18* (2013.01); *C12N 9/0069* (2013.01); *C12P 7/62* (2013.01); *C12Y 113/00* (2013.01)

(58) Field of Classification Search
CPC ........... C12N 9/18; C12N 9/0069; C12P 7/62
See application file for complete search history.

(56) References Cited

U.S. PATENT DOCUMENTS 6,071,955 A 6/2000 Elias et al.
7,214,507 B2 5/2007 Bouwmeester et al.
2019/0002925 A1 1/2019 Schalk et al.

FOREIGN PATENT DOCUMENTS

CN 1221317 A 6/1999
CN 1589327 A 3/2005
(Continued)

OTHER PUBLICATIONS

Fransceus. J Ind Microbiol Biotechnol. May 2017;44(4-5):687-695.*

(Continued)

*Primary Examiner* — Yong D Pak
(74) *Attorney, Agent, or Firm* — Armstrong Teasdale LLP

(57) ABSTRACT

Described herein are biocatalytic methods of producing terpene degradation products useful as starting material for the production of perfumery ingredients, such as, for example, ambrox. In particular novel terpene degrading polypeptides (enal-cleaving polypeptides) and novel peptides converting terpenes compounds to oxygenated derivatives (oxygenases) and mutants and variants derived therefrom are described which may be applied in novel types of fully enzymatic multistep degradation pathways allowing the controlled, stepwise conversion and degradation of linear or cyclic terpene substrates. Said novel biosynthetic strategies allow the fully biochemical synthesis of valuable terpene-derived compounds, like for example manooloxy or (Continued)

gamma ambrol. Also described herein are recombinant host organisms carrying the required set of genetic information for the functional expression of the set of enzymes necessary for catalyzing the combination of enzymatic conversion and degradation steps.

20 Claims, 34 Drawing Sheets

Specification includes a Sequence Listing.

(56) References Cited

FOREIGN PATENT DOCUMENTS

| | | | | |
|---|---|---|---|---|
| CN | 105579585 | A | | 5/2016 |
| CN | 107889506 | A | | 4/2018 |
| DE | 102015217657 | A1 | | 3/2017 |
| JP | S5441385 | A | | 4/1979 |
| JP | 2009060799 | A | | 3/2009 |
| WO | 2018/114839 | A2 | | 6/2018 |
| WO | WO-2023288292 | A2 | * | 1/2023 |

OTHER PUBLICATIONS

Sanavia. Computational and Structural Biotechnology Journal, vol. 18, 2020, pp. 1968-1979.*

Studer. Residue mutations and their impact on protein structure and function: detecting beneficial and pathogenic changes. Biochem. J. (2013) 449, 581-594.*

Database NCBI. Oct. 25, 2019, DUF4334 domain-containing protein [*Rhodococcus* sp. YH3-3], XP055678772, retrieved from NCBI Database accession No. WP_042451379.

Forster-Fromme, K. et al. Identification and characterization of the acyclic terpene utilization gene cluster of Pseudomonas citronellolis. FEMS Microbiology Letters, vol. 264, Nov. 1, 2016, pp. 220-225.

Hannes, Leisch et al. Baeyer-Villiger Monooxygenases: More Than Just Green Chemistry. Chemical Reviews, vol. 111, No. 7, Jul. 13, 2011, pp. 4165-5222.

Database NCBI. Aug. 1, 2019, Giroux, E. "putative sterigmatocystin biosynthesis monooxygenase [Lachnellula willkommii]". XP002798451, retrieved from NCBI Database accession No. TVY90099.

International Search Report and Written Opinion, mailed Dec. 17, 2020, for Application No. PCT/EP2020/069217, filing date Jul. 8, 2020.

* cited by examiner

```
                              SEQUENCE LISTING


<160> NUMBER OF SEQ ID NOS: 208

<210> SEQ ID NO 1
<211> LENGTH: 1767
<212> TYPE: DNA
<213> ORGANISM: Hyphozyma roseonigra
<220> FEATURE:
<221> NAME/KEY: CDS
<222> LOCATION: (1)..(1767)

<400> SEQUENCE: 1

atg cct tcc gca atc acc ccg ccg gtt gat cat cgc agt ctt cca ggt        48
Met Pro Ser Ala Ile Thr Pro Pro Val Asp His Arg Ser Leu Pro Gly
1               5                   10                  15

ctt ttc aag cca cag agg aag ctc aaa gtg ata tgt gtc gga gcc ggc        96
Leu Phe Lys Pro Gln Arg Lys Leu Lys Val Ile Cys Val Gly Ala Gly
            20                  25                  30

gcc tcg ggc tta ctt ctt tcc tac aag ata caa cga cac ttc gag gat       144
Ala Ser Gly Leu Leu Leu Ser Tyr Lys Ile Gln Arg His Phe Glu Asp
        35                  40                  45

ttc gag ctc caa gtc ttt gag aag aat ccc gag gta tca gga acc tgg       192
Phe Glu Leu Gln Val Phe Glu Lys Asn Pro Glu Val Ser Gly Thr Trp
    50                  55                  60

tac gag aac agg tat ccc ggc tgc gct tgt gat gtt ccc tcg cat aat       240
Tyr Glu Asn Arg Tyr Pro Gly Cys Ala Cys Asp Val Pro Ser His Asn
65                  70                  75                  80

tat aca tgg tct ttt gag ccc aaa acc gac tgg tcc gcc aac tat gca       288
Tyr Thr Trp Ser Phe Glu Pro Lys Thr Asp Trp Ser Ala Asn Tyr Ala
                85                  90                  95

tca tcg aag gag att ttc aaa tat ttc aag gac ttc acg agg aaa tat       336
Ser Ser Lys Glu Ile Phe Lys Tyr Phe Lys Asp Phe Thr Arg Lys Tyr
            100                 105                 110

ggt cta agc aag tac atc aag ctg gaa cat gag gtc gtg gga gcc acg       384
Gly Leu Ser Lys Tyr Ile Lys Leu Glu His Glu Val Val Gly Ala Thr
        115                 120                 125

tgg atg gag gcg gag gca cag tgg aaa gtt gac gtc aag gac ctt cga       432
Trp Met Glu Ala Glu Ala Gln Trp Lys Val Asp Val Lys Asp Leu Arg
    130                 135                 140

agt gga aac acg cag agc tcg ttt gcg cat ata ctg gtc aat gca gga       480
Ser Gly Asn Thr Gln Ser Ser Phe Ala His Ile Leu Val Asn Ala Gly
145                 150                 155                 160

ggc att ttg aat gct tgg cga tac ccg cca att cca gga atc aag gat       528
```

-continued

```
Gly Ile Leu Asn Ala Trp Arg Tyr Pro Pro Ile Pro Gly Ile Lys Asp
                165                 170                 175

ttc aag ggt gat ctt gtt cac tcc gca gct tgg cca gaa cat ctt gat      576
Phe Lys Gly Asp Leu Val His Ser Ala Ala Trp Pro Glu His Leu Asp
            180                 185                 190

ctt aat ggg aag gtt gtc ggt ctc atc gga aat gga tcc tcc ggc att      624
Leu Asn Gly Lys Val Val Gly Leu Ile Gly Asn Gly Ser Ser Gly Ile
        195                 200                 205

cag atc ctt ccg gcc atc aag aag gat gta aag caa ctc gtt aca ttc      672
Gln Ile Leu Pro Ala Ile Lys Lys Asp Val Lys Gln Leu Val Thr Phe
    210                 215                 220

att cgg gaa gca act tgg gtg gcg cct cct tta ggt caa gcc tat cgt      720
Ile Arg Glu Ala Thr Trp Val Ala Pro Pro Leu Gly Gln Ala Tyr Arg
225                 230                 235                 240

gcg ttc tcg act gat gaa cag gct cag ttt gcg caa gat ccg cgc cat      768
Ala Phe Ser Thr Asp Glu Gln Ala Gln Phe Ala Gln Asp Pro Arg His
                245                 250                 255

cac ctg gag aca cgg cgt gca act gag gct acc atg aat caa tca ttt      816
His Leu Glu Thr Arg Arg Ala Thr Glu Ala Thr Met Asn Gln Ser Phe
            260                 265                 270

ggt atc ttc cat tcg gga tcc gag gag cag aaa ggg gtt cgc caa tat      864
Gly Ile Phe His Ser Gly Ser Glu Glu Gln Lys Gly Val Arg Gln Tyr
        275                 280                 285

atg cag aat atc atg gaa acg aag ctc aac aac aaa cag ctc gag agt      912
Met Gln Asn Ile Met Glu Thr Lys Leu Asn Asn Lys Gln Leu Glu Ser
    290                 295                 300

gtg ctg att cct gag tgg tcg gtc ggt tgt cgg cgt ctt aca cca ggt      960
Val Leu Ile Pro Glu Trp Ser Val Gly Cys Arg Arg Leu Thr Pro Gly
305                 310                 315                 320

act aat tat cta gaa tcc ctg tca gac gac aat gtc aag gtc gtc tat     1008
Thr Asn Tyr Leu Glu Ser Leu Ser Asp Asp Asn Val Lys Val Val Tyr
                325                 330                 335

ggt gag atc aca caa att acc gaa tcg ggt gtc atc tgc gat gat ggt     1056
Gly Glu Ile Thr Gln Ile Thr Glu Ser Gly Val Ile Cys Asp Asp Gly
            340                 345                 350

aaa ggc gaa tat ccc gtt gaa gtt ctt att tgc gcc acc ggc ttc gac     1104
Lys Gly Glu Tyr Pro Val Glu Val Leu Ile Cys Ala Thr Gly Phe Asp
        355                 360                 365

acc acc ttc aaa cca cga ttc cca ctc atc ggt aca acc caa gag aaa     1152
Thr Thr Phe Lys Pro Arg Phe Pro Leu Ile Gly Thr Thr Gln Glu Lys
    370                 375                 380

ctc agt gat gtt tgg aaa gat gat ccg agg ggc tac ttt ggg atc gca     1200
Leu Ser Asp Val Trp Lys Asp Asp Pro Arg Gly Tyr Phe Gly Ile Ala
385                 390                 395                 400

acc aac aac tat ccc aac tac ttc ttc act ctt gga cca aat tgt cca     1248
Thr Asn Asn Tyr Pro Asn Tyr Phe Phe Thr Leu Gly Pro Asn Cys Pro
                405                 410                 415

atc ggt aat ggc ccc gtg ctg tgt gcc att gaa gct gag gtt gaa tat     1296
Ile Gly Asn Gly Pro Val Leu Cys Ala Ile Glu Ala Glu Val Glu Tyr
            420                 425                 430

ata atc aac atg ctc tcg aag ttt cag aag gag aac att cgt tct ttt     1344
Ile Ile Asn Met Leu Ser Lys Phe Gln Lys Glu Asn Ile Arg Ser Phe
        435                 440                 445

gat atc aag gca gat gct gtc gac gcc ttc aac gac tgg aag gat gac     1392
Asp Ile Lys Ala Asp Ala Val Asp Ala Phe Asn Asp Trp Lys Asp Asp
    450                 455                 460

ttc atg aaa gat acc atc tgg gca gaa caa tgc cgg tca tgg tac aag     1440
Phe Met Lys Asp Thr Ile Trp Ala Glu Gln Cys Arg Ser Trp Tyr Lys
465                 470                 475                 480
```

```
gca gga tcc gcc acc ggt aaa atc ctt gca ttg tgg cca ggc tcg act      1488
Ala Gly Ser Ala Thr Gly Lys Ile Leu Ala Leu Trp Pro Gly Ser Thr
                485                 490                 495

ttg cac tac ttg gaa gca ctc aag tcg ccg cgg tgg gag gac tgg gac      1536
Leu His Tyr Leu Glu Ala Leu Lys Ser Pro Arg Trp Glu Asp Trp Asp
            500                 505                 510

ttc aag tat cag cct ggt aga aat cgt ttc cac tac ttt gga aat ggt      1584
Phe Lys Tyr Gln Pro Gly Arg Asn Arg Phe His Tyr Phe Gly Asn Gly
        515                 520                 525

cat agc tgt gct gag cag gat ggc gat ctg agc tgg tac att cgc aac      1632
His Ser Cys Ala Glu Gln Asp Gly Asp Leu Ser Trp Tyr Ile Arg Asn
    530                 535                 540

gag gat gat tct tat att gat ccg gta ctc aag ccg aag ccg aag gca      1680
Glu Asp Asp Ser Tyr Ile Asp Pro Val Leu Lys Pro Lys Pro Lys Ala
545                 550                 555                 560

gca gtt gaa agc gag gca cat atc gcc ctg cca gga atc ggt ccg atg      1728
Ala Val Glu Ser Glu Ala His Ile Ala Leu Pro Gly Ile Gly Pro Met
                565                 570                 575

ttg atg gaa gac ccg cgt gat gtt gct gta gag gcc tag                  1767
Leu Met Glu Asp Pro Arg Asp Val Ala Val Glu Ala
            580                 585


<210> SEQ ID NO 2
<211> LENGTH: 588
<212> TYPE: PRT
<213> ORGANISM: Hyphozyma roseonigra

<400> SEQUENCE: 2

Met Pro Ser Ala Ile Thr Pro Pro Val Asp His Arg Ser Leu Pro Gly
1               5                   10                  15

Leu Phe Lys Pro Gln Arg Lys Leu Lys Val Ile Cys Val Gly Ala Gly
            20                  25                  30

Ala Ser Gly Leu Leu Leu Ser Tyr Lys Ile Gln Arg His Phe Glu Asp
        35                  40                  45

Phe Glu Leu Gln Val Phe Glu Lys Asn Pro Glu Val Ser Gly Thr Trp
    50                  55                  60

Tyr Glu Asn Arg Tyr Pro Gly Cys Ala Cys Asp Val Pro Ser His Asn
65                  70                  75                  80

Tyr Thr Trp Ser Phe Glu Pro Lys Thr Asp Trp Ser Ala Asn Tyr Ala
                85                  90                  95

Ser Ser Lys Glu Ile Phe Lys Tyr Phe Lys Asp Phe Thr Arg Lys Tyr
            100                 105                 110

Gly Leu Ser Lys Tyr Ile Lys Leu Glu His Glu Val Val Gly Ala Thr
        115                 120                 125

Trp Met Glu Ala Glu Ala Gln Trp Lys Val Asp Val Lys Asp Leu Arg
    130                 135                 140

Ser Gly Asn Thr Gln Ser Ser Phe Ala His Ile Leu Val Asn Ala Gly
145                 150                 155                 160

Gly Ile Leu Asn Ala Trp Arg Tyr Pro Pro Ile Pro Gly Ile Lys Asp
                165                 170                 175

Phe Lys Gly Asp Leu Val His Ser Ala Ala Trp Pro Glu His Leu Asp
            180                 185                 190

Leu Asn Gly Lys Val Val Gly Leu Ile Gly Asn Gly Ser Ser Gly Ile
        195                 200                 205

Gln Ile Leu Pro Ala Ile Lys Lys Asp Val Lys Gln Leu Val Thr Phe
    210                 215                 220

Ile Arg Glu Ala Thr Trp Val Ala Pro Pro Leu Gly Gln Ala Tyr Arg
```

-continued

```
225                 230                 235                 240

Ala Phe Ser Thr Asp Glu Gln Ala Gln Phe Ala Gln Asp Pro Arg His
                245                 250                 255

His Leu Glu Thr Arg Arg Ala Thr Glu Ala Thr Met Asn Gln Ser Phe
            260                 265                 270

Gly Ile Phe His Ser Gly Ser Glu Glu Gln Lys Gly Val Arg Gln Tyr
        275                 280                 285

Met Gln Asn Ile Met Glu Thr Lys Leu Asn Asn Lys Gln Leu Glu Ser
    290                 295                 300

Val Leu Ile Pro Glu Trp Ser Val Gly Cys Arg Arg Leu Thr Pro Gly
305                 310                 315                 320

Thr Asn Tyr Leu Glu Ser Leu Ser Asp Asp Asn Val Lys Val Val Tyr
                325                 330                 335

Gly Glu Ile Thr Gln Ile Thr Glu Ser Gly Val Ile Cys Asp Asp Gly
            340                 345                 350

Lys Gly Glu Tyr Pro Val Glu Val Leu Ile Cys Ala Thr Gly Phe Asp
        355                 360                 365

Thr Thr Phe Lys Pro Arg Phe Pro Leu Ile Gly Thr Thr Gln Glu Lys
    370                 375                 380

Leu Ser Asp Val Trp Lys Asp Asp Pro Arg Gly Tyr Phe Gly Ile Ala
385                 390                 395                 400

Thr Asn Asn Tyr Pro Asn Tyr Phe Phe Thr Leu Gly Pro Asn Cys Pro
                405                 410                 415

Ile Gly Asn Gly Pro Val Leu Cys Ala Ile Glu Ala Glu Val Glu Tyr
            420                 425                 430

Ile Ile Asn Met Leu Ser Lys Phe Gln Lys Glu Asn Ile Arg Ser Phe
        435                 440                 445

Asp Ile Lys Ala Asp Ala Val Asp Ala Phe Asn Asp Trp Lys Asp Asp
    450                 455                 460

Phe Met Lys Asp Thr Ile Trp Ala Glu Gln Cys Arg Ser Trp Tyr Lys
465                 470                 475                 480

Ala Gly Ser Ala Thr Gly Lys Ile Leu Ala Leu Trp Pro Gly Ser Thr
                485                 490                 495

Leu His Tyr Leu Glu Ala Leu Lys Ser Pro Arg Trp Glu Asp Trp Asp
            500                 505                 510

Phe Lys Tyr Gln Pro Gly Arg Asn Arg Phe His Tyr Phe Gly Asn Gly
        515                 520                 525

His Ser Cys Ala Glu Gln Asp Gly Asp Leu Ser Trp Tyr Ile Arg Asn
    530                 535                 540

Glu Asp Asp Ser Tyr Ile Asp Pro Val Leu Lys Pro Lys Pro Lys Ala
545                 550                 555                 560

Ala Val Glu Ser Glu Ala His Ile Ala Leu Pro Gly Ile Gly Pro Met
                565                 570                 575

Leu Met Glu Asp Pro Arg Asp Val Ala Val Glu Ala
            580                 585
```

<210> SEQ ID NO 3
<211> LENGTH: 1767
<212> TYPE: DNA
<213> ORGANISM: Hyphozyma roseonigra

<400> SEQUENCE: 3

```
atgccgtctg ccattactcc acctgttgat caccgttccc tgccgggcct gtttaaaccg      60

cagcgcaagc tgaaagtgat ttgcgtgggc gcgggtgcga gcggcctgct gttgagctac     120
```

```
aagattcagc gccacttcga agatttcgag ctgcaagtgt ttgagaagaa ccctgaagtt    180

agcggtacgt ggtacgagaa ccgttatccg ggttgtgcgt gcgatgtgcc gagccataac    240

tacacctgga gctttgagcc gaaaacggat tggtccgcca attatgcgag cagcaaagag    300

attttcaaat atttcaaaga ttttacgcgt aaatatggtc tgtctaaata cattaaattg    360

gaacatgaag tggtcggcgc gacctggatg gaagccgagg cgcagtggaa agttgacgtt    420

aaagatctgc gcagcggtaa cacccagtcc agcttcgcgc atatcctggt taacgccggc    480

ggcattctga atgcctggcg ttatccgccg attccgggca tcaaagattt caagggtgac    540

ctggtgcata gcgcagcatg gccggagcat ttggacctga atggcaaagt cgttggtctg    600

atcggcaacg gtagcagcgg tatccaaatc ctgccggcaa ttaagaaaga cgtgaagcaa    660

ctggtgacgt ttatccgtga agccacctgg gtcgcaccgc cgctgggtca agcgtaccgt    720

gcgttttcca ccgacgagca agcacagttt gcgcaggacc cgcgccacca cctggaaacc    780

cgtcgtgcga ccgaagccac catgaatcag agctttggta ttttccatag cggcagcgaa    840

gaacagaaag gtgtccgcca gtacatgcaa aacattatgg aaaccaagct gaataataag    900

caactggaga gcgtcctgat tccggagtgg agcgtcggct gtcgtcgtct gaccccgggc    960

acgaactacc tggaaagcct gagcgacgac aatgtcaaag ttgtgtacgg tgagattacc   1020

caaatcaccg agagcggtgt catctgcgat gacggcaagg gtgagtatcc ggttgaagtc   1080

ctgatctgcg ccaccggttt tgatacgacc tttaaaccgc gcttcccgct gatcggtacg   1140

acccaggaaa agctgagcga cgtgtggaaa gatgatccgc gcggttactt cggcatcgcg   1200

acgaataatt atccgaacta tttcttcacg ctgggtccga actgcccgat cggtaatggc   1260

ccggtcctgt gtgcgatcga agccgaagtt gagtacatca tcaacatgct gagcaagttt   1320

cagaaagaaa atattcgctc cttcgacatt aaagccgacg cggtggacgc gtttaatgat   1380

tggaaagacg atttcatgaa agataccatc tgggcagaac agtgccgtag ctggtacaag   1440

gccggcagcg cgaccggcaa gattctggca ctgtggccgg gcagcacgct gcactacctg   1500

gaagcgctga aaagcccgcg ttgggaagat tgggacttca agtatcaacc gggccgtaac   1560

cgtttccact actttggcaa cggtcacagc tgtgccgagc aagatggcga cctgtcctgg   1620

tacatccgta atgaagatga cagctacatt gacccggttc tgaaaccgaa gccgaaagcc   1680

gcggtggaga gcgaggcaca catcgcactg ccgggtattg gcccgatgct gatggaagat   1740

ccgcgtgatg tcgcggttga ggcgtaa                                       1767
```

<210> SEQ ID NO 4
<211> LENGTH: 1767
<212> TYPE: DNA
<213> ORGANISM: Hyphozyma roseonigra

<400> SEQUENCE: 4

```
atgccatctg ctatcactcc accagttgac cacagatctt tgccaggttt gttcaagcca     60

caaagaaagt tgaaggttat ctgtgttggt gctggtgctt ctggtttgtt gttgtcttac    120

aagatccaaa gacacttcga agacttcgaa ttgcaagttt tcgaaaagaa cccagaagtt    180

tctggtactt ggtacgaaaa cagataccca ggttgtgctt gtgacgttcc atctcacaac    240

tacacttggt ctttcgaacc aaagactgac tggtctgcta actacgcttc ttctaaggaa    300

atcttcaagt acttcaagga cttcactaga aagtacggtt tgtctaagta catcaagttg    360

gaacacgaag ttgttggtgc tacttggatg gaagctgaag ctcaatggaa ggttgacgtt    420
```

-continued

```
aaggacttga gatctggtaa cactcaatct tctttcgctc acatcttggt taacgctggt    480

ggtatcttga acgcttggag atacccacca atcccaggta tcaaggactt caagggtgac    540

ttggttcact ctgctgcttg gccagaacac ttggacttga acggtaaggt tgttggtttg    600

atcggtaacg gttcttctgg tatccaaatc ttgccagcta tcaagaagga cgttaagcaa    660

ttggttactt tcatcagaga agctacttgg gttgctccac cattgggtca agcttacaga    720

gctttctcta ctgacgaaca agctcaattc gctcaagacc caagacacca cttggaaact    780

agaagagcta ctgaagctac tatgaaccaa tctttcggta tcttccactc tggttctgaa    840

gaacaaaagg gtgttagaca atacatgcaa aacatcatgg aaactaagtt gaacaacaag    900

caattggaat ctgttttgat cccagaatgg tctgttggtt gtagaagatt gactccaggt    960

actaactact tggaatcttt gtctgacgac aacgttaagg ttgtttacgg tgaaatcact   1020

caaatcactg aatctggtgt tatctgtgac gacggtaagg gtgaataccc agttgaagtt   1080

ttgatctgtg ctactggttt cgacactact ttcaagccaa gattcccatt gatcggtact   1140

actcaagaaa agttgtctga cgtttggaag gacgacccaa gaggttactt cggtatcgct   1200

actaacaact acccaaacta cttcttcact ttgggtccaa actgtccaat cggtaacggt   1260

ccagttttgt gtgctatcga agctgaagtt gaatacatca tcaacatgtt gtctaagttc   1320

caaaaggaaa acatcagatc tttcgacatc aaggctgacg ctgttgacgc tttcaacgac   1380

tggaaggacg acttcatgaa ggacactatc tgggctgaac aatgtagatc ttggtacaag   1440

gctggttctg ctactggtaa gatcttggct ttgtggccag gttctacttt gcactacttg   1500

gaagctttga agtctccaag atgggaagac tgggacttca agtaccaacc aggtagaaac   1560

agattccact acttcggtaa cggtcactct tgtgctgaac aagacggtga cttgtcttgg   1620

tacatcagaa acgaagacga ctcttacatc gacccagttt tgaagccaaa gccaaaggct   1680

gctgttgaat ctgaagctca catcgctttg ccaggtatcg gtccaatgtt gatggaagac   1740

ccaagagacg ttgctgttga agcttaa                                        1767
```

<210> SEQ ID NO 5
<211> LENGTH: 1839
<212> TYPE: DNA
<213> ORGANISM: Filobasidium magnum
<220> FEATURE:
<221> NAME/KEY: CDS
<222> LOCATION: (1)..(1839)

<400> SEQUENCE: 5

```
atg act atc gat ttg cag cag ccc gac gcc gtg cca ttc acc tct tcg       48
Met Thr Ile Asp Leu Gln Gln Pro Asp Ala Val Pro Phe Thr Ser Ser
1               5                   10                  15

act ttt gtc gtg ccg gat cca tcg aac ctg gcc tct cag gca cag aat       96
Thr Phe Val Val Pro Asp Pro Ser Asn Leu Ala Ser Gln Ala Gln Asn
            20                  25                  30

tca cag ctc caa tct gct caa gaa gga gca gag tac cct gtg aac gca      144
Ser Gln Leu Gln Ser Ala Gln Glu Gly Ala Glu Tyr Pro Val Asn Ala
        35                  40                  45

cat ggg gtt cga gga gat gga acg att cat gaa cga ccg atc aac gat      192
His Gly Val Arg Gly Asp Gly Thr Ile His Glu Arg Pro Ile Asn Asp
    50                  55                  60

cgc agg aag atg cgc gtc atc tgc gtc ggt gca ggc atc tca ggt ctc      240
Arg Arg Lys Met Arg Val Ile Cys Val Gly Ala Gly Ile Ser Gly Leu
65                  70                  75                  80

tat atg gcc atc aag ctc cct cga agt acg gaa aat gta gag ctc aag      288
Tyr Met Ala Ile Lys Leu Pro Arg Ser Thr Glu Asn Val Glu Leu Lys
```

-continued

```
                85                  90                  95

atc tac gag aag aat cac gat ctc ggt ggg acc tgg ctg gag aat agg      336
Ile Tyr Glu Lys Asn His Asp Leu Gly Gly Thr Trp Leu Glu Asn Arg
            100                 105                 110

tat cca gga tgc gct tgt gat gta cca gcc cat gcc tac gca tac agc      384
Tyr Pro Gly Cys Ala Cys Asp Val Pro Ala His Ala Tyr Ala Tyr Ser
        115                 120                 125

ttc gag aac aac ccc gaa ttt cct aga ttc ttt tcg agc tcg gaa gac      432
Phe Glu Asn Asn Pro Glu Phe Pro Arg Phe Phe Ser Ser Ser Glu Asp
    130                 135                 140

atc cac aag tac ttg ctt cgc gtg gct gat aaa tat gat tgc aag aaa      480
Ile His Lys Tyr Leu Leu Arg Val Ala Asp Lys Tyr Asp Cys Lys Lys
145                 150                 155                 160

tac atc gca ttc aac acc aaa gta gtc gag gcc att tgg gac gaa gaa      528
Tyr Ile Ala Phe Asn Thr Lys Val Val Glu Ala Ile Trp Asp Glu Glu
                165                 170                 175

cag ggc atc tat aac gtc aag att gaa cgc tcg gat ggc aca gta ttc      576
Gln Gly Ile Tyr Asn Val Lys Ile Glu Arg Ser Asp Gly Thr Val Phe
            180                 185                 190

cag gac acg tgc gaa gtt cta ttg aac gct tct ggt atc ctt aac gcc      624
Gln Asp Thr Cys Glu Val Leu Leu Asn Ala Ser Gly Ile Leu Asn Ala
        195                 200                 205

tgg agg tac cct ggg att cct gga att aag gac tac aag ggc acg tta      672
Trp Arg Tyr Pro Gly Ile Pro Gly Ile Lys Asp Tyr Lys Gly Thr Leu
    210                 215                 220

atg cac tcg gct acc tgg gac cga tcc gtg tcc ctg aaa ggc aaa aag      720
Met His Ser Ala Thr Trp Asp Arg Ser Val Ser Leu Lys Gly Lys Lys
225                 230                 235                 240

gtt gcc ctc atc gga tca gga tca tca ggc att cag atc ttg ccc aac      768
Val Ala Leu Ile Gly Ser Gly Ser Ser Gly Ile Gln Ile Leu Pro Asn
                245                 250                 255

atc ctt gac gat tgc aaa gag gtc gtg aca tac atc att gat cca gcc      816
Ile Leu Asp Asp Cys Lys Glu Val Val Thr Tyr Ile Ile Asp Pro Ala
            260                 265                 270

tgg att gcc cct gcg aat ctt gtc acg gct gga gtc tcg gac gac ggt      864
Trp Ile Ala Pro Ala Asn Leu Val Thr Ala Gly Val Ser Asp Asp Gly
        275                 280                 285

gaa gag cct aag gag ccg acg cct gaa gaa ttg gcg tcg agt agt gac      912
Glu Glu Pro Lys Glu Pro Thr Pro Glu Glu Leu Ala Ser Ser Ser Asp
    290                 295                 300

ttc gcc tac tcg caa gag caa atc aat ggc ttc aag aag gac cct aag      960
Phe Ala Tyr Ser Gln Glu Gln Ile Asn Gly Phe Lys Lys Asp Pro Lys
305                 310                 315                 320

tca ctg atg gat cat cga gca acg ctc gaa agg acg atg aat cag tct     1008
Ser Leu Met Asp His Arg Ala Thr Leu Glu Arg Thr Met Asn Gln Ser
                325                 330                 335

ttc ccc atc tta ctc aga ggc tca ccg tcc aac ctt tat gcc gct tct     1056
Phe Pro Ile Leu Leu Arg Gly Ser Pro Ser Asn Leu Tyr Ala Ala Ser
            340                 345                 350

ctc ttt gaa gac ctg atg agg aaa cgc ctt gcc aag aag cct gag gta     1104
Leu Phe Glu Asp Leu Met Arg Lys Arg Leu Ala Lys Lys Pro Glu Val
        355                 360                 365

gcg gat gcc atc atc ccc gaa tgg tca atc ggt tgc cga cgt ctc act     1152
Ala Asp Ala Ile Ile Pro Glu Trp Ser Ile Gly Cys Arg Arg Leu Thr
    370                 375                 380

cct gga cca cac tat ctt gag gcc ttg tgc aat ccc aag gtc aag atc     1200
Pro Gly Pro His Tyr Leu Glu Ala Leu Cys Asn Pro Lys Val Lys Ile
385                 390                 395                 400

ttg acc caa gct atc aag tcc ttc tcc gat aag gga atg tac act gcc     1248
```

```
Leu Thr Gln Ala Ile Lys Ser Phe Ser Asp Lys Gly Met Tyr Thr Ala
                405                 410                 415

gat ggc gaa cac gaa gac ttt gac gtg gtg ata tgc gcg act gga ttc      1296
Asp Gly Glu His Glu Asp Phe Asp Val Val Ile Cys Ala Thr Gly Phe
            420                 425                 430

gac gta tcg ttc cga ccc cga ttc aaa ttt atc ggc aag gac ggg tat      1344
Asp Val Ser Phe Arg Pro Arg Phe Lys Phe Ile Gly Lys Asp Gly Tyr
        435                 440                 445

gag gtg ccc gag aac ttt ggt cag act ccc aaa ggt tac ctc gct ctc      1392
Glu Val Pro Glu Asn Phe Gly Gln Thr Pro Lys Gly Tyr Leu Ala Leu
    450                 455                 460

gct tac gcc ggt ttc cct aat tcg ttc atc ttc atg ggg ccg aac gga      1440
Ala Tyr Ala Gly Phe Pro Asn Ser Phe Ile Phe Met Gly Pro Asn Gly
465                 470                 475                 480

cct atc gcc aac gga tct gtc gtg gtc tcc ctg gag aaa caa ggc gac      1488
Pro Ile Ala Asn Gly Ser Val Val Val Ser Leu Glu Lys Gln Gly Asp
                485                 490                 495

tac ttc atc aag gcg atc aac aag atc caa agg cag aat ata aaa ggc      1536
Tyr Phe Ile Lys Ala Ile Asn Lys Ile Gln Arg Gln Asn Ile Lys Gly
            500                 505                 510

atg act gtc aga ttc gat gcg gtc gat gat ttc acc aac cac gta gac      1584
Met Thr Val Arg Phe Asp Ala Val Asp Asp Phe Thr Asn His Val Asp
        515                 520                 525

aaa tac atg gat agg acc gtg ctc acc gat gac tgc atc agc tgg tac      1632
Lys Tyr Met Asp Arg Thr Val Leu Thr Asp Asp Cys Ile Ser Trp Tyr
    530                 535                 540

aag aac ggg aaa cga gac gga cga gtc agt gcc gtc tgg cct ggg agc      1680
Lys Asn Gly Lys Arg Asp Gly Arg Val Ser Ala Val Trp Pro Gly Ser
545                 550                 555                 560

gca ctt cat tat atg gag gcc atc gcc gac cct aga tgg gag gat tac      1728
Ala Leu His Tyr Met Glu Ala Ile Ala Asp Pro Arg Trp Glu Asp Tyr
                565                 570                 575

acc tac act tat cgc gaa ccc ggt cat tct ttt tcg ttc ttg gga gat      1776
Thr Tyr Thr Tyr Arg Glu Pro Gly His Ser Phe Ser Phe Leu Gly Asp
            580                 585                 590

ggg acg tcc tgg gtc gaa cac acc gga gga gac acg gct tgg tac ctg      1824
Gly Thr Ser Trp Val Glu His Thr Gly Gly Asp Thr Ala Trp Tyr Leu
        595                 600                 605

aaa gag acc ctc taa                                                  1839
Lys Glu Thr Leu
    610
```

<210> SEQ ID NO 6
<211> LENGTH: 612
<212> TYPE: PRT
<213> ORGANISM: Filobasidium magnum

<400> SEQUENCE: 6

```
Met Thr Ile Asp Leu Gln Gln Pro Asp Ala Val Pro Phe Thr Ser Ser
1               5                   10                  15

Thr Phe Val Val Pro Asp Pro Ser Asn Leu Ala Ser Gln Ala Gln Asn
            20                  25                  30

Ser Gln Leu Gln Ser Ala Gln Glu Gly Ala Glu Tyr Pro Val Asn Ala
        35                  40                  45

His Gly Val Arg Gly Asp Gly Thr Ile His Glu Arg Pro Ile Asn Asp
    50                  55                  60

Arg Arg Lys Met Arg Val Ile Cys Val Gly Ala Gly Ile Ser Gly Leu
65                  70                  75                  80

Tyr Met Ala Ile Lys Leu Pro Arg Ser Thr Glu Asn Val Glu Leu Lys
```

```
                85                  90                  95

Ile Tyr Glu Lys Asn His Asp Leu Gly Gly Thr Trp Leu Glu Asn Arg
            100                 105                 110

Tyr Pro Gly Cys Ala Cys Asp Val Pro Ala His Ala Tyr Ala Tyr Ser
        115                 120                 125

Phe Glu Asn Asn Pro Glu Phe Pro Arg Phe Phe Ser Ser Ser Glu Asp
    130                 135                 140

Ile His Lys Tyr Leu Leu Arg Val Ala Asp Lys Tyr Asp Cys Lys Lys
145                 150                 155                 160

Tyr Ile Ala Phe Asn Thr Lys Val Val Glu Ala Ile Trp Asp Glu Glu
                165                 170                 175

Gln Gly Ile Tyr Asn Val Lys Ile Glu Arg Ser Asp Gly Thr Val Phe
            180                 185                 190

Gln Asp Thr Cys Glu Val Leu Leu Asn Ala Ser Gly Ile Leu Asn Ala
        195                 200                 205

Trp Arg Tyr Pro Gly Ile Pro Gly Ile Lys Asp Tyr Lys Gly Thr Leu
    210                 215                 220

Met His Ser Ala Thr Trp Asp Arg Ser Val Ser Leu Lys Gly Lys Lys
225                 230                 235                 240

Val Ala Leu Ile Gly Ser Gly Ser Ser Gly Ile Gln Ile Leu Pro Asn
                245                 250                 255

Ile Leu Asp Asp Cys Lys Glu Val Val Thr Tyr Ile Ile Asp Pro Ala
            260                 265                 270

Trp Ile Ala Pro Ala Asn Leu Val Thr Ala Gly Val Ser Asp Asp Gly
        275                 280                 285

Glu Glu Pro Lys Glu Pro Thr Pro Glu Glu Leu Ala Ser Ser Ser Asp
    290                 295                 300

Phe Ala Tyr Ser Gln Glu Gln Ile Asn Gly Phe Lys Lys Asp Pro Lys
305                 310                 315                 320

Ser Leu Met Asp His Arg Ala Thr Leu Glu Arg Thr Met Asn Gln Ser
                325                 330                 335

Phe Pro Ile Leu Leu Arg Gly Ser Pro Ser Asn Leu Tyr Ala Ala Ser
            340                 345                 350

Leu Phe Glu Asp Leu Met Arg Lys Arg Leu Ala Lys Lys Pro Glu Val
        355                 360                 365

Ala Asp Ala Ile Ile Pro Glu Trp Ser Ile Gly Cys Arg Arg Leu Thr
    370                 375                 380

Pro Gly Pro His Tyr Leu Glu Ala Leu Cys Asn Pro Lys Val Lys Ile
385                 390                 395                 400

Leu Thr Gln Ala Ile Lys Ser Phe Ser Asp Lys Gly Met Tyr Thr Ala
                405                 410                 415

Asp Gly Glu His Glu Asp Phe Asp Val Val Ile Cys Ala Thr Gly Phe
            420                 425                 430

Asp Val Ser Phe Arg Pro Arg Phe Lys Phe Ile Gly Lys Asp Gly Tyr
        435                 440                 445

Glu Val Pro Glu Asn Phe Gly Gln Thr Pro Lys Gly Tyr Leu Ala Leu
    450                 455                 460

Ala Tyr Ala Gly Phe Pro Asn Ser Phe Ile Phe Met Gly Pro Asn Gly
465                 470                 475                 480

Pro Ile Ala Asn Gly Ser Val Val Val Ser Leu Glu Lys Gln Gly Asp
                485                 490                 495

Tyr Phe Ile Lys Ala Ile Asn Lys Ile Gln Arg Gln Asn Ile Lys Gly
            500                 505                 510
```

```
Met Thr Val Arg Phe Asp Ala Val Asp Asp Phe Thr Asn His Val Asp
        515                 520                 525

Lys Tyr Met Asp Arg Thr Val Leu Thr Asp Asp Cys Ile Ser Trp Tyr
    530                 535                 540

Lys Asn Gly Lys Arg Asp Gly Arg Val Ser Ala Val Trp Pro Gly Ser
545                 550                 555                 560

Ala Leu His Tyr Met Glu Ala Ile Ala Asp Pro Arg Trp Glu Asp Tyr
                565                 570                 575

Thr Tyr Thr Tyr Arg Glu Pro Gly His Ser Phe Ser Phe Leu Gly Asp
            580                 585                 590

Gly Thr Ser Trp Val Glu His Thr Gly Gly Asp Thr Ala Trp Tyr Leu
        595                 600                 605

Lys Glu Thr Leu
    610
```

<210> SEQ ID NO 7
<211> LENGTH: 1839
<212> TYPE: DNA
<213> ORGANISM: Filobasidium magnum

<400> SEQUENCE: 7

```
atgaccatcg atttgcaaca gccagacgca gtcccgttta cgagcagcac tttcgtcgta     60

ccggacccgt ccaacctggc atcccaggct caaaacagcc aactgcagag cgcgcaagag    120

ggcgcagagt acccggtgaa tgcacacggt gtccgcggtg acggcaccat tcacgagcgt    180

ccgatcaatg accgtcgtaa aatgcgcgtc atctgcgttg gtgcgggtat tagcggcctg    240

tatatggcga tcaaactgcc gcgcagcacc gagaatgttg aactgaagat ctacgagaaa    300

aaccatgacc tcggcggcac gtggctggag aatcgctacc ctggctgcgc gtgcgatgtt    360

ccggcgcatg cgtatgcata ttcttttgag aataatccgg aatttccacg ctttttcagc    420

agcagcgagg atatccacaa gtacctgttg cgtgttgcgg acaagtacga ctgtaagaaa    480

tacatcgcct ttaacaccaa agtcgttgag gctatctggg acgaagaaca gggtatttac    540

aatgtgaaga ttgagcgtag cgacggcacc gtgttccagg acacctgtga ggtgctgctg    600

aacgcgagcg gtattctgaa tgcctggcgc tacccgggca tccctggcat taaggattac    660

aaaggtacgc tgatgcacag cgctacctgg gaccgtagcg tttctttgaa aggcaaaaaa    720

gtcgcactga ttggcagcgg tagcagcggt atccagattc tgccgaacat tctggacgac    780

tgcaaagaag tggtcacgta cattatcgac ccggcgtgga ttgctccggc taacctggtg    840

accgcgggtg tctccgatga tggtgaggaa ccgaaagagc caacccctga ggaactggcc    900

tcatcctccg acttcgctta tagccaggaa cagattaacg gcttcaagaa agatccgaag    960

tcgctgatgg atcaccgcgc cacgctggag cgtaccatga atcaatcgtt tccgattctg   1020

ctgcgtggct ctccgagcaa cttgtatgcc gcaagcctgt tcgaggattt gatgcgtaag   1080

cgtctggcga agaagccgga agttgcggac gcgattatcc cggagtggag catcggttgc   1140

agacgcctga cgccgggtcc gcattacctg gaagcactgt gtaacccgaa agtgaagatc   1200

ctgactcagg cgatcaagag ctttagcgat aagggcatgt atactgcgga cggtgagcat   1260

gaagatttcg atgttgtcat ttgtgcgacc ggtttcgatg tgagctttcg tccgcgcttc   1320

aagtttattg gtaaagatgg ctatgaagtc ccagagaatt tcggccaaac gccgaaaggt   1380

tatctggcac tggcgtacgc cggcttcccg aacagcttca tctttatggg tccgaacggt   1440

ccgattgcga acggtagcgt tgtggtgagc ctggagaagc aaggtgacta cttcattaaa   1500
```

```
gcgatcaata agatccagcg tcaaaacatt aagggtatga ccgttcgttt cgacgccgtg   1560

gatgatttta cgaatcacgt ggacaaatac atggaccgta cggtgctgac cgacgattgc   1620

atcagctggt acaagaatgg taaacgtgac ggtcgtgtta gcgcagtttg gccgggttcc   1680

gcgctgcact atatggaagc catcgcagac ccgcgttggg aagattacac ctacacctat   1740

cgcgaaccgg gtcactcttt tagcttcctg ggtgatggca ccagctgggt tgagcatacg   1800

ggtggcgata ccgcctggta tttgaaagaa accctgtaa                          1839
```

<210> SEQ ID NO 8
<211> LENGTH: 1839
<212> TYPE: DNA
<213> ORGANISM: Filobasidium magnum

<400> SEQUENCE: 8

```
atgactatcg acttgcaaca accagacgct gttccattca cttcttctac tttcgttgtt     60

ccagacccat ctaacttggc ttctcaagct caaaactctc aattgcaatc tgctcaagaa    120

ggtgctgaat acccagttaa cgctcacggt gttagaggtg acggtactat ccacgaaaga    180

ccaatcaacg acagaagaaa gatgagagtt atctgtgttg gtgctggtat ctctggtttg    240

tacatggcta tcaagttgcc aagatctact gaaaacgttg aattgaagat ctacgaaaag    300

aaccacgact tgggtggtac ttggttggaa aacagatacc caggttgtgc ttgtgacgtt    360

ccagctcacg cttacgctta ctctttcgaa aacaacccag aattcccaag attcttctct    420

tcttctgaag acatccacaa gtacttgttg agagttgctg acaagtacga ctgtaagaag    480

tacatcgctt tcaacactaa ggttgttgaa gctatctggg acgaagaaca aggtatctac    540

aacgttaaga tcgaaagatc tgacggtact gttttccaag acacttgtga agttttgttg    600

aacgcttctg gtatcttgaa cgcttggaga tacccaggta tcccaggtat caaggactac    660

aagggtactt tgatgcactc tgctacttgg gacagatctg tttctttgaa gggtaagaag    720

gttgctttga tcggttctgg ttcttctggt atccaaatct tgccaaacat cttggacgac    780

tgtaaggaag ttgttactta catcatcgac ccagcttgga tcgctccagc taacttggtt    840

actgctggtg tttctgacga cggtgaagaa ccaaaggaac caactccaga agaattggct    900

tcttcttctg acttcgctta ctctcaagaa caaatcaacg gtttcaagaa ggacccaaag    960

tctttgatgg accacagagc tactttggaa agaactatga accaatcttt cccaatcttg   1020

ttgagaggtt ctccatctaa cttgtacgct gcttctttgt tcgaagactt gatgagaaag   1080

agattggcta agaagccaga agttgctgac gctatcatcc cagaatggtc tatcggttgt   1140

agaagattga ctccaggtcc acactacttg gaagctttgt gtaacccaaa ggttaagatc   1200

ttgactcaag ctatcaagtc tttctctgac aagggtatgt acactgctga cggtgaacac   1260

gaagacttcg acgttgttat ctgtgctact ggtttcgacg tttctttcag accaagattc   1320

aagttcatcg gtaaggacgg ttacgaagtt ccagaaaact tcggtcaaac tccaaagggt   1380

tacttggctt tggcttacgc tggtttccca aactctttca tcttcatggg tccaaacggt   1440

ccaatcgcta acggttctgt tgttgtttct ttggaaaagc aaggtgacta cttcatcaag   1500

gctatcaaca agatccaaag acaaaacatc aagggtatga ctgttagatt cgacgctgtt   1560

gacgacttca ctaaccacgt tgacaagtac atggacagaa ctgttttgac tgacgactgt   1620

atctcttggt acaagaacgg taagagagac ggtagagttt ctgctgtttg gccaggttct   1680

gctttgcact acatggaagc tatcgctgac ccaagatggg aagactacac ttacacttac   1740
```

-continued

```
agagaaccag gtcactcttt ctctttcttg ggtgacggta cttcttgggt tgaacacact   1800

ggtggtgaca ctgcttggta cttgaaggaa actttgtaa                          1839


<210> SEQ ID NO 9
<211> LENGTH: 1767
<212> TYPE: DNA
<213> ORGANISM: Papiliotrema laurentii
<220> FEATURE:
<221> NAME/KEY: CDS
<222> LOCATION: (1)..(1767)

<400> SEQUENCE: 9

atg cct tcc gca atc acc ccg ccg gtt gat cat cgc agt ctt cca ggt       48
Met Pro Ser Ala Ile Thr Pro Pro Val Asp His Arg Ser Leu Pro Gly
1               5                   10                  15

ctt ttc aag cca cag agg aag ctc aaa gtg ata tgt gtc gga gcc ggc       96
Leu Phe Lys Pro Gln Arg Lys Leu Lys Val Ile Cys Val Gly Ala Gly
            20                  25                  30

gcc tcg ggc tta ctt ctt tcc tac aag ata caa cga cac ttc gag gat      144
Ala Ser Gly Leu Leu Leu Ser Tyr Lys Ile Gln Arg His Phe Glu Asp
        35                  40                  45

ttc gag ctc caa gtc ttt gag aag aat cct gaa gta tca gga acc tgg      192
Phe Glu Leu Gln Val Phe Glu Lys Asn Pro Glu Val Ser Gly Thr Trp
    50                  55                  60

tac gag aac aga tat ccc ggc tgc gct tgt gat gtt ccc tcg cat aat      240
Tyr Glu Asn Arg Tyr Pro Gly Cys Ala Cys Asp Val Pro Ser His Asn
65                  70                  75                  80

tat aca tgg tct ttt gag ccc aaa acc gac tgg tcc gcc aac tat gca      288
Tyr Thr Trp Ser Phe Glu Pro Lys Thr Asp Trp Ser Ala Asn Tyr Ala
                85                  90                  95

tca tcg aag gag att ttc aaa tat ttc aag gac ttc acg aag aag tat      336
Ser Ser Lys Glu Ile Phe Lys Tyr Phe Lys Asp Phe Thr Lys Lys Tyr
            100                 105                 110

ggt ctt agc aag tac atc aag ctg gag cat gag gtc gtg ggg gcc acg      384
Gly Leu Ser Lys Tyr Ile Lys Leu Glu His Glu Val Val Gly Ala Thr
        115                 120                 125

tgg atg gag gcg gag gca cag tgg aaa gtt gac gtc aag gac ctt cga      432
Trp Met Glu Ala Glu Ala Gln Trp Lys Val Asp Val Lys Asp Leu Arg
    130                 135                 140

agt gga aac acg cag agc tcg ttt gcg cat ata ctg gtc aat gca gga      480
Ser Gly Asn Thr Gln Ser Ser Phe Ala His Ile Leu Val Asn Ala Gly
145                 150                 155                 160

ggc att ctg aat gct tgg cga tat ccg cca att cca gga atc aag gat      528
Gly Ile Leu Asn Ala Trp Arg Tyr Pro Pro Ile Pro Gly Ile Lys Asp
                165                 170                 175

ttc aag ggt gat ctt gtc cac tcc gca gct tgg cca gaa cat ctt gat      576
Phe Lys Gly Asp Leu Val His Ser Ala Ala Trp Pro Glu His Leu Asp
            180                 185                 190

ctt aat ggg aag gtt gtc ggt ctc atc gga aat gga tcc tcc ggc att      624
Leu Asn Gly Lys Val Val Gly Leu Ile Gly Asn Gly Ser Ser Gly Ile
        195                 200                 205

cag atc ctt ccg gcc atc aag aag gat gta aag caa ctc gtt aca ttc      672
Gln Ile Leu Pro Ala Ile Lys Lys Asp Val Lys Gln Leu Val Thr Phe
    210                 215                 220

att cgg gaa gca act tgg gtg gcg cct cct tta ggt caa gcc tat cgt      720
Ile Arg Glu Ala Thr Trp Val Ala Pro Pro Leu Gly Gln Ala Tyr Arg
225                 230                 235                 240

gcg ttc tcg act gat gaa cag gct cag ttt gcg caa gat ccg cgc cat      768
Ala Phe Ser Thr Asp Glu Gln Ala Gln Phe Ala Gln Asp Pro Arg His
                245                 250                 255
```

-continued

```
cac ctg gag aca cgg cgt gca att gag gct acc atg aat caa tca ttt      816
His Leu Glu Thr Arg Arg Ala Ile Glu Ala Thr Met Asn Gln Ser Phe
            260                 265                 270

ggt atc ttc cat tcg gga tcc gag gag cag aaa ggg gtt cgc caa tat      864
Gly Ile Phe His Ser Gly Ser Glu Glu Gln Lys Gly Val Arg Gln Tyr
        275                 280                 285

atg cag aat atc atg gaa acg aag ctc aac aac aaa cag ctc gag agt      912
Met Gln Asn Ile Met Glu Thr Lys Leu Asn Asn Lys Gln Leu Glu Ser
    290                 295                 300

gtg ctg att cct gag tgg tcg gtc ggt tgt cgg cgt ctt aca cca ggt      960
Val Leu Ile Pro Glu Trp Ser Val Gly Cys Arg Arg Leu Thr Pro Gly
305                 310                 315                 320

act aat tac cta gaa tcc ctg tcg gac gac aat gtc aag gtc gtc tac     1008
Thr Asn Tyr Leu Glu Ser Leu Ser Asp Asp Asn Val Lys Val Val Tyr
                325                 330                 335

ggt gag atc aca caa att acc gaa ttg ggt gtc atc tgc gat gat ggc     1056
Gly Glu Ile Thr Gln Ile Thr Glu Leu Gly Val Ile Cys Asp Asp Gly
            340                 345                 350

aaa ggc gag tat ccc gtt gaa gtt ctt att tgc gcc act ggc ttc gac     1104
Lys Gly Glu Tyr Pro Val Glu Val Leu Ile Cys Ala Thr Gly Phe Asp
        355                 360                 365

acc acc ttc aaa cca cga ttc cca ctc atc ggt aca acc caa gag aaa     1152
Thr Thr Phe Lys Pro Arg Phe Pro Leu Ile Gly Thr Thr Gln Glu Lys
    370                 375                 380

ctc agt gat gtt tgg aaa gat gat ccg agg ggt tac ttc ggg att gca     1200
Leu Ser Asp Val Trp Lys Asp Asp Pro Arg Gly Tyr Phe Gly Ile Ala
385                 390                 395                 400

acc aac aac tat ccc aac tac ttc ttc act ctt gga ccg aat tgt cca     1248
Thr Asn Asn Tyr Pro Asn Tyr Phe Phe Thr Leu Gly Pro Asn Cys Pro
                405                 410                 415

atc ggt aat ggc ccc gtg ctg tgt gcc atc gaa gct gag gtt gat tat     1296
Ile Gly Asn Gly Pro Val Leu Cys Ala Ile Glu Ala Glu Val Asp Tyr
            420                 425                 430

ata atc aac atg ctc tca aag ttt caa atg gag aac att cgt tct ttt     1344
Ile Ile Asn Met Leu Ser Lys Phe Gln Met Glu Asn Ile Arg Ser Phe
        435                 440                 445

gat atc aag gca gat gct gtc gac gcc ttc aac gac tgg aag gat gac     1392
Asp Ile Lys Ala Asp Ala Val Asp Ala Phe Asn Asp Trp Lys Asp Asp
    450                 455                 460

ttc atg aaa gat acc atc tgg gca gaa caa tgc cgg tca tgg tac aag     1440
Phe Met Lys Asp Thr Ile Trp Ala Glu Gln Cys Arg Ser Trp Tyr Lys
465                 470                 475                 480

gca gga tct gcc acc ggt aaa atc ctt gca ttg tgg cca ggc tcg act     1488
Ala Gly Ser Ala Thr Gly Lys Ile Leu Ala Leu Trp Pro Gly Ser Thr
                485                 490                 495

ttg cac tac ttg gaa gca ctc aag tcg ccg cgg tgg gag gat tgg gac     1536
Leu His Tyr Leu Glu Ala Leu Lys Ser Pro Arg Trp Glu Asp Trp Asp
            500                 505                 510

ttc aag tat cag cct ggt aga aat cgt ttc cac tac ttt gga aat ggt     1584
Phe Lys Tyr Gln Pro Gly Arg Asn Arg Phe His Tyr Phe Gly Asn Gly
        515                 520                 525

cat agc tgt gct gag cag gat ggc gat ctg agc tgg tac att cgc aac     1632
His Ser Cys Ala Glu Gln Asp Gly Asp Leu Ser Trp Tyr Ile Arg Asn
    530                 535                 540

gag gat gat tct tat att gat ccg gta ctc aag cca aag tcg aag gca     1680
Glu Asp Asp Ser Tyr Ile Asp Pro Val Leu Lys Pro Lys Ser Lys Ala
545                 550                 555                 560

gca att gag agc gag gca cat atc gcc ctg cca gga atc ggt ccg atg     1728
Ala Ile Glu Ser Glu Ala His Ile Ala Leu Pro Gly Ile Gly Pro Met
                565                 570                 575
```

```
ttg atg gaa gac ccg cgt gat gtt gct gta gag gcc tag                1767
Leu Met Glu Asp Pro Arg Asp Val Ala Val Glu Ala
            580                 585


<210> SEQ ID NO 10
<211> LENGTH: 588
<212> TYPE: PRT
<213> ORGANISM: Papiliotrema laurentii

<400> SEQUENCE: 10

Met Pro Ser Ala Ile Thr Pro Pro Val Asp His Arg Ser Leu Pro Gly
1               5                   10                  15

Leu Phe Lys Pro Gln Arg Lys Leu Lys Val Ile Cys Val Gly Ala Gly
            20                  25                  30

Ala Ser Gly Leu Leu Leu Ser Tyr Lys Ile Gln Arg His Phe Glu Asp
        35                  40                  45

Phe Glu Leu Gln Val Phe Glu Lys Asn Pro Glu Val Ser Gly Thr Trp
    50                  55                  60

Tyr Glu Asn Arg Tyr Pro Gly Cys Ala Cys Asp Val Pro Ser His Asn
65                  70                  75                  80

Tyr Thr Trp Ser Phe Glu Pro Lys Thr Asp Trp Ser Ala Asn Tyr Ala
                85                  90                  95

Ser Ser Lys Glu Ile Phe Lys Tyr Phe Lys Asp Phe Thr Lys Lys Tyr
            100                 105                 110

Gly Leu Ser Lys Tyr Ile Lys Leu Glu His Glu Val Val Gly Ala Thr
        115                 120                 125

Trp Met Glu Ala Glu Ala Gln Trp Lys Val Asp Val Lys Asp Leu Arg
    130                 135                 140

Ser Gly Asn Thr Gln Ser Ser Phe Ala His Ile Leu Val Asn Ala Gly
145                 150                 155                 160

Gly Ile Leu Asn Ala Trp Arg Tyr Pro Pro Ile Pro Gly Ile Lys Asp
                165                 170                 175

Phe Lys Gly Asp Leu Val His Ser Ala Ala Trp Pro Glu His Leu Asp
            180                 185                 190

Leu Asn Gly Lys Val Val Gly Leu Ile Gly Asn Gly Ser Ser Gly Ile
        195                 200                 205

Gln Ile Leu Pro Ala Ile Lys Lys Asp Val Lys Gln Leu Val Thr Phe
    210                 215                 220

Ile Arg Glu Ala Thr Trp Val Ala Pro Pro Leu Gly Gln Ala Tyr Arg
225                 230                 235                 240

Ala Phe Ser Thr Asp Glu Gln Ala Gln Phe Ala Gln Asp Pro Arg His
                245                 250                 255

His Leu Glu Thr Arg Arg Ala Ile Glu Ala Thr Met Asn Gln Ser Phe
            260                 265                 270

Gly Ile Phe His Ser Gly Ser Glu Glu Gln Lys Gly Val Arg Gln Tyr
        275                 280                 285

Met Gln Asn Ile Met Glu Thr Lys Leu Asn Asn Lys Gln Leu Glu Ser
    290                 295                 300

Val Leu Ile Pro Glu Trp Ser Val Gly Cys Arg Arg Leu Thr Pro Gly
305                 310                 315                 320

Thr Asn Tyr Leu Glu Ser Leu Ser Asp Asp Asn Val Lys Val Val Tyr
                325                 330                 335

Gly Glu Ile Thr Gln Ile Thr Glu Leu Gly Val Ile Cys Asp Asp Gly
            340                 345                 350
```

```
Lys Gly Glu Tyr Pro Val Glu Val Leu Ile Cys Ala Thr Gly Phe Asp
        355                 360                 365

Thr Thr Phe Lys Pro Arg Phe Pro Leu Ile Gly Thr Thr Gln Glu Lys
    370                 375                 380

Leu Ser Asp Val Trp Lys Asp Asp Pro Arg Gly Tyr Phe Gly Ile Ala
385                 390                 395                 400

Thr Asn Asn Tyr Pro Asn Tyr Phe Phe Thr Leu Gly Pro Asn Cys Pro
                405                 410                 415

Ile Gly Asn Gly Pro Val Leu Cys Ala Ile Glu Ala Glu Val Asp Tyr
            420                 425                 430

Ile Ile Asn Met Leu Ser Lys Phe Gln Met Glu Asn Ile Arg Ser Phe
        435                 440                 445

Asp Ile Lys Ala Asp Ala Val Asp Ala Phe Asn Asp Trp Lys Asp Asp
    450                 455                 460

Phe Met Lys Asp Thr Ile Trp Ala Glu Gln Cys Arg Ser Trp Tyr Lys
465                 470                 475                 480

Ala Gly Ser Ala Thr Gly Lys Ile Leu Ala Leu Trp Pro Gly Ser Thr
                485                 490                 495

Leu His Tyr Leu Glu Ala Leu Lys Ser Pro Arg Trp Glu Asp Trp Asp
            500                 505                 510

Phe Lys Tyr Gln Pro Gly Arg Asn Arg Phe His Tyr Phe Gly Asn Gly
        515                 520                 525

His Ser Cys Ala Glu Gln Asp Gly Asp Leu Ser Trp Tyr Ile Arg Asn
    530                 535                 540

Glu Asp Asp Ser Tyr Ile Asp Pro Val Leu Lys Pro Lys Ser Lys Ala
545                 550                 555                 560

Ala Ile Glu Ser Glu Ala His Ile Ala Leu Pro Gly Ile Gly Pro Met
                565                 570                 575

Leu Met Glu Asp Pro Arg Asp Val Ala Val Glu Ala
            580                 585


<210> SEQ ID NO 11
<211> LENGTH: 1767
<212> TYPE: DNA
<213> ORGANISM: Papiliotrema laurentii

<400> SEQUENCE: 11

atgccatctg ccattactcc acctgttgat catcgtagcc tgccgggtct gttcaagccg      60

caacgtaagt tgaaagtgat ctgtgttggc gcgggcgcga gcggcctgtt gctgagctac     120

aagattcagc gtcactttga ggactttgag ttgcaagttt ttgagaaaaa ccctgaagtg     180

agcggcacct ggtacgagaa tcgctacccg ggttgcgcgt gcgatgttcc gagccataac     240

tatacctggt cttttgagcc gaaaacggat tggtccgcaa actatgccag cagcaaagaa     300

attttcaagt acttcaaaga tttcaccaag aaatatggtc tgtctaaata cattaaactg     360

gaacacgaag tcgtgggtgc gacgtggatg gaagcggaag ctcaatggaa agttgacgtc     420

aaagacttgc gtagcggcaa cacccagagc tccttcgcgc acattctggt caatgccggt     480

ggcattctga acgcttggcg ttacccgccg attccgggta tcaaagattt taagggtgac     540

ctggtgcact cggcagcgtg gccggagcat ctggatctga atggtaaagt cgttggcctg     600

attggtaacg gtagcagcgg catccaaatt ctgccggcca tcaaaaaaga cgtgaaacaa     660

ctggtcacgt ttatccgtga ggccacgtgg gtcgccccgc cgctgggcca agcgtaccgc     720

gcatttagca ccgacgaaca ggcgcagttt gcacaagacc cgcgtcacca tctggaaact     780
```

```
cgtcgcgcga ttgaagctac catgaatcag agcttcggta tcttccacag cggttcagag     840

gaacagaaag gtgtgcgtca gtacatgcag aatatcatgg aaacgaaatt gaataacaaa     900

cagctggaga gcgtgctgat tccggagtgg tccgtgggtt gtcgccgtct gaccccgggc     960

acgaactatc tggagagctt gagcgacgat aacgtgaaag ttgtttatgg cgagatcacc    1020

cagatcaccg agctgggtgt gatttgcgat gatggcaagg gtgagtaccc ggtcgaagtg    1080

ctgatttgcg ctaccggttt cgacaccacg ttcaaaccgc gcttcccgtt gattggcacc    1140

acccaggaaa agctgagcga cgtctggaaa gatgaccctc gcggttattt cggtatcgcg    1200

accaataact acccgaacta ctttttcacc ctgggtccga actgcccgat cggcaatggt    1260

ccggtcctgt gtgcaatcga agctgaagtg gactatatca tcaatatgct gagcaaattt    1320

cagatggaaa acattcgcag cttcgacatt aaagccgacg cagttgatgc gtttaacgac    1380

tggaaagatg actttatgaa agacaccatc tgggcagagc agtgtcgttc ttggtacaag    1440

gctggttctg cgacgggtaa gattttggca ctgtggccgg gcagcacgct gcattatctg    1500

gaagccctga aaagcccacg ctgggaagat tgggacttca agtatcaacc gggtcgtaat    1560

cgctttcact acttcggtaa cggccacagc tgcgcggagc aagatggtga tctgtcctgg    1620

tatatccgta atgaagatga cagctacatt gacccggtac tgaagccgaa gtccaaggca    1680

gcgatcgaga gcgaagcaca catcgcgctg ccaggcattg gtccgatgct gatggaggac    1740

ccgcgtgacg ttgcggttga ggcataa                                        1767


<210> SEQ ID NO 12
<211> LENGTH: 1767
<212> TYPE: DNA
<213> ORGANISM: Bensingtonia ciliata
<220> FEATURE:
<221> NAME/KEY: CDS
<222> LOCATION: (1)..(1767)

<400> SEQUENCE: 12

atg cct tcc gca atc acc cca ccg gtt gat cat cgc agt ctt cca ggt       48
Met Pro Ser Ala Ile Thr Pro Pro Val Asp His Arg Ser Leu Pro Gly
1               5                   10                  15

ctt ttc aag cca cag agg aag ctc aaa gtg ata tgt gtc gga gcc ggc       96
Leu Phe Lys Pro Gln Arg Lys Leu Lys Val Ile Cys Val Gly Ala Gly
            20                  25                  30

gcc tcg ggc tta ctt ctt tcc tac aag ata caa cga cac ttc gag gat      144
Ala Ser Gly Leu Leu Leu Ser Tyr Lys Ile Gln Arg His Phe Glu Asp
        35                  40                  45

ttc gag ctc caa gtc ttt gag aag aat cct gag gta tca gga acc tgg      192
Phe Glu Leu Gln Val Phe Glu Lys Asn Pro Glu Val Ser Gly Thr Trp
    50                  55                  60

tac gag aac agg tat ccc ggc tgt gct tgt gat gtt ccc tcg cat aat      240
Tyr Glu Asn Arg Tyr Pro Gly Cys Ala Cys Asp Val Pro Ser His Asn
65                  70                  75                  80

tat aca tgg tct ttt gag ccc aaa acc gac tgg tcc gcc aac tat gca      288
Tyr Thr Trp Ser Phe Glu Pro Lys Thr Asp Trp Ser Ala Asn Tyr Ala
                85                  90                  95

tca tcg aag gag att ttc aaa tat ttc aag gac ttc acg aag aag tat      336
Ser Ser Lys Glu Ile Phe Lys Tyr Phe Lys Asp Phe Thr Lys Lys Tyr
            100                 105                 110

ggt ctt agc aag tac atc aag ctg gag cat gag gtc gtg ggg gcc acg      384
Gly Leu Ser Lys Tyr Ile Lys Leu Glu His Glu Val Val Gly Ala Thr
        115                 120                 125

tgg atg gag gcg gag gca cag tgg aaa gtt gac gtc aag gac ctt cga      432
Trp Met Glu Ala Glu Ala Gln Trp Lys Val Asp Val Lys Asp Leu Arg
```

```
    130                 135                 140

agt gga aac acg cag agc tcg ttt gcg cat ata ctg gtc aat gca gga      480
Ser Gly Asn Thr Gln Ser Ser Phe Ala His Ile Leu Val Asn Ala Gly
145                 150                 155                 160

ggc att ctg aat gct tgg cga tat ccg cca att cca gga atc aag gat      528
Gly Ile Leu Asn Ala Trp Arg Tyr Pro Pro Ile Pro Gly Ile Lys Asp
                165                 170                 175

ttc aag ggt gat ctt gtc cac tcc gca gct tgg cca gaa cat ctt gat      576
Phe Lys Gly Asp Leu Val His Ser Ala Ala Trp Pro Glu His Leu Asp
            180                 185                 190

ctt aat ggg aag gtt gtc ggt cta atc gga aat gga tcc tcc ggc att      624
Leu Asn Gly Lys Val Val Gly Leu Ile Gly Asn Gly Ser Ser Gly Ile
        195                 200                 205

cag atc ctt ccg gcc atc aag aag gat gta aag caa ctc gtt aca ttt      672
Gln Ile Leu Pro Ala Ile Lys Lys Asp Val Lys Gln Leu Val Thr Phe
    210                 215                 220

att cgg gaa gca act tgg gtg gcg cct cct tta ggt caa gcc tat cgt      720
Ile Arg Glu Ala Thr Trp Val Ala Pro Pro Leu Gly Gln Ala Tyr Arg
225                 230                 235                 240

gcg ttc tcg act gat gaa cag gct cag ttt gcg caa gat ccg cgc cat      768
Ala Phe Ser Thr Asp Glu Gln Ala Gln Phe Ala Gln Asp Pro Arg His
                245                 250                 255

cac ctg gaa aca cgt cgt gca act gag gct acc atg aat caa tca ttt      816
His Leu Glu Thr Arg Arg Ala Thr Glu Ala Thr Met Asn Gln Ser Phe
            260                 265                 270

ggt atc ttc cat tcg gga tcc gag gag cag aaa gga gtt cgc caa tat      864
Gly Ile Phe His Ser Gly Ser Glu Glu Gln Lys Gly Val Arg Gln Tyr
        275                 280                 285

atg cag gat atc atg gaa acg aag ctc aac aac aaa cag ctc gag agt      912
Met Gln Asp Ile Met Glu Thr Lys Leu Asn Asn Lys Gln Leu Glu Ser
    290                 295                 300

gtg ctg att cct gag tgg tcg gtc ggt tgt cgg cgt ctt aca cca ggt      960
Val Leu Ile Pro Glu Trp Ser Val Gly Cys Arg Arg Leu Thr Pro Gly
305                 310                 315                 320

act aat tac cta gaa tcc cta tcg gac gac aat gtc aag gtc gtc tac     1008
Thr Asn Tyr Leu Glu Ser Leu Ser Asp Asp Asn Val Lys Val Val Tyr
                325                 330                 335

ggt gaa atc aca caa att acc gaa tca ggt gtc atc tgc gat gat ggt     1056
Gly Glu Ile Thr Gln Ile Thr Glu Ser Gly Val Ile Cys Asp Asp Gly
            340                 345                 350

aaa ggc gaa tat ccc gtc gaa gtt ctt att tgc gcc acc ggc ttc gac     1104
Lys Gly Glu Tyr Pro Val Glu Val Leu Ile Cys Ala Thr Gly Phe Asp
        355                 360                 365

acc acc ttc aaa cca cga ttt cca ctc atc ggc act acg aaa gag aag     1152
Thr Thr Phe Lys Pro Arg Phe Pro Leu Ile Gly Thr Thr Lys Glu Lys
    370                 375                 380

ctc agt gat gtt tgg aaa gat gat ccg agg ggc tac ttt ggg atc gca     1200
Leu Ser Asp Val Trp Lys Asp Asp Pro Arg Gly Tyr Phe Gly Ile Ala
385                 390                 395                 400

acc aac aac tat ccc aac tac ttc ttc act ctt gga ccg aat tgt cca     1248
Thr Asn Asn Tyr Pro Asn Tyr Phe Phe Thr Leu Gly Pro Asn Cys Pro
                405                 410                 415

atc ggt aat ggc ccc gtg ctg tgt gcc att gaa gct gag gtt gaa tat     1296
Ile Gly Asn Gly Pro Val Leu Cys Ala Ile Glu Ala Glu Val Glu Tyr
            420                 425                 430

ata atc aac atg ctc tcg aag ttt cag aag gag aac att cgt tct ttt     1344
Ile Ile Asn Met Leu Ser Lys Phe Gln Lys Glu Asn Ile Arg Ser Phe
        435                 440                 445

gat atc aag gca gat gct gtc gac gcc ttc aac gac tgg aag gat gac     1392
```

```
Asp Ile Lys Ala Asp Ala Val Asp Ala Phe Asn Asp Trp Lys Asp Asp
    450                 455                 460

ttc atg aaa gat acc atc tgg gca gaa caa tgc cgg tca tgg tac aag     1440
Phe Met Lys Asp Thr Ile Trp Ala Glu Gln Cys Arg Ser Trp Tyr Lys
465                 470                 475                 480

gca gga tcc gcc act ggt aaa atc ctt gca ttg tgg cca ggc tcg act     1488
Ala Gly Ser Ala Thr Gly Lys Ile Leu Ala Leu Trp Pro Gly Ser Thr
                485                 490                 495

ttg cac tac ttg gaa gca ctc aag tcg ccg cgg tgg gag gac tgg gac     1536
Leu His Tyr Leu Glu Ala Leu Lys Ser Pro Arg Trp Glu Asp Trp Asp
            500                 505                 510

ttc aag tat cag cct ggt aga aat cgt ttc cat tac ttt gga aat ggt     1584
Phe Lys Tyr Gln Pro Gly Arg Asn Arg Phe His Tyr Phe Gly Asn Gly
        515                 520                 525

cat agc tgt gct gag cag gat ggc gat ctg agc tgg tac atc cgc aac     1632
His Ser Cys Ala Glu Gln Asp Gly Asp Leu Ser Trp Tyr Ile Arg Asn
    530                 535                 540

gag gat gat tct tat att gat ccg gta ctc aag cca aag ccg aag gca     1680
Glu Asp Asp Ser Tyr Ile Asp Pro Val Leu Lys Pro Lys Pro Lys Ala
545                 550                 555                 560

gca gtt gag agc gag gca cat atc gcc ctg cca gga atc ggt ccg atg     1728
Ala Val Glu Ser Glu Ala His Ile Ala Leu Pro Gly Ile Gly Pro Met
                565                 570                 575

ttg atg gaa gac ccg cgt gat gtt gct gta gag gcc tag                 1767
Leu Met Glu Asp Pro Arg Asp Val Ala Val Glu Ala
            580                 585


<210> SEQ ID NO 13
<211> LENGTH: 588
<212> TYPE: PRT
<213> ORGANISM: Bensingtonia ciliata

<400> SEQUENCE: 13

Met Pro Ser Ala Ile Thr Pro Pro Val Asp His Arg Ser Leu Pro Gly
1               5                   10                  15

Leu Phe Lys Pro Gln Arg Lys Leu Lys Val Ile Cys Val Gly Ala Gly
            20                  25                  30

Ala Ser Gly Leu Leu Leu Ser Tyr Lys Ile Gln Arg His Phe Glu Asp
        35                  40                  45

Phe Glu Leu Gln Val Phe Glu Lys Asn Pro Glu Val Ser Gly Thr Trp
    50                  55                  60

Tyr Glu Asn Arg Tyr Pro Gly Cys Ala Cys Asp Val Pro Ser His Asn
65                  70                  75                  80

Tyr Thr Trp Ser Phe Glu Pro Lys Thr Asp Trp Ser Ala Asn Tyr Ala
                85                  90                  95

Ser Ser Lys Glu Ile Phe Lys Tyr Phe Lys Asp Phe Thr Lys Lys Tyr
            100                 105                 110

Gly Leu Ser Lys Tyr Ile Lys Leu Glu His Glu Val Val Gly Ala Thr
        115                 120                 125

Trp Met Glu Ala Glu Ala Gln Trp Lys Val Asp Val Lys Asp Leu Arg
    130                 135                 140

Ser Gly Asn Thr Gln Ser Ser Phe Ala His Ile Leu Val Asn Ala Gly
145                 150                 155                 160

Gly Ile Leu Asn Ala Trp Arg Tyr Pro Pro Ile Pro Gly Ile Lys Asp
                165                 170                 175

Phe Lys Gly Asp Leu Val His Ser Ala Ala Trp Pro Glu His Leu Asp
            180                 185                 190
```

-continued

```
Leu Asn Gly Lys Val Val Gly Leu Ile Gly Asn Gly Ser Ser Gly Ile
        195                 200                 205

Gln Ile Leu Pro Ala Ile Lys Lys Asp Val Lys Gln Leu Val Thr Phe
    210                 215                 220

Ile Arg Glu Ala Thr Trp Val Ala Pro Pro Leu Gly Gln Ala Tyr Arg
225                 230                 235                 240

Ala Phe Ser Thr Asp Glu Gln Ala Gln Phe Ala Gln Asp Pro Arg His
                245                 250                 255

His Leu Glu Thr Arg Arg Ala Thr Glu Ala Thr Met Asn Gln Ser Phe
            260                 265                 270

Gly Ile Phe His Ser Gly Ser Glu Glu Gln Lys Gly Val Arg Gln Tyr
        275                 280                 285

Met Gln Asp Ile Met Glu Thr Lys Leu Asn Asn Lys Gln Leu Glu Ser
    290                 295                 300

Val Leu Ile Pro Glu Trp Ser Val Gly Cys Arg Arg Leu Thr Pro Gly
305                 310                 315                 320

Thr Asn Tyr Leu Glu Ser Leu Ser Asp Asp Asn Val Lys Val Val Tyr
                325                 330                 335

Gly Glu Ile Thr Gln Ile Thr Glu Ser Gly Val Ile Cys Asp Asp Gly
            340                 345                 350

Lys Gly Glu Tyr Pro Val Glu Val Leu Ile Cys Ala Thr Gly Phe Asp
        355                 360                 365

Thr Thr Phe Lys Pro Arg Phe Pro Leu Ile Gly Thr Thr Lys Glu Lys
    370                 375                 380

Leu Ser Asp Val Trp Lys Asp Asp Pro Arg Gly Tyr Phe Gly Ile Ala
385                 390                 395                 400

Thr Asn Asn Tyr Pro Asn Tyr Phe Phe Thr Leu Gly Pro Asn Cys Pro
                405                 410                 415

Ile Gly Asn Gly Pro Val Leu Cys Ala Ile Glu Ala Glu Val Glu Tyr
            420                 425                 430

Ile Ile Asn Met Leu Ser Lys Phe Gln Lys Glu Asn Ile Arg Ser Phe
        435                 440                 445

Asp Ile Lys Ala Asp Ala Val Asp Ala Phe Asn Asp Trp Lys Asp Asp
    450                 455                 460

Phe Met Lys Asp Thr Ile Trp Ala Glu Gln Cys Arg Ser Trp Tyr Lys
465                 470                 475                 480

Ala Gly Ser Ala Thr Gly Lys Ile Leu Ala Leu Trp Pro Gly Ser Thr
                485                 490                 495

Leu His Tyr Leu Glu Ala Leu Lys Ser Pro Arg Trp Glu Asp Trp Asp
            500                 505                 510

Phe Lys Tyr Gln Pro Gly Arg Asn Arg Phe His Tyr Phe Gly Asn Gly
        515                 520                 525

His Ser Cys Ala Glu Gln Asp Gly Asp Leu Ser Trp Tyr Ile Arg Asn
    530                 535                 540

Glu Asp Asp Ser Tyr Ile Asp Pro Val Leu Lys Pro Lys Pro Lys Ala
545                 550                 555                 560

Ala Val Glu Ser Glu Ala His Ile Ala Leu Pro Gly Ile Gly Pro Met
                565                 570                 575

Leu Met Glu Asp Pro Arg Asp Val Ala Val Glu Ala
            580                 585
```

<210> SEQ ID NO 14
<211> LENGTH: 1767
<212> TYPE: DNA

<213> ORGANISM: Bensingtonia ciliata

<400> SEQUENCE: 14
atgccatctg ccattactcc acctgttgat catcgtagcc tgccgggtct gttcaagccg 60
caacgtaagt tgaaagtgat ctgtgttggc gcgggcgcga gcggcctgtt gctgagctac 120
aagattcagc gtcactttga ggactttgag ttgcaagttt ttgagaaaaa ccctgaagtg 180
agcggcacct ggtacgagaa tcgctacccg ggttgcgcgt gcgatgttcc gagccataac 240
tatacctggt cttttgagcc gaaaacggat tggtccgcaa actatgccag cagcaaagaa 300
attttcaagt acttcaaaga tttcaccaag aaatatggtc tgtctaaata cattaaactg 360
gaacacgaag tcgtgggtgc gacgtggatg gaagcggaag ctcaatggaa agttgacgtc 420
aaagacttgc gtagcggcaa cacccagagc tccttcgcgc acattctggt caatgccggt 480
ggcattctga acgcttggcg ttacccgccg attccgggta tcaaagattt taagggtgac 540
ctggtgcact cggcagcgtg gccggagcat ctggatctga atggtaaagt cgttggcctg 600
attggtaacg gtagcagcgg catccaaatt ctgccggcca tcaaaaaaga cgtgaaacaa 660
ctggtcacgt ttatccgtga ggccacgtgg gtcgccccgc cgctgggcca agcgtaccgc 720
gcatttagca ccgacgaaca ggcgcagttt gcacaagacc cgcgtcacca tctggaaact 780
cgtcgcgcga ccgaagctac catgaatcag agcttcggta tcttccacag cggttcagag 840
gaacagaaag gtgtgcgtca gtacatgcag gatatcatgg aaacgaaatt gaataacaaa 900
cagctggaga gcgtgctgat tccggagtgg tccgtgggtt gtcgccgtct gaccccgggc 960
acgaactatc tggagagctt gagcgacgat aacgtgaaag ttgtttatgg cgagatcacc 1020
cagatcaccg agtccggtgt gatttgcgat gatggcaagg gtgagtaccc ggtcgaagtg 1080
ctgatttgcg ctaccggttt cgacaccacg ttcaaaccgc gcttcccgtt gattggcacc 1140
accaaagaaa agctgagcga cgtctggaaa gatgaccctc gcggttattt cggtatcgcg 1200
accaataact acccgaacta ctttttcacc ctgggtccga actgcccgat cggcaatggt 1260
ccggtcctgt gtgcaatcga agctgaagtg gagtatatca tcaatatgct gagcaaattt 1320
cagaaagaaa acattcgcag cttcgacatt aaagccgacg cagttgatgc gtttaacgac 1380
tggaaagatg actttatgaa agacaccatc tgggcagagc agtgtcgttc ttggtacaag 1440
gctggttctg cgacgggtaa gattttggca ctgtggccgg gcagcacgct gcattatctg 1500
gaagccctga aaagcccacg ctgggaagat tgggacttca agtatcaacc gggtcgtaat 1560
cgctttcact acttcggtaa cggccacagc tgcgcggagc aagatggtga tctgtcctgg 1620
tatatccgta atgaagatga cagctacatt gacccggtac tgaagccgaa gccgaaggca 1680
gcggtggaga gcgaagcaca catcgcgctg ccaggcattg gtccgatgct gatggaggac 1740
ccgcgtgacg ttgcggttga ggcataa 1767

<210> SEQ ID NO 15
<211> LENGTH: 1674
<212> TYPE: DNA
<213> ORGANISM: Aspergillus wentii
<220> FEATURE:
<221> NAME/KEY: CDS
<222> LOCATION: (1)..(1674)

<400> SEQUENCE: 15 atg acc aaa gac aat acc aca tca ttc ccc tcg cac gcc atc tac gag 48
Met Thr Lys Asp Asn Thr Thr Ser Phe Pro Ser His Ala Ile Tyr Glu
1 5 10 15

-continued

```
cca cgc cgg aca tta aaa gtg ctg gtc ata ggg gct ggt gcg tcc ggt        96
Pro Arg Arg Thr Leu Lys Val Leu Val Ile Gly Ala Gly Ala Ser Gly
            20                  25                  30

cta tta tta gca tac aaa cta cag cgg cac ttt gat tgt gtg gaa atc       144
Leu Leu Leu Ala Tyr Lys Leu Gln Arg His Phe Asp Cys Val Glu Ile
        35                  40                  45

acg gtg ttt gag aag aac ccc gca gtg tcc ggc act tgg ttt gag aat       192
Thr Val Phe Glu Lys Asn Pro Ala Val Ser Gly Thr Trp Phe Glu Asn
    50                  55                  60

cga tat ccg gga tgt gcc tgt gac gtt cct tcg cat tgc tat aca tgg       240
Arg Tyr Pro Gly Cys Ala Cys Asp Val Pro Ser His Cys Tyr Thr Trp
65                  70                  75                  80

tcc ttc gag ccc aac ccc aac tgg tcc gcc aac tac gct gga gcc gac       288
Ser Phe Glu Pro Asn Pro Asn Trp Ser Ala Asn Tyr Ala Gly Ala Asp
                85                  90                  95

gag att cga caa tac ttt gtc gat ttc tgc cat cgc cac gac ttg cag       336
Glu Ile Arg Gln Tyr Phe Val Asp Phe Cys His Arg His Asp Leu Gln
            100                 105                 110

aaa tat atc cat ctg gaa cat gag gtg gtc cac gca gcg tgg aag tcg       384
Lys Tyr Ile His Leu Glu His Glu Val Val His Ala Ala Trp Lys Ser
        115                 120                 125

gag act ggc cac tgg gag gtg caa gtg cgc gat ata caa cac aat tct       432
Glu Thr Gly His Trp Glu Val Gln Val Arg Asp Ile Gln His Asn Ser
    130                 135                 140

cac aca cag cat act gcg cat atc ttg att aat gct act gga ata ctg       480
His Thr Gln His Thr Ala His Ile Leu Ile Asn Ala Thr Gly Ile Leu
145                 150                 155                 160

aat caa tgg aag tgg cca tcc att ccc gga tta cag tcg ttc cag gga       528
Asn Gln Trp Lys Trp Pro Ser Ile Pro Gly Leu Gln Ser Phe Gln Gly
                165                 170                 175

gat ctt ttg cac agt gca gca tgg gac tcg tca gtc aat cta gag gat       576
Asp Leu Leu His Ser Ala Ala Trp Asp Ser Ser Val Asn Leu Glu Asp
            180                 185                 190

aaa acg gtc gct gtc att gga aac gga tca tcc gga atc cag att gtc       624
Lys Thr Val Ala Val Ile Gly Asn Gly Ser Ser Gly Ile Gln Ile Val
        195                 200                 205

cca gcg att cta ccc caa gtg cgc aaa ctc gtg cac ttt act cgt caa       672
Pro Ala Ile Leu Pro Gln Val Arg Lys Leu Val His Phe Thr Arg Gln
    210                 215                 220

gcg gca tgg gtc gca cct cca gtc aat gaa gag tat cag gaa tac tcg       720
Ala Ala Trp Val Ala Pro Pro Val Asn Glu Glu Tyr Gln Glu Tyr Ser
225                 230                 235                 240

ccc gaa cag atc gaa cgc ttt cgc tca gac cca aca tac ctg ctt ggg       768
Pro Glu Gln Ile Glu Arg Phe Arg Ser Asp Pro Thr Tyr Leu Leu Gly
                245                 250                 255

gtt cgt cga cag att gaa gca cgg atg aac ggc tca ttt ctg aaa ttc       816
Val Arg Arg Gln Ile Glu Ala Arg Met Asn Gly Ser Phe Leu Lys Phe
            260                 265                 270

atc caa ggc tca gac atg caa cgt cgt gca cac gag tat gtc atg ctg       864
Ile Gln Gly Ser Asp Met Gln Arg Arg Ala His Glu Tyr Val Met Leu
        275                 280                 285

cac atg atg aag aga ctg gac gga gac gcc tcc ctg gca gag acc ttg       912
His Met Met Lys Arg Leu Asp Gly Asp Ala Ser Leu Ala Glu Thr Leu
    290                 295                 300

gta cca acc ttc cca ttt ggc tgt cga aga ccg acg cca gga acc ggg       960
Val Pro Thr Phe Pro Phe Gly Cys Arg Arg Pro Thr Pro Gly Thr Gly
305                 310                 315                 320

tat ctc gaa gca ctg aag gac tcg aaa gtg gaa aca att acc gga gcc      1008
Tyr Leu Glu Ala Leu Lys Asp Ser Lys Val Glu Thr Ile Thr Gly Ala
                325                 330                 335
```

```
cga atc gcg aat gtg acg ggt aac cag gtg gtc ctc gag aat ggc acg     1056
Arg Ile Ala Asn Val Thr Gly Asn Gln Val Val Leu Glu Asn Gly Thr
            340                 345                 350

tcg tat acg gtg gat gcg att gtg tgc gcc acg gga ttc gat acg tct     1104
Ser Tyr Thr Val Asp Ala Ile Val Cys Ala Thr Gly Phe Asp Thr Ser
        355                 360                 365

tac aaa cca cga ttc cca ctg gtc ggc aga gac agc acc act ctc agc     1152
Tyr Lys Pro Arg Phe Pro Leu Val Gly Arg Asp Ser Thr Thr Leu Ser
    370                 375                 380

gag gcc tgg aag gac gaa gtg tct gca tat ctg ggg ctt aca gtt cct     1200
Glu Ala Trp Lys Asp Glu Val Ser Ala Tyr Leu Gly Leu Thr Val Pro
385                 390                 395                 400

gga ttt ccc aac tat ttt tcc atc ttg gga ccg aac tgt ccg gtg ggt     1248
Gly Phe Pro Asn Tyr Phe Ser Ile Leu Gly Pro Asn Cys Pro Val Gly
                405                 410                 415

aac ggg ccg gtg ttg atc agt atc gaa aaa cag gtc gaa tat att gtt     1296
Asn Gly Pro Val Leu Ile Ser Ile Glu Lys Gln Val Glu Tyr Ile Val
            420                 425                 430

cag gta ctg ggg aaa atg cag aag gag aat cta cag tca ttt gaa gtc     1344
Gln Val Leu Gly Lys Met Gln Lys Glu Asn Leu Gln Ser Phe Glu Val
        435                 440                 445

cgg cgg acg gca aca gac tcg ttt aac caa tgg aag gat gca ttc atg     1392
Arg Arg Thr Ala Thr Asp Ser Phe Asn Gln Trp Lys Asp Ala Phe Met
    450                 455                 460

caa aac acg gtg tgg acg agt ggt tgt cgc agc tgg tat cag aat ggc     1440
Gln Asn Thr Val Trp Thr Ser Gly Cys Arg Ser Trp Tyr Gln Asn Gly
465                 470                 475                 480

tcg aaa ggg aac cag atc gtg gct ctc tgg cct gga tcc acg ttg cac     1488
Ser Lys Gly Asn Gln Ile Val Ala Leu Trp Pro Gly Ser Thr Leu His
                485                 490                 495

tat ttg gag gcg att cag cat cca cga tac gag gac tac atc tgg acc     1536
Tyr Leu Glu Ala Ile Gln His Pro Arg Tyr Glu Asp Tyr Ile Trp Thr
            500                 505                 510

agt cca cct ggt gtc aat cca tgg gcc ttt cta ggc aac ggg cag agt     1584
Ser Pro Pro Gly Val Asn Pro Trp Ala Phe Leu Gly Asn Gly Gln Ser
        515                 520                 525

acg gcc gaa acc cgt ccc gga ggc gac acg agt tgg tat ctg cgt tcg     1632
Thr Ala Glu Thr Arg Pro Gly Gly Asp Thr Ser Trp Tyr Leu Arg Ser
    530                 535                 540

aaa gat gat tca ttt ata gat cca tgt ctg aga cag ctt tag             1674
Lys Asp Asp Ser Phe Ile Asp Pro Cys Leu Arg Gln Leu
545                 550                 555


<210> SEQ ID NO 16
<211> LENGTH: 557
<212> TYPE: PRT
<213> ORGANISM: Aspergillus wentii

<400> SEQUENCE: 16

Met Thr Lys Asp Asn Thr Thr Ser Phe Pro Ser His Ala Ile Tyr Glu
1               5                   10                  15

Pro Arg Arg Thr Leu Lys Val Leu Val Ile Gly Ala Gly Ala Ser Gly
            20                  25                  30

Leu Leu Leu Ala Tyr Lys Leu Gln Arg His Phe Asp Cys Val Glu Ile
        35                  40                  45

Thr Val Phe Glu Lys Asn Pro Ala Val Ser Gly Thr Trp Phe Glu Asn
    50                  55                  60

Arg Tyr Pro Gly Cys Ala Cys Asp Val Pro Ser His Cys Tyr Thr Trp
65                  70                  75                  80
```

-continued

Ser Phe Glu Pro Asn Pro Asn Trp Ser Ala Asn Tyr Ala Gly Ala Asp
85 90 95

Glu Ile Arg Gln Tyr Phe Val Asp Phe Cys His Arg His Asp Leu Gln
100 105 110

Lys Tyr Ile His Leu Glu His Glu Val Val His Ala Ala Trp Lys Ser
115 120 125

Glu Thr Gly His Trp Glu Val Gln Val Arg Asp Ile Gln His Asn Ser
130 135 140

His Thr Gln His Thr Ala His Ile Leu Ile Asn Ala Thr Gly Ile Leu
145 150 155 160

Asn Gln Trp Lys Trp Pro Ser Ile Pro Gly Leu Gln Ser Phe Gln Gly
165 170 175

Asp Leu Leu His Ser Ala Ala Trp Asp Ser Ser Val Asn Leu Glu Asp
180 185 190

Lys Thr Val Ala Val Ile Gly Asn Gly Ser Ser Gly Ile Gln Ile Val
195 200 205

Pro Ala Ile Leu Pro Gln Val Arg Lys Leu Val His Phe Thr Arg Gln
210 215 220

Ala Ala Trp Val Ala Pro Pro Val Asn Glu Glu Tyr Gln Glu Tyr Ser
225 230 235 240

Pro Glu Gln Ile Glu Arg Phe Arg Ser Asp Pro Thr Tyr Leu Leu Gly
245 250 255

Val Arg Arg Gln Ile Glu Ala Arg Met Asn Gly Ser Phe Leu Lys Phe
260 265 270

Ile Gln Gly Ser Asp Met Gln Arg Arg Ala His Glu Tyr Val Met Leu
275 280 285

His Met Met Lys Arg Leu Asp Gly Asp Ala Ser Leu Ala Glu Thr Leu
290 295 300

Val Pro Thr Phe Pro Phe Gly Cys Arg Arg Pro Thr Pro Gly Thr Gly
305 310 315 320

Tyr Leu Glu Ala Leu Lys Asp Ser Lys Val Glu Thr Ile Thr Gly Ala
325 330 335

Arg Ile Ala Asn Val Thr Gly Asn Gln Val Val Leu Glu Asn Gly Thr
340 345 350

Ser Tyr Thr Val Asp Ala Ile Val Cys Ala Thr Gly Phe Asp Thr Ser
355 360 365

Tyr Lys Pro Arg Phe Pro Leu Val Gly Arg Asp Ser Thr Thr Leu Ser
370 375 380

Glu Ala Trp Lys Asp Glu Val Ser Ala Tyr Leu Gly Leu Thr Val Pro
385 390 395 400

Gly Phe Pro Asn Tyr Phe Ser Ile Leu Gly Pro Asn Cys Pro Val Gly
405 410 415

Asn Gly Pro Val Leu Ile Ser Ile Glu Lys Gln Val Glu Tyr Ile Val
420 425 430

Gln Val Leu Gly Lys Met Gln Lys Glu Asn Leu Gln Ser Phe Glu Val
435 440 445

Arg Arg Thr Ala Thr Asp Ser Phe Asn Gln Trp Lys Asp Ala Phe Met
450 455 460

Gln Asn Thr Val Trp Thr Ser Gly Cys Arg Ser Trp Tyr Gln Asn Gly
465 470 475 480

Ser Lys Gly Asn Gln Ile Val Ala Leu Trp Pro Gly Ser Thr Leu His
485 490 495

```
Tyr Leu Glu Ala Ile Gln His Pro Arg Tyr Glu Asp Tyr Ile Trp Thr
            500                 505                 510

Ser Pro Pro Gly Val Asn Pro Trp Ala Phe Leu Gly Asn Gly Gln Ser
        515                 520                 525

Thr Ala Glu Thr Arg Pro Gly Gly Asp Thr Ser Trp Tyr Leu Arg Ser
    530                 535                 540

Lys Asp Asp Ser Phe Ile Asp Pro Cys Leu Arg Gln Leu
545                 550                 555


<210> SEQ ID NO 17
<211> LENGTH: 1674
<212> TYPE: DNA
<213> ORGANISM: Aspergillus wentii

<400> SEQUENCE: 17

atgaccaaag ataacaccac gtcctttccg agccacgcca tttacgagcc gcgccgtacc      60

ctgaaagtcc tggtgatcgg tgctggcgcg agcggtttgt tgctggcata taagctgcag     120

cgccacttcg attgcgttga gattaccgta ttcgagaaga atccggcagt cagcggcacc     180

tggtttgaga atcgttaccc tggttgtgca tgtgacgtgc cgagccattg ctacacctgg     240

tcgttcgagc caaacccgaa ttggagcgca aactacgcgg gtgcggatga aattcgccag     300

tatttcgttg atttctgtca ccgtcatgat ctgcagaagt acatccatct ggagcacgaa     360

gtcgttcatg cggcatggaa atcggagact ggtcactggg aagtgcaagt ccgtgacatc     420

cagcacaaca gccataccca gcacacggcg cacattttga tcaacgcaac gggtatcctg     480

aatcaatgga aatggccgag cattccgggc ctgcagagct ttcagggtga tctgctgcat     540

agcgcagcgt gggacagctc cgtcaactta gaggataaga ccgtcgcggt gatcggtaat     600

ggcagcagcg gtatccagat tgtgccggcc atcctgccgc aagtgcgcaa actggttcac     660

tttacgcgtc aagcggcatg ggtggcaccg ccggtgaacg aagagtacca agagtacagc     720

ccggagcaaa ttgagcgttt ccgtagcgac ccgacctacc tgttgggcgt ccgccgtcaa     780

attgaagccc gtatgaacgg cagctttctg aagtttattc agggcagcga catgcagcgc     840

agagcgcacg aatacgttat gctgcacatg atgaagcgtc tggacggtga tgcgagcctt     900

gctgagactc tggtgccgac gtttccgttc ggctgccgtc gtccgacccc gggcaccggt     960

tatctggaag cgctgaaaga ctctaaagtt gaaacgatca cgggtgcccg tatcgcaaat    1020

gttacgggca accaagttgt cctggagaac ggtactagct atacggtcga tgctattgtc    1080

tgtgctaccg gtttcgacac cagctataag ccgcgtttcc cgctggttgg ccgcgactct    1140

accaccctga gcgaagcctg gaaagacgaa gtgtctgcgt acctgggtct gaccgttccg    1200

ggttttccga actatttcag catcctgggt cctaattgcc cggtcggtaa tggtccggtt    1260

ttgatcagca tcgagaaaca agtggagtat atcgtgcaag ttctgggtaa gatgcagaaa    1320

gaaaacttgc agtccttcga agttcgccgt accgccaccg acagcttcaa tcagtggaaa    1380

gatgcgttca tgcaaaacac ggtgtggacc tcaggttgcc gttcttggta tcagaatggc    1440

agcaagggca accaaattgt cgcgctgtgg ccgggttcca cgctgcacta cctggaagcg    1500

attcaacatc ctcgctacga agattatatc tggacgagcc caccgggtgt taatccgtgg    1560

gcgtttctgg gcaatggcca gagcaccgcg gaaacccgtc cgggtggcga cacttcctgg    1620

tatctccgct ccaaagatga cagctttatt gacccatgcc tgcgtcagct gtaa          1674


<210> SEQ ID NO 18
<211> LENGTH: 1674
```

<212> TYPE: DNA
<213> ORGANISM: Aspergillus wentii

<400> SEQUENCE: 18
atgactaagg acaacactac ttctttccca tctcacgcta tctacgaacc aagaagaact 60
ttgaaggttt tggttatcgg tgctggtgct tctggtttgt tgttggctta caagttgcaa 120
agacacttcg actgtgttga aatcactgtt ttcgaaaaga acccagctgt ttctggtact 180
tggttcgaaa acagataccc aggttgtgct tgtgacgttc catctcactg ttacacttgg 240
tctttcgaac caaacccaaa ctggtctgct aactacgctg gtgctgacga aatcagacaa 300
tacttcgttg acttctgtca cagacacgac ttgcaaaagt acatccactt ggaacacgaa 360
gttgttcacg ctgcttggaa gtctgaaact ggtcactggg aagttcaagt tagagacatc 420
caacacaact ctcacactca acacactgct cacatcttga tcaacgctac tggtatcttg 480
aaccaatgga agtggccatc tatcccaggt ttgcaatctt tccaaggtga cttgttgcac 540
tctgctgctt gggactcttc tgttaacttg gaagacaaga ctgttgctgt tatcggtaac 600
ggttcttctg gtatccaaat cgttccagct atcttgccac aagttagaaa gttggttcac 660
ttcactagac aagctgcttg ggttgctcca ccagttaacg aagaatacca agaatactct 720
ccagaacaaa tcgaaagatt cagatctgac ccaacttact tgttgggtgt tagaagacaa 780
atcgaagcta gaatgaacgg ttctttcttg aagttcatcc aaggttctga catgcaaaga 840
agagctcacg aatacgttat gttgcacatg atgaagagat tggacggtga cgcttctttg 900
gctgaaactt tggttccaac tttcccattc ggttgtagaa gaccaactcc aggtactggt 960
tacttggaag ctttgaagga ctctaaggtt gaaactatca ctggtgctag aatcgctaac 1020
gttactggta accaagttgt tttggaaaac ggtacttctt acactgttga cgctatcgtt 1080
tgtgctactg gtttcgacac ttcttacaag ccaagattcc cattggttgg tagagactct 1140
actactttgt ctgaagcttg gaaggacgaa gtttctgctt acttgggttt gactgttcca 1200
ggtttcccaa actacttctc tatcttgggt ccaaactgtc cagttggtaa cggtccagtt 1260
ttgatctcta tcgaaaagca agttgaatac atcgttcaag ttttgggtaa gatgcaaaag 1320
gaaaacttgc aatctttcga agttagaaga actgctactg actctttcaa ccaatggaag 1380
gacgctttca tgcaaaacac tgtttggact tctggttgta gatcttggta ccaaaacggt 1440
tctaagggta accaaatcgt tgctttgtgg ccaggttcta ctttgcacta cttggaagct 1500
atccaacacc caagatacga agactacatc tggacttctc caccaggtgt taacccatgg 1560
gctttcttgg gtaacggtca atctactgct gaaactagac caggtggtga cacttcttgg 1620
tacttgagat ctaaggacga ctctttcatc gacccatgtt tgagacaatt gtaa 1674

<210> SEQ ID NO 19
<211> LENGTH: 1038
<212> TYPE: DNA
<213> ORGANISM: Hyphozyma roseonigra
<220> FEATURE:
<221> NAME/KEY: CDS
<222> LOCATION: (1)..(1038)

<400> SEQUENCE: 19 atg cct tcc gat ctt ccc cga cca gca tat gac ccg gaa ata gag ccc 48
Met Pro Ser Asp Leu Pro Arg Pro Ala Tyr Asp Pro Glu Ile Glu Pro
1 5 10 15 ttc ctc tct atg gtc cca tta cca cca aca atc aat gcg gat atc atg 96
Phe Leu Ser Met Val Pro Leu Pro Pro Thr Ile Asn Ala Asp Ile Met
20 25 30

```
aaa gaa ttg cgt aaa gca cct ctg ctc agt caa gcg cct gac ctc gac      144
Lys Glu Leu Arg Lys Ala Pro Leu Leu Ser Gln Ala Pro Asp Leu Asp
        35                  40                  45

gca tta ctt tcc gac aag cca ata act cac cgc gaa gtc agc att cca      192
Ala Leu Leu Ser Asp Lys Pro Ile Thr His Arg Glu Val Ser Ile Pro
    50                  55                  60

ggt ctc aat tcc caa gat cca caa atc acg ttg tca ata ttc tcc agt      240
Gly Leu Asn Ser Gln Asp Pro Gln Ile Thr Leu Ser Ile Phe Ser Ser
65                  70                  75                  80

aca ttg gag ggt ggc ccg aaa cca tgt atc tat ttc gtt cat ggt ggc      288
Thr Leu Glu Gly Gly Pro Lys Pro Cys Ile Tyr Phe Val His Gly Gly
                85                  90                  95

ggt atg atc atc gga tgt cga ttc gtg ggt att gag gat tat ctt caa      336
Gly Met Ile Ile Gly Cys Arg Phe Val Gly Ile Glu Asp Tyr Leu Gln
            100                 105                 110

tac gtc gag cag aac gac gct gtc gtc gtg gct gta gag tat cgt ctc      384
Tyr Val Glu Gln Asn Asp Ala Val Val Val Ala Val Glu Tyr Arg Leu
        115                 120                 125

gct ccg gaa cac ccg gac cca gcg cct gtc aat gat tgt tac gct gga      432
Ala Pro Glu His Pro Asp Pro Ala Pro Val Asn Asp Cys Tyr Ala Gly
    130                 135                 140

ctt tta tgg acg gca gca aat gct gca gag cta ggc atc gat ctg gag      480
Leu Leu Trp Thr Ala Ala Asn Ala Ala Glu Leu Gly Ile Asp Leu Glu
145                 150                 155                 160

aga ctg ttg atc tgt ggc gct tct gct ggt ggt ggt ctt tct gct gga      528
Arg Leu Leu Ile Cys Gly Ala Ser Ala Gly Gly Gly Leu Ser Ala Gly
                165                 170                 175

gtg gca ttg atg gca cga gac aag aaa ggt cca aaa ttg gta gga caa      576
Val Ala Leu Met Ala Arg Asp Lys Lys Gly Pro Lys Leu Val Gly Gln
            180                 185                 190

ttg tta tgc tat cca atg ctc gac gat agg aat gat tca ctc tca agt      624
Leu Leu Cys Tyr Pro Met Leu Asp Asp Arg Asn Asp Ser Leu Ser Ser
        195                 200                 205

cag cag tac gtg gat gaa ggt gtt tgg agt cgt ggt agc aat gca ttt      672
Gln Gln Tyr Val Asp Glu Gly Val Trp Ser Arg Gly Ser Asn Ala Phe
    210                 215                 220

ggc tgg aag caa ttg ctt gga gac agg gcg ggc aaa gag gga gtc agt      720
Gly Trp Lys Gln Leu Leu Gly Asp Arg Ala Gly Lys Glu Gly Val Ser
225                 230                 235                 240

att tat gct gcg ccg gca aga gca act gat ttg agc gga ctg ccg aac      768
Ile Tyr Ala Ala Pro Ala Arg Ala Thr Asp Leu Ser Gly Leu Pro Asn
                245                 250                 255

act ttc atc gac gtt ggc agc gct gaa gtc ttc agg gat gag gac atc      816
Thr Phe Ile Asp Val Gly Ser Ala Glu Val Phe Arg Asp Glu Asp Ile
            260                 265                 270

gct tat gcc tcg agg tta tgg gct gtt ggt gtc caa gcg gaa ctt cat      864
Ala Tyr Ala Ser Arg Leu Trp Ala Val Gly Val Gln Ala Glu Leu His
        275                 280                 285

gtg tgg ccg ggt gga tat cat gct gcg gag aac atg gca cct ggg act      912
Val Trp Pro Gly Gly Tyr His Ala Ala Glu Asn Met Ala Pro Gly Thr
    290                 295                 300

gat tac tct aag aag gtg aaa gcg act cgc ttg gca tgg atg aag aga      960
Asp Tyr Ser Lys Lys Val Lys Ala Thr Arg Leu Ala Trp Met Lys Arg
305                 310                 315                 320

gtc ttc atg aaa gcc cca aag tcg acg aca gag tcg ttg cct gct cca     1008
Val Phe Met Lys Ala Pro Lys Ser Thr Thr Glu Ser Leu Pro Ala Pro
                325                 330                 335

aca gtg gat gaa gct gtt ggc aca ata tga                             1038
Thr Val Asp Glu Ala Val Gly Thr Ile
```

340 345

<210> SEQ ID NO 20
<211> LENGTH: 345
<212> TYPE: PRT
<213> ORGANISM: Hyphozyma roseonigra

<400> SEQUENCE: 20

Met Pro Ser Asp Leu Pro Arg Pro Ala Tyr Asp Pro Glu Ile Glu Pro
1 5 10 15

Phe Leu Ser Met Val Pro Leu Pro Pro Thr Ile Asn Ala Asp Ile Met
20 25 30

Lys Glu Leu Arg Lys Ala Pro Leu Leu Ser Gln Ala Pro Asp Leu Asp
35 40 45

Ala Leu Leu Ser Asp Lys Pro Ile Thr His Arg Glu Val Ser Ile Pro
50 55 60

Gly Leu Asn Ser Gln Asp Pro Gln Ile Thr Leu Ser Ile Phe Ser Ser
65 70 75 80

Thr Leu Glu Gly Gly Pro Lys Pro Cys Ile Tyr Phe Val His Gly Gly
85 90 95

Gly Met Ile Ile Gly Cys Arg Phe Val Gly Ile Glu Asp Tyr Leu Gln
100 105 110

Tyr Val Glu Gln Asn Asp Ala Val Val Val Ala Val Glu Tyr Arg Leu
115 120 125

Ala Pro Glu His Pro Asp Pro Ala Pro Val Asn Asp Cys Tyr Ala Gly
130 135 140

Leu Leu Trp Thr Ala Ala Asn Ala Ala Glu Leu Gly Ile Asp Leu Glu
145 150 155 160

Arg Leu Leu Ile Cys Gly Ala Ser Ala Gly Gly Gly Leu Ser Ala Gly
165 170 175

Val Ala Leu Met Ala Arg Asp Lys Lys Gly Pro Lys Leu Val Gly Gln
180 185 190

Leu Leu Cys Tyr Pro Met Leu Asp Asp Arg Asn Asp Ser Leu Ser Ser
195 200 205

Gln Gln Tyr Val Asp Glu Gly Val Trp Ser Arg Gly Ser Asn Ala Phe
210 215 220

Gly Trp Lys Gln Leu Leu Gly Asp Arg Ala Gly Lys Glu Gly Val Ser
225 230 235 240

Ile Tyr Ala Ala Pro Ala Arg Ala Thr Asp Leu Ser Gly Leu Pro Asn
245 250 255

Thr Phe Ile Asp Val Gly Ser Ala Glu Val Phe Arg Asp Glu Asp Ile
260 265 270

Ala Tyr Ala Ser Arg Leu Trp Ala Val Gly Val Gln Ala Glu Leu His
275 280 285

Val Trp Pro Gly Gly Tyr His Ala Ala Glu Asn Met Ala Pro Gly Thr
290 295 300

Asp Tyr Ser Lys Lys Val Lys Ala Thr Arg Leu Ala Trp Met Lys Arg
305 310 315 320

Val Phe Met Lys Ala Pro Lys Ser Thr Thr Glu Ser Leu Pro Ala Pro
325 330 335

Thr Val Asp Glu Ala Val Gly Thr Ile
340 345

<210> SEQ ID NO 21
<211> LENGTH: 1038

<212> TYPE: DNA
<213> ORGANISM: Hyphozyma roseonigra

<400> SEQUENCE: 21
atgccatcgg atctgccgcg cccagcctac gaccctgaaa tcgaaccgtt cttgagcatg 60
gttccgctgc ctccgaccat taacgcggac attatgaaag aactgcgtaa ggccccactg 120
ctgagccagg ctccggatct ggatgccctg ctgagcgaca agccgattac tcaccgtgag 180
gtgtccatcc cgggtctgaa cagccaggac ccgcagatta ccctgagcat ctttagctct 240
accctggagg gtggcccgaa gccgtgtatc tacttcgtgc acggtggcgg catgattatt 300
ggctgtcgct tcgtcggtat tgaggactac ttgcaatacg tggaacagaa tgacgcggtc 360
gttgtggccg ttgagtatcg tctggcaccg gaacatccgg acccggcacc ggtgaatgac 420
tgctacgcgg gtctgctgtg gaccgctgcg aacgcggcag aactgggcat cgatttggag 480
cgtctgctga tctgcggcgc ttctgcgggt ggcggtctgt cagcgggtgt ggcgctgatg 540
gcacgcgaca aaaagggtcc gaaactggtc ggtcagctgc tgtgctatcc gatgctcgac 600
gatcgtaacg atagcttgag cagccagcaa tacgtagatg agggtgtttg gagccgtggt 660
agcaatgcgt ttggttggaa gcaactgctg ggtgatcgtg ccggcaaaga gggcgtgtcc 720
atttacgcgg caccggctcg cgcaaccgac ctgtctggct tgcctaacac gtttatcgac 780
gttggttccg ccgaggtttt ccgtgatgaa gatatcgcgt atgcgagccg cttatgggca 840
gtcggtgttc aagcggagct gcatgtctgg ccgggtggtt atcacgctgc ggagaatatg 900
gcaccgggca ccgattatag caaaaaagtc aaggcgacgc gtctggcatg gatgaaacgc 960
gtctttatga aggccccgaa aagcaccacg gagagcctgc cggcaccgac ggttgacgaa 1020
gcggtgggca cgatctaa 1038

<210> SEQ ID NO 22
<211> LENGTH: 1038
<212> TYPE: DNA
<213> ORGANISM: Hyphozyma roseonigra

<400> SEQUENCE: 22
atgccatctg acttgccaag accagcttac gacccagaaa tcgaaccatt cttgtctatg 60
gttccattgc caccaactat caacgctgac atcatgaagg aattgagaaa ggctccattg 120
ttgtctcaag ctccagactt ggacgctttg ttgtctgaca agccaatcac tcacagagaa 180
gtttctatcc caggtttgaa ctctcaagac ccacaaatca ctttgtctat cttctcttct 240
actttggaag gtggtccaaa gccatgtatc tacttcgttc acggtggtgg tatgatcatc 300
ggttgtagat tcgttggtat cgaagactac ttgcaatacg ttgaacaaaa cgacgctgtt 360
gttgttgctg ttgaatacag attggctcca gaacacccag acccagctcc agttaacgac 420
tgttacgctg gtttgttgtg gactgctgct aacgctgctg aattgggtat cgacttggaa 480
agattgttga tctgtggtgc ttctgctggt ggtggtttgt ctgctggtgt tgctttgatg 540
gctagagaca agaagggtcc aaagttggtt ggtcaattgt tgtgttaccc aatgttggac 600
gacagaaacg actctttgtc ttctcaacaa tacgttgacg aaggtgtttg gtctagaggt 660
tctaacgctt tcggttggaa gcaattgttg ggtgacagag ctggtaagga aggtgtttct 720
atctacgctg ctccagctag agctactgac ttgtctggtt tgccaaacac tttcatcgac 780
gttggttctg ctgaagtttt cagagacgaa gacatcgctt acgcttctag attgtgggct 840
gttggtgttc aagctgaatt gcacgtttgg ccaggtggtt accacgctgc tgaaaacatg 900

-continued

```
gctccaggta ctgactactc taagaaggtt aaggctacta gattggcttg gatgaagaga    960

gttttcatga aggctccaaa gtctactact gaatctttgc cagctccaac tgttgacgaa   1020

gctgttggta ctatctaa                                                 1038


<210> SEQ ID NO 23
<211> LENGTH: 933
<212> TYPE: DNA
<213> ORGANISM: Filobasidium magnum
<220> FEATURE:
<221> NAME/KEY: CDS
<222> LOCATION: (1)..(933)

<400> SEQUENCE: 23

atg act cat agc cct cca ctc gat gcc gaa ctt tcg cta ctc cga tat       48
Met Thr His Ser Pro Pro Leu Asp Ala Glu Leu Ser Leu Leu Arg Tyr
1               5                   10                  15

gct cct gct gtt ccc gtg gga tgg cag ttg gga cga aaa ctc ttg cgg       96
Ala Pro Ala Val Pro Val Gly Trp Gln Leu Gly Arg Lys Leu Leu Arg
            20                  25                  30

atg aac aca ctc atg acg cgc cct atg gag ggt gtc atg cga gat gat      144
Met Asn Thr Leu Met Thr Arg Pro Met Glu Gly Val Met Arg Asp Asp
        35                  40                  45

gtg gtc ata cca aat ctt gat ggt act gcc aac atc aga ctg ttc att      192
Val Val Ile Pro Asn Leu Asp Gly Thr Ala Asn Ile Arg Leu Phe Ile
    50                  55                  60

tgt cgc cct caa gac cct act gag act atg ccg gtg ata ctt tgg tta      240
Cys Arg Pro Gln Asp Pro Thr Glu Thr Met Pro Val Ile Leu Trp Leu
65                  70                  75                  80

cac gga ggc ggt atg gtc gca ggt cat tac aaa caa gac tcc ggg ttc      288
His Gly Gly Gly Met Val Ala Gly His Tyr Lys Gln Asp Ser Gly Phe
                85                  90                  95

atg gac atc tgg gcc aag cgc cta gga gcc ttt gtg gtt tcg gtc gat      336
Met Asp Ile Trp Ala Lys Arg Leu Gly Ala Phe Val Val Ser Val Asp
            100                 105                 110

tat cgt ctg gct ccc gag gcc aag gct cca gcc gct cta gac gat tgc      384
Tyr Arg Leu Ala Pro Glu Ala Lys Ala Pro Ala Ala Leu Asp Asp Cys
        115                 120                 125

atc gct gct tgg caa tgg atc acc acg cag acc gct cga ggc atc gac      432
Ile Ala Ala Trp Gln Trp Ile Thr Thr Gln Thr Ala Arg Gly Ile Asp
    130                 135                 140

act acc cgc atg gcg gtg ggt ggt gcg agc gca gga gga ggc ctg gcg      480
Thr Thr Arg Met Ala Val Gly Gly Ala Ser Ala Gly Gly Gly Leu Ala
145                 150                 155                 160

gcc agt acc gtt cag cga ctt gtc gat ctc gga gga gtg aaa cct gtc      528
Ala Ser Thr Val Gln Arg Leu Val Asp Leu Gly Gly Val Lys Pro Val
                165                 170                 175

ttt caa ttg ctc atc tat ccc atg ttg gac gac agg acg gtg gtc aga      576
Phe Gln Leu Leu Ile Tyr Pro Met Leu Asp Asp Arg Thr Val Val Arg
            180                 185                 190

ttt gat ccc gac cga aga tat tac atg tgg aca ccg gat tgt aat cga      624
Phe Asp Pro Asp Arg Arg Tyr Tyr Met Trp Thr Pro Asp Cys Asn Arg
        195                 200                 205

tat ggc tgg acc tcg tac ctc gga gtc cct cca ggg agc gct gag gtg      672
Tyr Gly Trp Thr Ser Tyr Leu Gly Val Pro Pro Gly Ser Ala Glu Val
    210                 215                 220

cct ccc tat gcg tcg gcg gca cgt cga ccg gat cta tca ggt cta cct      720
Pro Pro Tyr Ala Ser Ala Ala Arg Arg Pro Asp Leu Ser Gly Leu Pro
225                 230                 235                 240

ccc acc tgg atc ggt gtt ggg tca ctg gat ctc ttt cac gac gag gac      768
Pro Thr Trp Ile Gly Val Gly Ser Leu Asp Leu Phe His Asp Glu Asp
```

```
                245                 250                 255

atg gat tat gcg cgc agg tta cgt gag agc gga gtt ccg gtt gag gaa      816
Met Asp Tyr Ala Arg Arg Leu Arg Glu Ser Gly Val Pro Val Glu Glu
            260                 265                 270

tat gtc gct gtc gga gcg cct cat gcc ttc gac acg ata tat gga aag      864
Tyr Val Ala Val Gly Ala Pro His Ala Phe Asp Thr Ile Tyr Gly Lys
        275                 280                 285

gcg aag gtc acc ttg gat ttc tgg gac tcg cat ttc aac gcc ctt cga      912
Ala Lys Val Thr Leu Asp Phe Trp Asp Ser His Phe Asn Ala Leu Arg
    290                 295                 300

agg gct ttg tgt ctc gac tga                                          933
Arg Ala Leu Cys Leu Asp
305                 310


<210> SEQ ID NO 24
<211> LENGTH: 310
<212> TYPE: PRT
<213> ORGANISM: Filobasidium magnum

<400> SEQUENCE: 24

Met Thr His Ser Pro Pro Leu Asp Ala Glu Leu Ser Leu Leu Arg Tyr
1               5                   10                  15

Ala Pro Ala Val Pro Val Gly Trp Gln Leu Gly Arg Lys Leu Leu Arg
            20                  25                  30

Met Asn Thr Leu Met Thr Arg Pro Met Glu Gly Val Met Arg Asp Asp
        35                  40                  45

Val Val Ile Pro Asn Leu Asp Gly Thr Ala Asn Ile Arg Leu Phe Ile
    50                  55                  60

Cys Arg Pro Gln Asp Pro Thr Glu Thr Met Pro Val Ile Leu Trp Leu
65                  70                  75                  80

His Gly Gly Gly Met Val Ala Gly His Tyr Lys Gln Asp Ser Gly Phe
                85                  90                  95

Met Asp Ile Trp Ala Lys Arg Leu Gly Ala Phe Val Val Ser Val Asp
            100                 105                 110

Tyr Arg Leu Ala Pro Glu Ala Lys Ala Pro Ala Ala Leu Asp Asp Cys
        115                 120                 125

Ile Ala Ala Trp Gln Trp Ile Thr Thr Gln Thr Ala Arg Gly Ile Asp
    130                 135                 140

Thr Thr Arg Met Ala Val Gly Gly Ala Ser Ala Gly Gly Gly Leu Ala
145                 150                 155                 160

Ala Ser Thr Val Gln Arg Leu Val Asp Leu Gly Gly Val Lys Pro Val
                165                 170                 175

Phe Gln Leu Leu Ile Tyr Pro Met Leu Asp Asp Arg Thr Val Val Arg
            180                 185                 190

Phe Asp Pro Asp Arg Arg Tyr Tyr Met Trp Thr Pro Asp Cys Asn Arg
        195                 200                 205

Tyr Gly Trp Thr Ser Tyr Leu Gly Val Pro Pro Gly Ser Ala Glu Val
    210                 215                 220

Pro Pro Tyr Ala Ser Ala Ala Arg Arg Pro Asp Leu Ser Gly Leu Pro
225                 230                 235                 240

Pro Thr Trp Ile Gly Val Gly Ser Leu Asp Leu Phe His Asp Glu Asp
                245                 250                 255

Met Asp Tyr Ala Arg Arg Leu Arg Glu Ser Gly Val Pro Val Glu Glu
            260                 265                 270

Tyr Val Ala Val Gly Ala Pro His Ala Phe Asp Thr Ile Tyr Gly Lys
        275                 280                 285
```

Ala Lys Val Thr Leu Asp Phe Trp Asp Ser His Phe Asn Ala Leu Arg
290 295 300

Arg Ala Leu Cys Leu Asp
305 310

<210> SEQ ID NO 25
<211> LENGTH: 933
<212> TYPE: DNA
<213> ORGANISM: Filobasidium magnum

<400> SEQUENCE: 25
atgacccact cgccgccact ggatgccgaa ctgagcttgc tgcgctacgc ccctgccgtt 60
ccggtgggtt ggcagctggg tcgcaaactg ctgcgtatga acaccttgat gacccgtccg 120
atggaaggtg tcatgcgcga cgatgtggtt attccgaatc tggacggcac ggctaacatc 180
cgtctgttta tctgtcgtcc gcaagacccg accgagacta tgccggttat cctgtggctg 240
cacggtggcg gcatggtcgc aggccactac aaacaagaca gcggtttcat ggacatttgg 300
gcgaagcgcc tgggtgcgtt tgttgttagc gttgattatc gcctggcgcc tgaggctaag 360
gcaccggcag cgctcgatga ctgcatcgcg gcgtggcagt ggattaccac ccagaccgcg 420
cgtggtattg acaccactcg tatggcagtg ggtggtgcga gcgcgggtgg cggtctggcg 480
gcaagcacgg ttcagcgtct tgtcgatctg ggcggtgtga aaccggtctt tcaactgctg 540
atctatccga tgctggacga tcgtaccgtg gtgcgcttcg acccggatcg tcgttattac 600
atgtggacgc cggactgcaa cagatacggc tggaccagct acctgggcgt gccaccgggt 660
agcgcagagg tcccgccgta tgcctccgcg gctcgtcgtc cggatctgtc cggcctgccg 720
ccgacgtgga tcggtgtcgg ctctctggat ctgttccatg acgaagatat ggattacgca 780
cgtcgtttgc gcgagagcgg tgtgccggtc gaagagtatg ttgctgtggg tgccccgcat 840
gcgttcgaca cgatttacgg caaggccaaa gttacgctgg acttttggga tagccacttc 900
aatgcgctgc gccgtgcgtt gtgtttagac taa 933

<210> SEQ ID NO 26
<211> LENGTH: 933
<212> TYPE: DNA
<213> ORGANISM: Filobasidium magnum

<400> SEQUENCE: 26
atgactcact ctccaccatt ggacgctgaa ttgtctttgt tgagatacgc tccagctgtt 60
ccagttggtt ggcaattggg tagaaagttg ttgagaatga acactttgat gactagacca 120
atggaaggtg ttatgagaga cgacgttgtt atcccaaact tggacggtac tgctaacatc 180
agattgttca tctgtagacc acaagaccca actgaaacta tgccagttat cttgtggttg 240
cacggtggtg gtatggttgc tggtcactac aagcaagact ctggtttcat ggacatctgg 300
gctaagagat tgggtgcttt cgttgtttct gttgactaca gattggctcc agaagctaag 360
gctccagctg ctttggacga ctgtatcgct gcttggcaat ggatcactac tcaaactgct 420
agaggtatcg acactactag aatggctgtt ggtggtgctt ctgctggtgg tggtttggct 480
gcttctactg ttcaaagatt ggttgacttg ggtggtgtta agccagtttt ccaattgttg 540
atctacccaa tgttggacga cagaactgtt gttagattcg acccagacag aagatactac 600
atgtggactc cagactgtaa cagatacggt tggacttctt acttgggtgt tccaccaggt 660
tctgctgaag ttccaccata cgcttctgct gctagaagac cagacttgtc tggtttgcca 720

-continued

```
ccaacttgga tcggtgttgg ttctttggac ttgttccacg acgaagacat ggactacgct    780

agaagattga gagaatctgg tgttccagtt gaagaatacg ttgctgttgg tgctccacac    840

gctttcgaca ctatctacgg taaggctaag gttactttgg acttctggga ctctcacttc    900

aacgctttga gaagagcttt gtgtttggac taa                                 933


<210> SEQ ID NO 27
<211> LENGTH: 1038
<212> TYPE: DNA
<213> ORGANISM: Papiliotrema laurentii
<220> FEATURE:
<221> NAME/KEY: CDS
<222> LOCATION: (1)..(1038)

<400> SEQUENCE: 27

atg cct tcc aat ctc ccc cga cca gca tat gac ccg gaa ata gag cca       48
Met Pro Ser Asn Leu Pro Arg Pro Ala Tyr Asp Pro Glu Ile Glu Pro
1               5                   10                  15

ttc ctc tct atg gtc cca tta cca cca aca atc aat gcg gat atc atg       96
Phe Leu Ser Met Val Pro Leu Pro Pro Thr Ile Asn Ala Asp Ile Met
            20                  25                  30

aga gaa ctg cgt aaa gcg cct cta ctc agt caa gcg cct gac ctc gac      144
Arg Glu Leu Arg Lys Ala Pro Leu Leu Ser Gln Ala Pro Asp Leu Asp
        35                  40                  45

gca tta ctt tcc ggc aaa cca ata act cac cgc gaa gtc agc att cca      192
Ala Leu Leu Ser Gly Lys Pro Ile Thr His Arg Glu Val Ser Ile Pro
    50                  55                  60

ggt ctc aat tct tca gat cca caa atc acg ttg tcg ata ttc tcc agt      240
Gly Leu Asn Ser Ser Asp Pro Gln Ile Thr Leu Ser Ile Phe Ser Ser
65                  70                  75                  80

aca ttg acg agc ggt cca aaa cca tgt att tat ttc gtt cat ggt ggc      288
Thr Leu Thr Ser Gly Pro Lys Pro Cys Ile Tyr Phe Val His Gly Gly
                85                  90                  95

ggt atg atc atc gga tgt cga ttc gtg ggt att gag gat tat ctt cag      336
Gly Met Ile Ile Gly Cys Arg Phe Val Gly Ile Glu Asp Tyr Leu Gln
            100                 105                 110

tac gtc gag cag aat gac gct gtc gtc gtg gct gtg gaa tat cgt ctt      384
Tyr Val Glu Gln Asn Asp Ala Val Val Val Ala Val Glu Tyr Arg Leu
        115                 120                 125

gcg ccg gaa aat cca gat cca gcg cct gtc aat gat tgt tac gct gga      432
Ala Pro Glu Asn Pro Asp Pro Ala Pro Val Asn Asp Cys Tyr Ala Gly
    130                 135                 140

ctt cta tgg acc gca gca aat gct gca gaa ctg ggc att gat ctg gag      480
Leu Leu Trp Thr Ala Ala Asn Ala Ala Glu Leu Gly Ile Asp Leu Glu
145                 150                 155                 160

aga ctg ttg atc tgt ggc gct tct gcc ggt ggt ggt ctt tct gct gga      528
Arg Leu Leu Ile Cys Gly Ala Ser Ala Gly Gly Gly Leu Ser Ala Gly
                165                 170                 175

gtg gct ttg atg gcg cga gac aag aaa ggt ccg aaa ctg gta gga caa      576
Val Ala Leu Met Ala Arg Asp Lys Lys Gly Pro Lys Leu Val Gly Gln
            180                 185                 190

ttg tta tgt tat ccg atg ctc gac gat agg aat gat tcc ctt tca agt      624
Leu Leu Cys Tyr Pro Met Leu Asp Asp Arg Asn Asp Ser Leu Ser Ser
        195                 200                 205

cag cag tac gtc gat gaa ggt gtt tgg agt cgt ggt agc aat gca ttc      672
Gln Gln Tyr Val Asp Glu Gly Val Trp Ser Arg Gly Ser Asn Ala Phe
    210                 215                 220

ggg tgg aag caa ttg ctt gga gac agg gca ggc aaa gaa ggt gtc agc      720
Gly Trp Lys Gln Leu Leu Gly Asp Arg Ala Gly Lys Glu Gly Val Ser
225                 230                 235                 240
```

-continued

```
atc tat gct gca ccg gcg agg gca act gat ttg agc gga ctg ccg aac      768
Ile Tyr Ala Ala Pro Ala Arg Ala Thr Asp Leu Ser Gly Leu Pro Asn
                245                 250                 255

act ttc atc gac gtt ggc agc gct gaa gtc ttc agg gat gag gac atc      816
Thr Phe Ile Asp Val Gly Ser Ala Glu Val Phe Arg Asp Glu Asp Ile
            260                 265                 270

gct tat gcc tcg agg tta tgg gct gtc ggt gtc caa gca gaa ctt cat      864
Ala Tyr Ala Ser Arg Leu Trp Ala Val Gly Val Gln Ala Glu Leu His
        275                 280                 285

gtg tgg ccg ggt gga tat cat gct gcg gaa aac atg gca ccg ggg act      912
Val Trp Pro Gly Gly Tyr His Ala Ala Glu Asn Met Ala Pro Gly Thr
    290                 295                 300

gac tac tct aac aag gtg aaa gct gcc cgc ttg gca tgg atg aag aga      960
Asp Tyr Ser Asn Lys Val Lys Ala Ala Arg Leu Ala Trp Met Lys Arg
305                 310                 315                 320

gtc ttc atg aaa gcc cca aag tcg acg aca gag tcg tta cct gct cca     1008
Val Phe Met Lys Ala Pro Lys Ser Thr Thr Glu Ser Leu Pro Ala Pro
                325                 330                 335

aca gtg gat gaa gct gtt ggc aca ata tga                             1038
Thr Val Asp Glu Ala Val Gly Thr Ile
            340                 345


<210> SEQ ID NO 28
<211> LENGTH: 345
<212> TYPE: PRT
<213> ORGANISM: Papiliotrema laurentii

<400> SEQUENCE: 28

Met Pro Ser Asn Leu Pro Arg Pro Ala Tyr Asp Pro Glu Ile Glu Pro
1               5                   10                  15

Phe Leu Ser Met Val Pro Leu Pro Pro Thr Ile Asn Ala Asp Ile Met
            20                  25                  30

Arg Glu Leu Arg Lys Ala Pro Leu Leu Ser Gln Ala Pro Asp Leu Asp
        35                  40                  45

Ala Leu Leu Ser Gly Lys Pro Ile Thr His Arg Glu Val Ser Ile Pro
    50                  55                  60

Gly Leu Asn Ser Ser Asp Pro Gln Ile Thr Leu Ser Ile Phe Ser Ser
65                  70                  75                  80

Thr Leu Thr Ser Gly Pro Lys Pro Cys Ile Tyr Phe Val His Gly Gly
                85                  90                  95

Gly Met Ile Ile Gly Cys Arg Phe Val Gly Ile Glu Asp Tyr Leu Gln
            100                 105                 110

Tyr Val Glu Gln Asn Asp Ala Val Val Val Ala Val Glu Tyr Arg Leu
        115                 120                 125

Ala Pro Glu Asn Pro Asp Pro Ala Pro Val Asn Asp Cys Tyr Ala Gly
    130                 135                 140

Leu Leu Trp Thr Ala Ala Asn Ala Ala Glu Leu Gly Ile Asp Leu Glu
145                 150                 155                 160

Arg Leu Leu Ile Cys Gly Ala Ser Ala Gly Gly Gly Leu Ser Ala Gly
                165                 170                 175

Val Ala Leu Met Ala Arg Asp Lys Lys Gly Pro Lys Leu Val Gly Gln
            180                 185                 190

Leu Leu Cys Tyr Pro Met Leu Asp Asp Arg Asn Asp Ser Leu Ser Ser
        195                 200                 205

Gln Gln Tyr Val Asp Glu Gly Val Trp Ser Arg Gly Ser Asn Ala Phe
    210                 215                 220

Gly Trp Lys Gln Leu Leu Gly Asp Arg Ala Gly Lys Glu Gly Val Ser
```

-continued

```
225                 230                 235                 240

Ile Tyr Ala Ala Pro Ala Arg Ala Thr Asp Leu Ser Gly Leu Pro Asn
                245                 250                 255

Thr Phe Ile Asp Val Gly Ser Ala Glu Val Phe Arg Asp Glu Asp Ile
            260                 265                 270

Ala Tyr Ala Ser Arg Leu Trp Ala Val Gly Val Gln Ala Glu Leu His
        275                 280                 285

Val Trp Pro Gly Gly Tyr His Ala Ala Glu Asn Met Ala Pro Gly Thr
    290                 295                 300

Asp Tyr Ser Asn Lys Val Lys Ala Ala Arg Leu Ala Trp Met Lys Arg
305                 310                 315                 320

Val Phe Met Lys Ala Pro Lys Ser Thr Thr Glu Ser Leu Pro Ala Pro
                325                 330                 335

Thr Val Asp Glu Ala Val Gly Thr Ile
            340                 345
```

<210> SEQ ID NO 29
<211> LENGTH: 1038
<212> TYPE: DNA
<213> ORGANISM: Papiliotrema laurentii

<400> SEQUENCE: 29

```
atgccaagca acttgccgcg cccagcctac gatccggaaa ttgagccttt tctgtctatg     60

gtcccgctgc cgccgaccat caacgcggac attatgcgtg agctgcgtaa agccccgctg    120

ctgagccagg caccggacct cgacgcactg ctgagcggca agccgatcac tcaccgtgaa    180

gtcagcattc cgggtctgaa cagcagcgac ccgcaaatca ccctgagcat tttctccagc    240

acgttgacca gcggtccgaa accgtgcatc tattttgtgc acggtggcgg tatgattatt    300

ggttgtcgct tcgtcggcat tgaagattat ctgcaatatg ttgagcaaaa tgacgcggtg    360

gttgtggcgg ttgagtatcg tctggcccct gaaaatccgg acccggcacc ggttaatgat    420

tgctacgcgg gtctgctgtg gaccgcagcg aacgcagcgg agctgggtat cgatttggaa    480

cgcctgctga tctgtggcgc gagcgctggc ggtggtctga gcgcgggtgt ggcgctgatg    540

gctcgcgaca aaaagggtcc aaaactggtc ggtcagctgt tgtgctaccc gatgctggac    600

gatcgtaacg acagcttgag ctctcaacag tacgtcgatg agggtgtttg gagccgtggc    660

agcaatgctt tcggctggaa acagctgctg ggcgatcgtg cgggtaagga aggcgtgtcg    720

atctatgccg ctccggcacg cgcaaccgat ctgtctggcc tgccgaacac gttcatcgat    780

gtcggtagcg ctgaggtgtt tcgtgacgaa gatatcgcgt acgcctcacg tctgtgggcc    840

gtcggtgtgc aggccgagct gcatgtttgg ccgggtggct accatgcagc cgagaatatg    900

gcgcctggca ccgactactc caataaagtg aaggcagcgc gcctggcgtg gatgaagcgt    960

gtgtttatga aagcgccgaa gtccacgacc gagagcctgc cggcaccgac cgttgacgaa   1020

gcggttggta cgatttaa                                                 1038
```

<210> SEQ ID NO 30
<211> LENGTH: 1038
<212> TYPE: DNA
<213> ORGANISM: Bensingtonia ciliata
<220> FEATURE:
<221> NAME/KEY: CDS
<222> LOCATION: (1)..(1038)

<400> SEQUENCE: 30

```
atg cct tcc aat ctc cct cga cca gca tat gac ccg gaa ata gag cca       48
```

-continued

```
Met Pro Ser Asn Leu Pro Arg Pro Ala Tyr Asp Pro Glu Ile Glu Pro
1               5                   10                  15

ttc ctc tct atg gtc cca tta cca cca aca atc aat gcg gat atc atg       96
Phe Leu Ser Met Val Pro Leu Pro Pro Thr Ile Asn Ala Asp Ile Met
            20                  25                  30

aga gaa ctg cgt aaa gca cct cta ctc agt caa gcg cct gac ctc gac      144
Arg Glu Leu Arg Lys Ala Pro Leu Leu Ser Gln Ala Pro Asp Leu Asp
        35                  40                  45

gca tta ctt tcc ggc aga ccg ata act cac cgc gaa gtc agc att cca      192
Ala Leu Leu Ser Gly Arg Pro Ile Thr His Arg Glu Val Ser Ile Pro
    50                  55                  60

ggt ctc aat tcc cag gat cca caa atc acg ttg tca ata ttc tcc agt      240
Gly Leu Asn Ser Gln Asp Pro Gln Ile Thr Leu Ser Ile Phe Ser Ser
65                  70                  75                  80

aca ttg acg agc ggt cca aaa cca tgt att tat ttc gtt cat ggt ggc      288
Thr Leu Thr Ser Gly Pro Lys Pro Cys Ile Tyr Phe Val His Gly Gly
                85                  90                  95

ggt atg atc atc gga tgt cga ttc gtg ggt att gag gat tat ctt caa      336
Gly Met Ile Ile Gly Cys Arg Phe Val Gly Ile Glu Asp Tyr Leu Gln
            100                 105                 110

tac gtc gag cag aac gac gct gtc gtt gtg gct gtg gaa tat cgt ctt      384
Tyr Val Glu Gln Asn Asp Ala Val Val Val Ala Val Glu Tyr Arg Leu
        115                 120                 125

gct ccg gaa aac ccg gac cca gcg cct gtt aat gat tgt tac gcc gga      432
Ala Pro Glu Asn Pro Asp Pro Ala Pro Val Asn Asp Cys Tyr Ala Gly
    130                 135                 140

ctt tta tgg acc gca gcg aat gct gca gag cta ggc atc gat ctg gag      480
Leu Leu Trp Thr Ala Ala Asn Ala Ala Glu Leu Gly Ile Asp Leu Glu
145                 150                 155                 160

aga ctg ttg atc tgt ggc gct tct gcc ggt ggt ggt ctt tct gct gga      528
Arg Leu Leu Ile Cys Gly Ala Ser Ala Gly Gly Gly Leu Ser Ala Gly
                165                 170                 175

gtg gca ttg atg gca cga gac aag aaa ggt cca aaa ttg gta gga caa      576
Val Ala Leu Met Ala Arg Asp Lys Lys Gly Pro Lys Leu Val Gly Gln
            180                 185                 190

ttg tta tgc tat cca atg ctc gac gat agg aat gat tca ctc tca agt      624
Leu Leu Cys Tyr Pro Met Leu Asp Asp Arg Asn Asp Ser Leu Ser Ser
        195                 200                 205

cag cag tac gtg gat gaa ggt gtt tgg agt cgt ggt agc aat gca ttt      672
Gln Gln Tyr Val Asp Glu Gly Val Trp Ser Arg Gly Ser Asn Ala Phe
    210                 215                 220

ggc tgg aag caa ttg ctt gga gac agg gcg ggc aaa gag gga gtc agt      720
Gly Trp Lys Gln Leu Leu Gly Asp Arg Ala Gly Lys Glu Gly Val Ser
225                 230                 235                 240

att tat gct gcg ccg gca aga gca act gat ttg agc gga ctg ccg aac      768
Ile Tyr Ala Ala Pro Ala Arg Ala Thr Asp Leu Ser Gly Leu Pro Asn
                245                 250                 255

act ttc atc gac gtt ggc agc gct gag gtc ttc agg gat gag gac atc      816
Thr Phe Ile Asp Val Gly Ser Ala Glu Val Phe Arg Asp Glu Asp Ile
            260                 265                 270

gct tat gcc tcg agg tta tgg gct gtc ggt gtc caa gca gaa ctt cat      864
Ala Tyr Ala Ser Arg Leu Trp Ala Val Gly Val Gln Ala Glu Leu His
        275                 280                 285

gtg tgg ccc ggt gga tat cat gct gcg gag aac atg gca ccg ggg act      912
Val Trp Pro Gly Gly Tyr His Ala Ala Glu Asn Met Ala Pro Gly Thr
    290                 295                 300

gac tac tct aag aag gtg aaa gct gcg cgc ttg gca tgg atg aag aga      960
Asp Tyr Ser Lys Lys Val Lys Ala Ala Arg Leu Ala Trp Met Lys Arg
305                 310                 315                 320
```

-continued

```
gtc ttc ctg aaa gcc cca aag ccg acg act gag tcg ttg cct gct cca      1008
Val Phe Leu Lys Ala Pro Lys Pro Thr Thr Glu Ser Leu Pro Ala Pro
                325                 330                 335

aca gtg gat gaa gct gtt ggc aca ata tga                              1038
Thr Val Asp Glu Ala Val Gly Thr Ile
            340                 345


<210> SEQ ID NO 31
<211> LENGTH: 345
<212> TYPE: PRT
<213> ORGANISM: Bensingtonia ciliata

<400> SEQUENCE: 31

Met Pro Ser Asn Leu Pro Arg Pro Ala Tyr Asp Pro Glu Ile Glu Pro
1               5                   10                  15

Phe Leu Ser Met Val Pro Leu Pro Pro Thr Ile Asn Ala Asp Ile Met
            20                  25                  30

Arg Glu Leu Arg Lys Ala Pro Leu Leu Ser Gln Ala Pro Asp Leu Asp
        35                  40                  45

Ala Leu Leu Ser Gly Arg Pro Ile Thr His Arg Glu Val Ser Ile Pro
    50                  55                  60

Gly Leu Asn Ser Gln Asp Pro Gln Ile Thr Leu Ser Ile Phe Ser Ser
65                  70                  75                  80

Thr Leu Thr Ser Gly Pro Lys Pro Cys Ile Tyr Phe Val His Gly Gly
                85                  90                  95

Gly Met Ile Ile Gly Cys Arg Phe Val Gly Ile Glu Asp Tyr Leu Gln
            100                 105                 110

Tyr Val Glu Gln Asn Asp Ala Val Val Val Ala Val Glu Tyr Arg Leu
        115                 120                 125

Ala Pro Glu Asn Pro Asp Pro Ala Pro Val Asn Asp Cys Tyr Ala Gly
    130                 135                 140

Leu Leu Trp Thr Ala Ala Asn Ala Ala Glu Leu Gly Ile Asp Leu Glu
145                 150                 155                 160

Arg Leu Leu Ile Cys Gly Ala Ser Ala Gly Gly Gly Leu Ser Ala Gly
                165                 170                 175

Val Ala Leu Met Ala Arg Asp Lys Lys Gly Pro Lys Leu Val Gly Gln
            180                 185                 190

Leu Leu Cys Tyr Pro Met Leu Asp Asp Arg Asn Asp Ser Leu Ser Ser
        195                 200                 205

Gln Gln Tyr Val Asp Glu Gly Val Trp Ser Arg Gly Ser Asn Ala Phe
    210                 215                 220

Gly Trp Lys Gln Leu Leu Gly Asp Arg Ala Gly Lys Glu Gly Val Ser
225                 230                 235                 240

Ile Tyr Ala Ala Pro Ala Arg Ala Thr Asp Leu Ser Gly Leu Pro Asn
                245                 250                 255

Thr Phe Ile Asp Val Gly Ser Ala Glu Val Phe Arg Asp Glu Asp Ile
            260                 265                 270

Ala Tyr Ala Ser Arg Leu Trp Ala Val Gly Val Gln Ala Glu Leu His
        275                 280                 285

Val Trp Pro Gly Gly Tyr His Ala Ala Glu Asn Met Ala Pro Gly Thr
    290                 295                 300

Asp Tyr Ser Lys Lys Val Lys Ala Ala Arg Leu Ala Trp Met Lys Arg
305                 310                 315                 320

Val Phe Leu Lys Ala Pro Lys Pro Thr Thr Glu Ser Leu Pro Ala Pro
                325                 330                 335
```

Thr Val Asp Glu Ala Val Gly Thr Ile
340 345

<210> SEQ ID NO 32
<211> LENGTH: 1038
<212> TYPE: DNA
<213> ORGANISM: Bensingtonia ciliata

<400> SEQUENCE: 32
atgccatcga atctgccgcg tccagcctac gaccctgaaa ttgaaccttt cttgagcatg 60
gtgccgctgc cgccgacgat taacgctgat atcatgcgtg agctgcgcaa ggcaccgctg 120
ctgagccaag cgccggacct ggatgcgctg ttgagcggtc gcccgatcac ccaccgcgaa 180
gtcagcatcc cgggtctgaa ctctcaggac ccgcagatca ccttgtcaat ctttagcagc 240
accttgactt ccggtccgaa gccgtgcatt tattttgtcc acggtggtgg catgattatc 300
ggctgtcgtt tcgttggtat tgaagattac ttacaatatg tggaacaaaa tgatgcagtg 360
gttgtggcag tggagtaccg cctggcgcct gagaacccgg acccagcgcc ggtgaacgac 420
tgctacgcgg gtctgttgtg gacggcagct aacgcagcag agctgggtat cgatctggag 480
cgcctgctga tctgcggtgc gagcgcgggt ggcggcctgt ccgctggcgt tgcgctgatg 540
gcccgtgaca aaaagggtcc gaaactggtt ggccagctgc tgtgttatcc gatgctggac 600
gaccgtaatg acagcctgag cagccagcaa tacgtggatg agggcgtctg gagccgtggt 660
agcaatgcgt tcggttggaa gcaactgctg ggcgatcgtg ccggcaaaga gggcgttagc 720
atctatgcgg caccggcgcg tgccacggat ctgtctggtc tgccgaacac cttcattgac 780
gttggtagcg ctgaagtttt tcgcgatgaa gatattgcgt acgcgagccg tctgtgggca 840
gtcggcgtcc aggcagagct ccatgtctgg ccgggtggct atcatgcggc cgagaatatg 900
gcaccgggta cggactacag caaaaaagtt aaagctgcgc gtctggcctg gatgaagcgt 960
gttttcctga aagcgccgaa gccgaccacc gagtccctgc cggcaccgac cgtggatgaa 1020
gccgtgggca ccatttaa 1038

<210> SEQ ID NO 33
<211> LENGTH: 474
<212> TYPE: DNA
<213> ORGANISM: Rhodococcus erythropolis
<220> FEATURE:
<221> NAME/KEY: CDS
<222> LOCATION: (1)..(474)

<400> SEQUENCE: 33 atg aat ctc aac gaa gcc cga act gct ttc gcc cgg ctc cgt gca gcg 48
Met Asn Leu Asn Glu Ala Arg Thr Ala Phe Ala Arg Leu Arg Ala Ala
1 5 10 15 gaa aat ggt tta tca cca gca gaa ctc gac gaa gtg tgg gcc gcg ctg 96
Glu Asn Gly Leu Ser Pro Ala Glu Leu Asp Glu Val Trp Ala Ala Leu
20 25 30 gaa acc gtc gcc gct gaa gaa atc ctc ggt gag tgg aaa ggt gac gac 144
Glu Thr Val Ala Ala Glu Glu Ile Leu Gly Glu Trp Lys Gly Asp Asp
35 40 45 ttc gcc acc ggt cat cgt ctg cac gaa aag ctg tcc gcg agc cgc tgg 192
Phe Ala Thr Gly His Arg Leu His Glu Lys Leu Ser Ala Ser Arg Trp
50 55 60 tac ggc aag act ttc aat tcc gtc gag gat gcc aag ccg ttg atc tgc 240
Tyr Gly Lys Thr Phe Asn Ser Val Glu Asp Ala Lys Pro Leu Ile Cys
65 70 75 80 cga gac gaa gac gga aat ctc tat tcc gac gtc aag agc ggc aat ggc 288

```
Arg Asp Glu Asp Gly Asn Leu Tyr Ser Asp Val Lys Ser Gly Asn Gly
                85                  90                  95

gag gca agt ctg tgg aac atc gag ttt cgt ggt gaa gtg acc gcg acc      336
Glu Ala Ser Leu Trp Asn Ile Glu Phe Arg Gly Glu Val Thr Ala Thr
            100                 105                 110

atg gtc tac gac ggc gcg ccg att ttc gac cac ttc aag aaa gtc gac      384
Met Val Tyr Asp Gly Ala Pro Ile Phe Asp His Phe Lys Lys Val Asp
        115                 120                 125

gat tcg acg ctc atg ggc atc atg aac gga aag tcg gcg ttg gtc ctc      432
Asp Ser Thr Leu Met Gly Ile Met Asn Gly Lys Ser Ala Leu Val Leu
    130                 135                 140

gac ggc ggg cag cac tac tac ttc ctg ctc gag cga gcg tga              474
Asp Gly Gly Gln His Tyr Tyr Phe Leu Leu Glu Arg Ala
145                 150                 155


<210> SEQ ID NO 34
<211> LENGTH: 157
<212> TYPE: PRT
<213> ORGANISM: Rhodococcus erythropolis

<400> SEQUENCE: 34

Met Asn Leu Asn Glu Ala Arg Thr Ala Phe Ala Arg Leu Arg Ala Ala
1               5                   10                  15

Glu Asn Gly Leu Ser Pro Ala Glu Leu Asp Glu Val Trp Ala Ala Leu
            20                  25                  30

Glu Thr Val Ala Ala Glu Glu Ile Leu Gly Glu Trp Lys Gly Asp Asp
        35                  40                  45

Phe Ala Thr Gly His Arg Leu His Glu Lys Leu Ser Ala Ser Arg Trp
    50                  55                  60

Tyr Gly Lys Thr Phe Asn Ser Val Glu Asp Ala Lys Pro Leu Ile Cys
65                  70                  75                  80

Arg Asp Glu Asp Gly Asn Leu Tyr Ser Asp Val Lys Ser Gly Asn Gly
                85                  90                  95

Glu Ala Ser Leu Trp Asn Ile Glu Phe Arg Gly Glu Val Thr Ala Thr
            100                 105                 110

Met Val Tyr Asp Gly Ala Pro Ile Phe Asp His Phe Lys Lys Val Asp
        115                 120                 125

Asp Ser Thr Leu Met Gly Ile Met Asn Gly Lys Ser Ala Leu Val Leu
    130                 135                 140

Asp Gly Gly Gln His Tyr Tyr Phe Leu Leu Glu Arg Ala
145                 150                 155


<210> SEQ ID NO 35
<211> LENGTH: 474
<212> TYPE: DNA
<213> ORGANISM: Rhodococcus erythropolis

<400> SEQUENCE: 35

atgaacttaa atgaagcgcg taccgcattt gcacgtctga gagctgccga gaacggtctg      60

agcccggctg agctggatga agtgtgggca gcgctggaga ctgtggcggc tgaagaaatc     120

ctgggtgagt ggaagggtga cgattttgcg acgggtcacc gtctgcacga gaaactgtcg     180

gcgagccgct ggtatggtaa gaccttcaac tctgttgaag atgcaaagcc gctgatttgc     240

cgtgacgaag atggcaatct gtactccgat gtcaagagcg gtaacggtga ggccagcctg     300

tggaatatcg agtttcgcgg cgaagtcacc gcgacgatgg tttacgatgg tgccccgatc     360

ttcgaccatt tcaaaaaagt tgacgacagc accctgatgg gcattatgaa tggcaaaagc     420
```

-continued gcgttggtgt tggacggtgg ccagcattac tatttcctgc tggagcgtgc gtaa 474

<210> SEQ ID NO 36
<211> LENGTH: 474
<212> TYPE: DNA
<213> ORGANISM: Rhodococcus erythropolis

<400> SEQUENCE: 36
atgaacttgg acgaagctag aactgctttc gctagattga gagctgctga atctggtgtt 60
tctccagctg aattggacga agtttgggct gctttggaaa ctgttgctgc tgaagaaatc 120
ttgggtgaat ggaagggtga cgacttcgct actggtcaca gattgcacga aaagttgttc 180
gcttctagat ggtacggtaa gactttcaac tctgttgaag acgctaagcc attgatctgt 240
agagacgaag acggtaactt gtactctgac gttaagtctg gtaacggtga agcttctttg 300
tggaacatcg aattcagagg tgaagttact gctactatgg tttacgacgg tgctccaatc 360
ttcgaccact tcaagaaggt tgacgactct actttgatgg gtatcatgaa cggtaagtct 420
gctttggttt tggacggtgg tcaacactac tacttcttgt tggaaagagc ttaa 474

<210> SEQ ID NO 37
<211> LENGTH: 474
<212> TYPE: DNA
<213> ORGANISM: Rhodococcus rhodochrous
<220> FEATURE:
<221> NAME/KEY: CDS
<222> LOCATION: (1)..(474)

<400> SEQUENCE: 37 atg aat ctc gac gaa gcc cga act gct ttc gcc cgg ctc cgt gct gcg 48
Met Asn Leu Asp Glu Ala Arg Thr Ala Phe Ala Arg Leu Arg Ala Ala
1 5 10 15 gaa agt ggt gta tca cca gca gaa ctc gac gaa gtg tgg gcc gcg ctg 96
Glu Ser Gly Val Ser Pro Ala Glu Leu Asp Glu Val Trp Ala Ala Leu
20 25 30 gaa acc gtc gcc gcc gaa gaa atc ctc ggc gag tgg aag ggt gac gac 144
Glu Thr Val Ala Ala Glu Glu Ile Leu Gly Glu Trp Lys Gly Asp Asp
35 40 45 ttc gcc acc ggt cac cgt ctt cac gaa aag ctg ttc gcg agc cgt tgg 192
Phe Ala Thr Gly His Arg Leu His Glu Lys Leu Phe Ala Ser Arg Trp
50 55 60 tac ggc aag acc ttc aac tcg gtc gag gac gcc aag ccg ttg atc tgc 240
Tyr Gly Lys Thr Phe Asn Ser Val Glu Asp Ala Lys Pro Leu Ile Cys
65 70 75 80 cga gac gaa gac ggc aac ctc tac tcc gac gtc aag agc ggc aat ggc 288
Arg Asp Glu Asp Gly Asn Leu Tyr Ser Asp Val Lys Ser Gly Asn Gly
85 90 95 gag gca agt ctg tgg aac atc gag ttt cgt ggc gaa gtc acg gcg acg 336
Glu Ala Ser Leu Trp Asn Ile Glu Phe Arg Gly Glu Val Thr Ala Thr
100 105 110 atg gtc tac gac ggc gcg ccg atc ttc gac cac ttc aag aag gtc gac 384
Met Val Tyr Asp Gly Ala Pro Ile Phe Asp His Phe Lys Lys Val Asp
115 120 125 gat tcg acg ctc atg ggc atc atg aac gga aaa tcg gcg ttg gtt ctc 432
Asp Ser Thr Leu Met Gly Ile Met Asn Gly Lys Ser Ala Leu Val Leu
130 135 140 gac ggc gga cag cac tac tac ttc ctg ctc gag cga gcg tga 474
Asp Gly Gly Gln His Tyr Tyr Phe Leu Leu Glu Arg Ala
145 150 155

<210> SEQ ID NO 38

<211> LENGTH: 157
<212> TYPE: PRT
<213> ORGANISM: Rhodococcus rhodochrous

<400> SEQUENCE: 38

Met Asn Leu Asp Glu Ala Arg Thr Ala Phe Ala Arg Leu Arg Ala Ala
1               5                   10                  15

Glu Ser Gly Val Ser Pro Ala Glu Leu Asp Glu Val Trp Ala Ala Leu
            20                  25                  30

Glu Thr Val Ala Ala Glu Glu Ile Leu Gly Glu Trp Lys Gly Asp Asp
        35                  40                  45

Phe Ala Thr Gly His Arg Leu His Glu Lys Leu Phe Ala Ser Arg Trp
    50                  55                  60

Tyr Gly Lys Thr Phe Asn Ser Val Glu Asp Ala Lys Pro Leu Ile Cys
65                  70                  75                  80

Arg Asp Glu Asp Gly Asn Leu Tyr Ser Asp Val Lys Ser Gly Asn Gly
                85                  90                  95

Glu Ala Ser Leu Trp Asn Ile Glu Phe Arg Gly Glu Val Thr Ala Thr
            100                 105                 110

Met Val Tyr Asp Gly Ala Pro Ile Phe Asp His Phe Lys Lys Val Asp
        115                 120                 125

Asp Ser Thr Leu Met Gly Ile Met Asn Gly Lys Ser Ala Leu Val Leu
    130                 135                 140

Asp Gly Gly Gln His Tyr Tyr Phe Leu Leu Glu Arg Ala
145                 150                 155

<210> SEQ ID NO 39
<211> LENGTH: 474
<212> TYPE: DNA
<213> ORGANISM: Rhodococcus rhodochrous

<400> SEQUENCE: 39
atgaatctgg acgaagcccg tactgctttc gcccgtctgc gcgctgctga atctggtgtt 60
agcccggcag agctggacga agtgtgggca gcgctggaaa ccgttgcggc ggaagaaatt 120
ctgggtgagt ggaagggcga tgacttcgca acgggccatc gcttgcacga gaaattgttc 180
gcgagccgct ggtatggtaa gacctttaac agcgtcgaag atgcgaaacc gctgatctgc 240
cgtgatgaag atggcaacct gtacagcgac gtcaagagcg gtaatggtga ggccagcctg 300
tggaatatcg agtttcgtgg cgaagtgacc gcgacgatgg tgtacgacgg tgcaccgatt 360
tttgatcatt tcaaaaaagt cgatgacagc accctgatgg gcatcatgaa cggtaagtcc 420
gcgctggttc tggacggtgg ccagcactat tactttctgc tggagcgtgc gtaa 474

<210> SEQ ID NO 40
<211> LENGTH: 474
<212> TYPE: DNA
<213> ORGANISM: Rhodococcus rhodochrous

<400> SEQUENCE: 40
atgaacttga acgaagctag aactgctttc gctagattga gagctgctga aaacggtttg 60
tctccagctg aattggacga agtttgggct gctttggaaa ctgttgctgc tgaagaaatc 120
ttgggtgaat ggaagggtga cgacttcgct actggtcaca gattgcacga aaagttgtct 180
gcttctagat ggtacggtaa gactttcaac tctgttgaag acgctaagcc attgatctgt 240
agagacgaag acggtaactt gtactctgac gttaagtctg gtaacggtga agcttctttg 300
tggaacatcg aattcagagg tgaagttact gctactatgg tttacgacgg tgctccaatc 360

```
ttcgaccact tcaagaaggt tgacgactct actttgatgg gtatcatgaa cggtaagtct    420

gctttggttt tggacggtgg tcaacactac tacttcttgt tggaaagagc ttaa          474


<210> SEQ ID NO 41
<211> LENGTH: 453
<212> TYPE: DNA
<213> ORGANISM: Penicillium digitatum
<220> FEATURE:
<221> NAME/KEY: CDS
<222> LOCATION: (1)..(453)

<400> SEQUENCE: 41

atg tcc aca agc acc cca cag gat cag ttt gct gcc cta gtt gca aaa       48
Met Ser Thr Ser Thr Pro Gln Asp Gln Phe Ala Ala Leu Val Ala Lys
1               5                   10                  15

aac agc aag ttg aat gaa acc gac atc gag gct gtt tat aac aag ctt       96
Asn Ser Lys Leu Asn Glu Thr Asp Ile Glu Ala Val Tyr Asn Lys Leu
            20                  25                  30

tca gct ctt ccc gtc gat ttc ctc cgt gga gaa tgg aag ggt gga agc      144
Ser Ala Leu Pro Val Asp Phe Leu Arg Gly Glu Trp Lys Gly Gly Ser
        35                  40                  45

ttc gac acc ggc cac cca ggc cac acc cag ctt ttg gct atg aac tgg      192
Phe Asp Thr Gly His Pro Gly His Thr Gln Leu Leu Ala Met Asn Trp
    50                  55                  60

gtt gga aag acg ttc cac gat acc gag cgc gtc gac cct att gtt gtg      240
Val Gly Lys Thr Phe His Asp Thr Glu Arg Val Asp Pro Ile Val Val
65                  70                  75                  80

tta aag gat gga aag cgt gta tgc gat gag aac tgg ggc cat gct atc      288
Leu Lys Asp Gly Lys Arg Val Cys Asp Glu Asn Trp Gly His Ala Ile
                85                  90                  95

gtc cgt gag gtt cgt ttc cgt ggt att gtg tca acc gct atg atc tat      336
Val Arg Glu Val Arg Phe Arg Gly Ile Val Ser Thr Ala Met Ile Tyr
            100                 105                 110

gac aag cac cct atc att gat cac ttc cgc tat gtt aat gag aac ctc      384
Asp Lys His Pro Ile Ile Asp His Phe Arg Tyr Val Asn Glu Asn Leu
        115                 120                 125

gtt gct ggc gcc atg gac act agc tcc ttc ggt gac gtt ggt acc tac      432
Val Ala Gly Ala Met Asp Thr Ser Ser Phe Gly Asp Val Gly Thr Tyr
    130                 135                 140

tac ttc tac cta tac aaa tag                                          453
Tyr Phe Tyr Leu Tyr Lys
145                 150


<210> SEQ ID NO 42
<211> LENGTH: 150
<212> TYPE: PRT
<213> ORGANISM: Penicillium digitatum

<400> SEQUENCE: 42

Met Ser Thr Ser Thr Pro Gln Asp Gln Phe Ala Ala Leu Val Ala Lys
1               5                   10                  15

Asn Ser Lys Leu Asn Glu Thr Asp Ile Glu Ala Val Tyr Asn Lys Leu
            20                  25                  30

Ser Ala Leu Pro Val Asp Phe Leu Arg Gly Glu Trp Lys Gly Gly Ser
        35                  40                  45

Phe Asp Thr Gly His Pro Gly His Thr Gln Leu Leu Ala Met Asn Trp
    50                  55                  60

Val Gly Lys Thr Phe His Asp Thr Glu Arg Val Asp Pro Ile Val Val
65                  70                  75                  80
```

-continued

```
Leu Lys Asp Gly Lys Arg Val Cys Asp Glu Asn Trp Gly His Ala Ile
                85                  90                  95

Val Arg Glu Val Arg Phe Arg Gly Ile Val Ser Thr Ala Met Ile Tyr
            100                 105                 110

Asp Lys His Pro Ile Ile Asp His Phe Arg Tyr Val Asn Glu Asn Leu
        115                 120                 125

Val Ala Gly Ala Met Asp Thr Ser Ser Phe Gly Asp Val Gly Thr Tyr
    130                 135                 140

Tyr Phe Tyr Leu Tyr Lys
145                 150


<210> SEQ ID NO 43
<211> LENGTH: 453
<212> TYPE: DNA
<213> ORGANISM: Penicillium digitatum

<400> SEQUENCE: 43

atgtccacta gcaccccaca agatcaattt gccgcactgg ttgccaaaaa ctctaaactg      60

aatgaaaccg acattgaagc tgtctataac aagttgagcg cgttgccggt ggatttcctg     120

cgtggcgagt ggaagggcgg cagcttcgac accggtcacc cgggtcacac gcagctgctg     180

gcaatgaatt gggtcggtaa gacctttcat gataccgagc gtgtggaccc gatcgtcgtt     240

ctgaaggacg gtaaacgtgt gtgcgacgag aattggggtc acgcgatcgt tcgcgaagtt     300

cgcttccgtg gtatcgtgag caccgcgatg atctatgata aacacccgat tattgatcat     360

ttccgctatg ttaacgaaaa cctggtcgcg ggtgcgatgg atacgtcgag ctttggcgac     420

gtgggcacgt actactttta cctgtacaaa taa                                  453


<210> SEQ ID NO 44
<211> LENGTH: 453
<212> TYPE: DNA
<213> ORGANISM: Penicillium digitatum

<400> SEQUENCE: 44

atgtctactt ctactccaca agaccaattc gctgctttgg ttgctaagaa ctctaagttg      60

aacgaaactg acatcgaagc tgtttacaac aagttgtctg ctttgccagt tgacttcttg     120

agaggtgaat ggaagggtgg ttctttcgac actggtcacc caggtcacac tcaattgttg     180

gctatgaact gggttggtaa gactttccac gacactgaaa gagttgaccc aatcgttgtt     240

ttgaaggacg gtaagagagt ttgtgacgaa aactggggtc acgctatcgt tagagaagtt     300

agattcagag gtatcgtttc tactgctatg atctacgaca agcacccaat catcgaccac     360

ttcagatacg ttaacgaaaa cttggttgct ggtgctatgg acacttcttc tttcggtgac     420

gttggtactt actacttcta cttgtacaag taa                                  453


<210> SEQ ID NO 45
<211> LENGTH: 453
<212> TYPE: DNA
<213> ORGANISM: Penicillium italicum
<220> FEATURE:
<221> NAME/KEY: CDS
<222> LOCATION: (1)..(453)

<400> SEQUENCE: 45

atg tcg gcc agt gac ccc aag gac cag ttt gct gcc cta gtt gcc aag       48
Met Ser Ala Ser Asp Pro Lys Asp Gln Phe Ala Ala Leu Val Ala Lys
1               5                   10                  15

gac ggc aag ttg aat gaa gac gaa atc gag gct gtt tac aac aag ctt       96
```

-continued

```
Asp Gly Lys Leu Asn Glu Asp Glu Ile Glu Ala Val Tyr Asn Lys Leu
            20                  25                  30

cct gct ctt ccc ctc gat ttc ctc cgt gga gaa tgg aag ggt gga agc      144
Pro Ala Leu Pro Leu Asp Phe Leu Arg Gly Glu Trp Lys Gly Gly Ser
        35                  40                  45

ttc gac acc ggt cac cct ggt cac acc caa ctc ttg gca atg aaa tgg      192
Phe Asp Thr Gly His Pro Gly His Thr Gln Leu Leu Ala Met Lys Trp
    50                  55                  60

gtt ggg aag aca ttc cat tcc acc gaa cgg gtt gac cct att gtt gtg      240
Val Gly Lys Thr Phe His Ser Thr Glu Arg Val Asp Pro Ile Val Val
65                  70                  75                  80

tta aag gat gaa aag cgt gta tgc aat gag gac tgg ggc cat gca gtc      288
Leu Lys Asp Glu Lys Arg Val Cys Asn Glu Asp Trp Gly His Ala Val
                85                  90                  95

ctc cgt gag att cgt ttc cgt ggt att gtg tca tct gct atg atc tat      336
Leu Arg Glu Ile Arg Phe Arg Gly Ile Val Ser Ser Ala Met Ile Tyr
            100                 105                 110

gac aag cac cct atc atc gac cac ttc cgc tat gtc aac gac aag ctc      384
Asp Lys His Pro Ile Ile Asp His Phe Arg Tyr Val Asn Asp Lys Leu
        115                 120                 125

att gct ggc gcc atg gac act agc agc ttc ggt gac gtt ggc acc tac      432
Ile Ala Gly Ala Met Asp Thr Ser Ser Phe Gly Asp Val Gly Thr Tyr
    130                 135                 140

tac ttc tac ctg tgc aaa tag                                          453
Tyr Phe Tyr Leu Cys Lys
145                 150


<210> SEQ ID NO 46
<211> LENGTH: 150
<212> TYPE: PRT
<213> ORGANISM: Penicillium italicum

<400> SEQUENCE: 46

Met Ser Ala Ser Asp Pro Lys Asp Gln Phe Ala Ala Leu Val Ala Lys
1               5                   10                  15

Asp Gly Lys Leu Asn Glu Asp Glu Ile Glu Ala Val Tyr Asn Lys Leu
            20                  25                  30

Pro Ala Leu Pro Leu Asp Phe Leu Arg Gly Glu Trp Lys Gly Gly Ser
        35                  40                  45

Phe Asp Thr Gly His Pro Gly His Thr Gln Leu Leu Ala Met Lys Trp
    50                  55                  60

Val Gly Lys Thr Phe His Ser Thr Glu Arg Val Asp Pro Ile Val Val
65                  70                  75                  80

Leu Lys Asp Glu Lys Arg Val Cys Asn Glu Asp Trp Gly His Ala Val
                85                  90                  95

Leu Arg Glu Ile Arg Phe Arg Gly Ile Val Ser Ser Ala Met Ile Tyr
            100                 105                 110

Asp Lys His Pro Ile Ile Asp His Phe Arg Tyr Val Asn Asp Lys Leu
        115                 120                 125

Ile Ala Gly Ala Met Asp Thr Ser Ser Phe Gly Asp Val Gly Thr Tyr
    130                 135                 140

Tyr Phe Tyr Leu Cys Lys
145                 150


<210> SEQ ID NO 47
<211> LENGTH: 453
<212> TYPE: DNA
<213> ORGANISM: Penicillium italicum
```

-continued

<400> SEQUENCE: 47

```
atgagcgctt cggacccaaa agatcaattc gcagcattgg tggcaaagga cggtaaactg     60

aacgaagatg aaatcgaagc cgtctataac aagctgcctg cgctgccgct ggacttcttg    120

cgtggtgagt ggaagggcgg cagctttgat accggtcatc cgggccacac tcagctgctg    180

gcgatgaaat gggtgggtaa aacctttcac agcaccgagc gcgtggaccc gatcgtcgtt    240

ctgaaagatg agaagcgtgt ctgtaatgaa gattggggtc acgccgtgct gcgcgagatt    300

cgttttcgcg gtatcgtttc tagcgcgatg atttatgaca agcatccgat tattgaccac    360

ttccgttacg ttaatgacaa gctgatcgcg ggtgcgatgg atacgtccag ctttggcgac    420

gttggcacgt actatttcta cctgtgcaaa taa                                 453
```

<210> SEQ ID NO 48
<211> LENGTH: 468
<212> TYPE: DNA
<213> ORGANISM: Aspergillus wentii
<220> FEATURE:
<221> NAME/KEY: CDS
<222> LOCATION: (1)..(468)

<400> SEQUENCE: 48

```
atg agc tgt tgc acc gcc gag gac cag gcc aaa cgg ctc ttc gaa gcg       48
Met Ser Cys Cys Thr Ala Glu Asp Gln Ala Lys Arg Leu Phe Glu Ala
1               5                   10                  15

acc agc ccc gtc caa cca tca gca gtc gaa gaa ctc ttc aac caa ctc       96
Thr Ser Pro Val Gln Pro Ser Ala Val Glu Glu Leu Phe Asn Gln Leu
            20                  25                  30

caa ccg ata aag ccc tca ttc ctg att ggc gaa tgg gac gga aat agc      144
Gln Pro Ile Lys Pro Ser Phe Leu Ile Gly Glu Trp Asp Gly Asn Ser
        35                  40                  45

ctg gac acc ggc cat ccc ggt ctc aag ctg ctc cag gcg atg cgg tgg      192
Leu Asp Thr Gly His Pro Gly Leu Lys Leu Leu Gln Ala Met Arg Trp
    50                  55                  60

gcg ggt aag aca ttt cga tcc gtg gat gac gcc gat ccg att gtg acg      240
Ala Gly Lys Thr Phe Arg Ser Val Asp Asp Ala Asp Pro Ile Val Thr
65                  70                  75                  80

ctg gac gat gct ggc aat cgc atc tgg aaa gag gag tac ggt aat gct      288
Leu Asp Asp Ala Gly Asn Arg Ile Trp Lys Glu Glu Tyr Gly Asn Ala
                85                  90                  95

gtg gta cga gaa atg gcg ttt cgc gga gtc gtt tcg gcg gcg atg atc      336
Val Val Arg Glu Met Ala Phe Arg Gly Val Val Ser Ala Ala Met Ile
            100                 105                 110

tac gac acc aag ccc atc atg gac cat ttt cga tac gtg gac gaa aag      384
Tyr Asp Thr Lys Pro Ile Met Asp His Phe Arg Tyr Val Asp Glu Lys
        115                 120                 125

aca gtg ctg ggt gtg atg gaa acc ccc aag cag gct gga agc gga acc      432
Thr Val Leu Gly Val Met Glu Thr Pro Lys Gln Ala Gly Ser Gly Thr
    130                 135                 140

ttt tat ttc tat ctg cag cgt cgt gct tct gtc taa                      468
Phe Tyr Phe Tyr Leu Gln Arg Arg Ala Ser Val
145                 150                 155
```

<210> SEQ ID NO 49
<211> LENGTH: 155
<212> TYPE: PRT
<213> ORGANISM: Aspergillus wentii

<400> SEQUENCE: 49

```
Met Ser Cys Cys Thr Ala Glu Asp Gln Ala Lys Arg Leu Phe Glu Ala
1               5                   10                  15
```

```
Thr Ser Pro Val Gln Pro Ser Ala Val Glu Glu Leu Phe Asn Gln Leu
            20                  25                  30

Gln Pro Ile Lys Pro Ser Phe Leu Ile Gly Glu Trp Asp Gly Asn Ser
        35                  40                  45

Leu Asp Thr Gly His Pro Gly Leu Lys Leu Leu Gln Ala Met Arg Trp
    50                  55                  60

Ala Gly Lys Thr Phe Arg Ser Val Asp Asp Ala Asp Pro Ile Val Thr
65                  70                  75                  80

Leu Asp Asp Ala Gly Asn Arg Ile Trp Lys Glu Glu Tyr Gly Asn Ala
                85                  90                  95

Val Val Arg Glu Met Ala Phe Arg Gly Val Val Ser Ala Ala Met Ile
            100                 105                 110

Tyr Asp Thr Lys Pro Ile Met Asp His Phe Arg Tyr Val Asp Glu Lys
        115                 120                 125

Thr Val Leu Gly Val Met Glu Thr Pro Lys Gln Ala Gly Ser Gly Thr
    130                 135                 140

Phe Tyr Phe Tyr Leu Gln Arg Arg Ala Ser Val
145                 150                 155
```

<210> SEQ ID NO 50
<211> LENGTH: 468
<212> TYPE: DNA
<213> ORGANISM: Aspergillus wentii

<400> SEQUENCE: 50

```
atgtcgtgtt gcaccgccga agatcaagcc aaacgtctgt tcgaagccac tagcccggtt      60

caaccgagcg cggtcgaaga actgttcaat cagctgcaac cgattaagcc ttccttcctg     120

atcggtgagt gggatggcaa cagcctggat accggtcatc cgggcttgaa gctgctgcag     180

gcaatgcgct gggcgggtaa gacctttcgt tctgtggatg acgctgaccc aattgttacc     240

ctggacgacg cgggtaatcg tatttggaaa gaggaatacg gtaacgcagt ggttcgcgag     300

atggcgtttc gtggtgtggt cagcgcggca atgatctatg acacgaagcc gatcatggat     360

cactttcgct atgttgacga gaaaacggtc ctgggcgtga tggaaacgcc gaaacaggct     420

ggtagcggca ccttctactt ttacttgcag cgtcgtgcga gcgtctaa                 468
```

<210> SEQ ID NO 51
<211> LENGTH: 468
<212> TYPE: DNA
<213> ORGANISM: Aspergillus wentii

<400> SEQUENCE: 51

```
atgtcttgtt gtactgctga agaccaagct aagagattgt tcgaagctac ttctccagtt      60

caaccatctg ctgttgaaga attgttcaac caattgcaac caatcaagcc atctttcttg     120

atcggtgaat gggacggtaa ctctttggac actggtcacc caggtttgaa gttgttgcaa     180

gctatgagat gggctggtaa gactttcaga tctgttgacg acgctgaccc aatcgttact     240

ttggacgacg ctggtaacag aatctggaag gaagaatacg gtaacgctgt tgttagagaa     300

atggctttca gaggtgttgt ttctgctgct atgatctacg acactaagcc aatcatggac     360

cacttcagat acgttgacga aaagactgtt ttgggtgtta tggaaactcc aaagcaagct     420

ggttctggta ctttctactt ctacttgcaa agaagagctt ctgtttaa                 468
```

<210> SEQ ID NO 52
<211> LENGTH: 477

```
<212> TYPE: DNA
<213> ORGANISM: Rhodococcus hoagii
<220> FEATURE:
<221> NAME/KEY: CDS
<222> LOCATION: (1)..(477)

<400> SEQUENCE: 52

atg aac gta cga gac gag gtc gcc gcg ctg cgg gcg cgc acc gac cgg       48
Met Asn Val Arg Asp Glu Val Ala Ala Leu Arg Ala Arg Thr Asp Arg
1               5                   10                  15

atc gat ccg cgg gaa ctc gat tcg atc tgg gac cgc ttg gcc ccg tgt       96
Ile Asp Pro Arg Glu Leu Asp Ser Ile Trp Asp Arg Leu Ala Pro Cys
            20                  25                  30

cgg ccc gtg gat ctg atc ggg tac cgc tgg agg ggt ttc gac ttc gac      144
Arg Pro Val Asp Leu Ile Gly Tyr Arg Trp Arg Gly Phe Asp Phe Asp
        35                  40                  45

acc gga cat cgc acg agt ggg ctc ctc cgt cga gct cat tgg tac ggc      192
Thr Gly His Arg Thr Ser Gly Leu Leu Arg Arg Ala His Trp Tyr Gly
    50                  55                  60

aag gca ttc gcc agc gag tcc gac gtg cag cct ctg ctg tgc cgc agc      240
Lys Ala Phe Ala Ser Glu Ser Asp Val Gln Pro Leu Leu Cys Arg Ser
65                  70                  75                  80

gag gac gga cag ctg ttc tcc gac atc gga acc ggg cac ggc gag gcc      288
Glu Asp Gly Gln Leu Phe Ser Asp Ile Gly Thr Gly His Gly Glu Ala
                85                  90                  95

agc ctg tgg gag gtc gtg ttc cgc ggg gag gtg acc gcg acg atg gtc      336
Ser Leu Trp Glu Val Val Phe Arg Gly Glu Val Thr Ala Thr Met Val
            100                 105                 110

tac gac ggc atg ccg gtg ttc gac cac ttc aag aag gtc gac gac gac      384
Tyr Asp Gly Met Pro Val Phe Asp His Phe Lys Lys Val Asp Asp Asp
        115                 120                 125

acc gtc atc ggc gtc atg aac ggc aag ggc acg ttg gtg ttc gac ggc      432
Thr Val Ile Gly Val Met Asn Gly Lys Gly Thr Leu Val Phe Asp Gly
    130                 135                 140

ggc gaa cac ttc tgg ttc ggg ctg gag cga gac gtc gca ctc tga          477
Gly Glu His Phe Trp Phe Gly Leu Glu Arg Asp Val Ala Leu
145                 150                 155


<210> SEQ ID NO 53
<211> LENGTH: 158
<212> TYPE: PRT
<213> ORGANISM: Rhodococcus hoagii

<400> SEQUENCE: 53

Met Asn Val Arg Asp Glu Val Ala Ala Leu Arg Ala Arg Thr Asp Arg
1               5                   10                  15

Ile Asp Pro Arg Glu Leu Asp Ser Ile Trp Asp Arg Leu Ala Pro Cys
            20                  25                  30

Arg Pro Val Asp Leu Ile Gly Tyr Arg Trp Arg Gly Phe Asp Phe Asp
        35                  40                  45

Thr Gly His Arg Thr Ser Gly Leu Leu Arg Arg Ala His Trp Tyr Gly
    50                  55                  60

Lys Ala Phe Ala Ser Glu Ser Asp Val Gln Pro Leu Leu Cys Arg Ser
65                  70                  75                  80

Glu Asp Gly Gln Leu Phe Ser Asp Ile Gly Thr Gly His Gly Glu Ala
                85                  90                  95

Ser Leu Trp Glu Val Val Phe Arg Gly Glu Val Thr Ala Thr Met Val
            100                 105                 110

Tyr Asp Gly Met Pro Val Phe Asp His Phe Lys Lys Val Asp Asp Asp
        115                 120                 125
```

```
Thr Val Ile Gly Val Met Asn Gly Lys Gly Thr Leu Val Phe Asp Gly
    130                 135                 140

Gly Glu His Phe Trp Phe Gly Leu Glu Arg Asp Val Ala Leu
145                 150                 155


<210> SEQ ID NO 54
<211> LENGTH: 477
<212> TYPE: DNA
<213> ORGANISM: Rhodococcus hoagii

<400> SEQUENCE: 54

atgaatgttc gtgatgaagt tgcagctctg cgtgcccgta ctgatagaat cgacccgcgt      60

gagctggata gcatttggga ccgtctggca ccatgtcgtc cggtggacct gatcggttac     120

cgttggcgcg gtttcgattt cgacaccggt caccgtacct ccggtctgtt gcgtcgcgcg     180

cattggtatg gtaaggcctt tgcgagcgag agcgacgtgc aaccgttgct gtgccgctct     240

gaggacggcc agctgtttag cgatattggc accggtcacg gtgaggcgag cctgtgggaa     300

gttgtctttc gcggcgaagt gaccgcgacg atggtttacg acggtatgcc ggtgttcgac     360

cacttcaaaa aagttgatga cgacacggtg atcggtgtca tgaacggcaa gggcacgctg     420

gtctttgatg gtggcgagca tttctggttt ggcctggaac gcgatgtcgc gctgtaa        477


<210> SEQ ID NO 55
<211> LENGTH: 477
<212> TYPE: DNA
<213> ORGANISM: Rhodococcus hoagii
<220> FEATURE:
<221> NAME/KEY: CDS
<222> LOCATION: (1)..(477)

<400> SEQUENCE: 55

atg aac gta cga gac gag gtc gcc gcg ctg cgg gcg cgc acc gac cgg       48
Met Asn Val Arg Asp Glu Val Ala Ala Leu Arg Ala Arg Thr Asp Arg
1               5                   10                  15

atc gat ccg cgg gaa ctc gat tcg atc tgg gac cgc ttg gcc ccg tgt       96
Ile Asp Pro Arg Glu Leu Asp Ser Ile Trp Asp Arg Leu Ala Pro Cys
            20                  25                  30

cgg ccc gtg gat ctg atc ggg tac cgc tgg agg ggt ttc gac ttc gac      144
Arg Pro Val Asp Leu Ile Gly Tyr Arg Trp Arg Gly Phe Asp Phe Asp
        35                  40                  45

acc gga cat cgc acg agt ggg ctc ctc cgt cga gct cat tgg tac ggc      192
Thr Gly His Arg Thr Ser Gly Leu Leu Arg Arg Ala His Trp Tyr Gly
    50                  55                  60

aag gca ttc gcc agc gag tcc gac gtg cag cct ctg ctg tgc cgc agc      240
Lys Ala Phe Ala Ser Glu Ser Asp Val Gln Pro Leu Leu Cys Arg Ser
65                  70                  75                  80

gac gac gga cag ctg ttc tcc gac atc gga acc ggg cac ggc gag gcc      288
Asp Asp Gly Gln Leu Phe Ser Asp Ile Gly Thr Gly His Gly Glu Ala
                85                  90                  95

agc ctg tgg gag gtc gtg ttc cgc ggg gag gtg acc gcg acg atg gtc      336
Ser Leu Trp Glu Val Val Phe Arg Gly Glu Val Thr Ala Thr Met Val
            100                 105                 110

tac gac ggc atg ccg gtg ttc gac cac ttc aag aag gtc gac gac gac      384
Tyr Asp Gly Met Pro Val Phe Asp His Phe Lys Lys Val Asp Asp Asp
        115                 120                 125

acc gtc atc ggc gtc atg aac ggc aag ggc acg ttg gtg ttc gac ggc      432
Thr Val Ile Gly Val Met Asn Gly Lys Gly Thr Leu Val Phe Asp Gly
    130                 135                 140

ggc gaa cac ttc tgg ttc ggg ctg gag cga gac gtc gca ctc tga          477
```

Gly Glu His Phe Trp Phe Gly Leu Glu Arg Asp Val Ala Leu
145 150 155

<210> SEQ ID NO 56
<211> LENGTH: 158
<212> TYPE: PRT
<213> ORGANISM: Rhodococcus hoagii

<400> SEQUENCE: 56

Met Asn Val Arg Asp Glu Val Ala Ala Leu Arg Ala Arg Thr Asp Arg
1 5 10 15

Ile Asp Pro Arg Glu Leu Asp Ser Ile Trp Asp Arg Leu Ala Pro Cys
20 25 30

Arg Pro Val Asp Leu Ile Gly Tyr Arg Trp Arg Gly Phe Asp Phe Asp
35 40 45

Thr Gly His Arg Thr Ser Gly Leu Leu Arg Arg Ala His Trp Tyr Gly
50 55 60

Lys Ala Phe Ala Ser Glu Ser Asp Val Gln Pro Leu Leu Cys Arg Ser
65 70 75 80

Asp Asp Gly Gln Leu Phe Ser Asp Ile Gly Thr Gly His Gly Glu Ala
85 90 95

Ser Leu Trp Glu Val Val Phe Arg Gly Glu Val Thr Ala Thr Met Val
100 105 110

Tyr Asp Gly Met Pro Val Phe Asp His Phe Lys Lys Val Asp Asp Asp
115 120 125

Thr Val Ile Gly Val Met Asn Gly Lys Gly Thr Leu Val Phe Asp Gly
130 135 140

Gly Glu His Phe Trp Phe Gly Leu Glu Arg Asp Val Ala Leu
145 150 155

<210> SEQ ID NO 57
<211> LENGTH: 477
<212> TYPE: DNA
<213> ORGANISM: Rhodococcus hoagii

<400> SEQUENCE: 57
atgaatgttc gtgatgaagt tgcagctctg cgtgcccgta ctgatagaat cgacccgcgt 60
gagctggata gcatttggga ccgtctggca ccatgtcgtc cggtggacct gatcggttac 120
cgttggcgcg gtttcgattt cgacaccggt caccgtacct ccggtctgtt gcgtcgcgcg 180
cattggtatg gtaaggcctt tgcgagcgag agcgacgtgc aaccgttgct gtgccgctct 240
gatgacggcc agctgtttag cgatattggc accggtcacg gtgaggcgag cctgtgggaa 300
gttgtctttc gcggcgaagt gaccgcgacg atggtttacg acggtatgcc ggtgttcgac 360
cacttcaaaa aagttgatga cgacacggtg atcggtgtca tgaacggcaa gggcacgctg 420
gtctttgatg gtggcgagca tttctggttt ggcctggaac gcgatgtcgc gctgtaa 477

<210> SEQ ID NO 58
<211> LENGTH: 477
<212> TYPE: DNA
<213> ORGANISM: Rhodococcus hoagii
<220> FEATURE:
<221> NAME/KEY: CDS
<222> LOCATION: (1)..(477)

<400> SEQUENCE: 58 atg aac gta cga gac gag gtc gcc gcg ctg cgg gcg cgc acc gac cgg 48
Met Asn Val Arg Asp Glu Val Ala Ala Leu Arg Ala Arg Thr Asp Arg
1 5 10 15

```
atc gat ccg cgg gaa ctc gat tcg atc tgg gac cgc ttg gcc ccg tgt       96
Ile Asp Pro Arg Glu Leu Asp Ser Ile Trp Asp Arg Leu Ala Pro Cys
            20                  25                  30

cgg ccc gtg gat ctg atc ggg tac cgc tgg cgg ggt ttc gac ttc gac      144
Arg Pro Val Asp Leu Ile Gly Tyr Arg Trp Arg Gly Phe Asp Phe Asp
        35                  40                  45

acc gga cat cgc acg agt ggg ctc ctc cgt cga gcg cat tgg tac ggc      192
Thr Gly His Arg Thr Ser Gly Leu Leu Arg Arg Ala His Trp Tyr Gly
    50                  55                  60

aag gca ttc gcc agc gag tcc gac gtg cag cct ctg ctg tgc cgc agc      240
Lys Ala Phe Ala Ser Glu Ser Asp Val Gln Pro Leu Leu Cys Arg Ser
65                  70                  75                  80

gag gac gga cag ctg ttc tcc gac atc gga acc ggg cac ggc gag gcc      288
Glu Asp Gly Gln Leu Phe Ser Asp Ile Gly Thr Gly His Gly Glu Ala
                85                  90                  95

agc ctg tgg gag gtc gtg ttc cgc ggg gag gtg acc gcg acg atg gtc      336
Ser Leu Trp Glu Val Val Phe Arg Gly Glu Val Thr Ala Thr Met Val
            100                 105                 110

tac gac ggc atg ccg gtg tcc gac cac ttc aag aag gtc gac gac gac      384
Tyr Asp Gly Met Pro Val Ser Asp His Phe Lys Lys Val Asp Asp Asp
        115                 120                 125

acc gtc atc ggc gtc atg aac ggc aag ggc acg ttg gtg ttc gac ggc      432
Thr Val Ile Gly Val Met Asn Gly Lys Gly Thr Leu Val Phe Asp Gly
    130                 135                 140

ggc gaa cac ttc tgg ttc ggg ctg gag cga gac gtc gca ctc tga          477
Gly Glu His Phe Trp Phe Gly Leu Glu Arg Asp Val Ala Leu
145                 150                 155


<210> SEQ ID NO 59
<211> LENGTH: 158
<212> TYPE: PRT
<213> ORGANISM: Rhodococcus hoagii

<400> SEQUENCE: 59

Met Asn Val Arg Asp Glu Val Ala Ala Leu Arg Ala Arg Thr Asp Arg
1               5                   10                  15

Ile Asp Pro Arg Glu Leu Asp Ser Ile Trp Asp Arg Leu Ala Pro Cys
            20                  25                  30

Arg Pro Val Asp Leu Ile Gly Tyr Arg Trp Arg Gly Phe Asp Phe Asp
        35                  40                  45

Thr Gly His Arg Thr Ser Gly Leu Leu Arg Arg Ala His Trp Tyr Gly
    50                  55                  60

Lys Ala Phe Ala Ser Glu Ser Asp Val Gln Pro Leu Leu Cys Arg Ser
65                  70                  75                  80

Glu Asp Gly Gln Leu Phe Ser Asp Ile Gly Thr Gly His Gly Glu Ala
                85                  90                  95

Ser Leu Trp Glu Val Val Phe Arg Gly Glu Val Thr Ala Thr Met Val
            100                 105                 110

Tyr Asp Gly Met Pro Val Ser Asp His Phe Lys Lys Val Asp Asp Asp
        115                 120                 125

Thr Val Ile Gly Val Met Asn Gly Lys Gly Thr Leu Val Phe Asp Gly
    130                 135                 140

Gly Glu His Phe Trp Phe Gly Leu Glu Arg Asp Val Ala Leu
145                 150                 155


<210> SEQ ID NO 60
<211> LENGTH: 477
<212> TYPE: DNA
```

<213> ORGANISM: Rhodococcus hoagii

<400> SEQUENCE: 60
atgaatgttc gtgatgaagt tgcagctctg cgtgcccgta ctgatagaat cgacccgcgt 60
gagctggata gcatttggga ccgtctggca ccatgtcgtc cggtggacct gatcggttac 120
cgttggcgcg gtttcgattt cgacaccggt caccgtacct ccggtctgtt gcgtcgcgcg 180
cattggtatg gtaaggcctt tgcgagcgag agcgacgtgc aaccgttgct gtgccgctct 240
gaggacggcc agctgtttag cgatattggc accggtcacg gtgaggcgag cctgtgggaa 300
gttgtctttc gcggcgaagt gaccgcgacg atggtttacg acggtatgcc ggtgagcgac 360
cacttcaaaa aagttgatga cgacacggtg atcggtgtca tgaacggcaa gggcacgctg 420
gtctttgatg gtggcgagca tttctggttt ggcctggaac gcgatgtcgc gctgtaa 477

<210> SEQ ID NO 61
<211> LENGTH: 585
<212> TYPE: DNA
<213> ORGANISM: Cupriavidus necator
<220> FEATURE:
<221> NAME/KEY: CDS
<222> LOCATION: (1)..(585)

<400> SEQUENCE: 61

```
atg ctg aca gaa atg ctg cgg aat cga gtc tct aca act gcg gcg gta       48
Met Leu Thr Glu Met Leu Arg Asn Arg Val Ser Thr Thr Ala Ala Val
1               5                   10                  15

ctg gcc gct ttc gat gaa ctt gat cca tta tcg agc gat tcg cta gtt       96
Leu Ala Ala Phe Asp Glu Leu Asp Pro Leu Ser Ser Asp Ser Leu Val
            20                  25                  30

ggc tgc tgg agt ggt ttt gtg atc gct acc ggg cac ccc atg gac ggt      144
Gly Cys Trp Ser Gly Phe Val Ile Ala Thr Gly His Pro Met Asp Gly
        35                  40                  45

ctt ctg agc gct gtc ggc tgg tac ggg aaa atg ttc caa agc gtg gat      192
Leu Leu Ser Ala Val Gly Trp Tyr Gly Lys Met Phe Gln Ser Val Asp
    50                  55                  60

gag gca tat ccg ctg atc atc cgg tcc ccg gac gcc agt acg ctt ttt      240
Glu Ala Tyr Pro Leu Ile Ile Arg Ser Pro Asp Ala Ser Thr Leu Phe
65                  70                  75                  80

tcg atc gat ccc agc cct ttg cca ctt ata ggc tgc gcg aag tta tct      288
Ser Ile Asp Pro Ser Pro Leu Pro Leu Ile Gly Cys Ala Lys Leu Ser
                85                  90                  95

ccc acg gat atg gtg tcg cgt ttt tca aca ctt tcc ccg ttg gcc ctg      336
Pro Thr Asp Met Val Ser Arg Phe Ser Thr Leu Ser Pro Leu Ala Leu
            100                 105                 110

agc aca acc gtc tct cac ggt cgg ctg cgt atg gtc gag tat cgc gga      384
Ser Thr Thr Val Ser His Gly Arg Leu Arg Met Val Glu Tyr Arg Gly
        115                 120                 125

aag gtc aca gga act ctg atc tac gac cag cag ccg ata ctc gat cat      432
Lys Val Thr Gly Thr Leu Ile Tyr Asp Gln Gln Pro Ile Leu Asp His
    130                 135                 140

ttc gtg atg att gat tcg caa acg gta ctt gga att atg gat ttt aaa      480
Phe Val Met Ile Asp Ser Gln Thr Val Leu Gly Ile Met Asp Phe Lys
145                 150                 155                 160

gag ttc ccg cag cca ggc gcg ttt gtg ctg cag cgc gat gac gac agt      528
Glu Phe Pro Gln Pro Gly Ala Phe Val Leu Gln Arg Asp Asp Asp Ser
                165                 170                 175

gcc gtc agc gtt gat cgc ggc gac tgg tcc caa ctg gcg gcg caa cgg      576
Ala Val Ser Val Asp Arg Gly Asp Trp Ser Gln Leu Ala Ala Gln Arg
            180                 185                 190
```

ctc ggg tga 585
Leu Gly

<210> SEQ ID NO 62
<211> LENGTH: 194
<212> TYPE: PRT
<213> ORGANISM: Cupriavidus necator

<400> SEQUENCE: 62

Met Leu Thr Glu Met Leu Arg Asn Arg Val Ser Thr Thr Ala Ala Val
1 5 10 15

Leu Ala Ala Phe Asp Glu Leu Asp Pro Leu Ser Ser Asp Ser Leu Val
20 25 30

Gly Cys Trp Ser Gly Phe Val Ile Ala Thr Gly His Pro Met Asp Gly
35 40 45

Leu Leu Ser Ala Val Gly Trp Tyr Gly Lys Met Phe Gln Ser Val Asp
50 55 60

Glu Ala Tyr Pro Leu Ile Ile Arg Ser Pro Asp Ala Ser Thr Leu Phe
65 70 75 80

Ser Ile Asp Pro Ser Pro Leu Pro Leu Ile Gly Cys Ala Lys Leu Ser
85 90 95

Pro Thr Asp Met Val Ser Arg Phe Ser Thr Leu Ser Pro Leu Ala Leu
100 105 110

Ser Thr Thr Val Ser His Gly Arg Leu Arg Met Val Glu Tyr Arg Gly
115 120 125

Lys Val Thr Gly Thr Leu Ile Tyr Asp Gln Gln Pro Ile Leu Asp His
130 135 140

Phe Val Met Ile Asp Ser Gln Thr Val Leu Gly Ile Met Asp Phe Lys
145 150 155 160

Glu Phe Pro Gln Pro Gly Ala Phe Val Leu Gln Arg Asp Asp Asp Ser
165 170 175

Ala Val Ser Val Asp Arg Gly Asp Trp Ser Gln Leu Ala Ala Gln Arg
180 185 190

Leu Gly

<210> SEQ ID NO 63
<211> LENGTH: 585
<212> TYPE: DNA
<213> ORGANISM: Cupriavidus necator

<400> SEQUENCE: 63
atgttgactg aaatgctgcg taaccgtgtg tctaccactg ccgctgtcct ggccgctttt 60
gacgagctgg acccgctgtc atccgacagc ctggttggct gctggagcgg tttcgttatc 120
gcgacgggtc accctatgga tggtctgctg agcgcggtgg gctggtacgg taaaatgttc 180
cagagcgttg atgaagcata cccgctgatc atccgctccc cggacgcgag cacgctgttt 240
agcattgatc cgtccccgct gccgctgatt ggttgtgcga agctgtcgcc aaccgatatg 300
gtgagccgct tcagcacctt aagcccgctg gcgctgagca ccaccgtatc tcacggtcgt 360
ctgcgtatgg ttgagtatcg tggtaaggtt accggcacgc tcatctatga ccaacagccg 420
attttggatc atttcgtcat gattgacagc caaacggtgc tgggcatcat ggatttcaaa 480
gaatttccgc agccgggtgc gtttgtcttg cagcgtgacg acgatagcgc agtcagcgtg 540
gatcgcggcg actggagcca actggcagcc caacgcctgg gctaa 585

<210> SEQ ID NO 64

<211> LENGTH: 585
<212> TYPE: DNA
<213> ORGANISM: Cupriavidus necator

<400> SEQUENCE: 64
atgttgactg aaatgttgag aaacagagtt tctactactg ctgctgtttt ggctgctttc 60
gacgaattgg acccattgtc ttctgactct ttggttggtt gttggtctgg tttcgttatc 120
gctactggtc acccaatgga cggtttgttg tctgctgttg gttggtacgg taagatgttc 180
caatctgttg acgaagctta cccattgatc atcagatctc cagacgcttc tactttgttc 240
tctatcgacc catctccatt gccattgatc ggttgtgcta agttgtctcc aactgacatg 300
gtttctagat tctctacttt gtctccattg gctttgtcta ctactgtttc tcacggtaga 360
ttgagaatgg ttgaatacag aggtaaggtt actggtactt tgatctacga ccaacaacca 420
atcttggacc acttcgttat gatcgactct caaactgttt tgggtatcat ggacttcaag 480
gaattcccac aaccaggtgc tttcgttttg caaagagacg acgactctgc tgtttctgtt 540
gacagaggtg actggtctca attggctgct caaagattgg gttaa 585

<210> SEQ ID NO 65
<211> LENGTH: 447
<212> TYPE: DNA
<213> ORGANISM: Penicillium italicum
<220> FEATURE:
<221> NAME/KEY: CDS
<222> LOCATION: (1)..(447)

<400> SEQUENCE: 65 atg aca atc caa ttc cca atc atg tca ttc gac tgt ttc cag cca agc 48
Met Thr Ile Gln Phe Pro Ile Met Ser Phe Asp Cys Phe Gln Pro Ser
1 5 10 15 cca gcc aag aaa ttc gtc tct ctc acc aaa cac cct cgg gtg act ggt 96
Pro Ala Lys Lys Phe Val Ser Leu Thr Lys His Pro Arg Val Thr Gly
20 25 30 ggg aaa atc aac acc gtc ttt cct gag ctc aag cct ctt cag cca gac 144
Gly Lys Ile Asn Thr Val Phe Pro Glu Leu Lys Pro Leu Gln Pro Asp
35 40 45 gac cta atc ggc gaa tgg gac gga tat att ctt gtc acg ggc cac ccc 192
Asp Leu Ile Gly Glu Trp Asp Gly Tyr Ile Leu Val Thr Gly His Pro
50 55 60 ttt gaa gaa gaa ctg gac acg ctg aat tgg ttc gga aat aca ttt tat 240
Phe Glu Glu Glu Leu Asp Thr Leu Asn Trp Phe Gly Asn Thr Phe Tyr
65 70 75 80 tcc acc gac gac gtg gca ccg ctg act gtt gcg cgg aac ggg gtg cgg 288
Ser Thr Asp Asp Val Ala Pro Leu Thr Val Ala Arg Asn Gly Val Arg
85 90 95 gtg ccc ttc gag gat tgg ggg cgt gca tct cta cgt gaa atc aaa tat 336
Val Pro Phe Glu Asp Trp Gly Arg Ala Ser Leu Arg Glu Ile Lys Tyr
100 105 110 caa gga gtc gtc tct gcg gct ttg gtc tat gat aaa cga cca atg atg 384
Gln Gly Val Val Ser Ala Ala Leu Val Tyr Asp Lys Arg Pro Met Met
115 120 125 gtc tat tat cga gcc gtg aaa cat aac atg gtg gct ggg ggt att gag 432
Val Tyr Tyr Arg Ala Val Lys His Asn Met Val Ala Gly Gly Ile Glu
130 135 140 agt aaa gag tgg tag 447
Ser Lys Glu Trp
145

<210> SEQ ID NO 66

<211> LENGTH: 148
<212> TYPE: PRT
<213> ORGANISM: Penicillium italicum

<400> SEQUENCE: 66

Met Thr Ile Gln Phe Pro Ile Met Ser Phe Asp Cys Phe Gln Pro Ser
1               5                   10                  15

Pro Ala Lys Lys Phe Val Ser Leu Thr Lys His Pro Arg Val Thr Gly
            20                  25                  30

Gly Lys Ile Asn Thr Val Phe Pro Glu Leu Lys Pro Leu Gln Pro Asp
        35                  40                  45

Asp Leu Ile Gly Glu Trp Asp Gly Tyr Ile Leu Val Thr Gly His Pro
    50                  55                  60

Phe Glu Glu Glu Leu Asp Thr Leu Asn Trp Phe Gly Asn Thr Phe Tyr
65                  70                  75                  80

Ser Thr Asp Asp Val Ala Pro Leu Thr Val Ala Arg Asn Gly Val Arg
                85                  90                  95

Val Pro Phe Glu Asp Trp Gly Arg Ala Ser Leu Arg Glu Ile Lys Tyr
            100                 105                 110

Gln Gly Val Val Ser Ala Ala Leu Val Tyr Asp Lys Arg Pro Met Met
        115                 120                 125

Val Tyr Tyr Arg Ala Val Lys His Asn Met Val Ala Gly Gly Ile Glu
    130                 135                 140

Ser Lys Glu Trp
145

<210> SEQ ID NO 67
<211> LENGTH: 447
<212> TYPE: DNA
<213> ORGANISM: Penicillium italicum

<400> SEQUENCE: 67
atgaccattc aatttcctat catgtctttt gattgttttc agccgagccc agcgaagaaa     60
ttcgtgagct tgacgaaaca tccgcgtgtt accggtggca agatcaatac ggttttcccg    120
gaactgaaac cgctgcaacc ggacgacctg atcggtgagt gggacggtta cattctggtg    180
acgggccacc cgttcgaaga agaactggat accttgaact ggttcggcaa tactttctat    240
agcaccgacg atgtcgctcc gctgaccgtc gcccgcaacg gtgtgcgtgt tccgtttgag    300
gattggggtc gtgcgtccct gcgtgagatc aagtaccagg gtgtggttag cgcagcgctg    360
gtctacgaca aacgcccgat gatggtgtat tatcgcgcag ttaagcacaa catggtcgcg    420
ggtggcattg agagcaaaga gtggtaa                                        447

<210> SEQ ID NO 68
<211> LENGTH: 501
<212> TYPE: DNA
<213> ORGANISM: Ralstonia insidiosa
<220> FEATURE:
<221> NAME/KEY: CDS
<222> LOCATION: (1)..(501)

<400> SEQUENCE: 68 atg aac acg aag cag aaa ttc gat caa ctc aag agc acg gaa cgc ctg      48
Met Asn Thr Lys Gln Lys Phe Asp Gln Leu Lys Ser Thr Glu Arg Leu
1               5                   10                  15 aat gac gaa atc ctg ttg gag ttc ttc gac acc ctt ccc ccc gtt tct      96
Asn Asp Glu Ile Leu Leu Glu Phe Phe Asp Thr Leu Pro Pro Val Ser
            20                  25                  30

-continued

```
acg gac gaa gcg ctg ggt cgc tgg aaa ggc ggt gac ttc aat acg ggg      144
Thr Asp Glu Ala Leu Gly Arg Trp Lys Gly Gly Asp Phe Asn Thr Gly
        35                  40                  45

cat tgg ggc aac ctc gct ctg aaa gca agg aag tgg tac gga aag tgg      192
His Trp Gly Asn Leu Ala Leu Lys Ala Arg Lys Trp Tyr Gly Lys Trp
    50                  55                  60

tat cgc agc aag ctg gat gcg gta ccg ctt atc tgt tac gac gac caa      240
Tyr Arg Ser Lys Leu Asp Ala Val Pro Leu Ile Cys Tyr Asp Asp Gln
65                  70                  75                  80

ggc cgc cta tat tcc agc aag gcc atg aag ggc gaa gcg tcg ctt tgg      288
Gly Arg Leu Tyr Ser Ser Lys Ala Met Lys Gly Glu Ala Ser Leu Trp
                85                  90                  95

gat gtg gcg ttc cgc gga aag gtc tcg acc acc atg atc tac gac ggc      336
Asp Val Ala Phe Arg Gly Lys Val Ser Thr Thr Met Ile Tyr Asp Gly
            100                 105                 110

gtg ccg atc ttc gat cat ttg cgc aag gtc gac gag aac acg ctg ttc      384
Val Pro Ile Phe Asp His Leu Arg Lys Val Asp Glu Asn Thr Leu Phe
        115                 120                 125

ggc atc atg gat ggc aaa tcg ttt gag ggg tcc ccc gac atc atc gac      432
Gly Ile Met Asp Gly Lys Ser Phe Glu Gly Ser Pro Asp Ile Ile Asp
    130                 135                 140

cgc ggc aag tac tac ttt ttc tac ctc gag agg gta gac agc ttc ccg      480
Arg Gly Lys Tyr Tyr Phe Phe Tyr Leu Glu Arg Val Asp Ser Phe Pro
145                 150                 155                 160

gcc gaa tat ctg gaa ggc tga                                          501
Ala Glu Tyr Leu Glu Gly
                165


<210> SEQ ID NO 69
<211> LENGTH: 166
<212> TYPE: PRT
<213> ORGANISM: Ralstonia insidiosa

<400> SEQUENCE: 69

Met Asn Thr Lys Gln Lys Phe Asp Gln Leu Lys Ser Thr Glu Arg Leu
1               5                   10                  15

Asn Asp Glu Ile Leu Leu Glu Phe Phe Asp Thr Leu Pro Pro Val Ser
            20                  25                  30

Thr Asp Glu Ala Leu Gly Arg Trp Lys Gly Gly Asp Phe Asn Thr Gly
        35                  40                  45

His Trp Gly Asn Leu Ala Leu Lys Ala Arg Lys Trp Tyr Gly Lys Trp
    50                  55                  60

Tyr Arg Ser Lys Leu Asp Ala Val Pro Leu Ile Cys Tyr Asp Asp Gln
65                  70                  75                  80

Gly Arg Leu Tyr Ser Ser Lys Ala Met Lys Gly Glu Ala Ser Leu Trp
                85                  90                  95

Asp Val Ala Phe Arg Gly Lys Val Ser Thr Thr Met Ile Tyr Asp Gly
            100                 105                 110

Val Pro Ile Phe Asp His Leu Arg Lys Val Asp Glu Asn Thr Leu Phe
        115                 120                 125

Gly Ile Met Asp Gly Lys Ser Phe Glu Gly Ser Pro Asp Ile Ile Asp
    130                 135                 140

Arg Gly Lys Tyr Tyr Phe Phe Tyr Leu Glu Arg Val Asp Ser Phe Pro
145                 150                 155                 160

Ala Glu Tyr Leu Glu Gly
                165


<210> SEQ ID NO 70
```

<211> LENGTH: 501
<212> TYPE: DNA
<213> ORGANISM: Ralstonia insidiosa

<400> SEQUENCE: 70

```
atgaacacca agcaaaagtt tgaccagctg aagtccaccg agcgcctgaa tgatgaaatc      60

ctgttggaat ttttcgatac cctgcctccg gtgagcaccg atgaagcgct gggccgttgg     120

aagggtggcg acttcaatac gggtcattgg ggtaacctgg ccctgaaagc gcgtaaatgg     180

tacggcaaat ggtatcgcag caaactggac gcagttccac tgatttgcta tgacgatcag     240

ggccgtctgt actctagcaa ggctatgaaa ggtgaggcga gcctgtggga tgttgcgttt     300

cgtggtaaag tgagcacgac tatgatctac gacggtgtcc cgattttcga ccacttgcgt     360

aaagtcgatg agaacacgct gtttggtatc atggatggta agtcgttcga gggtagcccg     420

gacattatcg accgtggcaa gtactatttc ttttatctgg agcgcgttga cagcttcccg     480

gcagagtacc tggaaggcta a                                               501
```

<210> SEQ ID NO 71
<211> LENGTH: 447
<212> TYPE: DNA
<213> ORGANISM: Cryptococcus gattii
<220> FEATURE:
<221> NAME/KEY: CDS
<222> LOCATION: (1)..(447)

<400> SEQUENCE: 71

```
atg tcc cct cag gaa cag tat att gct ctc gtc cag gcc ggc ggc aag       48
Met Ser Pro Gln Glu Gln Tyr Ile Ala Leu Val Gln Ala Gly Gly Lys
1               5                   10                  15

tcg gac cca tcc acc att gaa gct ctt ttc caa gcg ctt ccg ccg gtc       96
Ser Asp Pro Ser Thr Ile Glu Ala Leu Phe Gln Ala Leu Pro Pro Val
            20                  25                  30

aag ccc act cag ctg cta ggc gac tgg aat cac ggc gga ttt ttc gac      144
Lys Pro Thr Gln Leu Leu Gly Asp Trp Asn His Gly Gly Phe Phe Asp
        35                  40                  45

aca ggc cat ccg gtt aac gag caa ctc aaa gag att aaa tgg att gga      192
Thr Gly His Pro Val Asn Glu Gln Leu Lys Glu Ile Lys Trp Ile Gly
    50                  55                  60

aag tca ttt aag tcc gtc gaa gat gtt gat cct gtg att att gac cag      240
Lys Ser Phe Lys Ser Val Glu Asp Val Asp Pro Val Ile Ile Asp Gln
65                  70                  75                  80

gat ggt aag cca act agc tgg agg aag tgg ggg tca gcc agc ctg cga      288
Asp Gly Lys Pro Thr Ser Trp Arg Lys Trp Gly Ser Ala Ser Leu Arg
                85                  90                  95

gag atg gtg tat gaa ggc act gta tca acg tcg atg ata tat gat gac      336
Glu Met Val Tyr Glu Gly Thr Val Ser Thr Ser Met Ile Tyr Asp Asp
            100                 105                 110

cga cca atc atc gat cac ttc cgc tac gta gat gac gac ttt atg gcg      384
Arg Pro Ile Ile Asp His Phe Arg Tyr Val Asp Asp Asp Phe Met Ala
        115                 120                 125

ggg ata atg gaa ggg aag gct ctg ggg gag gcg ggg aag ttt tat ttc      432
Gly Ile Met Glu Gly Lys Ala Leu Gly Glu Ala Gly Lys Phe Tyr Phe
    130                 135                 140

tat ttg aga aga tag                                                  447
Tyr Leu Arg Arg
145
```

<210> SEQ ID NO 72
<211> LENGTH: 148
<212> TYPE: PRT

<213> ORGANISM: Cryptococcus gattii

<400> SEQUENCE: 72

Met Ser Pro Gln Glu Gln Tyr Ile Ala Leu Val Gln Ala Gly Gly Lys
1 5 10 15

Ser Asp Pro Ser Thr Ile Glu Ala Leu Phe Gln Ala Leu Pro Pro Val
20 25 30

Lys Pro Thr Gln Leu Leu Gly Asp Trp Asn His Gly Gly Phe Phe Asp
35 40 45

Thr Gly His Pro Val Asn Glu Gln Leu Lys Glu Ile Lys Trp Ile Gly
50 55 60

Lys Ser Phe Lys Ser Val Glu Asp Val Asp Pro Val Ile Ile Asp Gln
65 70 75 80

Asp Gly Lys Pro Thr Ser Trp Arg Lys Trp Gly Ser Ala Ser Leu Arg
85 90 95

Glu Met Val Tyr Glu Gly Thr Val Ser Thr Ser Met Ile Tyr Asp Asp
100 105 110

Arg Pro Ile Ile Asp His Phe Arg Tyr Val Asp Asp Asp Phe Met Ala
115 120 125

Gly Ile Met Glu Gly Lys Ala Leu Gly Glu Ala Gly Lys Phe Tyr Phe
130 135 140

Tyr Leu Arg Arg
145

<210> SEQ ID NO 73
<211> LENGTH: 447
<212> TYPE: DNA
<213> ORGANISM: Cryptococcus gattii

<400> SEQUENCE: 73
atgagcccac aagaacaata cattgcatta gtccaggccg gtggtaagag cgatcctagc 60
acgatcgaag cgctgtttca ggcattgccg ccggttaaac cgacccagct gctgggcgat 120
tggaatcacg gtggcttctt tgacacgggc catccggtga acgaacaact gaaagaaatc 180
aagtggattg gcaaatcctt caaatcggtc gaagatgttg atccggtgat catcgaccag 240
gacggtaagc cgactagctg gcgtaagtgg ggttctgcga gcctgcgtga gatggtttat 300
gagggcaccg tgagcaccag catgatttat gacgaccgcc cgatcattga tcactttcgt 360
tacgtcgatg acgacttcat ggctggtatt atggaaggca aggcactggg tgaggccggt 420
aaattctact tttatctgcg ccgttaa 447

<210> SEQ ID NO 74
<211> LENGTH: 459
<212> TYPE: DNA
<213> ORGANISM: Grosmannia clavigera
<220> FEATURE:
<221> NAME/KEY: CDS
<222> LOCATION: (1)..(459)

<400> SEQUENCE: 74 atg aca gct gta cag cga ttt aac gca ctc acc aaa gca gaa ggg ctt 48
Met Thr Ala Val Gln Arg Phe Asn Ala Leu Thr Lys Ala Glu Gly Leu
1 5 10 15 ctc aag gag tct gag ctt gca caa att ttc gac gag ctc cct cct gtt 96
Leu Lys Glu Ser Glu Leu Ala Gln Ile Phe Asp Glu Leu Pro Pro Val
20 25 30 tct cca gaa gct atg aca ggc aag tgg aat gga ggc agc ttt gac agt 144
Ser Pro Glu Ala Met Thr Gly Lys Trp Asn Gly Gly Ser Phe Asp Ser -continued

```
        35                  40                  45

ggc cat cct gtc cac aag ctg ctt caa act ttt aaa tgg gca ggg aaa      192
Gly His Pro Val His Lys Leu Leu Gln Thr Phe Lys Trp Ala Gly Lys
    50                  55                  60

gaa ttc cgc tcc gtt gac gat atc gac ccg att gtg atc ttc gac gaa      240
Glu Phe Arg Ser Val Asp Asp Ile Asp Pro Ile Val Ile Phe Asp Glu
65                  70                  75                  80

aat ggg gag cga aag tgg cta tcc gag tat gga cat gca aga ctg cgt      288
Asn Gly Glu Arg Lys Trp Leu Ser Glu Tyr Gly His Ala Arg Leu Arg
                85                  90                  95

gaa gtt aag ttt cgg gga gtt gta tct gcc gcc ttg gta tac gac aaa      336
Glu Val Lys Phe Arg Gly Val Val Ser Ala Ala Leu Val Tyr Asp Lys
            100                 105                 110

gtt gcc att atc gac tcg ttt cgt cgg gtt tcg gac aac gtg ctg atg      384
Val Ala Ile Ile Asp Ser Phe Arg Arg Val Ser Asp Asn Val Leu Met
        115                 120                 125

gga act atg gac gcc agg gac tgg ccg gat gct ggc atc tac tac ttt      432
Gly Thr Met Asp Ala Arg Asp Trp Pro Asp Ala Gly Ile Tyr Tyr Phe
    130                 135                 140

tac atc acc aag ttt gaa gaa ttg tga                                  459
Tyr Ile Thr Lys Phe Glu Glu Leu
145                 150


<210> SEQ ID NO 75
<211> LENGTH: 152
<212> TYPE: PRT
<213> ORGANISM: Grosmannia clavigera

<400> SEQUENCE: 75

Met Thr Ala Val Gln Arg Phe Asn Ala Leu Thr Lys Ala Glu Gly Leu
1               5                   10                  15

Leu Lys Glu Ser Glu Leu Ala Gln Ile Phe Asp Glu Leu Pro Pro Val
            20                  25                  30

Ser Pro Glu Ala Met Thr Gly Lys Trp Asn Gly Gly Ser Phe Asp Ser
        35                  40                  45

Gly His Pro Val His Lys Leu Leu Gln Thr Phe Lys Trp Ala Gly Lys
    50                  55                  60

Glu Phe Arg Ser Val Asp Asp Ile Asp Pro Ile Val Ile Phe Asp Glu
65                  70                  75                  80

Asn Gly Glu Arg Lys Trp Leu Ser Glu Tyr Gly His Ala Arg Leu Arg
                85                  90                  95

Glu Val Lys Phe Arg Gly Val Val Ser Ala Ala Leu Val Tyr Asp Lys
            100                 105                 110

Val Ala Ile Ile Asp Ser Phe Arg Arg Val Ser Asp Asn Val Leu Met
        115                 120                 125

Gly Thr Met Asp Ala Arg Asp Trp Pro Asp Ala Gly Ile Tyr Tyr Phe
    130                 135                 140

Tyr Ile Thr Lys Phe Glu Glu Leu
145                 150


<210> SEQ ID NO 76
<211> LENGTH: 459
<212> TYPE: DNA
<213> ORGANISM: Grosmannia clavigera

<400> SEQUENCE: 76

atgactgctg ttcaacgttt taacgcattg accaaagccg agggtttgct gaaagaatct      60

gagctggcac agattttcga cgaactgccg ccggttagcc cagaggccat gaccggtaag     120
```

```
tggaatggtg gcagctttga ttccggccat ccggtgcaca agctgctgca gacgttcaaa    180

tgggcgggta aagaatttcg tagcgttgac gacattgacc cgatcgtgat ctttgatgag    240

aatggcgagc gcaagtggct gagcgagtat ggtcacgcac gcctgcgtga agtgaagttc    300

cgtggtgtcg tcagcgcggc tctggtctat gacaaagtcg cgatcattga cagcttccgc    360

cgtgttagcg ataacgtgct gatgggtacg atggatgcgc gtgattggcc ggatgcgggc    420

atttactact tctacatcac caagtttgaa gaactgtaa                           459


<210> SEQ ID NO 77
<211> LENGTH: 642
<212> TYPE: DNA
<213> ORGANISM: Oidiodendron maius
<220> FEATURE:
<221> NAME/KEY: CDS
<222> LOCATION: (1)..(642)

<400> SEQUENCE: 77

atg gct tct act tta tat gaa gct aga gtt att ttg gca ctt aaa gct       48
Met Ala Ser Thr Leu Tyr Glu Ala Arg Val Ile Leu Ala Leu Lys Ala
1               5                   10                  15

att caa aac agc aac aat ctt agc tta cga gct gca gca aag ctg tat       96
Ile Gln Asn Ser Asn Asn Leu Ser Leu Arg Ala Ala Ala Lys Leu Tyr
            20                  25                  30

gat gta cag cca aca acc cta tat tac cga caa gct ggc cga cct gca      144
Asp Val Gln Pro Thr Thr Leu Tyr Tyr Arg Gln Ala Gly Arg Pro Ala
        35                  40                  45

cga cat gat att cca cct aac tct cgc aag ctt acg gat cta gaa gag      192
Arg His Asp Ile Pro Pro Asn Ser Arg Lys Leu Thr Asp Leu Glu Glu
    50                  55                  60

gag acg att gtt cgc ccg acg gaa cag ttt att gcc cta gct cag gcc      240
Glu Thr Ile Val Arg Pro Thr Glu Gln Phe Ile Ala Leu Ala Gln Ala
65                  70                  75                  80

cag ggc cgg ctt gat gcc aca ttg att gac gcg gtg ttt aac aag ttt      288
Gln Gly Arg Leu Asp Ala Thr Leu Ile Asp Ala Val Phe Asn Lys Phe
                85                  90                  95

ggc cca gtc aag cca gag ctg atg cta ggc aag tgg agt ggt ggg att      336
Gly Pro Val Lys Pro Glu Leu Met Leu Gly Lys Trp Ser Gly Gly Ile
            100                 105                 110

tta gac acc ggc cat cct atg gga gat aca ctg aag gag ata cga tgg      384
Leu Asp Thr Gly His Pro Met Gly Asp Thr Leu Lys Glu Ile Arg Trp
        115                 120                 125

gtg ggc aag aat ttc acc tcc act gaa cac gtg gac ccg gtt att atc      432
Val Gly Lys Asn Phe Thr Ser Thr Glu His Val Asp Pro Val Ile Ile
    130                 135                 140

gac aag aac ggc caa agg gcc agc tgg ggg aag tgg ggc ctt gct acc      480
Asp Lys Asn Gly Gln Arg Ala Ser Trp Gly Lys Trp Gly Leu Ala Thr
145                 150                 155                 160

cta cgt gag gtc ttg tat cga gat gtt gtc tcg acg gcg atg atc tac      528
Leu Arg Glu Val Leu Tyr Arg Asp Val Val Ser Thr Ala Met Ile Tyr
                165                 170                 175

gat gac cgc ccg gtc ttt gac tat ttc cgt ttc gct aat gat gat atg      576
Asp Asp Arg Pro Val Phe Asp Tyr Phe Arg Phe Ala Asn Asp Asp Met
            180                 185                 190

gtt gct ggt atc atg gaa ggg aag gag ttg gga ggg aga ctt ttc tat      624
Val Ala Gly Ile Met Glu Gly Lys Glu Leu Gly Gly Arg Leu Phe Tyr
        195                 200                 205

ttc tac ctg aag aga tag                                              642
Phe Tyr Leu Lys Arg
    210
```

<210> SEQ ID NO 78
<211> LENGTH: 213
<212> TYPE: PRT
<213> ORGANISM: Oidiodendron maius

<400> SEQUENCE: 78

```
Met Ala Ser Thr Leu Tyr Glu Ala Arg Val Ile Leu Ala Leu Lys Ala
1               5                   10                  15

Ile Gln Asn Ser Asn Asn Leu Ser Leu Arg Ala Ala Ala Lys Leu Tyr
            20                  25                  30

Asp Val Gln Pro Thr Thr Leu Tyr Tyr Arg Gln Ala Gly Arg Pro Ala
        35                  40                  45

Arg His Asp Ile Pro Pro Asn Ser Arg Lys Leu Thr Asp Leu Glu Glu
    50                  55                  60

Glu Thr Ile Val Arg Pro Thr Glu Gln Phe Ile Ala Leu Ala Gln Ala
65                  70                  75                  80

Gln Gly Arg Leu Asp Ala Thr Leu Ile Asp Ala Val Phe Asn Lys Phe
                85                  90                  95

Gly Pro Val Lys Pro Glu Leu Met Leu Gly Lys Trp Ser Gly Gly Ile
            100                 105                 110

Leu Asp Thr Gly His Pro Met Gly Asp Thr Leu Lys Glu Ile Arg Trp
        115                 120                 125

Val Gly Lys Asn Phe Thr Ser Thr Glu His Val Asp Pro Val Ile Ile
    130                 135                 140

Asp Lys Asn Gly Gln Arg Ala Ser Trp Gly Lys Trp Gly Leu Ala Thr
145                 150                 155                 160

Leu Arg Glu Val Leu Tyr Arg Asp Val Val Ser Thr Ala Met Ile Tyr
                165                 170                 175

Asp Asp Arg Pro Val Phe Asp Tyr Phe Arg Phe Ala Asn Asp Asp Met
            180                 185                 190

Val Ala Gly Ile Met Glu Gly Lys Glu Leu Gly Gly Arg Leu Phe Tyr
        195                 200                 205

Phe Tyr Leu Lys Arg
    210
```

<210> SEQ ID NO 79
<211> LENGTH: 642
<212> TYPE: DNA
<213> ORGANISM: Oidiodendron maius

<400> SEQUENCE: 79

```
atggcaagca ctttgtatga agctcgcgtg attctggcgc tgaaagcgat tcaaaatagc      60

aacaatctga gcttgcgtgc agccgcgaag ctctatgatg tccagccgac cacgctgtac     120

tatcgtcagg ccggtcgtcc agctcgccac gacatcccgc cgaactcccg taagctgacc     180

gatctggaag aggaaacgat cgttcgcccg accgagcaat tcatcgcgtt agcacaagca     240

cagggccgtc tggatgcgac cctgattgat gcagttttca ataagtttgg tccggtgaag     300

cctgagctga tgctgggtaa gtggagcggt ggcattctgg acacgggtca cccgatgggc     360

gataccctga aagaaatccg ttgggtgggt aaaaatttca ccagcaccga acatgttgat     420

ccggtcatca ttgacaaaaa cggtcagcgc gcttcttggg gcaagtgggg tctggccacc     480

ttgcgtgaag ttctgtaccg cgacgtcgtc agcacggcga tgatttacga tgaccgtccg     540

gtgtttgact attttcgttt cgcgaacgac gacatggttg cgggtatcat ggaaggcaaa     600
```

-continued

```
gaactgggtg gccgtctgtt ttacttctac ctgaaacgct aa                   642


<210> SEQ ID NO 80
<211> LENGTH: 447
<212> TYPE: DNA
<213> ORGANISM: Thermomonospora curvata
<220> FEATURE:
<221> NAME/KEY: CDS
<222> LOCATION: (1)..(447)

<400> SEQUENCE: 80

atg gat gcg gaa cag cgc ctt gcc aag atc atc gcg tcc ggc gac gag       48
Met Asp Ala Glu Gln Arg Leu Ala Lys Ile Ile Ala Ser Gly Asp Glu
1               5                   10                  15

tgc gac cgg gcc acc gtg gag gaa ctg tac gac cgg ctg gcc ccc gtg       96
Cys Asp Arg Ala Thr Val Glu Glu Leu Tyr Asp Arg Leu Ala Pro Val
            20                  25                  30

ccg gtg gac ttc atg ctc ggc acc tgg cgg ggc ggc atc ttc gac cgg      144
Pro Val Asp Phe Met Leu Gly Thr Trp Arg Gly Gly Ile Phe Asp Arg
        35                  40                  45

ggc gac gcg ctg gcg ggg atg ctg ctg ggg atg aac tgg tac ggc aag      192
Gly Asp Ala Leu Ala Gly Met Leu Leu Gly Met Asn Trp Tyr Gly Lys
    50                  55                  60

cgg ttc atc gac cgc gac cac gtc gag ccg ctg ctg tgc cgc tcc ccc      240
Arg Phe Ile Asp Arg Asp His Val Glu Pro Leu Leu Cys Arg Ser Pro
65                  70                  75                  80

gac ggc tcg atc tac tcc tac gag aag ctc ggg ctg gcc cgg ctg cgc      288
Asp Gly Ser Ile Tyr Ser Tyr Glu Lys Leu Gly Leu Ala Arg Leu Arg
                85                  90                  95

gag gtc gcc ctg cgc ggc acg gtc tcg gcg gcc atg atc tac gac aag      336
Glu Val Ala Leu Arg Gly Thr Val Ser Ala Ala Met Ile Tyr Asp Lys
            100                 105                 110

cag ccc atc atc gac cac ttc cgg cgg gtc aac gac gac atg gtg gtc      384
Gln Pro Ile Ile Asp His Phe Arg Arg Val Asn Asp Asp Met Val Val
        115                 120                 125

ggc gcc atg gac gcc aag ggc cag ccc gac atc ctc tac ttc cac ctc      432
Gly Ala Met Asp Ala Lys Gly Gln Pro Asp Ile Leu Tyr Phe His Leu
    130                 135                 140

acc cgg gaa cgc tga                                                  447
Thr Arg Glu Arg
145


<210> SEQ ID NO 81
<211> LENGTH: 148
<212> TYPE: PRT
<213> ORGANISM: Thermomonospora curvata

<400> SEQUENCE: 81

Met Asp Ala Glu Gln Arg Leu Ala Lys Ile Ile Ala Ser Gly Asp Glu
1               5                   10                  15

Cys Asp Arg Ala Thr Val Glu Glu Leu Tyr Asp Arg Leu Ala Pro Val
            20                  25                  30

Pro Val Asp Phe Met Leu Gly Thr Trp Arg Gly Gly Ile Phe Asp Arg
        35                  40                  45

Gly Asp Ala Leu Ala Gly Met Leu Leu Gly Met Asn Trp Tyr Gly Lys
    50                  55                  60

Arg Phe Ile Asp Arg Asp His Val Glu Pro Leu Leu Cys Arg Ser Pro
65                  70                  75                  80

Asp Gly Ser Ile Tyr Ser Tyr Glu Lys Leu Gly Leu Ala Arg Leu Arg
                85                  90                  95
```

```
Glu Val Ala Leu Arg Gly Thr Val Ser Ala Ala Met Ile Tyr Asp Lys
            100                 105                 110

Gln Pro Ile Ile Asp His Phe Arg Arg Val Asn Asp Asp Met Val Val
        115                 120                 125

Gly Ala Met Asp Ala Lys Gly Gln Pro Asp Ile Leu Tyr Phe His Leu
    130                 135                 140

Thr Arg Glu Arg
145


<210> SEQ ID NO 82
<211> LENGTH: 447
<212> TYPE: DNA
<213> ORGANISM: Thermomonospora curvata

<400> SEQUENCE: 82

atggatgcgg aacaaagact ggctaaaatt attgcatctg gtgatgagtg tgatcgtgca      60

accgtggaag aactgtatga ccgtttggcc cctgtcccgg ttgacttcat gctgggtacg     120

tggcgtggtg gcatcttcga tcgtggtgat gcgctggcgg gtatgctgct gggtatgaat     180

tggtatggca agcgctttat cgaccgcgac cacgtcgagc cactgctgtg ccgtagcccg     240

gatggctcca tctacagcta cgagaaactg ggtctggccc gtttgcgcga agtggcactg     300

cgtggcaccg ttagcgcggc tatgatttat gacaaacagc cgattatcga ccatttccgt     360

cgcgtgaacg acgacatggt tgtcggcgcg atggatgcga agggtcagcc ggacatcctg     420

tactttcacc tgacccgcga gcgttaa                                         447


<210> SEQ ID NO 83
<211> LENGTH: 492
<212> TYPE: DNA
<213> ORGANISM: Pseudomonas litoralis
<220> FEATURE:
<221> NAME/KEY: CDS
<222> LOCATION: (1)..(492)

<400> SEQUENCE: 83

atg act gca aca ctg gcc gcc ctc agc ctg acc acc ctg ctt gcc ggg       48
Met Thr Ala Thr Leu Ala Ala Leu Ser Leu Thr Thr Leu Leu Ala Gly
1               5                   10                  15

ccc agt ctg gcc gca gat acg gaa cag caa tgg ctg gag atg atc gcc       96
Pro Ser Leu Ala Ala Asp Thr Glu Gln Gln Trp Leu Glu Met Ile Ala
            20                  25                  30

agc ggt gaa gcc tat tcg gcg gac acc ctg gtg cct ctg ttc aaa caa      144
Ser Gly Glu Ala Tyr Ser Ala Asp Thr Leu Val Pro Leu Phe Lys Gln
        35                  40                  45

ctc gaa ccg gtg gat acc gac ttc atg gtc ggc aca tgg aag ggc ggc      192
Leu Glu Pro Val Asp Thr Asp Phe Met Val Gly Thr Trp Lys Gly Gly
    50                  55                  60

aag ttc gac ggc ggc gcc gag ccg gac ccg atc aac tgg tac ggc aaa      240
Lys Phe Asp Gly Gly Ala Glu Pro Asp Pro Ile Asn Trp Tyr Gly Lys
65                  70                  75                  80

cgt ttc acc tcg acc acc gat gtc gag ccg tta ttg gta aac gat gcc      288
Arg Phe Thr Ser Thr Thr Asp Val Glu Pro Leu Leu Val Asn Asp Ala
                85                  90                  95

gag ggc gag gtg atc acc cac gac cgg ctc ggc gcc gca cag atg cgc      336
Glu Gly Glu Val Ile Thr His Asp Arg Leu Gly Ala Ala Gln Met Arg
            100                 105                 110

cag gtg gtg ttc gat ggg aag gta tcg gcc gcg ttg atc tac gac agc      384
Gln Val Val Phe Asp Gly Lys Val Ser Ala Ala Leu Ile Tyr Asp Ser
        115                 120                 125
```

-continued

```
cag ccg atc atg gat tac ctc cgc aag gtc aac gag gat gtg gtc atc      432
Gln Pro Ile Met Asp Tyr Leu Arg Lys Val Asn Glu Asp Val Val Ile
    130                 135                 140

ggc ctg ggc gac atc aag ggc aag cct acc gat ttc ttt ttc tat ctg      480
Gly Leu Gly Asp Ile Lys Gly Lys Pro Thr Asp Phe Phe Phe Tyr Leu
145                 150                 155                 160

gta cgc gat taa                                                      492
Val Arg Asp


<210> SEQ ID NO 84
<211> LENGTH: 163
<212> TYPE: PRT
<213> ORGANISM: Pseudomonas litoralis

<400> SEQUENCE: 84

Met Thr Ala Thr Leu Ala Ala Leu Ser Leu Thr Thr Leu Leu Ala Gly
1               5                   10                  15

Pro Ser Leu Ala Ala Asp Thr Glu Gln Gln Trp Leu Glu Met Ile Ala
            20                  25                  30

Ser Gly Glu Ala Tyr Ser Ala Asp Thr Leu Val Pro Leu Phe Lys Gln
        35                  40                  45

Leu Glu Pro Val Asp Thr Asp Phe Met Val Gly Thr Trp Lys Gly Gly
    50                  55                  60

Lys Phe Asp Gly Gly Ala Glu Pro Asp Pro Ile Asn Trp Tyr Gly Lys
65                  70                  75                  80

Arg Phe Thr Ser Thr Thr Asp Val Glu Pro Leu Leu Val Asn Asp Ala
                85                  90                  95

Glu Gly Glu Val Ile Thr His Asp Arg Leu Gly Ala Ala Gln Met Arg
            100                 105                 110

Gln Val Val Phe Asp Gly Lys Val Ser Ala Ala Leu Ile Tyr Asp Ser
        115                 120                 125

Gln Pro Ile Met Asp Tyr Leu Arg Lys Val Asn Glu Asp Val Val Ile
    130                 135                 140

Gly Leu Gly Asp Ile Lys Gly Lys Pro Thr Asp Phe Phe Phe Tyr Leu
145                 150                 155                 160

Val Arg Asp


<210> SEQ ID NO 85
<211> LENGTH: 492
<212> TYPE: DNA
<213> ORGANISM: Pseudomonas litoralis

<400> SEQUENCE: 85

atgactgcga ctttggctgc tctgagcttg acgaccctgt tggctggccc atctttggct     60

gcggacaccg agcagcaatg gctggaaatg attgcaagcg gcgaggcgta tagcgcggac    120

accctggtgc cgctgttcaa gcaactggag cctgtcgata cggacttcat ggtcggcacg    180

tggaagggcg gcaaatttga tggtggtgcc gaaccggacc cgattaactg gtacggtaag    240

cgttttacca gcacgaccga tgtggagccg ctgctggtga atgacgccga gggtgaagtt    300

atcacccacg atcgtctggg tgcggcacag atgcgccaag ttgtttttga tggcaaagtc    360

tccgcagcgc tgatctacga cagccagccg attatggact atctgcgcaa agtgaacgaa    420

gatgttgtca tcggtctggg tgacatcaag ggtaaaccga ccgacttttt cttctacctg    480

gttcgtgatt aa                                                        492


<210> SEQ ID NO 86
```

<211> LENGTH: 498
<212> TYPE: DNA
<213> ORGANISM: Pseudomonas protegens
<220> FEATURE:
<221> NAME/KEY: CDS
<222> LOCATION: (1)..(498)

<400> SEQUENCE: 86

```
atg aat acg aaa gaa aag ttt gaa cag ctt aag agc acg caa ggt ctt       48
Met Asn Thr Lys Glu Lys Phe Glu Gln Leu Lys Ser Thr Gln Gly Leu
1               5                   10                  15

aat gat gaa gta ctg ttg gac ttc ttt gac tcg ctt tct cca gtc aca       96
Asn Asp Glu Val Leu Leu Asp Phe Phe Asp Ser Leu Ser Pro Val Thr
            20                  25                  30

atc gat ggc gcg ttg ggc cgt tgg caa ggt ggt gac ttc aag aca gga      144
Ile Asp Gly Ala Leu Gly Arg Trp Gln Gly Gly Asp Phe Lys Thr Gly
        35                  40                  45

cac tgg ggc aat gac gca ctt acc gga atg aag tgg tac gga aag tgg      192
His Trp Gly Asn Asp Ala Leu Thr Gly Met Lys Trp Tyr Gly Lys Trp
    50                  55                  60

tac cgg agc aag ttg gat gcc gtt ccc cta gtc tgc tac gac gaa cag      240
Tyr Arg Ser Lys Leu Asp Ala Val Pro Leu Val Cys Tyr Asp Glu Gln
65                  70                  75                  80

ggc cga cta ttt tcc aac aag atc atg aaa ggt gag gcc tct ctc tgg      288
Gly Arg Leu Phe Ser Asn Lys Ile Met Lys Gly Glu Ala Ser Leu Trp
                85                  90                  95

gag gtg gcg ttt cgt ggc aag gtt tcg act acg atg atc tac gat ggc      336
Glu Val Ala Phe Arg Gly Lys Val Ser Thr Thr Met Ile Tyr Asp Gly
            100                 105                 110

gtt ccg att tat gat cac ttg cgc aag gtc gat gac aac acc ctt ttc      384
Val Pro Ile Tyr Asp His Leu Arg Lys Val Asp Asp Asn Thr Leu Phe
        115                 120                 125

ggg atc atg gat ggt aag tcc ttt gag ggg cag ctc ccc gac atc atc      432
Gly Ile Met Asp Gly Lys Ser Phe Glu Gly Gln Leu Pro Asp Ile Ile
    130                 135                 140

gac aat ggc aag tac tac ttc ttc tac ctc gaa agg gtc gat ggc ttc      480
Asp Asn Gly Lys Tyr Tyr Phe Phe Tyr Leu Glu Arg Val Asp Gly Phe
145                 150                 155                 160

cct gtc gag ttc gtc tag                                              498
Pro Val Glu Phe Val
                165
```

<210> SEQ ID NO 87
<211> LENGTH: 165
<212> TYPE: PRT
<213> ORGANISM: Pseudomonas protegens

<400> SEQUENCE: 87

```
Met Asn Thr Lys Glu Lys Phe Glu Gln Leu Lys Ser Thr Gln Gly Leu
1               5                   10                  15

Asn Asp Glu Val Leu Leu Asp Phe Phe Asp Ser Leu Ser Pro Val Thr
            20                  25                  30

Ile Asp Gly Ala Leu Gly Arg Trp Gln Gly Gly Asp Phe Lys Thr Gly
        35                  40                  45

His Trp Gly Asn Asp Ala Leu Thr Gly Met Lys Trp Tyr Gly Lys Trp
    50                  55                  60

Tyr Arg Ser Lys Leu Asp Ala Val Pro Leu Val Cys Tyr Asp Glu Gln
65                  70                  75                  80

Gly Arg Leu Phe Ser Asn Lys Ile Met Lys Gly Glu Ala Ser Leu Trp
                85                  90                  95
```

```
Glu Val Ala Phe Arg Gly Lys Val Ser Thr Thr Met Ile Tyr Asp Gly
            100                 105                 110

Val Pro Ile Tyr Asp His Leu Arg Lys Val Asp Asp Asn Thr Leu Phe
        115                 120                 125

Gly Ile Met Asp Gly Lys Ser Phe Glu Gly Gln Leu Pro Asp Ile Ile
    130                 135                 140

Asp Asn Gly Lys Tyr Tyr Phe Phe Tyr Leu Glu Arg Val Asp Gly Phe
145                 150                 155                 160

Pro Val Glu Phe Val
                165
```

<210> SEQ ID NO 88
<211> LENGTH: 498
<212> TYPE: DNA
<213> ORGANISM: Pseudomonas protegens

<400> SEQUENCE: 88

```
atgaacacga aagaaaagtt tgaacagttg aaaagcaccc aaggtctgaa cgatgaagtt      60

ttgctggatt tcttcgatag cctgagccca gtgaccattg acggtgcact gggccgttgg     120

cagggtggcg acttcaagac cggtcactgg ggcaacgacg cgctgactgg catgaaatgg     180

tacggtaaat ggtatcgcag caaactggat gctgtgccgc tggtgtgcta cgacgaacag     240

ggtcgtctgt tttccaataa gatcatgaaa ggtgaggcca gcctgtggga agtcgcgttc     300

cgcggtaagg ttagcacgac gatgatttat gatggtgtgc cgatctatga ccatctgcgt     360

aaagttgatg acaataccct gtttggcatc atggatggca agtcttttga gggtcaactg     420

ccggacatca ttgacaatgg caagtactac ttcttctacc tggagcgtgt tgacggtttt     480

ccggtcgagt tcgtctaa                                                   498
```

<210> SEQ ID NO 89
<211> LENGTH: 157
<212> TYPE: PRT
<213> ORGANISM: Artificial Sequence
<220> FEATURE:
<223> OTHER INFORMATION: variant

<400> SEQUENCE: 89

```
Met Asn Leu Asn Glu Ala Arg Thr Ala Phe Ala Arg Leu Arg Ala Ala
1               5                   10                  15

Glu Asn Gly Leu Ser Pro Ala Glu Leu Asp Glu Val Trp Ala Ala Leu
            20                  25                  30

Glu Thr Val Ala Ala Glu Glu Ile Leu Gly Glu Ala Lys Gly Asp Asp
        35                  40                  45

Phe Ala Thr Gly His Arg Leu His Glu Lys Leu Ser Ala Ser Arg Trp
    50                  55                  60

Tyr Gly Lys Thr Phe Asn Ser Val Glu Asp Ala Lys Pro Leu Ile Cys
65                  70                  75                  80

Arg Asp Glu Asp Gly Asn Leu Tyr Ser Asp Val Lys Ser Gly Asn Gly
                85                  90                  95

Glu Ala Ser Leu Trp Asn Ile Glu Phe Arg Gly Glu Val Thr Ala Thr
            100                 105                 110

Met Val Tyr Asp Gly Ala Pro Ile Phe Asp His Phe Lys Lys Val Asp
        115                 120                 125

Asp Ser Thr Leu Met Gly Ile Met Asn Gly Lys Ser Ala Leu Val Leu
    130                 135                 140

Asp Gly Gly Gln His Tyr Tyr Phe Leu Leu Glu Arg Ala
```

145 150 155

<210> SEQ ID NO 90
<211> LENGTH: 474
<212> TYPE: DNA
<213> ORGANISM: Artificial Sequence
<220> FEATURE:
<223> OTHER INFORMATION: E. coli optimized

<400> SEQUENCE: 90
atgaacttaa atgaagcgcg taccgcattt gcacgtctga gagctgccga gaacggtctg 60
agcccggctg agctggatga agtgtgggca gcgctggaga ctgtggcggc tgaagaaatc 120
ctgggtgagg caaagggtga cgattttgcg acgggtcacc gtctgcacga gaaactgtcg 180
gcgagccgct ggtatggtaa gaccttcaac tctgttgaag atgcaaagcc gctgatttgc 240
cgtgacgaag atggcaatct gtactccgat gtcaagagcg gtaacggtga ggccagcctg 300
tggaatatcg agtttcgcgg cgaagtcacc gcgacgatgg tttacgatgg tgccccgatc 360
ttcgaccatt tcaaaaaagt tgacgacagc accctgatgg gcattatgaa tggcaaaagc 420
gcgttggtgt tggacggtgg ccagcattac tatttcctgc tggagcgtgc gtaa 474

<210> SEQ ID NO 91
<211> LENGTH: 157
<212> TYPE: PRT
<213> ORGANISM: Artificial Sequence
<220> FEATURE:
<223> OTHER INFORMATION: variant

<400> SEQUENCE: 91

Met Asn Leu Asn Glu Ala Arg Thr Ala Phe Ala Arg Leu Arg Ala Ala
1 5 10 15

Glu Asn Gly Leu Ser Pro Ala Glu Leu Asp Glu Val Trp Ala Ala Leu
20 25 30

Glu Thr Val Ala Ala Glu Glu Ile Leu Gly Glu Trp Lys Gly Asp Asp
35 40 45

Phe Ala Ala Gly His Arg Leu His Glu Lys Leu Ser Ala Ser Arg Trp
50 55 60

Tyr Gly Lys Thr Phe Asn Ser Val Glu Asp Ala Lys Pro Leu Ile Cys
65 70 75 80

Arg Asp Glu Asp Gly Asn Leu Tyr Ser Asp Val Lys Ser Gly Asn Gly
85 90 95

Glu Ala Ser Leu Trp Asn Ile Glu Phe Arg Gly Glu Val Thr Ala Thr
100 105 110

Met Val Tyr Asp Gly Ala Pro Ile Phe Asp His Phe Lys Lys Val Asp
115 120 125

Asp Ser Thr Leu Met Gly Ile Met Asn Gly Lys Ser Ala Leu Val Leu
130 135 140

Asp Gly Gly Gln His Tyr Tyr Phe Leu Leu Glu Arg Ala
145 150 155

<210> SEQ ID NO 92
<211> LENGTH: 474
<212> TYPE: DNA
<213> ORGANISM: Artificial Sequence
<220> FEATURE:
<223> OTHER INFORMATION: E. coli optimized

<400> SEQUENCE: 92
atgaacttaa atgaagcgcg taccgcattt gcacgtctga gagctgccga gaacggtctg 60
agcccggctg agctggatga agtgtgggca gcgctggaga ctgtggcggc tgaagaaatc 120
ctgggtgagt ggaagggtga cgattttgcg gccggtcacc gtctgcacga gaaactgtcg 180
gcgagccgct ggtatggtaa gaccttcaac tctgttgaag atgcaaagcc gctgatttgc 240
cgtgacgaag atggcaatct gtactccgat gtcaagagcg gtaacggtga ggccagcctg 300
tggaatatcg agtttcgcgg cgaagtcacc gcgacgatgg tttacgatgg tgccccgatc 360
ttcgaccatt tcaaaaaagt tgacgacagc accctgatgg gcattatgaa tggcaaaagc 420
gcgttggtgt tggacggtgg ccagcattac tatttcctgc tggagcgtgc gtaa 474

<210> SEQ ID NO 93
<211> LENGTH: 157
<212> TYPE: PRT
<213> ORGANISM: Artificial Sequence
<220> FEATURE:
<223> OTHER INFORMATION: variant

<400> SEQUENCE: 93

Met Asn Leu Asn Glu Ala Arg Thr Ala Phe Ala Arg Leu Arg Ala Ala
1 5 10 15

Glu Asn Gly Leu Ser Pro Ala Glu Leu Asp Glu Val Trp Ala Ala Leu
20 25 30

Glu Thr Val Ala Ala Glu Glu Ile Leu Gly Glu Trp Lys Gly Asp Asp
35 40 45

Phe Ala Thr Gly Ala Arg Leu His Glu Lys Leu Ser Ala Ser Arg Trp
50 55 60

Tyr Gly Lys Thr Phe Asn Ser Val Glu Asp Ala Lys Pro Leu Ile Cys
65 70 75 80

Arg Asp Glu Asp Gly Asn Leu Tyr Ser Asp Val Lys Ser Gly Asn Gly
85 90 95

Glu Ala Ser Leu Trp Asn Ile Glu Phe Arg Gly Glu Val Thr Ala Thr
100 105 110

Met Val Tyr Asp Gly Ala Pro Ile Phe Asp His Phe Lys Lys Val Asp
115 120 125

Asp Ser Thr Leu Met Gly Ile Met Asn Gly Lys Ser Ala Leu Val Leu
130 135 140

Asp Gly Gly Gln His Tyr Tyr Phe Leu Leu Glu Arg Ala
145 150 155

<210> SEQ ID NO 94
<211> LENGTH: 474
<212> TYPE: DNA
<213> ORGANISM: Artificial Sequence
<220> FEATURE:
<223> OTHER INFORMATION: E. coli optimized

<400> SEQUENCE: 94
atgaacttaa atgaagcgcg taccgcattt gcacgtctga gagctgccga gaacggtctg 60
agcccggctg agctggatga agtgtgggca gcgctggaga ctgtggcggc tgaagaaatc 120
ctgggtgagt ggaagggtga cgattttgcg acgggtgcac gtctgcacga gaaactgtcg 180
gcgagccgct ggtatggtaa gaccttcaac tctgttgaag atgcaaagcc gctgatttgc 240
cgtgacgaag atggcaatct gtactccgat gtcaagagcg gtaacggtga ggccagcctg 300
tggaatatcg agtttcgcgg cgaagtcacc gcgacgatgg tttacgatgg tgccccgatc 360
ttcgaccatt tcaaaaaagt tgacgacagc accctgatgg gcattatgaa tggcaaaagc 420

-continued gcgttggtgt tggacggtgg ccagcattac tatttcctgc tggagcgtgc gtaa 474

<210> SEQ ID NO 95
<211> LENGTH: 157
<212> TYPE: PRT
<213> ORGANISM: Artificial Sequence
<220> FEATURE:
<223> OTHER INFORMATION: variant

<400> SEQUENCE: 95

Met Asn Leu Asn Glu Ala Arg Thr Ala Phe Ala Arg Leu Arg Ala Ala
1               5                   10                  15

Glu Asn Gly Leu Ser Pro Ala Glu Leu Asp Glu Val Trp Ala Ala Leu
            20                  25                  30

Glu Thr Val Ala Ala Glu Glu Ile Leu Gly Glu Trp Lys Gly Asp Asp
        35                  40                  45

Phe Ala Thr Gly His Arg Leu His Glu Lys Ala Ser Ala Ser Arg Trp
    50                  55                  60

Tyr Gly Lys Thr Phe Asn Ser Val Glu Asp Ala Lys Pro Leu Ile Cys
65                  70                  75                  80

Arg Asp Glu Asp Gly Asn Leu Tyr Ser Asp Val Lys Ser Gly Asn Gly
                85                  90                  95

Glu Ala Ser Leu Trp Asn Ile Glu Phe Arg Gly Glu Val Thr Ala Thr
            100                 105                 110

Met Val Tyr Asp Gly Ala Pro Ile Phe Asp His Phe Lys Lys Val Asp
        115                 120                 125

Asp Ser Thr Leu Met Gly Ile Met Asn Gly Lys Ser Ala Leu Val Leu
    130                 135                 140

Asp Gly Gly Gln His Tyr Tyr Phe Leu Leu Glu Arg Ala
145                 150                 155

<210> SEQ ID NO 96
<211> LENGTH: 474
<212> TYPE: DNA
<213> ORGANISM: Artificial Sequence
<220> FEATURE:
<223> OTHER INFORMATION: E. coli optimized

<400> SEQUENCE: 96
atgaacttaa atgaagcgcg taccgcattt gcacgtctga gagctgccga gaacggtctg 60
agcccggctg agctggatga agtgtgggca gcgctggaga ctgtggcggc tgaagaaatc 120
ctgggtgagt ggaagggtga cgattttgcg acgggtcacc gtctgcacga gaaagcatcg 180
gcgagccgct ggtatggtaa gaccttcaac tctgttgaag atgcaaagcc gctgatttgc 240
cgtgacgaag atggcaatct gtactccgat gtcaagagcg gtaacggtga ggccagcctg 300
tggaatatcg agtttcgcgg cgaagtcacc gcgacgatgg tttacgatgg tgccccgatc 360
ttcgaccatt tcaaaaaagt tgacgacagc accctgatgg gcattatgaa tggcaaaagc 420
gcgttggtgt tggacggtgg ccagcattac tatttcctgc tggagcgtgc gtaa 474

<210> SEQ ID NO 97
<211> LENGTH: 157
<212> TYPE: PRT
<213> ORGANISM: Artificial Sequence
<220> FEATURE:
<223> OTHER INFORMATION: variant

<400> SEQUENCE: 97

Met Asn Leu Asn Glu Ala Arg Thr Ala Phe Ala Arg Leu Arg Ala Ala

```
1               5                   10                  15

Glu Asn Gly Leu Ser Pro Ala Glu Leu Asp Glu Val Trp Ala Ala Leu
            20                  25                  30

Glu Thr Val Ala Ala Glu Glu Ile Leu Gly Glu Trp Lys Gly Asp Asp
        35                  40                  45

Phe Ala Thr Gly His Arg Leu His Glu Lys Leu Ser Ala Ser Arg Ala
    50                  55                  60

Tyr Gly Lys Thr Phe Asn Ser Val Glu Asp Ala Lys Pro Leu Ile Cys
65                  70                  75                  80

Arg Asp Glu Asp Gly Asn Leu Tyr Ser Asp Val Lys Ser Gly Asn Gly
                85                  90                  95

Glu Ala Ser Leu Trp Asn Ile Glu Phe Arg Gly Glu Val Thr Ala Thr
            100                 105                 110

Met Val Tyr Asp Gly Ala Pro Ile Phe Asp His Phe Lys Lys Val Asp
        115                 120                 125

Asp Ser Thr Leu Met Gly Ile Met Asn Gly Lys Ser Ala Leu Val Leu
    130                 135                 140

Asp Gly Gly Gln His Tyr Tyr Phe Leu Leu Glu Arg Ala
145                 150                 155


<210> SEQ ID NO 98
<211> LENGTH: 474
<212> TYPE: DNA
<213> ORGANISM: Artificial Sequence
<220> FEATURE:
<223> OTHER INFORMATION: E. coli optimized

<400> SEQUENCE: 98

atgaacttaa atgaagcgcg taccgcattt gcacgtctga gagctgccga gaacggtctg      60

agcccggctg agctggatga agtgtgggca gcgctggaga ctgtggcggc tgaagaaatc     120

ctgggtgagt ggaagggtga cgattttgcg acgggtcacc gtctgcacga gaaactgtcg     180

gcgagccgcg cctatggtaa gaccttcaac tctgttgaag atgcaaagcc gctgatttgc     240

cgtgacgaag atggcaatct gtactccgat gtcaagagcg gtaacggtga ggccagcctg     300

tggaatatcg agtttcgcgg cgaagtcacc gcgacgatgg tttacgatgg tgccccgatc     360

ttcgaccatt tcaaaaaagt tgacgacagc accctgatgg gcattatgaa tggcaaaagc     420

gcgttggtgt tggacggtgg ccagcattac tatttcctgc tggagcgtgc gtaa           474


<210> SEQ ID NO 99
<211> LENGTH: 157
<212> TYPE: PRT
<213> ORGANISM: Artificial Sequence
<220> FEATURE:
<223> OTHER INFORMATION: variant

<400> SEQUENCE: 99

Met Asn Leu Asn Glu Ala Arg Thr Ala Phe Ala Arg Leu Arg Ala Ala
1               5                   10                  15

Glu Asn Gly Leu Ser Pro Ala Glu Leu Asp Glu Val Trp Ala Ala Leu
            20                  25                  30

Glu Thr Val Ala Ala Glu Glu Ile Leu Gly Glu Trp Lys Gly Asp Asp
        35                  40                  45

Phe Ala Thr Gly His Arg Leu His Glu Lys Leu Ser Ala Ser Arg Trp
    50                  55                  60

Tyr Gly Ala Thr Phe Asn Ser Val Glu Asp Ala Lys Pro Leu Ile Cys
65                  70                  75                  80
```

-continued

Arg Asp Glu Asp Gly Asn Leu Tyr Ser Asp Val Lys Ser Gly Asn Gly
85 90 95

Glu Ala Ser Leu Trp Asn Ile Glu Phe Arg Gly Glu Val Thr Ala Thr
100 105 110

Met Val Tyr Asp Gly Ala Pro Ile Phe Asp His Phe Lys Lys Val Asp
115 120 125

Asp Ser Thr Leu Met Gly Ile Met Asn Gly Lys Ser Ala Leu Val Leu
130 135 140

Asp Gly Gly Gln His Tyr Tyr Phe Leu Leu Glu Arg Ala
145 150 155

<210> SEQ ID NO 100
<211> LENGTH: 474
<212> TYPE: DNA
<213> ORGANISM: Artificial Sequence
<220> FEATURE:
<223> OTHER INFORMATION: E. coli optimized

<400> SEQUENCE: 100
atgaacttaa atgaagcgcg taccgcattt gcacgtctga gagctgccga gaacggtctg 60
agcccggctg agctggatga agtgtgggca gcgctggaga ctgtggcggc tgaagaaatc 120
ctgggtgagt ggaagggtga cgattttgcg acgggtcacc gtctgcacga gaaactgtcg 180
gcgagccgct ggtatggtgc aaccttcaac tctgttgaag atgcaaagcc gctgatttgc 240
cgtgacgaag atggcaatct gtactccgat gtcaagagcg gtaacggtga ggccagcctg 300
tggaatatcg agtttcgcgg cgaagtcacc gcgacgatgg tttacgatgg tgccccgatc 360
ttcgaccatt tcaaaaaagt tgacgacagc accctgatgg gcattatgaa tggcaaaagc 420
gcgttggtgt tggacggtgg ccagcattac tatttcctgc tggagcgtgc gtaa 474

<210> SEQ ID NO 101
<211> LENGTH: 157
<212> TYPE: PRT
<213> ORGANISM: Artificial Sequence
<220> FEATURE:
<223> OTHER INFORMATION: variant

<400> SEQUENCE: 101

Met Asn Leu Asn Glu Ala Arg Thr Ala Phe Ala Arg Leu Arg Ala Ala
1 5 10 15

Glu Asn Gly Leu Ser Pro Ala Glu Leu Asp Glu Val Trp Ala Ala Leu
20 25 30

Glu Thr Val Ala Ala Glu Glu Ile Leu Gly Glu Trp Lys Gly Asp Asp
35 40 45

Phe Ala Thr Gly His Arg Leu His Glu Lys Leu Ser Ala Ser Arg Trp
50 55 60

Tyr Gly Lys Thr Phe Asn Ala Val Glu Asp Ala Lys Pro Leu Ile Cys
65 70 75 80

Arg Asp Glu Asp Gly Asn Leu Tyr Ser Asp Val Lys Ser Gly Asn Gly
85 90 95

Glu Ala Ser Leu Trp Asn Ile Glu Phe Arg Gly Glu Val Thr Ala Thr
100 105 110

Met Val Tyr Asp Gly Ala Pro Ile Phe Asp His Phe Lys Lys Val Asp
115 120 125

Asp Ser Thr Leu Met Gly Ile Met Asn Gly Lys Ser Ala Leu Val Leu
130 135 140

```
Asp Gly Gly Gln His Tyr Tyr Phe Leu Leu Glu Arg Ala
145                 150                 155


<210> SEQ ID NO 102
<211> LENGTH: 474
<212> TYPE: DNA
<213> ORGANISM: Artificial Sequence
<220> FEATURE:
<223> OTHER INFORMATION: E. Coli optimized

<400> SEQUENCE: 102

atgaacttaa atgaagcgcg taccgcattt gcacgtctga gagctgccga gaacggtctg     60

agcccggctg agctggatga agtgtgggca gcgctggaga ctgtggcggc tgaagaaatc    120

ctgggtgagt ggaagggtga cgattttgcg acgggtcacc gtctgcacga gaaactgtcg    180

gcgagccgct ggtatggtaa gaccttcaac gcagttgaag atgcaaagcc gctgatttgc    240

cgtgacgaag atggcaatct gtactccgat gtcaagagcg gtaacggtga ggccagcctg    300

tggaatatcg agtttcgcgg cgaagtcacc gcgacgatgg tttacgatgg tgccccgatc    360

ttcgaccatt tcaaaaaagt tgacgacagc accctgatgg gcattatgaa tggcaaaagc    420

gcgttggtgt tggacggtgg ccagcattac tatttcctgc tggagcgtgc gtaa          474


<210> SEQ ID NO 103
<211> LENGTH: 157
<212> TYPE: PRT
<213> ORGANISM: Artificial Sequence
<220> FEATURE:
<223> OTHER INFORMATION: variant

<400> SEQUENCE: 103

Met Asn Leu Asn Glu Ala Arg Thr Ala Phe Ala Arg Leu Arg Ala Ala
1               5                   10                  15

Glu Asn Gly Leu Ser Pro Ala Glu Leu Asp Glu Val Trp Ala Ala Leu
            20                  25                  30

Glu Thr Val Ala Ala Glu Glu Ile Leu Gly Glu Trp Lys Gly Asp Asp
        35                  40                  45

Phe Ala Thr Gly His Arg Leu His Glu Lys Leu Ser Ala Ser Arg Trp
    50                  55                  60

Tyr Gly Lys Thr Phe Asn Ser Val Glu Asp Ala Lys Pro Leu Ile Cys
65                  70                  75                  80

Arg Asp Glu Asp Gly Asn Leu Tyr Ser Asp Val Lys Ser Gly Asn Gly
                85                  90                  95

Glu Ala Ser Leu Trp Asn Ile Glu Phe Ala Gly Glu Val Thr Ala Thr
            100                 105                 110

Met Val Tyr Asp Gly Ala Pro Ile Phe Asp His Phe Lys Lys Val Asp
        115                 120                 125

Asp Ser Thr Leu Met Gly Ile Met Asn Gly Lys Ser Ala Leu Val Leu
    130                 135                 140

Asp Gly Gly Gln His Tyr Tyr Phe Leu Leu Glu Arg Ala
145                 150                 155


<210> SEQ ID NO 104
<211> LENGTH: 474
<212> TYPE: DNA
<213> ORGANISM: Artificial Sequence
<220> FEATURE:
<223> OTHER INFORMATION: E. coli optimized

<400> SEQUENCE: 104
```

-continued

```
atgaacttaa atgaagcgcg taccgcattt gcacgtctga gagctgccga gaacggtctg     60

agcccggctg agctggatga agtgtgggca gcgctggaga ctgtggcggc tgaagaaatc    120

ctgggtgagt ggaagggtga cgattttgcg acgggtcacc gtctgcacga gaaactgtcg    180

gcgagccgct ggtatggtaa gaccttcaac tctgttgaag atgcaaagcc gctgatttgc    240

cgtgacgaag atggcaatct gtactccgat gtcaagagcg gtaacggtga ggccagcctg    300

tggaatatcg agtttgcagg cgaagtcacc gcgacgatgg tttacgatgg tgccccgatc    360

ttcgaccatt tcaaaaaagt tgacgacagc accctgatgg gcattatgaa tggcaaaagc    420

gcgttggtgt tggacggtgg ccagcattac tatttcctgc tggagcgtgc gtaa          474
```

<210> SEQ ID NO 105
<211> LENGTH: 157
<212> TYPE: PRT
<213> ORGANISM: Artificial Sequence
<220> FEATURE:
<223> OTHER INFORMATION: variant

<400> SEQUENCE: 105

```
Met Asn Leu Asn Glu Ala Arg Thr Ala Phe Ala Arg Leu Arg Ala Ala
1               5                   10                  15

Glu Asn Gly Leu Ser Pro Ala Glu Leu Asp Glu Val Trp Ala Ala Leu
            20                  25                  30

Glu Thr Val Ala Ala Glu Glu Ile Leu Gly Glu Trp Lys Gly Asp Asp
        35                  40                  45

Phe Ala Thr Gly His Arg Leu His Glu Lys Leu Ser Ala Ser Arg Trp
    50                  55                  60

Tyr Gly Lys Thr Phe Asn Ser Val Glu Asp Ala Lys Pro Leu Ile Cys
65                  70                  75                  80

Arg Asp Glu Asp Gly Asn Leu Tyr Ser Asp Val Lys Ser Gly Asn Gly
                85                  90                  95

Glu Ala Ser Leu Trp Asn Ile Glu Phe Arg Gly Glu Val Thr Ala Thr
            100                 105                 110

Met Val Ala Asp Gly Ala Pro Ile Phe Asp His Phe Lys Lys Val Asp
        115                 120                 125

Asp Ser Thr Leu Met Gly Ile Met Asn Gly Lys Ser Ala Leu Val Leu
    130                 135                 140

Asp Gly Gly Gln His Tyr Tyr Phe Leu Leu Glu Arg Ala
145                 150                 155
```

<210> SEQ ID NO 106
<211> LENGTH: 474
<212> TYPE: DNA
<213> ORGANISM: Artificial Sequence
<220> FEATURE:
<223> OTHER INFORMATION: E. coli optimized

<400> SEQUENCE: 106

```
atgaacttaa atgaagcgcg taccgcattt gcacgtctga gagctgccga gaacggtctg     60

agcccggctg agctggatga agtgtgggca gcgctggaga ctgtggcggc tgaagaaatc    120

ctgggtgagt ggaagggtga cgattttgcg acgggtcacc gtctgcacga gaaactgtcg    180

gcgagccgct ggtatggtaa gaccttcaac tctgttgaag atgcaaagcc gctgatttgc    240

cgtgacgaag atggcaatct gtactccgat gtcaagagcg gtaacggtga ggccagcctg    300

tggaatatcg agtttcgcgg cgaagtcacc gcgacgatgg ttgccgatgg tgccccgatc    360

ttcgaccatt tcaaaaaagt tgacgacagc accctgatgg gcattatgaa tggcaaaagc    420
```

gcgttggtgt tggacggtgg ccagcattac tatttcctgc tggagcgtgc gtaa 474

<210> SEQ ID NO 107
<211> LENGTH: 157
<212> TYPE: PRT
<213> ORGANISM: Artificial Sequence
<220> FEATURE:
<223> OTHER INFORMATION: variant

<400> SEQUENCE: 107

Met Asn Leu Asn Glu Ala Arg Thr Ala Phe Ala Arg Leu Arg Ala Ala
1 5 10 15

Glu Asn Gly Leu Ser Pro Ala Glu Leu Asp Glu Val Trp Ala Ala Leu
20 25 30

Glu Thr Val Ala Ala Glu Glu Ile Leu Gly Glu Trp Lys Gly Asp Asp
35 40 45

Phe Ala Thr Gly His Arg Leu His Glu Lys Leu Ser Ala Ser Arg Trp
50 55 60

Tyr Gly Lys Thr Phe Asn Ser Val Glu Asp Ala Lys Pro Leu Ile Cys
65 70 75 80

Arg Asp Glu Asp Gly Asn Leu Tyr Ser Asp Val Lys Ser Gly Asn Gly
85 90 95

Glu Ala Ser Leu Trp Asn Ile Glu Phe Arg Gly Glu Val Thr Ala Thr
100 105 110

Met Val Tyr Ala Gly Ala Pro Ile Phe Asp His Phe Lys Lys Val Asp
115 120 125

Asp Ser Thr Leu Met Gly Ile Met Asn Gly Lys Ser Ala Leu Val Leu
130 135 140

Asp Gly Gly Gln His Tyr Tyr Phe Leu Leu Glu Arg Ala
145 150 155

<210> SEQ ID NO 108
<211> LENGTH: 474
<212> TYPE: DNA
<213> ORGANISM: Artificial Sequence
<220> FEATURE:
<223> OTHER INFORMATION: E. coli optimized

<400> SEQUENCE: 108
atgaacttaa atgaagcgcg taccgcattt gcacgtctga gagctgccga gaacggtctg 60
agcccggctg agctggatga agtgtgggca gcgctggaga ctgtggcggc tgaagaaatc 120
ctgggtgagt ggaagggtga cgattttgcg acgggtcacc gtctgcacga gaaactgtcg 180
gcgagccgct ggtatggtaa gaccttcaac tctgttgaag atgcaaagcc gctgatttgc 240
cgtgacgaag atggcaatct gtactccgat gtcaagagcg gtaacggtga ggccagcctg 300
tggaatatcg agtttcgcgg cgaagtcacc gcgacgatgg tttacgccgg tgccccgatc 360
ttcgaccatt tcaaaaaagt tgacgacagc accctgatgg gcattatgaa tggcaaaagc 420
gcgttggtgt tggacggtgg ccagcattac tatttcctgc tggagcgtgc gtaa 474

<210> SEQ ID NO 109
<211> LENGTH: 157
<212> TYPE: PRT
<213> ORGANISM: Artificial Sequence
<220> FEATURE:
<223> OTHER INFORMATION: variant

<400> SEQUENCE: 109

```
Met Asn Leu Asn Glu Ala Arg Thr Ala Phe Ala Arg Leu Arg Ala Ala
1               5                   10                  15

Glu Asn Gly Leu Ser Pro Ala Glu Leu Asp Glu Val Trp Ala Ala Leu
            20                  25                  30

Glu Thr Val Ala Ala Glu Glu Ile Leu Gly Glu Trp Lys Gly Asp Asp
        35                  40                  45

Phe Ala Thr Gly His Arg Leu His Glu Lys Leu Ser Ala Ser Arg Trp
    50                  55                  60

Tyr Gly Lys Thr Phe Asn Ser Val Glu Asp Ala Lys Pro Leu Ile Cys
65                  70                  75                  80

Arg Asp Glu Asp Gly Asn Leu Tyr Ser Asp Val Lys Ser Gly Asn Gly
                85                  90                  95

Glu Ala Ser Leu Trp Asn Ile Glu Phe Arg Gly Glu Val Thr Ala Thr
            100                 105                 110

Met Val Tyr Asp Gly Ala Pro Ile Phe Ala His Phe Lys Lys Val Asp
        115                 120                 125

Asp Ser Thr Leu Met Gly Ile Met Asn Gly Lys Ser Ala Leu Val Leu
    130                 135                 140

Asp Gly Gly Gln His Tyr Tyr Phe Leu Leu Glu Arg Ala
145                 150                 155


<210> SEQ ID NO 110
<211> LENGTH: 474
<212> TYPE: DNA
<213> ORGANISM: Artificial Sequence
<220> FEATURE:
<223> OTHER INFORMATION: E. coli optimized

<400> SEQUENCE: 110

atgaacttaa atgaagcgcg taccgcattt gcacgtctga gagctgccga gaacggtctg      60

agcccggctg agctggatga agtgtgggca gcgctggaga ctgtggcggc tgaagaaatc     120

ctgggtgagt ggaagggtga cgattttgcg acgggtcacc gtctgcacga gaaactgtcg     180

gcgagccgct ggtatggtaa gaccttcaac tctgttgaag atgcaaagcc gctgatttgc     240

cgtgacgaag atggcaatct gtactccgat gtcaagagcg gtaacggtga ggccagcctg     300

tggaatatcg agtttcgcgg cgaagtcacc gcgacgatgg tttacgatgg tgccccgatc     360

ttcgcacatt tcaaaaaagt tgacgacagc accctgatgg gcattatgaa tggcaaaagc     420

gcgttggtgt tggacggtgg ccagcattac tatttcctgc tggagcgtgc gtaa           474


<210> SEQ ID NO 111
<211> LENGTH: 157
<212> TYPE: PRT
<213> ORGANISM: Artificial Sequence
<220> FEATURE:
<223> OTHER INFORMATION: variant

<400> SEQUENCE: 111

Met Asn Leu Asn Glu Ala Arg Thr Ala Phe Ala Arg Leu Arg Ala Ala
1               5                   10                  15

Glu Asn Gly Leu Ser Pro Ala Glu Leu Asp Glu Val Trp Ala Ala Leu
            20                  25                  30

Glu Thr Val Ala Ala Glu Glu Ile Leu Gly Glu Trp Lys Gly Asp Asp
        35                  40                  45

Phe Ala Thr Gly His Arg Leu His Glu Lys Leu Ser Ala Ser Arg Trp
    50                  55                  60

Tyr Gly Lys Thr Phe Asn Ser Val Glu Asp Ala Lys Pro Leu Ile Cys
```

```
65                  70                  75                  80

Arg Asp Glu Asp Gly Asn Leu Tyr Ser Asp Val Lys Ser Gly Asn Gly
                85                  90                  95

Glu Ala Ser Leu Trp Asn Ile Glu Phe Arg Gly Glu Val Thr Ala Thr
            100                 105                 110

Met Val Tyr Asp Gly Ala Pro Ile Phe Asp His Phe Lys Lys Val Asp
        115                 120                 125

Asp Ser Thr Leu Met Gly Ile Ala Asn Gly Lys Ser Ala Leu Val Leu
    130                 135                 140

Asp Gly Gly Gln His Tyr Tyr Phe Leu Leu Glu Arg Ala
145                 150                 155


<210> SEQ ID NO 112
<211> LENGTH: 474
<212> TYPE: DNA
<213> ORGANISM: Artificial Sequence
<220> FEATURE:
<223> OTHER INFORMATION: E. coli optimized

<400> SEQUENCE: 112

atgaacttaa atgaagcgcg taccgcattt gcacgtctga gagctgccga gaacggtctg      60

agcccggctg agctggatga agtgtgggca gcgctggaga ctgtggcggc tgaagaaatc     120

ctgggtgagt ggaagggtga cgattttgcg acgggtcacc gtctgcacga gaaactgtcg     180

gcgagccgct ggtatggtaa gaccttcaac tctgttgaag atgcaaagcc gctgatttgc     240

cgtgacgaag atggcaatct gtactccgat gtcaagagcg gtaacggtga ggccagcctg     300

tggaatatcg agtttcgcgg cgaagtcacc gcgacgatgg tttacgatgg tgccccgatc     360

ttcgaccatt tcaaaaaagt tgacgacagc accctgatgg gcattgcaaa tggcaaaagc     420

gcgttggtgt tggacggtgg ccagcattac tatttcctgc tggagcgtgc gtaa           474


<210> SEQ ID NO 113
<211> LENGTH: 157
<212> TYPE: PRT
<213> ORGANISM: Artificial Sequence
<220> FEATURE:
<223> OTHER INFORMATION: variant

<400> SEQUENCE: 113

Met Asn Leu Asn Glu Ala Arg Thr Ala Phe Ala Arg Leu Arg Ala Ala
1               5                   10                  15

Glu Asn Gly Leu Ser Pro Ala Glu Leu Asp Glu Val Trp Ala Ala Leu
            20                  25                  30

Glu Thr Val Ala Ala Glu Glu Ile Leu Gly Glu Trp Lys Gly Asp Asp
        35                  40                  45

Phe Ala Thr Gly His Arg Leu His Glu Lys Leu Ser Ala Ser Arg Trp
    50                  55                  60

Tyr Gly Lys Thr Phe Asn Ser Val Glu Asp Ala Lys Pro Leu Ile Cys
65                  70                  75                  80

Arg Asp Glu Asp Gly Asn Leu Tyr Ser Asp Val Lys Ser Gly Asn Gly
                85                  90                  95

Glu Ala Ser Leu Trp Asn Ile Glu Phe Arg Gly Glu Val Thr Ala Thr
            100                 105                 110

Met Val Tyr Asp Gly Ala Pro Ile Phe Asp His Phe Lys Lys Val Asp
        115                 120                 125

Asp Ser Thr Leu Met Gly Ile Met Asn Gly Ala Ser Ala Leu Val Leu
    130                 135                 140
```

```
Asp Gly Gly Gln His Tyr Tyr Phe Leu Leu Glu Arg Ala
145                 150                 155

<210> SEQ ID NO 114
<211> LENGTH: 474
<212> TYPE: DNA
<213> ORGANISM: Artificial Sequence
<220> FEATURE:
<223> OTHER INFORMATION: E. coli optimized

<400> SEQUENCE: 114

atgaacttaa atgaagcgcg taccgcattt gcacgtctga gagctgccga gaacggtctg      60

agcccggctg agctggatga agtgtgggca gcgctggaga ctgtggcggc tgaagaaatc     120

ctgggtgagt ggaagggtga cgattttgcg acgggtcacc gtctgcacga gaaactgtcg     180

gcgagccgct ggtatggtaa gaccttcaac tctgttgaag atgcaaagcc gctgatttgc     240

cgtgacgaag atggcaatct gtactccgat gtcaagagcg gtaacggtga ggccagcctg     300

tggaatatcg agtttcgcgg cgaagtcacc gcgacgatgg tttacgatgg tgccccgatc     360

ttcgaccatt tcaaaaaagt tgacgacagc accctgatgg gcattatgaa tggcgcaagc     420

gcgttggtgt tggacggtgg ccagcattac tatttcctgc tggagcgtgc gtaa           474

<210> SEQ ID NO 115
<211> LENGTH: 157
<212> TYPE: PRT
<213> ORGANISM: Artificial Sequence
<220> FEATURE:
<223> OTHER INFORMATION: variant

<400> SEQUENCE: 115

Met Asn Leu Asn Glu Ala Arg Thr Ala Phe Ala Arg Leu Arg Ala Ala
1               5                   10                  15

Glu Asn Gly Leu Ser Pro Ala Glu Leu Asp Glu Val Trp Ala Ala Leu
            20                  25                  30

Glu Thr Val Ala Ala Glu Glu Ile Leu Gly Glu Trp Lys Gly Asp Asp
        35                  40                  45

Phe Ala Thr Gly His Arg Leu His Glu Lys Leu Ser Ala Ser Arg Trp
    50                  55                  60

Tyr Gly Lys Thr Phe Asn Ser Val Glu Asp Ala Lys Pro Leu Ile Cys
65                  70                  75                  80

Arg Asp Glu Asp Gly Asn Leu Tyr Ser Asp Val Lys Ser Gly Asn Gly
                85                  90                  95

Glu Ala Ser Leu Trp Asn Ile Glu Phe Arg Gly Glu Val Thr Ala Thr
            100                 105                 110

Met Val Tyr Asp Gly Ala Pro Ile Phe Asp His Phe Lys Lys Val Asp
        115                 120                 125

Asp Ser Thr Leu Met Gly Ile Met Asn Gly Lys Ser Ala Leu Val Leu
    130                 135                 140

Asp Gly Gly Gln His Tyr Tyr Ala Leu Leu Glu Arg Ala
145                 150                 155

<210> SEQ ID NO 116
<211> LENGTH: 474
<212> TYPE: DNA
<213> ORGANISM: Artificial Sequence
<220> FEATURE:
<223> OTHER INFORMATION: E. coli optimized

<400> SEQUENCE: 116
```

atgaacttaa atgaagcgcg taccgcattt gcacgtctga gagctgccga gaacggtctg 60
agcccggctg agctggatga agtgtgggca gcgctggaga ctgtggcggc tgaagaaatc 120
ctgggtgagt ggaagggtga cgattttgcg acgggtcacc gtctgcacga gaaactgtcg 180
gcgagccgct ggtatggtaa gaccttcaac tctgttgaag atgcaaagcc gctgatttgc 240
cgtgacgaag atggcaatct gtactccgat gtcaagagcg gtaacggtga ggccagcctg 300
tggaatatcg agtttcgcgg cgaagtcacc gcgacgatgg tttacgatgg tgccccgatc 360
ttcgaccatt tcaaaaaagt tgacgacagc accctgatgg gcattatgaa tggcaaaagc 420
gcgttggtgt tggacggtgg ccagcattac tatgcactgc tggagcgtgc gtaa 474

<210> SEQ ID NO 117
<211> LENGTH: 157
<212> TYPE: PRT
<213> ORGANISM: Artificial Sequence
<220> FEATURE:
<223> OTHER INFORMATION: variant

<400> SEQUENCE: 117

Met Asn Leu Asn Glu Ala Arg Thr Ala Phe Ala Arg Leu Arg Ala Ala
1 5 10 15

Glu Asn Gly Leu Ser Pro Ala Glu Leu Asp Glu Val Trp Ala Ala Leu
20 25 30

Glu Thr Val Ala Ala Glu Glu Ile Leu Gly Glu Trp Lys Gly Asp Asp
35 40 45

Phe Ala Thr Gly His Arg Leu His Glu Lys Leu Ser Ala Ser Arg Trp
50 55 60

Tyr Gly Lys Thr Phe Asn Ser Val Glu Asp Ala Lys Pro Leu Ile Cys
65 70 75 80

Arg Asp Glu Asp Gly Asn Leu Tyr Ser Asp Val Lys Ser Gly Asn Gly
85 90 95

Glu Ala Ser Leu Trp Asn Ile Glu Phe Arg Gly Glu Val Thr Ala Thr
100 105 110

Met Val Tyr Asp Gly Ala Pro Ile Phe Asp His Phe Lys Lys Val Asp
115 120 125

Asp Ser Thr Leu Met Gly Ile Met Asn Gly Lys Ser Ala Leu Val Leu
130 135 140

Asp Gly Gly Gln His Tyr Tyr Phe Leu Ala Glu Arg Ala
145 150 155

<210> SEQ ID NO 118
<211> LENGTH: 474
<212> TYPE: DNA
<213> ORGANISM: Artificial Sequence
<220> FEATURE:
<223> OTHER INFORMATION: E. coli optimized

<400> SEQUENCE: 118
atgaacttaa atgaagcgcg taccgcattt gcacgtctga gagctgccga gaacggtctg 60
agcccggctg agctggatga agtgtgggca gcgctggaga ctgtggcggc tgaagaaatc 120
ctgggtgagt ggaagggtga cgattttgcg acgggtcacc gtctgcacga gaaactgtcg 180
gcgagccgct ggtatggtaa gaccttcaac tctgttgaag atgcaaagcc gctgatttgc 240
cgtgacgaag atggcaatct gtactccgat gtcaagagcg gtaacggtga ggccagcctg 300
tggaatatcg agtttcgcgg cgaagtcacc gcgacgatgg tttacgatgg tgccccgatc 360
ttcgaccatt tcaaaaaagt tgacgacagc accctgatgg gcattatgaa tggcaaaagc 420
gcgttggtgt tggacggtgg ccagcattac tatttcctgg ccgagcgtgc gtaa 474

<210> SEQ ID NO 119
<211> LENGTH: 157
<212> TYPE: PRT
<213> ORGANISM: Artificial Sequence
<220> FEATURE:
<223> OTHER INFORMATION: variant

<400> SEQUENCE: 119

Met Asn Leu Asn Glu Ala Arg Thr Ala Phe Ala Arg Leu Arg Ala Ala
1 5 10 15

Glu Asn Gly Leu Ser Pro Ala Glu Leu Asp Glu Val Trp Ala Ala Leu
20 25 30

Glu Thr Val Ala Ala Glu Glu Ile Leu Gly Glu Trp Lys Gly Asp Asp
35 40 45

Phe Ala Thr Gly His Arg Leu His Glu Lys Leu Ser Ala Ser Arg Trp
50 55 60

Tyr Gly Lys Thr Phe Asn Ser Val Glu Asp Ala Lys Pro Leu Ile Cys
65 70 75 80

Arg Asp Glu Asp Gly Asn Leu Tyr Ser Asp Val Lys Ser Gly Asn Gly
85 90 95

Glu Ala Ser Leu Trp Asn Ile Glu Phe Arg Gly Glu Val Thr Ala Thr
100 105 110

Met Val Tyr Asp Gly Ala Pro Ile Phe Asp His Phe Lys Lys Val Asp
115 120 125

Asp Ser Thr Leu Met Gly Ile Met Asn Gly Lys Ser Ala Leu Val Leu
130 135 140

Asp Gly Gly Gln His Tyr Tyr Phe Leu Leu Glu Ala Ala
145 150 155

<210> SEQ ID NO 120
<211> LENGTH: 474
<212> TYPE: DNA
<213> ORGANISM: Artificial Sequence
<220> FEATURE:
<223> OTHER INFORMATION: E. coli optimized

<400> SEQUENCE: 120
atgaacttaa atgaagcgcg taccgcattt gcacgtctga gagctgccga gaacggtctg 60
agcccggctg agctggatga agtgtgggca gcgctggaga ctgtggcggc tgaagaaatc 120
ctgggtgagt ggaagggtga cgattttgcg acgggtcacc gtctgcacga gaaactgtcg 180
gcgagccgct ggtatggtaa gaccttcaac tctgttgaag atgcaaagcc gctgatttgc 240
cgtgacgaag atggcaatct gtactccgat gtcaagagcg gtaacggtga ggccagcctg 300
tggaatatcg agtttcgcgg cgaagtcacc gcgacgatgg tttacgatgg tgccccgatc 360
ttcgaccatt tcaaaaaagt tgacgacagc accctgatgg gcattatgaa tggcaaaagc 420
gcgttggtgt tggacggtgg ccagcattac tatttcctgc tggaggcagc gtaa 474

<210> SEQ ID NO 121
<211> LENGTH: 60
<212> TYPE: DNA
<213> ORGANISM: Artificial Sequence
<220> FEATURE:
<223> OTHER INFORMATION: Integration cassette fragment 1

<400> SEQUENCE: 121
gcaggcagct ccatttcatg taggtgattt atccctccgg gcggtatttg agactctcgg 60

<210> SEQ ID NO 122
<211> LENGTH: 60
<212> TYPE: DNA
<213> ORGANISM: Artificial Sequence
<220> FEATURE:
<223> OTHER INFORMATION: Integration cassette fragment 2

<400> SEQUENCE: 122
actgctgggt actgttcagg cacgatagga aatgcgtcca gcgcatacac cagtcttagc 60

<210> SEQ ID NO 123
<211> LENGTH: 60
<212> TYPE: DNA
<213> ORGANISM: Artificial Sequence
<220> FEATURE:
<223> OTHER INFORMATION: Integration cassette fragment 3

<400> SEQUENCE: 123
agtcgacctt acagcgcctg ggactctaca taaacatgca gcgaacatgc tttccaacgc 60

<210> SEQ ID NO 124
<211> LENGTH: 79
<212> TYPE: DNA
<213> ORGANISM: Artificial Sequence
<220> FEATURE:
<223> OTHER INFORMATION: LEU2 yeast marker_primer 1

<400> SEQUENCE: 124
aggtgcagtt cgcgtgcaat tataacgtcg tggcaactgt tatcagtcgt accgcgccat 60
tcgactacgt cgtaaggcc 79

<210> SEQ ID NO 125
<211> LENGTH: 80
<212> TYPE: DNA
<213> ORGANISM: Artificial Sequence
<220> FEATURE:
<223> OTHER INFORMATION: LEU2 yeast marker_primer 2

<400> SEQUENCE: 125
tcgtggtcaa ggcgtgcaat tctcaacacg agagtgattc ttcggcgttg ttgctgacca 60
tcgacggtcg aggagaactt 80

<210> SEQ ID NO 126
<211> LENGTH: 85
<212> TYPE: DNA
<213> ORGANISM: Artificial Sequence
<220> FEATURE:
<223> OTHER INFORMATION: AmpR E. coli marker_primer 1

<400> SEQUENCE: 126
tggtcagcaa caacgccgaa gaatcactct cgtgttgaga attgcacgcc ttgaccacga 60
cacgttaagg gattttggtc atgag 85

<210> SEQ ID NO 127
<211> LENGTH: 80
<212> TYPE: DNA
<213> ORGANISM: Artificial Sequence
<220> FEATURE:
<223> OTHER INFORMATION: AmpR E. coli marker_primer 2

<400> SEQUENCE: 127
aacgcgtacc ctaagtacgg caccacagtg actatgcagt ccgcactttg ccaatgccaa 60
aaatgtgcgc ggaacccta 80

<210> SEQ ID NO 128
<211> LENGTH: 84
<212> TYPE: DNA
<213> ORGANISM: Artificial Sequence
<220> FEATURE:
<223> OTHER INFORMATION: Yeast origin of replication_primer 1

<400> SEQUENCE: 128
ttggcattgg caaagtgcgg actgcatagt cactgtggtg ccgtacttag ggtacgcgtt 60
cctgaacgaa gcatctgtgc ttca 84

<210> SEQ ID NO 129
<211> LENGTH: 85
<212> TYPE: DNA
<213> ORGANISM: Artificial Sequence
<220> FEATURE:
<223> OTHER INFORMATION: Yeast origin of replication_primer 2

<400> SEQUENCE: 129
ccgagatgcc aaaggatagg tgctatgttg atgactacga cacagaactg cgggtgacat 60
aatgatagca ttgaaggatg agact 85

<210> SEQ ID NO 130
<211> LENGTH: 82
<212> TYPE: DNA
<213> ORGANISM: Artificial Sequence
<220> FEATURE:
<223> OTHER INFORMATION: E. coli replication origin_primer 1

<400> SEQUENCE: 130
atgtcacccg cagttctgtg tcgtagtcat caacatagca cctatccttt ggcatctcgg 60
tgagcaaaag gccagcaaaa gg 82

<210> SEQ ID NO 131
<211> LENGTH: 81
<212> TYPE: DNA
<213> ORGANISM: Artificial Sequence
<220> FEATURE:
<223> OTHER INFORMATION: E. coli replication origin_primer 2

<400> SEQUENCE: 131
ctcagatgta cggtgatcgc caccatgtga cggaagctat cctgacagtg tagcaagtgc 60
tgagcgtcag accccgtaga a 81

<210> SEQ ID NO 132
<211> LENGTH: 60
<212> TYPE: DNA
<213> ORGANISM: Artificial Sequence
<220> FEATURE:
<223> OTHER INFORMATION: DNA fragment for S. cerevisiae
co-transformation

<400> SEQUENCE: 132
attcctagtg acggccttgg gaactcgata cacgatgttc agtagaccgc tcacacatgg 60

<210> SEQ ID NO 133
<211> LENGTH: 1056
<212> TYPE: DNA
<213> ORGANISM: Hyphozyma roseonigra
<220> FEATURE:

<221> NAME/KEY: CDS
<222> LOCATION: (1)..(1056)

<400> SEQUENCE: 133

```
atg caa ttc agc atc gga gat gta ctc gcc att gta gat aaa aca atc       48
Met Gln Phe Ser Ile Gly Asp Val Leu Ala Ile Val Asp Lys Thr Ile
1               5                   10                  15

ctc aac cca ctc gtc gtc agc gca gga ctt ctg tct ctg cac ttt ctc       96
Leu Asn Pro Leu Val Val Ser Ala Gly Leu Leu Ser Leu His Phe Leu
            20                  25                  30

acc aat gac aaa tac gca atc act gcg aat gac ggt cta ttc cct tat      144
Thr Asn Asp Lys Tyr Ala Ile Thr Ala Asn Asp Gly Leu Phe Pro Tyr
        35                  40                  45

caa att agc act cca gac tcg cat cga aaa gcc ctt ttt gca ctt ggc      192
Gln Ile Ser Thr Pro Asp Ser His Arg Lys Ala Leu Phe Ala Leu Gly
    50                  55                  60

ttt ggt cta ctt ctc aga gcc aat cgc tac atg agc aga aaa gct ctg      240
Phe Gly Leu Leu Leu Arg Ala Asn Arg Tyr Met Ser Arg Lys Ala Leu
65                  70                  75                  80

aac aac aac acc gcc gca caa ttc gac tgg aat cgt gag atc atc gtt      288
Asn Asn Asn Thr Ala Ala Gln Phe Asp Trp Asn Arg Glu Ile Ile Val
                85                  90                  95

gtt act ggt gga tct ggt ggt atc ggt gct cag gcc gcg cag aaa ttg      336
Val Thr Gly Gly Ser Gly Gly Ile Gly Ala Gln Ala Ala Gln Lys Leu
            100                 105                 110

gca gaa aga gga tcg aaa gtg att gtt att gat gtg cta cca ctt acc      384
Ala Glu Arg Gly Ser Lys Val Ile Val Ile Asp Val Leu Pro Leu Thr
        115                 120                 125

ttt gac aag ccc aag aat ttg tac cac tat aaa tgt gat ctc aca aac      432
Phe Asp Lys Pro Lys Asn Leu Tyr His Tyr Lys Cys Asp Leu Thr Asn
    130                 135                 140

tac aaa gag ctc caa gaa gtt gcg gct aag atc gaa aga gaa gtt ggc      480
Tyr Lys Glu Leu Gln Glu Val Ala Ala Lys Ile Glu Arg Glu Val Gly
145                 150                 155                 160

act ccg act tgt gta gtt gcg aat gca gga ata tgt cgt gga aag aac      528
Thr Pro Thr Cys Val Val Ala Asn Ala Gly Ile Cys Arg Gly Lys Asn
                165                 170                 175

ata ttc gat gct aca gaa cga gat gtt cag ctt acc ttt gga gtc aac      576
Ile Phe Asp Ala Thr Glu Arg Asp Val Gln Leu Thr Phe Gly Val Asn
            180                 185                 190

aat ctg gga ctt cta tgg aca gcc aaa acc ttt ctc cca tca atg gcc      624
Asn Leu Gly Leu Leu Trp Thr Ala Lys Thr Phe Leu Pro Ser Met Ala
        195                 200                 205

aaa gca aat cat ggc cat ttc ttg atc atc gcc tct caa acc ggc cat      672
Lys Ala Asn His Gly His Phe Leu Ile Ile Ala Ser Gln Thr Gly His
    210                 215                 220

cta gcg acc gca gga gta gtc gac tat gca gcg acc aaa gca gca gca      720
Leu Ala Thr Ala Gly Val Val Asp Tyr Ala Ala Thr Lys Ala Ala Ala
225                 230                 235                 240

atc gcc ata tat gaa ggt cta caa aca gag atg aag cac ttt tat aaa      768
Ile Ala Ile Tyr Glu Gly Leu Gln Thr Glu Met Lys His Phe Tyr Lys
                245                 250                 255

gcg cct gct gta cgc gta tct tgt atc tcc cca tcc gcg gtc aag acg      816
Ala Pro Ala Val Arg Val Ser Cys Ile Ser Pro Ser Ala Val Lys Thr
            260                 265                 270

aag atg ttt gca ggc atc aag act gga ggc aat ttc ttc atg cca atg      864
Lys Met Phe Ala Gly Ile Lys Thr Gly Gly Asn Phe Phe Met Pro Met
        275                 280                 285

ttg acg cct gat gat ctt gga gac ctg att gca aag act ttg tgg gac      912
Leu Thr Pro Asp Asp Leu Gly Asp Leu Ile Ala Lys Thr Leu Trp Asp
```

```
    290                 295                 300

ggt gtg gca gtc aat att ttg agc cct gcg gcg gca tat atc agc ccg      960
Gly Val Ala Val Asn Ile Leu Ser Pro Ala Ala Ala Tyr Ile Ser Pro
305                 310                 315                 320

ccc acg aga gct ttg cca gat tgg atg agg gtt ggc atg cag gat gct     1008
Pro Thr Arg Ala Leu Pro Asp Trp Met Arg Val Gly Met Gln Asp Ala
                325                 330                 335

ggt gct gag atc atg acg gaa ttg act cct cat aag ccg ttg gag tag     1056
Gly Ala Glu Ile Met Thr Glu Leu Thr Pro His Lys Pro Leu Glu
            340                 345                 350


<210> SEQ ID NO 134
<211> LENGTH: 351
<212> TYPE: PRT
<213> ORGANISM: Hyphozyma roseonigra

<400> SEQUENCE: 134

Met Gln Phe Ser Ile Gly Asp Val Leu Ala Ile Val Asp Lys Thr Ile
1               5                   10                  15

Leu Asn Pro Leu Val Val Ser Ala Gly Leu Leu Ser Leu His Phe Leu
            20                  25                  30

Thr Asn Asp Lys Tyr Ala Ile Thr Ala Asn Asp Gly Leu Phe Pro Tyr
        35                  40                  45

Gln Ile Ser Thr Pro Asp Ser His Arg Lys Ala Leu Phe Ala Leu Gly
    50                  55                  60

Phe Gly Leu Leu Leu Arg Ala Asn Arg Tyr Met Ser Arg Lys Ala Leu
65                  70                  75                  80

Asn Asn Asn Thr Ala Ala Gln Phe Asp Trp Asn Arg Glu Ile Ile Val
                85                  90                  95

Val Thr Gly Gly Ser Gly Gly Ile Gly Ala Gln Ala Ala Gln Lys Leu
            100                 105                 110

Ala Glu Arg Gly Ser Lys Val Ile Val Ile Asp Val Leu Pro Leu Thr
        115                 120                 125

Phe Asp Lys Pro Lys Asn Leu Tyr His Tyr Lys Cys Asp Leu Thr Asn
    130                 135                 140

Tyr Lys Glu Leu Gln Glu Val Ala Ala Lys Ile Glu Arg Glu Val Gly
145                 150                 155                 160

Thr Pro Thr Cys Val Val Ala Asn Ala Gly Ile Cys Arg Gly Lys Asn
                165                 170                 175

Ile Phe Asp Ala Thr Glu Arg Asp Val Gln Leu Thr Phe Gly Val Asn
            180                 185                 190

Asn Leu Gly Leu Leu Trp Thr Ala Lys Thr Phe Leu Pro Ser Met Ala
        195                 200                 205

Lys Ala Asn His Gly His Phe Leu Ile Ile Ala Ser Gln Thr Gly His
    210                 215                 220

Leu Ala Thr Ala Gly Val Val Asp Tyr Ala Ala Thr Lys Ala Ala Ala
225                 230                 235                 240

Ile Ala Ile Tyr Glu Gly Leu Gln Thr Glu Met Lys His Phe Tyr Lys
                245                 250                 255

Ala Pro Ala Val Arg Val Ser Cys Ile Ser Pro Ser Ala Val Lys Thr
            260                 265                 270

Lys Met Phe Ala Gly Ile Lys Thr Gly Gly Asn Phe Phe Met Pro Met
        275                 280                 285

Leu Thr Pro Asp Asp Leu Gly Asp Leu Ile Ala Lys Thr Leu Trp Asp
    290                 295                 300
```

```
Gly Val Ala Val Asn Ile Leu Ser Pro Ala Ala Ala Tyr Ile Ser Pro
305                 310                 315                 320

Pro Thr Arg Ala Leu Pro Asp Trp Met Arg Val Gly Met Gln Asp Ala
                325                 330                 335

Gly Ala Glu Ile Met Thr Glu Leu Thr Pro His Lys Pro Leu Glu
            340                 345                 350


<210> SEQ ID NO 135
<211> LENGTH: 1056
<212> TYPE: DNA
<213> ORGANISM: Hyphozyma roseonigra

<400> SEQUENCE: 135

atgcaattct ctatcggtga cgttttggct atcgttgaca agactatctt gaacccattg      60

gttgtttctg ctggtttgtt gtctttgcac ttcttgacta acgacaagta cgctatcact     120

gctaacgacg gtttgttccc ataccaaatc tctactccag actctcacag aaaggctttg     180

ttcgctttgg gtttcggttt gttgttgaga gctaacagat acatgtctag aaaggctttg     240

aacaacaaca ctgctgctca attcgactgg aacagagaaa tcatcgttgt tactggtggt     300

tctggtggta tcggtgctca agctgctcaa aagttggctg aaagaggttc taaggttatc     360

gttatcgacg ttttgccatt gactttcgac aagccaaaga acttgtacca ctacaagtgt     420

gacttgacta actacaagga attgcaagaa gttgctgcta agatcgaaag agaagttggt     480

actccaactt gtgttgttgc taacgctggt atctgtagag gtaagaacat cttcgacgct     540

actgaaagag acgttcaatt gactttcggt gttaacaact tgggtttgtt gtggactgct     600

aagactttct tgccatctat ggctaaggct aaccacggtc acttcttgat catcgcttct     660

caaactggtc acttggctac tgctggtgtt gttgactacg ctgctactaa ggctgctgct     720

atcgctatct acgaaggttt gcaaactgaa atgaagcact tctacaaggc tccagctgtt     780

agagtttctt gtatctctcc atctgctgtt aagactaaga tgttcgctgg tatcaagact     840

ggtggtaact tcttcatgcc aatgttgact ccagacgact tgggtgactt gatcgctaag     900

actttgtggg acggtgttgc tgttaacatc ttgtctccag ctgctgctta catctctcca     960

ccaactagag ctttgccaga ctggatgaga gttggtatgc aagacgctgg tgctgaaatc    1020

atgactgaat tgactccaca caagccattg gaataa                              1056


<210> SEQ ID NO 136
<211> LENGTH: 1023
<212> TYPE: DNA
<213> ORGANISM: Hyphozyma roseonigra
<220> FEATURE:
<221> NAME/KEY: CDS
<222> LOCATION: (1)..(1023)

<400> SEQUENCE: 136

atg gcg acg ata ccg acc aca atg acc gca gcg aca atc gtt gaa ttc       48
Met Ala Thr Ile Pro Thr Thr Met Thr Ala Ala Thr Ile Val Glu Phe
1               5                   10                  15

aac aag ccc atc gtg cta aag aac gac ata cca gtt cca gac cta cca       96
Asn Lys Pro Ile Val Leu Lys Asn Asp Ile Pro Val Pro Asp Leu Pro
            20                  25                  30

gag aac aag att ctt gtt agg ata gct gca aca tca tta tgc tca agc      144
Glu Asn Lys Ile Leu Val Arg Ile Ala Ala Thr Ser Leu Cys Ser Ser
        35                  40                  45

gac ttg atg gcg tac aaa ggt tac atg gat ttc atg acc aag acg cct      192
Asp Leu Met Ala Tyr Lys Gly Tyr Met Asp Phe Met Thr Lys Thr Pro
    50                  55                  60
```

-continued

```
tac tgc gga gga cac gag ccc gtg gga acg gtg gtg aaa gtc ggt tct      240
Tyr Cys Gly Gly His Glu Pro Val Gly Thr Val Val Lys Val Gly Ser
65                  70                  75                  80

tcg gta aaa ggc tac tcg gtt gga gat cgc gtt ggc ata ttg atg ttc      288
Ser Val Lys Gly Tyr Ser Val Gly Asp Arg Val Gly Ile Leu Met Phe
                85                  90                  95

ttc gat acc tgt gga aca tgc aat gac tgc ttc tcg ggt gaa cat cgc      336
Phe Asp Thr Cys Gly Thr Cys Asn Asp Cys Phe Ser Gly Glu His Arg
            100                 105                 110

ttt tgc agc aca aag aaa atc cta ggc ttc gcg gaa agc tgg gga gga      384
Phe Cys Ser Thr Lys Lys Ile Leu Gly Phe Ala Glu Ser Trp Gly Gly
        115                 120                 125

ttt tca gaa tac gca ctt gct gat ccc atc tcg acc atc aag ctc ccg      432
Phe Ser Glu Tyr Ala Leu Ala Asp Pro Ile Ser Thr Ile Lys Leu Pro
    130                 135                 140

gaa ggg ttg agt ttc gat gta gca gcg cct ttg ttc tgc gct ggg atc      480
Glu Gly Leu Ser Phe Asp Val Ala Ala Pro Leu Phe Cys Ala Gly Ile
145                 150                 155                 160

aca gcc tac agc gcg ctg ttg aag gtg aag agt cat gcc ggt caa ctc      528
Thr Ala Tyr Ser Ala Leu Leu Lys Val Lys Ser His Ala Gly Gln Leu
                165                 170                 175

atc aat atc atc ggc tgt gga ggc gta gga cat atg gct ata ttg tat      576
Ile Asn Ile Ile Gly Cys Gly Gly Val Gly His Met Ala Ile Leu Tyr
            180                 185                 190

gcg aga gct atg gga tat cga gtt cat gtt tac gat ata tcc gat tcc      624
Ala Arg Ala Met Gly Tyr Arg Val His Val Tyr Asp Ile Ser Asp Ser
        195                 200                 205

aag gtc gaa ttt gca ctc ttt ctc ggc gca gat gca gcc ttc aac act      672
Lys Val Glu Phe Ala Leu Phe Leu Gly Ala Asp Ala Ala Phe Asn Thr
    210                 215                 220

ctg acc tat acc ggt cca ata gaa tca gca tct tct acg tta gtc gta      720
Leu Thr Tyr Thr Gly Pro Ile Glu Ser Ala Ser Ser Thr Leu Val Val
225                 230                 235                 240

agt gga gca aat gca gca tac cag agc gct cta ggc atg acg agt aat      768
Ser Gly Ala Asn Ala Ala Tyr Gln Ser Ala Leu Gly Met Thr Ser Asn
                245                 250                 255

cat gga gtc gtc ctg ggt att gga cta cca gcg gga ggt gtg gtc att      816
His Gly Val Val Leu Gly Ile Gly Leu Pro Ala Gly Gly Val Val Ile
            260                 265                 270

gat gtg cca gct tgg ggt acg aaa ggc gtt aca ttc gtc cca tgc aac      864
Asp Val Pro Ala Trp Gly Thr Lys Gly Val Thr Phe Val Pro Cys Asn
        275                 280                 285

aca ggc tcg aaa cag gaa cta gaa gaa gcg cta gaa ttg gct gtg aga      912
Thr Gly Ser Lys Gln Glu Leu Glu Glu Ala Leu Glu Leu Ala Val Arg
    290                 295                 300

aag gat atc aaa cca tta ctt gac atc cgc cat atc gac aca att aat      960
Lys Asp Ile Lys Pro Leu Leu Asp Ile Arg His Ile Asp Thr Ile Asn
305                 310                 315                 320

gag gca tat caa gat ttg gcg gag gga aag atc aat ggg agg att gtt     1008
Glu Ala Tyr Gln Asp Leu Ala Glu Gly Lys Ile Asn Gly Arg Ile Val
                325                 330                 335

ttc cac ttc gag tga                                                 1023
Phe His Phe Glu
            340
```

<210> SEQ ID NO 137
<211> LENGTH: 340
<212> TYPE: PRT
<213> ORGANISM: Hyphozyma roseonigra

<400> SEQUENCE: 137

Met Ala Thr Ile Pro Thr Thr Met Thr Ala Ala Thr Ile Val Glu Phe
1 5 10 15

Asn Lys Pro Ile Val Leu Lys Asn Asp Ile Pro Val Pro Asp Leu Pro
20 25 30

Glu Asn Lys Ile Leu Val Arg Ile Ala Ala Thr Ser Leu Cys Ser Ser
35 40 45

Asp Leu Met Ala Tyr Lys Gly Tyr Met Asp Phe Met Thr Lys Thr Pro
50 55 60

Tyr Cys Gly Gly His Glu Pro Val Gly Thr Val Val Lys Val Gly Ser
65 70 75 80

Ser Val Lys Gly Tyr Ser Val Gly Asp Arg Val Gly Ile Leu Met Phe
85 90 95

Phe Asp Thr Cys Gly Thr Cys Asn Asp Cys Phe Ser Gly Glu His Arg
100 105 110

Phe Cys Ser Thr Lys Lys Ile Leu Gly Phe Ala Glu Ser Trp Gly Gly
115 120 125

Phe Ser Glu Tyr Ala Leu Ala Asp Pro Ile Ser Thr Ile Lys Leu Pro
130 135 140

Glu Gly Leu Ser Phe Asp Val Ala Ala Pro Leu Phe Cys Ala Gly Ile
145 150 155 160

Thr Ala Tyr Ser Ala Leu Leu Lys Val Lys Ser His Ala Gly Gln Leu
165 170 175

Ile Asn Ile Ile Gly Cys Gly Gly Val Gly His Met Ala Ile Leu Tyr
180 185 190

Ala Arg Ala Met Gly Tyr Arg Val His Val Tyr Asp Ile Ser Asp Ser
195 200 205

Lys Val Glu Phe Ala Leu Phe Leu Gly Ala Asp Ala Ala Phe Asn Thr
210 215 220

Leu Thr Tyr Thr Gly Pro Ile Glu Ser Ala Ser Ser Thr Leu Val Val
225 230 235 240

Ser Gly Ala Asn Ala Ala Tyr Gln Ser Ala Leu Gly Met Thr Ser Asn
245 250 255

His Gly Val Val Leu Gly Ile Gly Leu Pro Ala Gly Gly Val Val Ile
260 265 270

Asp Val Pro Ala Trp Gly Thr Lys Gly Val Thr Phe Val Pro Cys Asn
275 280 285

Thr Gly Ser Lys Gln Glu Leu Glu Glu Ala Leu Glu Leu Ala Val Arg
290 295 300

Lys Asp Ile Lys Pro Leu Leu Asp Ile Arg His Ile Asp Thr Ile Asn
305 310 315 320

Glu Ala Tyr Gln Asp Leu Ala Glu Gly Lys Ile Asn Gly Arg Ile Val
325 330 335

Phe His Phe Glu
340

<210> SEQ ID NO 138
<211> LENGTH: 1023
<212> TYPE: DNA
<213> ORGANISM: Hyphozyma roseonigra

<400> SEQUENCE: 138
atggctacta tcccaactac tatgactgct gctactatcg ttgaattcaa caagccaatc 60
gttttgaaga acgacatccc agttccagac ttgccagaaa acaagatctt ggttagaatc 120

```
gctgctactt ctttgtgttc ttctgacttg atggcttaca agggttacat ggacttcatg    180

actaagactc catactgtgg tggtcacgaa ccagttggta ctgttgttaa ggttggttct    240

tctgttaagg gttactctgt tggtgacaga gttggtatct tgatgttctt cgacacttgt    300

ggtacttgta acgactgttt ctctggtgaa cacagattct gttctactaa gaagatcttg    360

ggtttcgctg aatcttgggg tggtttctct gaatacgctt tggctgaccc aatctctact    420

atcaagttgc cagaaggttt gtctttcgac gttgctgctc cattgttctg tgctggtatc    480

actgcttact ctgctttgtt gaaggttaag tctcacgctg gtcaattgat caacatcatc    540

ggttgtggtg gtgttggtca catggctatc ttgtacgcta gagctatggg ttacagagtt    600

cacgtttacg acatctctga ctctaaggtt gaattcgctt tgttcttggg tgctgacgct    660

gctttcaaca ctttgactta cactggtcca atcgaatctg cttcttctac tttggttgtt    720

tctggtgcta acgctgctta ccaatctgct ttgggtatga cttctaacca cggtgttgtt    780

ttgggtatcg gtttgccagc tggtggtgtt gttatcgacg ttccagcttg ggtactaag    840

ggtgttactt tcgttccatg taacactggt tctaagcaag aattggaaga agctttggaa    900

ttggctgtta gaaaggacat caagccattg ttggacatca gacacatcga cactatcaac    960

gaagcttacc aagacttggc tgaaggtaag atcaacggta gaatcgtttt ccacttcgaa   1020

taa                                                                  1023


<210> SEQ ID NO 139
<211> LENGTH: 1116
<212> TYPE: DNA
<213> ORGANISM: Filobasidium magnum
<220> FEATURE:
<221> NAME/KEY: CDS
<222> LOCATION: (1)..(1116)

<400> SEQUENCE: 139

atg cca acc cct atc ttt ggc gcc cga gag ggt ttc act atc gac tcc       48
Met Pro Thr Pro Ile Phe Gly Ala Arg Glu Gly Phe Thr Ile Asp Ser
1               5                   10                  15

gta ctg agc atc ctg gat gcg acc gta ctt aac ccc tgg ttt acc ggc       96
Val Leu Ser Ile Leu Asp Ala Thr Val Leu Asn Pro Trp Phe Thr Gly
            20                  25                  30

gtg tgc cta ata gcc gtc tgc gcc cga gat cgc acc att acg tac ccg      144
Val Cys Leu Ile Ala Val Cys Ala Arg Asp Arg Thr Ile Thr Tyr Pro
        35                  40                  45

gac tgg ccg gcg gct ctg gac cag gtg ctc ccc ttc ttg tcg cag atg      192
Asp Trp Pro Ala Ala Leu Asp Gln Val Leu Pro Phe Leu Ser Gln Met
    50                  55                  60

tgg agg gaa act gtc aga ccg acc ttt ggc gac cgc aac gtc ctt cat      240
Trp Arg Glu Thr Val Arg Pro Thr Phe Gly Asp Arg Asn Val Leu His
65                  70                  75                  80

ctg ttg acc act gtg tgt gtc ggc ctt gcc atc cga acc aac aga cgg      288
Leu Leu Thr Thr Val Cys Val Gly Leu Ala Ile Arg Thr Asn Arg Arg
                85                  90                  95

atg agt cgg gga gcg agg aac aat tgg gtg tgg gat act agt tat gac      336
Met Ser Arg Gly Ala Arg Asn Asn Trp Val Trp Asp Thr Ser Tyr Asp
            100                 105                 110

tgg aag aag gag atc gta gtg gtt acg gga gga gct gcc ggg ttt ggt      384
Trp Lys Lys Glu Ile Val Val Val Thr Gly Gly Ala Ala Gly Phe Gly
        115                 120                 125

gca gac atc gta caa cag cta gac acg cgt gga atc cag gtc gtc gtc      432
Ala Asp Ile Val Gln Gln Leu Asp Thr Arg Gly Ile Gln Val Val Val
    130                 135                 140
```

```
ttg gat gtg gga tcc ctc acc tat agg cct tcg agc aga gtt cat tat      480
Leu Asp Val Gly Ser Leu Thr Tyr Arg Pro Ser Ser Arg Val His Tyr
145                 150                 155                 160

tac aag tgc gac gtg tcg aac cca caa gac gtc gcc agc gtg gct aaa      528
Tyr Lys Cys Asp Val Ser Asn Pro Gln Asp Val Ala Ser Val Ala Lys
                165                 170                 175

gct atc gta tcc aac gtc ggg cac ccg acc ata ttg gtc aac aac gct      576
Ala Ile Val Ser Asn Val Gly His Pro Thr Ile Leu Val Asn Asn Ala
            180                 185                 190

ggc gta ttc agg ggt gcg act att ctc tcc acg aca ccg cgc gac ctc      624
Gly Val Phe Arg Gly Ala Thr Ile Leu Ser Thr Thr Pro Arg Asp Leu
        195                 200                 205

gac atg acc tac gac atc aac gtc aaa gcg cac tat cat ctc acg aag      672
Asp Met Thr Tyr Asp Ile Asn Val Lys Ala His Tyr His Leu Thr Lys
    210                 215                 220

gcg ttc ctc ccg aac atg atc tcc aag aac cat gga cat att gtg act      720
Ala Phe Leu Pro Asn Met Ile Ser Lys Asn His Gly His Ile Val Thr
225                 230                 235                 240

gtg tca agc gcg acc gca tac gct caa gct tgt tct ggc gtg tca tac      768
Val Ser Ser Ala Thr Ala Tyr Ala Gln Ala Cys Ser Gly Val Ser Tyr
                245                 250                 255

tgt tcc tca aag gcc gcc atc ttg tca ttt cac gaa gga ctg agc gaa      816
Cys Ser Ser Lys Ala Ala Ile Leu Ser Phe His Glu Gly Leu Ser Glu
            260                 265                 270

gag att ttg tgg atc tat aag gcg ccc aaa gtc cgg acc tcg gtc atc      864
Glu Ile Leu Trp Ile Tyr Lys Ala Pro Lys Val Arg Thr Ser Val Ile
        275                 280                 285

tgc ccc gga cac gtc aat acg gcc atg ttt aca ggc att gga gcc gcc      912
Cys Pro Gly His Val Asn Thr Ala Met Phe Thr Gly Ile Gly Ala Ala
    290                 295                 300

gct ccc tcg ttc atg gca cct gca ctt cat ccc tcg aca gtc gcc gag      960
Ala Pro Ser Phe Met Ala Pro Ala Leu His Pro Ser Thr Val Ala Glu
305                 310                 315                 320

aca atc gtc gat gta ttg ctc tca tgc gag tct caa cac gtc ctg atg     1008
Thr Ile Val Asp Val Leu Leu Ser Cys Glu Ser Gln His Val Leu Met
                325                 330                 335

ccc gcc gcc atg cac atg tca gtc gcc gga cga gcg ctg ccc acc tgg     1056
Pro Ala Ala Met His Met Ser Val Ala Gly Arg Ala Leu Pro Thr Trp
            340                 345                 350

ttc ttc cgg ggg ttg ttg gca tcg ggc aag gat acc atg ggt agc gtt     1104
Phe Phe Arg Gly Leu Leu Ala Ser Gly Lys Asp Thr Met Gly Ser Val
        355                 360                 365

gtc cgc cga tga                                                     1116
Val Arg Arg
    370


<210> SEQ ID NO 140
<211> LENGTH: 371
<212> TYPE: PRT
<213> ORGANISM: Filobasidium magnum

<400> SEQUENCE: 140

Met Pro Thr Pro Ile Phe Gly Ala Arg Glu Gly Phe Thr Ile Asp Ser
1               5                   10                  15

Val Leu Ser Ile Leu Asp Ala Thr Val Leu Asn Pro Trp Phe Thr Gly
            20                  25                  30

Val Cys Leu Ile Ala Val Cys Ala Arg Asp Arg Thr Ile Thr Tyr Pro
        35                  40                  45

Asp Trp Pro Ala Ala Leu Asp Gln Val Leu Pro Phe Leu Ser Gln Met
```

-continued

```
    50                  55                  60

Trp Arg Glu Thr Val Arg Pro Thr Phe Gly Asp Arg Asn Val Leu His
65                  70                  75                  80

Leu Leu Thr Thr Val Cys Val Gly Leu Ala Ile Arg Thr Asn Arg Arg
                85                  90                  95

Met Ser Arg Gly Ala Arg Asn Asn Trp Val Trp Asp Thr Ser Tyr Asp
            100                 105                 110

Trp Lys Lys Glu Ile Val Val Val Thr Gly Gly Ala Ala Gly Phe Gly
        115                 120                 125

Ala Asp Ile Val Gln Gln Leu Asp Thr Arg Gly Ile Gln Val Val Val
    130                 135                 140

Leu Asp Val Gly Ser Leu Thr Tyr Arg Pro Ser Ser Arg Val His Tyr
145                 150                 155                 160

Tyr Lys Cys Asp Val Ser Asn Pro Gln Asp Val Ala Ser Val Ala Lys
                165                 170                 175

Ala Ile Val Ser Asn Val Gly His Pro Thr Ile Leu Val Asn Asn Ala
            180                 185                 190

Gly Val Phe Arg Gly Ala Thr Ile Leu Ser Thr Thr Pro Arg Asp Leu
        195                 200                 205

Asp Met Thr Tyr Asp Ile Asn Val Lys Ala His Tyr His Leu Thr Lys
    210                 215                 220

Ala Phe Leu Pro Asn Met Ile Ser Lys Asn His Gly His Ile Val Thr
225                 230                 235                 240

Val Ser Ser Ala Thr Ala Tyr Ala Gln Ala Cys Ser Gly Val Ser Tyr
                245                 250                 255

Cys Ser Ser Lys Ala Ala Ile Leu Ser Phe His Glu Gly Leu Ser Glu
            260                 265                 270

Glu Ile Leu Trp Ile Tyr Lys Ala Pro Lys Val Arg Thr Ser Val Ile
        275                 280                 285

Cys Pro Gly His Val Asn Thr Ala Met Phe Thr Gly Ile Gly Ala Ala
    290                 295                 300

Ala Pro Ser Phe Met Ala Pro Ala Leu His Pro Ser Thr Val Ala Glu
305                 310                 315                 320

Thr Ile Val Asp Val Leu Leu Ser Cys Glu Ser Gln His Val Leu Met
                325                 330                 335

Pro Ala Ala Met His Met Ser Val Ala Gly Arg Ala Leu Pro Thr Trp
            340                 345                 350

Phe Phe Arg Gly Leu Leu Ala Ser Gly Lys Asp Thr Met Gly Ser Val
        355                 360                 365

Val Arg Arg
    370
```

<210> SEQ ID NO 141
<211> LENGTH: 1116
<212> TYPE: DNA
<213> ORGANISM: Filobasidium magnum

<400> SEQUENCE: 141

```
atgccaactc caatcttcgg tgctagagaa ggtttcacta tcgactctgt tttgtctatc      60

ttggacgcta ctgttttgaa cccatggttc actggtgttt gtttgatcgc tgtttgtgct     120

agagacagaa ctatcactta cccagactgg ccagctgctt tggaccaagt tttgccattc     180

ttgtctcaaa tgtggagaga aactgttaga ccaactttcg gtgacagaaa cgttttgcac     240

ttgttgacta ctgtttgtgt tggtttggct atcagaacta acagaagaat gtctagaggt     300
```

```
gctagaaaca actgggtttg ggacacttct tacgactgga agaaggaaat cgttgttgtt    360

actggtggtg ctgctggttt cggtgctgac atcgttcaac aattggacac tagaggtatc    420

caagttgttg ttttggacgt tggttctttg acttacagac catcttctag agttcactac    480

tacaagtgtg acgtttctaa cccacaagac gttgcttctg ttgctaaggc tatcgtttct    540

aacgttggtc acccaactat cttggttaac aacgctggtg ttttcagagg tgctactatc    600

ttgtctacta ctccaagaga cttggacatg acttacgaca tcaacgttaa ggctcactac    660

cacttgacta aggctttctt gccaaacatg atctctaaga accacggtca catcgttact    720

gtttcttctg ctactgctta cgctcaagct tgttctggtg tttcttactg ttcttctaag    780

gctgctatct tgtctttcca cgaaggtttg tctgaagaaa tcttgtggat ctacaaggct    840

ccaaaggtta gaacttctgt tatctgtcca ggtcacgtta acactgctat gttcactggt    900

atcggtgctg ctgctccatc tttcatggct ccagctttgc acccatctac tgttgctgaa    960

actatcgttg acgttttgtt gtcttgtgaa tctcaacacg ttttgatgcc agctgctatg   1020

cacatgtctg ttgctggtag agctttgcca acttggttct tcagaggttt gttggcttct   1080

ggtaaggaca ctatgggttc tgttgttaga agataa                             1116


<210> SEQ ID NO 142
<211> LENGTH: 1023
<212> TYPE: DNA
<213> ORGANISM: Filobasidium magnum
<220> FEATURE:
<221> NAME/KEY: CDS
<222> LOCATION: (1)..(1023)

<400> SEQUENCE: 142

atg gag cca ccc cag act atg aag gcc gcc ttg gtc acc gca tac aac       48
Met Glu Pro Pro Gln Thr Met Lys Ala Ala Leu Val Thr Ala Tyr Asn
1               5                   10                  15

gag ccc ctg att gtg aaa gac gtt gct aca ccc gag ccg ggc cct gga       96
Glu Pro Leu Ile Val Lys Asp Val Ala Thr Pro Glu Pro Gly Pro Gly
            20                  25                  30

cag att ctc gtt cgg gtc aaa gct agt tcg ctt tgc atg tca gat atc      144
Gln Ile Leu Val Arg Val Lys Ala Ser Ser Leu Cys Met Ser Asp Ile
        35                  40                  45

gga ggc tat gtc gga gcg atg ggg gaa ttt atc acg ctc ccc tat tgt      192
Gly Gly Tyr Val Gly Ala Met Gly Glu Phe Ile Thr Leu Pro Tyr Cys
    50                  55                  60

cca ggt cat gaa ccc gcc gga gag atc gtc gcc ctt ggc gac aac gtg      240
Pro Gly His Glu Pro Ala Gly Glu Ile Val Ala Leu Gly Asp Asn Val
65                  70                  75                  80

tcc ggc ttc tcc gtt ggg gat cgg gtt act tat atg gcc gct cta gat      288
Ser Gly Phe Ser Val Gly Asp Arg Val Thr Tyr Met Ala Ala Leu Asp
                85                  90                  95

cct tgt atg ggc tgc cga gac tgt ctc cga ggt gcc att cga ttc tgc      336
Pro Cys Met Gly Cys Arg Asp Cys Leu Arg Gly Ala Ile Arg Phe Cys
            100                 105                 110

tcc aaa cgc tcg aat ctc ggc ttc agc cac cag tac ggc ggg ttc tcc      384
Ser Lys Arg Ser Asn Leu Gly Phe Ser His Gln Tyr Gly Gly Phe Ser
        115                 120                 125

gag tac tct ctc gcc agc cca tac tcg atg gcc aag gtg ccg gac gaa      432
Glu Tyr Ser Leu Ala Ser Pro Tyr Ser Met Ala Lys Val Pro Asp Glu
    130                 135                 140

ctg tcc ctc gag gaa gct gcg agc atg tcc tgt gcc ggg gtg acc gct      480
Leu Ser Leu Glu Glu Ala Ala Ser Met Ser Cys Ala Gly Val Thr Ala
145                 150                 155                 160
```

```
ttc ggt gct ctc aag cta ttg agc aag tat cag gct ccg gga ggc atc      528
Phe Gly Ala Leu Lys Leu Leu Ser Lys Tyr Gln Ala Pro Gly Gly Ile
                165                 170                 175

atc aat gtc ttg ggc tgc ggc ggc gtt ggt cat ctg gtc atc aag ttt      576
Ile Asn Val Leu Gly Cys Gly Gly Val Gly His Leu Val Ile Lys Phe
            180                 185                 190

gcc gtc gcg ctc ggc tac acc gtg cac gct ttc gac att aac gat ggc      624
Ala Val Ala Leu Gly Tyr Thr Val His Ala Phe Asp Ile Asn Asp Gly
        195                 200                 205

aaa ctc aaa ctg gcc gag gag tgc ggg gca tct aaa gcc ttc ctt tca      672
Lys Leu Lys Leu Ala Glu Glu Cys Gly Ala Ser Lys Ala Phe Leu Ser
    210                 215                 220

aag gga gat ccc acc cag gcg atg atg gca gag agt acg ata gtc atc      720
Lys Gly Asp Pro Thr Gln Ala Met Met Ala Glu Ser Thr Ile Val Ile
225                 230                 235                 240

tcg ggt gtc aac gcg gcc tat gat ttc gct att aaa gct act ctg gcc      768
Ser Gly Val Asn Ala Ala Tyr Asp Phe Ala Ile Lys Ala Thr Leu Ala
                245                 250                 255

ggt gga cgt atc att gcg att ggg cac cca cat tcg gcg act ccg atg      816
Gly Gly Arg Ile Ile Ala Ile Gly His Pro His Ser Ala Thr Pro Met
            260                 265                 270

cct ctc ggc tcg atg atc atc aac gac atc tcg ttg atc gtg agc aat      864
Pro Leu Gly Ser Met Ile Ile Asn Asp Ile Ser Leu Ile Val Ser Asn
        275                 280                 285

caa ggt aca agg gtg gat cta caa gaa gcc ttg gat ttc gcc gct cga      912
Gln Gly Thr Arg Val Asp Leu Gln Glu Ala Leu Asp Phe Ala Ala Arg
    290                 295                 300

tcc ggt gtc aga ccg aac att aca atc aac gaa ggt ctg gac ggc atc      960
Ser Gly Val Arg Pro Asn Ile Thr Ile Asn Glu Gly Leu Asp Gly Ile
305                 310                 315                 320

aat cag ggc tat aaa tcg gtc atg aca ggc gct gta gaa ggc aga ttg     1008
Asn Gln Gly Tyr Lys Ser Val Met Thr Gly Ala Val Glu Gly Arg Leu
                325                 330                 335

gtc tac aaa ttc tag                                                 1023
Val Tyr Lys Phe
            340
```

<210> SEQ ID NO 143
<211> LENGTH: 340
<212> TYPE: PRT
<213> ORGANISM: Filobasidium magnum

<400> SEQUENCE: 143

```
Met Glu Pro Pro Gln Thr Met Lys Ala Ala Leu Val Thr Ala Tyr Asn
1               5                   10                  15

Glu Pro Leu Ile Val Lys Asp Val Ala Thr Pro Glu Pro Gly Pro Gly
            20                  25                  30

Gln Ile Leu Val Arg Val Lys Ala Ser Ser Leu Cys Met Ser Asp Ile
        35                  40                  45

Gly Gly Tyr Val Gly Ala Met Gly Glu Phe Ile Thr Leu Pro Tyr Cys
    50                  55                  60

Pro Gly His Glu Pro Ala Gly Glu Ile Val Ala Leu Gly Asp Asn Val
65                  70                  75                  80

Ser Gly Phe Ser Val Gly Asp Arg Val Thr Tyr Met Ala Ala Leu Asp
                85                  90                  95

Pro Cys Met Gly Cys Arg Asp Cys Leu Arg Gly Ala Ile Arg Phe Cys
            100                 105                 110

Ser Lys Arg Ser Asn Leu Gly Phe Ser His Gln Tyr Gly Gly Phe Ser
```

```
        115                 120                 125

Glu Tyr Ser Leu Ala Ser Pro Tyr Ser Met Ala Lys Val Pro Asp Glu
    130                 135                 140

Leu Ser Leu Glu Glu Ala Ala Ser Met Ser Cys Ala Gly Val Thr Ala
145                 150                 155                 160

Phe Gly Ala Leu Lys Leu Leu Ser Lys Tyr Gln Ala Pro Gly Gly Ile
                165                 170                 175

Ile Asn Val Leu Gly Cys Gly Gly Val Gly His Leu Val Ile Lys Phe
            180                 185                 190

Ala Val Ala Leu Gly Tyr Thr Val His Ala Phe Asp Ile Asn Asp Gly
        195                 200                 205

Lys Leu Lys Leu Ala Glu Glu Cys Gly Ala Ser Lys Ala Phe Leu Ser
    210                 215                 220

Lys Gly Asp Pro Thr Gln Ala Met Met Ala Glu Ser Thr Ile Val Ile
225                 230                 235                 240

Ser Gly Val Asn Ala Ala Tyr Asp Phe Ala Ile Lys Ala Thr Leu Ala
                245                 250                 255

Gly Gly Arg Ile Ile Ala Ile Gly His Pro His Ser Ala Thr Pro Met
            260                 265                 270

Pro Leu Gly Ser Met Ile Ile Asn Asp Ile Ser Leu Ile Val Ser Asn
        275                 280                 285

Gln Gly Thr Arg Val Asp Leu Gln Glu Ala Leu Asp Phe Ala Ala Arg
    290                 295                 300

Ser Gly Val Arg Pro Asn Ile Thr Ile Asn Glu Gly Leu Asp Gly Ile
305                 310                 315                 320

Asn Gln Gly Tyr Lys Ser Val Met Thr Gly Ala Val Glu Gly Arg Leu
                325                 330                 335

Val Tyr Lys Phe
            340


<210> SEQ ID NO 144
<211> LENGTH: 1023
<212> TYPE: DNA
<213> ORGANISM: Filobasidium magnum

<400> SEQUENCE: 144

atggaaccac cacaaactat gaaggctgct ttggttactg cttacaacga accattgatc     60

gttaaggacg ttgctactcc agaaccaggt ccaggtcaaa tcttggttag agttaaggct    120

tcttctttgt gtatgtctga catcggtggt tacgttggtg ctatgggtga attcatcact    180

ttgccatact gtccaggtca cgaaccagct ggtgaaatcg ttgctttggg tgacaacgtt    240

tctggtttct ctgttggtga cagagttact tacatggctg ctttggaccc atgtatgggt    300

tgtagagact gtttgagagg tgctatcaga ttctgttcta agagatctaa cttgggtttc    360

tctcaccaat acggtggttt ctctgaatac tctttggctt ctccatactc tatggctaag    420

gttccagacg aattgtcttt ggaagaagct gcttctatgt cttgtgctgg tgttactgct    480

ttcggtgctt tgaagttgtt gtctaagtac caagctccag gtggtatcat caacgttttg    540

ggttgtggtg gtgttggtca cttggttatc aagttcgctg ttgctttggg ttacactgtt    600

cacgctttcg acatcaacga cggtaagttg aagttggctg aagaatgtgg tgcttctaag    660

gctttcttgt ctaagggtga cccaactcaa gctatgatgg ctgaatctac tatcgttatc    720

tctggtgtta acgctgctta cgacttcgct atcaaggcta ctttggctgg tggtagaatc    780

atcgctatcg gtcacccaca ctctgctact ccaatgccat tgggttctat gatcatcaac    840
```

```
gacatctctt tgatcgtttc taaccaaggt actagagttg acttgcaaga agctttggac    900

ttcgctgcta gatctggtgt tagaccaaac atcactatca acgaaggttt ggacggtatc    960

aaccaaggtt acaagtctgt tatgactggt gctgttgaag gtagattggt ttacaagttc   1020

taa                                                                 1023


<210> SEQ ID NO 145
<211> LENGTH: 1038
<212> TYPE: DNA
<213> ORGANISM: Rhodococcus sp.
<220> FEATURE:
<221> NAME/KEY: CDS
<222> LOCATION: (1)..(1038)

<400> SEQUENCE: 145

atg aaa gcc gtc cag tac acc gag atc ggc tcc gag ccg gtc gtt gtc      48
Met Lys Ala Val Gln Tyr Thr Glu Ile Gly Ser Glu Pro Val Val Val
1               5                   10                  15

gac atc ccc acc ccg acg ccc ggg ccg ggt gag atc ctg ctg aag gtc      96
Asp Ile Pro Thr Pro Thr Pro Gly Pro Gly Glu Ile Leu Leu Lys Val
            20                  25                  30

acc gcg gcc ggg ctg tgc cac tcg gac atc ttc gtg atg gac atg ccg     144
Thr Ala Ala Gly Leu Cys His Ser Asp Ile Phe Val Met Asp Met Pro
        35                  40                  45

gcg gcg cag tac gcc tac ggc ctg ccg ctc acc ctc ggc cac gag ggt     192
Ala Ala Gln Tyr Ala Tyr Gly Leu Pro Leu Thr Leu Gly His Glu Gly
    50                  55                  60

gtc ggc acc gtc gcc gaa ctc ggc gag ggc gtc acg gga ttc ggg gtg     240
Val Gly Thr Val Ala Glu Leu Gly Glu Gly Val Thr Gly Phe Gly Val
65                  70                  75                  80

ggg gac gcc gtc gcc gtg tac ggg ccg tgg ggc tgc ggt gcg tgc cac     288
Gly Asp Ala Val Ala Val Tyr Gly Pro Trp Gly Cys Gly Ala Cys His
                85                  90                  95

gcc tgc gcg cgc ggc cgg gag aac tac tgc acc cgc gcc gcc gac ctg     336
Ala Cys Ala Arg Gly Arg Glu Asn Tyr Cys Thr Arg Ala Ala Asp Leu
            100                 105                 110

ggc atc acg cca ccc ggt ctc ggc tcg ccc gga tcg atg gcc gag tac     384
Gly Ile Thr Pro Pro Gly Leu Gly Ser Pro Gly Ser Met Ala Glu Tyr
        115                 120                 125

atg atc gtc gat tcg gcg cgc cac ctc gtc ccg atc gga gac ctc gac     432
Met Ile Val Asp Ser Ala Arg His Leu Val Pro Ile Gly Asp Leu Asp
    130                 135                 140

ccg gtc gcc gcg gcg ccg ctc acc gac gcc ggt ctg acg ccg tac cac     480
Pro Val Ala Ala Ala Pro Leu Thr Asp Ala Gly Leu Thr Pro Tyr His
145                 150                 155                 160

gcg atc tcc cgg gtc ctg ccg ctg ctg ggg ccg ggc tcg acg gcc gtc     528
Ala Ile Ser Arg Val Leu Pro Leu Leu Gly Pro Gly Ser Thr Ala Val
                165                 170                 175

gtc atc ggt gtc ggc ggg ctc ggc cac gtc ggc atc cag atc ctg cgc     576
Val Ile Gly Val Gly Gly Leu Gly His Val Gly Ile Gln Ile Leu Arg
            180                 185                 190

gcc gtc agc gcg gcc cgt gtg atc gcc gtc gac ctc gac gac gac cgt     624
Ala Val Ser Ala Ala Arg Val Ile Ala Val Asp Leu Asp Asp Asp Arg
        195                 200                 205

ctc gcc ctc gcc cgc gag gtc ggc gcc gac gcg gcg gtg aag tcg ggc     672
Leu Ala Leu Ala Arg Glu Val Gly Ala Asp Ala Ala Val Lys Ser Gly
    210                 215                 220

gcc ggt gcg gcg gac gcg atc cgg gaa ctg acc ggc ggc cag ggc gcg     720
Ala Gly Ala Ala Asp Ala Ile Arg Glu Leu Thr Gly Gly Gln Gly Ala
225                 230                 235                 240
```

-continued

```
acg gcg gtg ttc gac ttc gtc ggc gcc cag tcg acg atc gac acg gcg      768
Thr Ala Val Phe Asp Phe Val Gly Ala Gln Ser Thr Ile Asp Thr Ala
                245                 250                 255

cag cag gtg gtc gcg gtc gac ggg cac atc tcg gtc gtg ggc atc cac      816
Gln Gln Val Val Ala Val Asp Gly His Ile Ser Val Val Gly Ile His
            260                 265                 270

gcc ggc gca cac gcc aag gtc ggg ttc ttc atg atc ccg ttc ggc gcc      864
Ala Gly Ala His Ala Lys Val Gly Phe Phe Met Ile Pro Phe Gly Ala
        275                 280                 285

tcc gtc gtg acc ccg tac tgg ggc acc cgg tcg gaa ctg atg gag gtc      912
Ser Val Val Thr Pro Tyr Trp Gly Thr Arg Ser Glu Leu Met Glu Val
    290                 295                 300

gtc gcg ctg gcc cgc gcc ggc cgg ctg gac atc cac acc gag acg ttc      960
Val Ala Leu Ala Arg Ala Gly Arg Leu Asp Ile His Thr Glu Thr Phe
305                 310                 315                 320

acc ctc gac gag ggg ccg gcg gcg tac cgg cgg ctg cgc gag ggc agc     1008
Thr Leu Asp Glu Gly Pro Ala Ala Tyr Arg Arg Leu Arg Glu Gly Ser
                325                 330                 335

atc cgc ggc cgc ggc gtg gtg gtt ccc tga                             1038
Ile Arg Gly Arg Gly Val Val Val Pro
            340                 345


<210> SEQ ID NO 146
<211> LENGTH: 345
<212> TYPE: PRT
<213> ORGANISM: Rhodococcus sp.

<400> SEQUENCE: 146

Met Lys Ala Val Gln Tyr Thr Glu Ile Gly Ser Glu Pro Val Val Val
1               5                   10                  15

Asp Ile Pro Thr Pro Thr Pro Gly Pro Gly Glu Ile Leu Leu Lys Val
            20                  25                  30

Thr Ala Ala Gly Leu Cys His Ser Asp Ile Phe Val Met Asp Met Pro
        35                  40                  45

Ala Ala Gln Tyr Ala Tyr Gly Leu Pro Leu Thr Leu Gly His Glu Gly
    50                  55                  60

Val Gly Thr Val Ala Glu Leu Gly Glu Gly Val Thr Gly Phe Gly Val
65                  70                  75                  80

Gly Asp Ala Val Ala Val Tyr Gly Pro Trp Gly Cys Gly Ala Cys His
                85                  90                  95

Ala Cys Ala Arg Gly Arg Glu Asn Tyr Cys Thr Arg Ala Ala Asp Leu
            100                 105                 110

Gly Ile Thr Pro Pro Gly Leu Gly Ser Pro Gly Ser Met Ala Glu Tyr
        115                 120                 125

Met Ile Val Asp Ser Ala Arg His Leu Val Pro Ile Gly Asp Leu Asp
    130                 135                 140

Pro Val Ala Ala Ala Pro Leu Thr Asp Ala Gly Leu Thr Pro Tyr His
145                 150                 155                 160

Ala Ile Ser Arg Val Leu Pro Leu Leu Gly Pro Gly Ser Thr Ala Val
                165                 170                 175

Val Ile Gly Val Gly Gly Leu Gly His Val Gly Ile Gln Ile Leu Arg
            180                 185                 190

Ala Val Ser Ala Ala Arg Val Ile Ala Val Asp Leu Asp Asp Asp Arg
        195                 200                 205

Leu Ala Leu Ala Arg Glu Val Gly Ala Asp Ala Ala Val Lys Ser Gly
    210                 215                 220
```

-continued

```
Ala Gly Ala Ala Asp Ala Ile Arg Glu Leu Thr Gly Gly Gln Gly Ala
225                 230                 235                 240

Thr Ala Val Phe Asp Phe Val Gly Ala Gln Ser Thr Ile Asp Thr Ala
                245                 250                 255

Gln Gln Val Val Ala Val Asp Gly His Ile Ser Val Val Gly Ile His
            260                 265                 270

Ala Gly Ala His Ala Lys Val Gly Phe Phe Met Ile Pro Phe Gly Ala
        275                 280                 285

Ser Val Val Thr Pro Tyr Trp Gly Thr Arg Ser Glu Leu Met Glu Val
    290                 295                 300

Val Ala Leu Ala Arg Ala Gly Arg Leu Asp Ile His Thr Glu Thr Phe
305                 310                 315                 320

Thr Leu Asp Glu Gly Pro Ala Ala Tyr Arg Arg Leu Arg Glu Gly Ser
                325                 330                 335

Ile Arg Gly Arg Gly Val Val Val Pro
            340                 345
```

<210> SEQ ID NO 147
<211> LENGTH: 1038
<212> TYPE: DNA
<213> ORGANISM: Rhodococcus sp.

<400> SEQUENCE: 147

```
atgaaagcag tgcaatatac ggaaattggc tcggaacctg ttgtggtgga catcccgacc     60

ccgaccccgg gtcctggtga aatcctgctg aaagttaccg ctgccggcct gtgccacagc    120

gacatcttcg tgatggacat gccggctgcc cagtacgctt acggtctgcc actgacgctg    180

ggtcacgaag gcgtgggtac ggtcgccgaa ctgggcgagg gtgtcaccgg tttcggtgtc    240

ggtgatgccg tggcagtgta cggtccgtgg ggttgcggtg cgtgccacgc gtgtgcgcgc    300

ggccgcgaga attactgtac gcgtgcagcg gacctgggta ttaccccgcc gggcctgggc    360

agcccgggta gcatggcaga gtacatgatc gttgatagcg cacgtcatct ggtgccgatt    420

ggcgatttgg acccggtcgc ggcagccccg ctgactgacg cgggcttgac cccgtatcat    480

gcaatctccc gtgtactgcc actgctcggt ccgggcagca ccgctgtggt tatcggcgtc    540

ggtggcctgg gtcatgttgg catccagatt ctgcgtgcag tcagcgcggc acgcgtgatc    600

gcggttgatc tggacgacga tcgcctggcc ctggcgcgtg aggtcggtgc ggatgctgcg    660

gttaagtctg gtgccggtgc agcggatgcg attcgtgagc tgacgggtgg ccagggtgcg    720

accgccgtgt ttgatttcgt tggcgcgcag agcaccattg atacggcgca acaagtcgtt    780

gcggtcgatg gtcacatttc cgttgtgggt atccacgcgg gtgcacatgc caaggtcggc    840

tttttcatga tcccgtttgg tgctagcgtt gttaccccgt attggggcac gcgcagcgag    900

ctgatggaag tcgtggcttt ggcgcgtgcg ggtcgtctgg acattcacac cgagactttc    960

accttggacg aaggcccggc agcgtatcgt cgtctgcgcg agggtagcat tcgtggccgt   1020

ggtgttgttg tcccgtaa                                                 1038
```

<210> SEQ ID NO 148
<211> LENGTH: 1113
<212> TYPE: DNA
<213> ORGANISM: Rhodococcus rhodochrous
<220> FEATURE:
<221> NAME/KEY: CDS
<222> LOCATION: (1)..(1113)

<400> SEQUENCE: 148

-continued

```
atg aag acc aaa gct gct gta ctg ctc gag ccc gga aag cct ttc gag       48
Met Lys Thr Lys Ala Ala Val Leu Leu Glu Pro Gly Lys Pro Phe Glu
1               5                   10                  15

atc atg gaa ctc gac ctc gac ggc ccg ggt gtg ggt gag gta ctg atc       96
Ile Met Glu Leu Asp Leu Asp Gly Pro Gly Val Gly Glu Val Leu Ile
            20                  25                  30

aag tac acc gct gcc gga ctg tgc cat tcg gat ctg cac ctg acc gac      144
Lys Tyr Thr Ala Ala Gly Leu Cys His Ser Asp Leu His Leu Thr Asp
        35                  40                  45

ggt gat ctc ccg ccg cgt tac ccg atc gtc ggc gga cac gaa ggc tcg      192
Gly Asp Leu Pro Pro Arg Tyr Pro Ile Val Gly Gly His Glu Gly Ser
    50                  55                  60

ggc atc atc gaa gag gtc ggc cca ggc gtc acg aag gtc aag ccg ggc      240
Gly Ile Ile Glu Glu Val Gly Pro Gly Val Thr Lys Val Lys Pro Gly
65                  70                  75                  80

gac cat gtc gtg tgt agc ttc atc ccc aac tgc ggc acc tgt cgc tac      288
Asp His Val Val Cys Ser Phe Ile Pro Asn Cys Gly Thr Cys Arg Tyr
                85                  90                  95

tgc tcg acc ggt cgc cag aac ctc tgc gac atg ggt gcc acc atc ctc      336
Cys Ser Thr Gly Arg Gln Asn Leu Cys Asp Met Gly Ala Thr Ile Leu
            100                 105                 110

gaa ggc tcg atg ccc gac ggt tcc ttc cgt ttc cac ggc aac gga atg      384
Glu Gly Ser Met Pro Asp Gly Ser Phe Arg Phe His Gly Asn Gly Met
        115                 120                 125

gat ttc ggc gga atg tgc atg ttg gga acg ttc tcc gag cgc gcc acc      432
Asp Phe Gly Gly Met Cys Met Leu Gly Thr Phe Ser Glu Arg Ala Thr
    130                 135                 140

att tct cag cac tcg gta gtc aag atc gac gac tgg ctt ccc ttg gag      480
Ile Ser Gln His Ser Val Val Lys Ile Asp Asp Trp Leu Pro Leu Glu
145                 150                 155                 160

aca gcg gtg gtc gtc ggc tgc ggc gtg cct tcg ggt tgg gga acg gca      528
Thr Ala Val Val Val Gly Cys Gly Val Pro Ser Gly Trp Gly Thr Ala
                165                 170                 175

gta aat gcc ggt aac ctt cgc gcc ggt gac acc gct gtg atc tac ggc      576
Val Asn Ala Gly Asn Leu Arg Ala Gly Asp Thr Ala Val Ile Tyr Gly
            180                 185                 190

atc ggt ggt ctc ggc atc aac gcc gtc cag ggc gcc gtt tcg gcc ggc      624
Ile Gly Gly Leu Gly Ile Asn Ala Val Gln Gly Ala Val Ser Ala Gly
        195                 200                 205

tgc aag tac gtc gtt gtg gtc gat ccg gtt gct ctc aag cgt gag acc      672
Cys Lys Tyr Val Val Val Val Asp Pro Val Ala Leu Lys Arg Glu Thr
    210                 215                 220

gca ctg aag ttc ggt gca acc cat gcc ttt gca gac gcc gag agc gct      720
Ala Leu Lys Phe Gly Ala Thr His Ala Phe Ala Asp Ala Glu Ser Ala
225                 230                 235                 240

gct gcc aag gtc aac gag ctg acg tgg gga cag ggt gcc gac gct gcg      768
Ala Ala Lys Val Asn Glu Leu Thr Trp Gly Gln Gly Ala Asp Ala Ala
                245                 250                 255

ctc atc ctt gtc ggc acc gtc gac gag gac gtg gtc agt gca gcg acg      816
Leu Ile Leu Val Gly Thr Val Asp Glu Asp Val Val Ser Ala Ala Thr
            260                 265                 270

gca gtg atc ggc aag ggt ggc acc gtg gtg atc acg gga ctc gcc gac      864
Ala Val Ile Gly Lys Gly Gly Thr Val Val Ile Thr Gly Leu Ala Asp
        275                 280                 285

ccc gcc aag ctg acc gtt cac gtg tcg ggt acc gac ctg acg ctg aat      912
Pro Ala Lys Leu Thr Val His Val Ser Gly Thr Asp Leu Thr Leu Asn
    290                 295                 300

cag aag acg atc aag ggc acg ttg ttc ggg tcc atg aat ccg cag tac      960
Gln Lys Thr Ile Lys Gly Thr Leu Phe Gly Ser Met Asn Pro Gln Tyr
305                 310                 315                 320
```

```
gac atc gtg cga ctg ctg cgt ctc tac gat gcc ggt cag ctc aag ctc      1008
Asp Ile Val Arg Leu Leu Arg Leu Tyr Asp Ala Gly Gln Leu Lys Leu
                325                 330                 335

gac gaa ctg atc acc aac acc tac agc ctc gaa gac gtc aac aag ggc      1056
Asp Glu Leu Ile Thr Asn Thr Tyr Ser Leu Glu Asp Val Asn Lys Gly
            340                 345                 350

tac cag gat cta cgt gac ggc aag aac atc cgt ggc gtg atc att cac      1104
Tyr Gln Asp Leu Arg Asp Gly Lys Asn Ile Arg Gly Val Ile Ile His
        355                 360                 365

gac aag taa                                                          1113
Asp Lys
    370
```

<210> SEQ ID NO 149
<211> LENGTH: 370
<212> TYPE: PRT
<213> ORGANISM: Rhodococcus rhodochrous

<400> SEQUENCE: 149

```
Met Lys Thr Lys Ala Ala Val Leu Leu Glu Pro Gly Lys Pro Phe Glu
1               5                   10                  15

Ile Met Glu Leu Asp Leu Asp Gly Pro Gly Val Gly Glu Val Leu Ile
            20                  25                  30

Lys Tyr Thr Ala Ala Gly Leu Cys His Ser Asp Leu His Leu Thr Asp
        35                  40                  45

Gly Asp Leu Pro Pro Arg Tyr Pro Ile Val Gly Gly His Glu Gly Ser
    50                  55                  60

Gly Ile Ile Glu Glu Val Gly Pro Gly Val Thr Lys Val Lys Pro Gly
65                  70                  75                  80

Asp His Val Val Cys Ser Phe Ile Pro Asn Cys Gly Thr Cys Arg Tyr
                85                  90                  95

Cys Ser Thr Gly Arg Gln Asn Leu Cys Asp Met Gly Ala Thr Ile Leu
            100                 105                 110

Glu Gly Ser Met Pro Asp Gly Ser Phe Arg Phe His Gly Asn Gly Met
        115                 120                 125

Asp Phe Gly Gly Met Cys Met Leu Gly Thr Phe Ser Glu Arg Ala Thr
    130                 135                 140

Ile Ser Gln His Ser Val Val Lys Ile Asp Asp Trp Leu Pro Leu Glu
145                 150                 155                 160

Thr Ala Val Val Val Gly Cys Gly Val Pro Ser Gly Trp Gly Thr Ala
                165                 170                 175

Val Asn Ala Gly Asn Leu Arg Ala Gly Asp Thr Ala Val Ile Tyr Gly
            180                 185                 190

Ile Gly Gly Leu Gly Ile Asn Ala Val Gln Gly Ala Val Ser Ala Gly
        195                 200                 205

Cys Lys Tyr Val Val Val Val Asp Pro Val Ala Leu Lys Arg Glu Thr
    210                 215                 220

Ala Leu Lys Phe Gly Ala Thr His Ala Phe Ala Asp Ala Glu Ser Ala
225                 230                 235                 240

Ala Ala Lys Val Asn Glu Leu Thr Trp Gly Gln Gly Ala Asp Ala Ala
                245                 250                 255

Leu Ile Leu Val Gly Thr Val Asp Glu Asp Val Val Ser Ala Ala Thr
            260                 265                 270

Ala Val Ile Gly Lys Gly Gly Thr Val Val Ile Thr Gly Leu Ala Asp
        275                 280                 285
```

-continued

```
Pro Ala Lys Leu Thr Val His Val Ser Gly Thr Asp Leu Thr Leu Asn
    290                 295                 300

Gln Lys Thr Ile Lys Gly Thr Leu Phe Gly Ser Met Asn Pro Gln Tyr
305                 310                 315                 320

Asp Ile Val Arg Leu Leu Arg Leu Tyr Asp Ala Gly Gln Leu Lys Leu
                325                 330                 335

Asp Glu Leu Ile Thr Asn Thr Tyr Ser Leu Glu Asp Val Asn Lys Gly
            340                 345                 350

Tyr Gln Asp Leu Arg Asp Gly Lys Asn Ile Arg Gly Val Ile Ile His
        355                 360                 365

Asp Lys
    370
```

<210> SEQ ID NO 150
<211> LENGTH: 1113
<212> TYPE: DNA
<213> ORGANISM: Rhodococcus rhodochrous

<400> SEQUENCE: 150

```
atgaaaacga aagccgcagt gttgttggag ccgggcaaac catttgagat catggaactg      60

gatctggacg gtccgggtgt cggtgaagtg ctgatcaagt acaccgcagc gggcttgtgc     120

cactctgatc tgcacctgac cgacggcgac ttgccgccac gttacccgat tgtgggtggc     180

catgagggta gcggtatcat tgaagaggtt ggtccgggcg ttaccaaggt caaaccgggt     240

gatcacgtcg tgtgctcttt catcccgaat tgtggtacgt gccgctattg tagcacgggt     300

cgtcagaacc tgtgcgacat gggtgccacc attttagagg gctccatgcc tgatggctcc     360

ttccgttttc acggcaacgg tatggacttt ggtggcatgt gcatgctggg tacgttcagc     420

gaacgcgcga ccatcagcca acatagcgtc gttaagatcg atgactggct cccgctggaa     480

accgcagttg ttgttggttg tggtgttccg agcggttggg gtactgcggt caatgccggt     540

aatctgcgtg ctggtgacac cgcggtcatt tatggtattg gcggcctggg tatcaacgct     600

gtgcagggcg cagttagcgc gggctgcaaa tacgtcgttg tggttgaccc ggttgcgctg     660

aaacgtgaga ctgcgctgaa atttggcgca acccacgcgt tcgcagacgc ggagagcgca     720

gctgcgaaag tgaacgaact gacctggggt cagggtgcgg atgcggcact gatcttggtc     780

ggcaccgtgg acgaagatgt cgtgagcgcg gcgactgctg ttatcggtaa gggtggcacc     840

gttgtgatca ccggtctggc cgatccggca aagctgaccg ttcatgtcag cggtacggac     900

ctgaccctga atcagaaaac cattaagggc acgctgttcg gttcgatgaa cccgcagtac     960

gacattgtgc gcctgctgcg tctgtacgat gcgggtcaac tgaaactgga cgaacttatt    1020

acgaatacgt atagcctgga agatgtgaac aaaggctacc aagatctgcg tgatggtaag    1080

aatattcgtg gtgtcattat ccacgacaag tga                                 1113
```

<210> SEQ ID NO 151
<211> LENGTH: 1041
<212> TYPE: DNA
<213> ORGANISM: Rhodococcus rhodochrous
<220> FEATURE:
<221> NAME/KEY: CDS
<222> LOCATION: (1)..(1041)

<400> SEQUENCE: 151

```
atg aag gca gcc cag ctc atg ggg ccc ggg ctc ctg gaa atc aac gac       48
Met Lys Ala Ala Gln Leu Met Gly Pro Gly Leu Leu Glu Ile Asn Asp
1               5                   10                  15
```

-continued

```
gtg ccg gtc ccg gag atc ggc ccg tcg gaa cta ctg att cgg gtg ggc       96
Val Pro Val Pro Glu Ile Gly Pro Ser Glu Leu Leu Ile Arg Val Gly
            20                  25                  30

gca gcg gga atc tgc cac tcc gat ctc cat ctc ctg cac ttt ccg tac      144
Ala Ala Gly Ile Cys His Ser Asp Leu His Leu Leu His Phe Pro Tyr
        35                  40                  45

aag atg cgc gaa gaa ccg ctg aca atc ggc cac gaa att gcc gga acg      192
Lys Met Arg Glu Glu Pro Leu Thr Ile Gly His Glu Ile Ala Gly Thr
    50                  55                  60

atc gaa gcc gtc ggg agt ggc gtc gac ggc cgt tcc gtc gga gag cgt      240
Ile Glu Ala Val Gly Ser Gly Val Asp Gly Arg Ser Val Gly Glu Arg
65                  70                  75                  80

ggc gtc gtc tac ctc tgt tgg tca tgt gga cag tgc cga gaa tgc atg      288
Gly Val Val Tyr Leu Cys Trp Ser Cys Gly Gln Cys Arg Glu Cys Met
                85                  90                  95

agc ggc aac gag aat atg tgc ctc gcc gct gga cgc acc gcg atg ccg      336
Ser Gly Asn Glu Asn Met Cys Leu Ala Ala Gly Arg Thr Ala Met Pro
            100                 105                 110

ccc tgc ccc gga ctc ggc cct gag ggc ggg atg gcc gag tac gtc aag      384
Pro Cys Pro Gly Leu Gly Pro Glu Gly Gly Met Ala Glu Tyr Val Lys
        115                 120                 125

atc ccg gct cgc tca ttc gta ccc atc gga gac ctc gac ttc ctg cag      432
Ile Pro Ala Arg Ser Phe Val Pro Ile Gly Asp Leu Asp Phe Leu Gln
    130                 135                 140

gcc gca cct ctc gcc gat gcg gca ctg acg agc tac cac gcc att cgc      480
Ala Ala Pro Leu Ala Asp Ala Ala Leu Thr Ser Tyr His Ala Ile Arg
145                 150                 155                 160

ggt gcc cgc gaa cat ctc cag ccc ggt gcc acc gcc gtc gtg atc ggc      528
Gly Ala Arg Glu His Leu Gln Pro Gly Ala Thr Ala Val Val Ile Gly
                165                 170                 175

gtc ggc gga ctc ggt cac gtt gca gta cag ata ctt cgc gcg atc agt      576
Val Gly Gly Leu Gly His Val Ala Val Gln Ile Leu Arg Ala Ile Ser
            180                 185                 190

gcc gtg cgc atc atc gcc gtc gat gtc gga cag gat caa ctc gat ctc      624
Ala Val Arg Ile Ile Ala Val Asp Val Gly Gln Asp Gln Leu Asp Leu
        195                 200                 205

gcc aaa cgt tgc ggc gcc gac atc acg ctc gaa tcg gga ccg gac acc      672
Ala Lys Arg Cys Gly Ala Asp Ile Thr Leu Glu Ser Gly Pro Asp Thr
    210                 215                 220

gcg cag cac atc ctc gac ctc aca tcg gcc aga ggc gca gaa gtc atc      720
Ala Gln His Ile Leu Asp Leu Thr Ser Ala Arg Gly Ala Glu Val Ile
225                 230                 235                 240

ttc gac ttc gtc ggt atc gac gca act gca cag atg tct gtt caa gcg      768
Phe Asp Phe Val Gly Ile Asp Ala Thr Ala Gln Met Ser Val Gln Ala
                245                 250                 255

gtt gcg ccg aac ggc gcg tat cgc atg gta ggt ctc gga ggc gga aac      816
Val Ala Pro Asn Gly Ala Tyr Arg Met Val Gly Leu Gly Gly Gly Asn
            260                 265                 270

ccc gga atc act gcc gaa gct gcc ggc gga cca ggc tgg cca tgg ggc      864
Pro Gly Ile Thr Ala Glu Ala Ala Gly Gly Pro Gly Trp Pro Trp Gly
        275                 280                 285

gca tcg atc cgg aag tcc tac ggc ggc acc aga aac gac ctc gtc gat      912
Ala Ser Ile Arg Lys Ser Tyr Gly Gly Thr Arg Asn Asp Leu Val Asp
    290                 295                 300

tcc atc gcc ctg gca cag gcc ggt ctg gta acg gta gaa gta gcc cgc      960
Ser Ile Ala Leu Ala Gln Ala Gly Leu Val Thr Val Glu Val Ala Arg
305                 310                 315                 320

ttc gac ctc gct gat gcc cgc gac gca ctc gac cgt ctc gaa cac ggc     1008
Phe Asp Leu Ala Asp Ala Arg Asp Ala Leu Asp Arg Leu Glu His Gly
                325                 330                 335
```

```
aag gtc acc gga cgc gca gtg ctc gta ccc tga                         1041
Lys Val Thr Gly Arg Ala Val Leu Val Pro
            340                 345


<210> SEQ ID NO 152
<211> LENGTH: 346
<212> TYPE: PRT
<213> ORGANISM: Rhodococcus rhodochrous

<400> SEQUENCE: 152

Met Lys Ala Ala Gln Leu Met Gly Pro Gly Leu Leu Glu Ile Asn Asp
1               5                   10                  15

Val Pro Val Pro Glu Ile Gly Pro Ser Glu Leu Leu Ile Arg Val Gly
            20                  25                  30

Ala Ala Gly Ile Cys His Ser Asp Leu His Leu Leu His Phe Pro Tyr
        35                  40                  45

Lys Met Arg Glu Glu Pro Leu Thr Ile Gly His Glu Ile Ala Gly Thr
    50                  55                  60

Ile Glu Ala Val Gly Ser Gly Val Asp Gly Arg Ser Val Gly Glu Arg
65                  70                  75                  80

Gly Val Val Tyr Leu Cys Trp Ser Cys Gly Gln Cys Arg Glu Cys Met
                85                  90                  95

Ser Gly Asn Glu Asn Met Cys Leu Ala Ala Gly Arg Thr Ala Met Pro
            100                 105                 110

Pro Cys Pro Gly Leu Gly Pro Glu Gly Gly Met Ala Glu Tyr Val Lys
        115                 120                 125

Ile Pro Ala Arg Ser Phe Val Pro Ile Gly Asp Leu Asp Phe Leu Gln
    130                 135                 140

Ala Ala Pro Leu Ala Asp Ala Ala Leu Thr Ser Tyr His Ala Ile Arg
145                 150                 155                 160

Gly Ala Arg Glu His Leu Gln Pro Gly Ala Thr Ala Val Val Ile Gly
                165                 170                 175

Val Gly Gly Leu Gly His Val Ala Val Gln Ile Leu Arg Ala Ile Ser
            180                 185                 190

Ala Val Arg Ile Ile Ala Val Asp Val Gly Gln Asp Gln Leu Asp Leu
        195                 200                 205

Ala Lys Arg Cys Gly Ala Asp Ile Thr Leu Glu Ser Gly Pro Asp Thr
    210                 215                 220

Ala Gln His Ile Leu Asp Leu Thr Ser Ala Arg Gly Ala Glu Val Ile
225                 230                 235                 240

Phe Asp Phe Val Gly Ile Asp Ala Thr Ala Gln Met Ser Val Gln Ala
                245                 250                 255

Val Ala Pro Asn Gly Ala Tyr Arg Met Val Gly Leu Gly Gly Gly Asn
            260                 265                 270

Pro Gly Ile Thr Ala Glu Ala Ala Gly Gly Pro Gly Trp Pro Trp Gly
        275                 280                 285

Ala Ser Ile Arg Lys Ser Tyr Gly Gly Thr Arg Asn Asp Leu Val Asp
    290                 295                 300

Ser Ile Ala Leu Ala Gln Ala Gly Leu Val Thr Val Glu Val Ala Arg
305                 310                 315                 320

Phe Asp Leu Ala Asp Ala Arg Asp Ala Leu Asp Arg Leu Glu His Gly
                325                 330                 335

Lys Val Thr Gly Arg Ala Val Leu Val Pro
            340                 345
```

<210> SEQ ID NO 153
<211> LENGTH: 1041
<212> TYPE: DNA
<213> ORGANISM: Rhodococcus rhodochrous

<400> SEQUENCE: 153
atgaaagctg cacaactgat gggtccgggt ctgttggaaa ttaatgatgt tccagtccca 60
gaaattggtc cgagcgagct gctgatccgt gttggcgctg ccggcatttg ccacagcgat 120
ctgcatctgc tgcacttccc gtacaagatg cgtgaggaac cgttaaccat tggtcacgaa 180
atcgcgggca cgatcgaagc cgttggtagc ggtgtggatg gccgcagcgt tggtgagcgt 240
ggcgtggttt acctgtgctg gtcctgtggt cagtgccgcg agtgcatgtc cggcaatgaa 300
aacatgtgtc tggcggctgg tcgtaccgca atgccgccat gtccgggttt gggtcctgag 360
ggtggcatgg ccgaatatgt caagatcccg gcgcgtagct tcgtgccgat tggcgatctg 420
gactttctgc aggcagcgcc tttggcggac gcagcactga ccagctacca cgcgatccgt 480
ggtgcccgcg aacacttgca gccgggtgca accgcagtgg tcattggtgt cggcggcttg 540
ggtcatgtgg cagtgcaaat cctgcgcgcg atttctgcgg tccgtatcat tgcggttgat 600
gtgggccagg accaactgga cctggcgaag cgttgtggcg cggacatcac cctggagagc 660
ggtcctgaca ccgcgcaaca tatcctggac ctgacctccg ctcgtggtgc cgaagtgatt 720
tttgacttcg tcggtatcga tgcgacggca cagatgagcg tccaagcggt agccccgaat 780
ggcgcatacc gtatggttgg tctgggtggt ggcaacccgg gcattactgc agaggcagcg 840
ggtggtcctg gttggccgtg ggtgcttcg atccgcaaaa gctatggcgg cacgcgtaac 900
gacctggttg attctattgc gttggcccag gctggtcttg ttaccgttga agtggcgcgc 960
tttgacctgg cagacgcccg tgatgcgctg gaccgtctgg agcatggtaa agtgacgggt 1020
cgcgctgtgc tggtgccgta a 1041

<210> SEQ ID NO 154
<211> LENGTH: 1047
<212> TYPE: DNA
<213> ORGANISM: Rhodococcus rhodochrous
<220> FEATURE:
<221> NAME/KEY: CDS
<222> LOCATION: (1)..(1047)

<400> SEQUENCE: 154 atg aag gca atc cag tac acg aga atc ggc gca gaa ccc gaa ctc acg 48
Met Lys Ala Ile Gln Tyr Thr Arg Ile Gly Ala Glu Pro Glu Leu Thr
1 5 10 15 gag att ccc aaa ccc gag ccc ggt cca ggt gaa gtg ctc ctg gaa gtc 96
Glu Ile Pro Lys Pro Glu Pro Gly Pro Gly Glu Val Leu Leu Glu Val
20 25 30 acc gct gcc ggc gtc tgc cac tcg gac gac ttc atc atg agc ctg ccc 144
Thr Ala Ala Gly Val Cys His Ser Asp Asp Phe Ile Met Ser Leu Pro
35 40 45 gaa gag cag tac acc tac ggc ctt cct ctc acg ctc ggc cac gaa ggc 192
Glu Glu Gln Tyr Thr Tyr Gly Leu Pro Leu Thr Leu Gly His Glu Gly
50 55 60 gcc ggc cgg gtc gcc gcc gtc ggc gag ggc gtc gaa gga ctc gac atc 240
Ala Gly Arg Val Ala Ala Val Gly Glu Gly Val Glu Gly Leu Asp Ile
65 70 75 80 gga acc aat gtc gtc gtc tac gga ccc tgg ggc tgt ggc agc tgt tgg 288
Gly Thr Asn Val Val Val Tyr Gly Pro Trp Gly Cys Gly Ser Cys Trp
85 90 95

```
cac tgc tcg caa gga ctc gaa aac tac tgt tct cgg gca aaa gaa ctc      336
His Cys Ser Gln Gly Leu Glu Asn Tyr Cys Ser Arg Ala Lys Glu Leu
            100                 105                 110

ggc atc aat cct cct ggt ctc ggt gca ccc ggc gcg ttg gcc gaa ttc      384
Gly Ile Asn Pro Pro Gly Leu Gly Ala Pro Gly Ala Leu Ala Glu Phe
        115                 120                 125

atg atc gtc gat tca cct cgc cac ctc gtc ccg atc ggc gac ctc gat      432
Met Ile Val Asp Ser Pro Arg His Leu Val Pro Ile Gly Asp Leu Asp
    130                 135                 140

ccg gtc aag acg gtg ccg ctg acc gac gcc ggt ctg act ccg tat cac      480
Pro Val Lys Thr Val Pro Leu Thr Asp Ala Gly Leu Thr Pro Tyr His
145                 150                 155                 160

gcg atc aag cgt tca ctg ccg aaa ctt cgc ggt ggc gcg tac gcc gtc      528
Ala Ile Lys Arg Ser Leu Pro Lys Leu Arg Gly Gly Ala Tyr Ala Val
                165                 170                 175

gtc atc ggt acc ggc ggt ctc ggc cat gtc gcc atc caa ctc ctc cgc      576
Val Ile Gly Thr Gly Gly Leu Gly His Val Ala Ile Gln Leu Leu Arg
            180                 185                 190

cac ctc tcg gca gca acc gtc atc gca ctc gac gtg agc gcg gac aag      624
His Leu Ser Ala Ala Thr Val Ile Ala Leu Asp Val Ser Ala Asp Lys
        195                 200                 205

ctc gaa ctg gca acc aag gta ggc gct cac gaa gtg gtc ctg tcc gac      672
Leu Glu Leu Ala Thr Lys Val Gly Ala His Glu Val Val Leu Ser Asp
    210                 215                 220

aag gac gcg gcc gag aac gtc cgc agg atc acc gga agt cag ggc gcc      720
Lys Asp Ala Ala Glu Asn Val Arg Arg Ile Thr Gly Ser Gln Gly Ala
225                 230                 235                 240

gca ctg gtt ctc gac ttc gtc ggc tat cag ccc acc atc gac acc gcg      768
Ala Leu Val Leu Asp Phe Val Gly Tyr Gln Pro Thr Ile Asp Thr Ala
                245                 250                 255

atg gct gtc gcc ggc gtc gga tcg gac gtc acg atc gtc ggg atc ggc      816
Met Ala Val Ala Gly Val Gly Ser Asp Val Thr Ile Val Gly Ile Gly
            260                 265                 270

gac ggg cag gcc cat gcc aaa gtc ggg ttc ttc caa agt cct tac gag      864
Asp Gly Gln Ala His Ala Lys Val Gly Phe Phe Gln Ser Pro Tyr Glu
        275                 280                 285

gct tct gtg aca gtt ccg tac tgg ggt gcc cgc aac gag ctg atc gaa      912
Ala Ser Val Thr Val Pro Tyr Trp Gly Ala Arg Asn Glu Leu Ile Glu
    290                 295                 300

ttg atc gac ctg gcg cac gcc ggc atc ttc gac atc gcg gtg gag acc      960
Leu Ile Asp Leu Ala His Ala Gly Ile Phe Asp Ile Ala Val Glu Thr
305                 310                 315                 320

ttc agt ctc gac aac ggc gcc gaa gcg tat cga cga ctg gcc gcc gga     1008
Phe Ser Leu Asp Asn Gly Ala Glu Ala Tyr Arg Arg Leu Ala Ala Gly
                325                 330                 335

acg ctc agc ggc cgc gcg gtt gtg gtc cct ggt ctg tga                 1047
Thr Leu Ser Gly Arg Ala Val Val Val Pro Gly Leu
            340                 345
```

<210> SEQ ID NO 155
<211> LENGTH: 348
<212> TYPE: PRT
<213> ORGANISM: Rhodococcus rhodochrous

<400> SEQUENCE: 155

```
Met Lys Ala Ile Gln Tyr Thr Arg Ile Gly Ala Glu Pro Glu Leu Thr
1               5                   10                  15

Glu Ile Pro Lys Pro Glu Pro Gly Pro Gly Glu Val Leu Leu Glu Val
            20                  25                  30

Thr Ala Ala Gly Val Cys His Ser Asp Asp Phe Ile Met Ser Leu Pro
```

```
        35                  40                  45

Glu Glu Gln Tyr Thr Tyr Gly Leu Pro Leu Thr Leu Gly His Glu Gly
    50                  55                  60

Ala Gly Arg Val Ala Ala Val Gly Glu Gly Val Glu Gly Leu Asp Ile
65                  70                  75                  80

Gly Thr Asn Val Val Val Tyr Gly Pro Trp Gly Cys Gly Ser Cys Trp
                85                  90                  95

His Cys Ser Gln Gly Leu Glu Asn Tyr Cys Ser Arg Ala Lys Glu Leu
            100                 105                 110

Gly Ile Asn Pro Pro Gly Leu Gly Ala Pro Gly Ala Leu Ala Glu Phe
        115                 120                 125

Met Ile Val Asp Ser Pro Arg His Leu Val Pro Ile Gly Asp Leu Asp
    130                 135                 140

Pro Val Lys Thr Val Pro Leu Thr Asp Ala Gly Leu Thr Pro Tyr His
145                 150                 155                 160

Ala Ile Lys Arg Ser Leu Pro Lys Leu Arg Gly Gly Ala Tyr Ala Val
                165                 170                 175

Val Ile Gly Thr Gly Gly Leu Gly His Val Ala Ile Gln Leu Leu Arg
            180                 185                 190

His Leu Ser Ala Ala Thr Val Ile Ala Leu Asp Val Ser Ala Asp Lys
        195                 200                 205

Leu Glu Leu Ala Thr Lys Val Gly Ala His Glu Val Val Leu Ser Asp
    210                 215                 220

Lys Asp Ala Ala Glu Asn Val Arg Arg Ile Thr Gly Ser Gln Gly Ala
225                 230                 235                 240

Ala Leu Val Leu Asp Phe Val Gly Tyr Gln Pro Thr Ile Asp Thr Ala
                245                 250                 255

Met Ala Val Ala Gly Val Gly Ser Asp Val Thr Ile Val Gly Ile Gly
            260                 265                 270

Asp Gly Gln Ala His Ala Lys Val Gly Phe Phe Gln Ser Pro Tyr Glu
        275                 280                 285

Ala Ser Val Thr Val Pro Tyr Trp Gly Ala Arg Asn Glu Leu Ile Glu
    290                 295                 300

Leu Ile Asp Leu Ala His Ala Gly Ile Phe Asp Ile Ala Val Glu Thr
305                 310                 315                 320

Phe Ser Leu Asp Asn Gly Ala Glu Ala Tyr Arg Arg Leu Ala Ala Gly
                325                 330                 335

Thr Leu Ser Gly Arg Ala Val Val Val Pro Gly Leu
            340                 345
```

<210> SEQ ID NO 156
<211> LENGTH: 1047
<212> TYPE: DNA
<213> ORGANISM: Rhodococcus rhodochrous

<400> SEQUENCE: 156

```
atgaaagcaa tccaatatac ccgcattggt gcagagcctg agttgaccga gatcccgaaa      60

ccggaaccgg gtcctggcga agttctgctc gaagttaccg ctgcgggtgt gtgccacagc     120

gatgacttta tcatgtcgct gccagaggaa caatacacgt acggcttacc gctgacgctg     180

ggtcatgagg gcgctggtcg tgttgcagcg gtgggtgagg gtgtcgaggg cctggacatt     240

ggcaccaacg ttgtcgtgta cggtccgtgg ggttgcggct cttgttggca ttgctcccag     300

ggcctggaga attactgttc ccgcgcgaaa gaactgggta tcaatccgcc tggtctgggt     360
```

-continued

```
gctccaggtg cgctggctga gttcatgatt gtcgatagcc cgcgtcactt ggttccgatc    420

ggtgacctgg acccggtgaa aaccgtcccg ctgaccgatg cgggcttgac gccgtatcac    480

gcgattaagc gcagcctgcc gaaactgcgt ggtggcgcgt atgcagtcgt catcggtact    540

ggtggcttgg gccatgttgc gattcagctg ctgcgtcatc tgtctgccgc gacggttatc    600

gcgctggacg tgagcgccga taagctcgaa ctggccacta aggttggcgc gcacgaagtc    660

gttctgagcg ataaagacgc agccgaaaat gtgcgtcgta ttaccggtag ccagggtgca    720

gcattggttc tggacttcgt tggttatcag ccgacgatcg acaccgcgat ggccgttgcg    780

ggcgttggta gcgatgtcac cattgtgggt attggcgatg gtcaagccca cgccaaggtt    840

ggtttctttc aaagcccgta tgaagcgagc gtcacggtgc cgtactgggg tgcgcgcaac    900

gaactgatcg agctgatcga tctggctcac gcgggtattt tcgacatcgc agtcgaaacc    960

tttagcctgg ataacggcgc agaggcatac cgtcgtctgg cggctggcac tctgagcggt   1020

cgcgcagtgg tagtgccggg tctgtaa                                        1047
```

```
<210> SEQ ID NO 157
<211> LENGTH: 1062
<212> TYPE: DNA
<213> ORGANISM: Rhodococcus rhodochrous
<220> FEATURE:
<221> NAME/KEY: CDS
<222> LOCATION: (1)..(1062)

<400> SEQUENCE: 157

atg ttg gca gtc cag ctg acg gcg tgg ggt cag cct ccg cag gtg cgt       48
Met Leu Ala Val Gln Leu Thr Ala Trp Gly Gln Pro Pro Gln Val Arg
1               5                   10                  15

gag atc ccc gta ccc gag ccc gct gag ggg caa ctg ttg atc aaa gtc       96
Glu Ile Pro Val Pro Glu Pro Ala Glu Gly Gln Leu Leu Ile Lys Val
            20                  25                  30

ggc gcc gct ggt ctg tgc cgc tcg gat ctg cac gtc atg gat tcg ccc      144
Gly Ala Ala Gly Leu Cys Arg Ser Asp Leu His Val Met Asp Ser Pro
        35                  40                  45

gcc gga cgt ttc gat tac ccg ttg ccg ctc aca ctc ggc cat gag gtt      192
Ala Gly Arg Phe Asp Tyr Pro Leu Pro Leu Thr Leu Gly His Glu Val
    50                  55                  60

gcc ggt acc gtc gtc ggt gcg gga ccg ctg gcc gat cac gcg tgg atc      240
Ala Gly Thr Val Val Gly Ala Gly Pro Leu Ala Asp His Ala Trp Ile
65                  70                  75                  80

ggt gaa aat gtt gtc att cat ggt gtt tgg cca tgt ggc cgg tgc cgc      288
Gly Glu Asn Val Val Ile His Gly Val Trp Pro Cys Gly Arg Cys Arg
                85                  90                  95

aat tgc cgg cgc gag cgc gag aac tac tgc ttg gag aaa gtc ccg cgt      336
Asn Cys Arg Arg Glu Arg Glu Asn Tyr Cys Leu Glu Lys Val Pro Arg
            100                 105                 110

ggg gac ggc cga ctc agc ccg atc gga aac ggg ttg ggc cat ccg ggc      384
Gly Asp Gly Arg Leu Ser Pro Ile Gly Asn Gly Leu Gly His Pro Gly
        115                 120                 125

ggg ctg gca gaa tac ctg ctg gtg ccc tcg gaa gct gtt ctc gtt cgc      432
Gly Leu Ala Glu Tyr Leu Leu Val Pro Ser Glu Ala Val Leu Val Arg
    130                 135                 140

gtc ggt tcg ctg agc ccc cag cag gcc gct ccg ctc gcc gac gcc ggc      480
Val Gly Ser Leu Ser Pro Gln Gln Ala Ala Pro Leu Ala Asp Ala Gly
145                 150                 155                 160

ctg acc gca tat cat gcg atc cgg acc aac agc gac gtc atc gac tcg      528
Leu Thr Ala Tyr His Ala Ile Arg Thr Asn Ser Asp Val Ile Asp Ser
                165                 170                 175
```

```
gac act gtg gct ttg gtg ata gga atc ggc ggt ctc ggc cat ctg gcg      576
Asp Thr Val Ala Leu Val Ile Gly Ile Gly Gly Leu Gly His Leu Ala
            180                 185                 190

gtg cag atc ctg cgc tct ttc ggc gtc aca gac atc atc gcc gtc gag      624
Val Gln Ile Leu Arg Ser Phe Gly Val Thr Asp Ile Ile Ala Val Glu
        195                 200                 205

aca aga acc cag aca cac gct ctc gcg ctc gaa tcg gga gca cac gcg      672
Thr Arg Thr Gln Thr His Ala Leu Ala Leu Glu Ser Gly Ala His Ala
    210                 215                 220

tgt ttt gcg acg ctc gcg gaa gcg aca gag gct gtg gcg agc ctc ggc      720
Cys Phe Ala Thr Leu Ala Glu Ala Thr Glu Ala Val Ala Ser Leu Gly
225                 230                 235                 240

ggt gcc gac gtg gtc ttc gac ttt gtc ggg gct cag gcg acg gtc gaa      768
Gly Ala Asp Val Val Phe Asp Phe Val Gly Ala Gln Ala Thr Val Glu
                245                 250                 255

ccc gct ccg gcg ctt ctc gct ccc ggc ggc cga gtt gtc gtc gtg gga      816
Pro Ala Pro Ala Leu Leu Ala Pro Gly Gly Arg Val Val Val Val Gly
            260                 265                 270

agt gcg ggc ggg caa ctg acc gtc ggc aaa agc ctt ggt ttg gtc aac      864
Ser Ala Gly Gly Gln Leu Thr Val Gly Lys Ser Leu Gly Leu Val Asn
        275                 280                 285

ggc tgg caa gtt cgg gcg ccg ttc tgg ggc acc atc gag gac ctg cgt      912
Gly Trp Gln Val Arg Ala Pro Phe Trp Gly Thr Ile Glu Asp Leu Arg
    290                 295                 300

cag gtg gtc gaa ctc gcc agt gca gga aag ctg cat gcc gag gtg acc      960
Gln Val Val Glu Leu Ala Ser Ala Gly Lys Leu His Ala Glu Val Thr
305                 310                 315                 320

acg ttc acg ttc gac agc gca ctg gag gca tac gat cgc ctg cgt tca     1008
Thr Phe Thr Phe Asp Ser Ala Leu Glu Ala Tyr Asp Arg Leu Arg Ser
                325                 330                 335

ggc gat ctg tcc ggc cgc gcc gta ctg gtt ccc aca gcc cct tca tcg     1056
Gly Asp Leu Ser Gly Arg Ala Val Leu Val Pro Thr Ala Pro Ser Ser
            340                 345                 350

ctg tga                                                             1062
Leu


<210> SEQ ID NO 158
<211> LENGTH: 353
<212> TYPE: PRT
<213> ORGANISM: Rhodococcus rhodochrous

<400> SEQUENCE: 158

Met Leu Ala Val Gln Leu Thr Ala Trp Gly Gln Pro Pro Gln Val Arg
1               5                   10                  15

Glu Ile Pro Val Pro Glu Pro Ala Glu Gly Gln Leu Leu Ile Lys Val
            20                  25                  30

Gly Ala Ala Gly Leu Cys Arg Ser Asp Leu His Val Met Asp Ser Pro
        35                  40                  45

Ala Gly Arg Phe Asp Tyr Pro Leu Pro Leu Thr Leu Gly His Glu Val
    50                  55                  60

Ala Gly Thr Val Val Gly Ala Gly Pro Leu Ala Asp His Ala Trp Ile
65                  70                  75                  80

Gly Glu Asn Val Val Ile His Gly Val Trp Pro Cys Gly Arg Cys Arg
                85                  90                  95

Asn Cys Arg Arg Glu Arg Glu Asn Tyr Cys Leu Glu Lys Val Pro Arg
            100                 105                 110

Gly Asp Gly Arg Leu Ser Pro Ile Gly Asn Gly Leu Gly His Pro Gly
        115                 120                 125
```

-continued

Gly Leu Ala Glu Tyr Leu Leu Val Pro Ser Glu Ala Val Leu Val Arg
    130                 135                 140

Val Gly Ser Leu Ser Pro Gln Gln Ala Ala Pro Leu Ala Asp Ala Gly
145                 150                 155                 160

Leu Thr Ala Tyr His Ala Ile Arg Thr Asn Ser Asp Val Ile Asp Ser
                165                 170                 175

Asp Thr Val Ala Leu Val Ile Gly Ile Gly Gly Leu Gly His Leu Ala
            180                 185                 190

Val Gln Ile Leu Arg Ser Phe Gly Val Thr Asp Ile Ile Ala Val Glu
        195                 200                 205

Thr Arg Thr Gln Thr His Ala Leu Ala Leu Glu Ser Gly Ala His Ala
    210                 215                 220

Cys Phe Ala Thr Leu Ala Glu Ala Thr Glu Ala Val Ala Ser Leu Gly
225                 230                 235                 240

Gly Ala Asp Val Val Phe Asp Phe Val Gly Ala Gln Ala Thr Val Glu
                245                 250                 255

Pro Ala Pro Ala Leu Leu Ala Pro Gly Gly Arg Val Val Val Val Gly
            260                 265                 270

Ser Ala Gly Gly Gln Leu Thr Val Gly Lys Ser Leu Gly Leu Val Asn
        275                 280                 285

Gly Trp Gln Val Arg Ala Pro Phe Trp Gly Thr Ile Glu Asp Leu Arg
    290                 295                 300

Gln Val Val Glu Leu Ala Ser Ala Gly Lys Leu His Ala Glu Val Thr
305                 310                 315                 320

Thr Phe Thr Phe Asp Ser Ala Leu Glu Ala Tyr Asp Arg Leu Arg Ser
                325                 330                 335

Gly Asp Leu Ser Gly Arg Ala Val Leu Val Pro Thr Ala Pro Ser Ser
            340                 345                 350

Leu

<210> SEQ ID NO 159
<211> LENGTH: 1062
<212> TYPE: DNA
<213> ORGANISM: Rhodococcus rhodochrous

<400> SEQUENCE: 159
atgttagctg ttcaactcac cgcatggggc caaccaccac aagttcgcga aatcccggtt 60
ccggaaccag ccgagggcca actgctgatt aaggttggcg cagccggtct gtgccgtagc 120
gaccttcacg ttatggacag ccctgctggt cgttttgatt acccgttgcc gctgacgctg 180
ggtcacgaag tggccggcac ggttgtcggt gccggtccgt tggcagacca cgcgtggatt 240
ggtgagaacg tcgtgattca cggtgtgtgg ccgtgtggcc gttgtcgtaa ttgccgtcgc 300
gagcgtgaga actactgttt ggaaaaagtg ccgcgtggtg acggtcgtct gtccccgatc 360
ggcaatggtc tgggtcatcc gggtggtctg gcagagtatc tgctggtgcc gagcgaagcc 420
gtcctggtgc gtgtcggctc tctgagcccg caacaggcag caccgctggc agatgcgggt 480
ctgaccgcgt atcacgcgat tcgcacgaat agcgacgtta tcgactctga taccgtggcg 540
ctggtcatcg gtattggtgg cctgggtcac ctggccgttc agattctgcg ttccttcggc 600
gtgacggaca tcattgcagt cgagactcgt acccagacgc atgcgttggc cctggagagc 660
ggtgcgcatg cgtgctttgc gaccctggcg gaagcaaccg aagcggttgc gagcttgggc 720
ggtgcagatg ttgtctttga cttcgttggt gcgcaggcga ctgttgagcc ggcaccagct 780
ctgctggcac ctggtggccg tgttgtcgtg gtgggttctg cgggtggcca actgaccgtc 840

```
ggcaaatccc tgggtctggt gaatggctgg caagtgcgtg cgccgttttg gggcaccatt     900

gaagatttgc gtcaagtcgt ggaactggcg tctgcaggca agttgcacgc cgaagttacc     960

acgttcacgt tcgatagcgc gctggaagcg tacgaccgcc tgcgtagcgg tgatctgagc    1020

ggtcgcgctg tactggttcc gaccgcccct agcagcctgt aa                       1062


<210> SEQ ID NO 160
<211> LENGTH: 1122
<212> TYPE: DNA
<213> ORGANISM: Rhodococcus erythropolis
<220> FEATURE:
<221> NAME/KEY: CDS
<222> LOCATION: (1)..(1122)

<400> SEQUENCE: 160

atg att cgc gcc gaa cag aat tcg aga tcc tcc atg cag atg aca gcg       48
Met Ile Arg Ala Glu Gln Asn Ser Arg Ser Ser Met Gln Met Thr Ala
1               5                   10                  15

gcg ctc tca cac ggc ccg cac tcc ccc ttc acg ctc gac acc gtc gag       96
Ala Leu Ser His Gly Pro His Ser Pro Phe Thr Leu Asp Thr Val Glu
            20                  25                  30

atc gac gac ccc cgc gca gac gag atc ctg gtt cgc atc gtc gcg acc      144
Ile Asp Asp Pro Arg Ala Asp Glu Ile Leu Val Arg Ile Val Ala Thr
        35                  40                  45

ggc ctg tgc cac aca gat ctg ttc acg aag tcg gcg cta ccg gaa aga      192
Gly Leu Cys His Thr Asp Leu Phe Thr Lys Ser Ala Leu Pro Glu Arg
    50                  55                  60

ctc ggc ccc tgc gtg ttc ggg cac gaa ggg gcg ggg gtg gtc gag gcc      240
Leu Gly Pro Cys Val Phe Gly His Glu Gly Ala Gly Val Val Glu Ala
65                  70                  75                  80

gtc ggc tcg tcg atc gac agc att gcg ccc ggt gat cac gtg ttg ctg      288
Val Gly Ser Ser Ile Asp Ser Ile Ala Pro Gly Asp His Val Leu Leu
                85                  90                  95

agc tac cgc agt tgc ggt gtg tgc agg cag tgt ctc agc ggc cat cgg      336
Ser Tyr Arg Ser Cys Gly Val Cys Arg Gln Cys Leu Ser Gly His Arg
            100                 105                 110

gcg tac tgc gaa agc tca cac ggg ctc aac agc tct ggc gca cgc acc      384
Ala Tyr Cys Glu Ser Ser His Gly Leu Asn Ser Ser Gly Ala Arg Thr
        115                 120                 125

gac ggc tcg acg ccg atc cgg cga gac gga acc ccg cta cgg tcc gcc      432
Asp Gly Ser Thr Pro Ile Arg Arg Asp Gly Thr Pro Leu Arg Ser Ala
    130                 135                 140

ttc ttc ggc cag tcc agc ttc gcg gaa tac gtc atc gcc tct gcc gac      480
Phe Phe Gly Gln Ser Ser Phe Ala Glu Tyr Val Ile Ala Ser Ala Asp
145                 150                 155                 160

aac acc gtc gtc gtc gat cct gcg gtg gac ctg acc gtc gca gct ccg      528
Asn Thr Val Val Val Asp Pro Ala Val Asp Leu Thr Val Ala Ala Pro
                165                 170                 175

ctc ggc tgc ggg ttt caa acc ggc gcc ggc gcg gta ctg aat ctg ctt      576
Leu Gly Cys Gly Phe Gln Thr Gly Ala Gly Ala Val Leu Asn Leu Leu
            180                 185                 190

cgc ccc gag ccc gac tcg acg ttt gtc gtt ttc ggg gca ggc agc gtc      624
Arg Pro Glu Pro Asp Ser Thr Phe Val Val Phe Gly Ala Gly Ser Val
        195                 200                 205

gga ctc gca gcg ctg ctg gcg gcg agg gct gcc ggc gtt tcc acc ctg      672
Gly Leu Ala Ala Leu Leu Ala Ala Arg Ala Ala Gly Val Ser Thr Leu
    210                 215                 220

gtc gcc gtg gac ccc gtt gcg cag cgg cgc gca ctc gcc gag gaa ttc      720
Val Ala Val Asp Pro Val Ala Gln Arg Arg Ala Leu Ala Glu Glu Phe
225                 230                 235                 240
```

```
ggc gcc gtc act gtc gat ccc tcg aat gaa gat gtg atc gac gcg gtc      768
Gly Ala Val Thr Val Asp Pro Ser Asn Glu Asp Val Ile Asp Ala Val
            245                 250                 255

cac gcc gcc acc gac gga ggt tcg acg cat tcc ctc gac acc acc gga      816
His Ala Ala Thr Asp Gly Gly Ser Thr His Ser Leu Asp Thr Thr Gly
        260                 265                 270

atc ggc tcc gtg atc aat caa gcc gtc aca tca ctt cga gca cgg gga      864
Ile Gly Ser Val Ile Asn Gln Ala Val Thr Ser Leu Arg Ala Arg Gly
    275                 280                 285

aca ctg gcg gta gtc gga ctc gga gca tcc acg gtc gag gtg aac atg      912
Thr Leu Ala Val Val Gly Leu Gly Ala Ser Thr Val Glu Val Asn Met
    290                 295                 300

gcc gac atc atg ctg agc gga aag aca att cga gga tgc atc gaa gga      960
Ala Asp Ile Met Leu Ser Gly Lys Thr Ile Arg Gly Cys Ile Glu Gly
305                 310                 315                 320

gag tcg gaa gtc tcg acg ttc atc ccc gaa ctc gtc gaa ctc ttc act     1008
Glu Ser Glu Val Ser Thr Phe Ile Pro Glu Leu Val Glu Leu Phe Thr
                325                 330                 335

ggt ggc cgg ttt ccg atc gac cgc ttg gtg acg cgc tac gca ttc gcc     1056
Gly Gly Arg Phe Pro Ile Asp Arg Leu Val Thr Arg Tyr Ala Phe Ala
            340                 345                 350

gac atc aac aaa gcc gtc gaa gat caa gcg tcg ggg cgc gtc atc aaa     1104
Asp Ile Asn Lys Ala Val Glu Asp Gln Ala Ser Gly Arg Val Ile Lys
        355                 360                 365

ccc gtt ctc gtg tgg tga                                             1122
Pro Val Leu Val Trp
    370


<210> SEQ ID NO 161
<211> LENGTH: 373
<212> TYPE: PRT
<213> ORGANISM: Rhodococcus erythropolis

<400> SEQUENCE: 161

Met Ile Arg Ala Glu Gln Asn Ser Arg Ser Ser Met Gln Met Thr Ala
1               5                   10                  15

Ala Leu Ser His Gly Pro His Ser Pro Phe Thr Leu Asp Thr Val Glu
            20                  25                  30

Ile Asp Asp Pro Arg Ala Asp Glu Ile Leu Val Arg Ile Val Ala Thr
        35                  40                  45

Gly Leu Cys His Thr Asp Leu Phe Thr Lys Ser Ala Leu Pro Glu Arg
    50                  55                  60

Leu Gly Pro Cys Val Phe Gly His Glu Gly Ala Gly Val Val Glu Ala
65                  70                  75                  80

Val Gly Ser Ser Ile Asp Ser Ile Ala Pro Gly Asp His Val Leu Leu
                85                  90                  95

Ser Tyr Arg Ser Cys Gly Val Cys Arg Gln Cys Leu Ser Gly His Arg
            100                 105                 110

Ala Tyr Cys Glu Ser Ser His Gly Leu Asn Ser Ser Gly Ala Arg Thr
        115                 120                 125

Asp Gly Ser Thr Pro Ile Arg Arg Asp Gly Thr Pro Leu Arg Ser Ala
    130                 135                 140

Phe Phe Gly Gln Ser Ser Phe Ala Glu Tyr Val Ile Ala Ser Ala Asp
145                 150                 155                 160

Asn Thr Val Val Val Asp Pro Ala Val Asp Leu Thr Val Ala Ala Pro
                165                 170                 175

Leu Gly Cys Gly Phe Gln Thr Gly Ala Gly Ala Val Leu Asn Leu Leu
```

-continued

```
            180                 185                 190

Arg Pro Glu Pro Asp Ser Thr Phe Val Val Phe Gly Ala Gly Ser Val
        195                 200                 205

Gly Leu Ala Ala Leu Leu Ala Ala Arg Ala Ala Gly Val Ser Thr Leu
    210                 215                 220

Val Ala Val Asp Pro Val Ala Gln Arg Arg Ala Leu Ala Glu Glu Phe
225                 230                 235                 240

Gly Ala Val Thr Val Asp Pro Ser Asn Glu Asp Val Ile Asp Ala Val
                245                 250                 255

His Ala Ala Thr Asp Gly Gly Ser Thr His Ser Leu Asp Thr Thr Gly
            260                 265                 270

Ile Gly Ser Val Ile Asn Gln Ala Val Thr Ser Leu Arg Ala Arg Gly
        275                 280                 285

Thr Leu Ala Val Val Gly Leu Gly Ala Ser Thr Val Glu Val Asn Met
    290                 295                 300

Ala Asp Ile Met Leu Ser Gly Lys Thr Ile Arg Gly Cys Ile Glu Gly
305                 310                 315                 320

Glu Ser Glu Val Ser Thr Phe Ile Pro Glu Leu Val Glu Leu Phe Thr
                325                 330                 335

Gly Gly Arg Phe Pro Ile Asp Arg Leu Val Thr Arg Tyr Ala Phe Ala
            340                 345                 350

Asp Ile Asn Lys Ala Val Glu Asp Gln Ala Ser Gly Arg Val Ile Lys
        355                 360                 365

Pro Val Leu Val Trp
    370
```

<210> SEQ ID NO 162
<211> LENGTH: 1122
<212> TYPE: DNA
<213> ORGANISM: Rhodococcus erythropolis

<400> SEQUENCE: 162

```
atgattagag cagaacagaa cagccgcagc tccatgcaaa tgaccgcggc actgtcacat      60

ggtccgcaca gcccgtttac gctggatacg gttgagattg acgatccacg cgccgacgaa     120

attctggtac gcatcgttgc gactggtctg tgtcatacgg acttgtttac caagagcgcg     180

ctgccggagc gcctgggtcc gtgcgtgttc ggccacgagg gtgcgggcgt ggttgaggca     240

gttggctcta gcattgacag catcgctccg ggtgatcacg tcctgttgtc ctaccgtagc     300

tgcggcgtct gccgtcagtg cctgagcggc caccgtgctt actgtgagag ctcccacggc     360

ctgaatagct ccggtgctcg taccgacggt agcaccccga tccgtcgtga tggtacgccg     420

cttcgtagcg cgttcttcgg tcaatccagc ttcgcggaat atgttatcgc aagcgcagac     480

aacaccgttg tggtcgatcc ggccgtggac ttgaccgttg cagcaccgct gggttgtggc     540

tttcagaccg gcgccggcgc ggtgctgaat ctgctgcgcc ctgagccgga cagcactttc     600

gtcgtctttg gtgccggcag cgtcggtttg gcggcactgc tggcggcgcg tgcggcgggt     660

gtttcgaccc tggtcgcagt tgatccggtc gcgcagcgcc gtgcgttggc cgaagaattt     720

ggtgccgtta ccgtcgatcc gagcaacgaa gatgttattg acgctgtgca cgcggcgacc     780

gacggtggca gcacgcattc tctggatacc acgggcatcg gttctgtgat taaccaagcc     840

gtgacctctc tgcgtgcgcg tggtactctg gctgtggttg gcctgggtgc tagcacggtc     900

gaggtgaata tggcagacat tatgctgagc ggtaaaacga tccgtggttg catcgagggc     960

gagagcgaag tttcgacgtt tatcccggaa ctggtcgagc tgttcaccgg tggccgtttc    1020
```

```
ccgattgacc gcctggttac ccgttatgca ttcgccgata tcaacaaagc tgtggaagat   1080

caagcgtccg gtcgcgtcat caagccagtg ctggtgtggt aa                      1122


<210> SEQ ID NO 163
<211> LENGTH: 1122
<212> TYPE: DNA
<213> ORGANISM: Rhodococcus rhodochrous
<220> FEATURE:
<221> NAME/KEY: CDS
<222> LOCATION: (1)..(1122)

<400> SEQUENCE: 163

atg att cgc gcc gaa cag aat tcg acg tcc gcc atg cag atg aca gcg       48
Met Ile Arg Ala Glu Gln Asn Ser Thr Ser Ala Met Gln Met Thr Ala
1               5                   10                  15

gcg ctc tca cac ggc ccg cac tcc ccc ttc aca ctc gac acc gtc gag       96
Ala Leu Ser His Gly Pro His Ser Pro Phe Thr Leu Asp Thr Val Glu
            20                  25                  30

atc gac gaa ccc cgc gca gac gag atc ctg gtt cgc atc gtc gcg acc      144
Ile Asp Glu Pro Arg Ala Asp Glu Ile Leu Val Arg Ile Val Ala Thr
        35                  40                  45

ggc ctg tgc cac aca gat ctg ttc acg aag tcg gtg cta ccg gaa cga      192
Gly Leu Cys His Thr Asp Leu Phe Thr Lys Ser Val Leu Pro Glu Arg
    50                  55                  60

ctc ggc ccc tgc gtg ttc ggg cac gaa ggg gcg ggg gtg gtc gag gcc      240
Leu Gly Pro Cys Val Phe Gly His Glu Gly Ala Gly Val Val Glu Ala
65                  70                  75                  80

gtc ggc tcg gcg atc gac aag gtc gtg ccc ggc gat cac gtg ttg ttg      288
Val Gly Ser Ala Ile Asp Lys Val Val Pro Gly Asp His Val Leu Leu
                85                  90                  95

agc tac cgc agt tgc ggt gtg tgc agg cag tgt ctc agc ggc cat cgg      336
Ser Tyr Arg Ser Cys Gly Val Cys Arg Gln Cys Leu Ser Gly His Arg
            100                 105                 110

gcg tac tgc gaa agc tca cac ggg ctc aac agc tct ggc gca cgc acc      384
Ala Tyr Cys Glu Ser Ser His Gly Leu Asn Ser Ser Gly Ala Arg Thr
        115                 120                 125

gac ggc tcg acg ccg gtc cgg cga agc gga act ccg ata cgg tcc gcc      432
Asp Gly Ser Thr Pro Val Arg Arg Ser Gly Thr Pro Ile Arg Ser Ala
    130                 135                 140

ttc ttc ggc cag tcc agc ttc gcg gaa tac gtc atc gcc act gcc gac      480
Phe Phe Gly Gln Ser Ser Phe Ala Glu Tyr Val Ile Ala Thr Ala Asp
145                 150                 155                 160

aac acc gtc gtc gtc gat cct gca gtg gac ctg acc gtc gcg gct ccc      528
Asn Thr Val Val Val Asp Pro Ala Val Asp Leu Thr Val Ala Ala Pro
                165                 170                 175

ctc ggc tgc gga ttt caa acc ggc gcg ggt gcc gtg ctg aat cta ctt      576
Leu Gly Cys Gly Phe Gln Thr Gly Ala Gly Ala Val Leu Asn Leu Leu
            180                 185                 190

cgc ccc gag ccc gac tcg acg ttt gtc gtc ttc gga gcc ggc agc gtc      624
Arg Pro Glu Pro Asp Ser Thr Phe Val Val Phe Gly Ala Gly Ser Val
        195                 200                 205

gga ctc gca gcg cta ctg gca gcg agg gct gcc ggc gtt tcc acc ctg      672
Gly Leu Ala Ala Leu Leu Ala Ala Arg Ala Ala Gly Val Ser Thr Leu
    210                 215                 220

gtc gcc gtg gac ccc gtt gcg cag cgg cgc gca ctc gcc gag gaa ttc      720
Val Ala Val Asp Pro Val Ala Gln Arg Arg Ala Leu Ala Glu Glu Phe
225                 230                 235                 240

ggc gcc gtc act gtc gat ccg acc acc gag gac gcg gtc gaa gca gta      768
Gly Ala Val Thr Val Asp Pro Thr Thr Glu Asp Ala Val Glu Ala Val
                245                 250                 255
```

```
cgc gcc gcc acc gac gga ggt tcg aca cat tcc ctc gac acc acc gga      816
Arg Ala Ala Thr Asp Gly Gly Ser Thr His Ser Leu Asp Thr Thr Gly
            260                 265                 270

atc ggc tcc gtg atc aat caa gcc gtc aca tca ctt cga gca cgg gga      864
Ile Gly Ser Val Ile Asn Gln Ala Val Thr Ser Leu Arg Ala Arg Gly
        275                 280                 285

aca ctg gcg gta gtc gga ctc gga gcg tcc acg gtc gag atg aac atg      912
Thr Leu Ala Val Val Gly Leu Gly Ala Ser Thr Val Glu Met Asn Met
    290                 295                 300

gcc gac atc atg ctg agc gga aag aca att cga gga tgc atc gaa gga      960
Ala Asp Ile Met Leu Ser Gly Lys Thr Ile Arg Gly Cys Ile Glu Gly
305                 310                 315                 320

gag tcg gaa gtc tcg acg ttc atc ccc gaa ctc gtc gaa ctc ttc act     1008
Glu Ser Glu Val Ser Thr Phe Ile Pro Glu Leu Val Glu Leu Phe Thr
                325                 330                 335

ggt ggc cgg ttt ccg atc gac cgc ttg gtg acg cgc tac gcc ttc tcc     1056
Gly Gly Arg Phe Pro Ile Asp Arg Leu Val Thr Arg Tyr Ala Phe Ser
            340                 345                 350

gac atc aac aaa gcc gtc gaa gat caa gcg tcg ggg cgc gtc atc aaa     1104
Asp Ile Asn Lys Ala Val Glu Asp Gln Ala Ser Gly Arg Val Ile Lys
        355                 360                 365

ccc gtt ctc gtg tgg tga                                             1122
Pro Val Leu Val Trp
    370
```

<210> SEQ ID NO 164
<211> LENGTH: 373
<212> TYPE: PRT
<213> ORGANISM: Rhodococcus rhodochrous

<400> SEQUENCE: 164

```
Met Ile Arg Ala Glu Gln Asn Ser Thr Ser Ala Met Gln Met Thr Ala
1               5                   10                  15

Ala Leu Ser His Gly Pro His Ser Pro Phe Thr Leu Asp Thr Val Glu
            20                  25                  30

Ile Asp Glu Pro Arg Ala Asp Glu Ile Leu Val Arg Ile Val Ala Thr
        35                  40                  45

Gly Leu Cys His Thr Asp Leu Phe Thr Lys Ser Val Leu Pro Glu Arg
    50                  55                  60

Leu Gly Pro Cys Val Phe Gly His Glu Gly Ala Gly Val Val Glu Ala
65                  70                  75                  80

Val Gly Ser Ala Ile Asp Lys Val Val Pro Gly Asp His Val Leu Leu
                85                  90                  95

Ser Tyr Arg Ser Cys Gly Val Cys Arg Gln Cys Leu Ser Gly His Arg
            100                 105                 110

Ala Tyr Cys Glu Ser Ser His Gly Leu Asn Ser Ser Gly Ala Arg Thr
        115                 120                 125

Asp Gly Ser Thr Pro Val Arg Arg Ser Gly Thr Pro Ile Arg Ser Ala
    130                 135                 140

Phe Phe Gly Gln Ser Ser Phe Ala Glu Tyr Val Ile Ala Thr Ala Asp
145                 150                 155                 160

Asn Thr Val Val Val Asp Pro Ala Val Asp Leu Thr Val Ala Ala Pro
                165                 170                 175

Leu Gly Cys Gly Phe Gln Thr Gly Ala Gly Ala Val Leu Asn Leu Leu
            180                 185                 190

Arg Pro Glu Pro Asp Ser Thr Phe Val Val Phe Gly Ala Gly Ser Val
        195                 200                 205
```

```
Gly Leu Ala Ala Leu Leu Ala Ala Arg Ala Ala Gly Val Ser Thr Leu
    210                 215                 220

Val Ala Val Asp Pro Val Ala Gln Arg Arg Ala Leu Ala Glu Glu Phe
225                 230                 235                 240

Gly Ala Val Thr Val Asp Pro Thr Thr Glu Asp Ala Val Glu Ala Val
                245                 250                 255

Arg Ala Ala Thr Asp Gly Gly Ser Thr His Ser Leu Asp Thr Thr Gly
            260                 265                 270

Ile Gly Ser Val Ile Asn Gln Ala Val Thr Ser Leu Arg Ala Arg Gly
        275                 280                 285

Thr Leu Ala Val Val Gly Leu Gly Ala Ser Thr Val Glu Met Asn Met
    290                 295                 300

Ala Asp Ile Met Leu Ser Gly Lys Thr Ile Arg Gly Cys Ile Glu Gly
305                 310                 315                 320

Glu Ser Glu Val Ser Thr Phe Ile Pro Glu Leu Val Glu Leu Phe Thr
                325                 330                 335

Gly Gly Arg Phe Pro Ile Asp Arg Leu Val Thr Arg Tyr Ala Phe Ser
            340                 345                 350

Asp Ile Asn Lys Ala Val Glu Asp Gln Ala Ser Gly Arg Val Ile Lys
        355                 360                 365

Pro Val Leu Val Trp
    370


<210> SEQ ID NO 165
<211> LENGTH: 1122
<212> TYPE: DNA
<213> ORGANISM: Rhodococcus rhodochrous

<400> SEQUENCE: 165

atgattagag cagaacagaa cagcaccagc gcgatgcaaa tgaccgcggc actgtcacat      60

ggtccgcaca gcccgtttac gctggatacg gttgagattg acgagccacg cgccgacgaa     120

attctggtac gcatcgttgc gactggtctg tgtcatacgg acttgtttac caagagcgtc     180

ctgccggagc gcctgggtcc gtgcgtgttc ggccacgagg gtgcgggcgt ggttgaggca     240

gttggctctg ccattgacaa agttgttccg ggtgatcacg tcctgttgtc ctaccgtagc     300

tgcggcgtct gccgtcagtg cctgagcggc caccgtgctt actgtgagag ctcccacggc     360

ctgaatagct ccggtgctcg taccgacggt agcaccccgg tgcgtcgtag cggtacgccg     420

attcgtagcg cgttcttcgg tcaatccagc ttcgcggaat atgttatcgc aaccgcagac     480

aacaccgttg tggtcgatcc ggccgtggac ttgaccgttg cagcaccgct gggttgtggc     540

tttcagaccg gcgccggcgc ggtgctgaat ctgctgcgcc ctgagccgga cagcactttc     600

gtcgtctttg gtgccggcag cgtcggtttg gcggcactgc tggcggcgcg tgcggcgggt     660

gtttcgaccc tggtcgcagt tgatccggtc gcgcagcgcc gtgcgttggc cgaagaattt     720

ggtgccgtta ccgtcgatcc gacgaccgaa gatgccgttg aagctgtgcg cgcggcgacc     780

gacggtggca gcacgcattc tctggatacc acgggcatcg gttctgtgat taaccaagcc     840

gtgacctctc tgcgtgcgcg tggtactctg gctgtggttg gcctgggtgc tagcacggtc     900

gagatgaata tggcagacat tatgctgagc ggtaaaacga tccgtggttg catcgagggc     960

gagagcgaag tttcgacgtt tatcccggaa ctggtcgagc tgttcaccgg tggccgtttc    1020

ccgattgacc gcctggttac ccgttatgca ttcagcgata tcaacaaagc tgtggaagat    1080

caagcgtccg gtcgcgtcat caagccagtg ctggtgtggt aa                       1122
```

<210> SEQ ID NO 166
<211> LENGTH: 1128
<212> TYPE: DNA
<213> ORGANISM: Azoarcus toluclasticus
<220> FEATURE:
<221> NAME/KEY: CDS
<222> LOCATION: (1)..(1128)

<400> SEQUENCE: 166

```
atg gga agc atc cag gat tcg ctg ttc att cgg gca cgc gct gcc gtg       48
Met Gly Ser Ile Gln Asp Ser Leu Phe Ile Arg Ala Arg Ala Ala Val
1               5                   10                  15

ctg cgt acg gtg ggc ggg ccg ctc gag atc gag aac gtg cgc atc agc       96
Leu Arg Thr Val Gly Gly Pro Leu Glu Ile Glu Asn Val Arg Ile Ser
            20                  25                  30

ccc ccc aag ggc gat gaa gtg ctg gtg cgc atg gtc gga gtc ggc gta      144
Pro Pro Lys Gly Asp Glu Val Leu Val Arg Met Val Gly Val Gly Val
        35                  40                  45

tgc cat acc gac gtg gtg tgc cgc gac ggt ttt ccc gtg ccg ctg ccg      192
Cys His Thr Asp Val Val Cys Arg Asp Gly Phe Pro Val Pro Leu Pro
    50                  55                  60

att gtg ctc ggg cac gaa ggc tcc ggc atc gtc gag gcc gtc ggc gag      240
Ile Val Leu Gly His Glu Gly Ser Gly Ile Val Glu Ala Val Gly Glu
65                  70                  75                  80

cgc gtg acg aaa gtg aag ccg ggc cag cgt gtc gtg ctg tcg ttc aac      288
Arg Val Thr Lys Val Lys Pro Gly Gln Arg Val Val Leu Ser Phe Asn
                85                  90                  95

tcc tgc ggg cac tgc gcg agc tgc tgc gag gat cac ccg gcg acc tgc      336
Ser Cys Gly His Cys Ala Ser Cys Cys Glu Asp His Pro Ala Thr Cys
            100                 105                 110

cac cag atg ctg ccg ctc aac ttc ggc gcg gcg cag cgc gtc gat ggg      384
His Gln Met Leu Pro Leu Asn Phe Gly Ala Ala Gln Arg Val Asp Gly
        115                 120                 125

ggc acg gtg atc gat gcg tcc ggc gaa gcg gtg cag agc ctc ttc ttc      432
Gly Thr Val Ile Asp Ala Ser Gly Glu Ala Val Gln Ser Leu Phe Phe
    130                 135                 140

ggt cag tcc tcg ttt ggc acc tac gcg ctc gcg cgc gaa gtg aat acg      480
Gly Gln Ser Ser Phe Gly Thr Tyr Ala Leu Ala Arg Glu Val Asn Thr
145                 150                 155                 160

gtc ccg gtt ccg gac gcc gtg ccg ctc gaa atc ctc ggc ccg ctc ggt      528
Val Pro Val Pro Asp Ala Val Pro Leu Glu Ile Leu Gly Pro Leu Gly
                165                 170                 175

tgc ggg atc cag acc ggg gcg ggt gcg gcg atc aat tcg ctc gcg ctg      576
Cys Gly Ile Gln Thr Gly Ala Gly Ala Ala Ile Asn Ser Leu Ala Leu
            180                 185                 190

aaa ccg ggc caa tcg ctc gcg atc ttc ggc ggg ggc agc gtc ggc ctg      624
Lys Pro Gly Gln Ser Leu Ala Ile Phe Gly Gly Gly Ser Val Gly Leu
        195                 200                 205

agc gcg ctg ctc ggc gcg ctc gcg gtc ggt gcc ggc ccg gtg gtc gtg      672
Ser Ala Leu Leu Gly Ala Leu Ala Val Gly Ala Gly Pro Val Val Val
    210                 215                 220

att gag ccc aac gaa cgg cgt cgc gcg ctg gcg ctc gat ctg ggt gca      720
Ile Glu Pro Asn Glu Arg Arg Arg Ala Leu Ala Leu Asp Leu Gly Ala
225                 230                 235                 240

agc cac gcc ttc gat ccc ttc aac acc gag gat ctc gtc gcg agc atc      768
Ser His Ala Phe Asp Pro Phe Asn Thr Glu Asp Leu Val Ala Ser Ile
                245                 250                 255

aag gct gcg acc ggc gga ggc gtc acg cac tcg ctc gat tcg acg ggc      816
Lys Ala Ala Thr Gly Gly Gly Val Thr His Ser Leu Asp Ser Thr Gly
            260                 265                 270
```

```
ctc ccc ccc gtc atc gcc aac gcg atc aac tgc acc ctc ccg ggc ggc      864
Leu Pro Pro Val Ile Ala Asn Ala Ile Asn Cys Thr Leu Pro Gly Gly
        275                 280                 285

acc gtc ggc ctg ctg ggg gtg ccg tca ccc gaa gcc gcg gtg cct gtg      912
Thr Val Gly Leu Leu Gly Val Pro Ser Pro Glu Ala Ala Val Pro Val
    290                 295                 300

acc ctg ctg gac ctg ctc gtg aaa agc gtc acc ctg cgc ccg atc acc      960
Thr Leu Leu Asp Leu Leu Val Lys Ser Val Thr Leu Arg Pro Ile Thr
305                 310                 315                 320

gaa ggc gac gcg aac ccg cag gaa ttc atc ccg cgc atg gtc caa ctc     1008
Glu Gly Asp Ala Asn Pro Gln Glu Phe Ile Pro Arg Met Val Gln Leu
                325                 330                 335

tac cgc gac ggc aag ttc ccc ttc gac aag ctg atc acc acc tat cgc     1056
Tyr Arg Asp Gly Lys Phe Pro Phe Asp Lys Leu Ile Thr Thr Tyr Arg
            340                 345                 350

ttc gac gac att aat caa gcc ttc aag gcg acc gag acc gga gag gcg     1104
Phe Asp Asp Ile Asn Gln Ala Phe Lys Ala Thr Glu Thr Gly Glu Ala
        355                 360                 365

atc aag ccg gtg ctg gtg ttc tga                                     1128
Ile Lys Pro Val Leu Val Phe
    370                 375


<210> SEQ ID NO 167
<211> LENGTH: 375
<212> TYPE: PRT
<213> ORGANISM: Azoarcus toluclasticus

<400> SEQUENCE: 167

Met Gly Ser Ile Gln Asp Ser Leu Phe Ile Arg Ala Arg Ala Ala Val
1               5                   10                  15

Leu Arg Thr Val Gly Gly Pro Leu Glu Ile Glu Asn Val Arg Ile Ser
            20                  25                  30

Pro Pro Lys Gly Asp Glu Val Leu Val Arg Met Val Gly Val Gly Val
        35                  40                  45

Cys His Thr Asp Val Val Cys Arg Asp Gly Phe Pro Val Pro Leu Pro
    50                  55                  60

Ile Val Leu Gly His Glu Gly Ser Gly Ile Val Glu Ala Val Gly Glu
65                  70                  75                  80

Arg Val Thr Lys Val Lys Pro Gly Gln Arg Val Val Leu Ser Phe Asn
                85                  90                  95

Ser Cys Gly His Cys Ala Ser Cys Cys Glu Asp His Pro Ala Thr Cys
            100                 105                 110

His Gln Met Leu Pro Leu Asn Phe Gly Ala Ala Gln Arg Val Asp Gly
        115                 120                 125

Gly Thr Val Ile Asp Ala Ser Gly Glu Ala Val Gln Ser Leu Phe Phe
    130                 135                 140

Gly Gln Ser Ser Phe Gly Thr Tyr Ala Leu Ala Arg Glu Val Asn Thr
145                 150                 155                 160

Val Pro Val Pro Asp Ala Val Pro Leu Glu Ile Leu Gly Pro Leu Gly
                165                 170                 175

Cys Gly Ile Gln Thr Gly Ala Gly Ala Ala Ile Asn Ser Leu Ala Leu
            180                 185                 190

Lys Pro Gly Gln Ser Leu Ala Ile Phe Gly Gly Gly Ser Val Gly Leu
        195                 200                 205

Ser Ala Leu Leu Gly Ala Leu Ala Val Gly Ala Gly Pro Val Val Val
    210                 215                 220
```

-continued

```
Ile Glu Pro Asn Glu Arg Arg Arg Ala Leu Ala Leu Asp Leu Gly Ala
225                 230                 235                 240

Ser His Ala Phe Asp Pro Phe Asn Thr Glu Asp Leu Val Ala Ser Ile
                245                 250                 255

Lys Ala Ala Thr Gly Gly Gly Val Thr His Ser Leu Asp Ser Thr Gly
            260                 265                 270

Leu Pro Pro Val Ile Ala Asn Ala Ile Asn Cys Thr Leu Pro Gly Gly
        275                 280                 285

Thr Val Gly Leu Leu Gly Val Pro Ser Pro Glu Ala Ala Val Pro Val
    290                 295                 300

Thr Leu Leu Asp Leu Leu Val Lys Ser Val Thr Leu Arg Pro Ile Thr
305                 310                 315                 320

Glu Gly Asp Ala Asn Pro Gln Glu Phe Ile Pro Arg Met Val Gln Leu
                325                 330                 335

Tyr Arg Asp Gly Lys Phe Pro Phe Asp Lys Leu Ile Thr Thr Tyr Arg
            340                 345                 350

Phe Asp Asp Ile Asn Gln Ala Phe Lys Ala Thr Glu Thr Gly Glu Ala
        355                 360                 365

Ile Lys Pro Val Leu Val Phe
    370                 375
```

<210> SEQ ID NO 168
<211> LENGTH: 1128
<212> TYPE: DNA
<213> ORGANISM: Azoarcus toluclasticus

<400> SEQUENCE: 168

```
atgggttcta ttcaagattc tctgttcatc cgtgcacgcg ccgctgttct gcgtactgtc      60

ggtggcccgc tggaaattga aaacgtccgc attagccctc cgaagggtga cgaagtgctc     120

gtgcgtatgg ttggtgttgg tgtgtgccat accgacgttg tgtgtcgcga tggcttcccg     180

gttccgctgc cgattgtgct gggtcacgag ggcagcggta ttgtcgaggc agtgggcgag     240

cgtgtgacca aggttaaacc gggtcagcgt gtcgttttat ccttcaatag ctgtggtcat     300

tgcgcgtcct gctgcgagga ccacccggcc acctgtcacc agatgctgcc actgaacttt     360

ggtgcggcgc agcgcgtgga tggtggcacc gttatcgacg cgagcggcga ggcagtgcag     420

agcctgtttt ttggtcaaag ctctttcggt acgtatgcat tggcgcgtga agtcaatacc     480

gtaccggtgc cggatgcagt tccgttggaa atcctgggcc cgttgggttg cggcatccag     540

acgggtgcgg gtgcggctat caacagcctg gcgctgaaac ctggtcaatc gctggcaatc     600

ttcggtggcg gcagcgtcgg tctgtccgcc ctgctgggcg cgctggccgt gggcgcgggc     660

ccggtcgttg tcattgagcc gaacgaacgt cgtcgtgcgt tggcgctgga cctgggtgcg     720

agccatgcat ttgatccgtt caacactgaa gatttggttg cgagcatcaa agccgctacg     780

ggtggcggcg ttacccacag cctggacagc acgggtctgc cgccggtcat cgcgaatgca     840

atcaactgta ccttgccggg cggcacggtc ggtctgctgg gcgtcccgag cccagaggct     900

gccgttccgg tgacgctgct ggatctgctg gttaaatcag ttaccctgcg tccgattacc     960

gagggtgacg ccaatccgca agaatttatt ccgcgtatgg tccagctgta ccgcgacggt    1020

aaatttccgt ttgataagct gattacgacc taccgcttcg acgacatcaa tcaagcgttc    1080

aaggcaaccg aaaccggtga agcgattaag ccagtgctgg tgttttaa                1128
```

<210> SEQ ID NO 169
<211> LENGTH: 852

```
<212> TYPE: DNA
<213> ORGANISM: Aspergillus wentii
<220> FEATURE:
<221> NAME/KEY: CDS
<222> LOCATION: (1)..(852)

<400> SEQUENCE: 169

atg gca tct gta cca gct ccc cca ttt gtc cac gtc gaa gga atg agc       48
Met Ala Ser Val Pro Ala Pro Pro Phe Val His Val Glu Gly Met Ser
1               5                   10                  15

aat ttc cga tcg ata gga gga tat ccc ctt gag aca gca tcg aca aac       96
Asn Phe Arg Ser Ile Gly Gly Tyr Pro Leu Glu Thr Ala Ser Thr Asn
            20                  25                  30

aat cac cgc tcc acg agg caa gga ttc gca ttt cgc agt gcc gat cca      144
Asn His Arg Ser Thr Arg Gln Gly Phe Ala Phe Arg Ser Ala Asp Pro
        35                  40                  45

acc tac gtc acc cag aaa ggc ctg gaa acc atc ctt tcg ctc gac atc      192
Thr Tyr Val Thr Gln Lys Gly Leu Glu Thr Ile Leu Ser Leu Asp Ile
    50                  55                  60

act cga gcc ttt gac ctc cgc tca ctg gaa gaa gca aag gca cag cgc      240
Thr Arg Ala Phe Asp Leu Arg Ser Leu Glu Glu Ala Lys Ala Gln Arg
65                  70                  75                  80

gca aaa ctc cag gcc gcc tca gga tgt ctc gac tgc agc atc agc cag      288
Ala Lys Leu Gln Ala Ala Ser Gly Cys Leu Asp Cys Ser Ile Ser Gln
                85                  90                  95

cac atg atc cac cag ccc aca ccc cta ttt cca gat ggg gac tgg agt      336
His Met Ile His Gln Pro Thr Pro Leu Phe Pro Asp Gly Asp Trp Ser
            100                 105                 110

cca gag gcc gca ggg gag cgg tat ctg cag tac gcc cag gct gag gga      384
Pro Glu Ala Ala Gly Glu Arg Tyr Leu Gln Tyr Ala Gln Ala Glu Gly
        115                 120                 125

gat ggg ata tcg ggc tac gtg gag gtc tac gga aac atg ctc gag gaa      432
Asp Gly Ile Ser Gly Tyr Val Glu Val Tyr Gly Asn Met Leu Glu Glu
    130                 135                 140

ggt tgg atg gcg att cgc gag att ctg ctt cat gtc cgg gac cgg cct      480
Gly Trp Met Ala Ile Arg Glu Ile Leu Leu His Val Arg Asp Arg Pro
145                 150                 155                 160

aca gag gcg ttt cta tgc cat tgt agt gca ggg aaa gat cgt acg ggg      528
Thr Glu Ala Phe Leu Cys His Cys Ser Ala Gly Lys Asp Arg Thr Gly
                165                 170                 175

att gtc att gcg gtt ttg ttg aag gtt gca ggg tgc tcg gat gat ctt      576
Ile Val Ile Ala Val Leu Leu Lys Val Ala Gly Cys Ser Asp Asp Leu
            180                 185                 190

gtg tgc aga gag tat gag ttg acc gag atc ggg ttg gct cga cgg agg      624
Val Cys Arg Glu Tyr Glu Leu Thr Glu Ile Gly Leu Ala Arg Arg Arg
        195                 200                 205

gag ttt atc gtg cag cat ctg ctt aag aag ccg gaa atg aat gga tcg      672
Glu Phe Ile Val Gln His Leu Leu Lys Lys Pro Glu Met Asn Gly Ser
    210                 215                 220

agg gaa ctg gcc gaa aga gtg gcg ggg gcc agg tat gag aat atg aag      720
Arg Glu Leu Ala Glu Arg Val Ala Gly Ala Arg Tyr Glu Asn Met Lys
225                 230                 235                 240

gaa acg ctg gag atg gtg caa act aga tat aga ggg atg agg ggc tat      768
Glu Thr Leu Glu Met Val Gln Thr Arg Tyr Arg Gly Met Arg Gly Tyr
                245                 250                 255

tgc aag gag att tgc ggc ttg acc gac gaa gat cta tct att atc cag      816
Cys Lys Glu Ile Cys Gly Leu Thr Asp Glu Asp Leu Ser Ile Ile Gln
            260                 265                 270

ggg aac ttg act agt ccg gag agt cct atc ttc taa                      852
Gly Asn Leu Thr Ser Pro Glu Ser Pro Ile Phe
        275                 280
```

<210> SEQ ID NO 170
<211> LENGTH: 283
<212> TYPE: PRT
<213> ORGANISM: Aspergillus wentii

<400> SEQUENCE: 170

```
Met Ala Ser Val Pro Ala Pro Pro Phe Val His Val Glu Gly Met Ser
1               5                   10                  15

Asn Phe Arg Ser Ile Gly Gly Tyr Pro Leu Glu Thr Ala Ser Thr Asn
            20                  25                  30

Asn His Arg Ser Thr Arg Gln Gly Phe Ala Phe Arg Ser Ala Asp Pro
        35                  40                  45

Thr Tyr Val Thr Gln Lys Gly Leu Glu Thr Ile Leu Ser Leu Asp Ile
    50                  55                  60

Thr Arg Ala Phe Asp Leu Arg Ser Leu Glu Glu Ala Lys Ala Gln Arg
65                  70                  75                  80

Ala Lys Leu Gln Ala Ala Ser Gly Cys Leu Asp Cys Ser Ile Ser Gln
                85                  90                  95

His Met Ile His Gln Pro Thr Pro Leu Phe Pro Asp Gly Asp Trp Ser
            100                 105                 110

Pro Glu Ala Ala Gly Glu Arg Tyr Leu Gln Tyr Ala Gln Ala Glu Gly
        115                 120                 125

Asp Gly Ile Ser Gly Tyr Val Glu Val Tyr Gly Asn Met Leu Glu Glu
    130                 135                 140

Gly Trp Met Ala Ile Arg Glu Ile Leu Leu His Val Arg Asp Arg Pro
145                 150                 155                 160

Thr Glu Ala Phe Leu Cys His Cys Ser Ala Gly Lys Asp Arg Thr Gly
                165                 170                 175

Ile Val Ile Ala Val Leu Leu Lys Val Ala Gly Cys Ser Asp Asp Leu
            180                 185                 190

Val Cys Arg Glu Tyr Glu Leu Thr Glu Ile Gly Leu Ala Arg Arg Arg
        195                 200                 205

Glu Phe Ile Val Gln His Leu Leu Lys Lys Pro Glu Met Asn Gly Ser
    210                 215                 220

Arg Glu Leu Ala Glu Arg Val Ala Gly Ala Arg Tyr Glu Asn Met Lys
225                 230                 235                 240

Glu Thr Leu Glu Met Val Gln Thr Arg Tyr Arg Gly Met Arg Gly Tyr
                245                 250                 255

Cys Lys Glu Ile Cys Gly Leu Thr Asp Glu Asp Leu Ser Ile Ile Gln
            260                 265                 270

Gly Asn Leu Thr Ser Pro Glu Ser Pro Ile Phe
        275                 280
```

<210> SEQ ID NO 171
<211> LENGTH: 852
<212> TYPE: DNA
<213> ORGANISM: Aspergillus wentii

<400> SEQUENCE: 171

```
atggcgtctg tccctgctcc accgtttgtt catgttgaag gtatgtctaa ttttcgtagc      60

atcggtggct acccgctgga gactgcctcc acgaataacc atcgctcgac ccgtcaaggc     120

ttcgcgtttc gtagcgcgga cccgacgtat gtgacgcaga aaggcctgga aaccattctg     180

tccctggata ttacccgcgc atttgacttg cgtagcttgg aagaagcaaa ggcacaacgt     240
```

```
gcgaagttgc aggccgcgag cggttgtctg gattgcagca ttagccaaca catgatccac    300

caaccgaccc cgctgttccc ggatggtgac tggtccccgg aagcggcggg tgagcgctac    360

ttgcagtacg cacaagctga gggtgatggt atcagcggtt atgtcgaagt ttatggtaat    420

atgctggaag agggctggat ggcgatccgt gagattctgc tgcacgtccg tgaccgcccg    480

accgaagcat tcctgtgcca ctgttccgcc ggtaaagatc gtacgggtat cgtgattgct    540

gttctgctca aagtcgcggg ttgcagcgac gacctggtgt gtcgtgagta cgaactgacc    600

gagattggcc tggcgcgccg tagagagttc atcgttcagc atctgctgaa gaaaccggaa    660

atgaacggca gccgtgagct ggcggagcgc gtcgcaggcg cccgttacga gaacatgaaa    720

gaaaccctgg aaatggtgca gacccgttac cgcggcatgc gcggctattg caaagaaatc    780

tgcggtctga ccgacgaaga tctgagcatt atccagggta acctgacgag cccggagagc    840

ccgattttct aa                                                        852


<210> SEQ ID NO 172
<211> LENGTH: 2892
<212> TYPE: DNA
<213> ORGANISM: Talaromyces verruculosus
<220> FEATURE:
<221> NAME/KEY: CDS
<222> LOCATION: (1)..(2892)

<400> SEQUENCE: 172

atg agc cca atg gat tta caa gaa tca gcg gca gct ttg gtg cgg cag       48
Met Ser Pro Met Asp Leu Gln Glu Ser Ala Ala Ala Leu Val Arg Gln
1               5                   10                  15

ttg ggg gag aga gtc gaa gat cgc cgt ggt ttt gga ttc atg agc cct       96
Leu Gly Glu Arg Val Glu Asp Arg Arg Gly Phe Gly Phe Met Ser Pro
            20                  25                  30

gcc atc tat gat acc gca tgg gtc tct atg att agc aag aca atc gat      144
Ala Ile Tyr Asp Thr Ala Trp Val Ser Met Ile Ser Lys Thr Ile Asp
        35                  40                  45

gac caa aaa aca tgg ttg ttt gca gaa tgt ttc cag tac att ctt tct      192
Asp Gln Lys Thr Trp Leu Phe Ala Glu Cys Phe Gln Tyr Ile Leu Ser
    50                  55                  60

cat cag ctc gaa gac ggt ggt tgg gca atg tat gca tct gaa atc gac      240
His Gln Leu Glu Asp Gly Gly Trp Ala Met Tyr Ala Ser Glu Ile Asp
65                  70                  75                  80

gcc atc cta aac act tcg gcc tca tta cta tca tta aag aga cat ctt      288
Ala Ile Leu Asn Thr Ser Ala Ser Leu Leu Ser Leu Lys Arg His Leu
                85                  90                  95

tca aat ccc tat caa att aca tct atc aca caa gag gat ctg tcc gcc      336
Ser Asn Pro Tyr Gln Ile Thr Ser Ile Thr Gln Glu Asp Leu Ser Ala
            100                 105                 110

cgc att aac agg gct cag aat gct tta cag aag ctt ctc aat gag tgg      384
Arg Ile Asn Arg Ala Gln Asn Ala Leu Gln Lys Leu Leu Asn Glu Trp
        115                 120                 125

aat gtc gac agc acg ctc cac gtg gga ttc gag atc cta gtt ccg gcc      432
Asn Val Asp Ser Thr Leu His Val Gly Phe Glu Ile Leu Val Pro Ala
    130                 135                 140

cta ctc agg tat ctc gaa gat gag ggc atc gct ttt gct ttt tct ggt      480
Leu Leu Arg Tyr Leu Glu Asp Glu Gly Ile Ala Phe Ala Phe Ser Gly
145                 150                 155                 160

aga gag cgc ctg ctt gag att gag aaa cag aaa tta tca aag ttc aaa      528
Arg Glu Arg Leu Leu Glu Ile Glu Lys Gln Lys Leu Ser Lys Phe Lys
                165                 170                 175

gca cag tat cta tac ctt cca atc aaa gtg aca gct ttg cat tct ctg      576
Ala Gln Tyr Leu Tyr Leu Pro Ile Lys Val Thr Ala Leu His Ser Leu
```

-continued

```
            180                 185                 190

gaa gcg ttc ata ggc gcc att gag ttt gat aaa gtc agt cac cac aaa      624
Glu Ala Phe Ile Gly Ala Ile Glu Phe Asp Lys Val Ser His His Lys
        195                 200                 205

gtc agc ggt gcg ttc atg gca tct cca tca tcc aca gca gct tac atg      672
Val Ser Gly Ala Phe Met Ala Ser Pro Ser Ser Thr Ala Ala Tyr Met
    210                 215                 220

atg cat gcg aca caa tgg gat gat gaa tgc gag gat tac cta cgc cac      720
Met His Ala Thr Gln Trp Asp Asp Glu Cys Glu Asp Tyr Leu Arg His
225                 230                 235                 240

gtc att gct cat gca tct ggg aaa gga tcc gga ggt gtt cca agc gct      768
Val Ile Ala His Ala Ser Gly Lys Gly Ser Gly Gly Val Pro Ser Ala
                245                 250                 255

ttt cct tcc acc atc ttt gaa agc gtt tgg cct cta tca act ctg cta      816
Phe Pro Ser Thr Ile Phe Glu Ser Val Trp Pro Leu Ser Thr Leu Leu
            260                 265                 270

aag gtg gga tat gat ctc aac tcg gca cct ttt atc gaa aaa atc aga      864
Lys Val Gly Tyr Asp Leu Asn Ser Ala Pro Phe Ile Glu Lys Ile Arg
        275                 280                 285

tca tac ttg cat gat gca tat att gct gaa aag gga att ctc ggc ttc      912
Ser Tyr Leu His Asp Ala Tyr Ile Ala Glu Lys Gly Ile Leu Gly Phe
    290                 295                 300

act cct ttt gtt ggc gct gat gca gat gat acc gct acc acc ata ttg      960
Thr Pro Phe Val Gly Ala Asp Ala Asp Asp Thr Ala Thr Thr Ile Leu
305                 310                 315                 320

gtg ctc aat ctt ttg aac caa cca gtc tca gtc gac gcg atg ttg aag     1008
Val Leu Asn Leu Leu Asn Gln Pro Val Ser Val Asp Ala Met Leu Lys
                325                 330                 335

gaa ttt gaa gaa gaa cat cac ttc aaa acc tac tct cag gag cgc aat     1056
Glu Phe Glu Glu Glu His His Phe Lys Thr Tyr Ser Gln Glu Arg Asn
            340                 345                 350

cct agt ttc tcg gcc aat tgt aac gtt ctt ctt gcc tta cta tac agt     1104
Pro Ser Phe Ser Ala Asn Cys Asn Val Leu Leu Ala Leu Leu Tyr Ser
        355                 360                 365

caa gag cca tcg ctt tat agc gcg cag atc gaa aaa gct ata agg ttc     1152
Gln Glu Pro Ser Leu Tyr Ser Ala Gln Ile Glu Lys Ala Ile Arg Phe
    370                 375                 380

ctc tat aag caa ttc aca gat tca gaa atg gac gtt cga gac aaa tgg     1200
Leu Tyr Lys Gln Phe Thr Asp Ser Glu Met Asp Val Arg Asp Lys Trp
385                 390                 395                 400

aat cta tca cca tac tat tct tgg atg ctc atg aca caa gcc atc acg     1248
Asn Leu Ser Pro Tyr Tyr Ser Trp Met Leu Met Thr Gln Ala Ile Thr
                405                 410                 415

cgg ttg acg act ctt cag aag act tcg aaa ctt tca aca ttg aga gat     1296
Arg Leu Thr Thr Leu Gln Lys Thr Ser Lys Leu Ser Thr Leu Arg Asp
            420                 425                 430

gat tct atc agc aaa ggc ttg att agt ctg ctg ttt agg ata gct tct     1344
Asp Ser Ile Ser Lys Gly Leu Ile Ser Leu Leu Phe Arg Ile Ala Ser
        435                 440                 445

acc gtg gtt aaa gac caa aag cca gga ggt tct tgg ggc act cga gct     1392
Thr Val Val Lys Asp Gln Lys Pro Gly Gly Ser Trp Gly Thr Arg Ala
    450                 455                 460

tcg aaa gaa gag act gcc tac gca gtg ttg att ctc aca tat gct ttc     1440
Ser Lys Glu Glu Thr Ala Tyr Ala Val Leu Ile Leu Thr Tyr Ala Phe
465                 470                 475                 480

tac ctc gat gag gtt acg gag tcg ttg cgg cat gat atc aag atc gcc     1488
Tyr Leu Asp Glu Val Thr Glu Ser Leu Arg His Asp Ile Lys Ile Ala
                485                 490                 495

att gag aat ggt tgc tca ttc cta tct gaa aga acc atg cag tcc gat     1536
```

-continued

```
Ile Glu Asn Gly Cys Ser Phe Leu Ser Glu Arg Thr Met Gln Ser Asp
            500                 505                 510

tcg gag tgg ctt tgg gtt gag aaa gtc aca tat aaa tca gag gtt ctt      1584
Ser Glu Trp Leu Trp Val Glu Lys Val Thr Tyr Lys Ser Glu Val Leu
        515                 520                 525

tcg gaa gca tat atc ttg gcc gct ctt aaa cgg gca gct gac tta ccc      1632
Ser Glu Ala Tyr Ile Leu Ala Ala Leu Lys Arg Ala Ala Asp Leu Pro
    530                 535                 540

gac gaa aat gca gaa gca gcc ccc gtc ata aat gga att tct aca aat      1680
Asp Glu Asn Ala Glu Ala Ala Pro Val Ile Asn Gly Ile Ser Thr Asn
545                 550                 555                 560

gga ttt gag cat acc gat aga att aac ggc aag ctt aaa gtc aat ggt      1728
Gly Phe Glu His Thr Asp Arg Ile Asn Gly Lys Leu Lys Val Asn Gly
                565                 570                 575

acc aac ggt aca aat ggc agt cat gag aca aac ggt atc aac ggt acg      1776
Thr Asn Gly Thr Asn Gly Ser His Glu Thr Asn Gly Ile Asn Gly Thr
            580                 585                 590

cat gaa att gaa cag atc aat ggc gtc aac ggc acg aat ggt cac tct      1824
His Glu Ile Glu Gln Ile Asn Gly Val Asn Gly Thr Asn Gly His Ser
        595                 600                 605

gat gtg cct cac gat aca aat ggc tgg gta gaa gag ccg acc gcc atc      1872
Asp Val Pro His Asp Thr Asn Gly Trp Val Glu Glu Pro Thr Ala Ile
    610                 615                 620

aat gag aca aat ggc cac tac gtg aat ggc acg aat cac gag act ccc      1920
Asn Glu Thr Asn Gly His Tyr Val Asn Gly Thr Asn His Glu Thr Pro
625                 630                 635                 640

ctt acc aac ggc att tcc aat gga gat tct gtt tcc gtt cat aca gac      1968
Leu Thr Asn Gly Ile Ser Asn Gly Asp Ser Val Ser Val His Thr Asp
                645                 650                 655

cac tcg gac agt tac tat cag cgc agt gat tgg aca gcc gac gaa gaa      2016
His Ser Asp Ser Tyr Tyr Gln Arg Ser Asp Trp Thr Ala Asp Glu Glu
            660                 665                 670

caa att ctt ctc ggt cca ttt gac tac ctg gag agc ctg cca ggc aag      2064
Gln Ile Leu Leu Gly Pro Phe Asp Tyr Leu Glu Ser Leu Pro Gly Lys
        675                 680                 685

aat atg cgc tca caa ctg att caa tca ttc aac aca tgg ctc aaa gtc      2112
Asn Met Arg Ser Gln Leu Ile Gln Ser Phe Asn Thr Trp Leu Lys Val
    690                 695                 700

cca act gag agc ttg gat gtt att att aag gtg att tca atg ttg cat      2160
Pro Thr Glu Ser Leu Asp Val Ile Ile Lys Val Ile Ser Met Leu His
705                 710                 715                 720

acg gcc tct ctc ttg atc gat gat att cag gat caa tca ata ctc cgc      2208
Thr Ala Ser Leu Leu Ile Asp Asp Ile Gln Asp Gln Ser Ile Leu Arg
                725                 730                 735

cgc ggg caa cct gta gcg cac agc atc ttt ggc aca gcg caa gca atg      2256
Arg Gly Gln Pro Val Ala His Ser Ile Phe Gly Thr Ala Gln Ala Met
            740                 745                 750

aac tca ggg aat tat gtc tac ttt cta gcc ctt agg gag gtt cag aaa      2304
Asn Ser Gly Asn Tyr Val Tyr Phe Leu Ala Leu Arg Glu Val Gln Lys
        755                 760                 765

cta caa aac ccg aaa gcc atc agt att tat gtt gac tct ttg att gat      2352
Leu Gln Asn Pro Lys Ala Ile Ser Ile Tyr Val Asp Ser Leu Ile Asp
    770                 775                 780

ctt cac cgt ggc caa ggc atg gag ctt ttc tgg cgg gat tct ctc atg      2400
Leu His Arg Gly Gln Gly Met Glu Leu Phe Trp Arg Asp Ser Leu Met
785                 790                 795                 800

tgc cca acc gaa gag cag tac ctt gac atg gtc gca aac aaa act ggc      2448
Cys Pro Thr Glu Glu Gln Tyr Leu Asp Met Val Ala Asn Lys Thr Gly
                805                 810                 815
```

```
ggc ctg ttt tgc ctt gct atc caa ttg atg caa gct gaa gcc act atc      2496
Gly Leu Phe Cys Leu Ala Ile Gln Leu Met Gln Ala Glu Ala Thr Ile
            820                 825                 830

caa gtc gac ttc ata cca ctt gtc cga cta ctc ggc atc atc ttc cag      2544
Gln Val Asp Phe Ile Pro Leu Val Arg Leu Leu Gly Ile Ile Phe Gln
        835                 840                 845

att tgt gat gat tac ttg aat ctg aag tct acg gcc tat aca gac aac      2592
Ile Cys Asp Asp Tyr Leu Asn Leu Lys Ser Thr Ala Tyr Thr Asp Asn
    850                 855                 860

aaa ggg ttg tgt gag gat ttg aca gag ggc aaa ttc tct ttt cct atc      2640
Lys Gly Leu Cys Glu Asp Leu Thr Glu Gly Lys Phe Ser Phe Pro Ile
865                 870                 875                 880

atc cat agc att cga tcc aac cct ggc aac cga cag cta atc aac atc      2688
Ile His Ser Ile Arg Ser Asn Pro Gly Asn Arg Gln Leu Ile Asn Ile
                885                 890                 895

ttg aag caa aag cca cgt gaa gac gac atc aaa cgc tat gct cta tcc      2736
Leu Lys Gln Lys Pro Arg Glu Asp Asp Ile Lys Arg Tyr Ala Leu Ser
            900                 905                 910

tat atg gaa agc acc aac tca ttt gag tat act cgg ggt gtc gtt aga      2784
Tyr Met Glu Ser Thr Asn Ser Phe Glu Tyr Thr Arg Gly Val Val Arg
        915                 920                 925

aaa ctg aag acc gag gca atc gat act att caa ggc ttg gag aag cac      2832
Lys Leu Lys Thr Glu Ala Ile Asp Thr Ile Gln Gly Leu Glu Lys His
    930                 935                 940

ggc ctg gaa gag aat att ggc att cga aag ata cta gct cgc atg tcc      2880
Gly Leu Glu Glu Asn Ile Gly Ile Arg Lys Ile Leu Ala Arg Met Ser
945                 950                 955                 960

ctt gag cta tga                                                      2892
Leu Glu Leu


<210> SEQ ID NO 173
<211> LENGTH: 963
<212> TYPE: PRT
<213> ORGANISM: Talaromyces verruculosus

<400> SEQUENCE: 173

Met Ser Pro Met Asp Leu Gln Glu Ser Ala Ala Ala Leu Val Arg Gln
1               5                   10                  15

Leu Gly Glu Arg Val Glu Asp Arg Arg Gly Phe Gly Phe Met Ser Pro
            20                  25                  30

Ala Ile Tyr Asp Thr Ala Trp Val Ser Met Ile Ser Lys Thr Ile Asp
        35                  40                  45

Asp Gln Lys Thr Trp Leu Phe Ala Glu Cys Phe Gln Tyr Ile Leu Ser
    50                  55                  60

His Gln Leu Glu Asp Gly Gly Trp Ala Met Tyr Ala Ser Glu Ile Asp
65                  70                  75                  80

Ala Ile Leu Asn Thr Ser Ala Ser Leu Leu Ser Leu Lys Arg His Leu
                85                  90                  95

Ser Asn Pro Tyr Gln Ile Thr Ser Ile Thr Gln Glu Asp Leu Ser Ala
            100                 105                 110

Arg Ile Asn Arg Ala Gln Asn Ala Leu Gln Lys Leu Leu Asn Glu Trp
        115                 120                 125

Asn Val Asp Ser Thr Leu His Val Gly Phe Glu Ile Leu Val Pro Ala
    130                 135                 140

Leu Leu Arg Tyr Leu Glu Asp Glu Gly Ile Ala Phe Ala Phe Ser Gly
145                 150                 155                 160

Arg Glu Arg Leu Leu Glu Ile Glu Lys Gln Lys Leu Ser Lys Phe Lys
                165                 170                 175
```

-continued

```
Ala Gln Tyr Leu Tyr Leu Pro Ile Lys Val Thr Ala Leu His Ser Leu
            180                 185                 190

Glu Ala Phe Ile Gly Ala Ile Glu Phe Asp Lys Val Ser His His Lys
        195                 200                 205

Val Ser Gly Ala Phe Met Ala Ser Pro Ser Ser Thr Ala Ala Tyr Met
    210                 215                 220

Met His Ala Thr Gln Trp Asp Asp Glu Cys Glu Asp Tyr Leu Arg His
225                 230                 235                 240

Val Ile Ala His Ala Ser Gly Lys Gly Ser Gly Gly Val Pro Ser Ala
                245                 250                 255

Phe Pro Ser Thr Ile Phe Glu Ser Val Trp Pro Leu Ser Thr Leu Leu
            260                 265                 270

Lys Val Gly Tyr Asp Leu Asn Ser Ala Pro Phe Ile Glu Lys Ile Arg
        275                 280                 285

Ser Tyr Leu His Asp Ala Tyr Ile Ala Glu Lys Gly Ile Leu Gly Phe
    290                 295                 300

Thr Pro Phe Val Gly Ala Asp Ala Asp Asp Thr Ala Thr Thr Ile Leu
305                 310                 315                 320

Val Leu Asn Leu Leu Asn Gln Pro Val Ser Val Asp Ala Met Leu Lys
                325                 330                 335

Glu Phe Glu Glu Glu His His Phe Lys Thr Tyr Ser Gln Glu Arg Asn
            340                 345                 350

Pro Ser Phe Ser Ala Asn Cys Asn Val Leu Leu Ala Leu Leu Tyr Ser
        355                 360                 365

Gln Glu Pro Ser Leu Tyr Ser Ala Gln Ile Glu Lys Ala Ile Arg Phe
    370                 375                 380

Leu Tyr Lys Gln Phe Thr Asp Ser Glu Met Asp Val Arg Asp Lys Trp
385                 390                 395                 400

Asn Leu Ser Pro Tyr Tyr Ser Trp Met Leu Met Thr Gln Ala Ile Thr
                405                 410                 415

Arg Leu Thr Thr Leu Gln Lys Thr Ser Lys Leu Ser Thr Leu Arg Asp
            420                 425                 430

Asp Ser Ile Ser Lys Gly Leu Ile Ser Leu Leu Phe Arg Ile Ala Ser
        435                 440                 445

Thr Val Val Lys Asp Gln Lys Pro Gly Gly Ser Trp Gly Thr Arg Ala
    450                 455                 460

Ser Lys Glu Glu Thr Ala Tyr Ala Val Leu Ile Leu Thr Tyr Ala Phe
465                 470                 475                 480

Tyr Leu Asp Glu Val Thr Glu Ser Leu Arg His Asp Ile Lys Ile Ala
                485                 490                 495

Ile Glu Asn Gly Cys Ser Phe Leu Ser Glu Arg Thr Met Gln Ser Asp
            500                 505                 510

Ser Glu Trp Leu Trp Val Glu Lys Val Thr Tyr Lys Ser Glu Val Leu
        515                 520                 525

Ser Glu Ala Tyr Ile Leu Ala Ala Leu Lys Arg Ala Ala Asp Leu Pro
    530                 535                 540

Asp Glu Asn Ala Glu Ala Ala Pro Val Ile Asn Gly Ile Ser Thr Asn
545                 550                 555                 560

Gly Phe Glu His Thr Asp Arg Ile Asn Gly Lys Leu Lys Val Asn Gly
                565                 570                 575

Thr Asn Gly Thr Asn Gly Ser His Glu Thr Asn Gly Ile Asn Gly Thr
            580                 585                 590
```

```
His Glu Ile Glu Gln Ile Asn Gly Val Asn Gly Thr Asn Gly His Ser
        595                 600                 605

Asp Val Pro His Asp Thr Asn Gly Trp Val Glu Glu Pro Thr Ala Ile
    610                 615                 620

Asn Glu Thr Asn Gly His Tyr Val Asn Gly Thr Asn His Glu Thr Pro
625                 630                 635                 640

Leu Thr Asn Gly Ile Ser Asn Gly Asp Ser Val Ser Val His Thr Asp
                645                 650                 655

His Ser Asp Ser Tyr Tyr Gln Arg Ser Asp Trp Thr Ala Asp Glu Glu
            660                 665                 670

Gln Ile Leu Leu Gly Pro Phe Asp Tyr Leu Glu Ser Leu Pro Gly Lys
        675                 680                 685

Asn Met Arg Ser Gln Leu Ile Gln Ser Phe Asn Thr Trp Leu Lys Val
    690                 695                 700

Pro Thr Glu Ser Leu Asp Val Ile Ile Lys Val Ile Ser Met Leu His
705                 710                 715                 720

Thr Ala Ser Leu Leu Ile Asp Asp Ile Gln Asp Gln Ser Ile Leu Arg
                725                 730                 735

Arg Gly Gln Pro Val Ala His Ser Ile Phe Gly Thr Ala Gln Ala Met
            740                 745                 750

Asn Ser Gly Asn Tyr Val Tyr Phe Leu Ala Leu Arg Glu Val Gln Lys
        755                 760                 765

Leu Gln Asn Pro Lys Ala Ile Ser Ile Tyr Val Asp Ser Leu Ile Asp
    770                 775                 780

Leu His Arg Gly Gln Gly Met Glu Leu Phe Trp Arg Asp Ser Leu Met
785                 790                 795                 800

Cys Pro Thr Glu Glu Gln Tyr Leu Asp Met Val Ala Asn Lys Thr Gly
                805                 810                 815

Gly Leu Phe Cys Leu Ala Ile Gln Leu Met Gln Ala Glu Ala Thr Ile
            820                 825                 830

Gln Val Asp Phe Ile Pro Leu Val Arg Leu Leu Gly Ile Ile Phe Gln
        835                 840                 845

Ile Cys Asp Asp Tyr Leu Asn Leu Lys Ser Thr Ala Tyr Thr Asp Asn
    850                 855                 860

Lys Gly Leu Cys Glu Asp Leu Thr Glu Gly Lys Phe Ser Phe Pro Ile
865                 870                 875                 880

Ile His Ser Ile Arg Ser Asn Pro Gly Asn Arg Gln Leu Ile Asn Ile
                885                 890                 895

Leu Lys Gln Lys Pro Arg Glu Asp Asp Ile Lys Arg Tyr Ala Leu Ser
            900                 905                 910

Tyr Met Glu Ser Thr Asn Ser Phe Glu Tyr Thr Arg Gly Val Val Arg
        915                 920                 925

Lys Leu Lys Thr Glu Ala Ile Asp Thr Ile Gln Gly Leu Glu Lys His
    930                 935                 940

Gly Leu Glu Glu Asn Ile Gly Ile Arg Lys Ile Leu Ala Arg Met Ser
945                 950                 955                 960

Leu Glu Leu
```

<210> SEQ ID NO 174
<211> LENGTH: 2892
<212> TYPE: DNA
<213> ORGANISM: Talaromyces verruculosus

<400> SEQUENCE: 174

-continued

```
atgagcccta tggatttgca agaaagcgcc gcagccctgg tccgtcaatt gggtgaacgc      60
gttgaggatc gccgcggttt tggtttcatg agcccggcca tttatgacac ggcctgggtt     120
agcatgatta gcaagaccat cgacgaccaa aaaacttggc tgtttgcgga gtgcttccag     180
tacattctgt ctcaccaact ggaagatggt ggctgggcga tgtacgcatc cgaaatcgat     240
gccatcttga atacttccgc gtcactgctg tccctgaaac gccacctgtc caacccttac     300
cagatcacca gcatcactca ggaagatctg agcgctcgca tcaaccgcgc tcaaaacgcc     360
ctgcagaaat tgctgaacga gtggaacgtt gactccacgc tgcacgtcgg tttcgagatt     420
ctggttccgg cgctgctgcg ctatctggaa gatgaaggca tcgcgtttgc gttctcgggt     480
cgtgagcgtt tgttagagat tgagaaacaa aaactgtcca agtttaaagc gcagtatttg     540
tacttaccga ttaaggtcac cgcactgcat agcctggaag ccttcatcgg cgctattgag     600
ttcgacaaag tcagccatca caaagtatcc ggtgctttca tggcgtcgcc gtctagcacc     660
gcagcataca tgatgcatgc gacgcaatgg gatgacgaat gtgaggatta cttgcgtcac     720
gtgatcgcgc atgcgtcagg taagggttct ggcggcgtgc cgagcgcctt tccgagcacc     780
atcttcgaga gcgtttggcc gctgtctact ctgctgaaag ttggctatga tctgaatagc     840
gctccgttca tcgagaaaat tcgtagctac ttgcacgatg cctatatcgc agagaaaggt     900
attctcggtt tcaccccgtt cgttggcgct gacgcggacg acaccgctac cacgattctg     960
gtgttgaatc tgctgaacca accggtgagc gtggacgcga tgttgaaaga atttgaagag    1020
gaacatcact tcaagaccta cagccaagag cgtaatccga gcttttccgc aaactgtaat    1080
gttctgctgg cgctgctgta cagccaggaa ccgagcctgt acagcgcgca aatcgaaaaa    1140
gcgatccgtt ttctgtataa gcaattcacc gactctgaga tggatgtgcg cgataaatgg    1200
aacctgtccc cgtattatag ctggatgctg atgacccagg ccatcacccg tctgacgacc    1260
ctgcaaaaga ccagcaagct gagcacgctg cgtgatgaca gcattagcaa gggcctgatt    1320
tctctgctgt tccgcattgc atccaccgtg gttaaagatc aaaaaccggg tggcagctgg    1380
ggcacgcgtg cgagcaaaga agaaacggca tacgccgtgc tgattctgac ctacgcgttt    1440
tatctggacg aggtgaccga gtctctgcgc cacgatatca aaattgcaat cgagaatggt    1500
tgctcgttcc tgagcgagcg caccatgcaa agcgacagcg agtggctgtg ggtcgaaaag    1560
gttacctaca agagcgaagt gctgagcgaa gcatacatcc tggcagctct gaaacgtgcg    1620
gcagacttgc cggatgagaa cgctgaggca gccccagtga tcaacggtat ctctaccaat    1680
ggctttgagc acaccgaccg cattaatggt aaactcaagg tcaatggtac gaatggcacc    1740
aacggttccc acgaaacgaa cggtatcaat ggcacccatg agattgagca aattaatggt    1800
gtcaacggca cgaatggcca tagcgacgtg ccacatgaca cgaatggttg ggtcgaggaa    1860
ccgacggcga ttaatgaaac gaacggtcac tacgttaacg gcaccaacca tgagactccg    1920
ctgaccaatg gtattagcaa tggtgactcc gtgagcgttc acaccgacca tagcgacagc    1980
tactatcagc gtagcgactg gaccgcggat gaagaacaga tcctgctggg tccattcgat    2040
tacctggaat ccctgcctgg taaaaatatg cgcagccagc tgatccagtc tttcaatacg    2100
tggctgaagg tcccgaccga gagcttggac gtgattatta aggtcattag catgctgcac    2160
actgctagcc tgctgatcga cgatattcag gaccaaagca tcctgcgtcg tggtcagcct    2220
gtggcgcact cgatcttcgg caccgcgcaa gcgatgaact ctggtaacta tgtttacttc    2280
ctggcattgc gtgaagttca gaaattgcaa aacccgaagg ctatcagcat ttatgtggac    2340
agcttgatcg atcttcatcg cggccagggc atggaactgt tctggcgtga ttctctgatg    2400
```

```
tgcccgactg aagaacagta tctggacatg gtggcgaaca agaccggtgg cctgttttgt   2460

ctggcgattc agctgatgca ggcagaagcg accattcagg ttgattttat tccgctggtg   2520

cgtctgctgg gtatcatttt ccagatttgc gacgactacc tgaacttgaa aagcactgcg   2580

tataccgaca acaaaggtct gtgtgaagat cttaccgagg gtaaattctc cttcccgatc   2640

attcacagca tccgtagcaa tccgggcaat cgtcagctga tcaatattct gaagcaaaaa   2700

ccgcgcgaag atgacatcaa gcgttacgca ctgtcctata tggagagcac gaatagcttc   2760

gagtacaccc gtggcgtcgt ccgtaaattg aaaaccgaag caattgacac gattcaaggt   2820

ctggagaagc atggcctgga agaaaacatt ggtattcgta agattctggc gcgtatgagc   2880

ctggaactgt aa                                                        2892
```

```
<210> SEQ ID NO 175
<211> LENGTH: 936
<212> TYPE: DNA
<213> ORGANISM: Talaromyces cellulolyticus
<220> FEATURE:
<221> NAME/KEY: CDS
<222> LOCATION: (1)..(936)

<400> SEQUENCE: 175

atg tct aat gac acc act agc acg gct tct gcc gga aca gca act tct      48
Met Ser Asn Asp Thr Thr Ser Thr Ala Ser Ala Gly Thr Ala Thr Ser
1               5                   10                  15

tcg cgg ttt ctt tct gtg ggc gga gtt gtg aat ttc cgt gaa ctg ggc      96
Ser Arg Phe Leu Ser Val Gly Gly Val Val Asn Phe Arg Glu Leu Gly
            20                  25                  30

ggt tat cca tgt gat tct gtc cct cct gct cct gcc tca aac ggc tca     144
Gly Tyr Pro Cys Asp Ser Val Pro Pro Ala Pro Ala Ser Asn Gly Ser
        35                  40                  45

ccg gac aac gca tct gaa gcg atc ctt tgg gtt ggc cac tcg tcc att     192
Pro Asp Asn Ala Ser Glu Ala Ile Leu Trp Val Gly His Ser Ser Ile
    50                  55                  60

cgg cct agg ttt ctc ttt cga tcg gca cag ccg tct cag att acc ccg     240
Arg Pro Arg Phe Leu Phe Arg Ser Ala Gln Pro Ser Gln Ile Thr Pro
65                  70                  75                  80

gcc ggt att gag aca ttg atc cgc cag ctt ggc atc cag gca att ttt     288
Ala Gly Ile Glu Thr Leu Ile Arg Gln Leu Gly Ile Gln Ala Ile Phe
                85                  90                  95

gac ttt cgt tca cgg acg gaa att cag ctt gtc gcc act cgc tat cct     336
Asp Phe Arg Ser Arg Thr Glu Ile Gln Leu Val Ala Thr Arg Tyr Pro
            100                 105                 110

gat tcg cta ctc gag ata cct ggt acg act cgc tat tcc gtg ccc gtc     384
Asp Ser Leu Leu Glu Ile Pro Gly Thr Thr Arg Tyr Ser Val Pro Val
        115                 120                 125

ttc acg gag ggc gac tat tcc ccg gcg tca tta gtc aag agg tac gga     432
Phe Thr Glu Gly Asp Tyr Ser Pro Ala Ser Leu Val Lys Arg Tyr Gly
    130                 135                 140

gtg tcc tcc gat act gca act gat tcc act tcc tcc aaa tgt gcc aag     480
Val Ser Ser Asp Thr Ala Thr Asp Ser Thr Ser Ser Lys Cys Ala Lys
145                 150                 155                 160

cct aca gga ttc gtc cac gca tat gag gct atc gca cgc agc gca gca     528
Pro Thr Gly Phe Val His Ala Tyr Glu Ala Ile Ala Arg Ser Ala Ala
                165                 170                 175

gaa aac ggc agt ttt cgt aaa ata acg gac cac ata ata caa cat ccg     576
Glu Asn Gly Ser Phe Arg Lys Ile Thr Asp His Ile Ile Gln His Pro
            180                 185                 190

gac cgg cct atc ctg ttt cac tgt aca ttg gga aaa gac cga acc ggt     624
```

```
Asp Arg Pro Ile Leu Phe His Cys Thr Leu Gly Lys Asp Arg Thr Gly
        195                 200                 205

gta ttt gca gca ttg tta ttg agt ctt tgc ggg gta cca aac gac acg      672
Val Phe Ala Ala Leu Leu Leu Ser Leu Cys Gly Val Pro Asn Asp Thr
    210                 215                 220

ata gtt gaa gac tat gct atg act acc gag gga ttt ggg gtc tgg cga      720
Ile Val Glu Asp Tyr Ala Met Thr Thr Glu Gly Phe Gly Val Trp Arg
225                 230                 235                 240

gaa cat cta att caa cgc ctg tta caa aga aag gat gca gct acg cgt      768
Glu His Leu Ile Gln Arg Leu Leu Gln Arg Lys Asp Ala Ala Thr Arg
                245                 250                 255

gag gat gca gaa ttc att att gcc agc cac ccg gag agt atg aag gct      816
Glu Asp Ala Glu Phe Ile Ile Ala Ser His Pro Glu Ser Met Lys Ala
            260                 265                 270

ttt cta gaa gat gtg gta gca acc aag ttc ggg gat gct cga aat tac      864
Phe Leu Glu Asp Val Val Ala Thr Lys Phe Gly Asp Ala Arg Asn Tyr
        275                 280                 285

ttt atc cag cac tgt gga ttg acg gaa gcg gag gtt gat aag cta att      912
Phe Ile Gln His Cys Gly Leu Thr Glu Ala Glu Val Asp Lys Leu Ile
    290                 295                 300

cgg aca ctg gtc att gcg aat tga                                      936
Arg Thr Leu Val Ile Ala Asn
305                 310


<210> SEQ ID NO 176
<211> LENGTH: 311
<212> TYPE: PRT
<213> ORGANISM: Talaromyces cellulolyticus

<400> SEQUENCE: 176

Met Ser Asn Asp Thr Thr Ser Thr Ala Ser Ala Gly Thr Ala Thr Ser
1               5                   10                  15

Ser Arg Phe Leu Ser Val Gly Gly Val Val Asn Phe Arg Glu Leu Gly
            20                  25                  30

Gly Tyr Pro Cys Asp Ser Val Pro Pro Ala Pro Ala Ser Asn Gly Ser
        35                  40                  45

Pro Asp Asn Ala Ser Glu Ala Ile Leu Trp Val Gly His Ser Ser Ile
    50                  55                  60

Arg Pro Arg Phe Leu Phe Arg Ser Ala Gln Pro Ser Gln Ile Thr Pro
65                  70                  75                  80

Ala Gly Ile Glu Thr Leu Ile Arg Gln Leu Gly Ile Gln Ala Ile Phe
                85                  90                  95

Asp Phe Arg Ser Arg Thr Glu Ile Gln Leu Val Ala Thr Arg Tyr Pro
            100                 105                 110

Asp Ser Leu Leu Glu Ile Pro Gly Thr Thr Arg Tyr Ser Val Pro Val
        115                 120                 125

Phe Thr Glu Gly Asp Tyr Ser Pro Ala Ser Leu Val Lys Arg Tyr Gly
    130                 135                 140

Val Ser Ser Asp Thr Ala Thr Asp Ser Thr Ser Ser Lys Cys Ala Lys
145                 150                 155                 160

Pro Thr Gly Phe Val His Ala Tyr Glu Ala Ile Ala Arg Ser Ala Ala
                165                 170                 175

Glu Asn Gly Ser Phe Arg Lys Ile Thr Asp His Ile Ile Gln His Pro
            180                 185                 190

Asp Arg Pro Ile Leu Phe His Cys Thr Leu Gly Lys Asp Arg Thr Gly
        195                 200                 205

Val Phe Ala Ala Leu Leu Leu Ser Leu Cys Gly Val Pro Asn Asp Thr
```

```
    210                 215                 220

Ile Val Glu Asp Tyr Ala Met Thr Thr Glu Gly Phe Gly Val Trp Arg
225                 230                 235                 240

Glu His Leu Ile Gln Arg Leu Leu Gln Arg Lys Asp Ala Ala Thr Arg
                245                 250                 255

Glu Asp Ala Glu Phe Ile Ile Ala Ser His Pro Glu Ser Met Lys Ala
            260                 265                 270

Phe Leu Glu Asp Val Val Ala Thr Lys Phe Gly Asp Ala Arg Asn Tyr
        275                 280                 285

Phe Ile Gln His Cys Gly Leu Thr Glu Ala Glu Val Asp Lys Leu Ile
    290                 295                 300

Arg Thr Leu Val Ile Ala Asn
305                 310


<210> SEQ ID NO 177
<211> LENGTH: 936
<212> TYPE: DNA
<213> ORGANISM: Talaromyces cellulolyticus

<400> SEQUENCE: 177

atgagcaacg acacgaccag caccgcatcc gcaggcaccg caacttcttc gcgctttctg      60

agcgtcggtg gcgtggttaa cttccgtgag ttgggtggct acccgtgcga cagcgttcct     120

cctgcaccag caagcaatgg tagcccggac aatgcgagcg aagcgattct gtgggttggt     180

cacagcagca ttcgtccgcg cttcttgttt cgtagcgcac agccgtccca gatcaccccg     240

gccggtattg aaacgctgat tcgccaactc ggtattcaag cgatctttga ctttcgttcc     300

cgtaccgaga tccaactggt ggcaacccgc tacccagata gcctgctgga aattccgggc     360

acgactcgtt actctgttcc ggtctttacc gagggcgact acagcccggc ttctctggtt     420

aagcgttatg gtgtctctag cgacacggca acggatagca ccagctcaaa gtgcgcgaaa     480

ccgaccggct ttgtgcatgc ttatgaagcg attgctcgtt ctgccgcgga gaacggtagc     540

ttccgcaaga tcaccgacca cattatccaa catccggatc gcccgatcct gtttcactgc     600

acgctgggca aagaccgtac cggtgttttc gcagcgctgc tgctgagctt gtgtggtgtc     660

ccgaatgaca ccatcgtgga agattatgcg atgacgaccg aaggcttcgg tgtgtggcgt     720

gagcacttga ttcagcgtct gctgcagcgc aaagatgcgg ctacgcgtga agatgccgag     780

ttcattatcg cgagccatcc ggagagcatg aaagcgttcc tggaagatgt cgttgcgacc     840

aaattcggtg acgcccgcaa ctactttatc cagcactgtg gtctgaccga agccgaagtg     900

gataagctga tccgtacgct ggtgatcgcg aattaa                               936


<210> SEQ ID NO 178
<211> LENGTH: 1122
<212> TYPE: DNA
<213> ORGANISM: Castellaniella defragrans
<220> FEATURE:
<221> NAME/KEY: CDS
<222> LOCATION: (1)..(1122)

<400> SEQUENCE: 178

atg aac gac acc cag gat ttc att tcc gcg cag gcc gcc gtg ctg cgc       48
Met Asn Asp Thr Gln Asp Phe Ile Ser Ala Gln Ala Ala Val Leu Arg
1               5                   10                  15

cag gtc ggc ggg ccg ctc gcg gtc gag ccc gtg cgc atc agc atg ccc       96
Gln Val Gly Gly Pro Leu Ala Val Glu Pro Val Arg Ile Ser Met Pro
            20                  25                  30
```

-continued

```
aaa ggc gac gag gtc ttg atc cgc atc gcc ggc gtg ggc gtc tgc cac      144
Lys Gly Asp Glu Val Leu Ile Arg Ile Ala Gly Val Gly Val Cys His
        35                  40                  45

acc gac ctg gtg tgc cgc gac gga ttt ccc gtg ccg ctg ccg atc gtg      192
Thr Asp Leu Val Cys Arg Asp Gly Phe Pro Val Pro Leu Pro Ile Val
    50                  55                  60

ctc ggc cac gaa ggc tcc ggc acc gtc gag gcg gtg ggc gag cag gtg      240
Leu Gly His Glu Gly Ser Gly Thr Val Glu Ala Val Gly Glu Gln Val
65                  70                  75                  80

cgc acg ctc aag ccc ggc gac cgg gtc gtg ctg tcc ttc aat tcc tgc      288
Arg Thr Leu Lys Pro Gly Asp Arg Val Val Leu Ser Phe Asn Ser Cys
                85                  90                  95

ggg cat tgc ggc aat tgc cac gac ggc cat ccg tcg aac tgc ctg cag      336
Gly His Cys Gly Asn Cys His Asp Gly His Pro Ser Asn Cys Leu Gln
            100                 105                 110

atg ctg ccc ctg aac ttc ggc ggc gcg cag cgc gtg gac ggc ggc cag      384
Met Leu Pro Leu Asn Phe Gly Gly Ala Gln Arg Val Asp Gly Gly Gln
        115                 120                 125

gtg ctg gac ggc gcc ggc cat ccc gtg cag agc atg ttc ttc ggc cag      432
Val Leu Asp Gly Ala Gly His Pro Val Gln Ser Met Phe Phe Gly Gln
    130                 135                 140

tcc tcg ttc ggc acg cat gcc gtg gcg cgc gaa atc aat gcg gtc aag      480
Ser Ser Phe Gly Thr His Ala Val Ala Arg Glu Ile Asn Ala Val Lys
145                 150                 155                 160

gtc ggc gac gac ctg ccg ctg gaa ctg ctg ggc ccg ctg ggc tgc ggc      528
Val Gly Asp Asp Leu Pro Leu Glu Leu Leu Gly Pro Leu Gly Cys Gly
                165                 170                 175

atc cag acc ggc gcg ggc gcg gcg atc aat tcg ctg ggg atc ggc ccg      576
Ile Gln Thr Gly Ala Gly Ala Ala Ile Asn Ser Leu Gly Ile Gly Pro
            180                 185                 190

ggc cag tcc ctg gcc atc ttc ggc ggt ggc ggc gtc ggc ctg agc gcg      624
Gly Gln Ser Leu Ala Ile Phe Gly Gly Gly Gly Val Gly Leu Ser Ala
        195                 200                 205

ctg ctg ggc gcg cgc gcc gtc ggg gcg gac cgg gtc gtg gtg atc gag      672
Leu Leu Gly Ala Arg Ala Val Gly Ala Asp Arg Val Val Val Ile Glu
    210                 215                 220

ccc aat gcc gcg cgc cgg gcc ctg gcc ctg gaa ctg ggc gcc agc cat      720
Pro Asn Ala Ala Arg Arg Ala Leu Ala Leu Glu Leu Gly Ala Ser His
225                 230                 235                 240

gcc ctc gac ccg cac gcc gaa ggc gac ctg gtg gcc gcg atc aag gcg      768
Ala Leu Asp Pro His Ala Glu Gly Asp Leu Val Ala Ala Ile Lys Ala
                245                 250                 255

gcc acc ggc ggc ggc gcg acc cac tcg ctg gac acg acg ggc ctg ccc      816
Ala Thr Gly Gly Gly Ala Thr His Ser Leu Asp Thr Thr Gly Leu Pro
            260                 265                 270

ccg gtc atc ggc agc gcg atc gcc tgc acc ctg ccg ggc ggc acc gtg      864
Pro Val Ile Gly Ser Ala Ile Ala Cys Thr Leu Pro Gly Gly Thr Val
        275                 280                 285

ggc atg gtc gga ctg ccg gcg ccc gat gcc ccg gtg ccg gcg acc ctg      912
Gly Met Val Gly Leu Pro Ala Pro Asp Ala Pro Val Pro Ala Thr Leu
    290                 295                 300

ctc gat ctg ctg agc aaa agc gtc acc ctg cgc ccg atc acc gag ggc      960
Leu Asp Leu Leu Ser Lys Ser Val Thr Leu Arg Pro Ile Thr Glu Gly
305                 310                 315                 320

gac gcg gac ccg cag cgc ttc atc ccg cgc atg ctg gat ttc cat cgc     1008
Asp Ala Asp Pro Gln Arg Phe Ile Pro Arg Met Leu Asp Phe His Arg
                325                 330                 335

gcg ggc aaa ttc ccg ttc gac cgg ctg atc acc cgc tac cgt ttc gac     1056
Ala Gly Lys Phe Pro Phe Asp Arg Leu Ile Thr Arg Tyr Arg Phe Asp
            340                 345                 350
```

```
cag atc aac gag gcc ctg cac gcc acc gag aag ggc gag gcg atc aag     1104
Gln Ile Asn Glu Ala Leu His Ala Thr Glu Lys Gly Glu Ala Ile Lys
        355                 360                 365

ccg gtg ctg gtg ttc tga                                             1122
Pro Val Leu Val Phe
    370


<210> SEQ ID NO 179
<211> LENGTH: 373
<212> TYPE: PRT
<213> ORGANISM: Castellaniella defragrans

<400> SEQUENCE: 179

Met Asn Asp Thr Gln Asp Phe Ile Ser Ala Gln Ala Ala Val Leu Arg
1               5                   10                  15

Gln Val Gly Gly Pro Leu Ala Val Glu Pro Val Arg Ile Ser Met Pro
            20                  25                  30

Lys Gly Asp Glu Val Leu Ile Arg Ile Ala Gly Val Gly Val Cys His
        35                  40                  45

Thr Asp Leu Val Cys Arg Asp Gly Phe Pro Val Pro Leu Pro Ile Val
    50                  55                  60

Leu Gly His Glu Gly Ser Gly Thr Val Glu Ala Val Gly Glu Gln Val
65                  70                  75                  80

Arg Thr Leu Lys Pro Gly Asp Arg Val Val Leu Ser Phe Asn Ser Cys
                85                  90                  95

Gly His Cys Gly Asn Cys His Asp Gly His Pro Ser Asn Cys Leu Gln
            100                 105                 110

Met Leu Pro Leu Asn Phe Gly Gly Ala Gln Arg Val Asp Gly Gly Gln
        115                 120                 125

Val Leu Asp Gly Ala Gly His Pro Val Gln Ser Met Phe Phe Gly Gln
    130                 135                 140

Ser Ser Phe Gly Thr His Ala Val Ala Arg Glu Ile Asn Ala Val Lys
145                 150                 155                 160

Val Gly Asp Asp Leu Pro Leu Glu Leu Leu Gly Pro Leu Gly Cys Gly
                165                 170                 175

Ile Gln Thr Gly Ala Gly Ala Ala Ile Asn Ser Leu Gly Ile Gly Pro
            180                 185                 190

Gly Gln Ser Leu Ala Ile Phe Gly Gly Gly Gly Val Gly Leu Ser Ala
        195                 200                 205

Leu Leu Gly Ala Arg Ala Val Gly Ala Asp Arg Val Val Val Ile Glu
    210                 215                 220

Pro Asn Ala Ala Arg Arg Ala Leu Ala Leu Glu Leu Gly Ala Ser His
225                 230                 235                 240

Ala Leu Asp Pro His Ala Glu Gly Asp Leu Val Ala Ala Ile Lys Ala
                245                 250                 255

Ala Thr Gly Gly Gly Ala Thr His Ser Leu Asp Thr Thr Gly Leu Pro
            260                 265                 270

Pro Val Ile Gly Ser Ala Ile Ala Cys Thr Leu Pro Gly Gly Thr Val
        275                 280                 285

Gly Met Val Gly Leu Pro Ala Pro Asp Ala Pro Val Pro Ala Thr Leu
    290                 295                 300

Leu Asp Leu Leu Ser Lys Ser Val Thr Leu Arg Pro Ile Thr Glu Gly
305                 310                 315                 320

Asp Ala Asp Pro Gln Arg Phe Ile Pro Arg Met Leu Asp Phe His Arg
                325                 330                 335
```

```
Ala Gly Lys Phe Pro Phe Asp Arg Leu Ile Thr Arg Tyr Arg Phe Asp
            340                 345                 350

Gln Ile Asn Glu Ala Leu His Ala Thr Glu Lys Gly Glu Ala Ile Lys
        355                 360                 365

Pro Val Leu Val Phe
    370


<210> SEQ ID NO 180
<211> LENGTH: 1122
<212> TYPE: DNA
<213> ORGANISM: Castellaniella defragrans

<400> SEQUENCE: 180

atgaacgata cgcaggattt tattagcgcc caagccgcag tgttacgtca ggtcggtggc      60

ccgctggccg ttgagcctgt tcgtatcagc atgccgaagg gtgacgaagt cctgattcgt     120

atcgcgggtg ttggtgtgtg ccacaccgac ttggtgtgcc gtgatggctt cccggtgccg     180

ctgccaattg tgctgggtca cgagggtagc ggtactgtcg aagccgtcgg tgaacaagtc     240

cgtaccctga aaccgggcga tcgcgtcgtg ctgagcttta acagctgcgg tcattgcggt     300

aactgtcacg acggtcaccc gagcaattgc ctgcagatgc tgccgctgaa cttcggtggc     360

gcgcaacgcg tggacggtgg ccaagttttg gacggtgcgg gtcatccggt tcagtccatg     420

tttttcggcc agtccagctt tggcacccac gcagtagcgc gcgagatcaa cgcagtcaag     480

gtcggcgatg atctgccact ggaactgctg ggtccgttgg gttgtggcat tcaaaccggt     540

gcgggtgcag ctatcaattc tctgggcatt ggtccgggtc agtctctggc tatcttcggc     600

ggcggcggcg tgggtctgag cgcactgctg ggcgcccgtg cggtgggtgc cgaccgtgtt     660

gttgtcattg agccgaatgc agcgcgccgt gcgctggcat tggaactggg tgccagccac     720

gcactggacc cgcatgccga gggcgacctt gttgcggcga ttaaagctgc gacgggtggc     780

ggcgctacgc atagcttgga tacgaccggc ctgccgccag tcattggctc cgcgatcgcg     840

tgtactctgc cgggtggcac cgttggtatg gttggtctgc cggcgccgga cgcaccggtc     900

cctgcgacgc tgttggatct gctgagcaaa tcggttaccc tgcgtccgat taccgagggt     960

gacgctgacc cgcaacgctt catcccgcgt atgctggatt tccatcgtgc gggcaagttt    1020

ccgttcgacc gcctgatcac ccgttaccgc tttgatcaga tcaatgaagc gctgcacgcg    1080

accgagaaag gtgaagcaat caaaccggtt ctggtgtttt aa                        1122


<210> SEQ ID NO 181
<211> LENGTH: 963
<212> TYPE: DNA
<213> ORGANISM: Blakeslea trispora
<220> FEATURE:
<221> NAME/KEY: CDS
<222> LOCATION: (1)..(963)

<400> SEQUENCE: 181

atg ttg acc tct agc aaa tca att gaa tcc ttc ccc aag aat gtt caa       48
Met Leu Thr Ser Ser Lys Ser Ile Glu Ser Phe Pro Lys Asn Val Gln
1               5                   10                  15

cct tat ggc aag cat tat caa aat ggc ttg gaa cct gtt gga aaa agc       96
Pro Tyr Gly Lys His Tyr Gln Asn Gly Leu Glu Pro Val Gly Lys Ser
            20                  25                  30

caa gaa gat att ctc ttg gag cca ttc cac tat ctc tgt tcg aat cct      144
Gln Glu Asp Ile Leu Leu Glu Pro Phe His Tyr Leu Cys Ser Asn Pro
        35                  40                  45
```

-continued

```
ggt aaa gat gtc cga acc aag atg att gaa gcg ttc aat gct tgg ctg      192
Gly Lys Asp Val Arg Thr Lys Met Ile Glu Ala Phe Asn Ala Trp Leu
    50                  55                  60

aaa gta ccc aag gac gat ttg atc gtc atc aca cgt gtg att gaa atg      240
Lys Val Pro Lys Asp Asp Leu Ile Val Ile Thr Arg Val Ile Glu Met
65                  70                  75                  80

ctt cat agt gct agt ttg tta att gat gat gtg gaa gat gat tcc gtg      288
Leu His Ser Ala Ser Leu Leu Ile Asp Asp Val Glu Asp Asp Ser Val
                85                  90                  95

ttg cgt cgt ggt gtt cct gca gct cat cat ata tat ggt act cct caa      336
Leu Arg Arg Gly Val Pro Ala Ala His His Ile Tyr Gly Thr Pro Gln
            100                 105                 110

act atc aat tgt gct aat tac gtg tac ttt ctt gca ctg aaa gaa att      384
Thr Ile Asn Cys Ala Asn Tyr Val Tyr Phe Leu Ala Leu Lys Glu Ile
        115                 120                 125

gcc aag ttg aac aag ccc aac atg att act atc tat acc gat gaa ttg      432
Ala Lys Leu Asn Lys Pro Asn Met Ile Thr Ile Tyr Thr Asp Glu Leu
    130                 135                 140

atc aat ttg cac aga ggg caa gga atg gaa ttg ttt tgg cgt gac acc      480
Ile Asn Leu His Arg Gly Gln Gly Met Glu Leu Phe Trp Arg Asp Thr
145                 150                 155                 160

tta act tgt cct aca gag aaa gaa ttt ctt gac atg gta aac gac aaa      528
Leu Thr Cys Pro Thr Glu Lys Glu Phe Leu Asp Met Val Asn Asp Lys
                165                 170                 175

act ggt ggc ctc ttg aga tta gct gtg aaa ctt atg caa gaa gct agt      576
Thr Gly Gly Leu Leu Arg Leu Ala Val Lys Leu Met Gln Glu Ala Ser
            180                 185                 190

caa tcg gga act gat tat acg gga ctc gta agt aag att ggt atc cat      624
Gln Ser Gly Thr Asp Tyr Thr Gly Leu Val Ser Lys Ile Gly Ile His
        195                 200                 205

ttc caa gta cgc gac gat tat atg aat ttg cag tca aaa aac tat gct      672
Phe Gln Val Arg Asp Asp Tyr Met Asn Leu Gln Ser Lys Asn Tyr Ala
    210                 215                 220

gac aac aaa gga ttc tgc gaa gac ttg aca gaa gga aaa ttc tct ttc      720
Asp Asn Lys Gly Phe Cys Glu Asp Leu Thr Glu Gly Lys Phe Ser Phe
225                 230                 235                 240

cct att ata cat tca atc cgc tct gac cca agc aat cgc cag ctt ttg      768
Pro Ile Ile His Ser Ile Arg Ser Asp Pro Ser Asn Arg Gln Leu Leu
                245                 250                 255

aac att tta aaa cag cgc agt agc tct atc gaa ctc aag caa ttt gcc      816
Asn Ile Leu Lys Gln Arg Ser Ser Ser Ile Glu Leu Lys Gln Phe Ala
            260                 265                 270

ttg cag cta ctg gaa aac aca aac act ttc caa tac tgt cgt gat ttc      864
Leu Gln Leu Leu Glu Asn Thr Asn Thr Phe Gln Tyr Cys Arg Asp Phe
        275                 280                 285

tta cgt gtc ttg gaa aag gaa gct aga gaa gaa att aag ctt tta ggg      912
Leu Arg Val Leu Glu Lys Glu Ala Arg Glu Glu Ile Lys Leu Leu Gly
    290                 295                 300

ggt aac atc atg ttg gag aaa att atg gat gtc ttg agt gtc aat gaa      960
Gly Asn Ile Met Leu Glu Lys Ile Met Asp Val Leu Ser Val Asn Glu
305                 310                 315                 320

taa                                                                  963
```

<210> SEQ ID NO 182
<211> LENGTH: 320
<212> TYPE: PRT
<213> ORGANISM: Blakeslea trispora

<400> SEQUENCE: 182

```
Met Leu Thr Ser Ser Lys Ser Ile Glu Ser Phe Pro Lys Asn Val Gln
```

```
1               5                   10                  15

Pro Tyr Gly Lys His Tyr Gln Asn Gly Leu Glu Pro Val Gly Lys Ser
            20                  25                  30

Gln Glu Asp Ile Leu Leu Glu Pro Phe His Tyr Leu Cys Ser Asn Pro
        35                  40                  45

Gly Lys Asp Val Arg Thr Lys Met Ile Glu Ala Phe Asn Ala Trp Leu
    50                  55                  60

Lys Val Pro Lys Asp Asp Leu Ile Val Ile Thr Arg Val Ile Glu Met
65                  70                  75                  80

Leu His Ser Ala Ser Leu Leu Ile Asp Asp Val Glu Asp Asp Ser Val
                85                  90                  95

Leu Arg Arg Gly Val Pro Ala Ala His His Ile Tyr Gly Thr Pro Gln
            100                 105                 110

Thr Ile Asn Cys Ala Asn Tyr Val Tyr Phe Leu Ala Leu Lys Glu Ile
        115                 120                 125

Ala Lys Leu Asn Lys Pro Asn Met Ile Thr Ile Tyr Thr Asp Glu Leu
    130                 135                 140

Ile Asn Leu His Arg Gly Gln Gly Met Glu Leu Phe Trp Arg Asp Thr
145                 150                 155                 160

Leu Thr Cys Pro Thr Glu Lys Glu Phe Leu Asp Met Val Asn Asp Lys
                165                 170                 175

Thr Gly Gly Leu Leu Arg Leu Ala Val Lys Leu Met Gln Glu Ala Ser
            180                 185                 190

Gln Ser Gly Thr Asp Tyr Thr Gly Leu Val Ser Lys Ile Gly Ile His
        195                 200                 205

Phe Gln Val Arg Asp Asp Tyr Met Asn Leu Gln Ser Lys Asn Tyr Ala
    210                 215                 220

Asp Asn Lys Gly Phe Cys Glu Asp Leu Thr Glu Gly Lys Phe Ser Phe
225                 230                 235                 240

Pro Ile Ile His Ser Ile Arg Ser Asp Pro Ser Asn Arg Gln Leu Leu
                245                 250                 255

Asn Ile Leu Lys Gln Arg Ser Ser Ser Ile Glu Leu Lys Gln Phe Ala
            260                 265                 270

Leu Gln Leu Leu Glu Asn Thr Asn Thr Phe Gln Tyr Cys Arg Asp Phe
        275                 280                 285

Leu Arg Val Leu Glu Lys Glu Ala Arg Glu Glu Ile Lys Leu Leu Gly
    290                 295                 300

Gly Asn Ile Met Leu Glu Lys Ile Met Asp Val Leu Ser Val Asn Glu
305                 310                 315                 320
```

<210> SEQ ID NO 183
<211> LENGTH: 963
<212> TYPE: DNA
<213> ORGANISM: Blakeslea trispora

<400> SEQUENCE: 183

```
atgttgacat cttctaagtc catcgaatct ttcccaaaga acgttcaacc atacggtaaa      60

cactatcaaa acggtttaga accagtcggt aagtctcaag aagacatctt gttggaacct     120

ttccactact tatgttctaa tccaggtaag gatgttagaa ccaagatgat tgaagctttc     180

aacgcctggt tgaaagtccc aaaggacgat ttgattgtta tcaccagagt cattgaaatg     240

ttgcactccg cttctttgtt gattgatgac gtcgaggacg attctgtctt gagaagaggt     300

gtcccagccg cccaccatat ctacggtacc cctcaaacca tcaactgcgc taactacgtt     360
```

-continued

```
tatttcttgg ccttgaaaga aatcgccaag ttgaacaagc caaatatgat tactatttat    420

accgatgaat tgatcaactt gcacagaggt caaggtatgg aattgttctg gcgtgatacc    480

ttgacctgcc caactgagaa agagtttttg gatatggtta acgataagac tggtggtttg    540

ttgagattgg ccgtcaagtt gatgcaagag gcttctcaat ctggtaccga ctatactggt    600

ttggtttcta agatcggtat ccattttcaa gttagagatg actacatgaa cttgcaatcc    660

aaaaactacg ccgataataa gggtttctgt gaagatttga ccgaaggtaa gttctccttt    720

ccaattattc actctatcag atctgaccca tccaacagac aattattgaa tattttgaag    780

caaagatctt cttctattga attgaaacaa ttcgctttac aattgttaga aaacactaac    840

acttttcaat actgtagaga tttcttgaga gttttggaaa aggaagccag agaagagatc    900

aaattattgg gtggtaacat catgttggaa aagattatgg acgtcttgtc tgttaatgaa    960

taa                                                                  963
```

```
<210> SEQ ID NO 184
<211> LENGTH: 2382
<212> TYPE: DNA
<213> ORGANISM: Salvia miltiorrhiza

<400> SEQUENCE: 184

atggcctcct tatcctctac aatcctcagc cgctctccgg cggcccgccg cagaattacg     60

ccggcgtcgg ctaagcttca ccggccggaa tgtttcgcca ccagtgcatg gatgggcagc    120

agcagtaaaa acctttctct cagctaccaa cttaatcaca agaaaatatc agttgccaca    180

gtagatgcgc cgcaggtgca tgaccacgac ggcactaccg ttcatcaagg ccatgatgcg    240

gtgaagaata ttgaggatcc cattgaatac atcaggacgt tgttgaggac gacgggggac    300

gggagaataa gcgtgtcgcc gtacgacacg gcgtgggtgg cgatgatcaa ggacgtggag    360

gggcgggacg gcccccagtt cccctccagc ctcgagtgga tcgtgcagaa tcaactcgag    420

gatggatcgt ggggcgatca gaagcttttc tgcgtctacg atcgcctcgt caataccatc    480

gcgtgcgtgg tagccttgag atcgtggaat gttcatgctc acaaggtcaa aagaggagtg    540

acgtacatca aggaaaatgt ggataaactt atggagggaa atgaggagca catgacttgt    600

gggttcgaag tggtgtttcc ggcgcttcta caaaaagcga aaagcttagg catcgaagat    660

cttccttacg attctccggc ggtgcaggag gtttatcatg tcagggaaca aaagttgaaa    720

aggattccac tggagattat gcacaaaata ccgacatcat tattatttag tttggaaggg    780

ctcgaaaatt tggattggga caaacttttg aaactgcagt cagccgacgg ttccttcctc    840

acctctccct cctccaccgc cttcgcgttc atgcaaacca aggatgaaaa atgctaccaa    900

ttcatcaaga acacgataga cactttcaac ggaggagcgc cacacactta tcccgtcgac    960

gtgtttggaa ggctctgggc gatcgaccgg ctgcagcgcc tcggaatttc ccgctttttt   1020

gagccggaga ttgctgattg cttaagccac atccacaaat tttggacgga taagggagtt   1080

ttcagtggga gagaatcgga gttttgcgac attgacgata catccatggg aatgaggctt   1140

atgaggatgc atggatatga tgttgatcca aatgtgctga ggaatttcaa gcagaaagat   1200

ggtaaattct cttgctacgg cgggcagatg atcgagtcgc cttctccgat atacaatctt   1260

tacagagctt ctcagctccg atttcccggc gaggaaatcc tcgaagatgc gaagagattc   1320

gcctacgatt tcttgaaaga aaaactagcc aacaatcaga ttctggataa atgggttatt   1380

tctaagcact tgcctgatga gatcaagctc gggctagaga tgccgtggct cgccacccta   1440

ccccgcgtcg aggcgaagta ctacatccag tactacgccg gctccggcga cgtgtggatc   1500
```

```
ggaaagacgc tgtacaggat gccggagatc agcaacgaca cgtaccacga cctagccaag   1560

acggatttca agagatgcca agcgaagcat cagttcgagt ggctctacat gcaagaatgg   1620

tacgagagct gcggcatcga ggaattcggg ataagcagaa aggaccttct gctttcctat   1680

ttcttggcga ccgcgagcat cttcgagctc gagaggacca acgagcgaat cgcgtgggcc   1740

aaatcgcaga tcatcgctaa gatgatcact tctttcttca acaaggaaac tacgtcggag   1800

gaggacaagc gagctctttt gaacgagctc ggaaacatta atggcctcaa cgacacaaac   1860

ggcgcaggga gagaaggtgg ggccggtagc attgcgctag cgaccctcac tcagttcctc   1920

gagggattcg acagatacac cagacaccag ctgaaaaatg cttggagcgt atggctgacg   1980

cagctgcaac atggcgaagc agacgacgcg gagctcctaa ccaacacgtt gaacatctgc   2040

gccggccaca tcgccttcag ggaagaaata ctggcgcaca acgagtacaa agctctctcc   2100

aacctaacca gcaaaatctg tcgacagctt tctttcattc aaagcgaaaa ggagatggga   2160

gtagagggcg agatcgcagc gaaatcgagc ataaaaaaca aggaactcga agaagacatg   2220

caaatgttgg tgaagttggt gcttgagaaa tatgggggca tagatagaaa tataaagaaa   2280

gcgtttttag cagttgcgaa gacttattat tacagagcgt atcatgccgc cgacaccata   2340

gacacacaca tgtttaaagt gcttttcgag ccagtcgcgt ga                      2382
```

<210> SEQ ID NO 185
<211> LENGTH: 736
<212> TYPE: PRT
<213> ORGANISM: Salvia miltiorrhiza

<400> SEQUENCE: 185

```
Met Ala Thr Val Asp Ala Pro Gln Val His Asp His Asp Gly Thr Thr
1               5                   10                  15

Val His Gln Gly His Asp Ala Val Lys Asn Ile Glu Asp Pro Ile Glu
            20                  25                  30

Tyr Ile Arg Thr Leu Leu Arg Thr Thr Gly Asp Gly Arg Ile Ser Val
        35                  40                  45

Ser Pro Tyr Asp Thr Ala Trp Val Ala Met Ile Lys Asp Val Glu Gly
    50                  55                  60

Arg Asp Gly Pro Gln Phe Pro Ser Ser Leu Glu Trp Ile Val Gln Asn
65                  70                  75                  80

Gln Leu Glu Asp Gly Ser Trp Gly Asp Gln Lys Leu Phe Cys Val Tyr
                85                  90                  95

Asp Arg Leu Val Asn Thr Ile Ala Cys Val Val Ala Leu Arg Ser Trp
            100                 105                 110

Asn Val His Ala His Lys Val Lys Arg Gly Val Thr Tyr Ile Lys Glu
        115                 120                 125

Asn Val Asp Lys Leu Met Glu Gly Asn Glu Glu His Met Thr Cys Gly
    130                 135                 140

Phe Glu Val Val Phe Pro Ala Leu Leu Gln Lys Ala Lys Ser Leu Gly
145                 150                 155                 160

Ile Glu Asp Leu Pro Tyr Asp Ser Pro Ala Val Gln Glu Val Tyr His
                165                 170                 175

Val Arg Glu Gln Lys Leu Lys Arg Ile Pro Leu Glu Ile Met His Lys
            180                 185                 190

Ile Pro Thr Ser Leu Leu Phe Ser Leu Glu Gly Leu Glu Asn Leu Asp
        195                 200                 205

Trp Asp Lys Leu Leu Lys Leu Gln Ser Ala Asp Gly Ser Phe Leu Thr
```

-continued

```
    210                 215                 220

Ser Pro Ser Ser Thr Ala Phe Ala Phe Met Gln Thr Lys Asp Glu Lys
225                 230                 235                 240

Cys Tyr Gln Phe Ile Lys Asn Thr Ile Asp Thr Phe Asn Gly Gly Ala
                245                 250                 255

Pro His Thr Tyr Pro Val Asp Val Phe Gly Arg Leu Trp Ala Ile Asp
            260                 265                 270

Arg Leu Gln Arg Leu Gly Ile Ser Arg Phe Phe Glu Pro Glu Ile Ala
        275                 280                 285

Asp Cys Leu Ser His Ile His Lys Phe Trp Thr Asp Lys Gly Val Phe
    290                 295                 300

Ser Gly Arg Glu Ser Glu Phe Cys Asp Ile Asp Asp Thr Ser Met Gly
305                 310                 315                 320

Met Arg Leu Met Arg Met His Gly Tyr Asp Val Asp Pro Asn Val Leu
                325                 330                 335

Arg Asn Phe Lys Gln Lys Asp Gly Lys Phe Ser Cys Tyr Gly Gly Gln
            340                 345                 350

Met Ile Glu Ser Pro Ser Pro Ile Tyr Asn Leu Tyr Arg Ala Ser Gln
        355                 360                 365

Leu Arg Phe Pro Gly Glu Glu Ile Leu Glu Asp Ala Lys Arg Phe Ala
    370                 375                 380

Tyr Asp Phe Leu Lys Glu Lys Leu Ala Asn Asn Gln Ile Leu Asp Lys
385                 390                 395                 400

Trp Val Ile Ser Lys His Leu Pro Asp Glu Ile Lys Leu Gly Leu Glu
                405                 410                 415

Met Pro Trp Leu Ala Thr Leu Pro Arg Val Glu Ala Lys Tyr Tyr Ile
            420                 425                 430

Gln Tyr Tyr Ala Gly Ser Gly Asp Val Trp Ile Gly Lys Thr Leu Tyr
        435                 440                 445

Arg Met Pro Glu Ile Ser Asn Asp Thr Tyr His Asp Leu Ala Lys Thr
    450                 455                 460

Asp Phe Lys Arg Cys Gln Ala Lys His Gln Phe Glu Trp Leu Tyr Met
465                 470                 475                 480

Gln Glu Trp Tyr Glu Ser Cys Gly Ile Glu Glu Phe Gly Ile Ser Arg
                485                 490                 495

Lys Asp Leu Leu Leu Ser Tyr Phe Leu Ala Thr Ala Ser Ile Phe Glu
            500                 505                 510

Leu Glu Arg Thr Asn Glu Arg Ile Ala Trp Ala Lys Ser Gln Ile Ile
        515                 520                 525

Ala Lys Met Ile Thr Ser Phe Phe Asn Lys Glu Thr Thr Ser Glu Glu
    530                 535                 540

Asp Lys Arg Ala Leu Leu Asn Glu Leu Gly Asn Ile Asn Gly Leu Asn
545                 550                 555                 560

Asp Thr Asn Gly Ala Gly Arg Glu Gly Gly Ala Gly Ser Ile Ala Leu
                565                 570                 575

Ala Thr Leu Thr Gln Phe Leu Glu Gly Phe Asp Arg Tyr Thr Arg His
            580                 585                 590

Gln Leu Lys Asn Ala Trp Ser Val Trp Leu Thr Gln Leu Gln His Gly
        595                 600                 605

Glu Ala Asp Asp Ala Glu Leu Leu Thr Asn Thr Leu Asn Ile Cys Ala
    610                 615                 620

Gly His Ile Ala Phe Arg Glu Glu Ile Leu Ala His Asn Glu Tyr Lys
625                 630                 635                 640
```

Ala Leu Ser Asn Leu Thr Ser Lys Ile Cys Arg Gln Leu Ser Phe Ile
645 650 655

Gln Ser Glu Lys Glu Met Gly Val Glu Gly Glu Ile Ala Ala Lys Ser
660 665 670

Ser Ile Lys Asn Lys Glu Leu Glu Glu Asp Met Gln Met Leu Val Lys
675 680 685

Leu Val Leu Glu Lys Tyr Gly Gly Ile Asp Arg Asn Ile Lys Lys Ala
690 695 700

Phe Leu Ala Val Ala Lys Thr Tyr Tyr Tyr Arg Ala Tyr His Ala Ala
705 710 715 720

Asp Thr Ile Asp Thr His Met Phe Lys Val Leu Phe Glu Pro Val Ala
725 730 735

<210> SEQ ID NO 186
<211> LENGTH: 2211
<212> TYPE: DNA
<213> ORGANISM: Salvia miltiorrhiza

<400> SEQUENCE: 186
atggctactg ttgacgctcc acaagttcac gaccacgacg gtactactgt tcaccaaggt 60
cacgacgctg ttaagaacat cgaagaccca atcgaataca tcagaacttt gttgagaact 120
actggtgacg gtagaatctc tgtttctcca tacgacactg cttgggttgc tatgatcaag 180
gacgttgaag gtagagacgg tccacaattc ccatcttctt tggaatggat cgttcaaaac 240
caattggaag acggttcttg gggtgaccaa aagttgttct gtgtttacga cagattggtt 300
aacactatcg cttgtgttgt tgctttgaga tcttggaacg ttcacgctca caaggttaag 360
agaggtgtta cttacatcaa ggaaaacgtt gacaagttga tggaaggtaa cgaagaacac 420
atgacttgtg gtttcgaagt tgttttccca gctttgttgc aaaaggctaa gtctttgggt 480
atcgaagact tgccatacga ctctccagct gttcaagaag tttaccacgt tagagaacaa 540
aagttgaaga gaatcccatt ggaaatcatg cacaagatcc caacttcttt gttgttctct 600
ttggaaggtt tggaaaactt ggactgggac aagttgttga agttgcaatc tgctgacggt 660
tctttcttga cttctccatc ttctactgct ttcgctttca tgcaaactaa ggacgaaaag 720
tgttaccaat tcatcaagaa cactatcgac actttcaacg gtggtgctcc acacacttac 780
ccagttgacg ttttcggtag attgtgggct atcgacagat tgcaaagatt gggtatctct 840
agattcttcg aaccagaaat cgctgactgt ttgtctcaca tccacaagtt ctggactgac 900
aagggtgttt tctctggtag agaatctgaa ttctgtgaca tcgacgacac ttctatgggt 960
atgagattga tgagaatgca cggttacgac gttgacccaa acgttttgag aaacttcaag 1020
caaaaggacg gtaagttctc ttgttacggt ggtcaaatga tcgaatctcc atctccaatc 1080
tacaacttgt acagagcttc tcaattgaga ttcccaggtg aagaaatctt ggaagacgct 1140
aagagattcg cttacgactt cttgaaggaa aagttggcta acaaccaaat cttggacaag 1200
tgggttatct ctaagcactt gccagacgaa atcaagttgg gtttggaaat gccatggttg 1260
gctactttgc caagagttga agctaagtac tacatccaat actacgctgg ttctggtgac 1320
gtttggatcg gtaagacttt gtacagaatg ccagaaatct ctaacgacac ttaccacgac 1380
ttggctaaga ctgacttcaa gagatgtcaa gctaagcacc aattcgaatg gttgtacatg 1440
caagaatggt acgaatcttg tggtatcgaa gaattcggta tctctagaaa ggacttgttg 1500
ttgtcttact tcttggctac tgcttctatc ttcgaattgg aaagaactaa cgaaagaatc 1560

```
gcttgggcta agtctcaaat catcgctaag atgatcactt ctttcttcaa caaggaaact   1620

acttctgaag aagacaagag agctttgttg aacgaattgg gtaacatcaa cggtttgaac   1680

gacactaacg gtgctggtag agaaggtggt gctggttcta tcgctttggc tactttgact   1740

caattcttgg aaggtttcga cagatacact agacaccaat tgaagaacgc ttggtctgtt   1800

tggttgactc aattgcaaca cggtgaagct gacgacgctg aattgttgac taacactttg   1860

aacatctgtg ctggtcacat cgctttcaga gaagaaatct tggctcacaa cgaatacaag   1920

gctttgtcta acttgacttc taagatctgt agacaattgt ctttcatcca atctgaaaag   1980

gaaatgggtg ttgaaggtga aatcgctgct aagtcttcta tcaagaacaa ggaattggaa   2040

gaagacatgc aaatgttggt taagttggtt ttggaaaagt acggtggtat cgacagaaac   2100

atcaagaagg ctttcttggc tgttgctaag acttactact acagagctta ccacgctgct   2160

gacactatcg acactcacat gttcaaggtt ttgttcgaac cagttgctta a            2211
```

<210> SEQ ID NO 187
<211> LENGTH: 2358
<212> TYPE: DNA
<213> ORGANISM: Salvia sclarea

<400> SEQUENCE: 187

```
atgacttctg taaatttgag cagagcacca gcagcgatta cccggcgcag gctgcagcta     60

cagccggaat ttcatgccga gtgttcatgg ctgaaaagca gcagcaaaca cgcgcccttg    120

accttgagtt gccaaatccg tcctaagcaa ctctcccaaa tagctgaatt gagagtaaca    180

agcctggatg cgtcgcaagc gagtgaaaaa gacatttccc ttgttcaaac tccgcataag    240

gttgaggtta atgaaaagat cgaggagtca atcgagtacg tccaaaatct gttgatgacg    300

tcgggcgacg ggcgaataag cgtgtcaccc tatgacacgg cagtgatcgc cctgatcaag    360

gacttgaaag ggcgcgacgc cccgcagttt ccgtcatgtc tcgagtggat cgcgcaccac    420

caactggctg atggctcatg gggcgacgaa ttcttctgta tttatgatcg gattctaaat    480

acattggcat gtgtcgtagc cttgaaatca tggaaccttc actctgatat tattgaaaaa    540

ggagtgacgt acatcaagga gaatgtgcat aaacttaaag gtgcaaatgt tgagcacagg    600

acagcggggt tcgaacttgt ggttcctact tttatgcaaa tggccacaga tttgggcatc    660

caagatctgc cctatgatca tcccctcatc aaggagattg ctgacacaaa acaacaaaga    720

ttgaaagaga tacccaagga tttggtttac caaatgccaa cgaatttact gtacagttta    780

gaagggttag gagatttgga gtgggaaagg ctactgaaac tgcagtcggg caatggctcc    840

ttcctcactt cgccgtcgtc caccgccgcc gtcttgatgc ataccaaaga tgaaaaatgt    900

ttgaaataca tcgaaaacgc cctcaagaat tgcgacggag gagcaccaca tacttatcca    960

gtcgatatct tctcaagact ttgggcaatc gataggctac aacgcctagg aatttctcgt   1020

ttcttccagc acgagatcaa gtatttctta gatcacatcg aaagcgtttg ggaggagacc   1080

ggagttttca gtggaagata tacgaaattt agcgatattg atgacacgtc catgggcgtt   1140

aggcttctca aaatgcacgg atacgacgtc gatccaaatg tactaaaaca tttcaagcaa   1200

caagatggta aattttcctg ctacattggt caatcggtcg agtctgcatc tccaatgtac   1260

aatctttata gggctgctca actaagattt ccaggagaag aagttcttga agaagccact   1320

aaatttgcct ttaacttctt gcaagaaatg ctagtcaaag atcgacttca agaaagatgg   1380

gtgatatccg accacttatt tgatgagata aagctggggt tgaagatgcc atggtacgcc   1440

actctacccc gagtcgaggc tgcatattat ctagaccatt atgctggttc tggtgatgta   1500
```

```
tggattggca agagtttcta caggatgcca gaaatcagca atgatacata caaggagctt   1560

gcgatattgg atttcaacag atgccaaaca caacatcagt tggagtggat ccacatgcag   1620

gaatggtacg acagatgcag ccttagcgaa ttcgggataa gcaaaagaga gttgcttcgc   1680

tcttactttc tggccgcagc aaccatattc gaaccggaga gaactcaaga gaggcttctg   1740

tgggccaaaa ccagaattct ttctaagatg atcacttcat ttgtcaacat tagtggaaca   1800

acactatctt tggactacaa tttcaatggc ctcgatgaaa taattagtag tgccaatgaa   1860

gatcaaggac tggctgggac tctgctggca accttccatc aacttctaga cggattcgat   1920

atatacactc tccatcaact caaacatgtt tggagccaat ggttcatgaa agtgcagcaa   1980

ggagagggaa gcggcgggga agacgcggtg ctcctagcga acacgctcaa catctgcgcc   2040

ggcctcaacg aagacgtgtt gtccaacaat gaatacacgg ctctgtccac cctcacaaat   2100

aaaatctgca atcgcctcgc ccaaattcaa gacaataaga ttctccaagt tgtggatggg   2160

agcataaagg ataaggagct agaacaggat atgcaggcgt tggtgaagtt agtgcttcaa   2220

gaaaatggcg gcgccgtaga cagaaacatc agacacacgt tttgtcggt ttccaagact    2280

ttctactacg atgcctacca cgacgatgag acgaccgatc ttcatatctt caaagtactc   2340

tttcgaccgg ttgtatga                                                 2358


<210> SEQ ID NO 188
<211> LENGTH: 723
<212> TYPE: PRT
<213> ORGANISM: Salvia sclarea

<400> SEQUENCE: 188

Met Ala Ser Gln Ala Ser Glu Lys Asp Ile Ser Leu Val Gln Thr Pro
1               5                   10                  15

His Lys Val Glu Val Asn Glu Lys Ile Glu Glu Ser Ile Glu Tyr Val
            20                  25                  30

Gln Asn Leu Leu Met Thr Ser Gly Asp Gly Arg Ile Ser Val Ser Pro
        35                  40                  45

Tyr Asp Thr Ala Val Ile Ala Leu Ile Lys Asp Leu Lys Gly Arg Asp
    50                  55                  60

Ala Pro Gln Phe Pro Ser Cys Leu Glu Trp Ile Ala His His Gln Leu
65                  70                  75                  80

Ala Asp Gly Ser Trp Gly Asp Glu Phe Phe Cys Ile Tyr Asp Arg Ile
                85                  90                  95

Leu Asn Thr Leu Ala Cys Val Val Ala Leu Lys Ser Trp Asn Leu His
            100                 105                 110

Ser Asp Ile Ile Glu Lys Gly Val Thr Tyr Ile Lys Glu Asn Val His
        115                 120                 125

Lys Leu Lys Gly Ala Asn Val Glu His Arg Thr Ala Gly Phe Glu Leu
    130                 135                 140

Val Val Pro Thr Phe Met Gln Met Ala Thr Asp Leu Gly Ile Gln Asp
145                 150                 155                 160

Leu Pro Tyr Asp His Pro Leu Ile Lys Glu Ile Ala Asp Thr Lys Gln
                165                 170                 175

Gln Arg Leu Lys Glu Ile Pro Lys Asp Leu Val Tyr Gln Met Pro Thr
            180                 185                 190

Asn Leu Leu Tyr Ser Leu Glu Gly Leu Gly Asp Leu Glu Trp Glu Arg
        195                 200                 205

Leu Leu Lys Leu Gln Ser Gly Asn Gly Ser Phe Leu Thr Ser Pro Ser
```

-continued

```
    210                 215                 220

Ser Thr Ala Ala Val Leu Met His Thr Lys Asp Glu Lys Cys Leu Lys
225                 230                 235                 240

Tyr Ile Glu Asn Ala Leu Lys Asn Cys Asp Gly Gly Ala Pro His Thr
                245                 250                 255

Tyr Pro Val Asp Ile Phe Ser Arg Leu Trp Ala Ile Asp Arg Leu Gln
            260                 265                 270

Arg Leu Gly Ile Ser Arg Phe Phe Gln His Glu Ile Lys Tyr Phe Leu
        275                 280                 285

Asp His Ile Glu Ser Val Trp Glu Glu Thr Gly Val Phe Ser Gly Arg
    290                 295                 300

Tyr Thr Lys Phe Ser Asp Ile Asp Asp Thr Ser Met Gly Val Arg Leu
305                 310                 315                 320

Leu Lys Met His Gly Tyr Asp Val Asp Pro Asn Val Leu Lys His Phe
                325                 330                 335

Lys Gln Gln Asp Gly Lys Phe Ser Cys Tyr Ile Gly Gln Ser Val Glu
            340                 345                 350

Ser Ala Ser Pro Met Tyr Asn Leu Tyr Arg Ala Ala Gln Leu Arg Phe
        355                 360                 365

Pro Gly Glu Glu Val Leu Glu Glu Ala Thr Lys Phe Ala Phe Asn Phe
    370                 375                 380

Leu Gln Glu Met Leu Val Lys Asp Arg Leu Gln Glu Arg Trp Val Ile
385                 390                 395                 400

Ser Asp His Leu Phe Asp Glu Ile Lys Leu Gly Leu Lys Met Pro Trp
                405                 410                 415

Tyr Ala Thr Leu Pro Arg Val Glu Ala Ala Tyr Tyr Leu Asp His Tyr
            420                 425                 430

Ala Gly Ser Gly Asp Val Trp Ile Gly Lys Ser Phe Tyr Arg Met Pro
        435                 440                 445

Glu Ile Ser Asn Asp Thr Tyr Lys Glu Leu Ala Ile Leu Asp Phe Asn
    450                 455                 460

Arg Cys Gln Thr Gln His Gln Leu Glu Trp Ile His Met Gln Glu Trp
465                 470                 475                 480

Tyr Asp Arg Cys Ser Leu Ser Glu Phe Gly Ile Ser Lys Arg Glu Leu
                485                 490                 495

Leu Arg Ser Tyr Phe Leu Ala Ala Ala Thr Ile Phe Glu Pro Glu Arg
            500                 505                 510

Thr Gln Glu Arg Leu Leu Trp Ala Lys Thr Arg Ile Leu Ser Lys Met
        515                 520                 525

Ile Thr Ser Phe Val Asn Ile Ser Gly Thr Thr Leu Ser Leu Asp Tyr
    530                 535                 540

Asn Phe Asn Gly Leu Asp Glu Ile Ile Ser Ser Ala Asn Glu Asp Gln
545                 550                 555                 560

Gly Leu Ala Gly Thr Leu Leu Ala Thr Phe His Gln Leu Leu Asp Gly
                565                 570                 575

Phe Asp Ile Tyr Thr Leu His Gln Leu Lys His Val Trp Ser Gln Trp
            580                 585                 590

Phe Met Lys Val Gln Gln Gly Glu Gly Ser Gly Gly Glu Asp Ala Val
        595                 600                 605

Leu Leu Ala Asn Thr Leu Asn Ile Cys Ala Gly Leu Asn Glu Asp Val
    610                 615                 620

Leu Ser Asn Asn Glu Tyr Thr Ala Leu Ser Thr Leu Thr Asn Lys Ile
625                 630                 635                 640
```

```
Cys Asn Arg Leu Ala Gln Ile Gln Asp Asn Lys Ile Leu Gln Val Val
                645                 650                 655

Asp Gly Ser Ile Lys Asp Lys Glu Leu Glu Gln Asp Met Gln Ala Leu
            660                 665                 670

Val Lys Leu Val Leu Gln Glu Asn Gly Gly Ala Val Asp Arg Asn Ile
        675                 680                 685

Arg His Thr Phe Leu Ser Val Ser Lys Thr Phe Tyr Tyr Asp Ala Tyr
    690                 695                 700

His Asp Asp Glu Thr Thr Asp Leu His Ile Phe Lys Val Leu Phe Arg
705                 710                 715                 720

Pro Val Val


<210> SEQ ID NO 189
<211> LENGTH: 2172
<212> TYPE: DNA
<213> ORGANISM: Salvia sclarea

<400> SEQUENCE: 189

atggcatccc aagcgtccga gaaagatatt agcctggttc aaaccccgca taaggtcgag     60

gtcaacgaaa agatcgaaga gagcatcgag tacgtccaaa atctgctgat gacgagcggt    120

gacggtcgta tctccgtgtc tccgtacgat accgcggtca tcgctctgat taaagatctg    180

aagggtcgcg acgcaccgca gttcccgagc tgtctggagt ggattgcgca ccaccagtta    240

gcggatggta gctggggcga cgagttcttt tgtatctatg accgcatttt gaataccctg    300

gcgtgcgtcg tcgcactgaa atcttggaat ctgcacagcg acattattga aaaaggcgtg    360

acctacatta aggaaaacgt ccataagctg aaaggcgcga atgttgagca tagaaccgcc    420

ggttttgagc tggttgttcc gaccttcatg cagatggcga ctgacctggg tattcaggat    480

ctgccgtacg atcatcctct tatcaaagaa atcgctgata cgaagcaaca gcgcctgaaa    540

gaaattccga aagatttggt ttatcagatg ccgaccaatc tgctgtatag cctggaaggc    600

ctgggcgatt tagagtggga gcgtttgctg aagctgcagt ctggtaatgg tagcttcctg    660

acgagcccaa gcagcacggc ggcagttctg atgcatacca aagacgagaa gtgtttgaaa    720

tacattgaga atgcgctgaa gaactgcgac ggtggcgctc ctcatacgta tccggttgac    780

atctttagcc gcttgtgggc gatcgaccgt ttgcaacgtc tgggcattag ccgtttcttc    840

caacacgaga tcaaatactt tctggaccac atcgagtcag tctgggaaga aaccggcgtg    900

tttagcggtc gttacacgaa gtttagcgac atcgatgaca cgagcatggg tgtccgcctg    960

ctgaaaatgc acggttacga cgtagaccca aacgtgttga aacactttaa gcagcaagac   1020

ggcaaattca gctgctacat cggccagagc gtcgagagcg cgagcccgat gtataatctg   1080

taccgtgccg cccagctgcg tttcccgggt gaagaagtgc ttgaagaagc aactaaattc   1140

gcgtttaact tcctgcaaga gatgctggtg aaggatcgct tgcaagagcg ttgggttatt   1200

agcgatcacc tgtttgacga gattaagctc ggtctgaaga tgccgtggta tgctaccctg   1260

ccgcgtgttg aggccgctta ttacctggat cactatgcgg gtagcggtga tgtgtggatt   1320

ggtaagtctt tttaccgcat gccggagatt agcaatgaca cctacaaaga attggccatc   1380

ctggacttta accgttgtca gactcagcat cagctggagt ggattcacat gcaagagtgg   1440

tatgaccgct gctctctgtc cgagtttggt attagcaagc gtgagctgct gcgtagctac   1500

ttcctggctg ccgcaaccat tttcgaaccg gaacgcaccc aagagcgtct gctctgggca   1560

aagacccgca tcctgagcaa gatgattacc agcttcgtca acatctccgg tacgaccctg   1620
```

```
agcctggatt acaacttcaa cggtttggat gagatcattt ccagcgcgaa tgaagatcag   1680

ggtctggcgg gtacgctgtt ggccacgttc catcaactgc tggatggttt cgacatttac   1740

accctgcacc aactgaaaca cgtctggtcg caatggttta tgaaagttca gcaaggcgag   1800

ggctccggcg gcgaagatgc ggtcctgctg gcaaatactc tgaatatctg cgcgggtctg   1860

aatgaagatg tgctgtcgaa caacgagtat accgcgctga gcacgctgac gaacaagatc   1920

tgcaaccgtc tggcccagat ccaggacaac aagattctgc aagtggtgga cggcagcatc   1980

aaagacaaag aactggaaca ggatatgcag gcattggtta aactggtgct gcaggaaaac   2040

ggtggcgcag tggaccgtaa catccgtcac acgtttctga gcgttagcaa gaccttctac   2100

tatgacgcgt atcacgacga tgaaaccacc gatctgcata tctttaaagt cctgttccgt   2160

ccggttgttt aa                                                        2172


<210> SEQ ID NO 190
<211> LENGTH: 924
<212> TYPE: DNA
<213> ORGANISM: Pantoea agglomerans
<220> FEATURE:
<221> NAME/KEY: CDS
<222> LOCATION: (1)..(924)

<400> SEQUENCE: 190

atg gtg agt ggc agt aaa gcg ggc gtt tcg cct cat cgc gaa ata gaa       48
Met Val Ser Gly Ser Lys Ala Gly Val Ser Pro His Arg Glu Ile Glu
1               5                   10                  15

gta atg aga caa tcc att gac gat cac ctg gct ggc ctg tta cct gaa       96
Val Met Arg Gln Ser Ile Asp Asp His Leu Ala Gly Leu Leu Pro Glu
            20                  25                  30

acc gac agc cag gat atc gtc agc ctt gcg atg cgt gaa ggc gtc atg      144
Thr Asp Ser Gln Asp Ile Val Ser Leu Ala Met Arg Glu Gly Val Met
        35                  40                  45

gca ccc ggt aaa cgg atc cgt ccg ctg ctg atg ctg ctg gcc gcc cgc      192
Ala Pro Gly Lys Arg Ile Arg Pro Leu Leu Met Leu Leu Ala Ala Arg
    50                  55                  60

gac ctc cgc tac cag ggc agt atg cct acg ctg ctc gat ctc gcc tgc      240
Asp Leu Arg Tyr Gln Gly Ser Met Pro Thr Leu Leu Asp Leu Ala Cys
65                  70                  75                  80

gcc gtt gaa ctg acc cat acc gcg tcg ctg atg ctc gac gac atg ccc      288
Ala Val Glu Leu Thr His Thr Ala Ser Leu Met Leu Asp Asp Met Pro
                85                  90                  95

tgc atg gac aac gcc gag ctg cgc cgc ggt cag ccc act acc cac aaa      336
Cys Met Asp Asn Ala Glu Leu Arg Arg Gly Gln Pro Thr Thr His Lys
            100                 105                 110

aaa ttt ggt gag agc gtg gcg atc ctt gcc tcc gtt ggg ctg ctc tct      384
Lys Phe Gly Glu Ser Val Ala Ile Leu Ala Ser Val Gly Leu Leu Ser
        115                 120                 125

aaa gcc ttt ggt ctg atc gcc gcc acc ggc gat ctg ccg ggg gag agg      432
Lys Ala Phe Gly Leu Ile Ala Ala Thr Gly Asp Leu Pro Gly Glu Arg
    130                 135                 140

cgt gcc cag gcg gtc aac gag ctc tct acc gcc gtg ggc gtg cag ggc      480
Arg Ala Gln Ala Val Asn Glu Leu Ser Thr Ala Val Gly Val Gln Gly
145                 150                 155                 160

ctg gta ctg ggg cag ttt cgc gat ctt aac gat gcc gcc ctc gac cgt      528
Leu Val Leu Gly Gln Phe Arg Asp Leu Asn Asp Ala Ala Leu Asp Arg
                165                 170                 175

acc cct gac gct atc ctc agc acc aac cac ctc aag acc ggc att ctg      576
Thr Pro Asp Ala Ile Leu Ser Thr Asn His Leu Lys Thr Gly Ile Leu
            180                 185                 190
```

```
ttc agc gcg atg ctg cag atc gtc gcc att gct tcc gcc tcg tcg ccg      624
Phe Ser Ala Met Leu Gln Ile Val Ala Ile Ala Ser Ala Ser Ser Pro
        195                 200                 205

agc acg cga gag acg ctg cac gcc ttc gcc ctc gac ttc ggc cag gcg      672
Ser Thr Arg Glu Thr Leu His Ala Phe Ala Leu Asp Phe Gly Gln Ala
    210                 215                 220

ttt caa ctg ctg gac gat ctg cgt gac gat cac ccg gaa acc ggt aaa      720
Phe Gln Leu Leu Asp Asp Leu Arg Asp Asp His Pro Glu Thr Gly Lys
225                 230                 235                 240

gat cgc aat aag gac gcg gga aaa tcg acg ctg gtc aac cgg ctg ggc      768
Asp Arg Asn Lys Asp Ala Gly Lys Ser Thr Leu Val Asn Arg Leu Gly
                245                 250                 255

gca gac gcg gcc cgg caa aag ctg cgc gag cat att gat tcc gcc gac      816
Ala Asp Ala Ala Arg Gln Lys Leu Arg Glu His Ile Asp Ser Ala Asp
            260                 265                 270

aaa cac ctc act ttt gcc tgt ccg cag ggc ggc gcc atc cga cag ttt      864
Lys His Leu Thr Phe Ala Cys Pro Gln Gly Gly Ala Ile Arg Gln Phe
        275                 280                 285

atg cat ctg tgg ttt ggc cat cac ctt gcc gac tgg tca ccg gtc atg      912
Met His Leu Trp Phe Gly His His Leu Ala Asp Trp Ser Pro Val Met
    290                 295                 300

aaa atc gcc tga                                                      924
Lys Ile Ala
305
```

<210> SEQ ID NO 191
<211> LENGTH: 307
<212> TYPE: PRT
<213> ORGANISM: Pantoea agglomerans

<400> SEQUENCE: 191

```
Met Val Ser Gly Ser Lys Ala Gly Val Ser Pro His Arg Glu Ile Glu
1               5                   10                  15

Val Met Arg Gln Ser Ile Asp Asp His Leu Ala Gly Leu Leu Pro Glu
            20                  25                  30

Thr Asp Ser Gln Asp Ile Val Ser Leu Ala Met Arg Glu Gly Val Met
        35                  40                  45

Ala Pro Gly Lys Arg Ile Arg Pro Leu Leu Met Leu Leu Ala Ala Arg
    50                  55                  60

Asp Leu Arg Tyr Gln Gly Ser Met Pro Thr Leu Leu Asp Leu Ala Cys
65                  70                  75                  80

Ala Val Glu Leu Thr His Thr Ala Ser Leu Met Leu Asp Asp Met Pro
                85                  90                  95

Cys Met Asp Asn Ala Glu Leu Arg Arg Gly Gln Pro Thr Thr His Lys
            100                 105                 110

Lys Phe Gly Glu Ser Val Ala Ile Leu Ala Ser Val Gly Leu Leu Ser
        115                 120                 125

Lys Ala Phe Gly Leu Ile Ala Ala Thr Gly Asp Leu Pro Gly Glu Arg
    130                 135                 140

Arg Ala Gln Ala Val Asn Glu Leu Ser Thr Ala Val Gly Val Gln Gly
145                 150                 155                 160

Leu Val Leu Gly Gln Phe Arg Asp Leu Asn Asp Ala Ala Leu Asp Arg
                165                 170                 175

Thr Pro Asp Ala Ile Leu Ser Thr Asn His Leu Lys Thr Gly Ile Leu
            180                 185                 190

Phe Ser Ala Met Leu Gln Ile Val Ala Ile Ala Ser Ala Ser Ser Pro
        195                 200                 205
```

```
Ser Thr Arg Glu Thr Leu His Ala Phe Ala Leu Asp Phe Gly Gln Ala
    210                 215                 220

Phe Gln Leu Leu Asp Asp Leu Arg Asp Asp His Pro Glu Thr Gly Lys
225                 230                 235                 240

Asp Arg Asn Lys Asp Ala Gly Lys Ser Thr Leu Val Asn Arg Leu Gly
                245                 250                 255

Ala Asp Ala Ala Arg Gln Lys Leu Arg Glu His Ile Asp Ser Ala Asp
            260                 265                 270

Lys His Leu Thr Phe Ala Cys Pro Gln Gly Gly Ala Ile Arg Gln Phe
        275                 280                 285

Met His Leu Trp Phe Gly His His Leu Ala Asp Trp Ser Pro Val Met
    290                 295                 300

Lys Ile Ala
305


<210> SEQ ID NO 192
<211> LENGTH: 924
<212> TYPE: DNA
<213> ORGANISM: Pantoea agglomerans

<400> SEQUENCE: 192

atggtttctg gttcgaaagc aggagtatca cctcataggg aaatcgaagt catgagacag      60

tccattgatg accacttagc aggattgttg ccagaaacag attcccagga tatcgttagc     120

cttgctatga gagaaggtgt tatggcacct ggtaaacgta tcagaccttt gctgatgtta     180

cttgctgcaa gagacctgag atatcagggt tctatgccta cactactgga tctagcttgt     240

gctgttgaac tgacacatac tgcttccttg atgctggatg acatgccttg tatggacaat     300

gcggaactta gaagaggtca accaacaacc cacaagaaat tcggagaatc tgttgccatt     360

ttggcttctg taggtctgtt gtcgaaagca tttggcttga ttgctgcaac tggtgatctt     420

ccaggtgaaa ggagagcaca agctgtaaac gagctatcta ctgcagttgg tgttcaaggt     480

ctagtcttag gacagttcag agatttgaat gacgcagctt tggacagaac tcctgatgct     540

atcctgtcta cgaaccatct gaagactggc atcttgttct cagctatgtt gcaaatcgta     600

gccattgctt ctgcttcttc accatctact agggaaacgt tacacgcatt cgcattggac     660

tttggtcaag cctttcaact gctagacgat ttgagggatg atcatccaga gacaggtaaa     720

gaccgtaaca aagacgctgg taaaagcact ctagtcaaca gattgggtgc tgatgcagct     780

agacagaaac tgagagagca cattgactct gctgacaaac acctgacatt tgcatgtcca     840

caaggaggtg ctataaggca gtttatgcac ctatggtttg gacaccatct tgctgattgg     900

tctccagtga tgaagatcgc ctaa                                            924


<210> SEQ ID NO 193
<211> LENGTH: 936
<212> TYPE: DNA
<213> ORGANISM: Talaromyces verruculosus
<220> FEATURE:
<221> NAME/KEY: CDS
<222> LOCATION: (1)..(936)

<400> SEQUENCE: 193

atg tct aat gac acc act acc acg gct tct gcc gga aca gca act tct       48
Met Ser Asn Asp Thr Thr Thr Thr Ala Ser Ala Gly Thr Ala Thr Ser
1               5                   10                  15

tcg cgg ttt ctt tcc gtg ggg gga gtt gtg aac ttc cgt gaa ctg ggc       96
Ser Arg Phe Leu Ser Val Gly Gly Val Val Asn Phe Arg Glu Leu Gly
```

-continued

```
            20                  25                  30

ggt tac cca tgt gat tct gtc cct cct gct cct gcc tca aac ggc tca       144
Gly Tyr Pro Cys Asp Ser Val Pro Pro Ala Pro Ala Ser Asn Gly Ser
        35                  40                  45

ccg gac aat gca tct gaa gcg acc ctt tgg gtt ggc cac tcg tcc att       192
Pro Asp Asn Ala Ser Glu Ala Thr Leu Trp Val Gly His Ser Ser Ile
    50                  55                  60

cgg cct gga ttt ctg ttt cga tcg gca cag ccg tct cag att acc ccg       240
Arg Pro Gly Phe Leu Phe Arg Ser Ala Gln Pro Ser Gln Ile Thr Pro
65                  70                  75                  80

gcc ggt att gag aca ttg atc cgc cag ctt ggc atc cag aca att ttt       288
Ala Gly Ile Glu Thr Leu Ile Arg Gln Leu Gly Ile Gln Thr Ile Phe
                85                  90                  95

gac ttt cgt tca agg acg gaa att gag ctt gtt gcc act cgc tat cct       336
Asp Phe Arg Ser Arg Thr Glu Ile Glu Leu Val Ala Thr Arg Tyr Pro
            100                 105                 110

gat tcg cta ctt gag ata cct ggc acg act cgc tat tcc gtg ccc gtc       384
Asp Ser Leu Leu Glu Ile Pro Gly Thr Thr Arg Tyr Ser Val Pro Val
        115                 120                 125

ttc tcg gaa ggc gac tat tcc cca gcg tca tta gtc aag agg tac gga       432
Phe Ser Glu Gly Asp Tyr Ser Pro Ala Ser Leu Val Lys Arg Tyr Gly
    130                 135                 140

gtg tcc tcc gat act gca acc gat tcc act tcc tcc aaa agt gct aag       480
Val Ser Ser Asp Thr Ala Thr Asp Ser Thr Ser Ser Lys Ser Ala Lys
145                 150                 155                 160

cct aca gga ttc gtc cac gca tat gag gct atc gca cgc agt gca gca       528
Pro Thr Gly Phe Val His Ala Tyr Glu Ala Ile Ala Arg Ser Ala Ala
                165                 170                 175

gaa aac ggc agt ttt cgt aag ata acg gac cac ata ata caa cat ccg       576
Glu Asn Gly Ser Phe Arg Lys Ile Thr Asp His Ile Ile Gln His Pro
            180                 185                 190

gac cgg cct att ctg ttt cac tgt aca ctg ggg aaa gac cga acc ggt       624
Asp Arg Pro Ile Leu Phe His Cys Thr Leu Gly Lys Asp Arg Thr Gly
        195                 200                 205

gtg ttt gca gca ttg tta ttg agt ctt tgc ggg gta cca gac gag acg       672
Val Phe Ala Ala Leu Leu Leu Ser Leu Cys Gly Val Pro Asp Glu Thr
    210                 215                 220

ata gtt gaa gac tat gct atg act acc gag gga ttt gga gcc tgg cgg       720
Ile Val Glu Asp Tyr Ala Met Thr Thr Glu Gly Phe Gly Ala Trp Arg
225                 230                 235                 240

gaa cat cta att caa cgc ttg cta caa agg aag gat gca gct acg cgc       768
Glu His Leu Ile Gln Arg Leu Leu Gln Arg Lys Asp Ala Ala Thr Arg
                245                 250                 255

gag gat gca gaa tcc att att gcc agc ccc ccg gag act atg aag gct       816
Glu Asp Ala Glu Ser Ile Ile Ala Ser Pro Pro Glu Thr Met Lys Ala
            260                 265                 270

ttt cta gaa gat gtg gta gca gcc aag ttc ggg ggt gct cga aat tac       864
Phe Leu Glu Asp Val Val Ala Ala Lys Phe Gly Gly Ala Arg Asn Tyr
        275                 280                 285

ttt atc cag cac tgt gga ttt acg gaa gct gag gtt gat aag tta agc       912
Phe Ile Gln His Cys Gly Phe Thr Glu Ala Glu Val Asp Lys Leu Ser
    290                 295                 300

cat aca ctg gcc att acg aat tga                                       936
His Thr Leu Ala Ile Thr Asn
305                 310
```

<210> SEQ ID NO 194
<211> LENGTH: 311
<212> TYPE: PRT
<213> ORGANISM: Talaromyces verruculosus

<400> SEQUENCE: 194

```
Met Ser Asn Asp Thr Thr Thr Thr Ala Ser Ala Gly Thr Ala Thr Ser
1               5                   10                  15

Ser Arg Phe Leu Ser Val Gly Gly Val Val Asn Phe Arg Glu Leu Gly
            20                  25                  30

Gly Tyr Pro Cys Asp Ser Val Pro Pro Ala Pro Ala Ser Asn Gly Ser
        35                  40                  45

Pro Asp Asn Ala Ser Glu Ala Thr Leu Trp Val Gly His Ser Ser Ile
    50                  55                  60

Arg Pro Gly Phe Leu Phe Arg Ser Ala Gln Pro Ser Gln Ile Thr Pro
65                  70                  75                  80

Ala Gly Ile Glu Thr Leu Ile Arg Gln Leu Gly Ile Gln Thr Ile Phe
                85                  90                  95

Asp Phe Arg Ser Arg Thr Glu Ile Glu Leu Val Ala Thr Arg Tyr Pro
            100                 105                 110

Asp Ser Leu Leu Glu Ile Pro Gly Thr Thr Arg Tyr Ser Val Pro Val
        115                 120                 125

Phe Ser Glu Gly Asp Tyr Ser Pro Ala Ser Leu Val Lys Arg Tyr Gly
    130                 135                 140

Val Ser Ser Asp Thr Ala Thr Asp Ser Thr Ser Ser Lys Ser Ala Lys
145                 150                 155                 160

Pro Thr Gly Phe Val His Ala Tyr Glu Ala Ile Ala Arg Ser Ala Ala
                165                 170                 175

Glu Asn Gly Ser Phe Arg Lys Ile Thr Asp His Ile Ile Gln His Pro
            180                 185                 190

Asp Arg Pro Ile Leu Phe His Cys Thr Leu Gly Lys Asp Arg Thr Gly
        195                 200                 205

Val Phe Ala Ala Leu Leu Leu Ser Leu Cys Gly Val Pro Asp Glu Thr
    210                 215                 220

Ile Val Glu Asp Tyr Ala Met Thr Thr Glu Gly Phe Gly Ala Trp Arg
225                 230                 235                 240

Glu His Leu Ile Gln Arg Leu Leu Gln Arg Lys Asp Ala Ala Thr Arg
                245                 250                 255

Glu Asp Ala Glu Ser Ile Ile Ala Ser Pro Pro Glu Thr Met Lys Ala
            260                 265                 270

Phe Leu Glu Asp Val Val Ala Ala Lys Phe Gly Gly Ala Arg Asn Tyr
        275                 280                 285

Phe Ile Gln His Cys Gly Phe Thr Glu Ala Glu Val Asp Lys Leu Ser
    290                 295                 300

His Thr Leu Ala Ile Thr Asn
305                 310
```

<210> SEQ ID NO 195
<211> LENGTH: 936
<212> TYPE: DNA
<213> ORGANISM: Talaromyces verruculosus

<400> SEQUENCE: 195

```
atgtctaacg acactactac tactgcttct gctggtactg ctacttcttc tagattcttg      60

tctgttggtg gtgttgttaa cttcagagaa ttgggtggtt acccatgtga ctctgttcca     120

ccagctccag cttctaacgg ttctccagac aacgcttctg aagctacttt gtgggttggt     180

cactcttcta tcagaccagg tttcttgttc agatctgctc aaccatctca aatcactcca     240
```

-continued

```
gctggtatcg aaactttgat cagacaattg ggtatccaaa ctatcttcga cttcagatct    300

agaactgaaa tcgaattggt tgctactaga tacccagact ctttgttgga aatcccaggt    360

actactagat actctgttcc agttttctct gaaggtgact actctccagc ttctttggtt    420

aagagatacg gtgtttcttc tgacactgct actgactcta cttcttctaa gtctgctaag    480

ccaactggtt tcgttcacgc ttacgaagct atcgctagat ctgctgctga aaacggttct    540

ttcagaaaga tcactgacca catcatccaa cacccagaca gaccaatctt gttccactgt    600

actttgggta aggacagaac tggtgttttc gctgctttgt tgttgtcttt gtgtggtgtt    660

ccagacgaaa ctatcgttga agactacgct atgactactg aaggtttcgg tgcttggaga    720

gaacacttga tccaaagatt gttgcaaaga aaggacgctg ctactagaga agacgctgaa    780

tctatcatcg cttctccacc agaaactatg aaggctttct tggaagacgt tgttgctgct    840

aagttcggtg gtgctagaaa ctacttcatc caacactgtg gtttcactga agctgaagtt    900

gacaagttgt ctcacacttt ggctatcact aactaa                              936


<210> SEQ ID NO 196
<211> LENGTH: 14
<212> TYPE: DNA
<213> ORGANISM: Artificial Sequence
<220> FEATURE:
<223> OTHER INFORMATION: RBS sequence

<400> SEQUENCE: 196

aaggaggtaa aaaa                                                       14


<210> SEQ ID NO 197
<211> LENGTH: 7
<212> TYPE: PRT
<213> ORGANISM: Artificial Sequence
<220> FEATURE:
<223> OTHER INFORMATION: BVMO sequence motif 1
<220> FEATURE:
<221> NAME/KEY: MISC_FEATURE
<222> LOCATION: (4)..(4)
<223> OTHER INFORMATION: Xaa can be any naturally occurring amino acid,
      particularly A or I

<400> SEQUENCE: 197

Gly Ala Gly Xaa Ser Gly Leu
1               5


<210> SEQ ID NO 198
<211> LENGTH: 32
<212> TYPE: PRT
<213> ORGANISM: Artificial Sequence
<220> FEATURE:
<223> OTHER INFORMATION: BVMO sequence motif 2
<220> FEATURE:
<221> NAME/KEY: MISC_FEATURE
<222> LOCATION: (4)..(4)
<223> OTHER INFORMATION: Xaa can be any naturally occurring amino acid,
      particularly H or P
<220> FEATURE:
<221> NAME/KEY: MISC_FEATURE
<222> LOCATION: (5)..(5)
<223> OTHER INFORMATION: Xaa can be any naturally occurring amino acid,
      particularly A, D, or E
<220> FEATURE:
<221> NAME/KEY: MISC_FEATURE
<222> LOCATION: (6)..(6)
<223> OTHER INFORMATION: Xaa can be any naturally occurring amino acid,
      particularly L or V
<220> FEATURE:
<221> NAME/KEY: MISC_FEATURE
<222> LOCATION: (7)..(7)
```

<223> OTHER INFORMATION: Xaa can be any naturally occurring amino acid, particularly G or S
<220> FEATURE:
<221> NAME/KEY: MISC_FEATURE
<222> LOCATION: (11)..(11)
<223> OTHER INFORMATION: Xaa can be any naturally occurring amino acid, particularly F, L, or Y
<220> FEATURE:
<221> NAME/KEY: MISC_FEATURE
<222> LOCATION: (24)..(24)
<223> OTHER INFORMATION: Xaa can be any naturally occurring amino acid, particularly A or S
<220> FEATURE:
<221> NAME/KEY: MISC_FEATURE
<222> LOCATION: (26)..(26)
<223> OTHER INFORMATION: Xaa can be any naturally occurring amino acid, particularly A, C, or N
<220> FEATURE:
<221> NAME/KEY: MISC_FEATURE
<222> LOCATION: (28)..(28)
<223> OTHER INFORMATION: Xaa can be any naturally occurring amino acid, particularly A or T
<220> FEATURE:
<221> NAME/KEY: MISC_FEATURE
<222> LOCATION: (29)..(29)
<223> OTHER INFORMATION: Xaa can be any naturally occurring amino acid, particularly W or Y

<400> SEQUENCE: 198

```
Glu Lys Asn Xaa Xaa Xaa Xaa Gly Thr Trp Xaa Glu Asn Arg Tyr Pro
1               5                   10                  15

Gly Cys Ala Cys Asp Val Pro Xaa His Xaa Tyr Xaa Xaa Ser Phe Glu
            20                  25                  30
```

<210> SEQ ID NO 199
<211> LENGTH: 18
<212> TYPE: PRT
<213> ORGANISM: Artificial Sequence
<220> FEATURE:
<223> OTHER INFORMATION: BVMO sequence motif 3
<220> FEATURE:
<221> NAME/KEY: MISC_FEATURE
<222> LOCATION: (2)..(2)
<223> OTHER INFORMATION: Xaa can be any naturally occurring amino acid, particularly I, L, or V
<220> FEATURE:
<221> NAME/KEY: MISC_FEATURE
<222> LOCATION: (5)..(5)
<223> OTHER INFORMATION: Xaa can be any naturally occurring amino acid, particularly G, S, or T
<220> FEATURE:
<221> NAME/KEY: MISC_FEATURE
<222> LOCATION: (10)..(10)
<223> OTHER INFORMATION: Xaa can be any naturally occurring amino acid, particularly A or Q
<220> FEATURE:
<221> NAME/KEY: MISC_FEATURE
<222> LOCATION: (12)..(12)
<223> OTHER INFORMATION: Xaa can be any naturally occurring amino acid, particularly K or R
<220> FEATURE:
<221> NAME/KEY: MISC_FEATURE
<222> LOCATION: (13)..(13)
<223> OTHER INFORMATION: Xaa can be any naturally occurring amino acid, particularly W or Y
<220> FEATURE:
<221> NAME/KEY: MISC_FEATURE
<222> LOCATION: (15)..(15)
<223> OTHER INFORMATION: Xaa can be any naturally occurring amino acid, particularly G, P, or S

<400> SEQUENCE: 199

```
Leu Xaa Asn Ala Xaa Gly Ile Leu Asn Xaa Trp Xaa Xaa Pro Xaa Ile
1               5                   10                  15
```

Pro Gly

<210> SEQ ID NO 200
<211> LENGTH: 22
<212> TYPE: PRT
<213> ORGANISM: Artificial Sequence
<220> FEATURE:
<223> OTHER INFORMATION: BVMO sequence motif 4
<220> FEATURE:
<221> NAME/KEY: MISC_FEATURE
<222> LOCATION: (2)..(2)
<223> OTHER INFORMATION: Xaa can be any naturally occurring amino acid, particularly E, K, or N
<220> FEATURE:
<221> NAME/KEY: MISC_FEATURE
<222> LOCATION: (3)..(3)
<223> OTHER INFORMATION: Xaa can be any naturally occurring amino acid, particularly D or G
<220> FEATURE:
<221> NAME/KEY: MISC_FEATURE
<222> LOCATION: (5)..(5)
<223> OTHER INFORMATION: Xaa can be any naturally occurring amino acid, particularly K, T, or V
<220> FEATURE:
<221> NAME/KEY: MISC_FEATURE
<222> LOCATION: (7)..(7)
<223> OTHER INFORMATION: Xaa can be any naturally occurring amino acid, particularly A or G
<220> FEATURE:
<221> NAME/KEY: MISC_FEATURE
<222> LOCATION: (8)..(8)
<223> OTHER INFORMATION: Xaa can be any naturally occurring amino acid, particularly L or V
<220> FEATURE:
<221> NAME/KEY: MISC_FEATURE
<222> LOCATION: (11)..(11)
<223> OTHER INFORMATION: Xaa can be any naturally occurring amino acid, particularly N or S
<220> FEATURE:
<221> NAME/KEY: MISC_FEATURE
<222> LOCATION: (19)..(19)
<223> OTHER INFORMATION: Xaa can be any naturally occurring amino acid, particularly L or V
<220> FEATURE:
<221> NAME/KEY: MISC_FEATURE
<222> LOCATION: (21)..(21)
<223> OTHER INFORMATION: Xaa can be any naturally occurring amino acid, particularly A or N

<400> SEQUENCE: 200

```
Leu Xaa Xaa Lys Xaa Val Xaa Xaa Ile Gly Xaa Gly Ser Ser Gly Ile
1               5                   10                  15

Gln Ile Xaa Pro Xaa Ile
            20
```

<210> SEQ ID NO 201
<211> LENGTH: 15
<212> TYPE: PRT
<213> ORGANISM: Artificial Sequence
<220> FEATURE:
<223> OTHER INFORMATION: BVMO sequence motif 5
<220> FEATURE:
<221> NAME/KEY: MISC_FEATURE
<222> LOCATION: (5)..(5)
<223> OTHER INFORMATION: Xaa can be any naturally occurring amino acid, particularly L or P
<220> FEATURE:
<221> NAME/KEY: MISC_FEATURE
<222> LOCATION: (9)..(9)
<223> OTHER INFORMATION: Xaa can be any naturally occurring amino acid, particularly P or T
<220> FEATURE:
<221> NAME/KEY: MISC_FEATURE
<222> LOCATION: (10)..(10)
<223> OTHER INFORMATION: Xaa can be any naturally occurring amino acid, particularly G, H, or N
<220> FEATURE:
<221> NAME/KEY: MISC_FEATURE
<222> LOCATION: (14)..(14)
<223> OTHER INFORMATION: Xaa can be any naturally occurring amino acid, particularly A or S

<400> SEQUENCE: 201

Gly Cys Arg Arg Xaa Thr Pro Gly Xaa Xaa Tyr Leu Glu Xaa Leu
1 5 10 15

<210> SEQ ID NO 202
<211> LENGTH: 17
<212> TYPE: PRT
<213> ORGANISM: Artificial Sequence
<220> FEATURE:
<223> OTHER INFORMATION: BVMO sequence motif 6
<220> FEATURE:
<221> NAME/KEY: MISC_FEATURE
<222> LOCATION: (7)..(7)
<223> OTHER INFORMATION: Xaa can be any naturally occurring amino acid, particularly T or V
<220> FEATURE:
<221> NAME/KEY: MISC_FEATURE
<222> LOCATION: (8)..(8)
<223> OTHER INFORMATION: Xaa can be any naturally occurring amino acid, particularly S or T
<220> FEATURE:
<221> NAME/KEY: MISC_FEATURE
<222> LOCATION: (9)..(9)
<223> OTHER INFORMATION: Xaa can be any naturally occurring amino acid, particularly F or Y
<220> FEATURE:
<221> NAME/KEY: MISC_FEATURE
<222> LOCATION: (10)..(10)
<223> OTHER INFORMATION: Xaa can be any naturally occurring amino acid, particularly K or R
<220> FEATURE:
<221> NAME/KEY: MISC_FEATURE
<222> LOCATION: (14)..(14)
<223> OTHER INFORMATION: Xaa can be any naturally occurring amino acid, particularly K or P
<220> FEATURE:
<221> NAME/KEY: MISC_FEATURE
<222> LOCATION: (15)..(15)
<223> OTHER INFORMATION: Xaa can be any naturally occurring amino acid, particularly F or L
<220> FEATURE:
<221> NAME/KEY: MISC_FEATURE
<222> LOCATION: (16)..(16)
<223> OTHER INFORMATION: Xaa can be any naturally occurring amino acid, particularly I or V

<400> SEQUENCE: 202

Cys Ala Thr Gly Phe Asp Xaa Xaa Xaa Xaa Pro Arg Phe Xaa Xaa Xaa
1 5 10 15

Gly

<210> SEQ ID NO 203
<211> LENGTH: 18
<212> TYPE: PRT
<213> ORGANISM: Artificial Sequence
<220> FEATURE:
<223> OTHER INFORMATION: BVMO sequence motif 7
<220> FEATURE:
<221> NAME/KEY: MISC_FEATURE
<222> LOCATION: (3)..(3)
<223> OTHER INFORMATION: Xaa can be any naturally occurring amino acid, particularly S or Y
<220> FEATURE:
<221> NAME/KEY: MISC_FEATURE
<222> LOCATION: (5)..(5)
<223> OTHER INFORMATION: Xaa can be any naturally occurring amino acid, particularly F, I, or S
<220> FEATURE:
<221> NAME/KEY: MISC_FEATURE
<222> LOCATION: (6)..(6)
<223> OTHER INFORMATION: Xaa can be any naturally occurring amino acid, particularly F, I, or T
<220> FEATURE:
<221> NAME/KEY: MISC_FEATURE
<222> LOCATION: (7)..(7)
<223> OTHER INFORMATION: Xaa can be any naturally occurring amino acid, particularly L or M
<220> FEATURE:
<221> NAME/KEY: MISC_FEATURE
<222> LOCATION: (11)..(11)
<223> OTHER INFORMATION: Xaa can be any naturally occurring amino acid, particularly C or G
<220> FEATURE:
<221> NAME/KEY: MISC_FEATURE
<222> LOCATION: (13)..(13)
<223> OTHER INFORMATION: Xaa can be any naturally occurring amino acid, particularly I or V
<220> FEATURE:
<221> NAME/KEY: MISC_FEATURE
<222> LOCATION: (14)..(14)
<223> OTHER INFORMATION: Xaa can be any naturally occurring amino acid, particularly A or G
<220> FEATURE:
<221> NAME/KEY: MISC_FEATURE
<222> LOCATION: (17)..(17)
<223> OTHER INFORMATION: Xaa can be any naturally occurring amino acid, particularly P or S

<400> SEQUENCE: 203

```
Pro Asn Xaa Phe Xaa Xaa Xaa Gly Pro Asn Xaa Pro Xaa Xaa Asn Gly
1               5                   10                  15

Xaa Val
```

<210> SEQ ID NO 204
<211> LENGTH: 21
<212> TYPE: PRT
<213> ORGANISM: Artificial Sequence
<220> FEATURE:
<223> OTHER INFORMATION: BVMO sequence motif 8
<220> FEATURE:
<221> NAME/KEY: MISC_FEATURE
<222> LOCATION: (2)..(2)
<223> OTHER INFORMATION: Xaa can be any naturally occurring amino acid, particularly L or V
<220> FEATURE:
<221> NAME/KEY: MISC_FEATURE
<222> LOCATION: (7)..(7)
<223> OTHER INFORMATION: Xaa can be any naturally occurring amino acid, particularly A or T
<220> FEATURE:
<221> NAME/KEY: MISC_FEATURE
<222> LOCATION: (11)..(11)
<223> OTHER INFORMATION: Xaa can be any naturally occurring amino acid, particularly L or M
<220> FEATURE:
<221> NAME/KEY: MISC_FEATURE
<222> LOCATION: (14)..(14)
<223> OTHER INFORMATION: Xaa can be any naturally occurring amino acid, particularly I or L
<220> FEATURE:
<221> NAME/KEY: MISC_FEATURE
<222> LOCATION: (15)..(15)
<223> OTHER INFORMATION: Xaa can be any naturally occurring amino acid, particularly A, K, or Q
<220> FEATURE:
<221> NAME/KEY: MISC_FEATURE
<222> LOCATION: (16)..(16)
<223> OTHER INFORMATION: Xaa can be any naturally occurring amino acid, particularly D, H, or S
<220> FEATURE:
<221> NAME/KEY: MISC_FEATURE
<222> LOCATION: (19)..(19)
<223> OTHER INFORMATION: Xaa can be any naturally occurring amino acid, particularly W or Y

<400> SEQUENCE: 204

Ala Xaa Trp Pro Gly Ser Xaa Leu His Tyr Xaa Glu Ala Xaa Xaa Xaa
1 5 10 15

Pro Arg Xaa Glu Asp
20

<210> SEQ ID NO 205
<211> LENGTH: 13
<212> TYPE: PRT
<213> ORGANISM: Artificial Sequence
<220> FEATURE:
<223> OTHER INFORMATION: enal-cleaving polypeptide sequence motif 1
<220> FEATURE:
<221> NAME/KEY: MISC_FEATURE
<222> LOCATION: (2)..(2)
<223> OTHER INFORMATION: Xaa can be Y or be deleted
<220> FEATURE:
<221> NAME/KEY: MISC_FEATURE
<222> LOCATION: (3)..(3)
<223> OTHER INFORMATION: Xaa can be any naturally occurring amino acid
<220> FEATURE:
<221> NAME/KEY: MISC_FEATURE
<222> LOCATION: (5)..(5)
<223> OTHER INFORMATION: Xaa can be any naturally occurring amino acid
<220> FEATURE:
<221> NAME/KEY: MISC_FEATURE
<222> LOCATION: (7)..(7)
<223> OTHER INFORMATION: Xaa can be any naturally occurring amino acid
<220> FEATURE:
<221> NAME/KEY: MISC_FEATURE
<222> LOCATION: (8)..(8)
<223> OTHER INFORMATION: Xaa can be any naturally occurring amino acid
<220> FEATURE:
<221> NAME/KEY: MISC_FEATURE
<222> LOCATION: (9)..(9)
<223> OTHER INFORMATION: Xaa can be F, L, or I
<220> FEATURE:
<221> NAME/KEY: MISC_FEATURE
<222> LOCATION: (10)..(10)
<223> OTHER INFORMATION: Xaa can be any naturally occurring amino acid
<220> FEATURE:
<221> NAME/KEY: MISC_FEATURE
<222> LOCATION: (11)..(11)
<223> OTHER INFORMATION: Xaa can be R, S, or T
<220> FEATURE:
<221> NAME/KEY: MISC_FEATURE
<222> LOCATION: (13)..(13)
<223> OTHER INFORMATION: Xaa can be H or D

<400> SEQUENCE: 205

Gly Xaa Xaa Trp Xaa Gly Xaa Xaa Xaa Xaa Xaa Gly Xaa
1 5 10

<210> SEQ ID NO 206
<211> LENGTH: 8
<212> TYPE: PRT
<213> ORGANISM: Artificial Sequence
<220> FEATURE:
<223> OTHER INFORMATION: enal-cleaving polypeptide sequence motif 2
<220> FEATURE:
<221> NAME/KEY: MISC_FEATURE
<222> LOCATION: (2)..(2)
<223> OTHER INFORMATION: Xaa can be A, V, or Y
<220> FEATURE:
<221> NAME/KEY: MISC_FEATURE
<222> LOCATION: (5)..(5)
<223> OTHER INFORMATION: Xaa can be any naturally occurring amino acid
<220> FEATURE:
<221> NAME/KEY: MISC_FEATURE
<222> LOCATION: (6)..(6)
<223> OTHER INFORMATION: Xaa can be F or Y
<220> FEATURE:

<221> NAME/KEY: MISC_FEATURE
<222> LOCATION: (7)..(7)
<223> OTHER INFORMATION: Xaa can be any naturally occurring amino acid
<220> FEATURE:
<221> NAME/KEY: MISC_FEATURE
<222> LOCATION: (8)..(8)
<223> OTHER INFORMATION: Xaa can be D or S

<400> SEQUENCE: 206

Trp Xaa Gly Lys Xaa Xaa Xaa Xaa
1               5

<210> SEQ ID NO 207
<211> LENGTH: 14
<212> TYPE: PRT
<213> ORGANISM: Artificial Sequence
<220> FEATURE:
<223> OTHER INFORMATION: enal-cleaving polypeptide sequence motif 3
<220> FEATURE:
<221> NAME/KEY: MISC_FEATURE
<222> LOCATION: (1)..(1)
<223> OTHER INFORMATION: Xaa can be G or S
<220> FEATURE:
<221> NAME/KEY: MISC_FEATURE
<222> LOCATION: (2)..(2)
<223> OTHER INFORMATION: Xaa can be any naturally occurring amino acid
<220> FEATURE:
<221> NAME/KEY: MISC_FEATURE
<222> LOCATION: (3)..(3)
<223> OTHER INFORMATION: Xaa can be A or G
<220> FEATURE:
<221> NAME/KEY: MISC_FEATURE
<222> LOCATION: (4)..(4)
<223> OTHER INFORMATION: Xaa can be any naturally occurring amino acid
<220> FEATURE:
<221> NAME/KEY: MISC_FEATURE
<222> LOCATION: (5)..(5)
<223> OTHER INFORMATION: Xaa can be L or V
<220> FEATURE:
<221> NAME/KEY: MISC_FEATURE
<222> LOCATION: (6)..(6)
<223> OTHER INFORMATION: Xaa can be any naturally occurring amino acid
<220> FEATURE:
<221> NAME/KEY: MISC_FEATURE
<222> LOCATION: (7)..(7)
<223> OTHER INFORMATION: Xaa can be any naturally occurring amino acid
<220> FEATURE:
<221> NAME/KEY: MISC_FEATURE
<222> LOCATION: (8)..(8)
<223> OTHER INFORMATION: Xaa can be any naturally occurring amino acid
<220> FEATURE:
<221> NAME/KEY: MISC_FEATURE
<222> LOCATION: (9)..(9)
<223> OTHER INFORMATION: Xaa can be any naturally occurring amino acid
<220> FEATURE:
<221> NAME/KEY: MISC_FEATURE
<222> LOCATION: (10)..(10)
<223> OTHER INFORMATION: Xaa can be F, L, or Y
<220> FEATURE:
<221> NAME/KEY: MISC_FEATURE
<222> LOCATION: (13)..(13)
<223> OTHER INFORMATION: Xaa can be any naturally occurring amino acid

<400> SEQUENCE: 207

Xaa Xaa Xaa Xaa Xaa Xaa Xaa Xaa Xaa Xaa Arg Gly Xaa Val
1               5                   10

<210> SEQ ID NO 208
<211> LENGTH: 12
<212> TYPE: PRT
<213> ORGANISM: Artificial Sequence
<220> FEATURE:
<223> OTHER INFORMATION: enal-cleaving polypeptide sequence motif 4
<220> FEATURE:
<221> NAME/KEY: MISC_FEATURE -continued
<222> LOCATION: (1)..(1)
<223> OTHER INFORMATION: Xaa can be L or M
<220> FEATURE:
<221> NAME/KEY: MISC_FEATURE
<222> LOCATION: (2)..(2)
<223> OTHER INFORMATION: Xaa can be I or V
<220> FEATURE:
<221> NAME/KEY: MISC_FEATURE
<222> LOCATION: (5)..(5)
<223> OTHER INFORMATION: Xaa can be any naturally occurring amino acid
<220> FEATURE:
<221> NAME/KEY: MISC_FEATURE
<222> LOCATION: (6)..(6)
<223> OTHER INFORMATION: Xaa can be any naturally occurring amino acid
<220> FEATURE:
<221> NAME/KEY: MISC_FEATURE
<222> LOCATION: (8)..(8)
<223> OTHER INFORMATION: Xaa can be I or V
<220> FEATURE:
<221> NAME/KEY: MISC_FEATURE
<222> LOCATION: (9)..(9)
<223> OTHER INFORMATION: Xaa can be any naturally occurring amino acid
<220> FEATURE:
<221> NAME/KEY: MISC_FEATURE
<222> LOCATION: (11)..(11)
<223> OTHER INFORMATION: Xaa can be H or S
<220> FEATURE:
<221> NAME/KEY: MISC_FEATURE
<222> LOCATION: (12)..(12)
<223> OTHER INFORMATION: Xaa can be F or L

<400> SEQUENCE: 208

Xaa Xaa Tyr Asp Xaa Xaa Pro Xaa Xaa Asp Xaa Xaa
1 5 10

BIOCATALYTIC METHOD FOR THE CONTROLLED DEGRADATION OF TERPENE COMPOUNDS

CROSS-REFERENCE TO RELATED APPLICATIONS

This application is a U.S. National Phase Application of International Patent Application No. PCT/EP2020/069217, filed Jul. 8, 2020, which claims priority to European Patent Application No. 19000332.7, filed Jul. 10, 2019, and which claims priority to European Patent Application No. 19208951.4, filed Nov. 13, 2019, the entire contents of which are hereby incorporated by reference herein.

REFERENCE TO AN ELECTRONIC SEQUENCE LISTING

This application contains an electronic sequence listing. The contents of the electronic sequence listing (36803-328_Imported_ST25.txt; Size: 489,442 bytes; and Date of Creation: Jul. 22, 2022) is herein incorporated by reference in its entirety.

TECHNICAL FIELD

Provided herein are biocatalytic methods of producing terpene degradation products useful as starting material for the production of perfumery ingredients, such as, for example, ambrox. In particular novel terpene degrading polypeptides (enal-cleaving polypeptides) and novel peptides converting terpenes compounds to oxygenated derivatives (oxygenases) and mutants and variants derived therefrom are provided which may be applied in novel types of fully enzymatic multistep degradation pathways allowing the controlled, stepwise conversion and degradation of linear or cyclic terpene substrates. Said novel biosynthetic strategies allow the fully biochemical synthesis of valuable terpene-derived compounds, like for example manooloxy or gamma ambrol. The invention also provides recombinant host organisms carrying the required set of genetic information for the functional expression of the set of enzymes necessary for catalyzing the combination of enzymatic conversion and degradation steps.

BACKGROUND

Terpenes are found in most organisms (microorganisms, animals and plants). These compounds are made up of five-carbon units, so-called isoprene units, and are classified by the number of these units present in their structure. Thus hemiterpenes, monoterpenes, sesquiterpenes and diterpenes are terpenes containing 5, 10, 15 and 20 carbon atoms (i.e. 1, 2, 3 and 4 isoprene units) respectively. Sesquiterpenes, for example, are widely found in the plant kingdom. Many sesquiterpene molecules are known for their flavor and fragrance properties and their cosmetic, medicinal and antimicrobial effects. Numerous sesquiterpene hydrocarbons and sesquiterpenoids have been identified.

Biosynthetic production of terpenes involves enzymes called terpene synthases. These enzymes convert an acyclic terpene precursor in one or more terpene products. In particular, diterpene synthases produce diterpenes by cyclization of the precursor geranylgeranyl diphosphate (GGPP). The cyclization of GGPP often requires two enzyme polypeptides, a type I and a type II diterpene synthase working in combination in two successive enzymatic reactions. The type II diterpene synthases catalyze a cyclization/rearrangement of GGPP initiated by the protonation of the terminal double bond of GGPP leading to a cyclic diterpene diphosphate intermediate. This intermediate is then further converted by a type I diterpene synthase catalyzing an ionization initiated cyclization.

Diterpene synthases are present in plants and other organisms and use substrates such as GGPP but they have different product profiles. Genes and cDNAs encoding diterpene synthases have been cloned and the corresponding recombinant enzymes characterized.

Enzymes that catalyze a specific or preferential cleavage or removal of diphosphate groups from terpene diphosphate intermediates, in particular from cyclic terpene diphosphate intermediates, like the diterpenes copalyl diphosphate (CPP) or labdendiol diphosphate (LPP) have only recently be described in an earlier European patent application. (EP application number 18182783.3). By said enzymes the number or carbon atoms of the terpene diphosphate remains unchanged.

There is, however, the need terpene-derived compounds which may be considered as degradation products of terpene precursors, such as non-cyclic or cyclic sesquiterpenes or diterpenes, which in turn may the be further converted chemically and/or enzymatically into end product, to be applied for example as perfumery ingredients.

The problem to be solved by the present invention is to provide polypeptides which show the enzymatic terpene degrading activity or polypeptides which convert such terpenes into degradable derivatives.

Another problem to be solved by the present invention is the establishing of novel fully biocatalytic degradation pathway for generating defined terpene degradation products.

SUMMARY

The above-mentioned problem could surprisingly be solved by providing a new class of polypeptides having enal-cleaving activity which allow for the first time the specific shortening of carbonyl-functionalized terpene compounds by 2 carbon atoms and respective bio catalytic processes. For example, the novel class of enzymes allows the conversion of the labdane-type compound copalal, which comprises a diterpene carbon skeleton and carries a terminal aldehyde group to the respective dinor-labdane compound manooloxy shortened by 2 carbon atoms, i.e. retaining a carbon skeleton composed of 18 carbon atoms.

The above-mentioned problem in an alternative approach could also surprisingly be solved by providing a new class of polypeptides having Baeyer-Villiger Monooxygenase (BVMO) activity which allow the specific oxidiation of terpene compounds to esters (Baeyer-Villiger oxygenation) and respective biocatalytic processes. For example, the novel class of BVMOs allows the conversion of the labdane-type compound copalal, which comprises a diterpene carbon skeleton and carries a terminal aldehyde group to the respective norlabdane formate ester. By said Baeyer-Villiger oxygenation the labdane compound may be easily converted to the respective norlabdane through the action of a polypeptide having esterase activity. This step results consequently in a shortening by one carbon atom. In case the terminal aldehyde group is replaced by a terminal keto group a shortening in the same manner but now by more than one carbonate is possible. Repetition of the combination of BVMO-catalysed oxygenation step and esterase-catalyzed cleavage step, allows the stepwise shortening of the hydrocarbon chain of the terpene molecule.

Combinations of degradation steps catalyzed by the above enal-cleaving enzymes and BVMO enzymes allow the construction of completely new biochemical degradation pathways applicable a greater variety of carbonyl functionalized chemical compounds, in particular cyclic or non-cyclic terpenes or terpenoids.

Said biocatalytic steps may be coupled to several other preceding (upstream) or successive (downstream) enzymatic steps and allow the provision of a biocatalytic multistep process for the fully enzymatic synthesis of numerous valuable complex terpene molecules from their respective precursors.

The subsequent scheme illustrates two particular embodiments of two alternative pathways ("Enal cleaving polypeptide pathway" and "BMVO pathway)" of the present invention allowing the degradation of the labdane aldehyde copalal to manooloxy, which pathways are explained in more detail in the subsequent sections of the present specification. The scheme also illustrates the degradation of manooloxy to gamma-ambrol by applying a further BMVO-based degradation step.

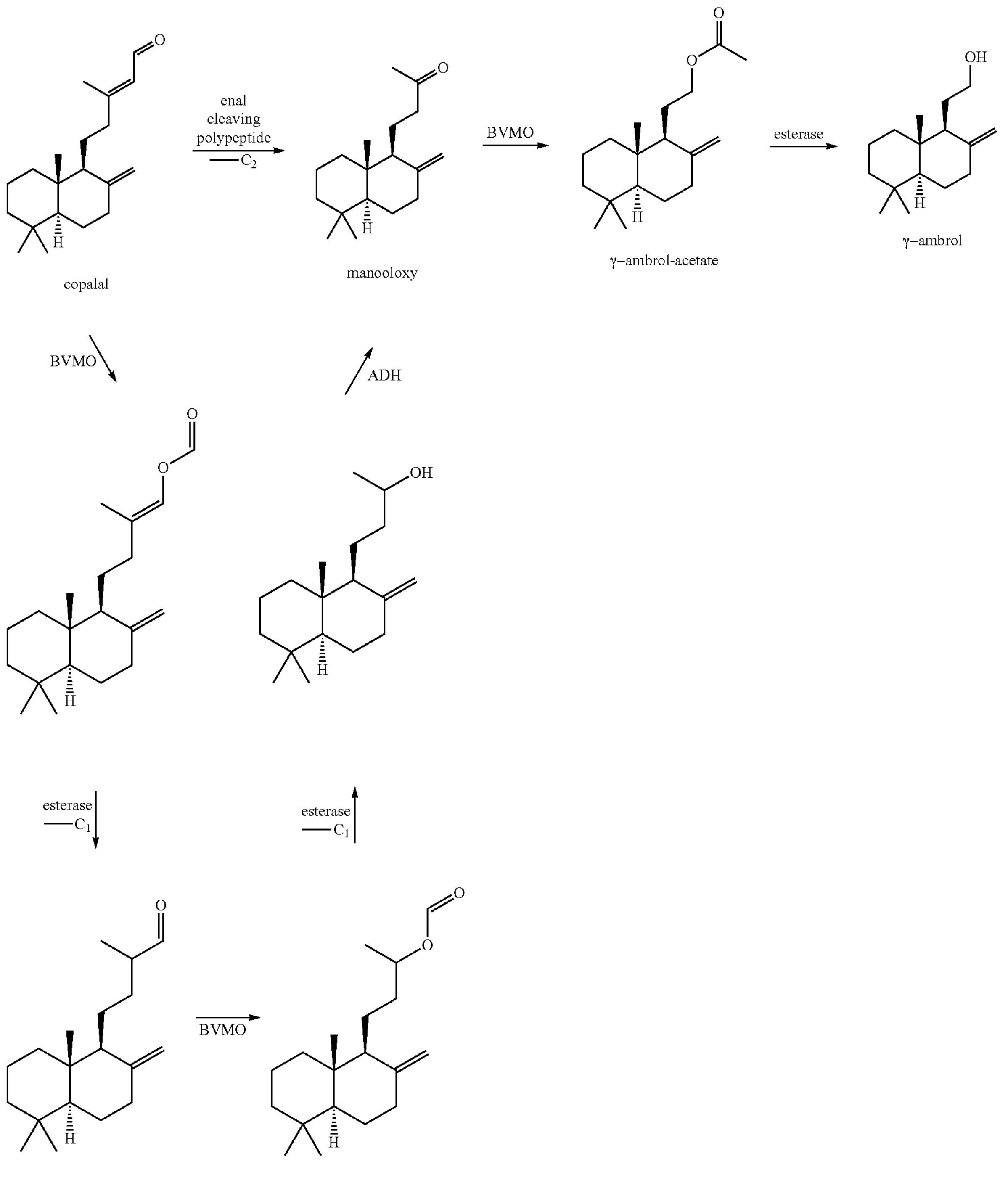

In full analogy to said exemplified reaction sequences this basic biosynthetic strategy my be applied to any other isomer of copalol or to any other labdane-type aldehyde in order to provide structurally related isomers of manooloxy, gamma-ambryl acetate or gamma-ambrol.

It also may be applied to structurally different monocyclic or non-cyclic carbonyl compounds as herein below specified in more detail.

ABBREVIATIONS USED

Figure 1:
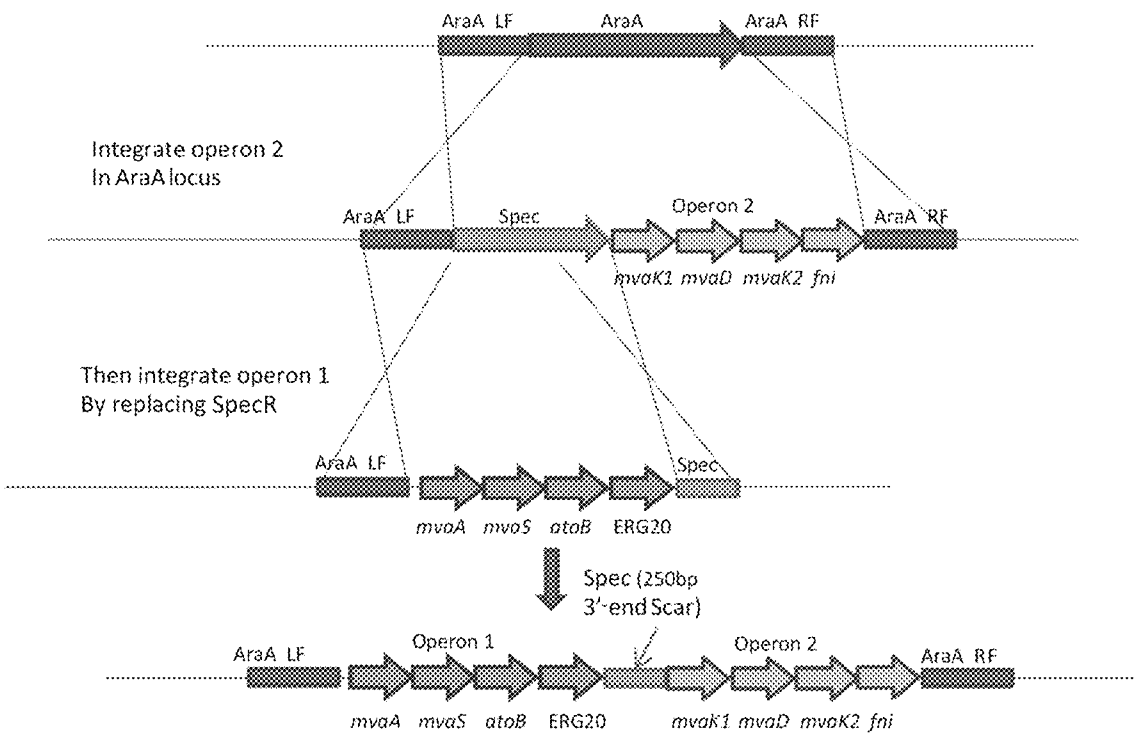
FIG. 1. Schematic representation of the chromosomal integration of the genes encoding for mevalonate pathway enzymes and organization of the two synthetic gene operons. mvaK1, a gene encoding a mevalonate kinase from *S. pneumoniae*; mvaD, a gene encoding a phosphomevalonate decarboxylase from *S. pneumoniae*; mvaK2, a gene encoding a phosphomevalonate kinase from *S. pneumoniae*; fni a gene encoding an isopentenyl diphosphate isomerase from *S. pneumoniae*; mvaA, a gene encoding an HMG-CoA synthase from *S. aureus*; mvaS a genes encoding an HMG-CoA reductase from *S. aureus*; atoB a gene encoding an acetoacetyl-CoA thiolase from *E. coli*; ERG20, a gene encoding an FPP synthase from *S. cerevisiae.*

ADH alcohol dehydrogenase
BVMO Baeyer-Villiger Monooxygenase
bp base pair
kb kilo base
CPP copalyl diphosphate
CPS copalyl diphosphate synthase
DNA deoxyribonucleic acid
cDNA complementary DNA
DMAPP dimethylallyl diphosphate
DTT dithiothreitol
FMO Flavin Monooxygenase
FPP farnesyl diphosphate
GPP geranyldiphosphate
GGPP geranylgeranyl diphosphate
GGPS geranylgeranyl diphosphate synthase
GC gas chromatograph
IPP isopentenyl diphosphate
LPP labdendiol diphosphate
LPS labdendiol diphosphate synthase
MS mass spectrometer/mass spectrometry
MVA mevalonic acid
PP diphosphate, pyrophosphate
PCR polymerase chain reaction
RNA ribonucleic acid
mRNA messenger ribonucleic acid
miRNA micro RNA
siRNA small interfering RNA
rRNA ribosomal RNA
tRNA transfer RNA
TPP terpenyl diphosphate

DEFINITIONS a) General Terms:

For the descriptions herein and the appended claims, the use of "or" means "and/or" unless stated otherwise. Similarly, "comprise", "comprises", "comprising", "include" "includes", and "including" are interchangeable and not intended to be limiting.

It is to be further understood that where descriptions of various embodiments use the term "comprising," those skilled in the art would understand that in some specific instances, an embodiment can be alternatively described using language "consisting essentially of" or "consisting of".

The terms "purified", "substantially purified", and "isolated" as used herein refer to the state of being free of other, dissimilar compounds with which a compound of the invention is normally associated in its natural state, so that the "purified", "substantially purified", and "isolated" subject comprises at least 0.5%, 1%, 5%, 10%, or 20%, or at least 50% or 75% of the mass, by weight, of a given sample. In one embodiment, these terms refer to the compound of the invention comprising at least 95, 96, 97, 98, 99 or 100%, of the mass, by weight, of a given sample. As used herein, the terms "purified," "substantially purified," and "isolated" when referring to a nucleic acid or protein, or nucleic acids or proteins, also refers to a state of purification or concentration different than that which occurs naturally, for example in an prokaryotic or eukaryotic environment, like, for example in a bacterial or fungal cell, or in the mammalian organism, especially human body. Any degree of purification or concentration greater than that which occurs naturally, including (1) the purification from other associated structures or compounds or (2) the association with structures or compounds to which it is not normally associated in said prokaryotic or eukaryotic environment, are within the meaning of "isolated". The nucleic acid or protein or classes of nucleic acids or proteins, described herein, may be isolated, or otherwise associated with structures or compounds to which they are not normally associated in nature, according to a variety of methods and processes known to those of skill in the art.

The term "about" indicates a potential variation of ±25% of the stated value, in particular ±15%, ±10%, more particularly ±5%, ±2% or ±1%.

The term "substantially" describes a range of values of from about 80 to 100%, such as, for example, 85-99.9%, in particular 90 to 99.9%, more particularly 95 to 99.9%, or 98 to 99.9% and especially 99 to 99.9%.

"Predominantly" refers to a proportion in the range of above 50%, as for example in the range of 51 to 100%, particularly in the range of 75 to 99.9%, more particularly 85 to 98.5%, like 95 to 99%.

A "main product" in the context of the present invention designates a single compound or a group of at least 2 compounds, like 2, 3, 4, 5 or more, particularly 2 or 3 compounds, which single compound or group of compounds is "predominantly" prepared by a reaction as described herein, and is contained in said reaction in a predominant proportion based on the total amount of the constituents of the product formed by said reaction. Said proportion may be a molar proportion, a weight proportion or, preferably based on chromatographic analytics, an area proportion calculated from the corresponding chromatogram of the reaction products.

A "side product" in the context of the present invention designates a single compound or a group of at least 2 compounds, like 2, 3, 4, 5 or more, particularly 2 or 3 compounds, which single compound or group of compounds is not "predominantly" prepared by a reaction as described herein.

Because of the reversibility of enzymatic reactions, the present invention relates, unless otherwise stated, to the enzymatic or biocatalytic reactions described herein in both directions of reaction.

"Functional mutants" of herein described polypeptides include the "functional equivalents" of such polypeptides as defined below.

The term "stereoisomers" includes conformational isomers and in particular configuration isomers.

Included in general are, according to the invention, all "stereoisomeric forms" of the compounds described herein, such as "constitutional isomers" and "stereoisomers".

"Stereoisomeric forms" encompass in particular, "stereoisomers" and mixtures thereof, e.g. configuration isomers (optical isomers), such as enantiomers, or geometric isomers (diastereomers), such as E- and Z-isomers, and combinations thereof. If one or more asymmetric centers are present in one molecule, the invention encompasses all combinations of different conformations of these asymmetry centers, e.g. enantiomeric pairs.

"Stereoselectivity" describes the ability to produce a particular stereoisomer of a compound in a stereoisomerically pure form or to specifically convert a particular stereoisomer in an enzyme catalyzed method as described herein out of a plurality of stereoisomers. More specifically, this means that a product of the invention is enriched with respect to a specific stereoisomer, or an educt may be depleted with respect to a particular stereoisomer. This may be quantified via the purity % ee-parameter calculated according to the formula:

$$\% \, ee=[X_A-X_B]/[X_A+X_B]*100,$$

wherein $X_A$ and $X_B$ represent the molar ratio (Molenbruch) of the stereoisomers A and B.

The terms "selectively converting" or "increasing the selectivity" in general means that a particular stereoisomeric form, as for example the E-form, of an unsaturated hydrocarbon, is converted in a higher proportion or amount (compared on a molar basis) than the corresponding other stereoisomeric form, as for example Z-form, either during the entire course of said reaction (i.e. between initiation and termination of the reaction), at a certain point of time of said reaction, or during an "interval" of said reaction. In particular, said selectivity may be observed during an "interval" corresponding 1 to 99%, 2 to 95%, 3 to 90%, 5 to 85%, 10 to 80%, 15 to 75%, 20 to 70%, 25 to 65%, 30 to 60%, or 40 to 50% conversion of the initial amount of the substrate. Said higher proportion or amount may, for example, be expressed in terms of

- a higher maximum yield of an isomer observed during the entire course of the reaction or said interval thereof;
- a higher relative amount of an isomer at a defined % degree of conversion value of the substrate; and/or
- an identical relative amount of an isomer at a higher % degree of conversion value;
- each of which preferably being observed relative to a reference method, said reference method being performed under otherwise identical conditions with known chemical or biochemical means.

Generally also comprised in accordance with the invention are all "isomeric forms" of the compounds described herein, such as constitutional isomers and in particular stereoisomers and mixtures of these, such as, for example, optical isomers or geometric isomers, such as E- and Z-isomers, and combinations of these. If several centers of asymmetry are present in a molecule, then the invention comprises all combinations of different conformations of these centers of asymmetry, such as, for example, pairs of enantiomers, or any mixtures of stereoisomeric forms.

"Yield" and/or the "conversion rate" of a reaction according to the invention is determined over a defined period of, for example, 4, 6, 8, 10, 12, 16, 20, 24, 36 or 48 hours, in which the reaction takes place. In particular, the reaction is carried out under precisely defined conditions, for example at "standard conditions" as herein defined.

The different yield parameters ("Yield" or $Y_{P/S}$; "Specific Productivity Yield"; or Space-Time-Yield (STY)) are well known in the art and are determined as described in the literature.

"Yield" and "$Y_{P/S}$" (each expressed in mass of product produced/mass of material consumed) are herein used as synonyms.

The specific productivity-yield describes the amount of a product that is produced per h and L fermentation broth per g of biomass. The amount of wet cell weight stated as WCW describes the quantity of biologically active microorganism in a biochemical reaction. The value is given as g product per g WCW per h (i.e. g/gWCW$^{-1}$ h$^{-1}$). Alternatively, the quantity of biomass can also be expressed as the amount of dry cell weight stated as DCW. Furthermore, the biomass concentration can be more easily determined by measuring the optical density at 600 nm ($OD_{600}$) and by using an experimentally determined correlation factor for estimating the corresponding wet cell or dry cell weight, respectively.

If the present disclosure refers to features, parameters and ranges thereof of different degree of preference (including general, not explicitly preferred features, parameters and ranges thereof) then, unless otherwise stated, any combination of two or more of such features, parameters and ranges thereof, irrespective of their respective degree of preference, is encompassed by the disclosure of the present description.

b) Biochemical Terms

The term "domain" refers to a set of amino acids or a partial sequence of amino acids residues conserved at specific positions along an alignment of sequences of evolutionarily related proteins. While amino acids at other positions can vary between protein homologues, amino acids that are highly conserved at specific positions of such domain indicate amino acids that are likely essential in the structure, stability or function of a protein. Identified by their high degree of conservation in aligned sequences of a family of protein homologues, they can be used as identifiers to determine if any polypeptide in question belongs to a previously identified polypeptide family.

The term "motif" or consensus sequence" or "signature" refers to a short conserved region in the sequence of evolutionarily related proteins. Motifs are frequently highly conserved parts of domains, but may also include only part of the domain.

A "protein family" is defined as a group of proteins that share a common evolutionary origin reflected by their related functions, similarities in sequence, or similar primary, secondary or tertiary structure. Proteins within protein families are usually homologous and have similar structure of conserved functional domains and motifs.

Specialist databases exist for the identification of domains, for example, SMART (Schultz et al. (1998) Proc. Natl. Acad. Sci. USA 95, 5857-5864; Letunic et al. (2002) Nucleic Acids Res 30, 242-244), InterPro (Mulder et al., (2003) Nucl. Acids. Res. 31, 315-318), Prosite (Bucher and Bairoch (1994), A generalized profile syntax for biomolecular sequences motifs and its function in automatic sequence interpretation. (In) ISMB-94; Proceedings 2nd International Conference on Intelligent Systems for Molecular Biology. Altman R., Brutlag D., Karp P., Lathrop R., Searls D., Eds., pp 53-61, AAAI Press, Menlo Park; Hulo et al., Nucl. Acids. Res. 32:D134-D137, (2004)), or Pfam (Bateman et al., Nucleic Acids Research 30(1): 276-280 (2002)). Domains or motifs may also be identified using routine techniques, such as by sequence alignment.

The term "Pfam" refers to a large collection of protein domains and protein families maintained by the Pfam Consortium and available at several sponsored world wide web sites, such as pfam.xfam.org// (European Molecular Biology Laboratory-European Bioinformatics Institute (EMBL_EBI). The latest release of Pfam is Pfam 32.0 (September 2018), based on the UniProt Reference Proteomes (El-Gebali S. et al, 2019, Nucleic Acids Res. 47, Database issue D427-D432). Pfam domains and families are identified using multiple sequence alignments and hidden Markov models (HMMs). Pfam-A family or domain assignments, are high quality assignments generated by a curated seed alignment using representative members of a protein family and profile hidden Markov models based on the seed alignment (Unless otherwise specified, matches of a queried protein to a Pfam domain or family are Pfam-A matches). All identified sequences belonging to the family are then used to automatically generate a full alignment for the family (Sonnhammer (1998) Nucleic Acids Research 26, 320-322; Bateman (2000) Nucleic Acids Research 26, 263-266; Bateman (2004) Nucleic Acids Research 32, Database Issue, D138-D141; Finn (2006) Nucleic Acids Research Database Issue 34, D247-251; Finn (2010) Nucleic Acids Research Database Issue 38, D211-222). By accessing the Pfam database, for example, using any of the above-reference websites, protein sequences can be queried against the HMMs using HMMER homology search software (e.g., HMMER2, HMMER3, or a higher version, hmmer.janelia.org/). Significant matches that identify a queried protein as being in a pfam family (or as having a particular Pfam domain) are those in which the bit score is greater than or equal to the gathering threshold for the Pfam domain. Expectation values (e-values) can also be used as a criterion for inclusion of a queried protein in a Pfam or for determining whether a queried protein has a particular Pfam domain, where low e-values, much less than 1.0, for example less than 0.1, or less.

The "E-value" (expectation value) is the number of hits that would be expected to have a score equal to or better than this value, by chance alone. This means that a good E-value which gives a confident prediction is much less than 1. E-values around 1 is what is expected by chance. Thus, the lower the E-value, the more specific the search for domains will be. Only positive numbers are allowed. (definition by Pfam))

A "precursor" molecule of a target compound as described herein is converted to said target compound, preferably through the enzymatic action of a suitable polypeptide performing at least one structural change on said precursor molecule. For example a "diphosphate precursor" (as for example a "terpenyl diphosphate precursor") is converted to said target compound (as for example a terpene alcohol) via enzymatic removal of the diphosphate moiety, for example by removal of mono- or diphosphate groups by a phosphatase enzyme. For example a "non-cyclic precursor" (like a non-cyclic terpenyl precursor") may be converted to the cyclic target molecule (like a cyclic terpene compound) through the action of a cyclase or synthase enzyme, irrespective of the particular enzymatic mechanism of such enzyme, in one or more steps.

The term "protein tyrosine phosphatase" represents a group of enzymes that are generally known to remove phosphate groups from phosphorylated tyrosine residues on proteins. A particular subgroup of said family as described herein are enzymes useful to dephosphorylate phosphorylated terpene molecules.

A "terpene synthase" designates a polypeptide which converts a terpene precursor molecule to the respective terpene target molecule, like in particular a processed target terpene alcohol or terpene hydrocarbon. Non-limiting examples of such terpene precursor molecules are for example non-cyclic compounds, selected from farnesyl pyrophosphate (FPP), geranylgeranyl-pyrophosphate (GGPP), or a mixture of isopentenyl pyrophosphate (IPP) and dimethyl allyl pyrophosphate (DMAPP). In case the obtained terpene contains a diphosphate moiety the synthase is designated "terpenyl diphosphate synthase" The terms "terpenyl diphosphate synthase" or "polypeptide having terpenyl diphosphate synthase activity" or "terpenyl diphosphate synthase protein" or "having the ability to produce terpenyl diphosphate" relate to a polypeptide capable of catalyzing the synthesis of a terpenyl diphosphate, in the form of any of its stereoisomers or a mixture thereof, starting from an acyclic terpene pyrophosphate, particularly GPP, FPP or GGPP or IPP together with DMAPP. The terpenyl diphosphate may be the only product or may be part of a mixture of terpenyl phosphates. Said mixture may comprise terpenyl monophosphate and/or a terpene alcohol. The above definition also applies to the group of "bicyclic terpenyl diphosphate synthases", which produce a bicyclic terpenyl diphosphate, like CPP or LPP. As example of such "terpenyl diphosphate synthase" enzymes there may be mentioned copalyl diphosphate synthase (CPS). Copalyl-diphosphate may be the only product or may be part of a mixture of copalyl phosphates. Said mixture may comprise copalyl-monophosphate and/or other terpenyl diphosphate. As another example of such "terpenyl diphosphate synthase" enzymes there may be mentioned and labdendiol diphosphate synthase (LPS). Labdendiol diphosphate may be the only product or may be part of a mixture of labdendiol phosphates. Said mixture may comprise labdendiol monophosphate and/or terpenyl diphosphate.

The terms "terpenyl diphosphate phosphatase" or "polypeptide having terpenyl diphosphate phosphatase activity" or "terpenyl diphosphate phosphatase protein" or "having the ability to produce terpene alcohol" relate to a polypeptide capable of catalyzing the removal (irrespective of a particular enzymatic mechanism) of a diphosphate moiety or monophosphate moieties, to form a dephosphorylated compound, in particular the corresponding alcohol compound of said terpenyl moiety. The terpene alcohol may be present in the product in any of its stereoisomers or as a mixture thereof. The terpene alcohol may be the only product or may be part of a mixture with other terpene compounds, as for example dephosphorylated analogs of the respective (for example non-cyclic) terpenyl diphosphate precursor of said terpenyl diphosphate. The above definition also applies to the group of "bicyclic terpenyl diphosphate phosphatase", which produce a bicyclic terpene alcohol, like copalol or labdendiol.

As example of such "terpenyl diphosphate phosphatase" enzymes there may be mentioned copalyl diphosphate phosphatase (CPP phosphatase). Copalol may be the only product or may be part of a mixture with dephosphorylated precursors, like for example farnesol and/or geranylgeraniol; and/or side products resulting from enzymatic side activities in the reaction mixture, like esters or aldehydes of such alcohols or other cyclic or non-cyclic diterpenes. As another example of such "terpenyl diphosphate phosphatase" enzymes there may be mentioned and labdendiol diphosphate phosphatase (LPP phosphatase). Labdendiol may be the only product or may be part of a mixture with dephosphorylated precursors, like for example farnesol and/or geranylgeraniol; and/or side products resulting from enzymatic side activities in the reaction mixture, like esters or aldehydes of such alcohols or other cyclic or non-cyclic diterpenes.

An "enal-cleaving enzyme" or "enal-cleaving protein" or "enal-cleaving polypeptide" in the context of the present invention designates an "α,β-unsaturated aldehyde carbon-carbon double bond-cleaving enzyme, which also may be called a "α,β-unsaturated aldehyde C═C bond-cleaving enzyme" or α,β-unsaturated aldehyde C═C-cleaving enzyme" or a "enal C═C-cleaving enzyme". The enal-cleaving protein of the invention, based on protein domain organization, may also be described as a member of the 'DUF4334 protein family" and/or as a member of the "GXWXG protein family".

More particularly, an enal cleaving enzyme of the invention has the ability to cleave labdane-type carbonyl compounds, like labdane aldehydes, in particular copalal to the respective dinorlabdane carbonyl compound. "Baeyer-Villiger monooxygenases" (BVMOs) are flavoenzymes and belong to the class of refers to a polypeptide having oxidoreductase activity (EC 1.14.13.X). They catalyze the oxidation of linear, cyclic (aromatic or non-aromatic) aldehydes or ketones to the corresponding esters or lactones, highly similar to the chemical Baeyer-Villiger oxidation. During the enzymatic oxidation one atom of molecular oxygen is incorporated into a carbon-carbon bond of a non-activated carbonyl compound. The BVMOs require NADPH or NADH as cofactor or accept both. They also require molecular oxygen as co-substrate. More particularly, a BVMO of the invention has the ability to oxidize terpene-derived aldehydes or ketones, like for example labdane-type carbonyl compounds, like labdane aldehydes, in particular copalal and/or manooloxy to the respective carbonyl ester An "esterase" refers to a polypeptide having hydrolase activity that splits esters into an acid and an alcohol in a chemical reaction with water (hydrolysis). Esterases in the context of the present invention are selected from the class of carboxylic ester hydrolases (EC 3.1.1.-), which splits off acyl groups, like acetyl or formyl groups, from the respective etser substrate. More particularly, an esterase of the invention has the ability to cleave labdane-type ester compounds, like gamma-ambryl-acetate, to form the respective labdane-type alcohol, like gamma-ambrol.

An "alcohol dehydrogenase" (ADH) in the context of the present invention refers to a polypeptide having the ability to oxidize an alcohol to the corresponding aldehyde in the presence of $NAD^+$ or $NADP^+$ as cofactor. Such enzymes are members of the E.C. families 1.1.1.1 ($NAD^+$ dependent) or 1.1.1.2 ($NADP^+$ dependent). More particularly, an ADH of the invention has the ability to oxidize labdane-type alkohols to the respective labdane-type carbonyl compounds (aldehydes or ketones), like copalol to copalal and/or labdendiol to the respective aldehyde or other labdane-type derivatives of copalol, labdendiol, for example the respective nor- or dinor-labdane derivatives of copalol or labdendiol. ADHs as used herein may either be endogenously present in the respective biocatalytic process or may be exogenous.

"Enal-cleaving activity" is determined under "standard conditions" as described herein below: It can be determined using recombinant enal-cleaving polypeptide expressing host cells, disrupted enal-cleaving polypeptide expressing cells, fractions of these or enriched or purified enal-cleaving polypeptide, in a culture medium or reaction medium, preferably buffered, having a pH in the range of 6 to 11, preferably 7 to 9, at a temperature in the range of about 20 to 45° C., like about 25 to 40° C., preferably 25 to 32° C. and in the presence of a reference substrate, here in particular copalal, either added at an initial concentration in the range of 1 to 100 μM mg/ml, preferably 5 to 50 μM, in particular 30 to 40 μM, or endogenously produced by the host cell. The conversion reaction to form the respective cleavage product, like manooloxy is conducted from 10 min to 5 h, preferably about 1 to 2 h. The cleavage product may then be determined in conventional matter, for example after extraction with an organic solvent, like ethyl acetate.

"BVMO activity" is determined under "standard conditions" as described herein below: It can be determined using recombinant BVMO expressing host cells, disrupted BVMO expressing cells, fractions of these or enriched or purified BVMO enzyme, in a culture medium or reaction medium, preferably buffered, having a pH in the range of 6 to 11, preferably 7 to 9, at a temperature in the range of about 20 to 45° C., like about 25 to 40° C., preferably 25 to 32° C. and in the presence of a reference substrate, here in particular copalal and/or manooloxy, either added at an initial concentration in the range of 1 to 100 μM mg/ml, preferably 5 to 50 μM, in particular 30 to 40 μM, or endogenously produced by the host cell and in the presence of molecular oxygen. For in-vitro assays a cofactor selected from NADH and NADPH has to be added in a suitable easily to be determined concentration range of The conversion reaction to form the respective cleavage product, like the formyl esters 1a and/or 1b in the case of copalal or gamma-ambryl acetate in the case of manooloxy is conducted from 10 min to 5 h, preferably about 1 to 2 h. The oxidation product may then be determined in conventional matter, for example after extraction with an organic solvent, like ethyl acetate.

"Terpenyl diphosphate synthase activity" (like CPS or LPS activity) is determined under "standard conditions" as described herein below: They can be determined using recombinant terpenyl diphosphate synthase expressing host cells, disrupted terpenyl diphosphate synthase expressing cells, fractions of these or enriched or purified terpenyl diphosphate synthase enzyme, in a culture medium or reaction medium, preferably buffered, having a pH in the range of 6 to 11, preferably 7 to 9, at a temperature in the range of about 20 to 45° C., like about 25 to 40° C., preferably 25 to 32° C. and in the presence of a reference substrate, here in particular GGPP, either added at an initial concentration in the range of 1 to 100 μM mg/ml, preferably 5 to 50 μM, in particular 30 to 40 μM, or endogenously produced by the host cell. The conversion reaction to form a terpenyl diphosphate is conducted from 10 min to 5 h, preferably about 1 to 2 h. If no endogenous phosphatase is present, one or more exogenous phosphatases, for example an alkaline phosphatase, are added to the reaction mixture to convert the terpenyl diphosphate as formed by the synthase to the respective terpene alcohol. The terpene alcohol may then be determined in conventional matter, for example after extraction with an organic solvent, like ethyl acetate.

"Terpenyl diphosphate phosphatase activity" (like CPP or LPP phosphatase activity) is determined under "standard conditions" as described herein below: They can be determined using recombinant terpenyl diphosphate phosphatase expressing host cells, disrupted terpenyl diphosphate phosphatase expressing cells, fractions of these, or enriched or purified terpenyl diphosphate phosphatase enzyme, in a culture medium or reaction medium, preferably buffered, having a pH in the range of 6 to 11, preferably 7 to 9, at a temperature in the range of about 20 to 45° C., like about 25 to 40° C., preferably 25 to 32° C. and in the presence of a reference substrate, here for example CPP or LPP, either added at an initial concentration in the range of 1 to 100 μM mg/ml, preferably 5 to 50 μM, in particular 30 to 40 μM, or endogenously produced by the host cell. The conversion reaction to form a terpenyl diphosphate is conducted from 10 min to 5 h, preferably about 1 to 2 h. The terpene alcohol may then be determined in conventional matter, for example after extraction with an organic solvent, like ethyl acetate.

Particular examples of suitable standard conditions for each of the above-described enzyme activates may be taken from the Experimental Part below.

The terms "biological function," "function", "biological activity" or "activity" of a terpenyl synthase refer to the ability of a terpenyl diphosphate synthase as described herein to catalyze the formation of at least one terpenyl diphosphate from the corresponding precursor terpene.

The terms "biological function," "function", "biological activity" or "activity" of a terpenyl diphosphate phosphatase refer to the ability of the terpenyl diphosphate phosphatase as described herein to catalyze the removal of a diphosphate group from said terpenyl compound to form the corresponding terpene alcohol.

The "mevalonate pathway" also known as the "isoprenoid pathway" or "HMG-CoA reductase pathway" is an essential metabolic pathway present in eukaryotes, archaea, and some bacteria. The mevalonate pathway begins with acetyl-CoA and produces two five-carbon building blocks called isopentenyl pyrophosphate (IPP) and dimethyl allyl pyrophosphate (DMAPP). Key enzymes are acetoacetyl-CoA thiolase (atoB), HMG-CoA synthase (mvaS), HMG-CoA reductase (mvaA), mevalonate kinase (MvaK1), phosphomevalonate kinase (MvaK2), a mevalonate diphosphate decarboxylase (MvaD), and an isopentenyl diphosphate isomerase (idi). Combining the mevalonate pathway with enzyme activity to generate the terpene precursors GPP, FPP or GGPP, like in particular FPP synthase (ERG20), allows the recombinant cellular production of terpenes.

As used herein, the term "host cell" or "transformed cell" refers to a cell (or organism) altered to harbor at least one nucleic acid molecule, for instance, a recombinant gene encoding a desired protein or nucleic acid sequence which upon transcription yields at least one functional polypeptide of the present invention, in particular a terpenyl diphosphate synthase protein or terpenyl diphosphate phosphatase enzyme as defined herein above. The host cell is particularly a bacterial cell, a fungal cell or a plant cell or plants. The host cell may contain a recombinant gene or several genes, as for example organized as an operon, which has been integrated into the nuclear or organelle genomes of the host cell. Alternatively, the host may contain the recombinant gene extra-chromosomally.

The term "organism" refers to any non-human multicellular or unicellular organism such as a plant, or a microorganism. Particularly, a micro-organism is a bacterium, a yeast, an algae or a fungus.

The term "plant" is used interchangeably to include plant cells including plant protoplasts, plant tissues, plant cell tissue cultures giving rise to regenerated plants, or parts of plants, or plant organs such as roots, stems, leaves, flowers, pollen, ovules, embryos, fruits and the like. Any plant can be used to carry out the methods of an embodiment herein.

A particular organism or cell is meant to be "capable of producing FPP" when it produces FPP naturally or when it does not produce FPP naturally but is transformed to produce FPP with a nucleic acid as described herein., Organisms or cells transformed to produce a higher amount of FPP than the naturally occurring organism or cell are also encompassed by the "organisms or cells capable of producing FPP".

A particular organism or cell is meant to be "capable of producing GGPP" when it produces GGPP naturally or when it does not produce GGPP naturally but is transformed to produce GGPP with a nucleic acid as described herein. Organisms or cells transformed to produce a higher amount of GGPP than the naturally occurring organism or cell are also encompassed by the "organisms or cells capable of producing GGPP".

A particular organism or cell is meant to be "capable of producing terpenyl diphosphate" when it produces a terpenyl diphosphate as defined herein naturally or when it does not produce said diphosphate naturally but is transformed to produce said diphosphate with a nucleic acid as described herein. Organisms or cells transformed to produce a higher amount of terpenyl diphosphate than the naturally occurring organism or cell are also encompassed by the "organisms or cells capable of producing a terpenyl diphosphate".

A particular organism or cell is meant to be "capable of producing terpene alcohol" when it produces a terpene alcohol as defined herein naturally or when it does not produce said alcohol naturally but is transformed to produce said alcohol with a nucleic acid as described herein. Organisms or cells transformed to produce a higher amount of a terpene alcohol than the naturally occurring organism or cell are also encompassed by the "organisms or cells capable of producing a terpene alcohol". The same applies to a particular organism "capable of producing labdane-type alcohol".

A particular organism or cell is meant to be "capable of producing an ester" when it produces an ester as defined herein naturally or when it does not produce said ester naturally but is transformed to produce said ester with a nucleic acid as described herein. Organisms or cells transformed to produce a higher amount of ester than the naturally occurring organism or cell are also encompassed by the "organisms or cells capable of producing an ester".

A particular organism or cell is meant to be "capable of producing a target product" when it produces a target product as defined herein (for example the esters, alcohol, or carbonyl compounds or more particularly the labdane type compounds) naturally or when it does not produce said target product naturally but is transformed to produce said target product with a nucleic acid as described herein. Organisms or cells transformed to produce a higher amount of target product than the naturally occurring organism or cell are also encompassed by the "organisms or cells capable of producing a target product".

The term "fermentative production" or "fermentation" refers to the ability of a microorganism (assisted by enzyme activity contained in or generated by said microorganism) to produce a chemical compound in cell culture utilizing at least one carbon source added to the incubation.

The term "fermentation broth" is understood to mean a liquid, particularly aqueous or aqueous/organic solution which is based on a fermentative process and has not been worked up or has been worked up, for example, as described herein.

An "enzymatically catalyzed" or "biocatalytic" method means that said method is performed under the catalytic action of an enzyme, including enzyme mutants, as herein defined. Thus the method can either be performed in the presence of said enzyme in isolated (purified, enriched) or crude form or in the presence of a cellular system, in particular, natural or recombinant microbial cells containing said enzyme in active form, and having the ability to catalyze the conversion reaction as disclosed herein.

c) Chemical Terms:

The term "alpha, beta-unsaturated carbonyl" compound describes organic molecules containing an aldehyde or keto group of the general formula $R^aR^b$ C═C($R^c$)—C═O, wherein the C═C bond may be of any stereoisomeric configuration and wherein residues $R^a$, $R^b$ and $R^c$ may be identical or different and may have the meanings as specified below for particular alpha, beta unsaturated carbonyl compounds.

A "labdane" compound in the context of the present invention will show the following basic structure of its carbon skeleton consisting of 20 carbon atoms. The depicted numbering of carbon atoms will be applied in order to further define certain positions within said carbon skeleton.

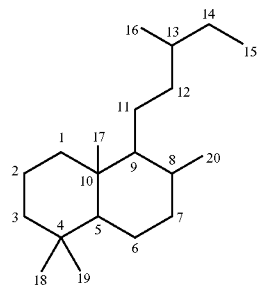

The term "labdane" encompasses any compounds of this basic $C_{20}$-structure, in any stereoisomeric form and encompassing any variant of this structure containing one or more unsaturated C—C bonds, in particular one or more C═C bonds, at any position, within the carbocyclic ring and/or the side chains. Also encompassed are variants thereof containing one or more substituents, as for example substituents selected from the group of —OH. ═O, —O—CO_R, wherein R may be straight chain or branched alkyl, in particular lower alkyl, more particularly $C_1$-$C_4$ aklyl, like methyl, ethyl, n- or i-propyl, or n-, i- or t-butyl; and —COOH at any of the indicated primary, secondary or tertiary C atoms.

A "labdane derived" compound of such "labdane" encompasses chemical compounds wherein the basic $C_{20}$-carbon skeleton is modified by deleting one or more carbon atoms. As examples there may be mentioned:

norlabdane ($C_{19}$-sceleton), dinorlabdane ($C_{18}$-sceleton), trinorlabdane ($C_{17}$-sceleton), and tetranorlabdane (C16-sceleton). The position of the deleted carbon atom is indicated by stating the carbon number. For example, in a norlabdane, wherein the carbonate in position 15 is missing is designated "15-norlabdane".

A "labdane derived" compound of such "labdane" also encompasses chemical compounds wherein the basic $C_{20}$-carbon skeleton is modified by inserting a hereoatom between two C-atoms of the labdane sceleoton. For example, insertion of an ether bridge between positions 14 and 15 converts the labdane to a norlabdane and particularly to a norlabdane ester.

Non-limiting examples of substituted labdanes or substituted labdane derived structures are given below:

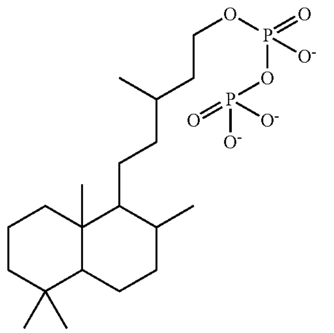

labdan-15-yl diphosphate
(labdane diphosphate)

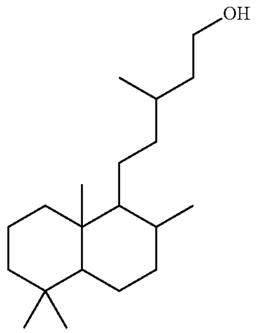

labdan-15-ol
(labdane alcohol)

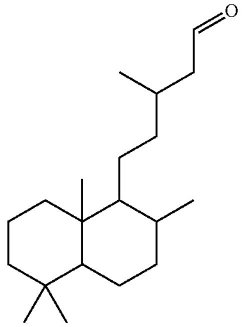

labdan-15-al
(labdane aldehyde)

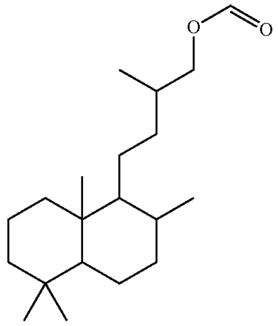

15-norlabdan-14-yl formate
(norlabdane formate)

-continued

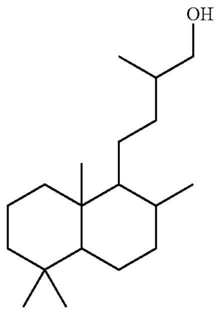

15-norlabdan-14-ol
(norlabdane alcohol)

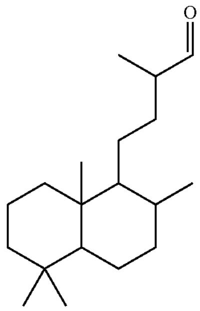

15-norlabdan-14-al
(norlabdane aldehyde)

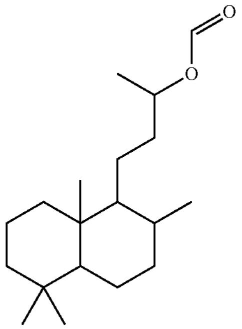

14,15-dinorlabdan-13-yl formate
(dinorlabdane formate)

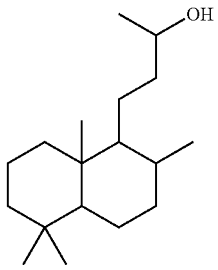

14,15-dinorlabdan-13-ol
(dinorlabdane alcohol)

-continued

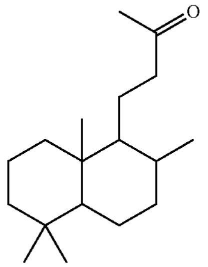

14,15-dinorlabdan-13-al
(dinorlabdane ketone)

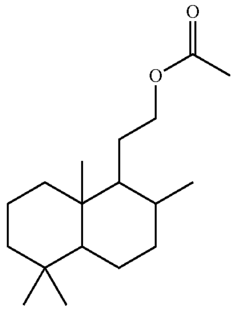

13,14,15,16-tetranorlabdan-12-yl acetate
(tetranorlabdane acetate)

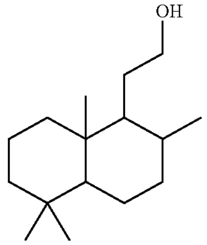

13,14,15,16-tetranorlabdan-12-ol
(tetranorlabdane alcohol)

"Diphosphate" and "pyrophosphate" as used herein are synonyms.

"Terpenes" are a large and diverse class of organic compounds, produced by a variety of plants, particularly conifers, and by some insects. Terpenes are hydrocarbons. Although sometimes used interchangeably with "terpenes", "terpenoids" or "isoprenoids" are modified terpenes as they contain additional functional groups, usually oxygen-containing.

"Terpenoids" ("isoprenoids") are a large and diverse class of naturally occurring organic chemicals derived from terpenes. Although sometimes used interchangeably with the term "terpenes", "terpenoids" contain additional functional groups, usually 0-containing groups, like for example hydroxyl, carbonyl or carboxyl groups. Most are multicyclic structures with oxygen-containing functional groups. Unless stated otherwise, in the context of the present description the term "terpene" and the term "terpenoid" may be used interchangeably.

Terpenes (and terpenoids) may be classified by the number of isoprene units in the molecule; a prefix in the name indicates the number of terpene units needed to assemble the molecule. Hemiterpenes consist of a single isoprene unit. Monoterpenes consist of two isoprene units and have the molecular formula $C_{10}H_{16}$. Sesquiterpenes consist of three isoprene units and have the molecular formula $C_{15}H_{24}$. Diterpenes are composed of four isoprene units and have the molecular formula $C_{20}H_{32}$.

"Terpenyl" designates noncyclic and cyclic chemical hydrocarbyl residues which are derived from the $C_5$ building block isoprene and in particular contain one or more such building blocks.

"Cyclic terpene"or cyclic terpenyl" or "cyclic diterpene" or cyclic diterpenyl" relates to a terpene compound or terpenyl residue which comprises in its structure at least on, as for example 1, 2, 3, 4 or 5 carbocyclic condensed and/or non-condensed rings, preferably two carbocyclic condensed rings.

"Bicyclic terpene"or bicyclic terpenyl" or "bicyclic diterpene" or bicyclic diterpenyl" relates to a terpene compound or terpenyl residue which comprises in its structure two carbocyclic rings, preferably two carbocyclic condensed rings.

"Derivatives of terpenes" or "derivatives of terpenoids" in the context of the present invention in particular refer to such chemical compounds which are obtained from a terpene or terpenoid by chemical and/or enzymatic modification. More particularly, such derivatives encompass "hydrocarbon chain-degraded" derivatives.

A "hydrocarbon chain-degraded" terpene or terpenoid differs from the non-degraded precursor by a reduced number of carbon items of the precursor's carbon skeleton.

A "hydrocarbyl" residue is a chemical group which essentially is composed of carbon and hydrogen atoms and may be a non-cyclic, linear or branched, saturated or unsaturated moiety, or a cyclic saturated or unsaturated moiety, aromatic or non-aromatic moiety. A hydrocarbyl residue comprises 1 to 30, 1 to 25, 1 to 20, 1 to 15 or 1 to 10 or 1 to 5 carbon atoms in the case of a non-cyclic structure. It comprises 4 to 30, 4 to 25, 4 to 20, 4 to 15, 4 to 10 or in particular 4, 5, 6 or 7 carbon atoms in the case of a cyclic structure.

Said hydrocarbyl residues may be non-substituted or may carry at least one, like 1 to 5, preferably 0, 1 or 2 substituents.

Particular examples of such hydrocarbyl residues are noncyclic linear or branched alkyl or alkenyl residues as defined below; or mono- or polycyclic, in particular mono- or bicyclic, saturated or unsaturated, nonaromatic moieties, as for example found in cyclic (for example bicyclic) or noncyclic terpene type compound, and labdane type compounds as defined herein.

An "alkyl" residue represents linear or branched, saturated hydrocarbon residues. It comprises 1 to 30, 1 to 25, 1 to 20, 1 to 15 or 1 to 10 or 1 to 7, 1 to 6, 1 to 5, or 1 to 4 carbon atoms.

An "alkenyl" residue represents linear or branched, mono- or polyunsaturated hydrocarbon residues. It comprises 2 to 30, 2 to 25, 2 to 20, 2 to 15 or 2 to 10 or 2 to 7, 2 to 6, 2 to 5, or 2 to 4 carbon atoms. I may have up to 10, like 1, 2, 3, 4 or 5 C═C double bonds.

The term "lower alkyl" or "short chain alkyl" represents saturated, straight-chain or branched hydrocarbon radicals having 1 to 4, 1 to 5, 1 to 6, or 1 to 7, in particular 1 to 4 carbon atoms. As examples there may be mentioned: methyl, ethyl, n-propyl, 1-methylethyl, n-butyl, 1-methylpropyl, 2-methylpropyl, 1,1-dimethylethyl, n-pentyl, 1-methylbutyl, 2-methylbutyl, 3-methylbutyl, 2,2-dimethylpropyl, 1-ethylpropyl, n-hexyl, 1,1-dimethylpropyl, 1,2-dimethylpropyl, 1-methylpentyl, 2-methylpentyl, 3-methylpentyl, 4-methylpentyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-ethylbutyl, 2-ethylbutyl, 1,1,2-trimethylpropyl, 1,2, 2-trimethylpropyl, 1-ethyl-1-methylpropyl and 1-ethyl-2-methylpropyl; and also n-heptyl, and the singly or multiply branched analogs thereof.

"Long-chain alkyl" represents, for example, saturated straight-chain or branched hydrocarbyl radicals having 8 to 30, for example 8 to 20 or 8 to 15, carbon atoms, such as octyl, nonyl, decyl, undecyl, dodecyl, tridecyl, tetradecyl, pentadecyl, hexadecyl, heptadecyl, octadecyl, nonadecyl, eicosyl, hencosyl, docosyl, tricosyl, tetracosyl, pentacosyl, hexacosyl, heptacosyl, octacosyl, nonacosyl, squalyl, constitutional isomers, especially singly or multiply branched isomers thereof.

"Long-chain alkenyl" represents the mono- or polyunsaturated analogues of the above mentioned "long-chain alkyl" groups, "Short chain alkenyl" (or "lower alkenyl") represents mono- or polyunsaturated, especially monounsaturated, straight-chain or branched hydrocarbon radicals having 2 to 4, 2 to 6, or 2 to 7 carbon atoms and one double bond in any position, e.g. $C_2$-$C_6$-alkenyl such as ethenyl, 1-propenyl, 2-propenyl, 1-methylethenyl, 1-butenyl, 2-butenyl, 3-butenyl, 1-methyl-1-propenyl, 2-methyl-1-propenyl, 1-methyl-2-propenyl, 2-methyl-2-propenyl, 1-pentenyl, 2-pentenyl, 3-pentenyl, 4-pentenyl, 1-methyl-1-butenyl, 2-methyl-1-butenyl, 3-methyl-1-butenyl, 1-methyl-2-butenyl, 2-methyl-2-butenyl, 3-methyl-2-butenyl, 1-methyl-3-butenyl, 2-methyl-3-butenyl, 3-methyl-3-butenyl, 1,1-dimethyl-2-propenyl, 1,2-dimethyl-1-propenyl, 1,2-dimethyl-2-propenyl, 1-ethyl-1-propenyl, 1-ethyl-2-propenyl, 1-hexenyl, 2-hexenyl, 3-hexenyl, 4-hexenyl, 5-hexenyl, 1-methyl-1-pentenyl, 2-methyl-1-pentenyl, 3-methyl-1-pentenyl, 4-methyl-1-pentenyl, 1-methyl-2-pentenyl, 2-methyl-2-pentenyl, 3-methyl-2-pentenyl, 4-methyl-2-pentenyl, 1-methyl-3-pentenyl, 2-methyl-3-pentenyl, 3-methyl-3-pentenyl, 4-methyl-3-pentenyl, 1-methyl-4-pentenyl, 2-methyl-4-pentenyl, 3-methyl-4-pentenyl, 4-methyl-4-pentenyl, 1,1-dimethyl-2-butenyl, 1,1-dimethyl-3-butenyl, 1,2-dimethyl-1-butenyl, 1,2-dimethyl-2-butenyl, 1,2-dimethyl-3-butenyl, 1,3-dimethyl-1-butenyl, 1,3-dimethyl-2-butenyl, 1,3-dimethyl-3-butenyl, 2,2-dimethyl-3-butenyl, 2,3-dimethyl-1-butenyl, 2,3-dimethyl-2-butenyl, 2,3-dimethyl-3-butenyl, 3,3-dimethyl-1-butenyl, 3,3-dimethyl-2-butenyl, 1-ethyl-1-butenyl, 1-ethyl-2-butenyl, 1-ethyl-3-butenyl, 2-ethyl-1-butenyl, 2-ethyl-2-butenyl, 2-ethyl-3-butenyl, 1,1,2-trimethyl-2-propenyl, 1-ethyl-1-methyl-2-propenyl, 1-ethyl-2-methyl-1-propenyl and 1-ethyl-2-methyl-2-propenyl.

"Alkylene" represents straight-chain or singly or multiply branched hydrocarbon bridging groups having 1 to 10 carbon atoms, for example $C_1$-$C_7$-alkylene groups selected from $—CH_2—$, $—(CH_2)_2—$, $—(CH_2)_3—$, $—(CH_2)_4—$, $—(CH_2)_2—CH(CH_3)—$, $—CH_2—CH(CH_3)—CH_2—$, $(CH_2)_4—$, $—(CH_2)_5—$, $—(CH_2)_6$, $—(CH_2)_7—$, $—CH(CH_3)—CH_2—CH_2—CH(CH_3)—$ or $—CH(CH_3)—CH_2—CH_2—CH_2—CH(CH_3)—$, and in particular $C_1$-$C_4$-alkylene groups selected from $—CH_2—$, $—(CH_2)_2—$, $—(CH_2)_3—$, $—(CH_2)_4—$, $—(CH_2)_2—CH(CH_3)—$, $—CH_2—CH(CH_3)—CH_2—$.

An "alkylidene" group represents a straight chain or branched hydrocarbon substituent linked via a double bond to the body of the molecule. It comprises 1 to 6 carbon atoms. As examples of such "$C_1$-$C_6$-alkylidenes" there may be mentioned methylidene ($=CH_2$) ethylidene, ($=CH—CH_2$), n-propylidene, n-butylidene, n-pentlyiden, n-hexylidene and the constitutional isomers thereof, as for example iso-propylidene.

An "alkenylidene" represents the mono-unsaturated analogue of the above mentioned alkylidenes with more than 2 carbon atoms and may be called "$C_3$-$C_6$-alkenylidenes". n-propenylidene, n-butenylidene, n-pentenlyiden, and n-hexenylidene may be mentioned as examples.

The "substituent" of the above mentioned residues contains one hetero atom, like O or N. Preferably the substituents are independently selected from —OH, C=O, or —COOH. Most preferably said substituent is —OH.

A "mono- or polycyclic hydrocarbyl residue" comprise 1, 2 or 3 condensed (anellated) or non-condensed, optionally substituted, saturated or unsaturated hydrocarbon ring groups (or "carbocyclic" groups). Each cycle may comprise independently of each other 3 to 8, in particular 5 to 7, more particularly 6 ring carbon atoms. As examples of monocyclic residues there may be mentioned "cycloalkyl" groups which are carbocyclic radicals having 3 to 7 ring carbon atoms, such as cyclopropyl, cyclobutyl, cyclopentyl, cyclohexyl, cycloheptyl, and cyclooctyl; and the corresponding "cycloalkenyl" groups. Cycloalkenyl" (or "mono- or polyunsaturated cycloalkyl") represents, in particular, monocyclic, mono- or polyunsaturated carbocyclic groups having 5 to 8, preferably up to 6, carbon ring members, for example monounsaturated cyclopentenyl, cyclohexenyl, cycloheptenyl and cyclooctenyl radicals.

As examples of polycyclic residues there may be mentioned groups wherein 1, 2 or 3 of such cycloalkyl and/or cycloalkenyl are linked together, as for example anellated, in order to form a polycyclic cycloalkyl or cycloalkenyl ring. As non-limiting example the bicyclic decalinyl residue composed of two anellated 6-membered carbon rings may be mentioned.

The number of substituents in such mono- or polycyclic hydrocarbyl residues may vary from 1 to 10, in particular 1 to 5 substituents. Suitable substituents of such cyclic residues are selected from lower alkyl, lower alkenyl, alkylidene, alkenylidene, or residues containing one hetero atom, like O or N as for example —OH or —COOH. In particular the substituents are independently selected from —OH, —COOH, methyl and methylidene.

Unsaturated cyclic groups may contain 1 or more, as for example 1, 2 or 3 C=C bonds and are aromatic, or in particular nonaromatic.

The above-mentioned mono- or polycyclic saturated or unsaturated groups may also contain at least one, like 1, 2, 3 or 4 ring heteroatoms, such as 0, N or S.

Overview of Particular Compound Names and their Structural Formulae

| Structure | IUPAC name | other names |
|---|---|---|
| 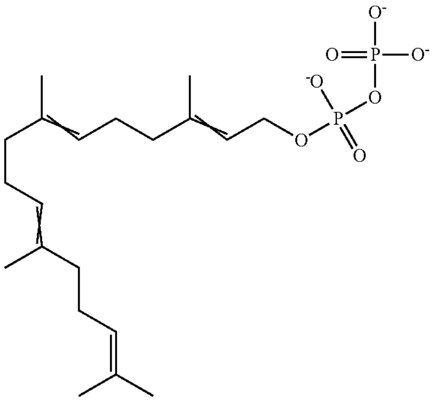 | [oxido(3,7,11,15-tetramethylhexadeca-2,6,10,14-tetraenoxy)phosphoryl] phosphate | cis/trans-geranylgeranyl pyrophosphate, cis/trans-GPP |
| 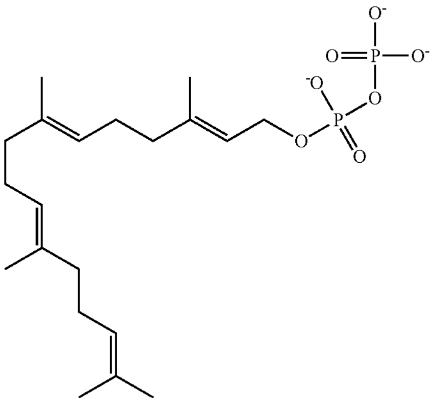 | [oxido-[(2E,6E,10E)-3,7,11,15-tetramethylhexadeca-2,6,10,14-tetraenoxy]phosphoryl] phosphate | (E,E,E)-geranylgeranyl pyrophosphate, (E,E,E)-GPP |

| Structure | IUPAC name | No. in examples | Labdane nomenclature | Short names |
|---|---|---|---|---|
| 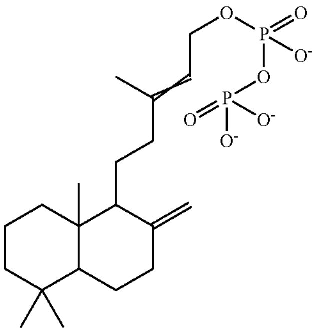 [SMILES: C=C1CCC2C(C)(C)CCCC2(C)C1CCC(C)=CCOP(=O)([O-])OP(=O)([O-])[O-]] | [[5-(5,5,8a-trimethyl-2-methylene-decalin-1-yl]-3-methyl-pent-2-enoxy]-oxido-phosphoryl] phosphate | | labda-8(20), 13-dien-15-yl diphosphate | |
| 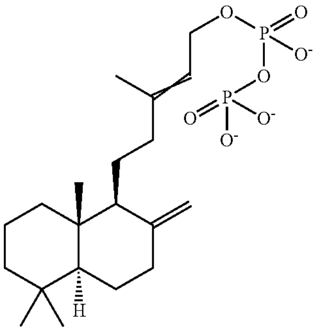 [SMILES: C=C1CC[C@H]2C(C)(C)CCC[C@]2(C)[C@H]1CCC(C)=CCOP(=O)([O-])OP(=O)([O-])[O-]] | [[5-[(1S,4aS,8aS)-5,5,8a-trimethyl-2-methylene-decalin-1-yl]-3-methyl-pent-2-enoxy]-oxido-phosphoryl] phosphate | | (5S,9S,10S)-labda-8(20), 13-dien-15-yl diphosphate | cis/trans-copalyl diphosphate, cis/trans-CPP |

-continued

| Structure | IUPAC name | No. in examples | Labdane nomenclature | Short names |
|---|---|---|---|---|
| 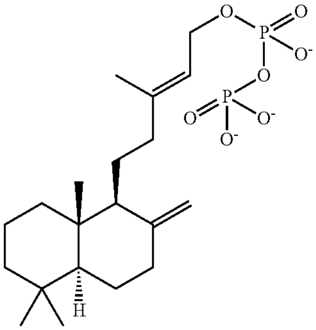 [SMILES: C=C1CC[C@H]2C(C)(C)CCC[C@]2(C)[C@H]1CC/C(C)=C/COP(=O)([O-])OP(=O)([O-])[O-]] | [[(E)-5-[(1S,4aS,8aS)-5,5,8a-trimethyl-2-methylene-decalin-1-yl]-3-methyl-pent-2-enoxy]-oxido-phosphoryl] phosphate | | (5S,9S,10S)--(13E)-labda-8(20), 13-dien-15-yl diphosphate | trans-copalyl diphosphate, Trans-CPP, CPP |
| 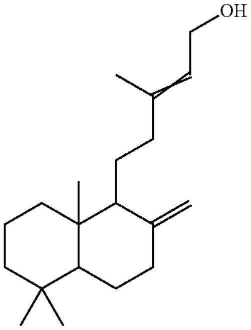 [SMILES: C=C1CCC2C(C)(C)CCCC2(C)C1CCC(C)=CCO] | 5-(5,5,8a-trimethyl-2-methylene-decalin-(1-yl)-3-methyl-pent-2-en-1-ol | | labda-8(20), 13-dien-15-ol | |
| 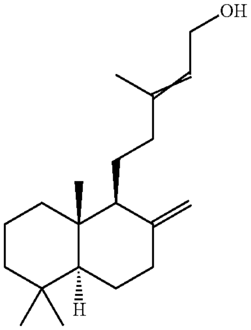 [SMILES: C=C1CC[C@H]2C(C)(C)CCC[C@]2(C)[C@H]1CCC(C)=CCO] | 5-[(1S,4aS,8aS)-5,5,8a-trimethyl-2-methylene-decalin-1-yl]-3-methyl-pent-2-en-1-ol | | (5S,9S,10S)-labda-8(20), 13-dien-15-ol | cis/trans-copalol |
| 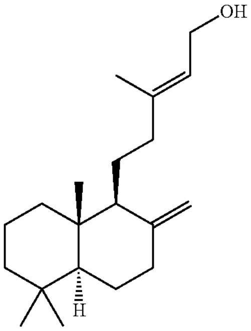 [SMILES: C=C1CC[C@H]2C(C)(C)CCC[C@]2(C)[C@H]1CC/C(C)=C/CO] | (E)-5-[(1S,4aS,8aS)-5,5,8a-trimethyl-2-methylene-decalin-1-yl]-3-methyl-pent-2-en-1-ol | | (5S,9S,10S)-(13E)-labda-8(20), 13-dien-15-ol | (+)-trans copalol |

-continued

| Structure | IUPAC name | No. in examples | Labdane nomenclature | Short names |
|---|---|---|---|---|
| 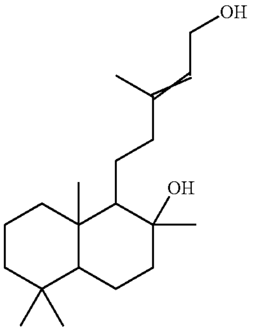 [SMILES: CC(=CCO)CCC1C(C)(O)CCC2C(C)(C)CCCC21C] | 1-(5-hydroxy-3-methyl-pent-3-enyl]-2,5,5,8a-tetramethyl-decalin-2-ol | | labd-13-en-8,15-diol | |
| 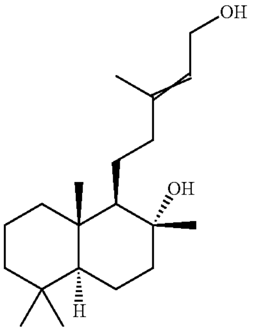 [SMILES: CC(=CCO)CC[C@@H]1[C@@]2(C)CCCC(C)(C)[C@@H]2CC[C@@]1(C)O] | (1R,2R,4aS,8aS)-1-(5-hydroxy-3-methyl-pent-3-enyl)-2,5,5,8a-tetramethyl-decalin-2-ol | | (5S,8R,9R,10S)-labd-13-en-8,15-diol | cis/trans-labdendiol |
| 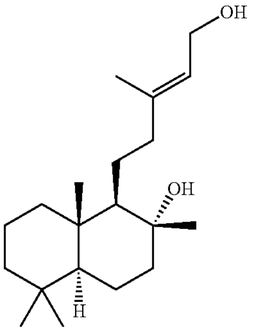 [SMILES: C/C(=C\CO)CC[C@@H]1[C@@]2(C)CCCC(C)(C)[C@@H]2CC[C@@]1(C)O] | (1R,2R,4aS,8aS)-1-[(E)-5-hydroxy-3-methyl-pent-3-enyl)-2,5,5,8a-tetramethyl-decalin-2-ol | | (5S,8R,9R,10S)-(13E)-5-labd-13 en-8,15-diol | trans-labdendiol |
| 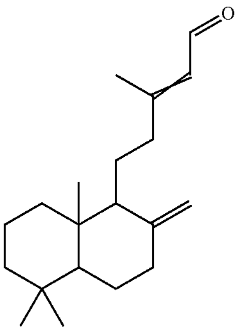 [SMILES: C=C1CCC2C(C)(C)CCCC2(C)C1CCC(C)=CC=O] | 5-(5,5,8a-trimethyl-2-methylene-decalin-1-yl)-3-methyl-pent-2-enal | | labda-8(20), 13-dien-15-al | |

-continued

| Structure | IUPAC name | No. in examples | Labdane nomenclature | Short names |
|---|---|---|---|---|
| 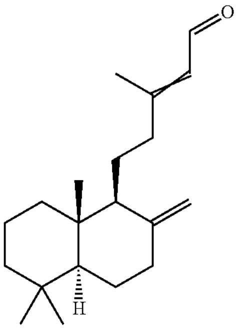 [SMILES: C=C1CC[C@H]2C(C)(C)CCC[C@]2(C)[C@H]1CCC(C)=CC=O] | 5-[(1S,4aS,8aS)-5,5,8a-trimethyl-2-methylene-decalin-1-yl]-3-methyl-pent-2-enal | | (5S,9S,10S)-labda-8(20), 13-dien-15-al | cis/trans-copalol |
| 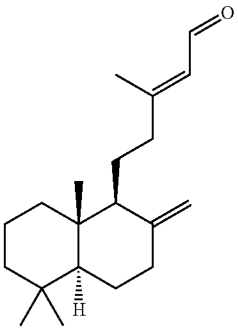 [SMILES: C=C1CC[C@H]2C(C)(C)CCC[C@]2(C)[C@H]1CC/C(C)=C/C=O] | (E)-5-[(1S,4aS,8aS)-5,5,8a-trimethyl-2-methylene-decalin-1-yl]-3-methyl-pent-2-enal | | (5S,9S,10S)-(13E)-labda-8(20), 13-dien-15-al | trans-copalol |
| 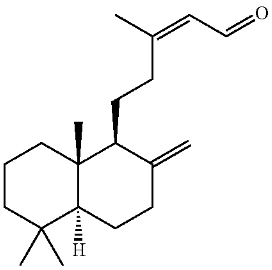 [SMILES: C=C1CC[C@H]2C(C)(C)CCC[C@]2(C)[C@H]1CC/C(C)=C\C=O] | (Z)-5-[(1S,4aS,8aS)-5,5,8a-trimethyl-2-methylene-decalin-1-yl]-3-methyl-pent-2-enal | | (5S,9S,10S)-(13Z)-labda-8(20), 13-dien-15-al | cis-copalal |
| 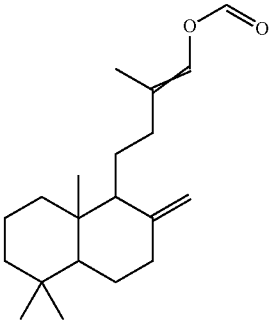 [SMILES: C=C1CCC2C(C)(C)CCCC2(C)C1CCC(C)=COC=O] | [4-(5,5,8a-trimethyl-2-methylene-decalin-1-yl)-2-methyl-but-1-enyl] formate | | (5S,9S,10S)-15-norlabda-8(20),13-dien-14-yl formate | |

-continued

| Structure | IUPAC name | No. in examples | Labdane nomenclature | Short names |
|---|---|---|---|---|
| 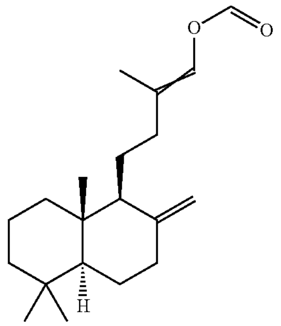 [SMILES: C=C1CC[C@H]2C(C)(C)CCC[C@]2(C)[C@H]1CCC(C)=COC=O] | [4-[(1S,4aS,8aS)-5,5,8a-trimethyl-2-methylene-decalin-1-yl]-2-methyl-but-1-enyl]formate | 1a, 1b | (5S,9S,10S)-15-norlabda-8(20), 13-dien-14-yl formate | |
| 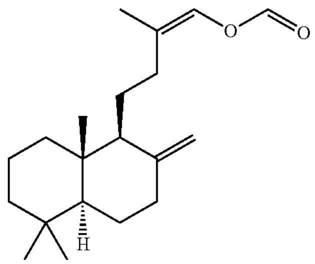 [SMILES: C=C1CC[C@H]2C(C)(C)CCC[C@]2(C)[C@H]1CC/C(C)=C\OC=O] | [(Z)-4-[(1S,4aS,8aS)-5,5,8a-trimethyl-2-methylene-decalin-1-yl]-2-methyl-but-1-enyl] formate | 1a | (5S,9S,10S)-(13Z)-15-norlabda-8(20), 13-dien-14-yl formate | |
| 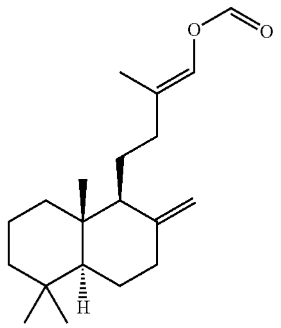 [SMILES: C=C1CC[C@H]2C(C)(C)CCC[C@]2(C)[C@H]1CC/C(C)=C/OC=O] | [(E)-4-[(1S,4aS,8aS)-5,5,8a-trimethyl-2-methylene-decalin-1-yl]-2-methyl-but-1-enyl] formate | 1b | (5S,9S,10S)-(13E)-15-norlabda-8(20), 13-dien-14-yl formate | |
| 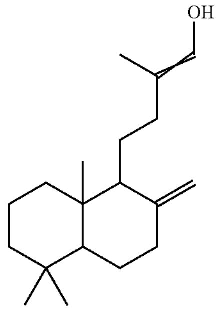 [SMILES: C=C1CCC2C(C)(C)CCCC2(C)C1CCC(C)=CO] | 4-(5,5,8a-trimethyl-2-methylene-decalin-1-yl)-2-methyl-but-1-en-1-ol formate (not stable) | | 15-norlabda-8(20), 13-dien-14-ol | |
| 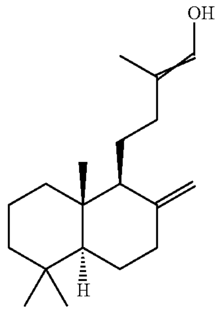 [SMILES: C=C1CC[C@H]2C(C)(C)CCC[C@]2(C)[C@H]1CCC(C)=CO] | 4-[(1S,4aS,8aS)-5,5,8a-trimethyl-2-methylene-decalin-1-yl]-2-methyl-but-1-en-1-ol (not stable) | 2a, 2b | (5S,9S,10S)-15-norlabda-8(20), 13-dien-14-ol | |

-continued

| Structure | IUPAC name | No. in examples | Labdane nomenclature | Short names |
|---|---|---|---|---|
| 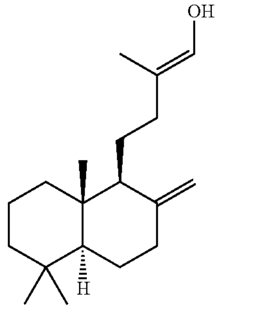 [SMILES: C=C1CC[C@H]2C(C)(C)CCC[C@]2(C)[C@H]1CC/C(C)=C/O] | (E)-4-[(1S,4aS,8aS)-5,5,8a-trimethyl-2-methylene-decalin-1-yl]-2-methyl-but-1-en-1-ol (not stable) | 2a | (5S,9S,10S)-(13E)-15-norlabda-8(20),13-dien-14-ol | |
| 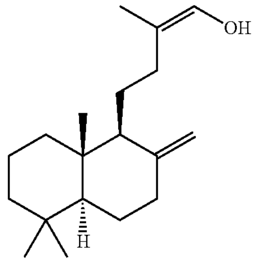 [SMILES: C=C1CC[C@H]2C(C)(C)CCC[C@]2(C)[C@H]1CC/C(C)=C\O] | (Z)-4-[(1S,4aS,8aS)-45,5,8a-trimethyl-2-methylene-decalin-1-yl]-2-methyl-but-1-en-1-ol (not stable) | 2b | (5S,9S,10S)-(13Z)-15-norlabda-8(20),13-dien-14-ol | |
| 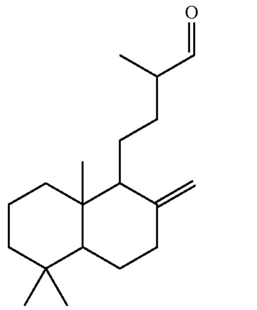 [SMILES: C=C1CCC2C(C)(C)CCCC2(C)C1CCC(C)C=O] | 4-(5,5,8a-trimethyl-2-methylene-decalin-1-yl)-2-methyl-butanal | | 15-norlabd-8(20)-en-14-al | |
| 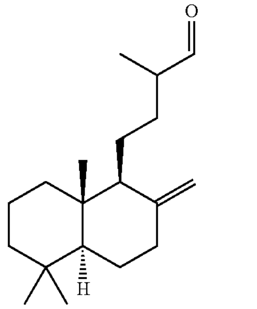 [SMILES: C=C1CC[C@H]2C(C)(C)CCC[C@]2(C)[C@H]1CCC(C)C=O] | 4-[(1S,4aS,8aS)-5,5,8a-trimethyl-2-methylene-decalin-1-yl]-2-methyl-butanal | 3a, 3b | (5S,9S,10S)-norlabd-8(20)-en-14-al | |
| 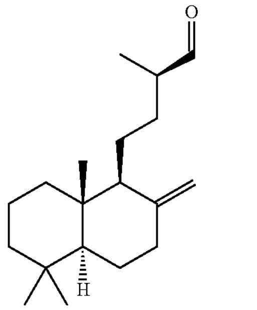 [SMILES: C=C1CC[C@H]2C(C)(C)CCC[C@]2(C)[C@H]1CC[C@@H](C)C=O] | (2R)-4-[(1S,4aS,8aS)-5,5,8a-trimethyl-2-methylene-decalin-1-yl]-2-methyl-butanal | 3a | (5S,9S,10S,13R)-15-norlabd-8(20)-en-14-al | |

-continued

| Structure | IUPAC name | No. in examples | Labdane nomenclature | Short names |
|---|---|---|---|---|
| 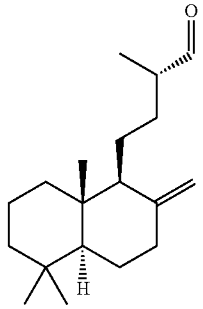 [SMILES: C=C1CC[C@H]2C(C)(C)CCC[C@]2(C)[C@H]1CC[C@H](C)C=O] | (2S)-4-[(1S,4aS,8aS)-5,5,8a-trimethyl-2-methylene-decalin-1-yl]-2-methyl-butanal | 3b | (5S,9S,10S,13S)-15-norlabd-8(20)-en-14-al | |
| 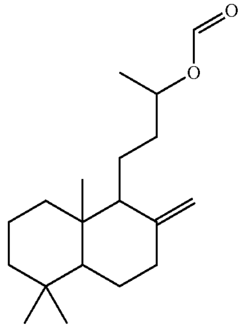 [SMILES: C=C1CCC2C(C)(C)CCCC2(C)C1CCC(C)OC=O] | [3-(5,5,8a-trimethyl-2-methylene-decalin-1-yl]-1-methyl-propyl] formate | | 14,15-dinorlabd-8(20)-en-13-yl formate | |
| 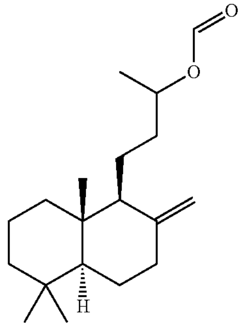 [SMILES: C=C1CC[C@H]2C(C)(C)CCC[C@]2(C)[C@H]1CCC(C)OC=O] | [3-[(1S,4aS,8aS)-5,5,8a-trimethyl-2-methylene-decalin-1-yl]-1-methyl-propyl] formate | 4a, 4b | (5S,9S,10S)-14,15-dinorlabd-8(20)-en-13-yl formate | |
| 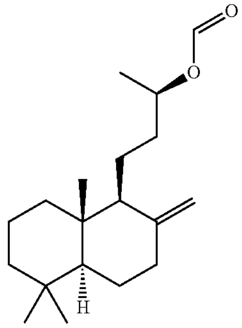 [SMILES: C=C1CC[C@H]2C(C)(C)CCC[C@]2(C)[C@H]1CC[C@@H](C)OC=O] | [(1R)-3-[(1S,4aS,8aS)-5,5,8a-trimethyl-2-methylene-decalin-1-yl]-1-methyl-propyl]formate | 4a | (5S,9S,10S,13R)-14,15-dinorlabd-8(20)-en-13-yl formate | |

-continued

| Structure | IUPAC name | No. in examples | Labdane nomenclature | Short names |
|---|---|---|---|---|
| 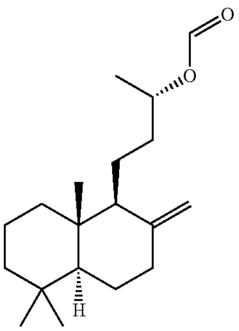 | [(1S)-3-[(1S,4aS,8aS)-5,5,8a-trimethyl-2-methylene-decalin-1-yl]-1-methyl-propyl] formate | 4b | (5S,9S,10S,13R)-14,15-dinorlabd-8(20)-en-13-yl formate | |
| 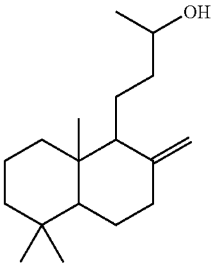 [SMILES: C=C1CCC2C(C)(C)CCCC2(C)C1CCC(C)O] | 4-(5,5,8a-trimethyl-2-methylene-decalin-1-yl)butan-2-ol | | 14,15-dinorlabd-8(20)-en-13-ol | |
| 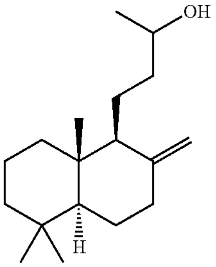 [SMILES: C=C1CC[C@H]2C(C)(C)CCC[C@]2(C)[C@H]1CCC(C)O] | 4-[(1S,4aS,8aS)-5,5,8a-trimethyl-2-methylene-decalin-1-yl] butan-2-ol | 5a, 5b | (5S,9S,10S)-14,15-dinorlabd-8(20)-en-13-ol | |
| 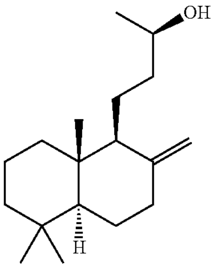 [SMILES: C=C1CC[C@H]2C(C)(C)CCC[C@]2(C)[C@H]1CC[C@@H](C)O] | (2R)-4-[(1S,4aS,8aS)-5,5,8a-trimethyl-2-methylene-decalin-1-yl]butan-2-ol | 5a | (5S,9S,10S,13R)-14,15-dinorlabd-8(20)-en-13-ol | |
| 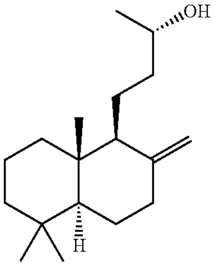 | (2S)-4-[(1S,4aS,8aS)-5,5,8a-trimethyl-2-methylene-decalin-1-yl]butan-2-ol | 5b | (5S,9S,10S,13S)-14,15-dinorlabd-8(20)-en-13-ol | |

-continued

| Structure | IUPAC name | No. in examples | Labdane nomenclature | Short names |
|---|---|---|---|---|
| 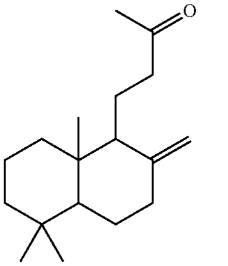 [SMILES: C=C1CCC2C(C)(C)CCCC2(C)C1CCC(C)=O] | 4-5(,5,8a-trimethyl-2-2-methylene-decalin-1-yl)butan-2-one | | 14,15-dinorlabd-8(20)-en-13-one | |
| 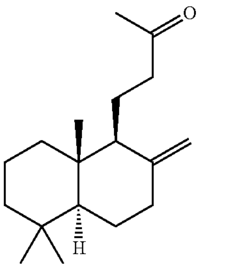 [SMILES: C=C1CC[C@H]2C(C)(C)CCC[C@]2(C)[C@H]1CCC(C)=O] | 4-[(1S,4aS,8aS)-5,5,8a-trimethyl-2-methylene-decalin-1-yl]butan-2-one | | (5S,9S,10S)-14,15-dinorlabd-8(20)-en-13-one | (+) manooloxy |
| 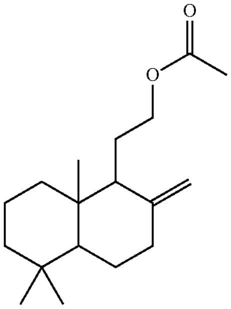 [SMILES: C=C1CCC2C(C)(C)CCCC2(C)C1CCOC(C)=O] | 2-(5,5,8a-trimethyl-2-methylene-decalin-1-yl)ethyl acetate | | 13,14,15,16-tetranor-labda-8(20)-en-12-yl acetate | 13,14,15,16-tetranorlabdenyl acetate |
| 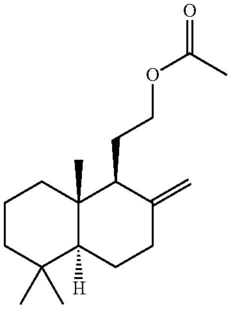 [SMILES: C=C1CC[C@H]2C(C)(C)CCC[C@]2(C)[C@H]1CCOC(C)=O] | 2-[(1S,4aS,8aS)-5,5,8a-trimethyl-2-methylene-decalin-1-yl]ethyl acetate | | (5S,9R,10S)-13,14,15,16-tetranor-labde-8(20)-en-12-yl acetate | (+)-γ-ambryl acetate |
| 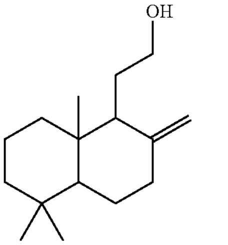 [SMILES: C=C1CCC2C(C)(C)CCCC2(C)C1CCO] | 2-(5,5,8a-trimethyl-2-methylene-decalin-1-yl)ethanol | | 13,14,15,16-tetranorlabda-8(20)-en-12-ol | 13,14,15,16-tetranorlabden-ol |

-continued

| Structure | IUPAC name | No. in examples | Labdane nomenclature | Short names |
|---|---|---|---|---|
| 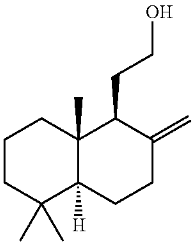 [SMILES: C=C1CC[C@H]2C(C)(C)CCC[C@]2(C)[C@H]1CCO] | 2-[(1S,4aS,8aS)-5,5,8a-trimethyl-2-methylene-decalin-1-yl]ethanol | | (5S,9S,10S)-13,14,15,16-tetranorlabda-8(20)-en-12-ol | (+)-γ-ambrol |
| 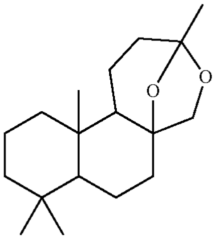 [SMILES: CC12CCC3C(CCC4C(C)(C)CCCC43C)(CO1)O2] | 3,8,8,11a-tetramethyldodecahy-dro-3,5a-epoxynaphtho [2,1-c]oxepin | | 8,13:13,20-diepoxy-15,16-dinorlabdane | diepoxy-dinorlabdane |
| 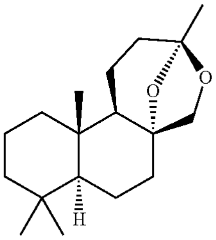 [SMILES: CC1(C)CCC[C@@]2(C)[C@H]1CC[C@]13CO[C@](C)(CC[C@@H]12)O3] | (3S,5aR,7aS,11aS,11bR)-3,8,8,11a-tetramethyldodecahydro-3,5a-epoxynaphtho [2,1-c]oxepin | | (5S,8R,9R,10S,13S)-8, 13:13,20-diepoxy-15,16-dinorlabdane | Z-11 |
| 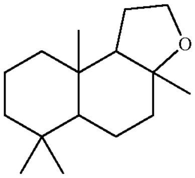 [SMILES: CC1(C)CCCC2(C)C1CCC1(C)OCCC12] | 3a,6,6,9a-tetramethyl-2,4,5,5a,7,8,9,9b-octahydro-1H-benzo[e]benzofuran | 8,12-epoxy-13,14,15,16-tetranorlabdane | | epoxy-tetranorlabdane |
| 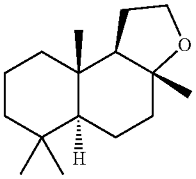 [SMILES: CC1(C)CCC[C@]2(C)[C@H]3CCO[C@]3(C)CC[C@@H]12] | (3aR,5aS,9aS,9bR)-3a,6,6,9a-tetramethyl-2,4,5,5a,7,8,9,9b-octahydro-1H-benzo[e]benzofuran | | (5S,8R,9R,10S)-8,12-epoxy-13,14,15,16-tetranorlabdane | Ambrox |
| 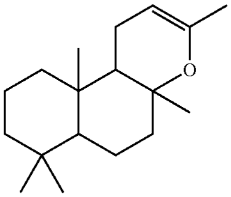 [SMILES: CC1=CCC2C(C)(CCC3C(C)(C)CCCC32C)O1] | 3,4a,7,7,10a-pentamethyl-1,5,6,6a,8,9,10,10b-octahydrobenzo[f] chromene | | 8,13-epoxy-13,14,15,16-dinorlabd-12-ene | |
| 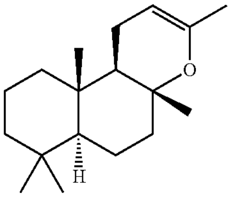 [SMILES: CC1=CC[C@@H]2[C@@]3(C)CCCC(C)(C)[C@@H]3CC[C@@]2(C)O1] | (4aR,6aS,10aS,10b R)-3,4a,7,7,10a-pentamethyl-1,5,6,6a,8,9,10,10b-octahydrobenzo[f] chromene | | (5S,8R,9R,10S)-8,13-epoxy-13,14,15,16-dinorlabd-12-ene | sclareol oxide |

DETAILED DESCRIPTION a. Particular Embodiments of the Invention i) The present invention relates to the following particular embodiments of biocatalytic methods involving the use of polypeptides with BMVO activity:

1. A biocatalytic method for preparing an ester compound, comprising:
   (1) contacting a carbonyl precursor compound of general formula I (I)

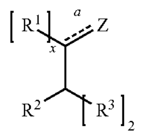

wherein
   "a" denotes a single or double bond,
   "x" is integer 1 if "a" denotes a double bond, or "x" is integer 2 if "a" denotes a single bond,
   $R^1$ represent independently of each other H or lower alkyl, like $C_1$-$C_4$-alkyl, in particular H or methyl,
   $R^2$ represents H, a linear or branched, saturated or unsaturated, optionally substituted hydrocarbyl residue, in particular having 2 to 20, more particularly 5 to 15 carbon atoms, or a group Cyc-A-,
   wherein
   Cyc represents an optionally substituted, saturated or unsaturated, mono- or polycyclic hydrocarbyl residue, and
   A represents a chemical bond or an optionally substituted, straight chain or branched alkylene bridge, in particular methylene,
   $R^3$ represent independently of each other H or a $C_1$-$C_{30}$, $C_1$-$C_{20}$ or in particular $C_1$-$C_{15}$ hydrocarbyl group, or a lower alkyl group, like $C_1$-$C_4$-alkyl, in particular H or methyl, and more particularly are each H,
   and
   when "a" denotes a single bond, then Z represents a hydrocarbyl residue containing a carbonyl group, in particular aldehyde or keto group, or,
   when "a" denotes a double bond, then Z forms, together with the carbon atom which it is attached to, either a carbonyl group (C═O, in particular aldehyde or keto group, or an alkylidene residue, in particular a $C_1$-$C_6$-alkylidene, residue carrying a terminal carbonyl group, in particular aldehyde or keto group, and
   when "a" denotes a double bond, and Z forms, together with the carbon atom which it is attached to, either a carbonyl group (C═O), then $R^2$ and $R^1$, together with the carbon atoms which they are attached to, may also form a cyclic, in particular monocyclic, saturated or unsaturated, optionally substituted carbocyclic ring group, in particular 5-7-membered ring;
   wherein said carbonyl compound of general formula I is provided in stereoisomerically pure form, or as a mixture of stereoisomers;
   with a natural or recombinant polypeptide having Baeyer-Villiger monooxygenase (BVMO) (EC 1.13.14.-) activity so as to form the respective carbonyl ester product, in particular by introducing a oxygen atom between the carbonyl group and the alpha-carbon atom of the precursor,
   (2) and optionally isolating the carbonyl ester formed in step (1), wherein said carbonyl ester compound is obtained in stereoisomerically pure form, or as a mixture of stereoisomers.
2. The biocatalytic method of embodiment 1, wherein in the carbonyl compound of general formula I
   "a" represents a chemical double bond and Z represents ═O (cf. Manooloxy) or ═C($R^4$)—C($R^5$)═O (cf. Copalal); or
   "a" represents a chemical single bond and Z represents —C($R^5$)═O (cf. Norlabdane compound 3a, 3b);
   wherein
   $R^4$ and $R^5$ independently of each other represent H or lower alkyl, like $C_1$-$C_4$-alkyl, in particular H or methyl.
3. The biocatalytic method of anyone of the preceding embodiments, wherein the carbonyl compound of general formula I possesses a labdane-type structure, in particular a labdane, norlabdane or di-norlabdane structure.
4. The biocatalytic method of anyone of the preceding embodiments wherein the carbonyl ester formed is of the formula II (II)

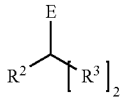

wherein
   $R^2$ and $R^3$ are as defined above, and
   E represents a hydrocarbyl residue containing said carbonyl ester group, or wherein E and $R^2$ together with the carbon atom which they are attached to form a cyclic ester group.
5. The biocatalytic method of embodiment 4, wherein the carbonyl ester group E is selected from
   —O—C(O)—$R^1$,
   —C($R^1$)$_2$—O—C(O)$R^5$
   —C($R^1$)═C($R^4$)—O—C($R^5$)═O; and
   a cyclic ester group formed by E and $R^2$ together with the carbon atom which they are attached to, wherein the cyclic ester ring represents a 5- to 7-membered, in particular 6-membered ring, as for example in esters of the formulae IIa and IIb (IIa)

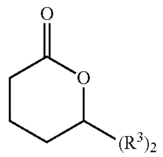

-continued (IIb)

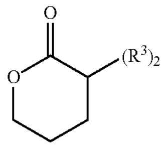

wherein $R^1$, $R^3$, $R^4$ and $R^5$ are as defined above.

6. The biocatalytic method of anyone of the preceding embodiments, wherein
   $R^2$ represents a group Cyc-A-, wherein A represents a straight chain or branched $C_1$-$C_4$-alkylene bridge, in particular methylene, and Cyc represents a mono- or polycyclic, in particular bicyclic, saturated or unsaturated hydrocarbyl residue, in particular a bicyclic anellated hydrocarbyl residue comprising 5-7, in particular 6, ring atoms per cycle; wherein Cyc is optionally substituted with 1-10, in particular 1-5 substituents, wherein said substituents in particular may be independently selected from $C_1$-$C_4$-alkyl, $C_1$-$C_4$-alkylidene, $C_3$-$C_6$-alkenylidene, $C_2$-$C_4$-alkenyl, oxo (=O), hydroxy, or amino; and in particular $C_1$-$C_4$-alkyl, like methyl, and $C_1$-$C_4$-alkylidene, like methylidene.
7. The method of anyone of the preceding embodiments, wherein the Cyc residue of $R^2$ forms an optionally substituted decalinyl residue, like in particular bicyclic residue obtainable through terpene cyclization.
8. The method of embodiment 7, wherein Cyc-A represents a bicyclic residue having 15 carbon atoms of formula IIIa, IIIb or IIIc (IIIa)

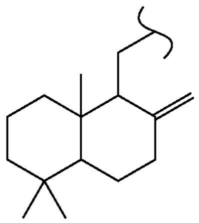

(IIIb)

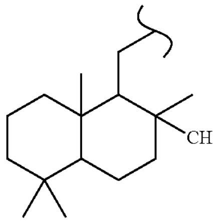

(IIIc)

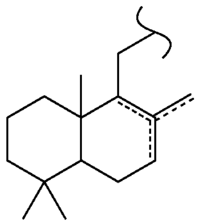

9. The method of anyone of the preceding embodiments, wherein the polypeptide having BVMO activity is selected from:

(1) the group of polypeptides containing a flavin-containing monooxygenase (FMO) protein family domain having the Pfam ID number PF00743 within their amino acid sequence; or a domain retaining at least 90%, 95%, 96%, 97%, 98%, or 99% sequence identity to PF00743;
   In particular, a polypeptide of the invention having BVMO activity is identified as member of the FMO protein family comprising said domain PF00743 if it matches with said domain with an e-value of less than $1\times10^{-5}$ or less than $1\times10^{-10}$, or less than or equal to $1\times10^{-15}$, or less than or equal to $1\times10^{-18}$; in particular in a range of $1\times10^{-10}$ to $1\times10^{-18}$ and more particular in a range of $1\times10^{-14}$ to $1\times10^{-17}$. As the query sequence the sequence of a polypeptide having BVMO activity is applied.
   For example, the following website may be applied for the search and calculating such e-value: pfam.xfam.org/, www.ebi.ac.uk/Tools/hmmer/search/hmmscan or www.ebi.ac.uk/Tools/pfa/pfamscan/.

and/or (2) selected from the group of polypeptides that comprise at least 1, 2, 3, 4, 5, 6, 7 or all of the sequence motif/domain selected from
   GAGxSGL set forth in SEQ ID NO:197
   EKNxxxxGTWxENRYPGCACDVPxHxYXXSFE set forth in SEQ ID NO: 198 or any partial motif thereof comprising up to 15, up to 10 or up to 5 consecutive amino acid residues, as for example corresponding to residues in positions 1-10, 11-20 or 21-32 of SEQ ID NO:198;
   LxNAxGILNxWxxPxIPG set forth in SEQ ID NO:199 or any partial motif thereof comprising up to 15, up to 10 or up to 5 consecutive amino acid residues, as for example corresponding to residues in positions 1-10 or 11-18 of SEQ ID NO:199;
   LxxKxVxxIGxGSSGIQIxPxI set forth in SEQ ID NO:200 or any partial motif thereof comprising up to 15, up to 10 or up to 5 consecutive amino acid residues, as for example corresponding to residues in positions 1-10 or 11-18 of SEQ ID NO:200;
   GCRRxTPGxxYLExL set forth in SEQ ID NO:201 or any partial motif thereof comprising up to 15, up to 10 or up to 5 consecutive amino acid residues, as for example corresponding to residues in positions 1-10, 11-15 of SEQ ID NO:201;
   CATGFDxxxxPRFxxxG set forth in SEQ ID NO:202 or any partial motif thereof comprising up to 15, up to 10 or up to 5 consecutive amino acid residues, as for example corresponding to residues in positions 1-10 or 11-17 of SEQ ID NO:202
   PNxFxxxGPNxPxxNGxV set forth in SEQ ID NO:203 or any partial motif thereof comprising up to 15, up to 10 or up to 5 consecutive amino acid residues, as for example corresponding to residues in positions 1-10 or 11-18 of SEQ ID NO:203;
   AxWPGSxLHYxEAxxxPRxED set forth in SEQ ID NO:204 or any partial motif thereof comprising up to 15, up to 10 or up to 5 consecutive amino acid residues, as for example corresponding to residues in positions 1-10 or 11-21 of SEQ ID NO:204;
   wherein
   in the above motifs residues x represent independently of each other any natural amino acid residue, and wherein optionally in each of the above motifs 1 to 5, like 1, 2, 3, 4 or 5 of the conserved amino acid residues (i.e. different from the x residues) may be modified, for example by amino acid substitution, in particular by conservative substitutions, provided that the enzymes retains, at least to analytically detectable extent, BVMO enzyme activity.

and/or (3) the group of polypeptides consisting of (a) polypeptides comprising the amino acid sequence of SCH23-BVMO1 set forth in SEQ ID NO:2;

(b) polypeptides comprising the amino acid sequence of SCH24-BVMO1 set forth in SEQ ID NO:6;

(c) polypeptides comprising the amino acid sequence of SCH25-BVMO1 set forth in SEQ ID NO:10;

(d) polypeptides comprising the amino acid sequence of SCH46-BVMO1 set forth in SEQ ID NO:13;

(e) polypeptides comprising the amino acid sequence of AspWeBVMO set forth in SEQ ID NO:16 (preferential substrate Manooloxa and its isomers)

(f) polypeptides comprising an amino acid sequence that has at least 70%, 75%, 80%, 85%, 90%, 95%, 96%, 97%, 98%, or 99% identity to any one of the amino acid sequences of a) to e).

Figure 32:
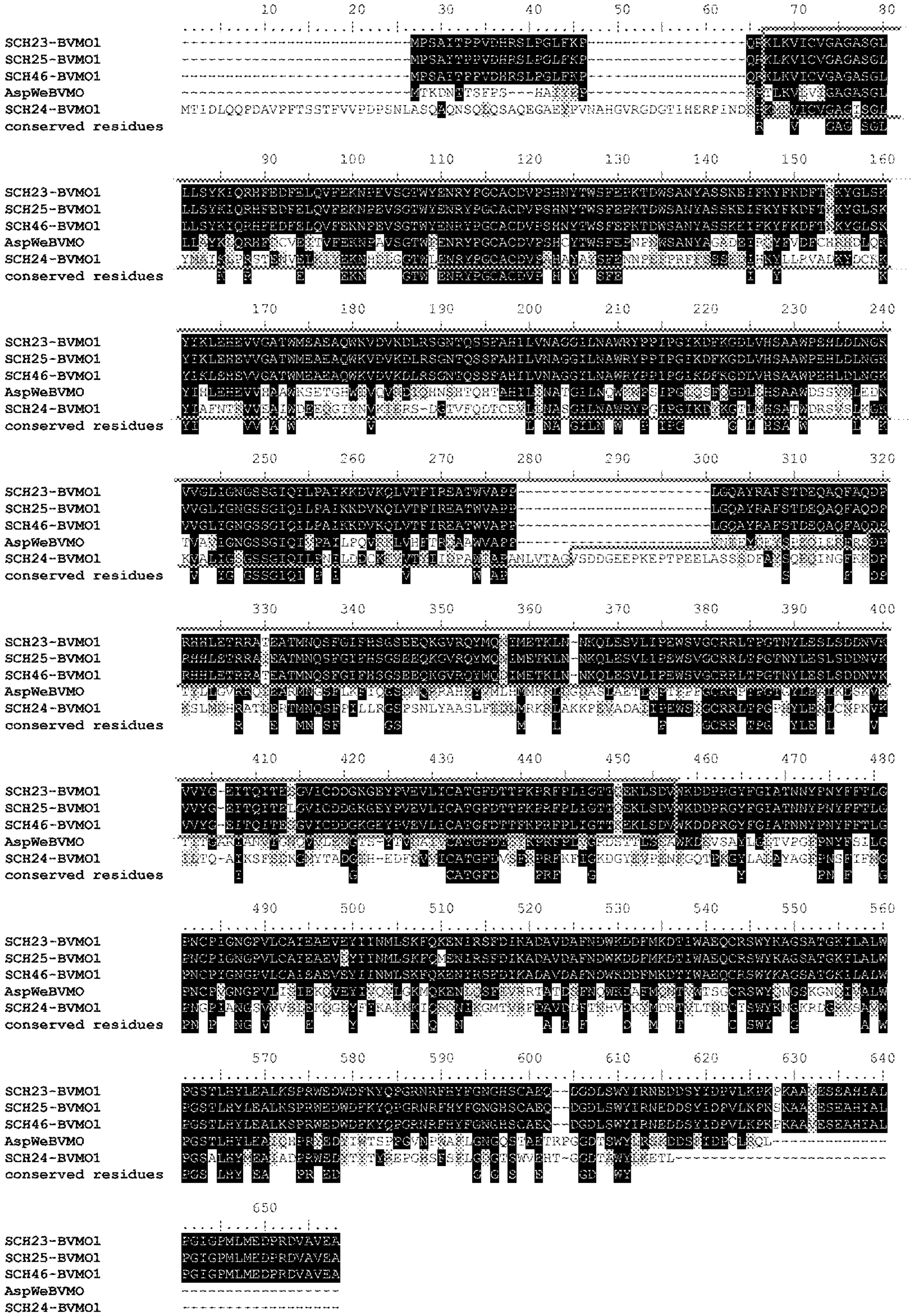
FIG. 32. Alignment and conserved amino acids of FMO-like domain containing proteins with BVMO activity. The boxes show the predicted localization of the respective protein family domains. The depicted sequence listings correspond to the following: SCH23-BVMO1 is set forth in SEQ ID NO:2, SCH24-BVMO1 is set forth in SEQ ID NO:6, SCH25-BVMO1 is set forth in SEQ ID NO:10, SCH46-BVMO1 is set forth in SEQ ID NO:13, and AspWeBVMO is set forth in SEQ ID NO: 16.

In the above referenced five particular BVMO polypeptides the protein family domain having the Pfam ID number PF00743 may be located at amino acid residue positions given in the following table (see also alignment depicted in FIG. 32 and the framed sequence sections therein)

| Protein sequence | From | To | E-Value | Accession Id | Protein domain |
|---|---|---|---|---|---|
| SCH23-BVMO1 | 23 | 388 | 2.9e−16 | Pf00743 | Flavin-binding monooxygenase-like |
| SCH24-BVMO2 | 67 | 283 | 6.8e−15 | Pf00743 | Flavin-binding monooxygenase-like |
| SCH25-BVMO1 | 23 | 246 | 1.2e−15 | Pf00743 | Flavin-binding monooxygenase-like |
| SCH46-BVMO1 | 23 | 388 | 1.8e−16 | Pf00743 | Flavin-binding monooxygenase-like |
| AspWe BVMO | 20 | 249 | 1.7e−16 | Pf00743 | Flavin-binding monooxygenase-like |

The numbering of amino acid residues refers to the residue number in the respective SEQ ID NO of the respective protein sequence in the attached sequence listing Another particular embodiment refers to polypeptide variants of the novel polypeptides of the invention having a BVMO activity as identified above by anyone of the particular amino acid sequences of SEQ ID NO: 2, 6, 10, and 13, and wherein the polypeptide variants are selected from an amino acid sequence having at least 70%, 75%, 80%, 85%, 90%, 95%, 96%, 97%, 98%, or 99% sequence identity to anyone of SEQ ID NO: 2, 6, 10, 13 and 16, and contain at least one substitution modification relative to anyone of the non-modified SEQ ID NO: 2, 6, 10, 13 and 16.

10. The method of anyone of the preceding embodiments performed in vitro or in vitro.

11. The method of embodiment 10 performed in vivo, that comprises, prior to step (1), the recombinant expression, in particular in a non-human host cell, of one or more polypeptides having the enzyme activity required for performing the BVMO catalyzed enzymatic step.

12. The method of embodiment 11, wherein the non-human host cell is transformed with a nucleic acid which is encoding at least one polypeptide having BVMO activity 13. The method of embodiment 11 or 12, wherein said non-human host cell is a eukaryotic or a prokaryotic cell, in particular a plant cell, a bacterial or a fungal cell, in particular a yeast cell.

14. The method of any one of embodiments 11 to 13, wherein the non-human host cell is a unicellular organism, a cultured cell derived from a multi-cellular organism, a cell present in a cultured tissue derived from a multicellular organism, or a cell present in a living multicellular organism.

15. The method of one of the embodiments 10 to 13, wherein the non-human host cell is a bacterium of the genus *Escherichia*, in particular *E. coli* and said yeast is of the genus *Saccharomyces*, or *Pichia*, in particular *S. cerevisiae*, or a plant cell.

16. The method of one of the preceding embodiments, wherein the carbonyl compound of general formula I is a labdane-type compound, selected from a) a labdane aldehyde, in particular copalal (or any stereoisomerically different form thereof, for example comprising cis- or trans-form or a mixture of cis- and trans-forms) which is converted by said BVMO to the respective norlabdane formate, in particular particular (5S,9S,10S)-15-norlabda-8(20),13-dien-14-yl-formate or any stereoisomerically different form thereof;

b) a dinorlabdane ketone, in particular manooloxy or any stereoisomerically different form thereof, which is converted by said BVMO to gamma-ambryl acetate or any stereoisomerically different form thereof; or c) a norlabdane aldehyde, in particular the $C_1$-degraded analog of copalal or any stereoisomerically different form thereof, in particular of the formula

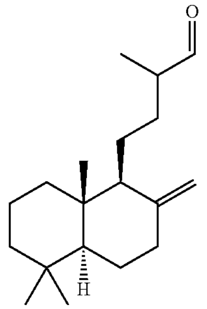 [SMILES: C=C1CC[C@H]2C(C)(C)CCC[C@]2(C)[C@H]1CCC(C)C=O]

or any stereoisomerically different form thereof which is converted by said BVMO to the respective dinorlabdane formate ester in particular of the formula

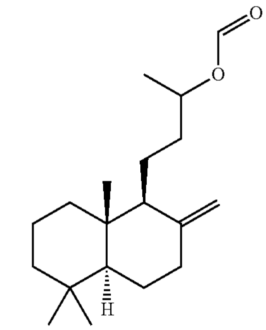 [SMILES: C=C1CC[C@H]2C(C)(C)CCC[C@]2(C)[C@H]1CCC(C)OC=O]

or any stereoisomerically different form thereof, and wherein optionally the obtained product is isolated in stereoisomerically essentially pure form or as a mixture of stereoisomers.

Further particular inventive examples of BVMO-catalyzed conversions of carbonyl compounds to the respective ester are summarized in the following schematic overview:

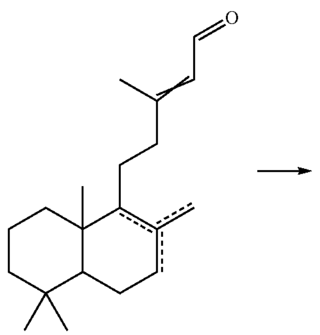

labdane aldehyde

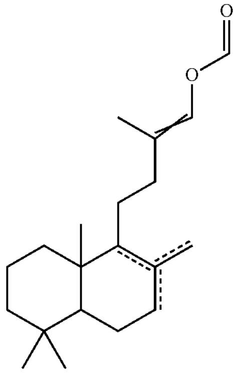

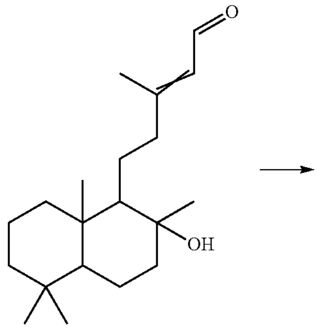

8-hydroxy labdane aldehyde

-continued

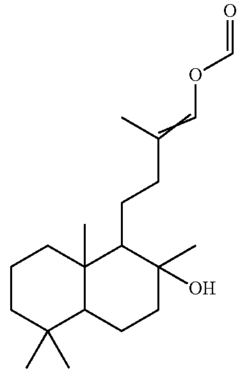

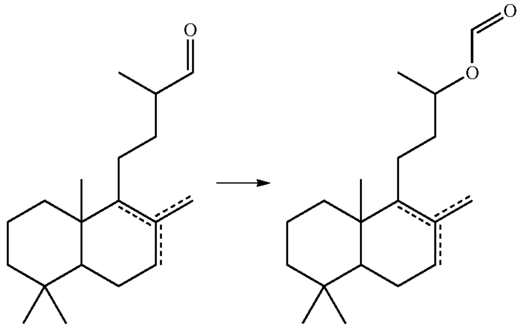

norlabdane aldehyde

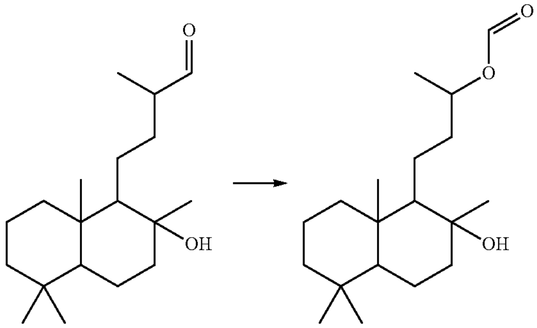

8-hydroxy morlabdane aldehyde

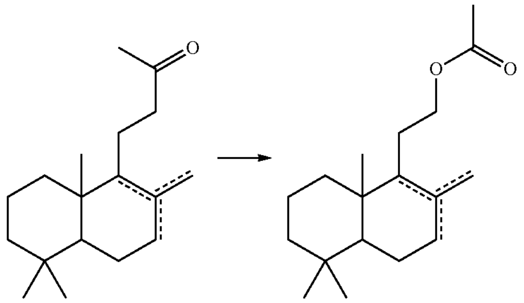

dinorlabdane aldehyde

-continued

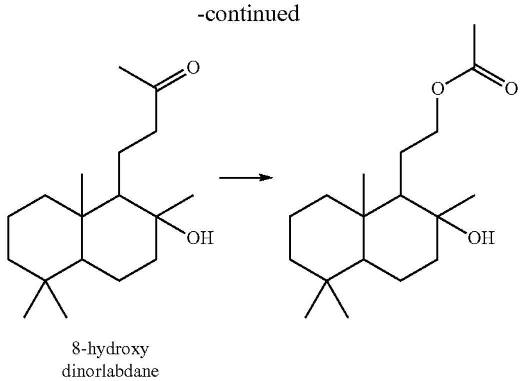

8-hydroxy dinorlabdane aldehyde

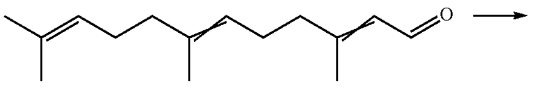

farnesal isomers

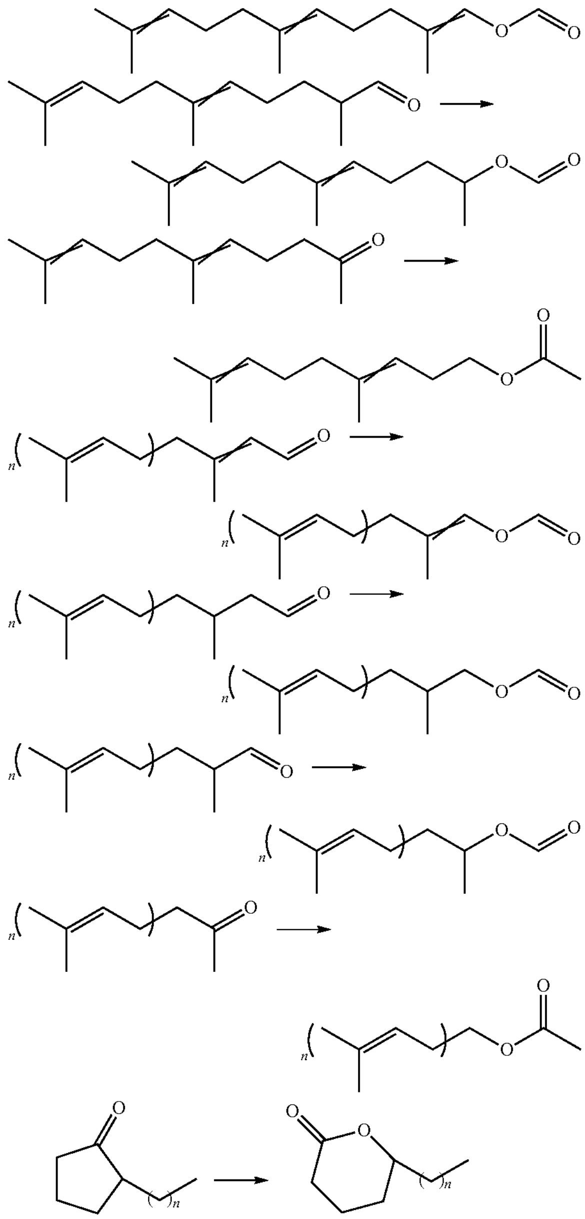

-continued

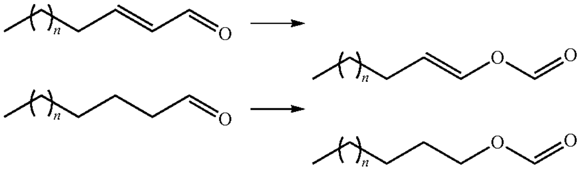

wherein parameter "n" is an integer from 1 to 20, 1 to 15, 1 to 10 or 1, 2, 3, 4 or 5.

17. The method of embodiment 16a, which comprises prior to step (1)

the biocatalytic oxidation of a labdane alcohol to a labdane aldehyde, in particular of copalol to copalal, which labdane alcohol is optionally formed by the biocatalytic conversion of at least one terpenly diphosphate precursor, selected from IPP, DMAPP, FPP and GGPP, in particular in a single step or a combination of at least two steps, known in the prior art.

Said labdane alcohol may for example be biocatalytically produced:

a) from geranylgeranyl diphosphate (GGPP) in one step in a cyclisation reaction/dephosphorylation reaction b) from GGPP in two steps by a cyclisation forming labdane diphosphate, as for example copalyl diphosphate (CPP) which is then dephosphorylated to the labdane alcohol;

c) from IPP and DMAPP which is directly converted through the action of a bifunctional GGPP synthase/CPP synthase to the labdane diphosphate, as for example CPP which is then dephosphorylated;

GGPP as used in these steps may also be provided by different biocatalytic steps:

d) GGPP synthases are available which produce GGPP directly from IPP and DMAPP; or e) GGPP may be provided from IPP and DMAPP via FPP through the action of a FPP synthase, and the subsequent conversion of FPP to GGPP through the action of a GGPP synthase.

18. The method of embodiment 17, wherein said biocatalytic oxidation of a labdane alcohol, in particular of copalol to copalal, is catalyzed by an exogenous or endogenous polypeptide having alcohol dehydrogenase (ADH) (EC 1.1.1.-) activity; and/or said biocatalytic formation of the labdane alcohol comprises at least one step selected from i) a biocatalytic dephosphorylation of a labdane diphosphate to a labdane alcohol, in particular of copalyl diphosphate (CPP) to copalol, which is catalyzed by a polypeptide having terpenyl diphosphate (TPP) phosphatase activity, and/or ii) a biocatalytic cyclisation of a terpenly diphosphate precursor, as for example of geranylgeranyl diphosphate (GGPP) to CPP, which is catalyzed by a polypeptide having CPP synthase activity, like SmCPS2 (SEQ ID NO: 185); or as for example of IPP and DMAPP to CPP, which is catalyzed by a bifunctional polypeptide having prenyl-transferase and copalyl-diphosphate synthase activity, like PvCPS, and/or iii) a biocatalytic formation of GGPP from FPP or a biocatalytic formation from IPP and DMAPP, each of which being catalyzed by a polypeptide having GGPP synthase activity.

19. The method of embodiment 18, wherein
   said biocatalytic oxidation, in particular of copalol to copalal, is catalyzed by a polypeptide having alcohol dehydrogenase (ADH) activity selected from
   a) polypeptides comprising the amino acid sequence of SCH23-ADH1_wt set forth in SEQ ID NO: 134
   b) polypeptides comprising the amino acid sequence of SCH24-ADH1_wt set forth in SEQ ID NO: 140
   c) polypeptides comprising the amino acid sequence of SCH94-3945_wt set forth in SEQ ID NO:161
   d) polypeptides comprising the amino acid sequence of SCH80-0540_wt set forth in SEQ ID NO:164
   e) polypeptides comprising the amino acid sequence of AzTolADH1_wt set forth in SEQ ID NO:167
   f) polypeptides comprising the amino acid sequence of CdGeoA_wt set forth in SEQ ID NO:179
   g) polypeptides comprising an amino acid sequence that has at least 70%, 75%, 80%, 85%, 90%, 95%, 96%, 97%, 98%, or 99% identity to any one of the amino acid sequences of a) to f) and having ADH activity.

and/or said biocatalytic dephosphorylation, in particular of copalyl diphosphate (CPP) to copalol, is catalyzed by a polypeptide having terpenyl diphosphate (TPP) phosphatase activity selected from
   a) polypeptides comprising an amino acid sequence of AspWE TPP as set forth in SEQ ID NO:170 or a polypeptide comprising an amino acid sequence that has at least 70%, 75%, 80%, 85%, 90%, 95%, 96%, 97%, 98%, or 99% identity thereto;
   b) polypeptides comprising an amino acid sequence of TalCeTPP as set forth in SEQ ID NO: 176 or a polypeptide comprising an amino acid sequence that has at least 70%, 75%, 80%, 85%, 90%, 95%, 96%, 97%, 98%, or 99% identity thereto; and
   c) polypeptides comprising an amino acid sequence of TalVeTPP as set forth in SEQ ID NO: 194 or a polypeptide comprising an amino acid sequence that has at least 70%, 75%, 80%, 85%, 90%, 95%, 96%, 97%, 98%, or 99% identity thereto;

Further suitable phosphatases are also disclosed in earlier the applicant's EP application number 18182783.3, incorporated by reference.

and/or said biocatalytic cyclisation, in particular of geranylgeranyl diphosphate (GGPP) to CPP, is catalyzed by a polypeptide selected from
   polypeptides having copalyl-diphosphate synthase activity comprising the amino acid sequence of SmCPS2 as set forth in SEQ ID NO:185 or a polypeptide comprising an amino acid sequence that has at least 70%, 75%, 80%, 85%, 90%, 95%, 96%, 97%, 98%, or 99% 70% identity thereto;

said biocatalytic cyclisation, in particular of IPP and DNMAPP to CPP, is catalyzed by a polypeptide selected from
   polypeptides having prenyl-transferase and copalyl-diphosphate synthase activities comprising the amino acid sequence of PvCPS as set forth in SEQ ID NO:173 or a polypeptide comprising an amino acid sequence that has at least 70%, 75%, 80%, 85%, 90%, 95%, 96%, 97%, 98%, or 99% identity thereto;

and/or said biocatalytic formation of GGPP is catalyzed by a polypeptide having GGPP synthase activity and is selected from
   a) polypeptides comprising the amino acid sequence of carG as set forth in SEQ ID NO:182 or a polypeptide comprising an amino acid sequence that has at least 70%, 75%, 80%, 85%, 90%, 95%, 96%, 97%, 98%, or 99% identity thereto;
   b) polypeptides comprising the amino acid sequence of CrtE as set forth in SEQ ID NO:191 or a polypeptide comprising an amino acid sequence that has at least 70%, 75%, 80%, 85%, 90%, 95%, 96%, 97%, 98%, or 99% identity thereto;
   c) polypeptides comprising the amino acid sequence of PvCPS as set forth in SEQ ID NO:173 or a polypeptide comprising an amino acid sequence that has at least 70%, 75%, 80%, 85%, 90%, 95%, 96%, 97%, 98%, or 99% identity thereto.
20. The method of anyone of the preceding embodiments further comprising as step (3) the processing of the carbonyl ester formed in step (1) or isolated in step (2) to obtain a derivative thereof using chemical or biocatalytic synthesis or a combination of both, wherein said derivative may in particular be selected from a hydrocarbon, alcohol, diol, triol, acetal, ketal, aldehyde, acid, ether, amide, ketone, lactone, epoxide, acetate, glycoside and/or an ester, and optionally isolating the derivative of step (3).
21. The method of embodiment 20, wherein step (3) comprises the hydrolysis of the carbonyl ester compound with an esterase activity EC 3.1.1 (Carboxylic Ester Hydrolases) to the corresponding de-esterified product (which may be an alcohol or an isomerization product thereof, and optionally isolating the derivative of step (3).
22. The method of embodiment 21, wherein the de-esterified product of step (3) is subjected in a further step (4) to an enzymatic redox reaction, wherein in particular the redox reaction comprises the oxidation of an alcohol group as formed in step (3) to the corresponding keto-group through the enzymatic action of an an exogenous or endogenous alcohol dehydrogenase (ADH) (EC 1.1.1.-).
23. The method of embodiment 21, wherein the esterase is selected from the group consisting of
   a) polypeptides comprising the amino acid sequence of SCH23-Esterase set forth in SEQ ID NO:20;
   b) polypeptides comprising the amino acid sequence of SCH24-Esterase set forth in SEQ ID NO:24;
   c) polypeptides comprising the amino acid sequence of SCH25-Esterase set forth in SEQ ID NO:28;
   d) polypeptides comprising the amino acid sequence of SCH46-Esterase set forth in SEQ ID NO:31; or
   e) polypeptides comprising an amino acid sequence that has at least 70%, 75%, 80%, 85%, 90%, 95%, 96%, 97%, 98%, or 99% identity to any one of the amino acid sequences of a) to d) and having esterase activity.
24. The method of embodiment 23, wherein
   a) a norlabdane ester, in particular a norlabdane-formate is de-esterified by said esterase to a norlabdane carbonyl compound, in particular a carbonyl compound if the formula

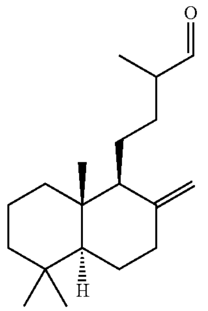

or the respective enol thereof which is the converted via isomerisation to said carbonyl compound;

or b) a tetranorlabdane ester, in particular gamma-ambryl acetate is de-esterified by said esterase to a tetranorlabdane, in particular gamma ambrol; or c) a dinorlabdane formate ester, in particular the formate ester of the formula

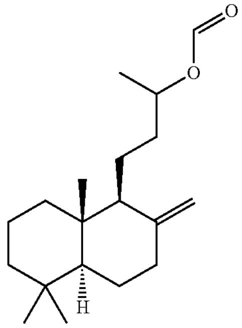 [SMILES: C=C1CC[C@H]2C(C)(C)CCC[C@]2(C)[C@H]1CCC(C)OC=O]

or any stereoisomerically different form thereof is de-esterified by said esterase to the corresponding dinorlabdane alcohol, in particular to the alcohol-compound of the formula

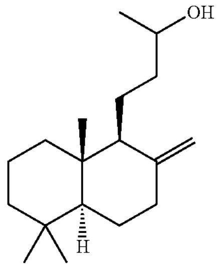 [SMILES: C=C1CC[C@H]2C(C)(C)CCC[C@]2(C)[C@H]1CCC(C)O]

or any stereoisomerically different form thereof and wherein optionally the obtained product is isolated in stereoisomerically essentially pure form or as a mixture of stereoisomers.

25. The method of embodiment 22, wherein the ADH is selected from the group consisting of a) polypeptides comprising the amino acid sequence of SCH23-ADH2_wt set forth in SEQ ID NO: 137 b) polypeptides comprising the amino acid sequence of SCH24-ADH2_wt set forth in SEQ ID NO: 143 c) polypeptides comprising the amino acid sequence of RrhSecADH_wt set forth in SEQ ID NO:146 d) polypeptides comprising the amino acid sequence of SCH80-06135_wt set forth in SEQ ID NO:155 e) polypeptides comprising an amino acid sequence that has at least 70%, 75%, 80%, 85%, 90%, 95%, 96%, 97%, 98%, or 99% identity to any one of the amino acid sequences of a) to d) and having ADH activity.

26. The method of embodiment 24, wherein the obtained dinorlabdane alcohol, in particular the alcohol of the formula

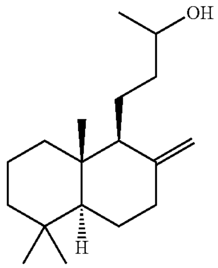 [SMILES: C=C1CC[C@H]2C(C)(C)CCC[C@]2(C)[C@H]1CCC(C)O]

or any stereoisomerically different form thereof is oxidized by said ADH to the corresponding dinorlabdane carbonyl compound, in particular to manoooloxy, and wherein optionally the obtained product is isolated in stereoisomerically essentially pure form or as a mixture of stereoisomers.

ii) The present invention relates to the following particular embodiments of biocatalytic methods involving the use of polypeptides with enal-cleaving activity:

27. A biocatalytic method of preparing a compound of the general formula IV (IV)

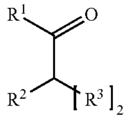

wherein $R^1$ represents H or lower alkyl, in particular methyl, $R^2$ represents H, a linear or branched, saturated or unsaturated, optionally substituted hydrocarbyl group, in particular alkyl or alkenyl group, in particular having up to 30, up to 20, up to 15 or up to 10 carbon atoms, or a residue Cyc-A- wherein

Cyc represents an optionally substituted, saturated or unsaturated, in particular nonaromatic, mono- or polycyclic, in particular mono- or bicyclic, hydrocarbyl residue, in particular having 5 to 7 ring carbon atoms, and A represents a chemical bond or an optionally substituted, straight chain or branched alkylene bridge, in particular methylene, and $R^3$ represent independently of each other H or lower alkyl, like $C_1$-$C_4$-alkyl, in particular H or methyl, and more particularly are each H, comprising the steps of (1) contacting the corresponding non-degraded precursor of the general formula V (V)

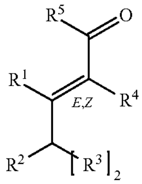

wherein $R^1$, $R^2$ and $R^3$ are as defined above; and $R^4$ represents H or lower alkyl, in particular H or methyl, $R^5$ represents H or lower alkyl, in particular H, and wherein said compound may be present in stereoisomerically essentially pure form (as for example in E- or Z-Form) or as a mixture of stereoisomers, with a natural or recombinant polypeptide having enal-cleaving activity, in particular a polypeptide having an α,β-unsaturated aldehyde C═C bond-cleaving, and (2) optionally isolating the degraded product of formula IV as obtained in step (1), wherein said compound of general formula IV may be obtained in stereoisomerically pure form, or as a mixture of stereoisomers 28. The method of embodiment 27, wherein said polypeptide having said enal-cleaving activity is selected from the group of polypeptides containing a) at least one DUF4334 protein family domain having the Pfam ID number PF14232 (in particular within the C-terminal region of their amino acid sequence); and/or b) at least one GXWXG protein family domain having the Pfam ID number PF14231 (in particular within the N-terminal region of their amino acid sequence); or c) a domain retaining at least 90% sequence identity to PF14232 or PF14231;

In particular, a polypeptide of the invention having enal-cleaving activity is identified as a member of the DUF4334 protein family comprising said domain PF14232 if it matches with said domain with an e-value of less than $1\times10^{-5}$, or less than $1\times10^{-10}$, or less than $1\times10^{-15}$, or less than $1\times10^{-20}$, or less than $1\times10^{-25}$, or less than $1\times10^{-30}$, or less than or equal to $1\times10^{-35}$, in particular in a range of $1\times10^{-20}$ to $1\times10^{-32}$ and more particular in a range of $1\times10^{-25}$ to $1\times10^{-31}$ For example, the following website may be applied for the search and calculating such e-value: pfam.xfam.org/, www.ebi.ac.uk/Tools/hmmer/search/hmmscan or www.ebi.ac.uk/Tools/pfa/pfamscan/

In particular, a polypeptide of the invention having enal-cleaving activity is identified as a member of GXWXG protein family comprising said domain PF14231 if it matches with an e-value of less than $1\times10^{-5}$, or less than $1\times10^{-10}$, or less than $1\times10^{-15}$, or less than $1\times10^{-20}$, or less than $1\times10^{-25}$, or less than $1\times10^{-30}$, or less than or equal to $1\times10^{-35}$, in particular in a range of $1\times10^{-20}$ to $1\times10^{-30}$ As the query sequence the sequence of a polypeptide having enal-cleaving activity is applied.

For example, the following website may be applied for the search and calculating such e-value: pfam.xfam.org/, www.ebi.ac.uk/Tools/hmmer/search/hmmscan or www.ebi.ac.uk/Tools/pfa/pfamscan/ and/or wherein said polypeptide having said enal-cleaving activity is selected from the group of polypeptides selected from the group of polypeptides that comprise at least one sequence motif/domain selected from G-[Y or "-" ]-x-W-x-G-x-x-[F,L or I]-x-[T,S or R]-G-[H or D] set forth in SEQ ID NO:205, or any partial motif thereof comprising up to 10 or up to 5 consecutive amino acid residues, as for example corresponding to residues in positions 1-8 or 9-13 of SEQ ID NO:205;

W-[Y, A or V]-G-K-x-[F or Y]-x-[S or D] set forth in SEQ ID NO:206, or any partial motif thereof comprising up to 4 consecutive amino acid residues, as for example corresponding to residues in positions 1-4 or 5-8 of SEQ ID NO:206;

[G or S]-x-[A or G]-x-[L or V]-x-x-x-x-[F, Y or L]-R-G-x-V set forth in SEQ ID NO:207, or any partial motif thereof comprising up to 10 or up to 5 consecutive amino acid residues, as for example corresponding to residues in positions 1-8 or 9-14 of SEQ ID NO:207;

[M or L]-[V or I]-Y-D-x-x-P-[I or V]-x-D-[H or S]-[F or L] set forth in SEQ ID NO:208, or any partial motif thereof comprising up to 10 or up to 5 consecutive amino acid residues, as for example corresponding to residues in positions 1-6 or 7-12 of SEQ ID NO:208;

wherein in the above motifs residues x represent independently of each other any natural amino acid residue, and wherein optionally in each of the above motifs 1 to 5, like 1, 2, 3, 4 or 5 amino acid residues different from the x residues may be modified, for example by amino acid substitution, in particular by conservative substitutions, provided that the enzymes retains, at least to analytically detectable extent, enal-cleaving enzyme activity.

and/or said polypeptide having said enal-cleaving activity is selected from the group consisting of the following polypeptides comprising the respective amino acid sequence:

a) SCH94-3944 set forth in SEQ ID NO: 34
b) SCH80-05241 set forth in SEQ ID NO:38
c) Pdigit7033 set forth in SEQ ID NO: 42
d) PitalDUF4334-1 set forth in SEQ ID NO: 46
e) AspWeDUF4334 set forth in SEQ ID NO: 49
f) RhoagDUF4334-2 set forth in SEQ ID NO: 53,
g) RhoagDUF4334-3 set forth in SEQ ID NO: 56,
h) RhoagDUF4334-4 set forth in SEQ ID NO: 59,
i) CnecaDUF4334 set forth in SEQ ID NO: 62,
j) Rins-DUF4334 set forth in SEQ ID NO: 69,
k) CgatDUF4334 set forth in SEQ ID NO: 72,
l) GclavDUF4334 set forth in SEQ ID NO: 75
m) TcurvaDUF4334 set forth in SEQ ID NO:81,
n) PprotDUF4334 set forth in SEQ ID NO: 87, and
o) polypeptides comprising an amino acid sequence that has at least 40%, 45%, 50%, 55%, 60%, 65%, 75%, 80%, 85%, 90%, 95%, 96%, 97%, 98%, or 99% sequence identity to any one of the amino acid sequences of a) to n) and retaining said enzymatic activity of degrading an terpene precursor of formula (1).

Another particular embodiment refers to polypeptide variants of the novel polypeptides of the invention having a enal-cleaving activity as identified above by anyone of the particular amino acid sequences of SEQ ID NO: 34, 38, 42, 46, 49, 53, 56, 59, 62, 69, 72, 75, 81 and 87 and wherein the polypeptide variants are selected from an amino acid sequence having at least 70%, 75%, 80%, 85%, 90%, 95% 96%, 97%, 98%, or 99% sequence identity to anyone of SEQ ID NO: 34, 38, 42, 46, 49, 53, 56, 59, 62, 69, 72, 75, 81 and 87, and containing at least one substitution modification relative to anyone of SEQ ID NO: 34, 38, 42, 46, 49, 53, 56, 59, 62, 69, 72, 75, 81 and 87.

In the above referenced 14 particular enal cleaving polypeptides the protein family domains having the Pfam ID number PF14232 and PF14231 may be located at amino acid residue positions given in the following table (see also alignment depicted in FIG. 31 and the framed sequence sections therein)

| Protein sequence | From | To | E-Value | Accession Id | Protein domain |
|---|---|---|---|---|---|
| SCH94-3944 | 96 | 153 | 1.63E−30 | pf14232 | DUF4334 |
| SCH94-3944 | 27 | 85 | 3.24E−28 | pf14231 | GXWXG |
| SCH80-05241 | 96 | 153 | 7.42E−30 | pf14232 | DUF4334 |
| SCH80-05241 | 27 | 85 | 2.30E−27 | pf14231 | GXWXG |
| Pdigit7033 | 93 | 147 | 9.46E−28 | pf14232 | DUF4334 |
| Pdigit7033 | 27 | 83 | 9.73E−24 | pf14231 | GXWXG |
| PitalDUF4334-1 | 93 | 147 | 1.03E−26 | pf14232 | DUF4334 |
| PitalDUF4334-1 | 27 | 84 | 7.88E−25 | pf14231 | GXWXG |
| AspWeDUF4334 | 94 | 148 | 5.62E−26 | pf14232 | DUF4334 |
| AspWeDUF4334 | 27 | 85 | 6.95E−26 | pf14231 | GXWXG |
| RhoagDUF4334-2 | 94 | 150 | 8.64E−27 | pf14232 | DUF4334 |
| RhoagDUF4334-2 | 24 | 83 | 9.35E−23 | pf14231 | GXWXG |
| RhoagDUF4334-3 | 94 | 150 | 1.33E−26 | pf14232 | DUF4334 |
| RhoagDUF4334-3 | 24 | 83 | 9.55E−23 | pf14231 | GXWXG |
| RhoagDUF4334-4 | 94 | 150 | 8.31E−26 | pf14232 | DUF4334 |
| RhoagDUF4334-4 | 24 | 83 | 8.03E−23 | pf14231 | GXWXG |
| CnecaDUF4334 | 117 | 168 | 1.10E−21 | pf14232 | DUF4334 |
| CnecaDUF4334 | 20 | 75 | 1.20E−20 | pf14231 | GXWXG |
| Rins-DUF4334 | 91 | 152 | 2.57E−27 | pf14232 | DUF4334 |
| Rins-DUF4334 | 23 | 81 | 5.84E−26 | pf14231 | GXWXG |
| CgatDUF4334 | 91 | 145 | 4.15E−26 | pf14232 | DUF4334 |
| CgatDUF4334 | 24 | 82 | 8.78E−23 | pf14231 | GXWXG |
| GelavDUF4334 | 91 | 145 | 3.09E−30 | pf14232 | DUF4334 |
| GelavDUF4334 | 24 | 82 | 5.12E−29 | pf14231 | GXWXG |
| TcurvaDUF4334 | 24 | 82 | 2.85E−27 | pf14231 | GXWXG |
| TcurvaDUF4334 | 91 | 143 | 1.69E−25 | pf14232 | DUF4334 |
| PprotDUF4334 | 91 | 153 | 3.71E−27 | pf14232 | DUF4334 |
| PprotDUF4334 | 23 | 81 | 6.37E−24 | pf14231 | GXWXG |

The numbering of amino acid residues refers to the residue number in the respective SEQ ID NO of the respective protein sequence in the attached sequence listing 29. The method of embodiment 28, wherein said enal-cleaving polypeptide is selected from the following group of mutants consisting of the following polypeptides and comprising the respective amino acid sequence:
    a) SCH94-3944-T51A_variant set forth in SEQ ID NO:91
    b) SCH94-3944-H53A_variant set forth in SEQ ID NO: 93
    c) SCH94-3944-L59A_variant set forth in SEQ ID NO:95
    d) SCH94-3944-W64A_variant set forth in SEQ ID NO:97
    e) SCH94-3944-S71A_variant set forth in SEQ ID NO:101
    f) SCH94-3944-R106A_variant set forth in SEQ ID NO:103
    g) SCH94-3944-Y115A_variant set forth in SEQ ID NO:105
    h) SCH94-3944-D116A_variant set forth in SEQ ID NO:107
    i) SCH94-3944-M136A_variant set forth in SEQ ID NO:111
    j) SCH94-3944-K139A_variant set forth in SEQ ID NO:113
    k) SCH94-3944-R156A_variant set forth in SEQ ID NO:119 and
    l) polypeptides comprising an amino acid sequence that has at least 90%, 95%, 96%, 97%, 98% or 99% sequence identity to any one of the amino acid sequences of a) to l) and retaining said enzymatic activity of degrading an terpene precursor of formula (1) and retaining said mutated amino acid sequence position.
30. The method of anyone of the embodiments 27 to 29, wherein a compound, for example a terpene-type compound, of formula V is applied, wherein $R^1$ represents H or methyl, $R^2$ represents H or
    a) a non-cyclic, linear or branched, saturated or unsaturated, hydrocarbyl residue having 1 to 20, in particular 1 to 10, 1 to 15 or 1 to 20 carbon atoms; or
    b) a group Cyc-A-, wherein A represents a straight chain or branched $C_1$-$C_4$-alkylene bridge, in particular methylene, and Cyc represents a mono- or polycyclic, in particular bicyclic, saturated or unsaturated hydrocarbyl residue, in particular a bicyclic annulated hydrocarbyl residue, comprising 5-7, in particular 6 ring atoms per cycle, optionally substituted with 1-10, 1-5 substituents which are independently selected from $C_1$-$C_4$-alkyl, $C_1$-$C_4$-alkylidene, $C_2$-$C_4$-alkenyl, oxo, hydroxy, or amino, in particular $C_1$-$C_4$-alkyl. like methyl, and $C_1$-$C_4$-alkylidene, like methylidene, each $R^3$ represents H, $R^4$ represents H or methyl, and $R^5$ represents H or methyl.
31. The method of embodiment 30 wherein the compound of general formula V possesses a labdane-type structure, and/or Cyc-A represents a residue of formula IIIa, IIIb or IIIc (IIIa)

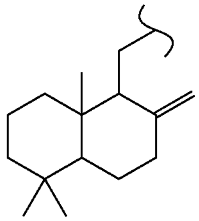

-continued (IIIb)

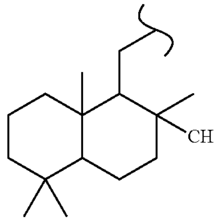

(IIIc)

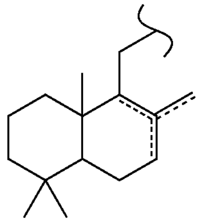

32. The method of any one of the embodiments 27 to 31, wherein the precursor of formula (V) is selected from farnesal, geranylgeranial, citral, dodecanal, labdane-type compounds, like 8-hydroxy-labd-13-en-15-al and copalal, each in the form of a mixture of its stereoisomers or in stereoisomerically pure form.

33. The method of one of the embodiments 27 to 32, wherein the degraded product of formula (IV) is selected from geranylacetone, farnesylacetone, methylheptenone, decanal; or manooloxy, or 8-hydroxy-14,15-dinorlabdan-13-one each in the form of a mixture of its stereoisomers or in stereoisomerically pure form.

Further particular inventive examples of enal-cleaving enzyme-catalyzed conversions of carbonyl compounds to the respective cleavage product are summarized in the following schematic overview:

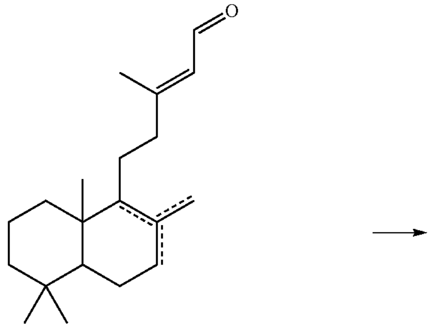

cis-labdane aldehyde isomers

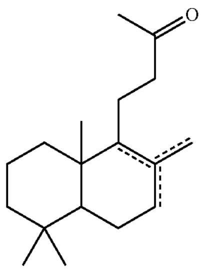

-continued

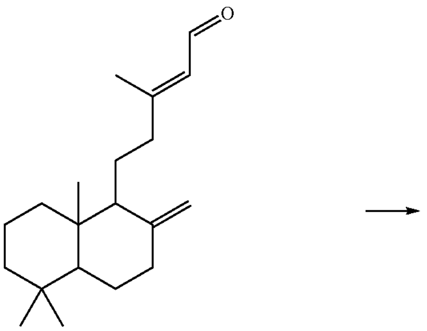

(13E)-labda-8(20), 13-dien-15-al(preferred labdane aldehyde)

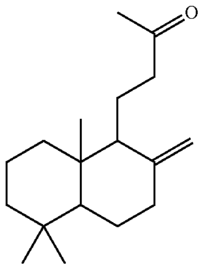

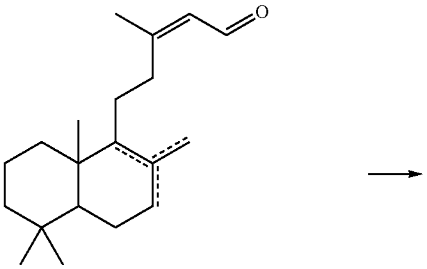

trans-labdane aldehyde isomers

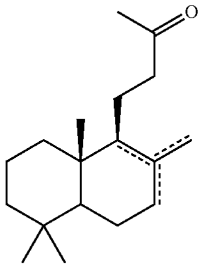

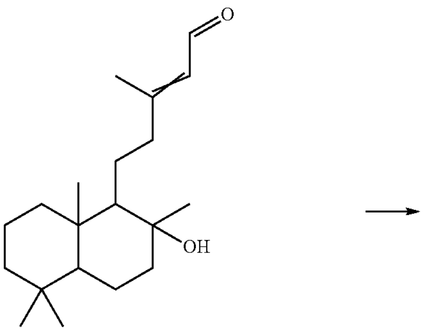

8-hydroxy-labdane aldehyde

-continued

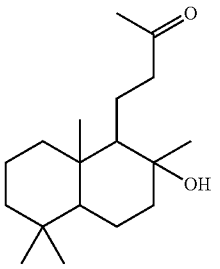

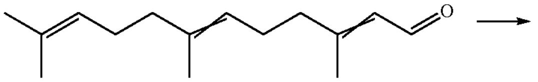

farnesal isomers

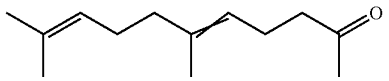

garanylacetone isomers

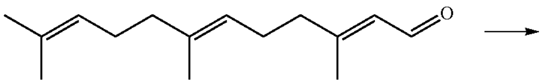

trans,trans-farnesal
(preferred farnesal)

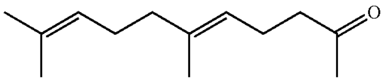

geranylacetone

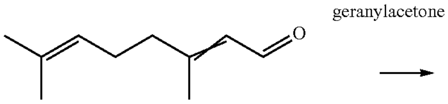

citral

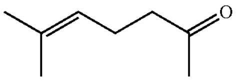

methylheptenone

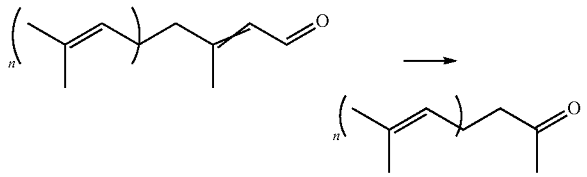

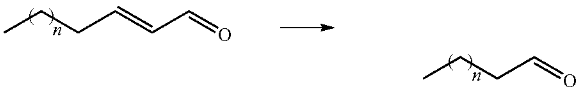

wherein parameter "n" is an integer from 1 to 20, 1 to 15, 1 to 10 or 1, 2, 3, 4 or 5.

34. The method of anyone of embodiments 27 to 33 performed in vitro or in vitro.

35. The method of embodiment 34 performed in vivo that comprises, prior to step (1), the recombinant expression, in particular in a non-human host cell, of one or more polypeptides having the enzyme activity required for performing the chain degradation step.

36. The method of embodiment 35, wherein the non-human host cell is transformed with a nucleic acid which is encoding at least one polypeptide having enal-cleaving activity.

37. The method of embodiment 35 or 36, wherein said non-human host cell is a eukaryotic or a prokaryotic cell, in particular a plant cell, a bacterial or a fungal cell, in particular a yeast cell.

38. The method of any one of embodiments 35 to 37, wherein the non-human host cell is a unicellular organism, a cultured cell derived from a multi-cellular organism, a cell present in a cultured tissue derived from a multicellular organism, or a cell present in a living multicellular organism.

39. The method of one of the embodiments 35 to 38, wherein the non-human host cell is a bacterium of the genus *Escherichia*, preferably *E. coli* and said yeast is of the genus *Saccharomyces*, or *Pichia*, preferably *S. cerevisiae*, or a plant cell.

40. The method of anyone of the embodiments 27 to 39 further comprising as step (3) the processing of the compound of formula IV formed in step (1) or isolated in step (2) to obtain a derivative thereof using chemical or biocatalytic synthesis or a combination of both, wherein said derivative may in particular be selected from a hydrocarbon, alcohol, diol, triol, acetal, ketal, aldehyde, acid, ether, amide, ketone, lactone, epoxide, acetate, glycoside and/or an ester and (4) optionally isolating the derivative of step (3).

41. The method of embodiment 40, wherein step (3) comprises the processing of the compound of formula IV formed in step (1) or isolated in step (2) with a polypeptide having Baeyer-Villiger monooxygenase (BVMO) activity so as to form the respective carbonyl ester.

42. The method of embodiment 41, further comprising the hydrolysis of the carbonyl ester compound with an esterase to the corresponding de-esterified product, which may be an alcohol or an isomerization product thereof, and and optionally isolating the derivative of step (3).

43. The method of embodiment 41, wherein the polypeptide having BVMO activity is as defined above in embodiment 9.

44. The method of embodiment 42, wherein the esterase is selected from the group consisting of
a) polypeptides comprising the amino acid sequence of SCH23-Esterase set forth in SEQ ID NO:20;
b) polypeptides comprising the amino acid sequence of SCH24-Esterase set forth in SEQ ID NO:24;
c) polypeptides comprising the amino acid sequence of SCH25-Esterase set forth in SEQ ID NO:28;
d) polypeptides comprising the amino acid sequence of SCH46-Esterase set forth in SEQ ID NO:31; or
e) polypeptides comprising an amino acid sequence that has at least 70%, 75%, 80%, 85%, 90%, 95%, 96%, 97%, 98%, or 99%, identity to any one of the amino acid sequences of a) to d) and having esterase activity.

45. The method of embodiment 41 to 44, wherein the carbonyl compound is a dinorlabdane ketone, in particular manooloxy, which is converted by said BVMO to the respective tetranorlabdanyl acetate, in particular to gamma-ambryl acetate.

46. The method of embodiment 45, wherein tetranorlabdanyl acetate, in particular gamma-ambryl acetate is deesterified by said esterase to the respective tetranorlabdane, in particular to gamma-ambrol.

47. The method of one of the preceding embodiments 27 to 46, which method comprises prior to step (1)

the biocatalytic oxidation of a labdane alcohol to a labdane aldehyde, in particular of copalol to copalal, which labdane alcohol is optionally formed by the biocatalytic conversion of at least one terpenly diphosphate precursor, selected from IPP, DMAPP, FPP and GGPP, in particular in a single step or a combination of at least two steps, known in the prior art.

Said labdane alcohol may for example be biocatalytically produced:

a) from geranylgeranyl diphosphate (GGPP) in one step in a cyclisation reaction/dephosphorylation reaction b) from GGPP in two steps by a cyclisation forming labdane diphosphate, as for example copalyl diphosphate (CPP) which is then dephosphorylated to the labdane alcohol;

c) from IPP and DMAPP which is directly converted through the action of a bifunctional GGPP synthase/CPP synthase to the labdane diphosphate, as for example CPP which is then dephosphorylated; GGPP as used in these steps may also be provided by different biocatalytic steps:

d) GGPP synthases are available which produce GGPP directly from IPP and DMAPP; or e) GGPP may be provided from IPP and DMAPP via FPP through the action of a FPP synthase, and the subsequent conversion of FPP to GGPP through the action of a GGPP synthase.

48. The method of embodiment 47, wherein said biocatalytic oxidation of a labdane alcohol, in particular of copalol to copalal, is catalyzed by an exogenous or endogenous polypeptide having alcohol dehydrogenase (ADH) (EC 1.1.1.-) activity; and/or said biocatalytic formation of the labdane alcohol comprises at least one step selected from i) a biocatalytic dephosphorylation of a labdane diphosphate to a labdane aldehyde, in particular of copalyl diphosphate (CPP) to copalol, which is catalyzed by a polypeptide having terpenyl diphosphate (TPP) phosphatase activity, and/or ii) a biocatalytic cyclisation of a terpenly diphosphate precursor, as for example of geranylgeranyl diphosphate (GGPP) to CPP, which is catalyzed by a polypeptide having CPP synthase activity, like SmCPS2 (SEQ ID NO: 185); or as for example of IPP and DMAPP to CPP, which is catalyzed by a bifunctional polypeptide having prenyl-transferase and copalyl-diphosphate synthase activity, like PvCPS, and/or iii) a biocatalytic formation of GGPP from FPP or a biocatalytic formation from IPP and DMAPP, each of which being catalyzed by a polypeptide having GGPP synthase activity.

49. The method of embodiment 48, wherein said biocatalytic oxidation, in particular of copalol to copalal, is catalyzed by a polypeptide having alcohol dehydrogenase (ADH) activity selected from a) polypeptides comprising the amino acid sequence of SCH23-ADH1_wt set forth in SEQ ID NO: 134 b) polypeptides comprising the amino acid sequence of SCH24-ADH1_wt set forth in SEQ ID NO: 140 c) polypeptides comprising the amino acid sequence of SCH94-3945_wt set forth in SEQ ID NO:161 d) polypeptides comprising the amino acid sequence of SCH80-0540_wt set forth in SEQ ID NO:164 e) polypeptides comprising the amino acid sequence of AzTolADH1_wt set forth in SEQ ID NO:167 f) polypeptides comprising the amino acid sequence of CdGeoA_wt set forth in SEQ ID NO:179 g) polypeptides comprising an amino acid sequence that has at least 70%, 75%, 80%, 85%, 90%, 95%, 96%, 97%, 98%, or 99% identity to any one of the amino acid sequences of a) to f) and having ADH activity.

and/or said biocatalytic dephosphorylation, in particular of copalyl diphosphate (CPP) to copalol, is catalyzed by a polypeptide having terpenyl diphosphate (TPP) phosphatase activity selected from d) polypeptides comprising an amino acid sequence of AspWE TPP as set forth in SEQ ID NO:170 or a polypeptide comprising an amino acid sequence that has at least 70%, 75%, 80%, 85%, 90%, 95%, 96%, 97%, 98%, or 99% identity thereto;

e) polypeptides comprising an amino acid sequence of TalCeTPP as set forth in SEQ ID NO: 176 or a polypeptide comprising an amino acid sequence that has at least 70%, 75%, 80%, 85%, 90%, 95%, 96%, 97%, 98%, or 99% identity thereto; and f) polypeptides comprising an amino acid sequence of TalVeTPP as set forth in SEQ ID NO: 194 or a polypeptide comprising an amino acid sequence that has at least 70%, 75%, 80%, 85%, 90%, 95%, 96%, 97%, 98%, or 99% identity thereto;

Further suitable phosphatases are also disclosed in earlier the applicant's EP application number 18182783.3, incorporated by reference.

and/or said biocatalytic cyclisation, in particular of geranylgeranyl diphosphate (GGPP) to CPP, is catalyzed by a polypeptide selected from polypeptides having copalyl-diphosphate synthase activity comprising the amino acid sequence of SmCPS2 as set forth in SEQ ID NO:185 or a polypeptide comprising an amino acid sequence that has at least 70%, 75%, 80%, 85%, 90%, 95%, 96%, 97%, 98%, or 99% 70% identity thereto;

said biocatalytic cyclisation, in particular of IPP and DNMAPP to CPP, is catalyzed by a polypeptide selected from polypeptides having prenyl-transferase and copalyl-diphosphate synthase activities comprising the amino acid sequence of PvCPS as set forth in SEQ ID NO:173 or a polypeptide comprising an amino acid sequence that has at least 70%, 75%, 80%, 85%, 90%, 95%, 96%, 97%, 98%, or 99% identity thereto;

and/or said biocatalytic formation of GGPP is catalyzed by a polypeptide having GGPP synthase activity and is selected from d) polypeptides comprising the amino acid sequence of carG as set forth in SEQ ID NO:182 or a polypeptide comprising an amino acid sequence that has at least 70%, 75%, 80%, 85%, 90%, 95%, 96%, 97%, 98%, or 99% identity thereto;

e) polypeptides comprising the amino acid sequence of CrtE as set forth in SEQ ID NO:191 or a polypeptide comprising an amino acid sequence that has at least 70%, 75%, 80%, 85%, 90%, 95%, 96%, 97%, 98%, or 99% identity thereto;

f) polypeptides comprising the amino acid sequence of PvCPS as set forth in SEQ ID NO:173 or a polypeptide comprising an amino acid sequence that has at least 70%, 75%, 80%, 85%, 90%, 95%, 96%, 97%, 98%, or 99% identity thereto.

iii) The present invention relates to the following particular embodiments related to enal-cleaving enzymes and corresponding coding sequences 50. An isolated polypeptide having enal-cleaving activity in particular the activity of an α,β-unsaturated aldehyde C═C bond-cleaving enzyme, as defined in anyone of the embodiments 28 and 29.

The polypeptides of the invention include all active forms, including active subsequences, e.g., catalytic domains or active sites, of an enzyme with enal cleaving activity.

51. An isolated nucleic acid molecule comprising a nucleic acid sequence encoding a polypeptide of embodiment 50 in particular a nucleic acid sequence selected from SEQ ID NOs: 33, 35, 36, 37, 39, 40, 41, 43, 44, 45, 47, 48, 50, 51, 52, 54, 55, 57, 58, 60, 61, 63, 64, 68, 70, 71, 73, 74, 76, 80, 82, 86, 88, 92, 94, 96, 98, 102, 104, 106, 108, 112, and 120, and nucleic acid sequences having a degree of sequence identity of at least 70%, 75%, 80%, 85%, 90%, 95%, 96%, 97%, 98%, or 99% to any one of said sequences of SEQ ID NO: 33, 35, 36, 37, 39, 40, 41, 43, 44, 45, 47, 48, 50, 51, 52, 54, 55, 57, 58, 60, 61, 63, 64, 68, 70, 71, 73, 74, 76, 80, 82, 86, 88, 92, 94, 96, 98, 102, 104, 106, 108, 112, and 120.

52. An expression cassette comprising the nucleotide sequence of at least one nucleic acid molecule of embodiment 50.

53. An expression vector comprising the nucleotide sequence of at least one nucleic acid molecule of embodiment 51, or at least one expression cassette of embodiment 52.

54. The expression vector of embodiment 53, wherein the vector is a prokaryotic vector, viral vector or eukaryotic vector.

55. The expression vector of anyone of the embodiments 53 to 54, which is a plasmid or a combination of two or more plasmids.

56. A recombinant non-human host cell comprising at least one nucleic acid molecule as defined in embodiment 51, or at least one expression cassette of embodiment 52, or at least one expression vector of any one of embodiments 53 to 55.

57. The host cell of embodiment 56, wherein the at least one nucleic acid molecule or the at least one expression cassette is stably integrated into the genome of the cell.

58. The host cell of embodiment 56 or 57 which is a prokaryotic or eukaryotic cell, in particular a plant cell, a bacterium or a fungal cell, in particular a yeast.

59. The host cell of anyone of the embodiments 56 to 58 which is a unicellular organism, a cultured cell derived from a multi-cellular organism, a cell present in a cultured tissue derived from a multicellular organism, or a cell present in a living multicellular organism.

60. The host cell of embodiment 59 which is a bacterium of the genus *Escherichia*, preferably *E. coli*, or a yeast cells of the genus *Saccharomyces*, preferably *S. cerevisiae*, or of the genus *Pichia*, preferably *P. pastoris*.

61. A method of producing at least one polypeptide having enal-cleaving activity according to embodiment 51, the method comprising:

(i) expressing said at least one polypeptide in a non-human host cell of any one of embodiments 57 to 60; and (ii) optionally isolating said at least one polypeptide from the non-human host cell used in step (i).

62. The method of embodiment 61 further comprising, prior to step (i): preparing the non-human host cell used in step (i) by introducing at least on nucleic acid molecule as defined in embodiment 51, or at least one expression cassette of embodiment 52, or at least one expression vector of any one of embodiments 53 to 55 into a non-human cell, thus yielding a host cell capable of expressing or over-expressing the at least one polypeptide having enal cleaving activity according to embodiment 50.

63. A method for preparing a mutant polypeptide having enal-cleaving activity, which method comprises the steps of:

(i) providing a nucleic acid molecule according to embodiment 51;

(ii) modifying the nucleotide sequence of said nucleic acid molecule, in particular the nucleotide sequence encoding a polypeptide of embodiment 50, so as to obtain at least one mutant nucleic acid molecule;

(iii) recombinantly expressing said mutant nucleic acid molecule in a non-human host cell;

(iv) screening the expression product obtained in step (iii) for at least one mutant polypeptide having enal cleaving activity; and (v) optionally repeating steps (ii) to (iv) with the mutant nucleic acid molecule until the expression product comprises a mutant polypeptide having the desired enal cleaving activity; and (vi) optionally isolating the mutant polypeptide having the desired enal cleaving activity.

iv) The present invention relates to the following particular embodiments related to BVMO enzymes and corresponding coding sequences 64. An isolated polypeptide having BVMO activity, as defined in embodiment 9.

The polypeptides of the invention include all active forms, including active subsequences, e.g., catalytic domains or active sites, of an enzyme with BVMO activity.

65. An isolated nucleic acid molecule comprising a nucleic acid sequence encoding a polypeptide of embodiment 64, in particular a nucleic acid sequence selected from SEQ ID NOs: 1, 3, 4, 5, 7, 8, 9, 11, 12, 14, 15, 17 and 18 and nucleic acid sequences having a degree of sequence identity of at least 70%, 75%, 80%, 85%, 90%, 95%, 96%, 97%, 98%, or 99% to any one of said sequences of SEQ ID NO: 1, 3, 4, 5, 7, 8, 9, 11, 12, 14, 15, 17 and 18.

66. An expression cassette comprising the nucleotide sequence of at least one nucleic acid molecule of embodiment 65.

67. An expression vector comprising the nucleotide sequence of at least one nucleic acid molecule of embodiment 65, or at least one expression cassette of embodiment 66.

68. The expression vector of embodiment 67, wherein the vector is a prokaryotic vector, viral vector or eukaryotic vector.

69. The expression vector of anyone of the embodiments 67 to 68, which is a plasmid or a combination of two or more plasmids.

70. A recombinant non-human host cell comprising at least one nucleic acid molecule as defined in embodiment 65, or at least one expression cassette of embodiment 66, or at least one expression vector of any one of embodiments 67 to 69.
71. The host cell of embodiment 70, wherein the at least one nucleic acid molecule or the at least one expression cassette is stably integrated into the genome of the cell.
72. The host cell of embodiment 70 or 71 which is a prokaryotic or eukaryotic cell, in particular a plant cell, a bacterium or a fungal cell, in particular a yeast.
73. The host cell of anyone of the embodiments 70 to 72 which is a unicellular organism, a cultured cell derived from a multi-cellular organism, a cell present in a cultured tissue derived from a multicellular organism, or a cell present in a living multicellular organism.
74. The host cell of embodiment 72 which is a bacterium of the genus *Escherichia*, preferably *E. coli*, or a yeast cells of the genus *Saccharomyces*, preferably *S. cerevisiae*, or of the genus *Pichia*, preferably *P. pastoris.*
75. A method of producing at least one polypeptide having BVMO activity according to embodiment 64, the method comprising:
    (i) expressing said at least one polypeptide in a non-human host cell of any one of embodiments 70 to 74; and
    (ii) optionally isolating said at least one polypeptide from the non-human host cell used in step (i).
76. The method of embodiment 75 further comprising, prior to step (i): preparing the non-human host cell used in step (i) by introducing at least on nucleic acid molecule as defined in embodiment 65, or at least one expression cassette of embodiment 66, or at least one expression vector of any one of embodiments 67 to 69 into a non-human cell, thus yielding a host cell capable of expressing or over-expressing the at least one polypeptide having BVMO activity according to embodiment 64.
77. A method for preparing a mutant polypeptide having BVMO activity, which method comprises the steps of:
    (i) providing a nucleic acid molecule according to embodiment 65;
    (ii) modifying the nucleotide sequence of said nucleic acid molecule, in particular the nucleotide sequence encoding a polypeptide of embodiment 64, so as to obtain at least one mutant nucleic acid molecule;
    (iii) recombinantly expressing said mutant nucleic acid molecule in a non-human host cell;
    (iv) screening the expression product obtained in step (iii) for at least one mutant polypeptide having BVMO activity; and
    (v) optionally repeating steps (ii) to (iv) with the mutant nucleic acid molecule until the expression product comprises a mutant polypeptide having the desired BVMO activity; and
    (vi) optionally isolating the mutant polypeptide having the desired BVMO activity.

v) The present invention relates to the following particular embodiments related to biocatalytic multistep in vivo methods of converting labdane compounds by applying polypeptides with enal-cleaving activity and/or BVMO activity 78. An in vivo method for preparing labdane-type terpenes which method comprises providing a recombinant host expressing a set of polypeptides having enzymatic activities required for catalyzing the following sequence of reaction steps
    (1) optionally converting a labdane alcohol, in particular a copalol, to the respective labdane aldehyde, in particular a copalal, through the enzymatic action of an exogenous or endogenous ADH polypeptide, in particular an ADH as defined in anyone of the embodiments 19 or 49;
    (2) converting said ladbane aldehyde of step (1), in particular a copalal, to the respective dinorlabdane carbonyl compound, in particular manooloxy, through the action a polypeptide having enal-cleaving activity, in particular a polypeptide as defined in anyone of the embodiments 28 and 29;
    (3) optionally converting said dinorlabdane carbonyl compound of step (2), in particular manooloxy, to the respective tetranorlabdanyl acetate, in particular to gamma-ambryl acetate through the action a polypeptide having BVMO activity, in particular BVMO as defined in embodiment 9;
    (4) optionally converting said tetranorlabdanyl acetate of step (3), in particular to gamma-ambryl acetate, to the respective tetranorlabdane alcohol, in particular gamma, ambrol, through the action a polypeptide having esterase activity, in particular an esterase as defined in anyone of the embodiment 23 and 44; and optionally
    (5) isolating the product of step (2), (3) or (4).
79. An in vivo method for preparing labdane-type cycloterpenes which method comprises providing a recombinant host expressing a set of polypeptides having enzymatic activities required for catalyzing the following sequence of reaction steps
    (1) optionally converting a labdane alcohol, in particular a copalol, to the respective labdane aldehyde, in particular a copalal, through the enzymatic action of an exogenous or endogenous ADH polypeptide, in particular an ADH as defined in anyone of the embodiments 19 or 49;
    (2) converting said labdane aldehyde of step (1), in particular a copalal, to the respective norlabdane ester compound, in particular [4-[(1S,4aS,8aS)-5,5,8a-trimethyl-2-methylene-decalin-1-yl]-2-methyl-but-1-enyl]formate (compound 1a, 1b), through the action a polypeptide having BVMO activity, in particular a BVMO as defined in anyone of the embodiments 9;
    (3) converting said labdane ester compound of step (2), in particular in particular [4-[(1S,4aS,8aS)-5,5,8a-trimethyl-2-methylene-decalin-1-yl]-2-methyl-but-1-enyl]formate (compound 1a, 1b) to the respective norlabdane aldehyde, in particular 4-[(1S,8aS)-5,5,8a-trimethyl-2-methylene-decalin-1-yl]-2-methyl-butanal (compound 3a, 3b), optionally through the action a polypeptide having esterase activity, in particular an esterase as defined in anyone of the embodiments 23 or 44;
    (4) converting said norlabdane aldehyde of step (3), in particular 4-[(1S,4aS,8aS)-5,5,8a-trimethyl-2-methylene-decalin-1-yl]-2-methyl-butanal (compound 3a, 3b), to the respective dinorlabdane ester, in particular [3-[(1S,4aS,8aS)-5,5,8a-trimethyl-2-methylene-decalin-1-yl]-1-methyl-propyl]formate (compound 4a, 4b), through the action a polypeptide having BVMO activity, in particular a BVMO as defined in anyone of the embodiments 9;
    (5) converting said dinorlabdane ester of step (4) in particular [3-[(1S,4aS,8aS)-5,5,8a-trimethyl-2-methylene-decalin-1-yl]-1-methyl-propyl]formate (compound 4a, 4b), to the respective dinorlabdane alcohol, in particular 4-[(1S,4aS,8aS)-5,5,8a-trimethyl-2-methylene-decalin-1-yl]butan-2-ol, (compound 5a, 5b), through the action a polypeptide having esterase activity, in particular an esterase as defined in anyone of the embodiments 23 or 44;

(6) optionally converting said dinorlabdane alcohol of step (5), in particular 4-[(1S,8aS)-5,5,8a-trimethyl-2-methylene-decalin-1-yl]butan-2-ol, (compound 5a, 5b), to the respective dinorlabdane carbonyl compound, in particular manooloxy, through the action an exogenous or endogenous polypeptide having ADH activity, in particular an ADH as defined in anyone of the embodiments 19 or 49;

(7) optionally converting said dinorlabdane carbonyl compound of step (6), in particular manooloxy, to the respective tetranorlabdanyl acetate, in particular to gamma-ambryl acetate through the action a polypeptide having BVMO activity, in particular a BVMO as defined in anyone of the embodiments 9;

(8) converting said tetranorlabdanyl acetate of step (7), in particular to gamma-ambryl acetate, to the respective tetranorlabdane alcohol, in particular gamma, ambrol through the action a polypeptide having esterase activity, in particular an esterase as defined in anyone of the embodiments 23 or 44; and optionally (9) isolating the product of step (5), (6), (7) or (8).

80. The method of embodiment 79, wherein the ADHs as applied in steps (1) and (6) are identical or different; exogenous or endogenous, and/or the BVMOs as applied in steps (2), (4) and (7) are identical or different; and/or the esterases as applied in steps (3), (5) and (8) are identical or different.

81. The method of anyone of the embodiments 78 to 80, wherein a recombinant host is applied additionally expressing a set of polypeptides having enzymatic activities required for catalyzing the following sequence of reaction steps in advance of step (1):

(i) the biocatalytic formation of geranylgeranyl diphosphate (GGPP) through the action a polypeptide having GGPP synthase activity, in particular a GGPP synthase as defined in anyone of the embodiments 19 and 49;

(ii) the biocatalytic cyclisation of GGPP to said labdane diphosphate, in particular to a copalyl diphosphate (CPP) through the action a polypeptide having labdane diphosphate synthase activity, in particular a polypeptide comprising CPP synthase activity as defined in anyone of embodiments 19 and 49;

(iii) the biocatalytic dephosphorylation of said labdane diphosphate to said labdane alcohol, in particular of CPP to copalol, through the action a polypeptide having labdane diphosphate phosphatase activity, in particular a polypeptide comprising TPP phosphatase activity as defined in anyone of embodiments 19 and 49.

82. The method of anyone of the embodiments 78 to 81, wherein a recombinant host is applied additionally expressing at least one of the polypeptide catalyzing an enzymatic step of the mevalonate pathway or the MEP pathway.

83. The method of one of the embodiments 78 to 82 wherein the a recombinant host is applied which carries the coding sequences of the respective catalytically active polypeptides on one or more expression vectors and/or stably integrated into the genome of the host.

84. The method of anyone of the embodiments 1 to 49 and 78 to 83 performed in vivo, which comprises prior to step (1) introducing into a non-human host organism or cell and optionally stably integrated into the respective genome; one or more nucleic acid molecules encoding one or more polypeptides having the enzyme activities required for performing the respective biocatalytic conversion step or steps.

85. The method of anyone of the embodiments 1 to 49 and 78 to 83 performed by applying a non-human host organism or cell endogenously producing FPP and/or GGPP; or a mixture of IPP and DMAPP; or a non-human host organism which is genetically modified to produce increased amounts of FPP and/or of GGPP and/or of a mixture of IPP and DMAPP.

Some of these host cells or organisms applicable in the invention do not produce FPP or GGPP or a mixture of IPP and DMAPP naturally. Such organisms or cells that do not produce an acyclic terpene pyrophosphate precursor, e.g. FPP or GGPP or a mixture of IPP and DMAPP, naturally may be genetically modified to produce said precursor. They can be, for example, so transformed either before the modification with nucleic acids described herein. Methods to transform organisms so that they produce an acyclic terpene pyrophosphate precursor, e.g. FPP or GGPP or a mixture of IPP and DMAPP, are already known in the art. For example, introducing enzyme activities of the mevalonate pathway, is a suitable strategy to make the organism produce FPP or GGPP or a mixture of IPP and DMAPP.

86. The recombinant microorganism as defined in anyone of the embodiments 78 to 85.

vi) The present invention relates to the following particular embodiments related to the further conversion of chemical intermediate compounds as obtained by a biocatalytic method described herein to further final products of particular interest 87. A method of preparing an epoxy-tetranorlabdane compound, in particular ambrox, which method comprises (1) providing a tetranorlabdane alcohol, in particular gamma-ambrol, or a tetranorlabdane acetate, in particular gamma-ambryl acetate, or a dinorlabdane carbonyl compound, in particular manooloxy, by applying a biocatalytic method comprising one or more method steps as defined in anyone of the claims herein, optionally isolating said product; and (2) converting said product of step (1) to epoxy-tetranorlabdane in particular ambrox, by applying one or more chemical and/or biochemical conversion steps.

88. A method of preparing a diepoxy-dinorlabdabe, in particular Z11, which method comprises (1) providing a dinorlabdane carbonyl compound, in particular manooloxy by applying a method which results in the formation of said dinorlabdane carbonyl compound, in particular manooloxy and which comprising one or more method steps as defined in anyone of the claims herein, optionally isolating said dinorlabdane carbonyl compound, in particular manooloxy; and (2) converting said dinorlabdane carbonyl compound, in particular manooloxy of step (1) to said diepoxy-dinorlabdabe, in particular Z-11, by applying one or more chemical and/or biochemical conversion steps.

b. Polypeptides Applicable According to the Invention

In this context the following definitions apply:

The generic terms "polypeptide" or "peptide", which may be used interchangeably, refer to a natural or synthetic linear chain or sequence of consecutive, peptidically linked amino acid residues, comprising about 10 to up to more than 1.000 residues. Short chain polypeptides with up to 30 residues are also designated as "oligopeptides".

The term "protein" refers to a macromolecular structure consisting of one or more polypeptides. The amino acid sequence of its polypeptide(s) represents the "primary structure" of the protein. The amino acid sequence also predetermines the "secondary structure" of the protein by the formation of special structural elements, such as alpha-helical and beta-sheet structures formed within a polypeptide chain. The arrangement of a plurality of such secondary structural elements defines the "tertiary structure" or spatial arrangement of the protein. If a protein comprises more than one polypeptide chains said chains are spatially arranged forming the "quaternary structure" of the protein. A correct spacial arrangement or "folding" of the protein is prerequisite of protein function. Denaturation or unfolding destroys protein function. If such destruction is reversible, protein function may be restored by refolding.

A typical protein function referred to herein is an "enzyme function", i.e. the protein acts as biocatalyst on a substrate, for example a chemical compound, and catalyzes the conversion of said substrate to a product. An enzyme may show a high or low degree of substrate and/or product specificity.

A "polypeptide" referred to herein as having a particular "activity" thus implicitly refers to a correctly folded protein showing the indicated activity, as for example a specific enzyme activity.

Thus, unless otherwise indicated the term "polypeptide" also encompasses the terms "protein" and "enzyme".

Similarly, the term "polypeptide fragment" encompasses the terms "protein fragment" and "enzyme fragment".

The term "isolated polypeptide" refers to an amino acid sequence that is removed from its natural environment by any method or combination of methods known in the art and includes recombinant, biochemical and synthetic methods.

"Target peptide" refers to an amino acid sequence which targets a protein, or polypeptide to intracellular organelles, i.e., mitochondria, or plastids, or to the extracellular space (secretion signal peptide). A nucleic acid sequence encoding a target peptide may be fused to the nucleic acid sequence encoding the amino terminal end, e.g., N-terminal end, of the protein or polypeptide, or may be used to replace a native targeting polypeptide.

The present invention also relates to "functional equivalents" (also designated as "analogs" or "functional mutations") of the polypeptides specifically described herein.

For example, "functional equivalents" refer to polypeptides which, in a test used for determining enzymatic terpenyl diphosphate synthase activity, or terpenyl diphosphate phosphatase activity display at least a 1 to 10%, or at least 20%, or at least 50%, or at least 75%, or at least 90% higher or lower activity, as that of the polypeptides specifically described herein.

"Functional equivalents", according to the invention, also cover particular mutants, which, in at least one sequence position of an amino acid sequences stated herein, have an amino acid that is different from that concretely stated one, but nevertheless possess one of the aforementioned biological activities, as for example enzyme activity. "Functional equivalents" thus comprise mutants obtainable by one or more, like 1 to 20, in particular 1 to 15 or 5 to 10 amino acid additions, substitutions, in particular conservative substitutions, deletions and/or inversions, where the stated changes can occur in any sequence position, provided they lead to a mutant with the profile of properties according to the invention. Functional equivalence is in particular also provided if the activity patterns coincide qualitatively between the mutant and the unchanged polypeptide, i.e. if, for example, interaction with the same agonist or antagonist or substrate, however at a different rate, (i.e. expressed by a $EC_{50}$ or $IC_{50}$ value or any other parameter suitable in the present technical field) is observed. Examples of suitable (conservative) amino acid substitutions are shown in the following table:

| Original residue | Examples of substitution |
|---|---|
| Ala | Ser |
| Arg | Lys |
| Asn | Gln; His |
| Asp | Glu |
| Cys | Ser |
| Gln | Asn |
| Glu | Asp |
| Gly | Pro |
| His | Asn; Gln |
| He | Leu; Val |
| Leu | Ile; Val |
| Lys | Arg; Gln; Glu |
| Met | Leu; He |
| Phe | Met; Leu; Tyr |
| Ser | Thr |
| Thr | Ser |
| Trp | Tyr |
| Tyr | Trp; Phe |
| Val | Ile; Leu |

"Functional equivalents" in the above sense are also "precursors" of the polypeptides described herein, as well as "functional derivatives" and "salts" of the polypeptides.

"Precursors" are in that case natural or synthetic precursors of the polypeptides with or without the desired biological activity.

The expression "salts" means salts of carboxyl groups as well as salts of acid addition of amino groups of the protein molecules according to the invention. Salts of carboxyl groups can be produced in a known way and comprise inorganic salts, for example sodium, calcium, ammonium, iron and zinc salts, and salts with organic bases, for example amines, such as triethanolamine, arginine, lysine, piperidine and the like. Salts of acid addition, for example salts with inorganic acids, such as hydrochloric acid or sulfuric acid and salts with organic acids, such as acetic acid and oxalic acid, are also covered by the invention.

"Functional derivatives" of polypeptides according to the invention can also be produced on functional amino acid side groups or at their N-terminal or C-terminal end using known techniques. Such derivatives comprise for example aliphatic esters of carboxylic acid groups, amides of carboxylic acid groups, obtainable by reaction with ammonia or with a primary or secondary amine; N-acyl derivatives of free amino groups, produced by reaction with acyl groups; or O-acyl derivatives of free hydroxyl groups, produced by reaction with acyl groups.

"Functional equivalents" naturally also comprise polypeptides that can be obtained from other organisms, as well as naturally occurring variants. For example, areas of homologous sequence regions can be established by sequence comparison, and equivalent polypeptides can be determined on the basis of the concrete parameters of the invention.

"Functional equivalents" also comprise "fragments", like individual domains or sequence motifs, of the polypeptides according to the invention, or N- and or C-terminally truncated forms, which may or may not display the desired biological function. Preferably such "fragments" retain the desired biological function at least qualitatively.

"Functional equivalents" are, moreover, fusion proteins, which have one of the polypeptide sequences stated herein or functional equivalents derived there from and at least one further, functionally different, heterologous sequence in functional N-terminal or C-terminal association (i.e. without substantial mutual functional impairment of the fusion protein parts). Non-limiting examples of these heterologous sequences are e.g. signal peptides, histidine anchors or enzymes.

"Functional equivalents" which are also comprised in accordance with the invention are homologs to the specifically disclosed polypeptides. These have at least 60%, preferably at least 75%, in particular at least 80 or 85%, such as, for example, 90, 91, 92, 93, 94, 95, 96, 97, 98 or 99%, homology (or identity) to one of the specifically disclosed amino acid sequences, calculated by the algorithm of Pearson and Lipman, Proc. Natl. Acad, Sci. (USA) 85(8), 1988, 2444-2448. A homology or identity, expressed as a percentage, of a homologous polypeptide according to the invention means in particular an identity, expressed as a percentage, of the amino acid residues based on the total length of one of the amino acid sequences described specifically herein.

The identity data, expressed as a percentage, may also be determined with the aid of BLAST alignments, algorithm blastp (protein-protein BLAST), or by applying the Clustal settings specified herein below.

In the case of a possible protein glycosylation, "functional equivalents" according to the invention comprise polypeptides as described herein in deglycosylated or glycosylated form as well as modified forms that can be obtained by altering the glycosylation pattern.

Functional equivalents or homologues of the polypeptides according to the invention can be produced by mutagenesis, e.g. by point mutation, lengthening or shortening of the protein or as described in more detail below.

Functional equivalents or homologs of the polypeptides according to the invention can be identified by screening combinatorial databases of mutants, for example shortening mutants. For example, a variegated database of protein variants can be produced by combinatorial mutagenesis at the nucleic acid level, e.g. by enzymatic ligation of a mixture of synthetic oligonucleotides. There are a great many methods that can be used for the production of databases of potential homologues from a degenerated oligonucleotide sequence. Chemical synthesis of a degenerated gene sequence can be carried out in an automatic DNA synthesizer, and the synthetic gene can then be ligated in a suitable expression vector. The use of a degenerated genome makes it possible to supply all sequences in a mixture, which code for the desired set of potential protein sequences. Methods of synthesis of degenerated oligonucleotides are known to a person skilled in the art.

In the prior art, several techniques are known for the screening of gene products of combinatorial databases, which were produced by point mutations or shortening, and for the screening of cDNA libraries for gene products with a selected property. These techniques can be adapted for the rapid screening of the gene banks that were produced by combinatorial mutagenesis of homologues according to the invention. The techniques most frequently used for the screening of large gene banks, which are based on a high-throughput analysis, comprise cloning of the gene bank in expression vectors that can be replicated, transformation of the suitable cells with the resultant vector database and expression of the combinatorial genes in conditions in which detection of the desired activity facilitates isolation of the vector that codes for the gene whose product was detected. Recursive Ensemble Mutagenesis (REM), a technique that increases the frequency of functional mutants in the databases, can be used in combination with the screening tests, in order to identify homologues.

An embodiment provided herein provides orthologs and paralogs of polypeptides disclosed herein as well as methods for identifying and isolating such orthologs and paralogs. A definition of the terms "ortholog" and "paralog" is given below and applies to amino acid and nucleic acid sequences.

The polypeptides of the invention include all active forms, including active subsequences, e.g., catalytic domains or active sites, of an enzyme of the invention. In one aspect, the invention provides catalytic domains or active sites as set forth below. In one aspect, the invention provides a peptide or polypeptide comprising or consisting of an active site domain as predicted through use of a database such as Pfam (pfam.wustl.edu/hmmsearch.shtml) (which is a large collection of multiple sequence alignments and hidden Markov models covering many common protein families, The Pfam protein families database, A. Bateman, E. Birney, L. Cerruti, R. Durbin, L. Etwiller, S. R. Eddy, S. Griffiths-Jones, K. L. Howe, M. Marshall, and E. L. L. Sonnhammer, Nucleic Acids Research, 30(1):276-280, 2002) or equivalent, as for example InterPro and SMART databases (www.ebi.ac.uk/interpro/scan.html, smart.embl-heidelberg.de/).

The invention also encompasses "polypeptide variant" having the desired activity, wherein the variant polypeptide is selected from an amino acid sequence having at least 40%, 45%, 50%, 55%, 60%, 65%, 70%, 75%, 80%, 85%, 90%, 91%, 92%, 93%, 94%, 95%, 96%, 97%, 98% or 99%, sequence identity to a specific, in particular natural, amino acid sequence as referred to by a specific SEQ ID NO and contains at least one substitution modification relative said SEQ ID NO.

c. Coding Nucleic Acid Sequences Applicable According to the Invention

In this context the following definitions apply:

The terms "nucleic acid sequence," "nucleic acid," "nucleic acid molecule" and "polynucleotide" are used interchangeably meaning a sequence of nucleotides. A nucleic acid sequence may be a single-stranded or double-stranded deoxyribonucleotide, or ribonucleotide of any length, and include coding and non-coding sequences of a gene, exons, introns, sense and anti-sense complimentary sequences, genomic DNA, cDNA, miRNA, siRNA, mRNA, rRNA, tRNA, recombinant nucleic acid sequences, isolated and purified naturally occurring DNA and/or RNA sequences, synthetic DNA and RNA sequences, fragments, primers and nucleic acid probes. The skilled artisan is aware that the nucleic acid sequences of RNA are identical to the DNA sequences with the difference of thymine (T) being replaced by uracil (U). The term "nucleotide sequence" should also be understood as comprising a polynucleotide molecule or an oligonucleotide molecule in the form of a separate fragment or as a component of a larger nucleic acid.

An "isolated nucleic acid" or "isolated nucleic acid sequence" relates to a nucleic acid or nucleic acid sequence that is in an environment different from that in which the nucleic acid or nucleic acid sequence naturally occurs and can include those that are substantially free from contaminating endogenous material.

The term "naturally-occurring" as used herein as applied to a nucleic acid refers to a nucleic acid that is found in a cell of an organism in nature and which has not been intentionally modified by a human in the laboratory.

A "fragment" of a polynucleotide or nucleic acid sequence refers to contiguous nucleotides that is particularly at least 15 bp, at least 30 bp, at least 40 bp, at least 50 bp and/or at least 60 bp in length of the polynucleotide of an embodiment herein. Particularly the fragment of a polynucleotide comprises at least 25, more particularly at least 50, more particularly at least 75, more particularly at least 100, more particularly at least 150, more particularly at least 200, more particularly at least 300, more particularly at least 400, more particularly at least 500, more particularly at least 600, more particularly at least 700, more particularly at least 800, more particularly at least 900, more particularly at least 1000 contiguous nucleotides of the polynucleotide of an embodiment herein. Without being limited, the fragment of the polynucleotides herein may be used as a PCR primer, and/or as a probe, or for anti-sense gene silencing or RNAi.

As used herein, the term "hybridization" or hybridizes under certain conditions is intended to describe conditions for hybridization and washes under which nucleotide sequences that are significantly identical or homologous to each other remain bound to each other. The conditions may be such that sequences, which are at least about 70%, such as at least about 80%, and such as at least about 85%, 90%, or 95% identical, remain bound to each other. Definitions of low stringency, moderate, and high stringency hybridization conditions are provided herein below. Appropriate hybridization conditions can also be selected by those skilled in the art with minimal experimentation as exemplified in Ausubel et al. (1995, *Current Protocols in Molecular Biology*, John Wiley & Sons, sections 2, 4, and 6). Additionally, stringency conditions are described in Sambrook et al. (1989, *Molecular Cloning: A Laboratory Manual,* 2nd ed., Cold Spring Harbor Press, chapters 7, 9, and 11).

"Recombinant nucleic acid sequences" are nucleic acid sequences that result from the use of laboratory methods (for example, molecular cloning) to bring together genetic material from more than on source, creating or modifying a nucleic acid sequence that does not occur naturally and would not be otherwise found in biological organisms.

"Recombinant DNA technology" refers to molecular biology procedures to prepare a recombinant nucleic acid sequence as described, for instance, in Laboratory Manuals edited by Weigel and Glazebrook, 2002, Cold Spring Harbor Lab Press; and Sambrook et al., 1989, Cold Spring Harbor, NY, Cold Spring Harbor Laboratory Press.

The term "gene" means a DNA sequence comprising a region, which is transcribed into a RNA molecule, e.g., an mRNA in a cell, operably linked to suitable regulatory regions, e.g., a promoter. A gene may thus comprise several operably linked sequences, such as a promoter, a 5' leader sequence comprising, e.g., sequences involved in translation initiation, a coding region of cDNA or genomic DNA, introns, exons, and/or a 3'non-translated sequence comprising, e.g., transcription termination sites.

"Polycistronic" refers to nucleic acid molecules, in particular mRNAs, that can encode more than one polypeptide separately within the same nucleic acid molecule A "chimeric gene" refers to any gene which is not normally found in nature in a species, in particular, a gene in which one or more parts of the nucleic acid sequence are present that are not associated with each other in nature. For example the promoter is not associated in nature with part or all of the transcribed region or with another regulatory region. The term "chimeric gene" is understood to include expression constructs in which a promoter or transcription regulatory sequence is operably linked to one or more coding sequences or to an antisense, i.e., reverse complement of the sense strand, or inverted repeat sequence (sense and antisense, whereby the RNA transcript forms double stranded RNA upon transcription). The term "chimeric gene" also includes genes obtained through the combination of portions of one or more coding sequences to produce a new gene.

A "3' UTR" or "3' non-translated sequence" (also referred to as "3' untranslated region," or "3'end") refers to the nucleic acid sequence found downstream of the coding sequence of a gene, which comprises, for example, a transcription termination site and (in most, but not all eukaryotic mRNAs) a polyadenylation signal such as AAUAAA or variants thereof. After termination of transcription, the mRNA transcript may be cleaved downstream of the polyadenylation signal and a poly(A) tail may be added, which is involved in the transport of the mRNA to the site of translation, e.g., cytoplasm.

The term "primer" refers to a short nucleic acid sequence that is hybridized to a template nucleic acid sequence and is used for polymerization of a nucleic acid sequence complementary to the template.

The term "selectable marker" refers to any gene which upon expression may be used to select a cell or cells that include the selectable marker. Examples of selectable markers are described below. The skilled artisan will know that different antibiotic, fungicide, auxotrophic or herbicide selectable markers are applicable to different target species.

The invention also relates to nucleic acid sequences that code for polypeptides as defined herein.

In particular, the invention also relates to nucleic acid sequences (single-stranded and double-stranded DNA and RNA sequences, e.g. cDNA, genomic DNA and mRNA), coding for one of the above polypeptides and their functional equivalents, which can be obtained for example using artificial nucleotide analogs.

The invention relates both to isolated nucleic acid molecules, which code for polypeptides according to the invention or biologically active segments thereof, and to nucleic acid fragments, which can be used for example as hybridization probes or primers for identifying or amplifying coding nucleic acids according to the invention.

The present invention also relates to nucleic acids with a certain degree of "identity" to the sequences specifically disclosed herein. "Identity" between two nucleic acids means identity of the nucleotides, in each case over the entire length of the nucleic acid.

The "identity" between two nucleotide sequences (the same applies to peptide or amino acid sequences) is a function of the number of nucleotide residues (or amino acid residues) or that are identical in the two sequences when an alignment of these two sequences has been generated. Identical residues are defined as residues that are the same in the two sequences in a given position of the alignment. The percentage of sequence identity, as used herein, is calculated from the optimal alignment by taking the number of residues identical between two sequences dividing it by the total number of residues in the shortest sequence and multiplying by 100. The optimal alignment is the alignment in which the percentage of identity is the highest possible. Gaps may be introduced into one or both sequences in one or more positions of the alignment to obtain the optimal alignment. These gaps are then taken into account as non-identical residues for the calculation of the percentage of sequence identity. Alignment for the purpose of determining the percentage of amino acid or nucleic acid sequence identity can be achieved in various ways using computer programs and for instance publicly available computer programs available on the world wide web.

Particularly, the BLAST program (Tatiana et al, *FEMS Microbiol Lett.,* 1999, 174:247-250, 1999) set to the default parameters, available from the National Center for Biotechnology Information (NCBI) website at ncbi.nlm.nih.gov/BLAST/bl2seq/wblast2.cgi, can be used to obtain an optimal alignment of protein or nucleic acid sequences and to calculate the percentage of sequence identity.

In another example the identity may be calculated by means of the Vector NTI Suite 7.1 program of the company Informax (USA) employing the Clustal Method (Higgins D G, Sharp P M. ((1989))) with the following settings:
Multiple Alignment Parameters:

| | |
|---|---|
| Gap opening penalty | 10 |
| Gap extension penalty | 10 |
| Gap separation penalty range | 8 |
| Gap separation penalty | off |
| % identity for alignment delay | 40 |
| Residue specific gaps | off |
| Hydrophilic residue gap | off |
| Transition weighing | 0 |
| Pairwise alignment parameter: | |
| FAST algorithm | on |
| K-tuple size | 1 |
| Gap penalty | 3 |
| Window size | 5 |
| Number of best diagonals | 5 |

Alternatively the identity may be determined according to Chenna, et al. (2003), the web page: www.ebi.ac.uk/Tools/clustalw/index.html # and the following settings

| | |
|---|---|
| DNA Gap Open Penalty | 15.0 |
| DNA Gap Extension Penalty | 6.66 |
| DNA Matrix | Identity |
| Protein Gap Open Penalty | 10.0 |
| Protein Gap Extension Penalty | 0.2 |
| Protein matrix | Gonnet |
| Protein/DNA ENDGAP | −1 |
| Protein/DNA GAPDIST | 4 |

All the nucleic acid sequences mentioned herein (single-stranded and double-stranded DNA and RNA sequences, for example cDNA and mRNA) can be produced in a known way by chemical synthesis from the nucleotide building blocks, e.g. by fragment condensation of individual overlapping, complementary nucleic acid building blocks of the double helix. Chemical synthesis of oligonucleotides can, for example, be performed in a known way, by the phosphoamidite method (Voet, Voet, 2nd edition, Wiley Press, New York, pages 896-897). The accumulation of synthetic oligonucleotides and filling of gaps by means of the Klenow fragment of DNA polymerase and ligation reactions as well as general cloning techniques are described in Sambrook et al. (1989), see below.

The nucleic acid molecules according to the invention can in addition contain non-translated sequences from the 3' and/or 5' end of the coding genetic region.

The invention further relates to the nucleic acid molecules that are complementary to the concretely described nucleotide sequences or a segment thereof.

The nucleotide sequences according to the invention make possible the production of probes and primers that can be used for the identification and/or cloning of homologous sequences in other cellular types and organisms. Such probes or primers generally comprise a nucleotide sequence region which hybridizes under "stringent" conditions (as defined herein elsewhere) on at least about 12, preferably at least about 25, for example about 40, 50 or 75 successive nucleotides of a sense strand of a nucleic acid sequence according to the invention or of a corresponding antisense strand.

"Homologous" sequences include orthologous or paralogous sequences. Methods of identifying orthologs or paralogs including phylogenetic methods, sequence similarity and hybridization methods are known in the art and are described herein.

"Paralogs" result from gene duplication that gives rise to two or more genes with similar sequences and similar functions. Paralogs typically cluster together and are formed by duplications of genes within related plant species. Paralogs are found in groups of similar genes using pair-wise Blast analysis or during phylogenetic analysis of gene families using programs such as CLUSTAL. In paralogs, consensus sequences can be identified characteristic to sequences within related genes and having similar functions of the genes.

"Orthologs", or orthologous sequences, are sequences similar to each other because they are found in species that descended from a common ancestor. For instance, plant species that have common ancestors are known to contain many enzymes that have similar sequences and functions. The skilled artisan can identify orthologous sequences and predict the functions of the orthologs, for example, by constructing a polygenic tree for a gene family of one species using CLUSTAL or BLAST programs. A method for identifying or confirming similar functions among homologous sequences is by comparing of the transcript profiles in host cells or organisms, such as plants or microorganisms, overexpressing or lacking (in knockouts/knockdowns) related polypeptides. The skilled person will understand that genes having similar transcript profiles, with greater than 50% regulated transcripts in common, or with greater than 70% regulated transcripts in common, or greater than 90% regulated transcripts in common will have similar functions. Homologs, paralogs, orthologs and any other variants of the sequences herein are expected to function in a similar manner by making the host cells, organism such as plants or microorganisms producing terpene synthase proteins.

The term "selectable marker" refers to any gene which upon expression may be used to select a cell or cells that include the selectable marker. Examples of selectable markers are described below. The skilled artisan will know that different antibiotic, fungicide, auxotrophic or herbicide selectable markers are applicable to different target species.

A nucleic acid molecule according to the invention can be recovered by means of standard techniques of molecular biology and the sequence information supplied according to the invention. For example, cDNA can be isolated from a suitable cDNA library, using one of the concretely disclosed complete sequences or a segment thereof as hybridization probe and standard hybridization techniques (as described for example in Sambrook, (1989)).

In addition, a nucleic acid molecule comprising one of the disclosed sequences or a segment thereof, can be isolated by the polymerase chain reaction, using the oligonucleotide primers that were constructed on the basis of this sequence. The nucleic acid amplified in this way can be cloned in a suitable vector and can be characterized by DNA sequencing. The oligonucleotides according to the invention can also be produced by standard methods of synthesis, e.g. using an automatic DNA synthesizer.

Nucleic acid sequences according to the invention or derivatives thereof, homologues or parts of these sequences, can for example be isolated by usual hybridization techniques or the PCR technique from other bacteria, e.g. via genomic or cDNA libraries. These DNA sequences hybridize in standard conditions with the sequences ac-cording to the invention.

"Hybridize" means the ability of a polynucleotide or oligonucleotide to bind to an almost complementary sequence in standard conditions, whereas nonspecific binding does not occur between non-complementary partners in these conditions. For this, the sequences can be 90-100% complementary. The property of complementary sequences of being able to bind specifically to one another is utilized for example in Northern Blotting or Southern Blotting or in primer binding in PCR or RT-PCR.

Short oligonucleotides of the conserved regions are used advantageously for hybridization. However, it is also possible to use longer fragments of the nucleic acids according to the invention or the complete sequences for the hybridization. These "standard conditions" vary depending on the nucleic acid used (oligonucleotide, longer fragment or complete sequence) or depending on which type of nucleic acid—DNA or RNA—is used for hybridization. For example, the melting temperatures for DNA:DNA hybrids are approx. 10° C. lower than those of DNA:RNA hybrids of the same length.

For example, depending on the particular nucleic acid, standard conditions mean temperatures between 42 and 58° C. in an aqueous buffer solution with a concentration between 0.1 to 5×SSC (1×SSC=0.15 M NaCl, 15 mM sodium citrate, pH 7.2) or additionally in the presence of 50% formamide, for example 42° C. in 5×SSC, 50% formamide. Advantageously, the hybridization conditions for DNA:DNA hybrids are 0.1×SSC and temperatures between about 20° C. to 45° C., preferably between about 30° C. to 45° C. For DNA:RNA hybrids the hybridization conditions are advantageously 0.1×SSC and temperatures between about 30° C. to 55° C., preferably between about 45° C. to 55° C. These stated temperatures for hybridization are examples of calculated melting temperature values for a nucleic acid with a length of approx. 100 nucleotides and a G+C content of 50% in the absence of formamide. The experimental conditions for DNA hybridization are described in relevant genetics textbooks, for example Sambrook et al., 1989, and can be calculated using formulae that are known by a person skilled in the art, for example depending on the length of the nucleic acids, the type of hybrids or the G+C content. A person skilled in the art can obtain further information on hybridization from the following textbooks: Ausubel et al. (eds), (1985), Brown (ed) (1991).

"Hybridization" can in particular be carried out under stringent conditions. Such hybridization conditions are for example described in Sambrook (1989), or in Current Protocols in Molecular Biology, John Wiley & Sons, N.Y. (1989), 6.3.1-6.3.6.

As used herein, the term hybridization or hybridizes under certain conditions is intended to describe conditions for hybridization and washes under which nucleotide sequences that are significantly identical or homologous to each other remain bound to each other. The conditions may be such that sequences, which are at least about 70%, such as at least about 80%, and such as at least about 85%, 90%, or 95% identical, remain bound to each other. Definitions of low stringency, moderate, and high stringency hybridization conditions are provided herein.

Appropriate hybridization conditions can be selected by those skilled in the art with minimal experimentation as exemplified in Ausubel et al. (1995*, Current Protocols in Molecular Biology*, John Wiley & Sons, sections 2, 4, and 6). Additionally, stringency conditions are described in Sambrook et al. (1989*, Molecular Cloning: A Laboratory Manual,* 2nd ed., Cold Spring Harbor Press, chapters 7, 9, and 11).

As used herein, defined conditions of low stringency are as follows. Filters containing DNA are pretreated for 6 h at 40° C. in a solution containing 35% formamide, 5×SSC, 50 mM Tris-HCl (pH 7.5), 5 mM EDTA, 0.1% PVP, 0.1% Ficoll, 1% BSA, and 500 μg/ml denatured salmon sperm DNA. Hybridizations are carried out in the same solution with the following modifications: 0.02% PVP, 0.02% Ficoll, 0.2% BSA, 100 μg/ml salmon sperm DNA, 10% (wt/vol) dextran sulfate, and 5-20×106 32P-labeled probe is used. Filters are incubated in hybridization mixture for 18-20 h at 40° C., and then washed for 1.5 h at 55° C. In a solution containing 2×SSC, 25 mM Tris-HCl (pH 7.4), 5 mM EDTA, and 0.1% SDS. The wash solution is replaced with fresh solution and incubated an additional 1.5 h at 60° C. Filters are blotted dry and exposed for autoradiography.

As used herein, defined conditions of moderate stringency are as follows. Filters containing DNA are pretreated for 7 h at 50° C. in a solution containing 35% formamide, 5×SSC, 50 mM Tris-HCl (pH 7.5), 5 mM EDTA, 0.1% PVP, 0.1% Ficoll, 1% BSA, and 500 μg/ml denatured salmon sperm DNA. Hybridizations are carried out in the same solution with the following modifications: 0.02% PVP, 0.02% Ficoll, 0.2% BSA, 100 μg/ml salmon sperm DNA, 10% (wt/vol) dextran sulfate, and 5-20×106 32P-labeled probe is used. Filters are incubated in hybridization mixture for 30 h at 50° C., and then washed for 1.5 h at 55° C. In a solution containing 2×SSC, 25 mM Tris-HCl (pH 7.4), 5 mM EDTA, and 0.1% SDS. The wash solution is replaced with fresh solution and incubated an additional 1.5 h at 60° C. Filters are blotted dry and exposed for autoradiography.

As used herein, defined conditions of high stringency are as follows. Prehybridization of filters containing DNA is carried out for 8 h to overnight at 65° C. in buffer composed of 6×SSC, 50 mM Tris-HCl (pH 7.5), 1 mM EDTA, 0.02% PVP, 0.02% Ficoll, 0.02% BSA, and 500 μg/ml denatured salmon sperm DNA. Filters are hybridized for 48 h at 65° C. in the prehybridization mixture containing 100 μg/ml denatured salmon sperm DNA and 5-20×106 cpm of 32P-labeled probe. Washing of filters is done at 37° C. for 1 h in a solution containing 2×SSC, 0.01% PVP, 0.01% Ficoll, and 0.01% BSA. This is followed by a wash in 0.1×SSC at 50° C. for 45 minutes.

Other conditions of low, moderate, and high stringency well known in the art (e.g., as employed for cross-species hybridizations) may be used if the above conditions are inappropriate (e.g., as employed for cross-species hybridizations).

A detection kit for nucleic acid sequences encoding a polypeptide of the invention may include primers and/or probes specific for nucleic acid sequences encoding the polypeptide, and an associated protocol to use the primers and/or probes to detect nucleic acid sequences encoding the polypeptide in a sample. Such detection kits may be used to determine whether a plant, organism, microorganism or cell has been modified, i.e., transformed with a sequence encoding the polypeptide.

To test a function of variant DNA sequences according to an embodiment herein, the sequence of interest is operably linked to a selectable or screenable marker gene and expression of said reporter gene is tested in transient expression assays, for example, with microorganisms or with protoplasts or in stably transformed plants.

The invention also relates to derivatives of the concretely disclosed or derivable nucleic acid sequences.

Thus, further nucleic acid sequences according to the invention can be derived from the sequences specifically disclosed herein and can differ from it by one or more, like 1 to 20, in particular 1 to 15 or 5 to 10 additions, substitutions, insertions or deletions of one or several (like for example 1 to 10) nucleotides, and furthermore code for polypeptides with the desired profile of properties.

The invention also encompasses nucleic acid sequences that comprise so-called silent mutations or have been altered, in comparison with a concretely stated sequence, according to the codon usage of a special original or host organism.

According to a particular embodiment of the invention variant nucleic acids may be prepared in order to adapt its nucleotide sequence to a specific expression system. For example, bacterial expression systems are known to more efficiently express polypeptides if amino acids are encoded by particular codons. Due to the degeneracy of the genetic code, more than one codon may encode the same amino acid sequence, multiple nucleic acid sequences can code for the same protein or polypeptide, all these DNA sequences being encompassed by an embodiment herein. Where appropriate, the nucleic acid sequences encoding the polypeptides described herein may be optimized for increased expression in the host cell. For example, nucleic acids of an embodiment herein may be synthesized using codons particular to a host for improved expression.

The invention also encompasses naturally occurring variants, e.g. splicing variants or allelic variants, of the sequences described therein.

Allelic variants may have at least 60% homology at the level of the derived amino acid, preferably at least 80% homology, quite especially preferably at least 90% homology over the entire sequence range (regarding homology at the amino acid level, reference should be made to the details given above for the polypeptides). Advantageously, the homologies can be higher over partial regions of the sequences.

The invention also relates to sequences that can be obtained by conservative nucleotide substitutions (i.e. as a result thereof the amino acid in question is replaced by an amino acid of the same charge, size, polarity and/or solubility).

The invention also relates to the molecules derived from the concretely disclosed nucleic acids by sequence polymorphisms. Such genetic polymorphisms may exist in cells from different populations or within a population due to natural allelic variation. Allelic variants may also include functional equivalents. These natural variations usually produce a variance of 1 to 5% in the nucleotide sequence of a gene. Said polymorphisms may lead to changes in the amino acid sequence of the polypeptides disclosed herein. Allelic variants may also include functional equivalents.

Furthermore, derivatives are also to be understood to be homologs of the nucleic acid sequences according to the invention, for example animal, plant, fungal or bacterial homologs, shortened sequences, single-stranded DNA or RNA of the coding and noncoding DNA sequence. For example, homologs have, at the DNA level, a homology of at least 40%, preferably of at least 60%, especially preferably of at least 70%, quite especially preferably of at least 80% over the entire DNA region given in a sequence specifically disclosed herein.

Moreover, derivatives are to be understood to be, for example, fusions with promoters. The promoters that are added to the stated nucleotide sequences can be modified by at least one nucleotide exchange, at least one insertion, inversion and/or deletion, though without impairing the functionality or efficacy of the promoters. Moreover, the efficacy of the promoters can be increased by altering their sequence or can be exchanged completely with more effective promoters even of organisms of a different genus.

d. Generation of Functional Polypeptide Mutants

Moreover, a person skilled in the art is familiar with methods for generating functional mutants, that is to say nucleotide sequences which code for a polypeptide with at least 40%, 45%, 50%, 55%, 60%, 65%, 70%, 75%, 80%, 81%, 82%, 83%, 84%, 85%, 86%, 87%, 88%, 89%, 90%, 91%, 92%, 93%, 94%, 95%, 96%, 97%, 98% or 99% sequence identity to anyone of amino acid related SEQ ID NOs as disclosed herein and/or encoded by a nucleic acid molecule comprising a nucleotide sequence having at least 70% sequence identity to anyone of the nucleotide related SEQ ID NOs as disclosed herein.

Depending on the technique used, a person skilled in the art can introduce entirely random or else more directed mutations into genes or else noncoding nucleic acid regions (which are for example important for regulating expression) and subsequently generate genetic libraries. The methods of molecular biology required for this purpose are known to the skilled worker and for example described in Sambrook and Russell, Molecular Cloning. 3rd Edition, Cold Spring Harbor Laboratory Press 2001.

Methods for modifying genes and thus for modifying the polypeptide encoded by them have been known to the skilled worker for a long time, such as, for example

- site-specific mutagenesis, where individual or several nucleotides of a gene are replaced in a directed fashion (Trower MK (Ed.) 1996; In vitro mutagenesis protocols. Humana Press, New Jersey),
- saturation mutagenesis, in which a codon for any amino acid can be exchanged or added at any point of a gene (Kegler-Ebo D M, Docktor C M, DiMaio D (1994) Nucleic Acids Res 22:1593; Barettino D, Feigenbutz M, Valcárel R, Stunnenberg H G (1994) Nucleic Acids Res 22:541; Bank S (1995) Mol Biotechnol 3:1),
- error-prone polymerase chain reaction, where nucleotide sequences are mutated by error-prone DNA polymerases (Eckert K A, Kunkel T A (1990) Nucleic Acids Res 18:3739);
- the SeSaM method (sequence saturation method), in which preferred exchanges are prevented by the polymerase. Schenk et al., Biospektrum, Vol. 3, 2006, 277-279
- the passaging of genes in mutator strains, in which, for example owing to defective DNA repair mechanisms, there is an increased mutation rate of nucleotide sequences (Greener A, Callahan M, Jerpseth B (1996) An efficient random mutagenesis technique using an *E. coli* mutator strain. In: Trower M K (Ed.) In vitro mutagenesis protocols. Humana Press, New Jersey), or
- DNA shuffling, in which a pool of closely related genes is formed and digested and the fragments are used as templates for a polymerase chain reaction in which, by repeated strand separation and reassociation, full-length mosaic genes are ultimately generated (Stemmer WPC (1994) Nature 370:389; Stemmer WPC (1994) Proc Natl Acad Sci USA 91:10747).

Using so-called directed evolution (described, inter alia, in Reetz M T and Jaeger K-E (1999), Topics Curr Chem 200:31; Zhao H, Moore J C, Volkov A A, Arnold F H (1999), Methods for optimizing industrial polypeptides by directed evolution, In: Demain A L, Davies J E (Ed.) Manual of industrial microbiology and biotechnology. American Society for Microbiology), a skilled worker can produce functional mutants in a directed manner and on a large scale. To this end, in a first step, gene libraries of the respective polypeptides are first produced, for example using the methods given above. The gene libraries are expressed in a suitable way, for example by bacteria or by phage display systems.

The relevant genes of host organisms which express functional mutants with properties that largely correspond to the desired properties can be submitted to another mutation cycle. The steps of the mutation and selection or screening can be repeated iteratively until the present functional mutants have the desired properties to a sufficient extent. Using this iterative procedure, a limited number of mutations, for example 1, 2, 3, 4 or 5 mutations, can be performed in stages and assessed and selected for their influence on the activity in question. The selected mutant can then be submitted to a further mutation step in the same way. In this way, the number of individual mutants to be investigated can be reduced significantly.

The results according to the invention also provide important information relating to structure and sequence of the relevant polypeptides, which is required for generating, in a targeted fashion, further polypeptides with desired modified properties. In particular, it is possible to define so-called "hot spots", i.e. sequence segments that are potentially suitable for modifying a property by introducing targeted mutations.

Information can also be deduced regarding amino acid sequence positions, in the region of which mutations can be effected that should probably have little effect on the activity, and can be designated as potential "silent mutations".

e. Constructs for Expressing Polypeptides of the Invention

In this context the following definitions apply:

"Expression of a gene" encompasses "heterologous expression" and "over-expression" and involves transcription of the gene and translation of the mRNA into a protein. Overexpression refers to the production of the gene product as measured by levels of mRNA, polypeptide and/or enzyme activity in transgenic cells or organisms that exceeds levels of production in non-transformed cells or organisms of a similar genetic background.

"Expression vector" as used herein means a nucleic acid molecule engineered using molecular biology methods and recombinant DNA technology for delivery of foreign or exogenous DNA into a host cell. The expression vector typically includes sequences required for proper transcription of the nucleotide sequence. The coding region usually codes for a protein of interest but may also code for an RNA, e.g., an antisense RNA, siRNA and the like.

An "expression vector" as used herein includes any linear or circular recombinant vector including but not limited to viral vectors, bacteriophages and plasmids. The skilled person is capable of selecting a suitable vector according to the expression system. In one embodiment, the expression vector includes the nucleic acid of an embodiment herein operably linked to at least one "regulatory sequence", which controls transcription, translation, initiation and termination, such as a transcriptional promoter, operator or enhancer, or an mRNA ribosomal binding site and, optionally, including at least one selection marker. Nucleotide sequences are "operably linked" when the regulatory sequence functionally relates to the nucleic acid of an embodiment herein.

An "expression system" as used herein encompasses any combination of nucleic acid molecules required for the expression of one, or the co-expression of two or more polypeptides either in vivo of a given expression host, or in vitro. The respective coding sequences may either be located on a single nucleic acid molecule or vector, as for example a vector containing multiple cloning sites, or on a polycistronic nucleic acid, or may be distributed over two or more physically distinct vectors. As a particular example there may be mentioned an operon comprising a promotor sequence, one or more operator sequences and one or more structural genes each encoding an enzyme as described herein As used herein, the terms "amplifying" and "amplification" refer to the use of any suitable amplification methodology for generating or detecting recombinant of naturally expressed nucleic acid, as described in detail, below. For example, the invention provides methods and reagents (e.g., specific degenerate oligonucleotide primer pairs, oligo dT primer) for amplifying (e.g., by polymerase chain reaction, PCR) naturally expressed (e.g., genomic DNA or mRNA) or recombinant (e.g., cDNA) nucleic acids of the invention in vivo, ex vivo or in vitro.

"Regulatory sequence" refers to a nucleic acid sequence that determines expression level of the nucleic acid sequences of an embodiment herein and is capable of regulating the rate of transcription of the nucleic acid sequence operably linked to the regulatory sequence. Regulatory sequences comprise promoters, enhancers, transcription factors, promoter elements and the like.

A "promoter", a "nucleic acid with promoter activity" or a "promoter sequence" is understood as meaning, in accordance with the invention, a nucleic acid which, when functionally linked to a nucleic acid to be transcribed, regulates the transcription of said nucleic acid. "Promoter" in particular refers to a nucleic acid sequence that controls the expression of a coding sequence by providing a binding site for RNA polymerase and other factors required for proper transcription including without limitation transcription factor binding sites, repressor and activator protein binding sites. The meaning of the term promoter also includes the term "promoter regulatory sequence". Promoter regulatory sequences may include upstream and downstream elements that may influences transcription, RNA processing or stability of the associated coding nucleic acid sequence. Promoters include naturally-derived and synthetic sequences. The coding nucleic acid sequences is usually located downstream of the promoter with respect to the direction of the transcription starting at the transcription initiation site.

In this context, a "functional" or "operative" linkage is understood as meaning for example the sequential arrangement of one of the nucleic acids with a regulatory sequence. For example the sequence with promoter activity and of a nucleic acid sequence to be transcribed and optionally further regulatory elements, for example nucleic acid sequences which ensure the transcription of nucleic acids, and for example a terminator, are linked in such a way that each of the regulatory elements can perform its function upon transcription of the nucleic acid sequence. This does not necessarily require a direct linkage in the chemical sense. Genetic control sequences, for example enhancer sequences, can even exert their function on the target sequence from more remote positions or even from other DNA molecules. Preferred arrangements are those in which the nucleic acid sequence to be transcribed is positioned behind (i.e. at the 3'-end of) the promoter sequence so that the two sequences are joined together covalently. The distance between the promoter sequence and the nucleic acid sequence to be expressed recombinantly can be smaller than 200 base pairs, or smaller than 100 base pairs or smaller than 50 base pairs.

In addition to promoters and terminator, the following may be mentioned as examples of other regulatory elements: targeting sequences, enhancers, polyadenylation signals, selectable markers, amplification signals, replication origins and the like. Suitable regulatory sequences are described, for example, in Goeddel, Gene Expression Technology: Methods in Enzymology 185, Academic Press, San Diego, CA (1990).

The term "constitutive promoter" refers to an unregulated promoter that allows for continual transcription of the nucleic acid sequence it is operably linked to.

As used herein, the term "operably linked" refers to a linkage of polynucleotide elements in a functional relationship. A nucleic acid is "operably linked" when it is placed into a functional relationship with another nucleic acid sequence. For instance, a promoter, or rather a transcription regulatory sequence, is operably linked to a coding sequence if it affects the transcription of the coding sequence. Operably linked means that the DNA sequences being linked are typically contiguous. The nucleotide sequence associated with the promoter sequence may be of homologous or heterologous origin with respect to the plant to be transformed. The sequence also may be entirely or partially synthetic. Regardless of the origin, the nucleic acid sequence associated with the promoter sequence will be expressed or silenced in accordance with promoter properties to which it is linked after binding to the polypeptide of an embodiment herein. The associated nucleic acid may code for a protein that is desired to be expressed or suppressed throughout the organism at all times or, alternatively, at a specific time or in specific tissues, cells, or cell compartment. Such nucleotide sequences particularly encode proteins conferring desirable phenotypic traits to the host cells or organism altered or transformed therewith. More particularly, the associated nucleotide sequence leads to the production of the product or products of interest as herein defined in the cell or organism. Particularly, the nucleotide sequence encodes a polypeptide having an enzyme activity as herein defined.

The nucleotide sequence as described herein above may be part of an "expression cassette". The terms "expression cassette" and "expression construct" are used synonymously. The (preferably recombinant) expression construct contains a nucleotide sequence which encodes a polypeptide according to the invention and which is under genetic control of regulatory nucleic acid sequences.

In a process applied according to the invention, the expression cassette may be part of an "expression vector", in particular of a recombinant expression vector.

An "expression unit" is understood as meaning, in accordance with the invention, a nucleic acid with expression activity which comprises a promoter as defined herein and, after functional linkage with a nucleic acid to be expressed or a gene, regulates the expression, i.e. the transcription and the translation of said nucleic acid or said gene. It is therefore in this connection also referred to as a "regulatory nucleic acid sequence". In addition to the promoter, other regulatory elements, for example enhancers, can also be present.

An "expression cassette" or "expression construct" is understood as meaning, in accordance with the invention, an expression unit which is functionally linked to the nucleic acid to be expressed or the gene to be expressed. In contrast to an expression unit, an expression cassette therefore comprises not only nucleic acid sequences which regulate transcription and translation, but also the nucleic acid sequences that are to be expressed as protein as a result of transcription and translation.

The terms "expression" or "overexpression" describe, in the context of the invention, the production or increase in intracellular activity of one or more polypeptides in a microorganism, which are encoded by the corresponding DNA. To this end, it is possible for example to introduce a gene into an organism, replace an existing gene with another gene, increase the copy number of the gene(s), use a strong promoter or use a gene which encodes for a corresponding polypeptide with a high activity; optionally, these measures can be combined.

Preferably such constructs according to the invention comprise a promoter 5'-upstream of the respective coding sequence and a terminator sequence 3'-downstream and optionally other usual regulatory elements, in each case in operative linkage with the coding sequence.

Nucleic acid constructs according to the invention comprise in particular a sequence coding for a polypeptide for example derived from the amino acid related SEQ ID NOs as described therein or the reverse complement thereof, or derivatives and homologs thereof and which have been linked operatively or functionally with one or more regulatory signals, advantageously for controlling, for example increasing, gene expression.

In addition to these regulatory sequences, the natural regulation of these sequences may still be present before the actual structural genes and optionally may have been genetically modified so that the natural regulation has been switched off and expression of the genes has been enhanced. The nucleic acid construct may, however, also be of simpler construction, i.e. no additional regulatory signals have been inserted before the coding sequence and the natural promoter, with its regulation, has not been removed. Instead, the natural regulatory sequence is mutated such that regulation no longer takes place and the gene expression is increased.

A preferred nucleic acid construct advantageously also comprises one or more of the already mentioned "enhancer" sequences in functional linkage with the promoter, which sequences make possible an enhanced expression of the nucleic acid sequence. Additional advantageous sequences may also be inserted at the 3'-end of the DNA sequences, such as further regulatory elements or terminators. One or more copies of the nucleic acids according to the invention may be present in a construct. In the construct, other markers, such as genes which complement auxotrophisms or antibiotic resistances, may also optionally be present so as to select for the construct.

Examples of suitable regulatory sequences are present in promoters such as cos, tac, trp, tet, trp-tet, lpp, lac, lpp-lac, $lacI^q$; T7, T5, T3, gal, trc, ara, rhaP ($rhaP_{BAD}$) SP6, lambda-$P_R$ or in the lambda-$P_L$ promoter, and these are advantageously employed in Gram-negative bacteria. Further advantageous regulatory sequences are present for example in the Gram-positive promoters amy and SPO2, in the yeast or fungal promoters ADC1, MFalpha, AC, P-60, CYC1, GAPDH, TEF, rp28, ADH. Artificial promoters may also be used for regulation.

For expression in a host organism, the nucleic acid construct is inserted advantageously into a vector such as, for example, a plasmid or a phage, which makes possible optimal expression of the genes in the host. Vectors are also understood as meaning, in addition to plasmids and phages, all the other vectors which are known to the skilled worker, that is to say for example viruses such as SV40, CMV, baculovirus and adenovirus, transposons, IS elements, phasmids, cosmids and linear or circular DNA or artificial chromosomes. These vectors are capable of replicating autonomously in the host organism or else chromosomally. These vectors are a further development of the invention. Binary or cpo-integration vectors are also applicable.

Suitable plasmids are, for example, in *E. coli* pLG338, pACYC184, pBR322, pUC18, pUC19, pKC30, pRep4, pHS1, pKK223-3, pDHE19.2, pHS2, pPLc236, pMBL24, pLG200, pUR290, pIN-III$^{113}$-B1, λgt11 or pBdCI, in *Streptomyces* pIJ101, pIJ364, pIJ702 or pIJ361, in *Bacillus* pUB110, pC194 or pBD214, in *Corynebacterium* pSA77 or pAJ667, in fungi pALS1, pIL2 or pBB116, in yeasts 2alphaM, pAG-1, YEp6, YEp13 or pEMBLYe23 or in plants pLGV23, pGHlac$^{+}$, pBIN19, pAK2004 or pDH51. The abovementioned plasmids are a small selection of the plasmids which are possible. Further plasmids are well known to the skilled worker and can be found for example in the book Cloning Vectors (Eds. Pouwels P. H. et al. Elsevier, Amsterdam-New York-Oxford, 1985, ISBN 0 444 904018).

In a further development of the vector, the vector which comprises the nucleic acid construct according to the invention or the nucleic acid according to the invention can advantageously also be introduced into the microorganisms in the form of a linear DNA and integrated into the host organism's genome via heterologous or homologous recombination. This linear DNA can consist of a linearized vector such as a plasmid or only of the nucleic acid construct or the nucleic acid according to the invention.

For optimal expression of heterologous genes in organisms, it is advantageous to modify the nucleic acid sequences to match the specific "codon usage" used in the organism. The "codon usage" can be determined readily by computer evaluations of other, known genes of the organism in question.

An expression cassette according to the invention is generated by fusing a suitable promoter to a suitable coding nucleotide sequence and a terminator or polyadenylation signal. Customary recombination and cloning techniques are used for this purpose, as are described, for example, in T. Maniatis, E. F. Fritsch and J. Sambrook, Molecular Cloning: A Laboratory Manual, Cold Spring Harbor Laboratory, Cold Spring Harbor, NY (1989) and in T. J. Silhavy, M. L. Berman and L. W. Enquist, Experiments with Gene Fusions, Cold Spring Harbor Laboratory, Cold Spring Harbor, NY (1984) and in Ausubel, F. M. et al., Current Protocols in Molecular Biology, Greene Publishing Assoc. and Wiley Interscience (1987).

For expression in a suitable host organism, the recombinant nucleic acid construct or gene construct is advantageously inserted into a host-specific vector which makes possible optimal expression of the genes in the host. Vectors are well known to the skilled worker and can be found for example in "cloning vectors" (Pouwels P. H. et al., Ed., Elsevier, Amsterdam-New York-Oxford, 1985).

An alternative embodiment of an embodiment herein provides a method to "alter gene expression" in a host cell. For instance, the polynucleotide of an embodiment herein may be enhanced or overexpressed or induced in certain contexts (e.g. upon exposure to certain temperatures or culture conditions) in a host cell or host organism.

Alteration of expression of a polynucleotide provided herein may also result in ectopic expression which is a different expression pattern in an altered and in a control or wild-type organism. Alteration of expression occurs from interactions of polypeptide of an embodiment herein with exogenous or endogenous modulators, or as a result of chemical modification of the polypeptide. The term also refers to an altered expression pattern of the polynucleotide of an embodiment herein which is altered below the detection level or completely suppressed activity.

In one embodiment, provided herein is also an isolated, recombinant or synthetic polynucleotide encoding a polypeptide or variant polypeptide provided herein.

In one embodiment, several polypeptide encoding nucleic acid sequences are co-expressed in a single host, particularly under control of different promoters. In another embodiment, several polypeptide encoding nucleic acid sequences can be present on a single transformation vector or be co-transformed at the same time using separate vectors and selecting transformants comprising both chimeric genes. Similarly, one or polypeptide encoding genes may be expressed in a single plant, cell, microorganism or organism together with other chimeric genes.

f. Hosts to be Applied for the Present Invention

Depending on the context, the term "host" can mean the wild-type host or a genetically altered, recombinant host or both.

In principle, all prokaryotic or eukaryotic organisms may be considered as host or recombinant host organisms for the nucleic acids or the nucleic acid constructs according to the invention.

Using the vectors according to the invention, recombinant hosts can be produced, which are for example transformed with at least one vector according to the invention and can be used for producing the polypeptides according to the invention. Advantageously, the recombinant constructs according to the invention, described above, are introduced into a suitable host system and expressed. Preferably common cloning and transfection methods, known by a person skilled in the art, are used, for example co-precipitation, protoplast fusion, electroporation, retroviral transfection and the like, for expressing the stated nucleic acids in the respective expression system. Suitable systems are described for example in Current Protocols in Molecular Biology, F. Ausubel et al., Ed., Wiley Interscience, New York 1997, or Sambrook et al. Molecular Cloning: A Laboratory Manual. 2nd edition, Cold Spring Harbor Laboratory, Cold Spring Harbor Laboratory Press, Cold Spring Harbor, NY, 1989.

Advantageously, microorganisms such as bacteria, fungi or yeasts are used as host organisms. Advantageously, gram-positive or gram-negative bacteria are used, preferably bacteria of the families Enterobacteriaceae, Pseudomonadaceae, Rhizobiaceae, Streptomycetaceae, Streptococcaceae or Nocardiaceae, especially preferably bacteria of the genera *Escherichia, Pseudomonas, Streptomyces, Lactococcus, Nocardia, Burkholderia, Salmonella, Agrobacterium, Clostridium* or *Rhodococcus*. The genus and species *Escherichia coli* is quite especially preferred. Furthermore, other advantageous bacteria are to be found in the group of alpha-Proteobacteria, beta-Proteobacteria or gamma-Proteobacteria. Advantageously also yeasts of families like *Saccharomyces* or *Pichia* are suitable hosts.

Alternatively, entire plants or plant cells may serve as natural or recombinant host. As non-limiting examples the following plants or cells derived therefrom may be mentioned the genera *Nicotiana*, in particular *Nicotiana benthamiana* and *Nicotiana tabacum* (tobacco); as well as *Arabidopsis*, in particular *Arabidopsis thaliana.*

Depending on the host organism, the organisms used in the method according to the invention are grown or cultured in a manner known by a person skilled in the art. Culture can be batchwise, semi-batchwise or continuous. Nutrients can be present at the beginning of fermentation or can be supplied later, semicontinuously or continuously. This is also described in more detail below.

g. Recombinant Production of Polypeptides According to the Invention

The invention further relates to methods for recombinant production of polypeptides according to the invention or functional, biologically active fragments thereof, wherein a polypeptide-producing microorganism is cultured, optionally the expression of the polypeptides is induced by applying at least one inducer inducing gene expression and the expressed polypeptides are isolated from the culture. The polypeptides can also be produced in this way on an industrial scale, if desired.

The microorganisms produced according to the invention can be cultured continuously or discontinuously in the batch method or in the fed-batch method or repeated fed-batch method. A summary of known cultivation methods can be found in the textbook by Chmiel (Bioprozesstechnik 1. Einführung in die Bioverfahrenstechnik [Bioprocess technology 1. Introduction to bioprocess technology](Gustav Fischer Verlag, Stuttgart, 1991)) or in the textbook by Storhas (Bioreaktoren und periphere Einrichtungen [Bioreactors and peripheral equipment](Vieweg Verlag, Braunschweig/Wiesbaden, 1994)).

The culture medium to be used must suitably meet the requirements of the respective strains. Descriptions of culture media for various microorganisms are given in the manual "Manual of Methods for General Bacteriology" of the American Society for Bacteriology (Washington D.C., USA, 1981).

These media usable according to the invention usually comprise one or more carbon sources, nitrogen sources, inorganic salts, vitamins and/or trace elements.

Preferred carbon sources are sugars, such as mono-, di- or polysaccharides. Very good carbon sources are for example glucose, fructose, mannose, galactose, ribose, sorbose, ribulose, lactose, maltose, sucrose, raffinose, starch or cellulose. Sugars can also be added to the media via complex compounds, such as molasses, or other by-products of sugar refining. It can also be advantageous to add mixtures of different carbon sources. Other possible carbon sources are oils and fats, for example soybean oil, sunflower oil, peanut oil and coconut oil, fatty acids, for example palmitic acid, stearic acid or linoleic acid, alcohols, for example glycerol, methanol or ethanol and organic acids, for example acetic acid or lactic acid.

Nitrogen sources are usually organic or inorganic nitrogen compounds or materials that contain these compounds. Examples of nitrogen sources comprise ammonia gas or ammonium salts, such as ammonium sulfate, ammonium chloride, ammonium phosphate, ammonium carbonate or ammonium nitrate, nitrates, urea, amino acids or complex nitrogen sources, such as corn-steep liquor, soya flour, soya protein, yeast extract, meat extract and others. The nitrogen sources can be used alone or as a mixture.

Inorganic salt compounds that can be present in the media comprise the chloride, phosphorus or sulfate salts of calcium, magnesium, sodium, cobalt, molybdenum, potassium, manganese, zinc, copper and iron.

Inorganic sulfur-containing compounds, for example sulfates, sulfites, dithionites, tetrathionates, thiosulfates, sulfides, as well as organic sulfur compounds, such as mercaptans and thiols, can be used as the sulfur source.

Phosphoric acid, potassium dihydrogen phosphate or dipotassium hydrogen phosphate or the corresponding sodium-containing salts can be used as the phosphorus source.

Chelating agents can be added to the medium, in order to keep the metal ions in solution. Especially suitable chelating agents comprise dihydroxyphenols, such as catechol or protocatechuate, or organic acids, such as citric acid.

The fermentation media used according to the invention usually also contain other growth factors, such as vitamins or growth promoters, which include for example biotin, riboflavin, thiamine, folic acid, nicotinic acid, pantothenate and pyridoxine. Growth factors and salts often originate from the components of complex media, such as yeast extract, molasses, corn-steep liquor and the like. Moreover, suitable precursors can be added to the culture medium. The exact composition of the compounds in the medium is strongly dependent on the respective experiment and is decided for each specific case individually. Information on media optimization can be found in the textbook "Applied Microbiol. Physiology, A Practical Approach" (Ed. P. M. Rhodes, P. F. Stanbury, IRL Press (1997) p. 53-73, ISBN 0 19 963577 3). Growth media can also be obtained from commercial suppliers, such as Standard 1 (Merck) or BHI (brain heart infusion, DIFCO) and the like.

All components of the medium are sterilized, either by heat (20 min at 1.5 bar and 121° C.) or by sterile filtration. The components can either be sterilized together, or separately if necessary. All components of the medium can be present at the start of culture or can be added either continuously or batchwise.

The culture temperature is normally between 15° C. and 45° C., preferably 25° C. to 40° C. and can be varied or kept constant during the experiment. The pH of the medium should be in the range from 5 to 8.5, preferably around 7.0. The pH for growing can be controlled during growing by adding basic compounds such as sodium hydroxide, potassium hydroxide, ammonia or ammonia water or acid compounds such as phosphoric acid or sulfuric acid. Antifoaming agents, for example fatty acid polyglycol esters, can be used for controlling foaming. To maintain the stability of plasmids, suitable selective substances, for example antibiotics, can be added to the medium. To maintain aerobic conditions, oxygen or oxygen-containing gas mixtures, for example ambient air, are fed into the culture. The temperature of the culture is normally in the range from 20° C. to 45° C. The culture is continued until a maximum of the desired product has formed. This target is normally reached within 10 hours to 160 hours.

The fermentation broth is then processed further. Depending on requirements, the biomass can be removed from the fermentation broth completely or partially by separation techniques, for example centrifugation, filtration, decanting or a combination of these methods or can be left in it completely.

If the polypeptides are not secreted in the culture medium, the cells can also be lysed and the product can be obtained from the lysate by known methods for isolation of proteins. The cells can optionally be disrupted with high-frequency ultrasound, high pressure, for example in a French press, by osmolysis, by the action of detergents, lytic enzymes or organic solvents, by means of homogenizers or by a combination of several of the aforementioned methods.

The polypeptides can be purified by known chromatographic techniques, such as molecular sieve chromatography (gel filtration), such as Q-sepharose chromatography, ion exchange chromatography and hydrophobic chromatography, and with other usual techniques such as ultrafiltration, crystallization, salting-out, dialysis and native gel electrophoresis. Suitable methods are described for example in Cooper, T. G., Biochemische Arbeitsmethoden [Biochemical processes], Verlag Walter de Gruyter, Berlin, New York or in Scopes, R., Protein Purification, Springer Verlag, New York, Heidelberg, Berlin.

For isolating the recombinant protein, it can be advantageous to use vector systems or oligonucleotides, which lengthen the cDNA by defined nucleotide sequences and therefore code for altered polypeptides or fusion proteins, which for example serve for easier purification. Suitable modifications of this type are for example so-called "tags" functioning as anchors, for example the modification known as hexa-histidine anchor or epitopes that can be recognized as antigens of antibodies (described for example in Harlow, E. and Lane, D., 1988, Antibodies: A Laboratory Manual. Cold Spring Harbor (N.Y.) Press). These anchors can serve for attaching the proteins to a solid carrier, for example a polymer matrix, which can for example be used as packing in a chromatography column, or can be used on a microtiter plate or on some other carrier.

At the same time these anchors can also be used for recognition of the proteins. For recognition of the proteins, it is moreover also possible to use usual markers, such as fluorescent dyes, enzyme markers, which form a detectable reaction product after reaction with a substrate, or radioactive markers, alone or in combination with the anchors for derivatization of the proteins.

h. Polypeptide Immobilization

The enzymes or polypeptides according to the invention can be used free or immobilized in the method described herein. An immobilized enzyme is an enzyme that is fixed to an inert carrier. Suitable carrier materials and the enzymes immobilized thereon are known from EP-A-1149849, EP-A-1 069 183 and DE-OS 100193773 and from the references cited therein. Reference is made in this respect to the disclosure of these documents in their entirety. Suitable carrier materials include for example clays, clay minerals, such as kaolinite, diatomaceous earth, perlite, silica, aluminum oxide, sodium carbonate, calcium carbonate, cellulose powder, anion exchanger materials, synthetic polymers, such as polystyrene, acrylic resins, phenol formaldehyde resins, polyurethanes and polyolefins, such as polyethylene and polypropylene. For making the supported enzymes, the carrier materials are usually employed in a finely-divided, particulate form, porous forms being preferred. The particle size of the carrier material is usually not more than 5 mm, in particular not more than 2 mm (particle-size distribution curve). Similarly, when using dehydrogenase as whole-cell catalyst, a free or immobilized form can be selected. Carrier materials are e.g. Ca-alginate, and carrageenan. Enzymes as well as cells can also be crosslinked directly with glutaraldehyde (cross-linking to CLEAs). Corresponding and other immobilization techniques are described for example in J. Lalonde and A. Margolin "Immobilization of Enzymes" in K. Drauz and H. Waldmann, Enzyme Catalysis in Organic Synthesis 2002, Vol. III, 991-1032, Wiley-VCH, Weinheim. Further information on biotransformations and bioreactors for carrying out methods according to the invention are also given for example in Rehm et al. (Ed.) Biotechnology, 2nd Edn, Vol 3, Chapter 17, VCH, Weinheim.

i. Reaction Conditions for Biocatalytic Production Methods of the Invention

The reaction of the present invention may be performed under in vivo or in vitro conditions.

The at least one polypeptide/enzyme which is present during a method of the invention or an individual step of a multistep-method as defined herein above, can be present in living cells naturally or recombinantly producing the enzyme or enzymes, in harvested cells. i.e. under in vivo conditions, or, in dead cells, in permeabilized cells, in crude cell extracts, in purified extracts, or in essentially pure or completely pure form, i.e. under in vitro conditions. The at least one enzyme may be present in solution or as an enzyme immobilized on a carrier. One or several enzymes may simultaneously be present in soluble and/or immobilised form.

The methods according to the invention can be performed in common reactors, which are known to those skilled in the art, and in different ranges of scale, e.g. from a laboratory scale (few millilitres to dozens of litres of reaction volume) to an industrial scale (several litres to thousands of cubic meters of reaction volume). If the polypeptide is used in a form encapsulated by non-living, optionally permeabilized cells, in the form of a more or less purified cell extract or in purified form, a chemical reactor can be used. The chemical reactor usually allows controlling the amount of the at least one enzyme, the amount of the at least one substrate, the pH, the temperature and the circulation of the reaction medium. When the at least one polypeptide/enzyme is present in living cells, the process will be a fermentation. In this case the biocatalytic production will take place in a bioreactor (fermenter), where parameters necessary for suitable living conditions for the living cells (e.g. culture medium with nutrients, temperature, aeration, presence or absence of oxygen or other gases, antibiotics, and the like) can be controlled. Those skilled in the art are familiar with chemical reactors or bioreactors, e.g. with procedures for up-scaling chemical or biotechnological methods from laboratory scale to industrial scale, or for optimizing process parameters, which are also extensively described in the literature (for biotechnological methods see e.g. Crueger und Crueger, Biotechnologie-Lehrbuch der angewandten Mikrobiologie, 2. Ed., R. Oldenbourg Verlag, München, Wien, 1984).

Cells containing the at least one enzyme can be permeabilized by physical or mechanical means, such as ultrasound or radiofrequency pulses, French presses, or chemical means, such as hypotonic media, lytic enzymes and detergents present in the medium, or combination of such methods. Examples for detergents are digitonin, n-dodecylmaltoside, octylglycoside, Triton® X-100, Tween® 20, deoxycholate, CHAPS (3-[(3-Cholamidopropyl)dimethylammonio]-1-propansulfonate), Nonidet® P40 (Ethylphenolpoly(ethyleneglycolether), and the like.

Instead of living cells biomass of non-living cells containing the required biocatalyst(s) may be applied of the biotransformation reactions of the invention as well.

If the at least one enzyme is immobilised, it is attached to an inert carrier as described above.

The conversion reaction can be carried out batch wise, semi-batch wise or continuously. Reactants (and optionally nutrients) can be supplied at the start of reaction or can be supplied subsequently, either semi-continuously or continuously.

The reaction of the invention, depending on the particular reaction type, may be performed in an aqueous, aqueous-organic or non-aqueous reaction medium.

An aqueous or aqueous-organic medium may contain a suitable buffer in order to adjust the pH to a value in the range of 5 to 11, like 6 to 10.

In an aqueous-organic medium an organic solvent miscible, partly miscible or immiscible with water may be applied. Non-limiting examples of suitable organic solvents are listed below. Further examples are mono- or polyhydric, aromatic or aliphatic alcohols, in particular polyhydric aliphatic alcohols like glycerol.

The non-aqueous medium may contain is substantially free of water, i.e. will contain less that about 1 wt.-% or 0.5 wt.-% of water.

Biocatalytic methods may also be performed in an organic non-aqueous medium. As suitable organic solvents there may be mentioned aliphatic hydrocarbons having for example 5 to 8 carbon atoms, like pentane, cyclopentane, hexane, cyclohexane, heptane, octane or cyclooctane; aromatic carbohydrates, like benzene, toluene, xylenes, chlorobenzene or dichlorobenzene, aliphatic acyclic and ethers, like diethylether, methyl-tert.-butylether, ethyl-tert.-butylether, dipropylether, diisopropylether, dibutylether; or mixtures thereof.

The concentration of the reactants/substrates may be adapted to the optimum reaction conditions, which may depend on the specific enzyme applied. For example, the initial substrate concentration may be in the 0.1 to 0.5 M, as for example 10 to 100 mM.

The reaction temperature may be adapted to the optimum reaction conditions, which may depend on the specific enzyme applied. For example, the reaction may be performed at a temperature in a range of from 0 to 70° C., as for example 20 to 50 or 25 to 40° C. Examples for reaction temperatures are about 30° C., about 35° C., about 37° C., about 40° C., about 45° C., about 50° C., about 55° C. and about 60° C.

The process may proceed until equilibrium between the substrate and then product(s) is achieved, but may be stopped earlier. Usual process times are in the range from 1 minute to 25 hours, in particular 10 min to 6 hours, as for example in the range from 1 hour to 4 hours, in particular 1.5 hours to 3.5 hours. These parameters are non-limiting examples of suitable process conditions.

If the host is a transgenic plant, optimal growth conditions can be provided, such as optimal light, water and nutrient conditions, for example.

k. Product Isolation

The methodology of the present invention can further include a step of recovering an end or intermediate product, optionally in stereoisomerically or enantiomerically substantially pure form. The term "recovering" includes extracting, harvesting, isolating or purifying the compound from culture or reaction media. Recovering the compound can be performed according to any conventional isolation or purification methodology known in the art including, but not limited to, treatment with a conventional resin (e.g., anion or cation exchange resin, non-ionic adsorption resin, etc.), treatment with a conventional adsorbent (e.g., activated charcoal, silicic acid, silica gel, cellulose, alumina, etc.), alteration of pH, solvent extraction (e.g., with a conventional solvent such as an alcohol, ethyl acetate, hexane and the like), distillation, dialysis, filtration, concentration, crystallization, recrystallization, pH adjustment, lyophilization and the like.

Identity and purity of the isolated product may be determined by known techniques, like High Performance Liquid Chromatography (HPLC), gas chromatography (GC), Spektroskopy (like IR, UV, NMR), Colouring methods, TLC, NIRS, enzymatic or microbial assays. (see for example: Patek et al. (1994) Appl. Environ. Microbiol. 60:133-140; Malakhova et al. (1996) Biotekhnologiya 11 27-32; und Schmidt et al. (1998) Bioprocess Engineer. 19:67-70. Ullmann's Encyclopedia of Industrial Chemistry (1996) Bd. A27, VCH: Weinheim, S. 89-90, S. 521-540, S. 540-547, S. 559-566, 575-581 und S. 581-587; Michal, G (1999) Biochemical Pathways: An Atlas of Biochemistry and Molecular Biology, John Wiley and Sons; Fallon, A. et al. (1987) Applications of HPLC in Biochemistry in: Laboratory Techniques in Biochemistry and Molecular Biology, Bd. 17.)

The cyclic terpene compound produced in any of the method described herein can be converted to derivatives such as, but not limited to hydrocarbons, esters, amides, glycosides, ethers, epoxides, aldehydes, ketons, alcohols, diols, acetals or ketals. The terpene compound derivatives can be obtained by a chemical method such as, but not limited to oxidation, reduction, alkylation, acylation and/or rearrangement. Alternatively, the terpene compound derivatives can be obtained using a biochemical method by contacting the terpene compound with an enzyme such as, but not limited to an oxidoreductase, a monooxygenase, a dioxygenase, a transferase. The biochemical conversion can be performed in-vitro using isolated enzymes, enzymes from lysed cells or in-vivo using whole cells.

l. Fermentative Production of Terpene/Terpenoid Compounds, Like Labdane Type compounds The invention also relates to methods for the fermentative production of terpene/terpenoid compounds like labdane type compounds.

A fermentation as used according to the present invention can, for example, be performed in stirred fermenters, bubble columns and loop reactors. A comprehensive overview of the possible method types including stirrer types and geometric designs can be found in "Chmiel: Bioprozesstechnik: Einführung in die Bioverfahrenstechnik, Band 1". In the process of the invention, typical variants available are the following variants known to those skilled in the art or explained, for example, in "Chmiel, Hammes and Bailey: Biochemical Engineering", such as batch, fed-batch, repeated fed-batch or else continuous fermentation with and without recycling of the biomass. Depending on the production strain, sparging with air, oxygen, carbon dioxide, hydrogen, nitrogen or appropriate gas mixtures may be effected in order to achieve good yield (YP/S).

The culture medium that is to be used must satisfy the requirements of the particular strains in an appropriate manner. Descriptions of culture media for various microorganisms are given in the handbook "Manual of Methods for General Bacteriology" of the American Society for Bacteriology (Washington D.C., USA, 1981).

These media that can be used according to the invention may comprise one or more sources of carbon, sources of nitrogen, inorganic salts, vitamins and/or trace elements.

Preferred sources of carbon are sugars, such as mono-, di- or polysaccharides. Very good sources of carbon are for example glucose, fructose, mannose, galactose, ribose, sorbose, ribulose, lactose, maltose, sucrose, raffinose, starch or cellulose. Sugars can also be added to the media via complex compounds, such as molasses, or other by-products from sugar refining. It may also be advantageous to add mixtures of various sources of carbon. Other possible sources of carbon are oils and fats such as soybean oil, sunflower oil, peanut oil and coconut oil, fatty acids such as palmitic acid, stearic acid or linoleic acid, alcohols such as glycerol, methanol or ethanol and organic acids such as acetic acid or lactic acid.

Sources of nitrogen are usually organic or inorganic nitrogen compounds or materials containing these compounds. Examples of sources of nitrogen include ammonia gas or ammonium salts, such as ammonium sulfate, ammonium chloride, ammonium phosphate, ammonium carbonate or ammonium nitrate, nitrates, urea, amino acids or complex sources of nitrogen, such as com-steep liquor, soybean flour, soy-bean protein, yeast extract, meat extract and others. The sources of nitrogen can be used separately or as a mixture.

Inorganic salt compounds that may be present in the media comprise the chloride, phosphate or sulfate salts of calcium, magnesium, sodium, cobalt, molybdenum, potassium, manganese, zinc, copper and iron.

Inorganic sulfur-containing compounds, for example sulfates, sulfites, di-thionites, tetrathionates, thiosulfates, sulfides, but also organic sulfur compounds, such as mercaptans and thiols, can be used as sources of sulfur.

Phosphoric acid, potassium dihydrogenphosphate or dipotassium hydrogenphosphate or the corresponding sodium-containing salts can be used as sources of phosphorus.

Chelating agents can be added to the medium, in order to keep the metal ions in solution. Especially suitable chelating agents comprise dihydroxyphenols, such as catechol or protocatechuate, or organic acids, such as citric acid.

The fermentation media used according to the invention may also contain other growth factors, such as vitamins or growth promoters, which include for example biotin, riboflavin, thiamine, folic acid, nicotinic acid, pantothenate and pyridoxine. Growth factors and salts often come from complex components of the media, such as yeast extract, molasses, com-steep liquor and the like. In addition, suitable precursors can be added to the culture medium. The precise composition of the compounds in the medium is strongly dependent on the particular experiment and must be decided individually for each specific case. Information on media optimization can be found in the textbook "Applied Microbiol. Physiology, A Practical Approach" (1997) Growing media can also be obtained from commercial suppliers, such as Standard 1 (Merck) or BHI (Brain heart infusion, DIFCO) etc.

All components of the medium are sterilized, either by heating (20 min at 1.5 bar and 121° C.) or by sterile filtration. The components can be sterilized either together, or if necessary separately. All the components of the medium can be present at the start of growing, or optionally can be added continuously or by batch feed.

The temperature of the culture is normally between 15° C. and 45° C., preferably 25° C. to 40° C. and can be kept constant or can be varied during the experiment. The pH value of the medium should be in the range from 5 to 8.5, preferably around 7.0. The pH value for growing can be controlled during growing by adding basic compounds such as sodium hydroxide, potassium hydroxide, ammonia or ammonia water or acid compounds such as phosphoric acid or sulfuric acid. Antifoaming agents, e.g. fatty acid polyglycol esters, can be used for controlling foaming. To maintain the stability of plasmids, suitable substances with selective action, e.g. antibiotics, can be added to the medium. Oxygen or oxygen-containing gas mixtures, e.g. the ambient air, are fed into the culture in order to maintain aerobic conditions.

The temperature of the culture is normally from 20° C. to 45° C. Culture is continued until a maximum of the desired product has formed. This is normally achieved within 1 hour to 160 hours.

The methodology of the present invention can further include a step of recovering said terpene alcohol.

The term "recovering" includes extracting, harvesting, isolating or purifying the compound from culture media. Recovering the compound can be performed according to any conventional isolation or purification methodology known in the art including, but not limited to, treatment with a conventional resin (e.g., anion or cation exchange resin, non-ionic adsorption resin, etc.), treatment with a conventional adsorbent (e.g., activated charcoal, silicic acid, silica gel, cellulose, alumina, etc.), alteration of pH, solvent extraction (e.g., with a conventional solvent such as an alcohol, ethyl acetate, hexane and the like), distillation, dialysis, filtration, concentration, crystallization, recrystallization, pH adjustment, lyophilization and the like.

Before the intended isolation the biomass of the broth can be removed. Processes for removing the biomass are known to those skilled in the art, for example filtration, sedimentation and flotation. Consequently, the biomass can be removed, for example, with centrifuges, separators, decanters, filters or in flotation apparatus. For maximum recovery of the product of value, washing of the biomass is often advisable, for example in the form of a diafiltration. The selection of the method is dependent upon the biomass content in the fermenter broth and the properties of the biomass, and also the interaction of the biomass with the product of value.

In one embodiment, the fermentation broth can be sterilized or pasteurized. In a further embodiment, the fermentation broth is concentrated. Depending on the requirement, this concentration can be done batch wise or continuously. The pressure and temperature range should be selected such that firstly no product damage occurs, and secondly minimal use of apparatus and energy is necessary. The skillful selection of pressure and temperature levels for a multistage evaporation in particular enables saving of energy.

The following examples are illustrative only and are not intended to limit the scope of the embodiments an embodiments described herein.

The numerous possible variations that will become immediately evident to a person skilled in the art after heaving considered the disclosure provided herein also fall within the scope of the invention.

EXPERIMENTAL PART

The invention will now be described in further detail by way of the following Examples, a) MATERIALS

Unless otherwise stated, all chemical and biochemical materials and microorganisms or cells employed herein are commercially available products.

Unless otherwise specified, recombinant proteins are cloned and expressed by standard methods, such as, for example, as described by Sambrook, J., Fritsch, E. F. and Maniatis, T., Molecular cloning: A Laboratory Manual, $2^{nd}$ Edition, Cold Spring Harbor Laboratory, Cold Spring Harbor Laboratory Press, Cold Spring Harbor, NY, 1989.

b) GENERAL METHODS

Cell Free Protein Fractions Preparation.

The expression vectors were transformed into *E. coli* KRX cells (Promega Corporation, Madison, WI, USA) and the transformed cells were selected on LB medium plates supplemented with the appropriate antibiotic. The cells were then grown in 25 mL liquid LB medium supplemented with the appropriate antibiotic at 37° C. to an OD of 1. The expression of the recombinant proteins was induced with 1 mM isopropyl-1-thio-β-D-galactopyranoside and 0.1% (w/v) L-rhamnose monohydrate, and the cells were incubated 24 hours at 25° C. with moderate shaking.

The bacterial cells were harvested by centrifugation (5000 g, 12 min) and disrupted by sonication (Sonics, Vibra cell X 130 sonicator equipped with a 6 mm diameter tip microprobe; 3 times 20 second 20 kHz pulses at 80% of maximum power) on ice, in 1.8 mL of 50 mM MOPSO buffer pH 7.4 containing 15% glycerol. The lysates were cleared by centrifugation (3500 g, 8 min, 4° C.) and the resulting supernatants were stored frozen and used as the enzyme source for in vitro assays.

In Vitro Enzyme Assays.

The protein fractions containing one of the recombinant proteins was incubated 4 hours at 24° C. with shaking at 230 rpm in assays consisting of 20 μl of cell-free extract, 160 to 320 mg/L of substrate (using a 40 g/L substrate stock solution in DMSO), 1 mM of cofactor whenever relevant, and 50 mM MOPSO pH 7.4 in a final volume of 0.5 to 1 mL in borosilicate glass and PTFE sealed screw-capped tubes (11 mL capacity) (Wheaton, Millville, NJ 08332 USA). Assays were extracted with 1 volume of methyl-tert-butyl-ether (MTBE) and analyzed by GC-MS as described below.

Whole-Cell Bioconversion Assays.

Bioconversions of compounds were performed using *E. coli* cells expressing recombinant enzymes. The expression vectors are transformed into *E. coli* KRX cells (Promega Corporation, Madison, WI, USA) and the transformed cells were selected on LB medium plates supplemented with the appropriate antibiotic. The cells were first cultivated overnight at 30° C. in 5 mL LB medium supplemented 1% glucose and with the appropriate antibiotic. The next day, 20 mL of TB medium (Terrific Broth) supplemented with the appropriate antibiotic were inoculated with an initial optical density of 0.2 to 0.75. The culture were incubated in shake flasks at 37° C. until an optical density of 1 to 4 was reached and the expression of the recombinant proteins was induced by the addition of 0.1 mM isopropyl-1-thio-β-D-galactopyranoside IPTG and 0.1% rhamnose. The cultures were then distributed in 0.5 to 1 mL aliquotes in 12 mL glass tubes and incubated at 20° C. with moderate shaking.

The substrate was added to each tube 90 minutes after induction of the expression of the recombinant protein. The substrate was either added to a final concentration of 0.25 to 1 g/L using a 40 g/L stock solution in DMSO. Alternatively, an emulsion was prepared containing 150 mg/mL of Tween® 80 (Sigma-Aldrich) and 300 mg/mL of substrate in water and added to the assays to reach a final concentration of 12 mg/mL of substrate.

After 8 to 48 hours of incubation, the cultures were extracted with one volume of MTBE and analyzed by GC-MS as described below.

Cultivation of Engineered Bacteria Cells Under Conditions Enabling Production of Terpene Compounds.

The DP1205 *E. coli* cells were transformed with one or two expression plasmids carrying terpene biosynthesis genes and/or terpene modification enzymes and the transformed cells were cultured with the appropriate antibiotics (kanamycin (50 μg/mL) and/or chloramphenicol (34 μg/mL)) on LB-agarose plates. Single colonies were used to inoculate 5 mL liquid LB medium supplemented with the same antibiotics, 4 g/L glucose and 10% (v/v) dodecane. The next day 2 mL of TB medium supplemented with the same antibiotics and 10% (v/v) dodecane were inoculated with 0.2 mL of the overnight culture. The cultures were incubated at 37° C. until an optical density of 3 was reached. The expression of the recombinant proteins was then induced by addition of 1 mM IPTG and the cultures were incubated for 72 h at 20° C.

The cultures were then extracted with one volume of (MTBE) and the composition of the organic phase was analyzed by GC-MS as described below. For quantification an internal standard (α-longipinene (Aldrich)) was added to the extract prior to GC-MS analysis and concentrations of the components were estimated based on comparison of the peak areas.

GC-MS Analysis Methods.

Samples of whole cell bioconversion assays were analyzed using an Agilent 7890A GC system coupled with a 5975C series Mass Selective Detector (MSD) and equipped with a split/splitless injector (Agilent Technologies, CA).

The GC inlet temperature was set to 230° C. and 1.0 μL of sample was injected in split mode (split ratio 20:1) and analyzed on a DB-5 ms capillary column (30 m×0.25 mm inner diameter×0.25 μm film thickness; Agilent J&W) using helium as a carrier gas at a constant flow of 1 mL/min. The initial temperature of the oven was set at 80° C. and was programmed to 240° C. (10° C./min; hold 1 min) and then to 300° C. (20° C./min; hold 1 min).

Samples of in vitro assays were analyzed using an Agilent 6890N GC system coupled with a 5975 series Mass Selective Detector (MSD) and equipped with a split/splitless injector (Agilent Technologies, CA) and a CombiPAL autosampler (CTC Analytics, Zwingen, Switzerland) injection system. The GC inlet temperature was set to 250° C. and 1.0 μL of sample was injected in pulsed-splitless mode (pulse pressure 1.56 bar, pulse time 0.6 min) and analyzed on a DB-Ims capillary column (30 m×0.25 mm inner diameter×0.25 μm film thickness; Agilent J&W) using helium as a carrier gas at a constant flow of 1.2 mL/min. The initial temperature of the oven was set at 100° C. (hold 1 min) and was programmed to 260° C. (10 to 20° C./min) and then to 300° C. (30° C./min; hold 1 min). For smaller molecular mass compounds, the same conditions were used for analysis except that the oven initial temperature was lowered down to 80° C.

Engineering of Recombinant Strains for Degradation of Terpene Compounds.

Recombinant strains capable of producing or converting compounds were engineered by introducing nucleotide sequences encoding for one or more of the following proteins:

a Baeyer-Villiger monooxygenase (BVMO) selected from

SCH23-BVMO1 from *Hyphozyma roseonigra* (SEQ ID NO: 2),

SCH24-BVMO1 from *Filobasidium magnum* (SEQ ID NO: 6),

SCH25-BVMO1 from *Papiliotrema laurentii* (SEQ ID NO: 10), and

SCH46-BVMO1 from *Bensingtonia ciliata* (SEQ ID NO: 13);

an esterase selected from

SCH23-EST from *Hyphozyma roseonigra* (SEQ ID NO: 20),

SCH24-EST from *Filobasidium magnum* (SEQ ID NO: 24),

SCH25-EST from *Papiliotrema laurentii* (SEQ ID NO: 28); and an enal-cleaving enzyme (lyase) selected from SCH94-3944 *Rhodococcus erythropolis* (SEQ ID NO: 34), SCH80-05241 *Rhodococcus rhodochrous* (SEQ ID NO: 38), Pdigit7033 *Penicillium digitatum* (SEQ ID NO: 42), PitalDUF4334-1 *Penicillium italicum* (SEQ ID NO: 46), AspWeDUF4334 *Aspergillus wentii* (SEQ ID NO: 49), RhoagDUF4334-2 *Rhodococcus hoagii* strain PAM2288 (SEQ ID NO: 53), RhoagDUF4334-3 *Rhodococcus hoagii* strain N128 (SEQ ID NO: 56), RhoagDUF4334-4 *Rhodococcus hoagii* NBRC 10125 (SEQ ID NO: 59), CnecaDUF4334 *Cupriavidus necator* (SEQ ID NO: 62), Rins-DUF4334 *Ralstonia insidiosa* (SEQ ID NO: 69), CgatDUF4334 *Cryptococcus gattii* EJB2 (SEQ ID NO: 72), GclavDUF4334 *Grosmannia clavigera* kw1407 (SEQ ID NO: 75), TcurvaDUF4334 *Thermomonospora curvata* (SEQ ID NO:81), PprotDUF4334 *Pseudomonas protegens* (SEQ ID NO: 87), Bacterial host cells for in vitro enzyme assays or whole cell bioconversion assays were selected from *E. coli* KRX cells (Promega Corporation, Madison, WI, USA) and *E. coli* BL21 Star™ (DE3) cells (ThermoFisher).

For the biochemical production of terpene compounds using one or more enzyme(s) selected from the enzymes listed above, the host cell was engineered to produce increased amounts of farnesyl-pyrophosphate (FPP) using a mevalonate enzyme pathway and was further transformed to express sesquiterpene or diterpene biosynthesis enzymes.

Engineering of a Recombinant *E. coli* Strain for Production of FPP by Chromosomal Integration of the Genes Encoding Mevalonate Pathway Enzymes.

An *E. coli* strain was engineered to produce farnesyl-pyrophosphate (FPP) by chromosomal integration of recombinant genes encoding mevalonate pathway enzymes. See also construction scheme and recombination events depicted in FIG. 1.

An upper pathway operon (operon 1 from acetyl-CoA to mevalonate) was designed consisting of the atoB gene from *E. coli* encoding an acetoacetyl-CoA thiolase, and the mvaA and mvaS genes from *Staphylococcus aureus* encoding a HMG-CoA synthase and a HMG-CoA reductase, respectively.

As a lower mevalonate pathway operon (operon 2 from mevalonate to farnesyl pyrophosphate), a natural operon from the gram-negative bacteria *Streptococcus pneumoniae* was selected, encoding a mevalonate kinase (mvaK1), a phosphomevalonate kinase (mvaK2), a phosphomevalonate decarboxylase (mvaD), and an isopentenyl diphosphate isomerase (fni).

A codon optimized *Saccharomyces cerevisiae* FPP synthase encoding gene (ERG20) was introduced at the 3'-end of the upper pathway operon to convert isopentenyl-diphosphate (IPP) and dimethylallyl-diphosphate (DMAPP) into FPP.

The above described operons were synthesized by DNA 2.0 and integrated into the araA gene of the *Escherichia coli* strain BL21(DE3). The heterologous pathway was introduced in two separate recombination steps using the CRISPR/Cas9 genome engineering system. The first operon (lower pathway; operon 2) to be integrated carries a spectinomycin (Spec) marker which was used to screen for Spec resistant candidate integrants. The second operon was designed to displace the Spec marker of the previously integrated operon and was accordingly screened for Spec candidate integrants following the second recombination event (see FIG. 1). Guide RNA expression vectors targeting the araA gene were designed and synthetized by DNA 2.0. PCR was used to verify operon integration by designing PCR primers to amplify across the araA gene integration target and across recombination junctions of integrants. One clone yielding correct PCR results was then fully sequenced and archived as strain DP1205.

Engineering of Recombinant Bacterial Cells for the Production of Copalol.

An operon was constructed containing two cDNAs encoding for:

AspWeTPP, a protein with terpenyl diphosphate phosphatase activity from *Aspergillus wentii* (SEQ ID NO: 170) (GenBank accession OJJ34585.1) having the ability to dephosphorylate terpenyl diphosphate compounds, like copalyl PP; and PvCPS, a protein having prenyl-transferase and copalyl-diphosphate synthase activities from *Talaromyces verruculosus* (SED ID NO: 173) (GenBank accession BBF88128.1). PvCPS catalyzes the production of copalyl PP from IPP and DMAPP.

The cDNAs encoding for AspWeTPP and PvCPS were codon optimized (SEQ ID NOs: 171 and 174). An operon was designed containing the two cDNAs and an RBS sequence (AAGGAGGTAAAAAA) (SEQ ID NO: 196) placed upstream of the cDNAs. The operon was synthesized and cloned into the pJ401 expression plasmid (ATUM, Newark, California) providing the plasmid pJ401-CPOL-4.

Transformation of *E. coli* cells such as the DP1205 *E. coli* cells with the plasmid pJ401-CPOL-4 provides recombinant cells capable of producing copalol when cultivated under conditions enabling production of terpene compounds.

Engineering of Recombinant Bacteria Cells for the Production of Copalal.

An operon was constructed containing 3 cDNAs encoding for:

AspWeTPP, a protein with terpenyl diphosphate phosphatase activity from *Aspergillus wentii* (SEQ ID NO: 170) (GenBank accession OJJ34585.1) having the ability to dephosphorylate terpenyl diphosphate compounds, like copalyl PP;

AzTolADH1, a protein with alcohol dehydrogenase (ADH) activity from *Azoarcus toluclasticus* (SEQ ID NO: 167) (GenBank accession WP_018990713.1), having the ability to oxidize terpene alcohols like copalol to the respective carbonyl compound like copalal; and PvCPS, a protein having prenyl-transferase and copalyl-diphosphate synthase activities from *Talaromyces verruculosus* (SEQ ID NO: 173) (GenBank accession BBF88128.1) having the ability to produce cyclic terpenyl diphosphate compounds, like copalyl diphosphate, from IPP and DMAPP.

The cDNAs encoding for AspWeTPP, AzTolADH1 and PvCPS were codon optimized (SEQ ID NOs: 171, 168 and 174). An operon was designed containing successively the three cDNAs and an RBS sequence (AAGGAGGTAAAAAA) (SEQ ID NO: 196) placed upstream of each cDNA. The operon was synthesized and cloned into the pJ401 expression plasmid (ATUM, Newark, California) providing the plasmid pJ401-CPAL-1.

Transformation of *E. coli* cells such as the DP1205 *E. coli* cells with the plasmid pJ401-CPAL-1 provides recombinant cells capable of producing copalal when cultivated under conditions enabling production of terpene compounds.

Engineering of Recombinant Bacteria Cells for the Production of Farnesal.

An operon was constructed containing two cDNAs encoding for:

- TalCeTPP, a protein with terpenyl diphosphate phosphatase activity from *Talaromyces cellulolyticus* (GenBank: GAM42000.1) (SEQ ID NO: 176) having the ability to dephosphorylate terpenyl diphosphate compounds, like farnesyl diphosphate; and
- CdGeoA, a protein with alcohol dehydrogenase (ADH) activity from *Castellaniella defragrans* (NCBI accession WP_043683915.1) (SEQ ID NO: 179) having the ability to oxidize terpene alcohols like farnesol to the respective carbonyl compound like farnesal.

The cDNAs encoding for TalCeTPP and CdGeoA were codon optimized (SEQ ID NOs: 177 and 180). An operon was designed containing successively the two cDNAs and an RBS sequence (AAGGAGGTAAAAAA) (SEQ ID NO: 196) placed upstream of each cDNA. The operon was synthesized and cloned into the pJ401 expression plasmid (ATUM, Newark, California) providing the plasmid pJ401-FAL-1.

Transformation of *E. coli* cells such as the DP1205 *E. coli* cells with the plasmid pJ401-FAL-1 provides recombinant cells capable of producing farnesal when cultivated under conditions enabling production of terpene compounds.

Engineering of Recombinant Bacteria Cells for the Production of Labdendiol.

An operon was constructed containing three cDNAs encoding for:

- TalVeTPP, a protein with terpenyl diphosphate phosphatase activity from *Talaromyces verruculosus* (Genbank accession KUL89334.1) (SEQ ID NO: 194); having the ability to dephosphorylate terpenyl diphosphate compounds, like labdenediol PP
- SsLPS, a protein with labdendiol-phyrophosphate (LPP) synthase activity from *Salvia sclarea* (Genbank accession AET21247.1) (SEQ ID NO: 188) having the ability to produce cyclic terpenyl diphosphate compounds, like labdenediol diphosphate, from GGPP; and
- CrtE, a geranylgeranyl-diphosphate synthase from *Pantoea agglomerans* (GenBank accession AAA24819.1) (SEQ ID NO: 191) having the ability to produce GGPP from FPP.

The cDNAs encoding for TalVeTPP, SsLPS and CrtE were codon optimized (SEQ ID NOs: 195, 189 and 192). An operon was designed containing successively the three cDNAs and an RBS sequence (AAGGAGGTAAAAAA) (SEQ ID NO: 196) placed upstream of each cDNA. The operon was synthesized and cloned in the pJ401 expression plasmid (ATUM, Newark, California) providing the plasmid pJ401-LOH-2.

Transformation of *E. coli* cells such as the DP1205 *E. coli* cells with the plasmid pJ401-LOH-2 provides recombinant cells capable of producing labdendiol when cultivated under conditions enabling production of terpene compounds.

Transformation, Selection and Cultivation of Yeast Cells.

All yeast cell transformations were performed with the lithium acetate protocol as described in Gietz and Woods, *Methods Enzymol.,* 2002, 350:87-96. Transformation mixtures were plated on SmUra- or SmLeu-media plates containing 6.7 g/L of Yeast Nitrogen Base without amino acids (BD Difco, New Jersey, USA), 1.92 g/L Dropout supplement without uracil (Sigma Aldrich, Missouri, USA) or 1.6 g/L Dropout supplement without leucine (Sigma Aldrich, Missouri, USA), 20 g/L glucose and 20 g/L agar. Plates were incubated for 3-4 days at 30° C.

Engineering of Yeast Cells for an Increased Level of Endogenous Farnesyl-Diphosphate.

To increase the level of endogenous farnesyl-diphosphate (FPP) pool in *S. cerevisiae* cells, an extra copy of all yeast endogenous genes involved in the mevalonate pathway, from ERG10 coding for acetyl-CoA C-acetyltransferase to ERG20 coding for FPP synthetase, were integrated into the genome of the *S. cerevisiae* strain CEN.PK2-1C (Euroscarf, Frankfurt, Germany) under the control of galactose-inducible promoters, similarly as described in Paddon et al., *Nature,* 2013, 496:528-532. Briefly, three cassettes were integrated in the LEU2, TRP1 and URA3 loci respectively. A first cassette contained the genes ERG20 and a truncated HMG1 (tHMG1 as described in Donald et al., *Proc Natl Acad Sci USA,* 1997, 109:E111-8) under the control of the bidirectional promoter of GAL10/GAL1 and the genes ERG19 and ERG13 also under the control of the GAL10/GAL1 promoter. The cassette was flanked by two 100 nucleotides regions corresponding to the up- and down-stream sections of LEU2. A second cassette contained the genes IDI1 and tHMG1 which were under the control of the GAL10/GAL1 promoter and the gene ERG13 under the control of the promoter region of GAL7. The cassette was flanked by two 100 nucleotides regions corresponding to the up- and down-stream sections of TRP1. A third cassette contained the genes ERG10, ERG12, tHMG1 and ERG8, all under the control of GAL10/GAL1 promoters. The cassette was flanked by two 100 nucleotides regions corresponding to the up- and down-stream sections of URA3. All genes in the three cassettes included 200 nucleotides of their own terminator regions. Also, an extra copy of GAL4 under the control of a mutated version of its own promoter, as described in Griggs and Johnston, *Proc Natl Acad Sci USA,* 1991, 88:8597-8601, was integrated upstream of the ERG9 promoter region. In addition, the expression of ERG9 was modified by promoter exchange. The GAL7, GAL10 and GAL1 genes were deleted using a cassette containing the HIS3 gene with its own promoter and terminator. The resulting strain was mated with the strain CEN.PK2-1D (Euroscarf, Frankfurt, Germany) obtaining a diploid strain termed YST045 which was induced for sporulation according to Solis-Escalante et al., *FEMS Yeast Res,* 2015, 15:2. Spore separation was achieved by resuspension of asci in 200 μL 0.5M sorbitol with 2 μL zymolyase (1000 U $mL^{-1}$, Zymo research, Irvine, CA) and incubation at 37° C. for 20 minutes. The mixture was then plated on media containing 20 g/L peptone, 10 g/L yeast extract and 20 g/L agar, and one germinated spore was isolated and termed YST075.

Engineering of Recombinant Yeast Cells for the Production of Copalol.

For copalol production, expression of the GGPP synthase carG (from *Blakeslea trispora*, NCBI accession JQ289995.1) (SEQ ID NO: 182), the copalyl-pyrophosphate synthase SmCPS2 (from *Salvia miltiorrhiza*, NCBI accession ABV57835.1) (SEQ ID NO: 185) and the copalyl-pyrophosphate phosphatase TalVeTPP (from *Talaromyces verruculosus*, NCBI accession KUL89334.1) (SEQ ID NO: 194) in the different engineered yeast cells was achieved with a plasmid system constructed in vivo using yeast endogenous homologous recombination as previously described in Kuijpers et al., *Microb Cell Fact.,* 2013, 12:47.

The plasmid is composed of six DNA fragments which were used for *S. cerevisiae* co-transformation. The fragments were:

a) LEU2 yeast marker, constructed by PCR using the primers 5'-AGGTGCAGTTCGCGTGCAAT-TATAACGTCGTGGCAACTGTTATCAGTCG TACCGCGCCATTCGACTACGTCGTAAGGCC-3' (SEQ ID NO: 124) and 5'-TCGTGGT-CAAGGCGTGCAATTCTCAACACGAGAGTGAT-TCTTCGGCGTT GTTGCTGACCATCGACGG-TCGAGGAGAACTT-3' (SEQ ID NO: 125) with the plasmid pESC-LEU (Agilent Technologies, California, USA) as template;

b) AmpR *E. coli* marker, constructed by PCR using the primers 5'-TGGTCAGCAACAACGCCGAAGAAT-CACTCTCGTGTTGAGAATTGCACG CCTTGAC-CACGACACGTTAAGGGATTTGGTCATGAG-3' (SEQ ID NO: 126) and 5'-AACGCGTACCC-TAAGTACGGCACCACAGTGACTATGCAGTC-CGCACTTT GCCAATGCCAAAAATGTGCGCG-GAACCCCTA-3' (SEQ ID NO: 127) with the plasmid pESC-URA as template;

c) Yeast origin of replication, obtained by PCR using the primers 5'-TTGGCATTGGCAAAGTGCGGACTG-CATAGTCACTGTGGTGCCGTACTTA GGGTA-CGCGTTCCTGAACGAAGCATCTGTGCTTCA-3' (SEQ ID NO: 128) and 5'-CCGAGATGCCAAAGGA-TAGGTGCTATGTTGATGACTACGACACAGAAC TGCGGGTGACATAATGATAGCATTGAAGGAT-GAGACT-3' (SEQ ID NO: 129) with pESC-URA as template;

d) *E. coli* replication origin, obtained by PCR using the primers 5'-ATGTCACCCGCAGTTCTGTGTCG-TAGTCATCAACATAGCACCTATCCTT TGG-CATCTCGGTGAGCAAAAGGCCAGCAAAAGG-3' (SEQ ID NO: 130) and 5'-CTCAGATGTACGGT-GATCGCCACCATGTGACGGAAGCTATCCTG-ACAGT GTAGCAAGTGCTGAGCGTCAGACC-CCGTAGAA-3' (SEQ ID NO: 131) with the plasmid pESC-URA as template;

e) a fragment composed by the last 60 nucleotides of the fragment "d", 200 nucleotides downstream the stop codon of the yeast gene PGK1, the GGPP synthase coding sequence carG, the bidirectional yeast promoter of GAL10/GAL1, the coding sequence of TalVeTPP, 200 nucleotides downstream the stop codon of the yeast gene CYC1 and the sequence 5'-AT-TCCTAGTGACGGCCTTGGGAACTCGATACAC-GATGTTCAGTAGACCG CTCACACATGG-3'(SEQ ID NO: 132), this fragment was obtained by DNA synthesis (ATUM, Menlo Park, CA 94025) and f) a fragment composed by the last 60 nucleotides of fragment "e", 200 nucleotides downstream the stop codon of the yeast gene CYC1, the SmCPS2 copalyl-pyrophosphate synthase coding sequence, the bidirectional yeast promoter of GAL10/GAL1 and 60 nucleotides corresponding to the beginning of the fragment "a", this fragment was obtained by DNA synthesis (ATUM, Menlo Park, CA 94025).

Optionally, the GGPP synthase carG and the copalyl-pyrophosphate synthase were replaced by the bi-functional PvCPS.

Engineering of Recombinant Yeast Cells for the Production of Manooloxy.

For degradation of copalol to manooloxy using different alcohol dehydrogenases (ADHs), Baeyer-Villiger monooxygenases (BVMOs) and esterases (ESTs), genome integrations in the strain YST075 were performed. Each integration cassette was formed by four fragments:

1) A fragment containing 658 bp corresponding to the upstream section of the NDT80 gene and the sequence 5'-GCAGGCAGCTCCATTTCATGTAGGTGATT-TATCCCTCCGGGCGGTATTT GAGACTCTCGG-3' (SEQ ID NO: 121), this fragment was obtained by PCR with genomic DNA from the strain YST075 as template;

2) a fragment containing the sequence 5'-GCAGGCAGCTCCATTTCATGTAGGTGATT-TATCCCTCCGGGCGGTATTT GAGACTCTCGG-3' (SEQ ID NO: 121), the CYC1 terminator region, one of the genes coding for a BVMO, the intergenic region between GAL1 and GAL10 genes, one of the genes encoding for an esterase, the terminator region of the ADH1 gene and the sequence 5'-ACTGCTGGGTACTGTTCAGGCACGATAG-GAAATGCGTCCAGCGCATAC ACCAGTCTTAGC-3' (SEQ ID NO: 122), this fragment was obtained by DNA synthesis (ATUM, Menlo Park, CA 94025), 3) a fragment containing the sequence 5'-ACTGCTGGGTACTGTTCAGGCACGATAG-GAAATGCGTCCAGCGCATAC ACCAGTCTTAGC-3' (SEQ ID NO: 122), the PGK1 terminator region, one of the genes encoding for an alcohol dehydrogenase, the promoter region of the genes GAL1 and GAL10, one of the genes encoding an alcohol dehydrogenase, the CYC1 terminator region and the sequence 5'-AGTCGACCTTACAGCGCCTGGGACTCTA-CATAAACATGCAGCGAACAT GCTTTCCAACGC-3' (SEQ ID NO: 123), This fragment might contain one or two alcohol dehydrogenase depending on the experiment performed. They were obtained by DNA synthesis (ATUM, Menlo Park, CA 94025); and 4) a fragment containing the sequence 5'-AGTCGACCT-TACAGCGCCTGGGACTCTACATAAACATGCA-GCGAACAT GCTTTCCAACGC-3' (SEQ ID NO: 123), and 405 bp corresponding to the NDT80 gene. This fragment was obtained by PCR with genomic DNA from the strain YST075 as template.

Engineering of Recombinant Yeast Cells for the Degradation of Copalol to Manooloxy.

For degradation of copalol to manooloxy, using an alcohol dehydrogenase and different enal-cleaving polypeptides, genome integrations in the strain YST075 were performed, each integration cassette was formed by three fragments:

1) A fragment containing 658 bp corresponding to the upstream section of the NDT80 gene and the sequence 5'-GCAGGCAGCTCCATTTCATGTAGGTGATT-TATCCCTCCGGGCGGTATTTGAGACT CTCGG-3' (SEQ ID NO: 121), this fragment was obtained by PCR with genomic DNA from the strain YST075 as template;

2) a fragment containing the sequence 5'-GCAGGCAGCTCCATTTCATGTAGGTGATT-TATCCCTCCGGGCGGTATTTGAGACT CTCGG-3' (SEQ ID NO: 121), the intergenic region between GAL1 and GAL10 genes, one of the genes encoding for an enal-cleaving polypeptide, the terminator region of the ADH1 gene and the sequence 5'-ACTGCTGGGTACTGTTCAGGCACGATAG-GAAATGCGTCCAGCGCATACACCAGT CTTA-GC-3' (SEQ ID NO: 122), this fragment was obtained by DNA synthesis (ATUM, Menlo Park, CA 94025); and 3) a fragment containing the sequence 5'-ACTGCTGGGTACTGTTCAGGCACGATAGGAAATGCGTCCAGCGCATACACCAGT CTTAGC-3' (SEQ ID NO: 122), the PGK1 terminator region, the gene coding for an alcohol dehydrogenase, the promoter region of the genes GAL1 and GAL10, the sequence 5'-AGTCGACCTTACAGCGCCTGGGACTCTACATAAACATGCAGCGAACATGCTTTCC AACGC-3' (SEQ ID NO: 123) and 405 bp corresponding to the NDT80 gene. This fragment was obtained by DNA synthesis (ATUM, Menlo Park, CA 94025).

In all cases, copalol production was achieved by expressing the biosynthetic pathway in a plasmid system as described above.

Engineering of Recombinant Yeast Cells for the Production of Gamma-Ambryl Acetate.

For degradation of copalol to gamma-ambryl acetate using an alcohol dehydrogenase, an enal-cleaving polypeptide and different Baeyer-Villiger monooxygenases (BVMOs), genome integrations in the strain YST075 were performed; each integration cassette was formed by three fragments:

(1) A fragment containing 658 bp corresponding to the upstream section of the NDT80 gene and the sequence 5'-GCAGGCAGCTCCATTTCATGTAGGTGATTTATCCCTCCGGGCGGTATTTGAGACT CTCGG-3' (SEQ ID NO: 121), this fragment was obtained by PCR with genomic DNA from the strain YST075 as template;

(2) a fragment containing the sequence 5'-GCAGGCAGCTCCATTTCATGTAGGTGATTTATCCCTCCGGGCGGTATTTGAGACT CTCGG-3' (SEQ ID NO: 121), the terminator region of the CYC1 gene, one of the genes coding for the tested BVMOs, the intergenic region between GAL1 and GAL10 genes, the gene encoding for an enal-cleaving polypeptide, the terminator region of the ADH1 gene and the sequence 5'-ACTGCTGGGTACTGTTCAGGCACGATAGGAAATGCGTCCAGCGCATACACCAGT CTTAGC-3' (SEQ ID NO: 122), this fragment was obtained by DNA synthesis (ATUM, Menlo Park, CA 94025); and (3) a fragment containing the sequence 5'-ACTGCTGGGTACTGTTCAGGCACGATAGGAAATGCGTCCAGCGCATACACCAGT CTTAGC-3' (SEQ ID NO: 122), the PGK1 terminator region, the gene coding for an alcohol dehydrogenase, the promoter region of the genes GAL1 and GAL10, the sequence 5'-AGTCGACCTTACAGCGCCTGGGACTCTACATAAACATGCAGCGAACATGCTTTCC AACGC-3' (SEQ ID NO: 123) and 405 bp corresponding to the NDT80 gene. This fragment was obtained by DNA synthesis (ATUM, Menlo Park, CA 94025).

In all cases, copalol production was achieved by expressing the biosynthetic pathway in a plasmid system as described above.

Engineering of Recombinant Yeast Cells for the Production Gamma-Ambrol.

For degradation of copalol to gamma-ambrol using an alcohol dehydrogenase, an enal-cleaving polypeptide, a Baeyer-Villiger monooxygenases (BVMOs) and different esterases (EST), genome integrations in the strain YST075 were performed; each integration cassette was formed by four overlapping fragments:

1) A fragment containing at least 300 bp corresponding to the upstream section of the BUD9 gene and at least 60 bp overlapping sequence for in vivo assembly. This fragment was obtained by PCR with genomic DNA from the strain YST075 as template;

2) a fragment containing the terminator region of the ADH1 gene, one of the genes coding for the tested esterases and the intergenic region between GAL1 and GAL10 genes. The fragment was flanked by sequences allowing in vivo assembly. This fragment was obtained by DNA synthesis (ATUM, Menlo Park, CA 94025);

3) a fragment containing the URA3 yeast marker with its own promoter and terminator, flanked by sequences to allow homologous recombination. This fragment was obtained by PCR; and 4) a fragment containing at least 300 bp corresponding to the downstream section of the BUD9 gene and at least 60 bp overlapping sequences to allow in vivo assembly. This fragment was obtained by PCR with genomic DNA from the strain YST075 as template.

In all cases, copalol production was achieved by expressing the biosynthetic pathway in a plasmid system as described above.

Cultivation of Engineered Yeast Cells Under Conditions Enabling the Production of Terpene Compounds and GC-MS Analysis Methods.

Evaluation of the production of terpenes and derivatives from engineered yeast cells was achieved by culturing cells under conditions similarly as described in Westfall et al., *Proc Natl Acad Sci USA,* 2012, 109:E111-118 with 10% dodecane or 10% isopropyl myristate (IPM) as organic overlay. The cultures were then extracted with two volumes of MTBE and the composition of the organic phase was analyzed by GC-MS using an Agilent 7890A GC system coupled with a 5975C series Mass Selective Detector (MSD) and equipped with a split/splitless injector and a GC Injector 80 injection system (Agilent Technologies, CA). The GC inlet temperature was set to 260° C. and 1.0 μl of sample was injected in splitless mode and analyzed on a HP-5 GC column (30 m×0.25 mm×0.25 μm; Agilent J&W) using helium as a carrier gas at a constant flow of 1.2 mL/min. The initial temperature of the oven was set at 100° C. and was programmed to 300° C. (10° C./min).

c) EXAMPLES

Figure 2:
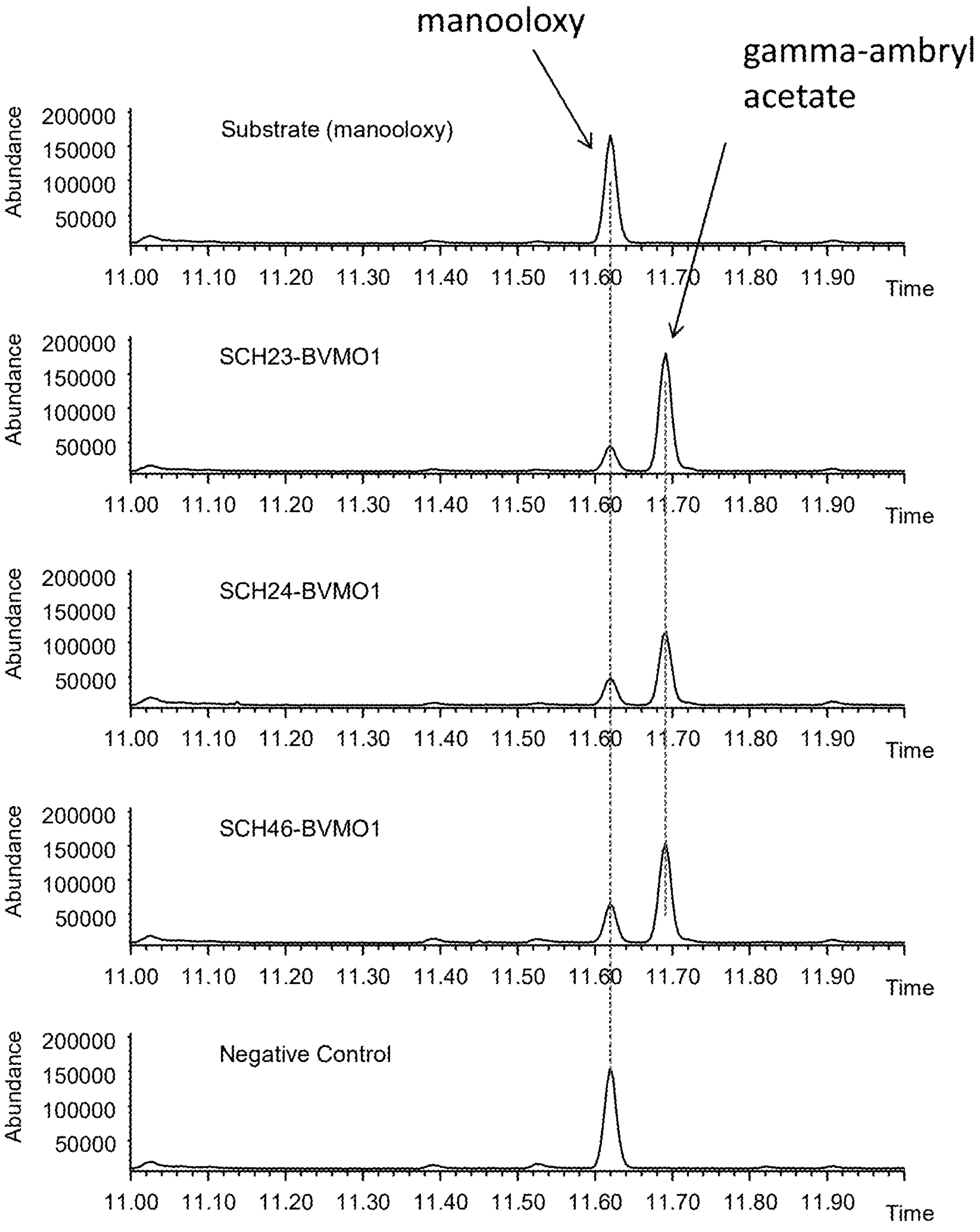
FIG. 2. Conversion of manooloxy to gamma-ambryl acetate using BVMOs in an whole-cells bioconversion assay. GC-MS analysis of the products formed during the bioconversion of manooloxy by different BVMOs: SCH23-BVMO1, SCH24-BVMO1, SCH46-BVMO1. The upper chromatogram shows the GC-MS analysis of manooloxy. The lower chromatogram shows the GC-MS analysis of a bioconversion using control cells not expressing a recombinant BVMO.

Example 1: In-Vivo-Conversion of Manooloxy to Gamma-Ambryl Acetate Using BVMOs Codon optimized cDNAs encoding for SCH23-BVMO1 from *Hyphozyma roseonigra* (SEQ ID NO: 2), SCH24-BVMO1 from *Filobasidium magnum* (SEQ ID NO: 6) and SCH46-BVMO1 from *Bensingtonia ciliata* (SEQ ID NO: 13) were synthesized and cloned in the pJ414 expression plasmid (ATUM, Newark, California) providing the plasmids pJ414-SCH23-BVMO1, pJ414-SCH24-BVMO1 and pJ414-SCH46-BVMO1. KRX *E. coli* cells (Promega Corporation, Madison, WI, USA) were transformed with these expression plasmids. The transformed cells were grown and used in whole cell bioconversion assay as described above using manooloxy as substrate. A negative control was included consisting of the cells transformed with an empty plasmid. In the presence of the SCH23-BVMO1, SCH24-BVMO1 or SCH46-BVMO1 recombinant proteins, conversion of manooloxy to gamma-ambryl acetate was observed (FIG. 2). No conversion was observed in the negative control. This experience shows that SCH23-BVMO1, SCH24-BVMO1 or SCH46-BVMO1 can catalyse the following conversion:

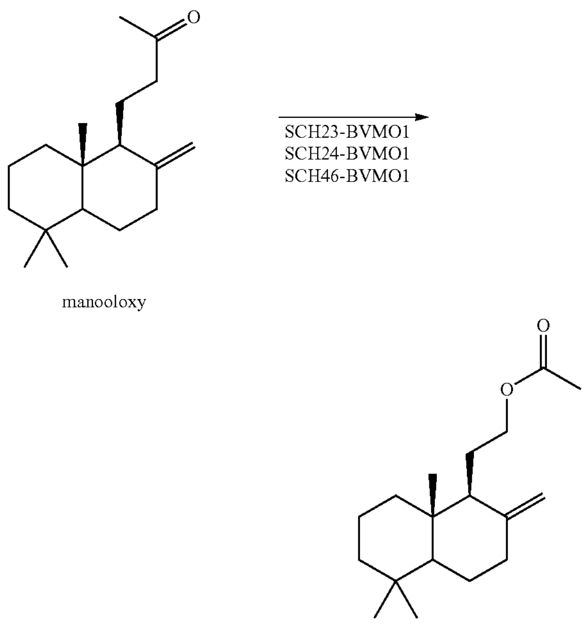

manooloxy gamma-ambryl acetate

These results show that SCH23-BVMO1, SCH24-BVMO1 and SCH46-BVMO1 catalyse a Baeyer-Villiger type oxidation of manooloxy.

Example 2: In-Vivo Conversion of Copalal to Compound 4 Using BVMOs

Figure 3:
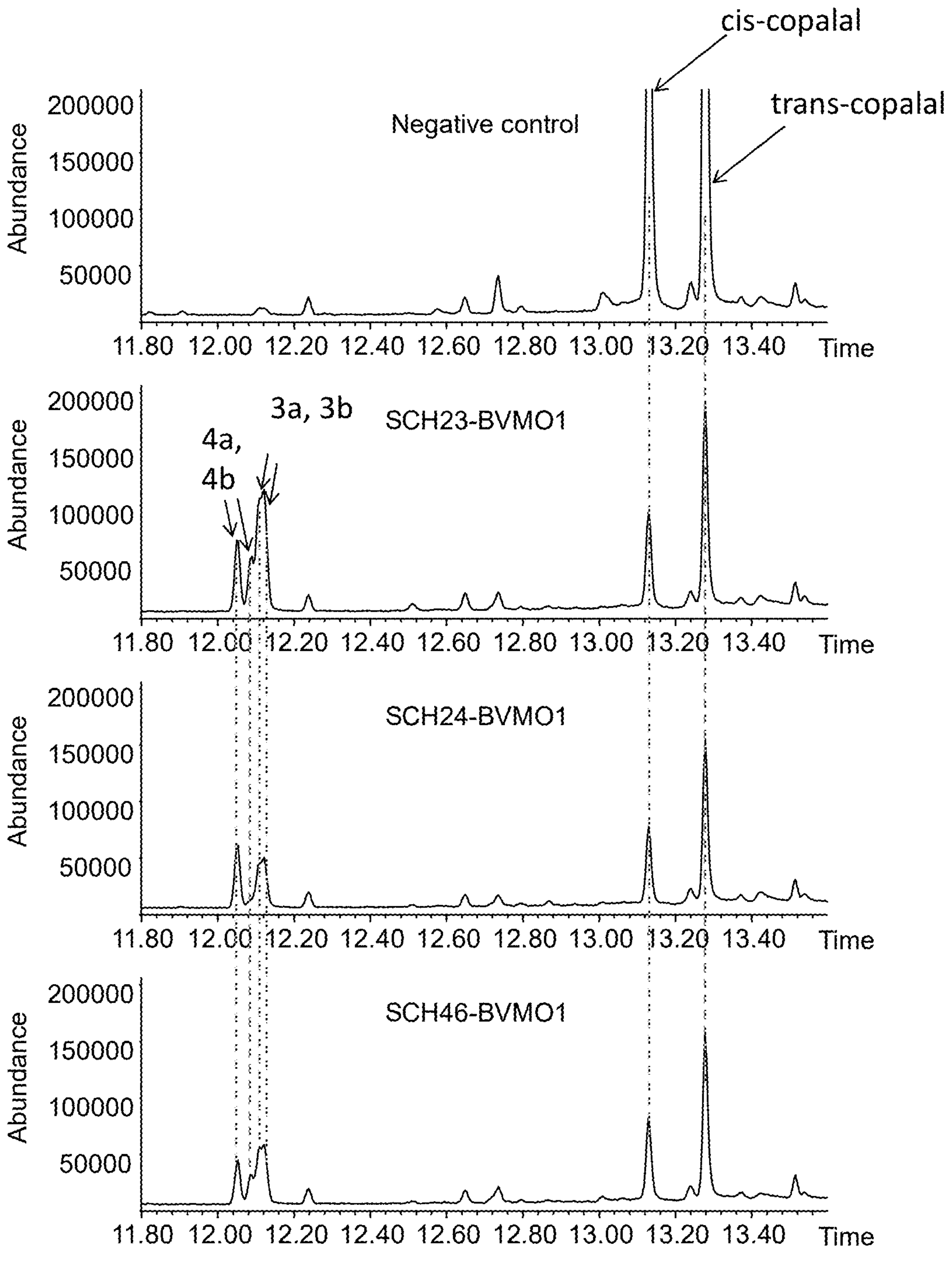
FIG. 3. Conversion of copalal using BVMOs in whole-cells bioconversion assays. GC-MS analysis of the products formed (compounds 3a, 3b, 4a, 4b as described in the experimental part) during the bioconversion of cis-copalal and trans-copalal by different BVMOs: SCH23-BVMO1, SCH24-BVMO1, SCH46-BVMO1. The upper chromatogram shows the GC-MS analysis of a bioconversion using control cells not expressing a recombinant BVMO.

Codon optimized cDNAs encoding for SCH23-BVMO1 from *Hyphozyma roseonigra* (SEQ ID NO: 3), SCH24-BVMO1 from *Filobasidium magnum* (SEQ ID NO: 7) and SCH46-BVMO1 from *Bensingtonia ciliata* (SEQ ID NO: 14) were synthesized and cloned in the pJ414 expression plasmid (ATUM, Newark, California) providing the plasmids pJ414-SCH23-BVMO1, pJ414-SCH24-BVMO1 and pJ414-SCH46-BVMO1. KRX *E. coli* cells (Promega Corporation, Madison, WI, USA) were transformed with these expression plasmids. The cells were grown and used in whole cell bioconversion assay as described above using a mixture of cis-copalal and trans-copalal as substrate. A negative control was included consisting of the cells transformed with an empty plasmid. In the presence of the SCH23-BVMO1, SCH24-BVMO1 or SCH46-BVMO1 recombinant proteins, conversion of cis-copalal and trans-copalal was observed. The GC-MS analysis of the products (FIG. 3) of the bioconversion after 42 hours of incubation shows the formation of four major products, the two stereoisomers 3a and 3b and the two stereoisomers 4a and 4b.

Figure 4:
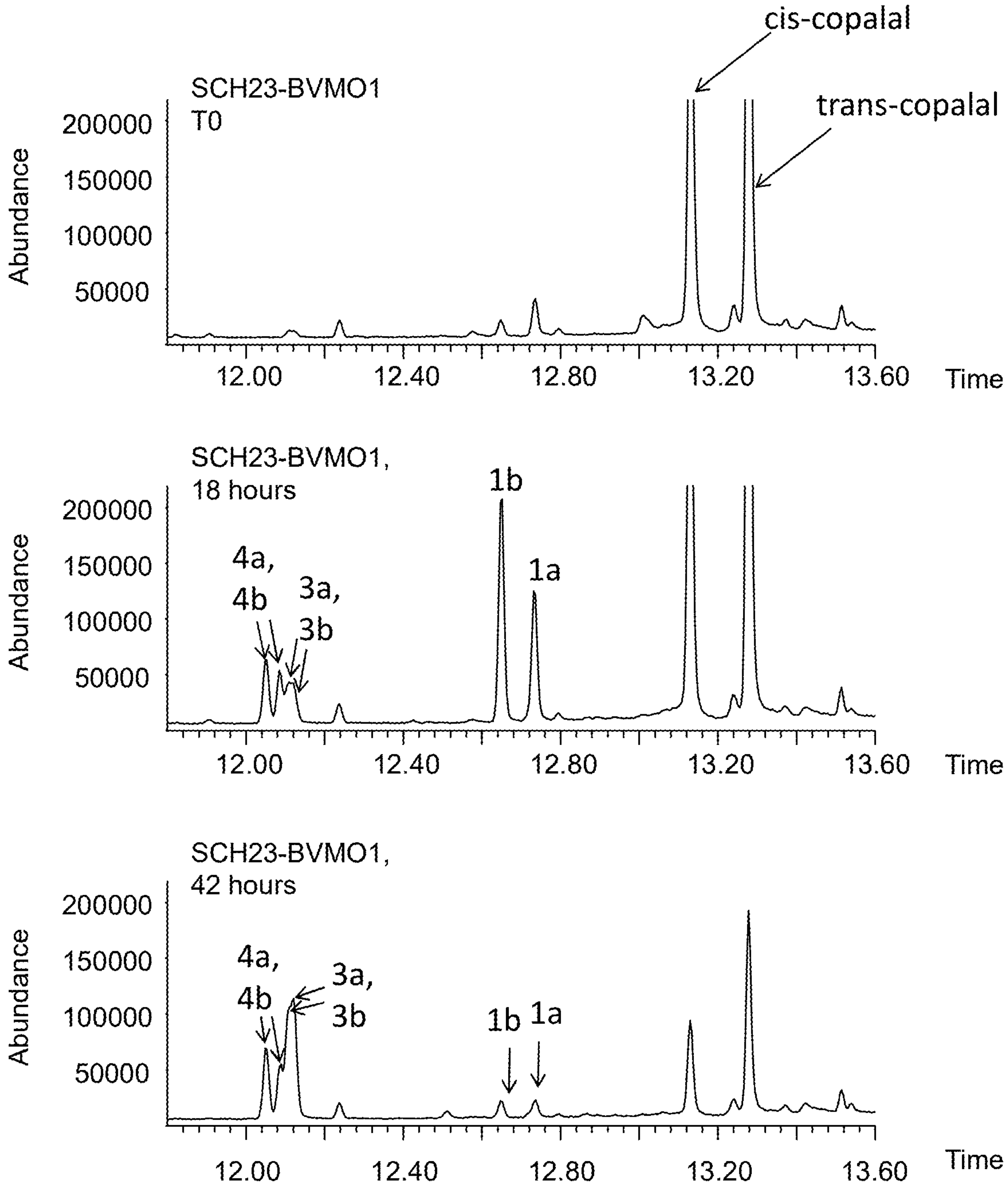
FIG. 4. Kinetic of the conversion of copalal using SCH23-BVMO1 in whole-cells bioconversion assays. GC-MS analysis of the products (compounds 1a, 1b, 3a, 3b, 4a, 4b as described in the experimental part) formed during the bioconversion of cis-copalal and trans-copalal by SCH23-BVMO1 after 0, 18 and 42 hours of incubation.

Time point measurements of the bioconversion show the formation of compounds 1a and 1b as intermediate products. FIG. 4 compares GC-MS analysis of the conversion of cis-copalal and trans-copalal by SCH23-BVMO1 at different times; similar evolution of the product profiles is observed with SCH24-BVMO1 and SCH46-BVMO1. The sequential formation of these compounds shows that trans-copalal and cis-copalal are converted to compound 4a and 4b in several steps. Compounds 1a and 1b and compounds 4a and 4b are formate esters. Such functional groups can be formed from aldehyde compounds by Baeyer-Villiger monooxygenases. Thus, the following reaction scheme, involving enzymatic and non-enzymatic (chemical reactions), can be drawn to describe the conversion of trans-copalal by SCH23-BVMO1, SCH24-BVMO1 or SCH46-BVMO1.

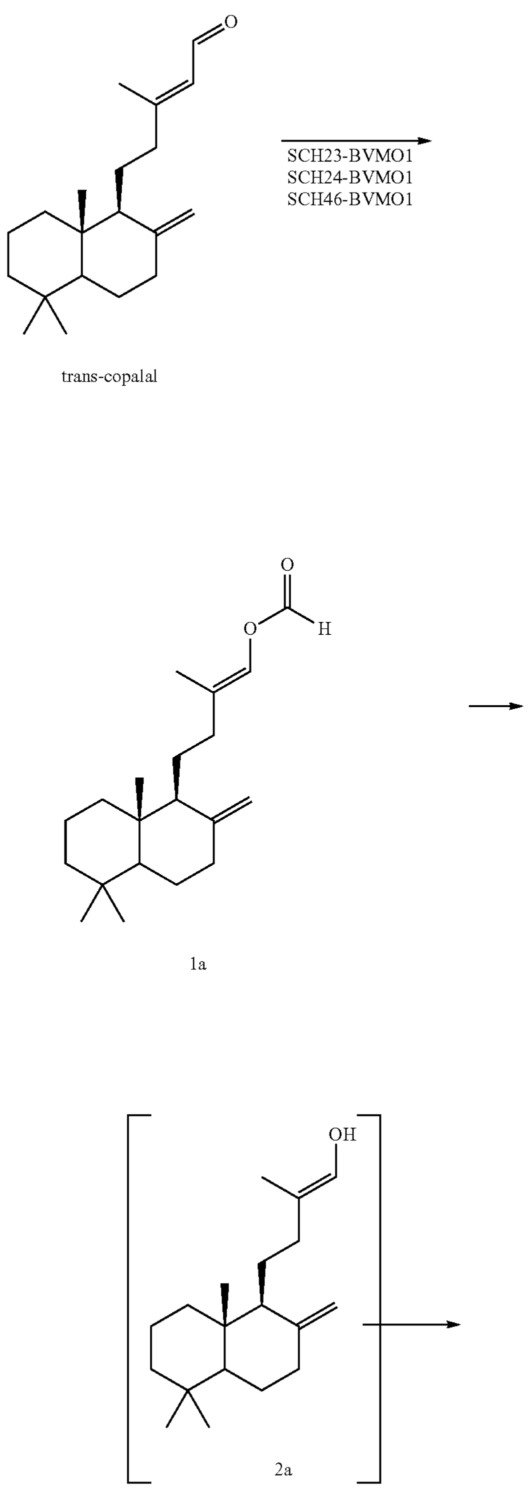

trans-copalal

1a

2a

-continued

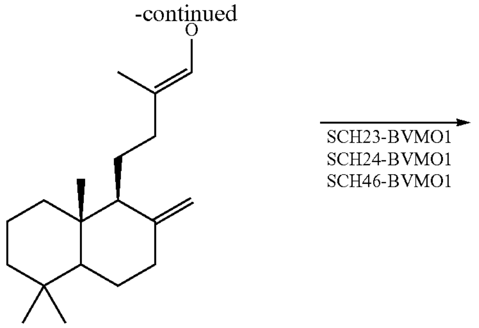

3a, 3b

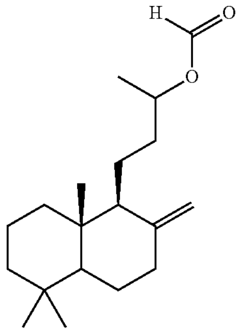

4a, 4b

In this scheme, the recombinant enzymes catalyse two Baeyer-Villiger type oxidations on two different aldehydes. First, the α,β-unsaturated aldehyde group of trans-copalal is oxidized to form compound 1a in the first Baeyer-Villiger oxidations by the recombinant enzyme. The enol formate functional group of compounds 1a is unstable under the experimental conditions and is partially hydrolysed to form compound 2a. This latter compound is rapidly converted via a keto-enol tautomerization to compound 3 (3a and 3b) and is therefore not detected in the GC-MS analysis. Compound 3 (3a and 3b) is the substrate of the same enzyme which catalyses a second Baeyer-Villiger oxidations to form compound 4 (4a and 4b).

The reaction scheme bellow depicts the similar reactions in the transformation of cis-copalal by SCH23-BVMO1, SCH24-BVMO1 or SCH46-BVMO1.

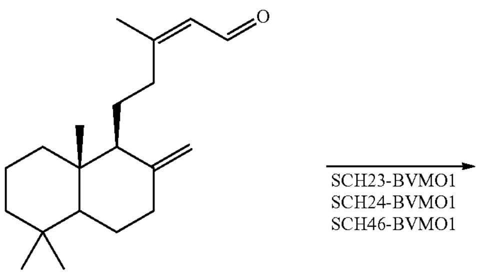

cis-copalal

-continued

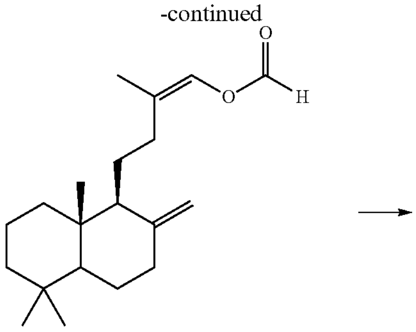

1b

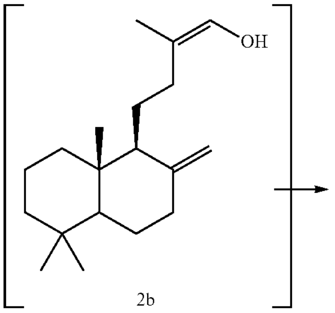

2b

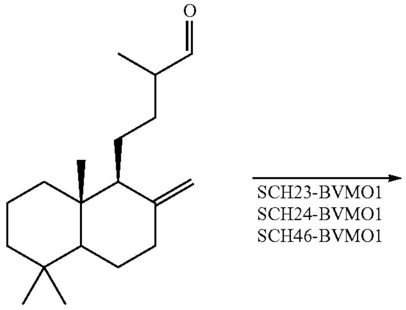

3a, 3b

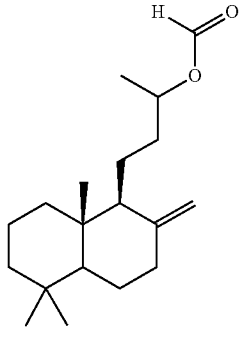

4a, 4b

These results show that SCH23-BVMO1, SCH24-BVMO1 and SCH46-BVMO1 catalyse a Baeyer-Villiger type oxidation on labdane aldehyde compounds.

Example 3: In Vitro Conversion of Manooloxy Using BVMOs and Esterases

For this experiment the following recombinant proteins were used: SCH23-BVMO1 from *Hyphozyma roseonigra* (SEQ ID NO: 2) SCH24-BVMO1 from *Filobasidium magnum* (SEQ ID NO: 6), SCH23-EST from *Hyphozyma roseonigra* (SEQ ID NO: 20) and SCH24-EST from *Filobasidium magnum* (SEQ ID NO: 24). Codon optimized cDNAs encoding for SCH23-BVMO1 (SEQ ID NO: 3) and SCH24-BVMO1 (SEQ ID NO: 7) were synthesized and cloned in the pJ414 expression plasmid (ATUM, Newark, California) providing the plasmids pJ414-SCH23-BVMO1 and pJ414-SCH24-BVMO1. Codon optimized cDNAs encoding for SCH23-EST (SEQ ID NO: 21) and SCH24-EST (SEQ ID NO: 25) were synthesized and cloned in the pJ431 expression plasmid (ATUM, Newark, California) providing the plasmids pJ414-SCH23-EST, pJ414-SCH24-EST.

KRX *E. coli* cells (Promega Corporation, Madison, WI, USA) were transformed with each of these expression plasmids. The transformed cells were grown and cell free lysates were prepared as described. In vitro enzymatic assays were performed with either of these protein fractions or with a combination of two of these protein fractions. The in vitro assays conditions were as described above with addition of 160 mg/L of manooloxy, 60 μM flavine adenine dinucleotide (FAD) and 500 μM reduced β-Nicotinamide adenine dinucleotide phosphate (NADPH).

Figure 5:
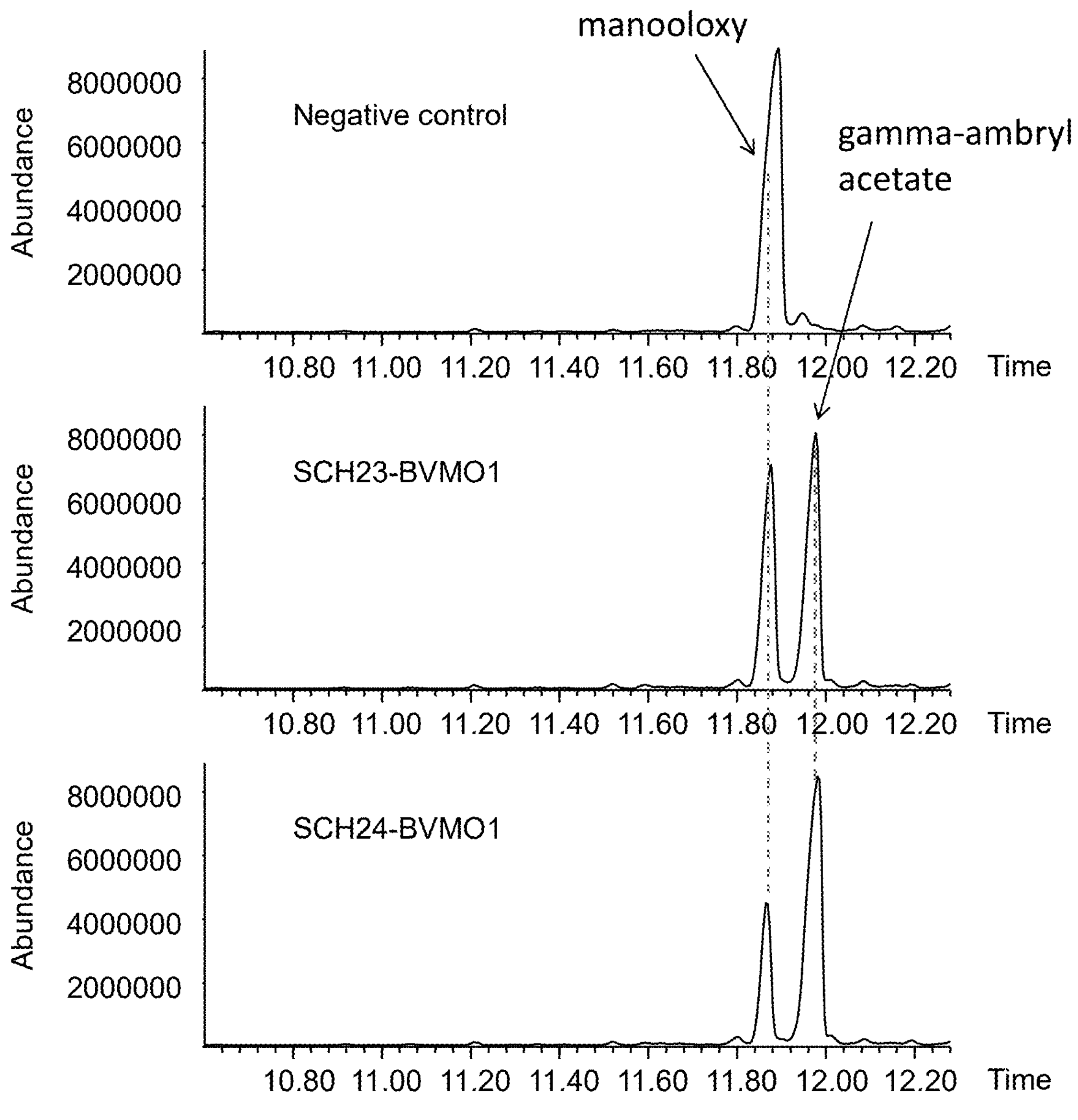
FIG. 5. In vitro conversion of manooloxy using BVMOs. GC-MS analysis of the conversion of manooloxy by SCH23-BVMO1 and SCH24-BVMO1 showing the formation of gamma-ambrol acetate. The upper chromatogram shows the GC-MS analysis of a conversion using control protein without recombinant BVMO.

Using crude fractions containing the recombinant SCH23-BVMO1 and SCH24-BVMO1 proteins, conversion of manooloxy to gamma-ambrol acetate was observed. No conversion was detected when using a control lysate obtained from *E. coli* cells transformed with an empty plasmid (FIG. 5). From these experiments, the following enzymatic reaction can be drawn:

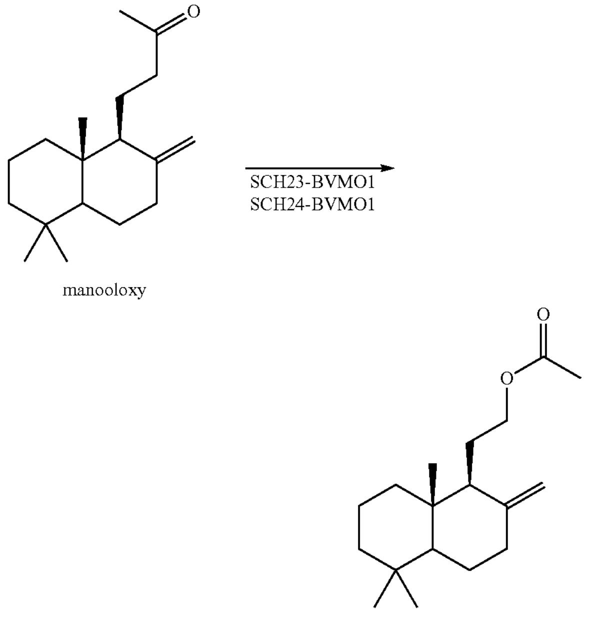

manooloxy gamma-ambryl acetate

Figure 6:
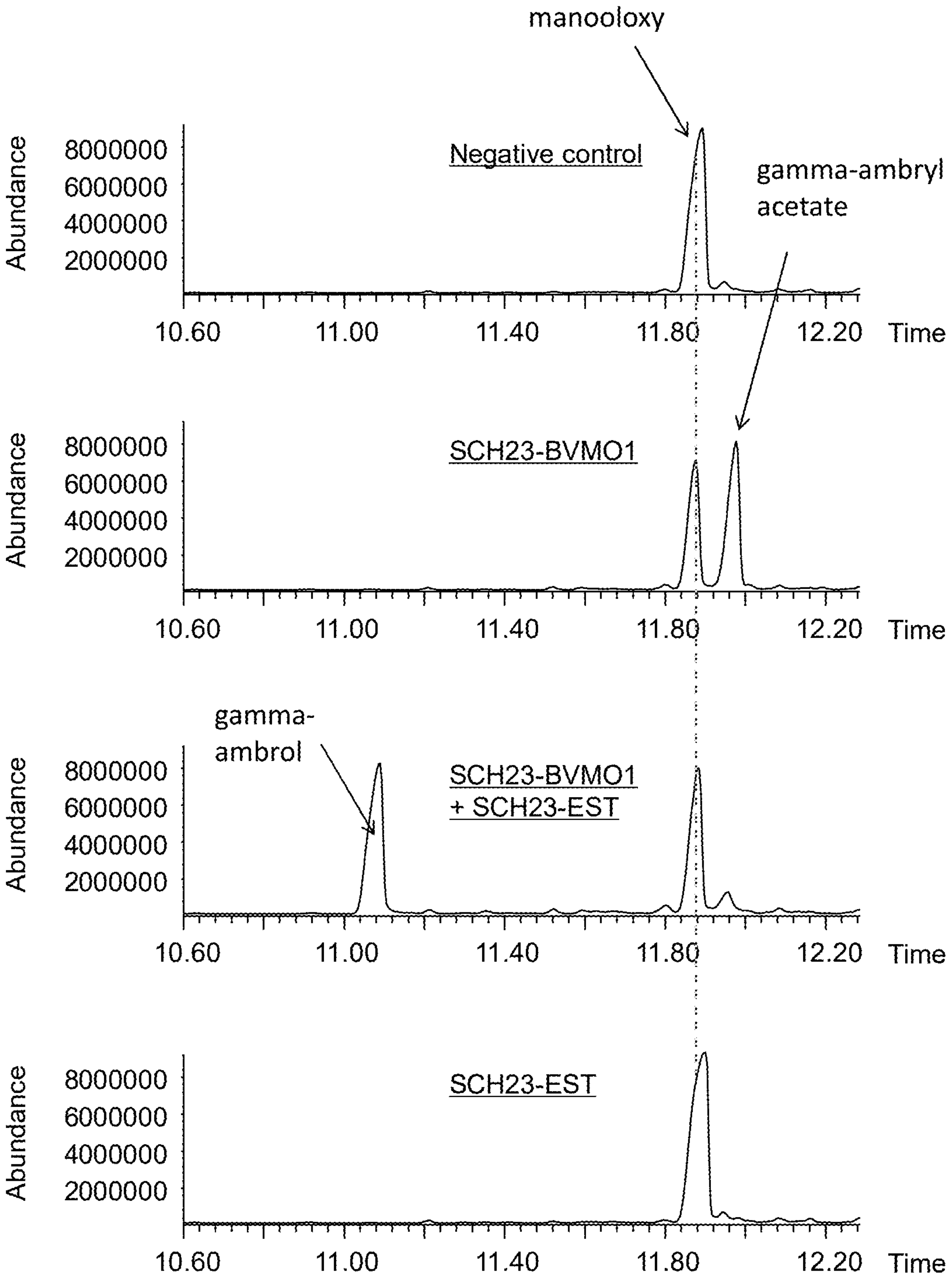
FIG. 6. In vitro conversion of manooloxy using BVMOs and esterases. GC-MS analysis of the conversion of manooloxy by SCH23-BVMO1, SCH23-EST and the combination of SCH23-BVMO1 and SCH23-EST showing the formation of gamma-ambrol. The upper chromatogram shows the GC-MS analysis of a conversion using control protein without recombinant enzymes.
Figure 7:
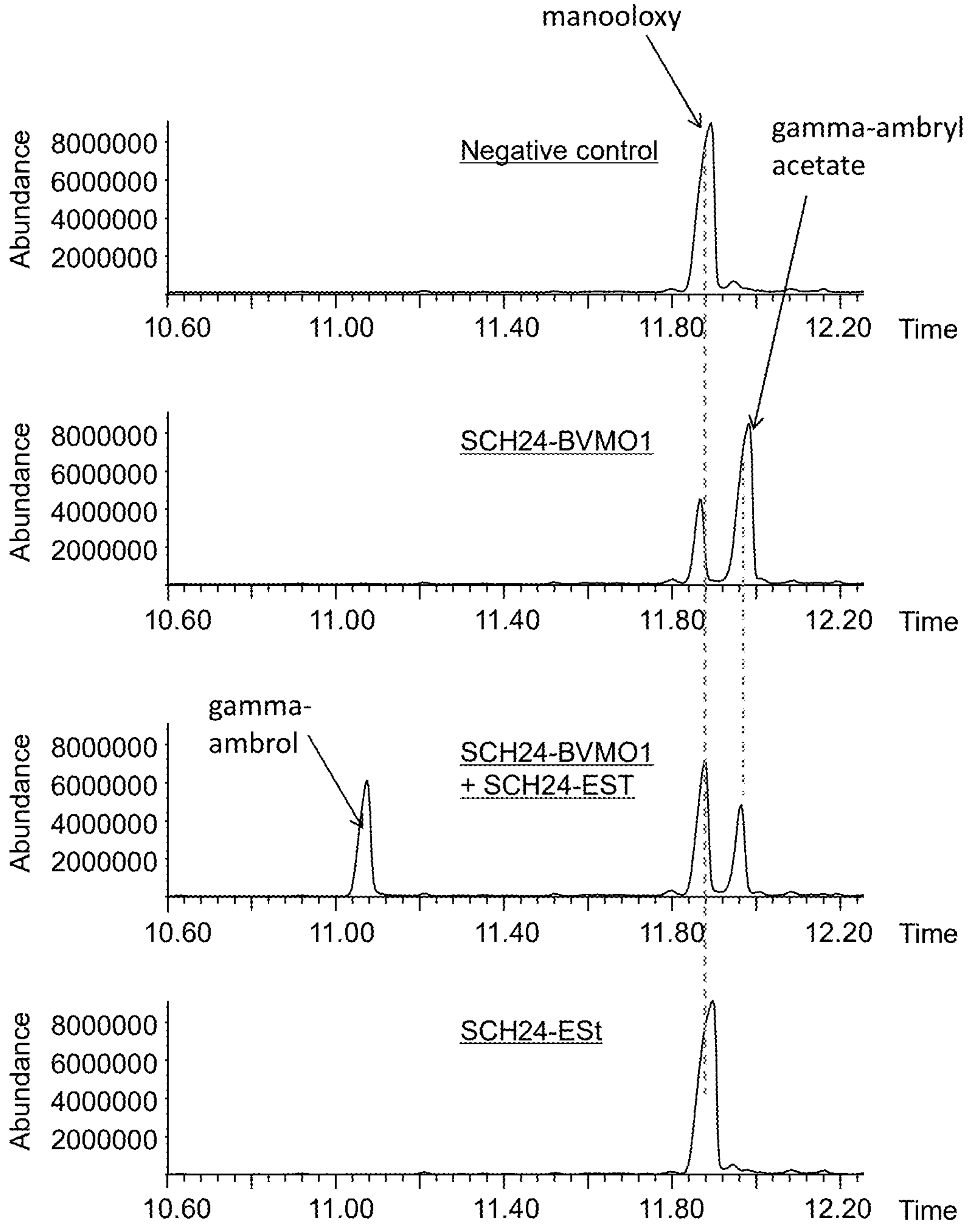
FIG. 7. In vitro conversion of manooloxy using BVMOs and esterases. GC-MS analysis of the conversion of manooloxy by SCH24-BVMO1, SCH24-EST and the combination of SCH24-BVMO1 and SCH24-EST showing the formation of gamma-ambrol. The upper chromatogram shows the GC-MS analysis of a conversion using control protein without recombinant enzymes.

In vitro enzymatic assays were also performed using protein fractions containing a recombinant esterase enzyme and using a combination of protein fractions containing a recombinant BVMO and a recombinant esterase enzyme. These assays were performed as described above using manooloxy as substrate. The GC-MS analysis of the products formed (FIGS. 6 and 7) shows conversion of manooloxy to gamma-ambryl acetate in the presence of a BVMO enzymes (SCH23-BVMO1 or SCH24-BVMO1) and further conversion of gamma-ambryl acetate to gamma-ambrol when an esterase enzyme (SCH23-EST or SCH24-EST) is present in the assay. When the esterase is used in the absence of a BVMO no substrate conversion is observed (FIGS. 6 and 7).

This experiment shows that in the presence of a BVMO and esterase, manooloxy can be converted to gamma-ambrol following the reaction scheme depicted bellow:

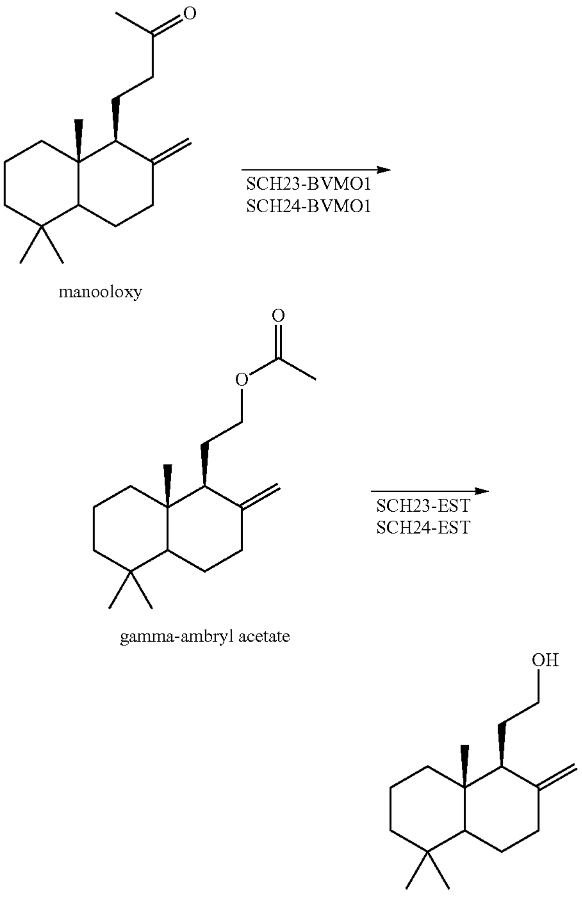

manooloxy gamma-ambryl acetate gamma-ambrol

Example 4: In Vitro Conversion of Compounds 4a and 4b to Compounds 5a and 5b Using Esterases Codon optimized cDNAs encoding for SCH23-EST from *Hyphozyma roseonigra* (SEQ ID NO: 21), SCH24-EST from *Filobasidium magnum* (SEQ ID NO: 25) and SCH46-EST from *Bensingtonia ciliata* (SEQ ID NO: 32) were synthesized and cloned in the pJ414 expression plasmid (ATUM, Newark, California) providing the plasmids pJ414-SCH23-EST1, pJ414-SCH24-EST1 and pJ414-SCH46-EST1. KRX *E. coli* cells (Promega Corporation, Madison, WI, USA) were transformed with these expression plasmids. The transformed cells were grown and cell free lysates were prepared as described. In vitro enzymatic assays were performed with these protein fractions following the conditions described above.

Figure 8:
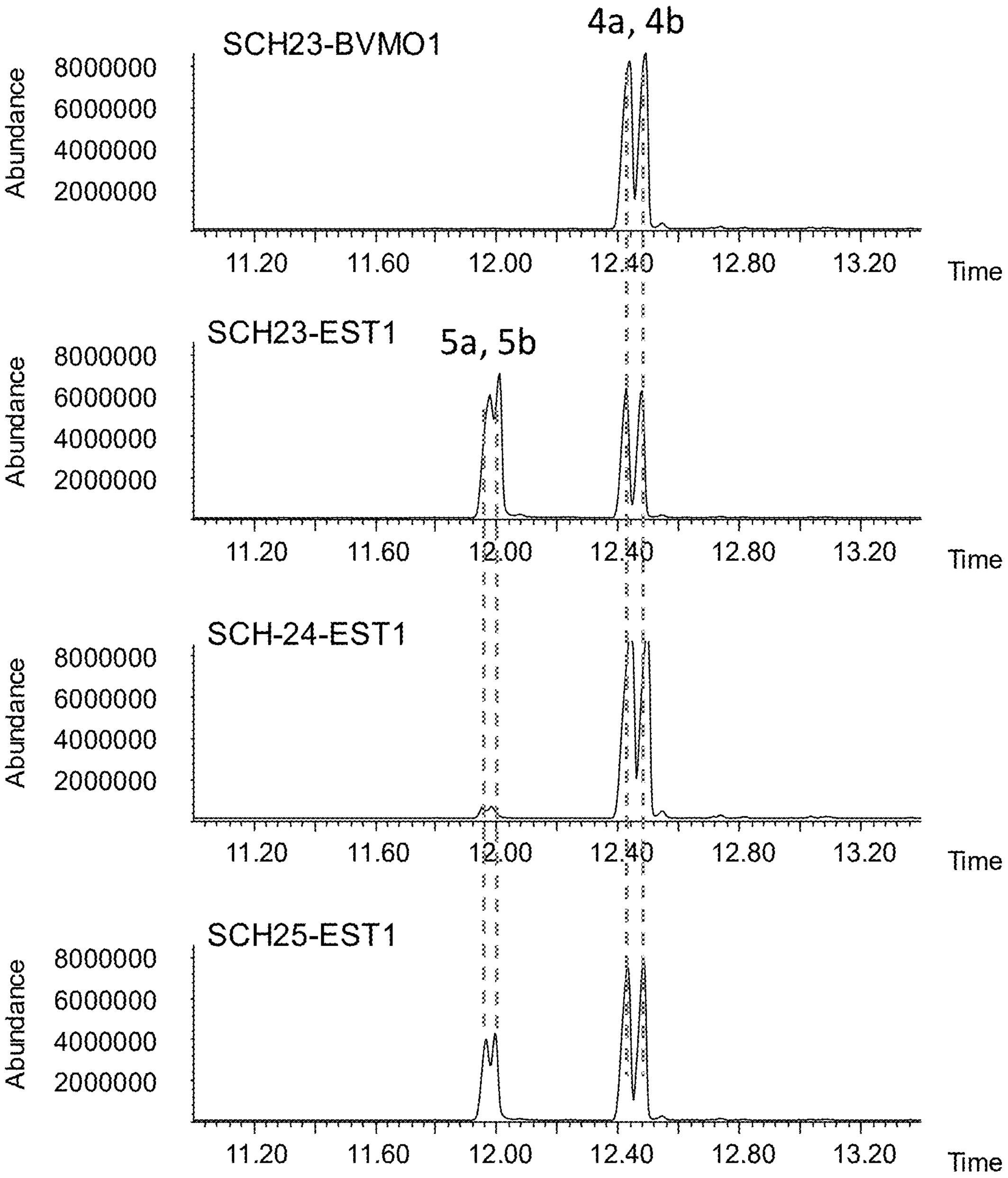
FIG. 8. In vitro conversion of compounds 4a and 4b to compounds 5a and 5b using esterases. GC-MS analysis of the in-vitro conversion of compounds 4a and 4b by SCH23-EST1, SCH24-EST1 and SCH25-EST1 showing the formation of compounds 5a and 5b.

As shown in FIG. 8, using crude fractions containing the recombinant SCH23-EST1, SCH24-EST1 and SCH25-EST1 proteins, the conversions of the two stereoisomers 4a and 4b to compounds 5a and 5b were observed. In comparison, no conversion was detected when using a lysate containing a recombinant BVMO enzyme (these proteins were thus used for the control reactions in this experiment series). Under these conditions the enzymatic activities of SCH23-EST1 and SCH25-EST1 were higher than the enzymatic activity of SCH24-EST.

From these experiments, the following enzymatic reaction can be drawn:

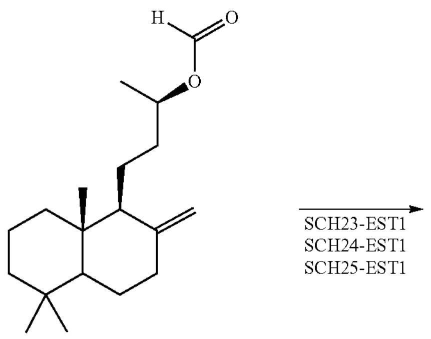

4a

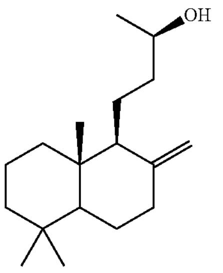

5a

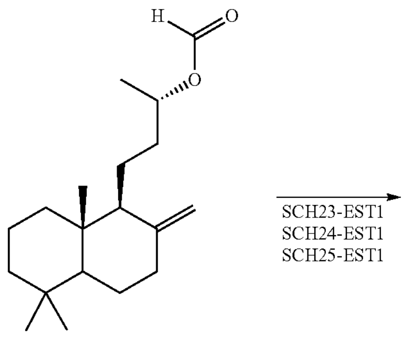

4b

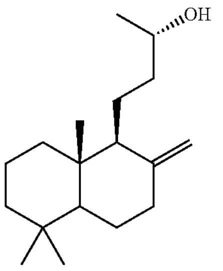

5b

Example 5: In Vitro Conversion of Copalal Using BVMOs and Esterases

For this experiment the following recombinant proteins were used: SCH23-BVMO1 from *Hyphozyma roseonigra* (SEQ ID NO: 2), SCH24-BVMO1 from *Filobasidium magnum* (SEQ ID NO: 6), SCH25-BVMO1 from *Papiliotrema laurentii* (SEQ ID NO: 10), SCH23-EST from *Hyphozyma roseonigra* (SEQ ID NO: 20), SCH24-EST from *Filobasidium magnum* (SEQ ID NO: 24), SCH25-EST from *Papiliotrema laurentii* (SEQ ID NO: 28).

Codon optimized cDNAs encoding for SCH23-BVMO1 (SEQ ID NO: 3), SCH24-BVMO1 (SEQ ID NO: 7) and SCH25-BVMO1 (SEQ ID NO: 11) were synthesized and cloned in the pJ414 expression plasmid (ATUM, Newark, California) providing the plasmids pJ414-SCH23-BVMO1, pJ414-SCH24-BVMO1 and pJ414-SCH25-BVMO1. Codon optimized cDNAs encoding for SCH23-EST (SEQ ID NO: 21), SCH24-EST (SEQ ID NO: 25) and SCH25-EST (SEQ ID NO: 29) were synthesized and cloned in the pJ431 expression plasmid (ATUM, Newark, California) providing the plasmids pJ414-SCH23-EST, pJ414-SCH25-EST.

KRX *E. coli* cells (Promega Corporation, Madison, WI, USA) were transformed with these expression plasmids. The transformed cells were grown and cell free lysates were prepared as described. In vitro enzymatic assays were performed with protein fractions containing a recombinant BVMO enzyme or a recombinant esterase enzyme or by combining of protein fractions containing recombinant BVMO and esterase enzymes. The assays were performed as described above with addition of 320 mg/L of a mixture of cis-copalal and trans-copalal as substrate, 60 μM flavine adenine dinucleotide (FAD) and 500 μM reduced β-Nicotinamide adenine dinucleotide phosphate (NADPH).

Figure 9:
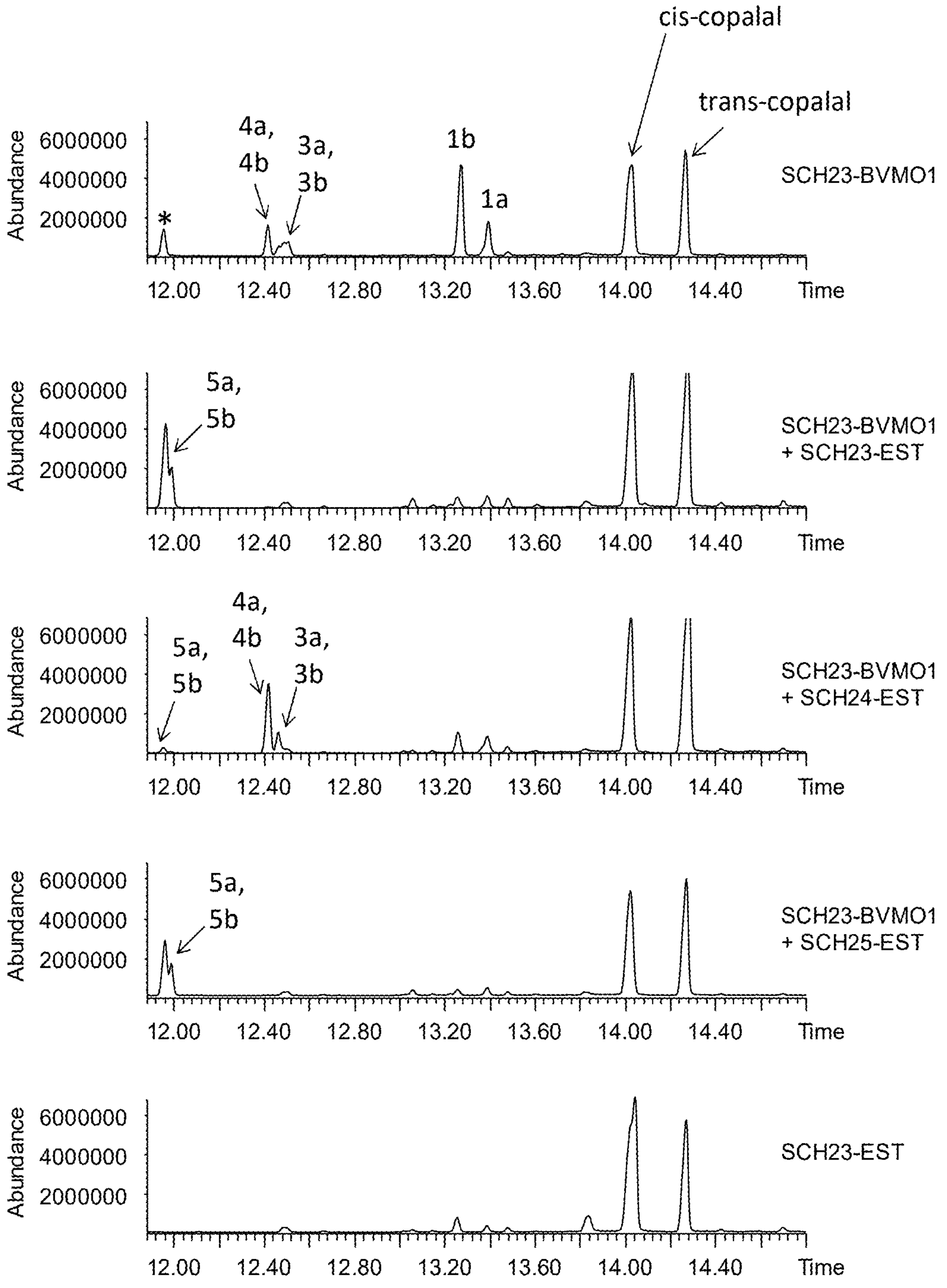
FIG. 9. In vitro conversion of copalal to compounds 5a and 5b using SCH23-BVMO1 and esterases. GCMS analysis of the in-vitro conversion of cis-copalal and trans-copalal by SCH23-BVMOs in combination with SCH23-EST1, SCH24-EST1 and SCH25-EST1 showing the formation of compounds 5a and 5b. The peak labelled with an * and at retention time of 11.95 minutes correspond to gamma-ambryl acetate; the observation of this compound in samples incubated with the BVMO alone is due to presence of small amounts of manooloxy in the mixture of copalal used in these assay.

FIG. 9 compares the products of the conversion of copalal in the presence of SCH23-BVMO1 only and in combination with different esterase enzymes. In the presence of SCH23-BVMO1, the major products are the formate compounds 1a, 1b and 4a, 4b. When the assays were conducted in the additional presence of the SCH23-EST or SCH25-EST, the major products of the conversion were compounds 5a and 5b showing that these two esterase enzymes can efficiently hydrolyse the formate intermediates produced by the BVMO enzyme. In the additional presence of SCH24-EST, the hydrolysis of the same intermediates (1a, 1b, and 4a, 4b) was observed, however with this enzyme the hydrolysis of the intermediates 1a and 1b by SCH24-EST seems more efficient than the hydrolysis of the intermediates 4a and 4b.

Figure 10:
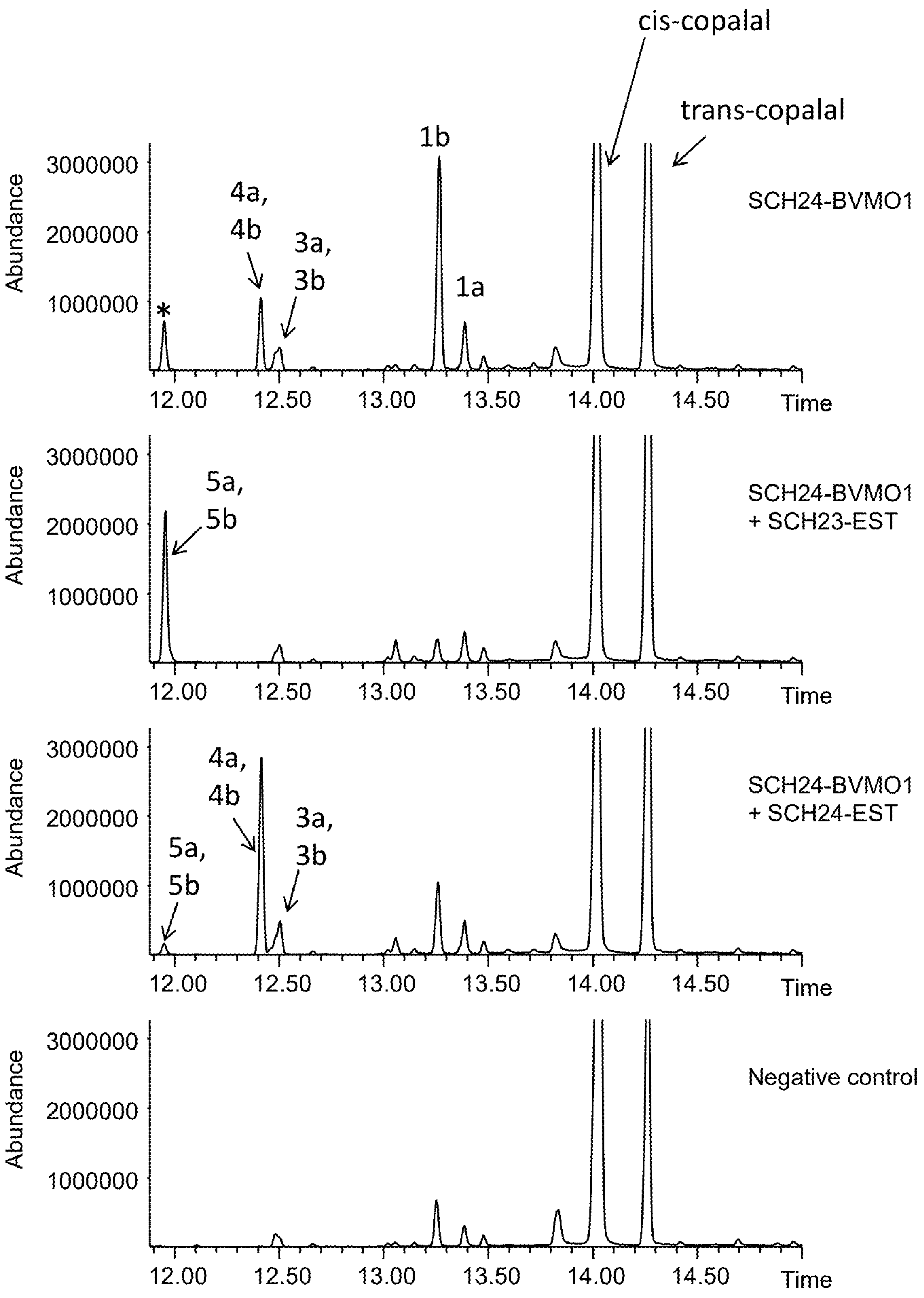
FIG. 10. In vitro conversion of copalal to compounds 5a and 5b using SCH24-BVMO1 and esterases. GCMS analysis of the in-vitro conversion of cis-copalal and trans-copalal by SCH23-BVMOs in combination with SCH23-EST1 and SCH25-EST1 showing the formation of compounds 5a and 5b. The peak labelled with an * at retention time of 11.95 minutes correspond to gamma-ambryl acetate; the observation of this compound in samples incubated with the BVMO alone is due to presence of small amounts of manooloxy in the mixture of copalal used in these assay.

Similar conversion of cis- and trans-copalal was observed when SCH24-BVMO1 was combined with esterase SCH23-EST or SCH24-EST (FIG. 10). In control experiments, when copalal was incubated only with an esterase, no conversion was observed.

From these experiments the following enzyme pathway can be deduced.

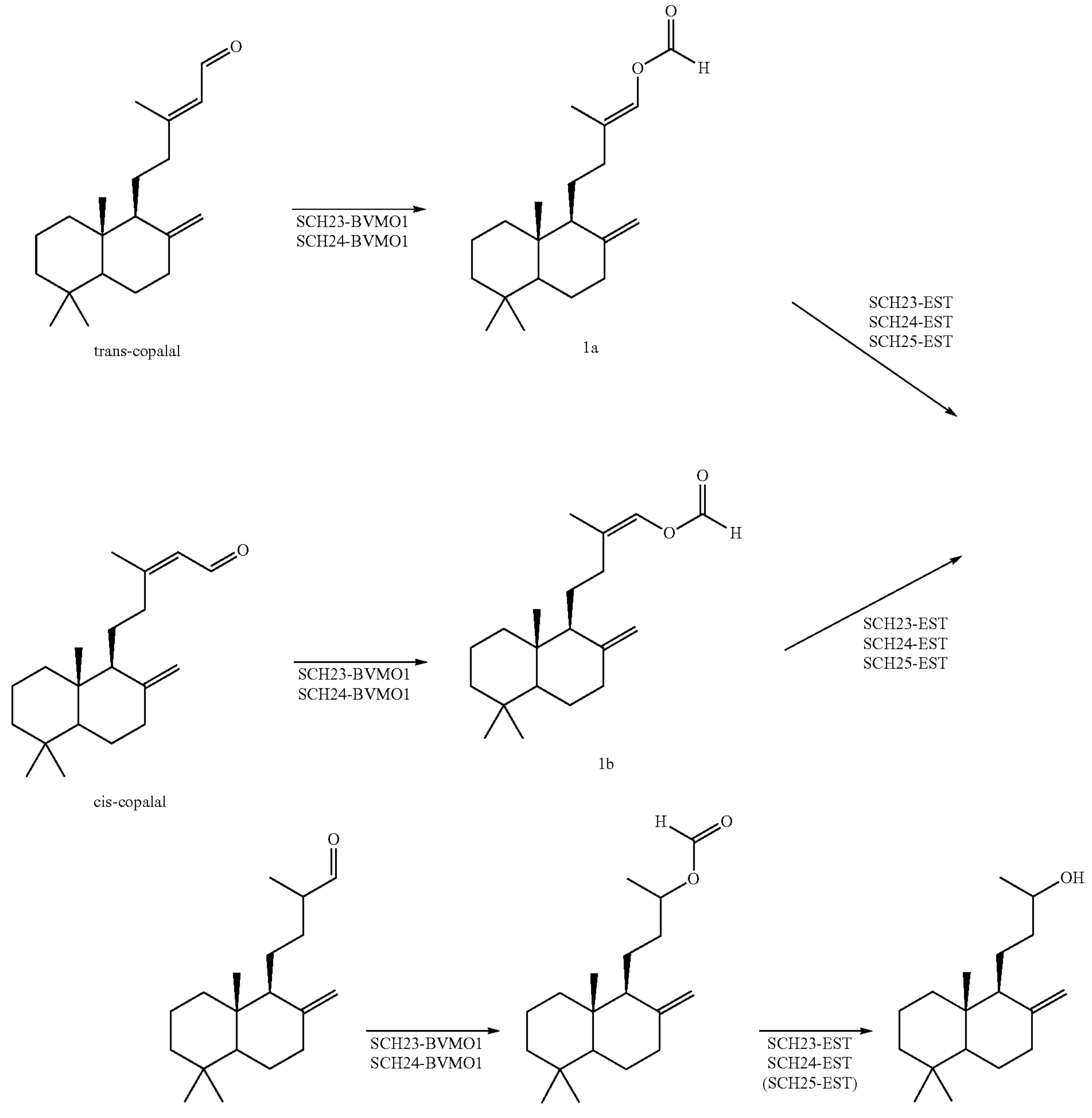

trans-copalal, 1a, cis-copalal, 1b, 3a, 3b, 4a, 4b, 5a, 5b

Figure 11:
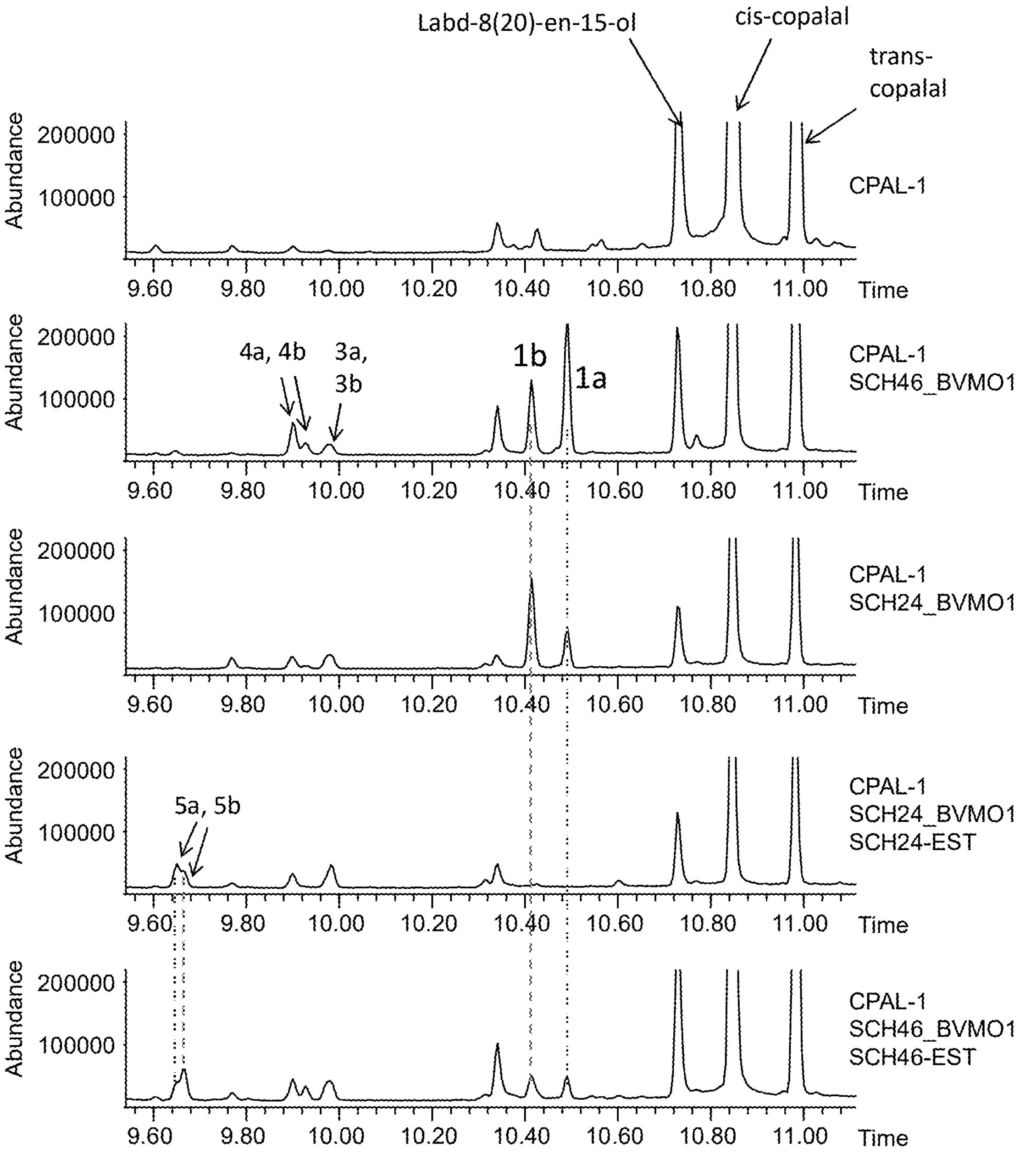
FIG. 11. Biochemical production of the 14,15-dinor-labdane compounds 5a and 5b and biosynthetic intermediates in engineered bacteria cells expression a BVMO and an esterase. The upper chromatogram shows the GC-MS analysis of compounds produced by *E coli* cells transformed with the pJ401-CPAL-1 plasmid allowing the expression of enzymes of a copalal biosynthetic pathway. The following chromatograms show the GC-MS analysis of cells further transformed with a second plasmid carrying nucleotide sequences encoding for a BVMO enzyme or a BVMO enzyme together with an esterase.

Example 6: In-Vivo Production of the 14,15-Dinor-Labdane Compounds 5a and 5b and Biosynthetic Intermediates in Engineered Bacteria Cells Expressing a BVMO and an Esterase In this experiment, the plasmid pJ401-CPAL-1 (described above) was used to transform *E. coli* cells to produce copalal as described in the experimental section. When DP1205 *E. coli* cells were transformed and cultivated unter the conditions described in the experimental section, formation of trans-copalal and cis-copalal was observed (FIG. 11, upper chromatogram). The detection of the two double-bond isomers of copalal is due to the relative easy isomerization of (E)-α,β-unsaturated aldehydes (Konning et al, Org. Lett., 2012, 14 (20), pp 5258-5261). The additional detection of labd-8(20)-en-15-ol is due to *E. coli* endogenous enoate reductase activity.

The bacteria cells were then transformed with a second expression plasmid carrying a codon optimized cDNA encoding for SCH24-BVMO1 from *Filobasidium magnum* (ATCC® 20918™) (SEQ ID NO: 7) or SCH46-BVMO1 from *Bensingtonia ciliata* (SEQ ID NO: 14). These plasmid was prepared by cloning the optimized cDNAs in the pJ423 expression plasmid (ATUM, Newark, California) providing the plasmids pJ423-SCH23-BVMO and pJ423-SCH46-BVMO, respectively. The cells transformed with two plasmids were cultivated and the production of terpene compounds and terpene derivatives was analysed using the conditions described in the experimental section. Under these conditions the compounds 1a and 1b, 3a and 3b, and 4a and 4b were detected in the solvent extract of the culture broth (FIG. 11). These results show that, using these combinations of enzymes, the biosynthesis of a labdane diterpene such as copalol and the sequential enzymatic cleavage of two carbon-carbon bounds in the side chain can be introduced in a recombinant cell.

Similarly, bacteria cells were co-transformed with the plasmid pJ401-CPAL-1 and with a second plasmid carrying a gene encoding for a BVMO and a gene encoding for an esterase. : pJ423-SCH24-BVMO-SCH24-EST, prepared by inserting a synthetic operon composed of a codon optimized cDNA encoding SCH24-BVMO1 (SEQ ID NO: 7) and a codon optimized cDNA encoding SCH24-EST (SEQ ID NO: 25) into the pJ423 expression plasmid (ATUM, Newark, California), or pJ423-SCH46-BVMO-SCH46-EST, a plasmid prepared by inserting a synthetic operon composed of a codon optimized cDNA encoding SCH46-BVMO (SEQ ID NO: 14) and a codon optimized cDNA encoding SCH46-EST (SEQ ID NO: 32) into the pJ423 expression plasmid (ATUM, Newark, California). The cells were cultivated and the production of terpene compounds and terpene derivatives was analysed using the conditions described in the experimental section. Under these conditions, the compounds 5a and 5b were detected and decreased amounts of the pathway intermediates (compounds 1a, 1b, 3a, 3b, 4a and 4b) were observed.

This experiment series shows that the following biosynthetic pathway can be introduced in a host cells transformed to express diterpene biosynthesis enzymes in combination with a BVMO and an esterase.

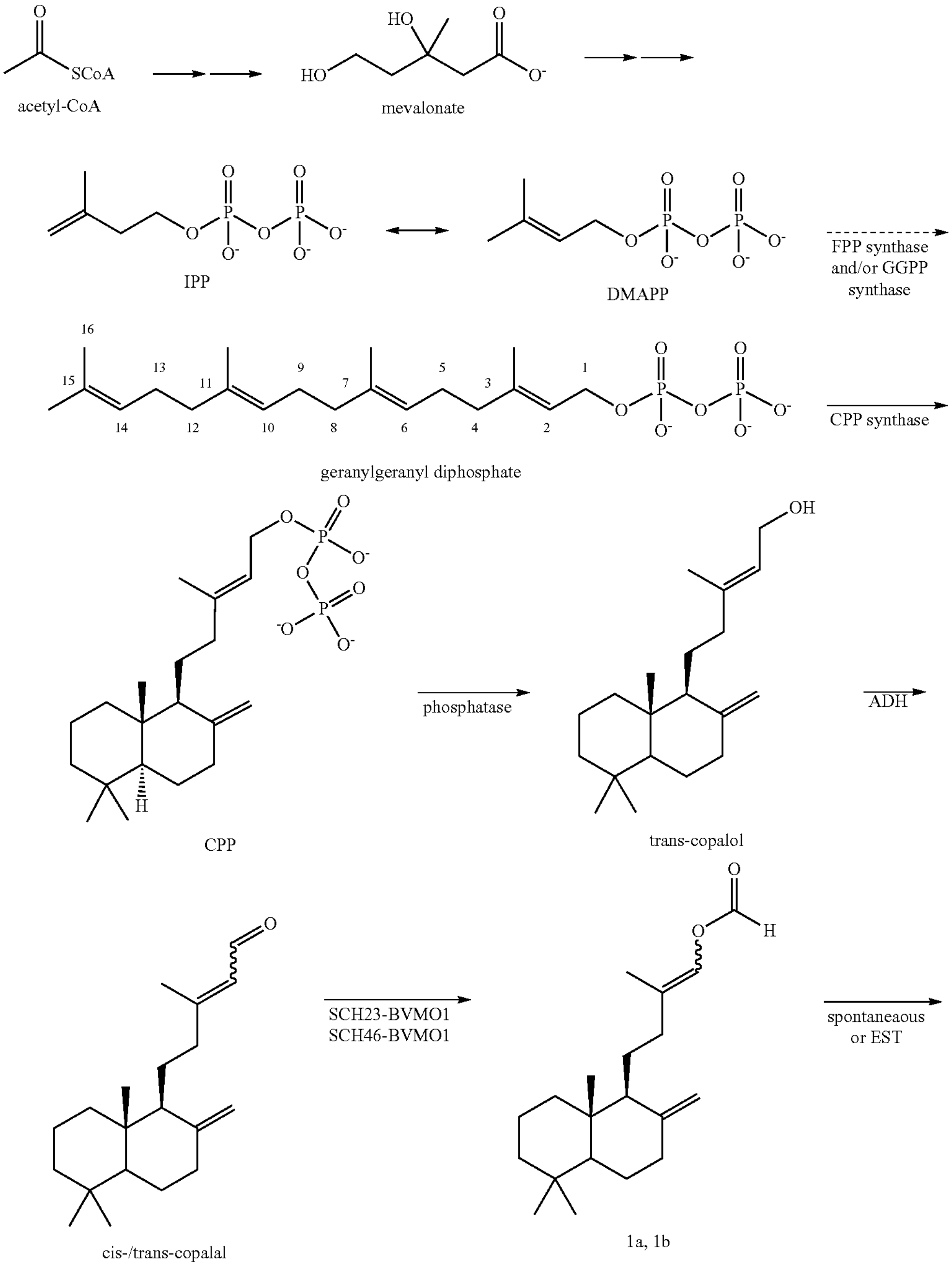

acetyl-CoA
mevalonate
IPP
DMAPP
geranylgeranyl diphosphate
CPP
trans-copalol
cis-/trans-copalal
1a, 1b -continued

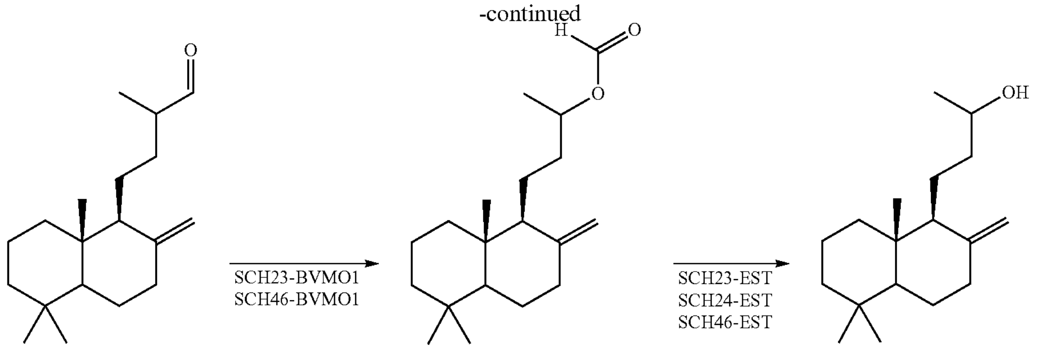

3a, 3b 4a, 4b 5a, 5b

Example 7: In-Vivo Conversion of Compounds 5a and 5b to Manooloxy Using Alcohol Dehydrogenases For this experiment, the following alcohol dehydrogenases were evaluated for the oxidation of compounds 5a and 5b to manooloxy:

RrhSecADH from *Rhodococcus rhodochrous* (SEQ ID NO: 146),

SCH80-00043 from *Rhodococcus rhodochrous* (SEQ ID NO: 149),

SCH80-04254 from *Rhodococcus rhodochrous* (SEQ ID NO: 152),

SCH80-06135 from *Rhodococcus rhodochrous* (SEQ ID NO: 155),

SCH80-06582 from *Rhodococcus rhodochrous* (SEQ ID NO: 158), (see also WO2005/026338); the above ADHs are merely non-limiting examples and may be replaced by other known ADHs may Codon optimized cDNAs encoding for each of these proteins were synthesized and cloned in the vector pJ401 providing plasmids pJ401-RrhSecADH, pJ401-SCH80-00043, pJ401-SCH80-04254, pJ401-SCH80-06135 and pJ401-SCH80-06582 (ATUM, Newark, California).

Figure 12:
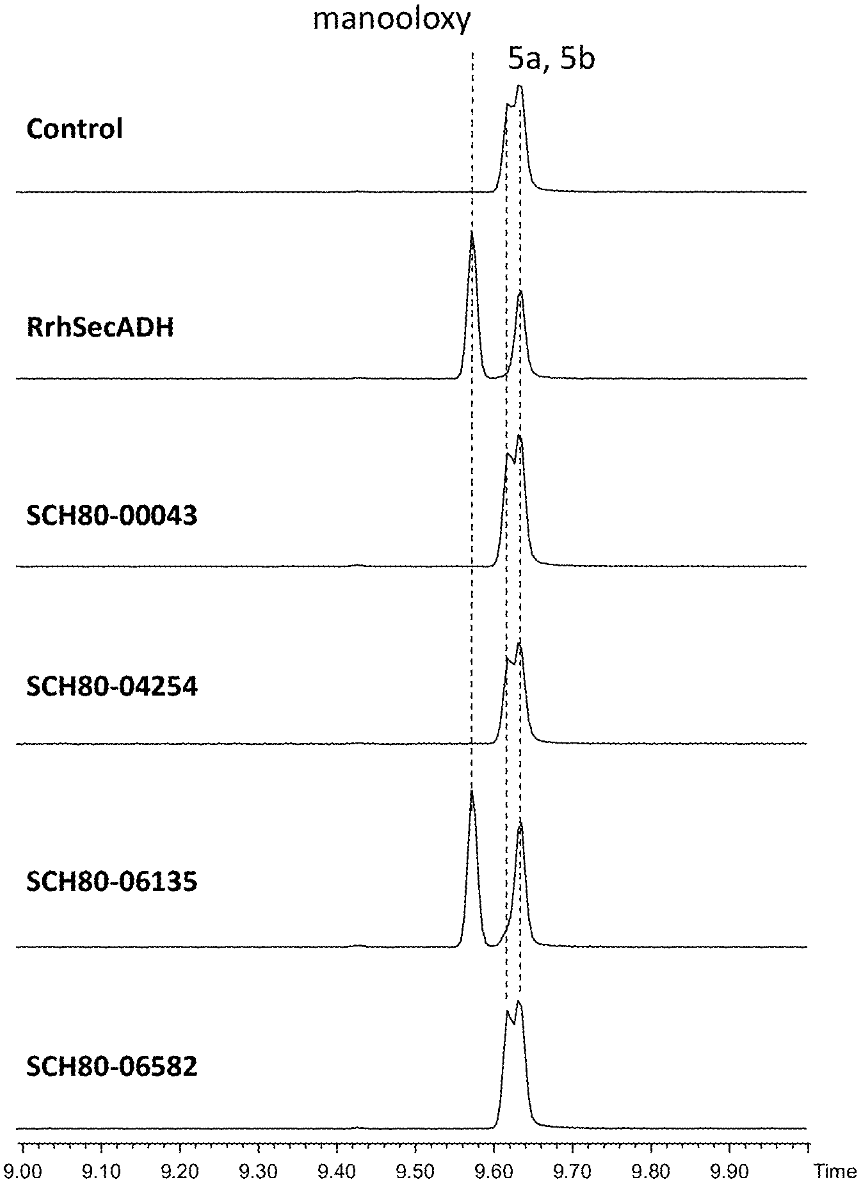
FIG. 12. GC-MS analysis of the products of the biotransformation of compounds 5a and 5b by *E coli* cells expressing various alcohol dehydrogenases. The upper chromatogram shows the GC-MS analysis of a bioconversion using control cells not expressing a recombinant alcohol dehydrogenase. The following chromatograms show the GC-MS analysis of a conversion using cells expressing the recombinant RrhSec-ADH, SCH80-00043, SCH80-04254, SCH80-06135 or SCH80-06582 protein.

KRX *E. coli* cells (Promega Corporation, Madison, WI, USA) were transformed with these expression plasmids. The transformed cells were grown and used in a whole cell bioconversion assay as described above using a mixture of compounds 5a and 5b as substrate. Five hours after the induction of the expression of the recombinant proteins, the substrate was added to a final concentration of 0.55 mg/mL using an emulsion containing 50 mg/mL of tween 80 and 25 mg/mL of substrate in water. A negative control was included consisting of the cells transformed with an empty plasmid. The oxidation reaction was observed only in the presence of the SCH80-06135 and RrhSecADH recombinant proteins (FIG. 12) showing that these enzymes can catalyse the following reaction.

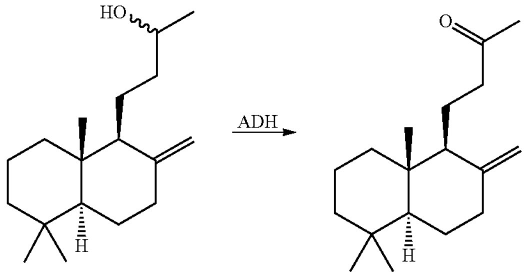

5a, 5b manooloxy

Example 8: In-Vivo Production of the Tetranor-Labdane Compounds Gamma-Ambrol and Biosynthetic Intermediates in Engineered Bacteria Cells Expressing a BVMO, an Esterase and an Alcohol Dehydrogenase In this experiment, the plasmid pJ401-CPAL-1 (described above) was used to transform the DP1205 *E. coli* cells creating a background strain producing copalal (cis- and trans-isomer) as described in the previous section.

This strain was then co-transformed with the plasmid pJ423-SCH24-BVMO-SCH24-EST (described above) allowing a further expression of a BVMO and an esterase in the same cells. In accordance with the observation made in the previous section, this recombinant organism produces 14,15-dinor-labdane compounds.

Figure 13:
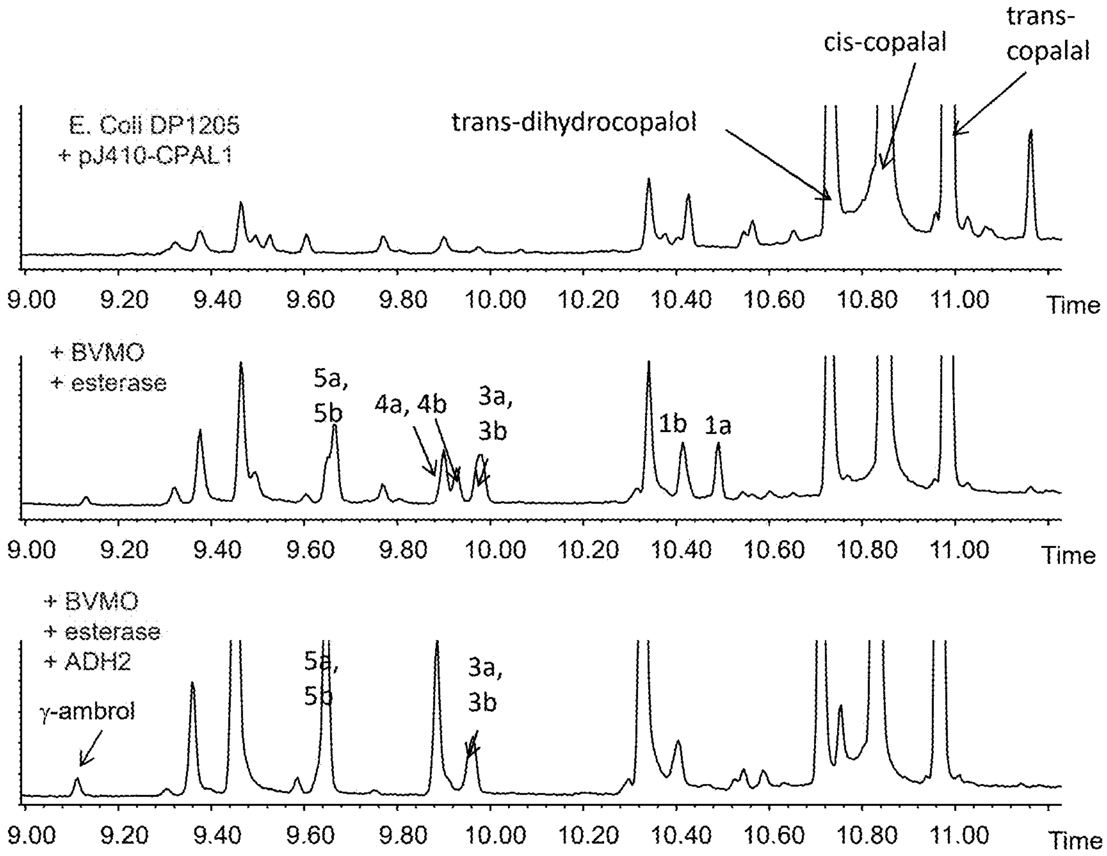
FIG. 13. Biochemical production of gamma-ambryl acetate and biosynthetic intermediates in engineered bacteria cells expression a BVMO, an esterase and an alcohol dehydrogenase. The upper chromatogram shows the GC-MS analysis of the compounds produced by *E coli* cells transformed with the pJ401-CPAL-1 plasmid allowing the expression of the enzymes of a copalal biosynthetic pathway. The middle chromatogram show the GC-MS analysis of cells further transformed with a second plasmid carrying nucleotide sequences encoding for a SCH-BVMO1 and SCH24-EST. The bottom chromatogram show the GC-MS analysis of cells transformed with pJ401-CPAL-1 and with the plasmid pJ423-secADH-23BVMO-EST allowing the expression of the RrhSecADH, SCH23-BVMO1 and SCH23-EST proteins.

To allow the side-chain degradation to continue to the formation of tetranor-labdane derivatives, the secondary alcohol group of compounds 5a and 5b must be oxidized to the corresponding ketone. A plasmid was thus constructed containing nucleotide sequences encoding for a BVMO, an esterase and an appropriate alcohol dehydrogenase (identified in Example 7). For the alcohol dehydrogenase, a codon optimized cDNA encoding for RrhSecADH from a *Rhodococcus* species (Accession number WP_043801412.1) (SEQ ID NO: 147) was synthesised and a synthetic operon was designed combining the RrhSecADH cDNA and the cDNAs encoding for SCH24-BVMO and SCH24-EST. The operon was cloned into the pJ423 expression plasmid providing the pJ423-secADH-23BVMO-EST plasmid. When DP1205 *E. coli* cells co-transformed with the vector pJ401-CPAL-1 and the vector pJ423-secADH-23BVMO-EST were cultivated under the conditions described above, gamma-ambrol was detected in the GC-MS analysis of the cultivation broth (FIG. 13). These data show that when compound 5 (5a and 5b) is oxidized to manooloxy in the presence of an appropriate ADH, the BVMO can catalyse the following step in the pathway providing gamma-ambrol.
This experiment series shows that the following biosynthetic pathway can be introduced in a recombinant host cells.
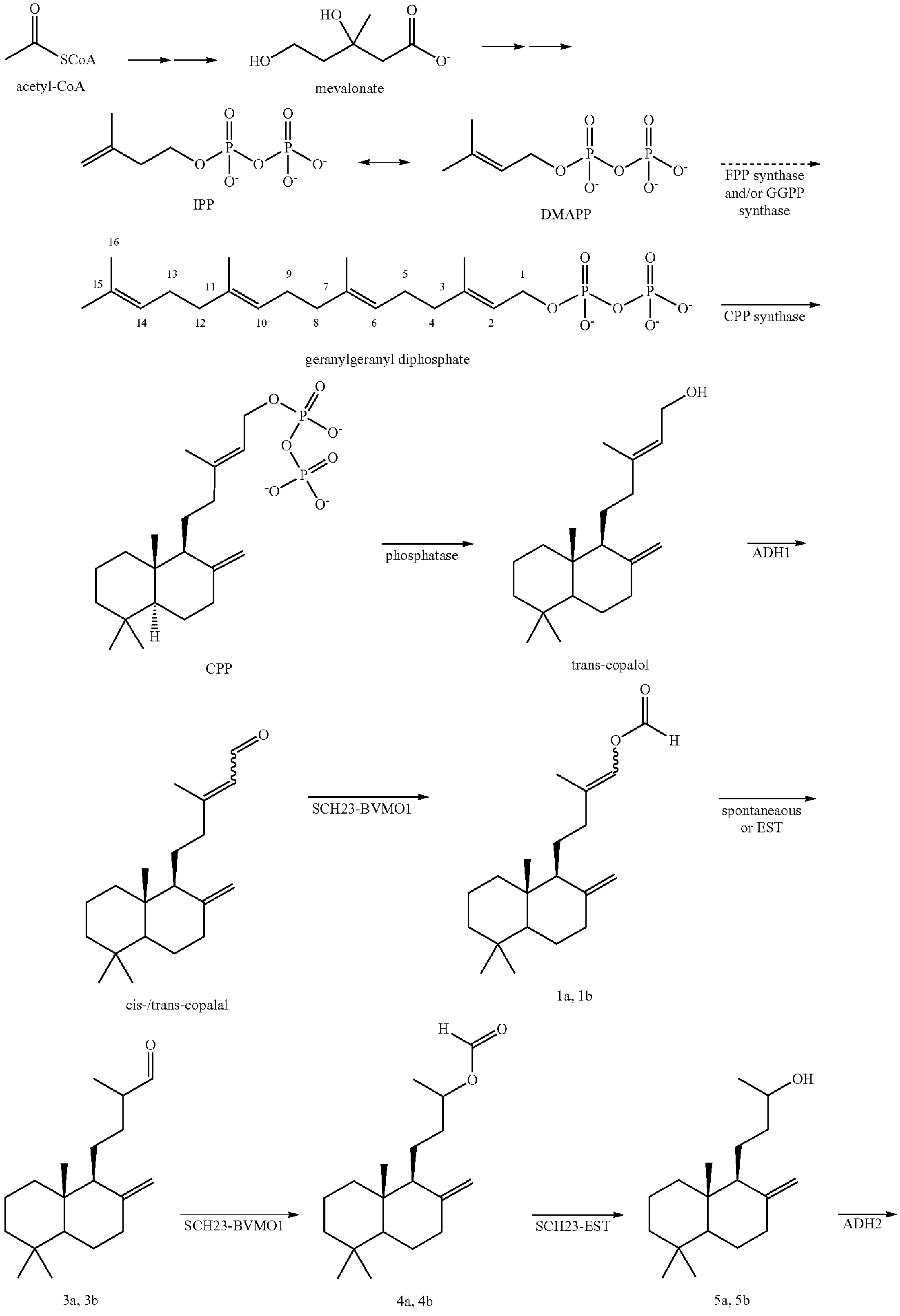
acetyl-CoA, mevalonate, IPP, DMAPP, geranylgeranyl diphosphate, CPP, trans-copalol, cis-/trans-copalal, 1a, 1b, 3a, 3b, 4a, 4b, 5a, 5b -continued

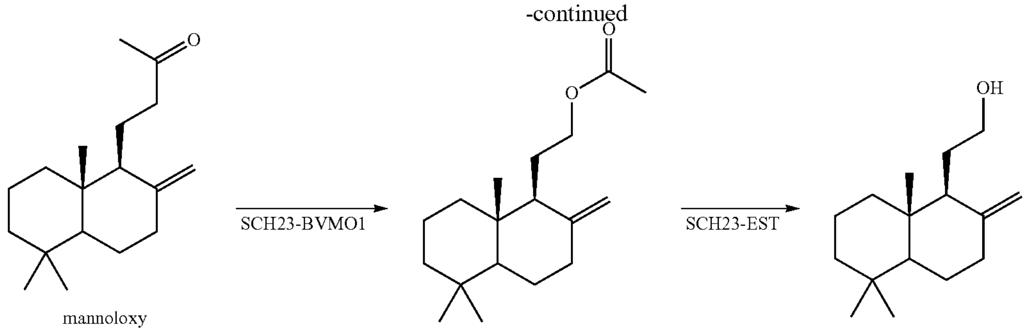

mannoloxy gamma-ambrol

Example 9: In Vivo Manooloxy Production in *Saccharomyces cerevisiae* Cells Using Alcohol Dehydrogenases (ADHs), Baeyer-Villiger Monooxygenases (BVMOs) and Esterases (ESTs) from *Hyphozyma roseonigra* or *Cryptococcus albidus*

For the production of manooloxy, the genes encoding for the GGPP synthase carG (from *Blakeslea trispora*, NCBI accession JQ289995.1) (SEQ ID NOs: 182), the copalyl-pyrophosphate synthase SmCPS2 (from *Salvia miltiorrhiza*, NCBI accession ABV57835.1) (SEQ ID NOs: 185), the copalyl-pyrophosphate phosphatase TalVeTPP (from *Talaromyces verruculosus*, NCBI accession KUL89334.1) (SEQ ID NOs: 194) and either the alcohol dehydrogenase SCH23-ADH1 (SEQ ID NOs: 134), the Baeyer-Villiger monooxygenase SCH23-BVMO1 (SEQ ID NOs: 2), the esterase SCH23-EST (SEQ ID NOs: 20) and the alcohol dehydrogenase SCH23-ADH2 (from *Hyphozyma roseonigra*) (SEQ ID NOs: 137) or the alcohol dehydrogenase SCH24-ADH1 (SEQ ID NOs: 140), the Baeyer-Villiger monooxygenase SCH24-BVMO1 (SEQ ID NOs: 6), the esterase SCH24-EST1 (SEQ ID NOs: 24) and the alcohol dehydrogenase SCH24-ADH2 (from *Filobasidium magnum*) (SEQ ID NOs: 143) were expressed in the engineered *Saccharomyces cerevisiae* strain YST075 as described in the general methods section above. All genes were codon optimized for their expression in *S. cerevisiae* (SCH23-ADH1, SEQ ID NO: 135; SCH23-BVMO1, SEQ ID NO: 4; SCH23-EST, SEQ ID NO: 22; SCH23-ADH2, SEQ ID NO: 138; SCH24-ADH1, SEQ ID NO: 141; SCH24-BVMO1, SEQ ID NO: 8; SCH24-EST, SEQ ID NO: 26; SCH24-ADH2, SEQ ID NO: 144; carG, SEQ ID NO: 183; SmCPS2, SEQ ID NO: 186; and TalVeTPP, SEQ ID NO: 195).

The strains YST120 (with SCH23-ADH1, SCH23-BVMO1, SCH23-EST and SCH23-ADH2) and YST121 (with SCH24-ADH1a, SCH24-BVMO1, SCH24-EST and SCH24-ADH2) harboring also the plasmid system for copalol biosynthesis were obtained and cultivated under the conditions described in the general methods section above.

Figure 14:
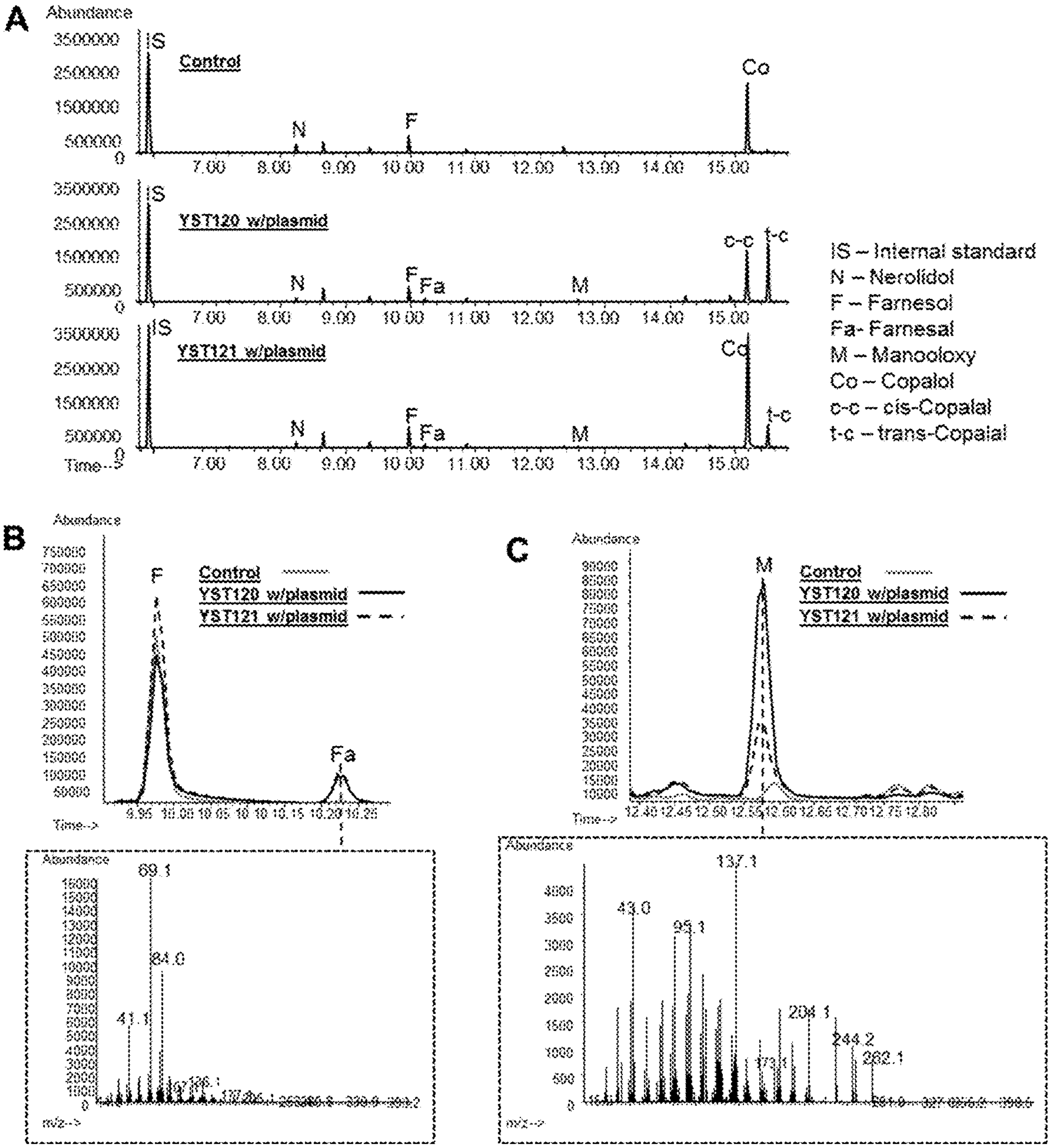
FIG. 14. A) GC-MS analysis of terpenes and derivatives produced using the modified *S. cerevisiae* strains expressing the GGPP synthase carG, the CPP synthase SmCPS2, the CPP phosphatase TalVeTPP and either SCH23-ADH1, SCH23-BVMO1, SCH23-EST1 and SCH23-ADH2 (YST120 w/plasmid) or SCH24-ADH1a, SCH24-BVMO1, SCH24-EST1 and SCH24-ADH2a (YST121 w/plasmid). The control strain was YST075 expressing only the copalol biosynthetic pathway. B) GC-MS analysis of the region where farnesal was identified, the farnesal mass spectrum is shown. C) GC-MS analysis of the region where manooloxy was identified, the manooloxy mass spectrum is shown.

Under these conditions, copalol was identified in all cultures. Only strains containing SCH23-ADH1 or SCH24-ADH1 were able to convert copalol into copalal (FIG. 14A). In addition, farnesal was detected in the cultures where the alcohol dehydrogenases were expressed (FIG. 14B). Accumulation of nerolidol and farnesol was identified in all cultures (FIG. 14A).

In addition, manooloxy was identified in the cultures containing the strains YST120 and YST121 harboring the plasmid with copalol biosynthetic genes (FIG. 14C). Neither gamma-ambryl acetate nor gamma-ambrol was identified. However, the presence of manooloxy suggests that the BVMOs, ESTs and ADHs were functionally expressed in the engineered yeast cells. We hypothesize that the amount obtained of manooloxy was limiting for the BVMOs to catalyze the conversion to gamma-ambryl acetate.

Example 10: In Vivo Manooloxy Production in *Saccharomyces cerevisiae* Cells Using Alcohol Dehydrogenases (ADHs), Baeyer-Villiger Monooxygenases (BVMOs) and Esterases (ESTs) from *Hyphozyma roseonigra* or *Cryptococcus albidus*

For the production of manooloxy, the genes encoding for the GGPP synthase carG (from *Blakeslea trispora*, NCBI accession JQ289995.1), the copalyl-pyrophosphate synthase SmCPS2 (from *Salvia miltiorrhiza*, NCBI accession ABV57835.1), the copalyl-pyrophosphate phosphatase TalVeTPP (from *Talaromyces verruculosus*, NCBI accession KUL89334.1), the alcohol dehydrogenase SCH23-ADH1 and either the Baeyer-Villiger monooxygenase SCH23-BVMO1 and the esterase SCH23-EST (from *Hyphozyma roseonigra*) or the Baeyer-Villiger monooxygenase SCH24-BVMO1 and the esterase SCH24-EST (from *Cryptococcus albidus*) were expressed in the engineered *Saccharomyces cerevisiae* strain YST075 as described in the general methods section.

The obtained strains were termed YST177 (with carG, SmCPS2, TalVeTPP, SCH23-ADH1, SCH23-BVMO1 and SCH23-EST) and YST178 (with carG, SmCPS2, TalVeTPP, SCH23-ADH1, SCH24-BVMO1 and SCH24-EST) and were cultivated as described in the general methods section above. Cultures were analyzed by GC-MS as described above.

Figure 15:
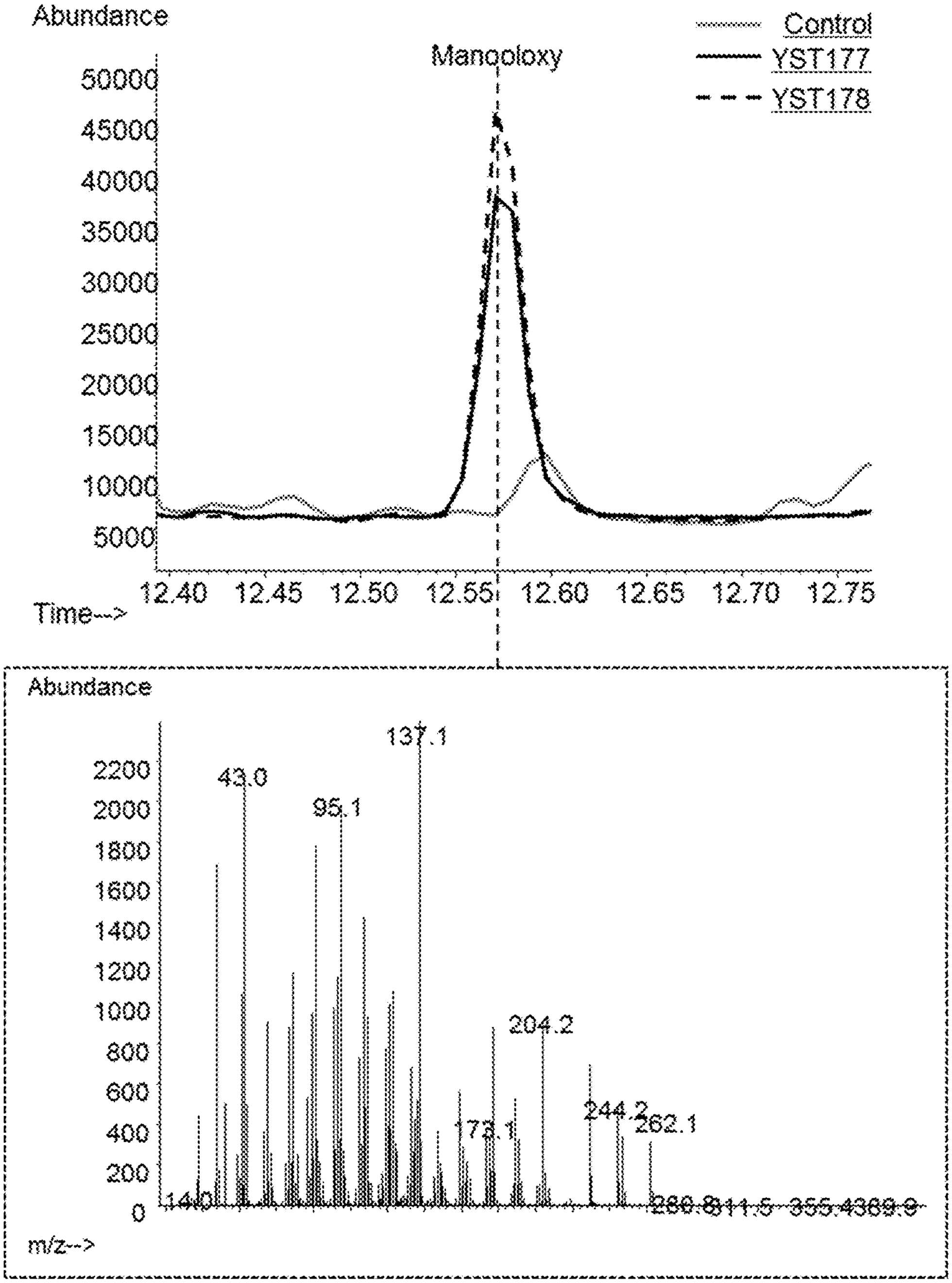
FIG. 15. GC-MS analysis of Manooloxy produced using the modified *S. cerevisiae* strains expressing the GGPP synthase carG, the CPP synthase SmCPS2, the CPP phosphatase TalVeTPP and either SCH23-ADH1, SCH23-BVMO1 and SCH23-EST1 (YST177) or SCH24-ADH1a, SCH24-BVMO1 and SCH24-EST1 (YST178). The control strain was YST075 expressing only the copalol biosynthetic pathway. The manooloxy mass spectrum is shown.

Copalol, copalal, nerolidol, farnesol and farnesal were identified in the cultures after extraction. The engineered cells not containing the alcohol dehydrogenases SCH23-ADH2 or SCH24-ADH2 were expected to accumulate the intermediate 5a (or 5b) and to be incapable to produce manooloxy. Interestingly, manooloxy was identified (FIG. 15) and molecule 5a (or 5b) was not detected. These results suggest that SCH23-ADH2 and SCH24-ADH2 might contribute to the production of manooloxy in yeast cells but are not essential for its production under the conditions tested. We hypothesize that endogenous alcohol dehydrogenase activities in yeast are responsible for the conversion.

Figure 16:
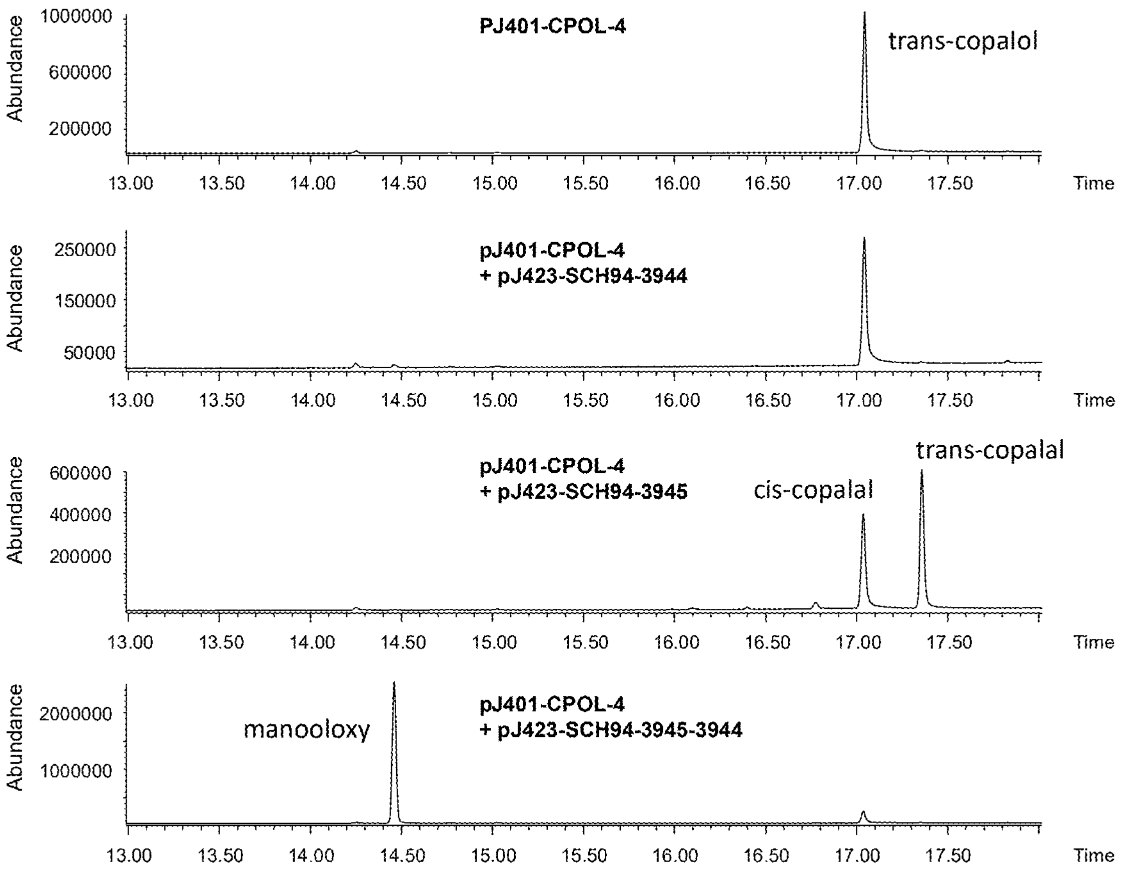
FIG. 16. GC-MS analysis of diterpenes and derivatives produced using *E coli* cells expressing a CPP synthase, a phosphatase, an alcohol dehydrogenase and/or SCH94-3944. The upper chromatogram shows the diterpene region the GC-MS analysis of compounds produced by *E coli* cells transformed with the pJ401-CPOL-4 plasmid allowing the expression of the enzymes of a copalol biosynthetic pathway. The following chromatograms shows the GC-MS analysis of the compounds produced by the same *E coli* cells further transformed with the plasmids pJ423-SCH94-3945, pJ423-SCH94-3944 or pJ423-SCH94-3944-3945 allowing the expression of SCH94-3945, SCH94-3944 or the combination of SCH94-3944 and SCH94-3945.

Example 11: Characterisation of a SCH94-3944, an Enzyme from *Rhodococcus erytheropolis* with Carbon-Carbon Bond Cleavage Activity In this experiment, the plasmid pJ401-CPOL-4 (described above) was used to transform the DP1205 *E. coli* cells creating a background strain producing copalol. The transformed strain produced copalol as major product with a concentration of up to 500 mg/L in the culture media in the tube assay (FIG. 16).

This strain was then further transformed with a second plasmid carrying one or more *E. coli* codon optimized cDNAs derived from *R. erytheropolis*. Two cDNAs were selected:

SCH94-3945, encoding for a putative alcohol dehydrogenase (SEQ ID NO: 161),

SCH94-3944, encoding for a 157 amino acid protein containing two protein family domains: a "GXWXG" protein domain (pfam14231, pfam.xfam.org/) and a domain of unknown function "DUF4334" (pfam14232, pfam.xfam.org/) (SEQ ID NO: 34).

Expression vectors were prepared using pJ423 as background and containing either a codon optimized cDNA encoding for SCH94-3945 (pJ423-SCH94-3945) or SCH94-3944 (pJ423-SCH94-3944) or a bicistronic operon comprised of the optimized cDNAs encoding for SCH94-3945 and SCH94-3944 (pJ423-SCH94-3944-3945).

When cells were transformed with the vector pJ401-CPOL-4 and the vector pJ423-SCH94-3944, no difference was observed in comparison with cells transformed with pJ401-CPOL-4 only, showing that the SCH94-3944 recombinant protein does not transform copalol. When cells were transformed with the vector pJ401-CPOL-4 and the vector pJ423-SCH94-3945, formation of cis-copalal and trans-copalal was observed showing that the SCH94-3945 is an alcohol dehydrogenase able to oxidase copalol to copalal (FIG. 16).

When cells were transformed with the vector pJ401-CPOL-4 and the vector pJ423-SCH94-3944-3945, formation of manooloxy was observed as major product with a concentration of up to 1 g/L in the culture media in the tube assay. Under this assay condition, the conversion of cis- and trans-copalal was nearly complete (FIG. 16).

This experiment shows that the SCH94-3944 enzyme can cleave the alpha-beta carbon-carbon double-bound of copalal and catalyse the direct conversion of cis-copalal and trans-copalal to the 14,15-dinor-labdane compound manooloxy, as shown in the scheme below.

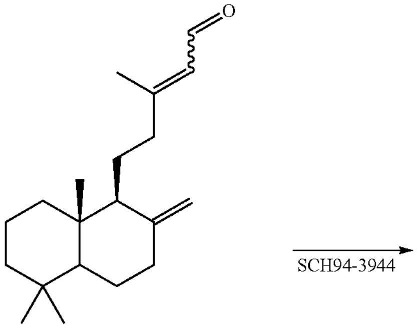

cis-trans-copalal

-continued

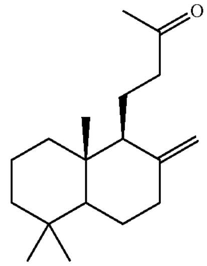

Manooloxy

Example 12: In-Vivo Conversion of Cis- and Trans-Farnesal Using an Enal-Cleaving Polypeptide from *Rhodococcus erythropolis*

Figure 17:
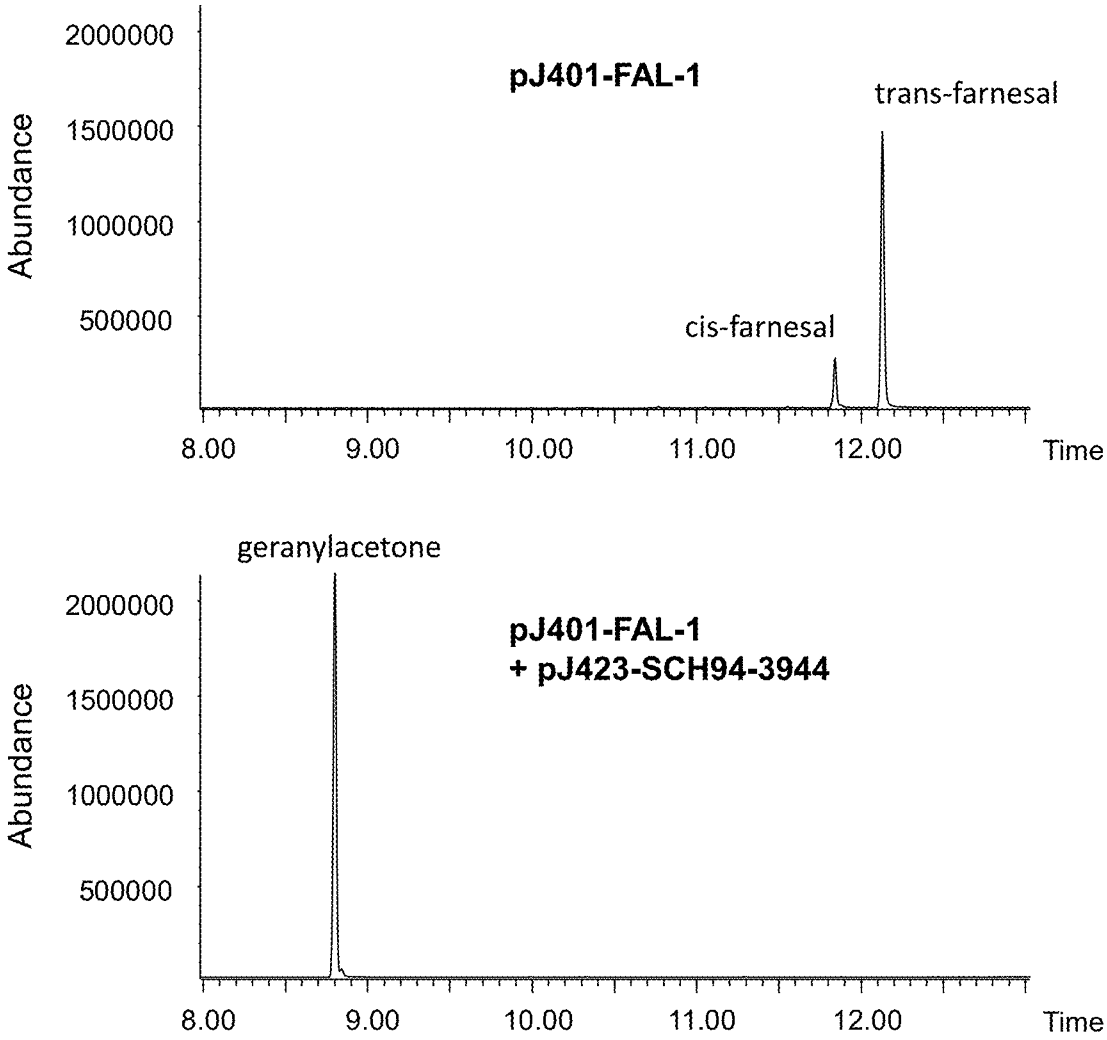
FIG. 17. GC-MS analysis of sesquiterpene and derivatives produced using *E coli* cells expressing a phosphatase, an alcohol dehydrogenase and SCH94-3944. The upper chromatogram shows the GC-MS analysis of the compounds produced by *E coli* cells transformed with the pJ401-FAL-1 plasmid allowing the expression of the enzymes of a farnesal biosynthetic pathway. The lower chromatograms shows the GC-MS analysis of the compounds produced by the same *E coli* cells further transformed with the plasmids pJ423-SCH94-3944 allowing the expression of the SCH94-3944 protein.

In this experiment, the plasmid pJ401-FAL-1 (described above) was used to transform the DP1205 *E. coli* cells creating a background strain producing cis-farnesal and trans-farnesal as major products with a concentration up to 500 mg/L in the culture media in tube assay conditions (FIG. 17).

This strain was then further transformed with the plasmid pJ423-SCH94-3944 carrying a cDNA encoding for SCH94-3944 from *R. erytheropolis*. The GC-MS analysis of the compounds produced by the cells showed formation of geranylacetone (FIG. 17). This experiment thus shows that the SCH94-3944 enzyme can cleave the alpha-beta carbon-carbon double-bound of the acyclic compound farnesal and catalyse the direct conversion of cis-farnesal and trans-farnesal to geranylacetone as shown in the scheme below.

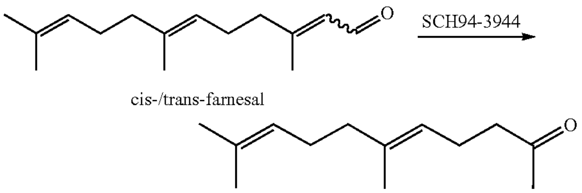

cis-/trans-farnesal geranylacetone

No conversion with farnesol was observed un ed the applied test conditions.

Example 13. In-Vivo Conversion of Citral Using an Enal-Cleaving Polypeptide from *Rhodococcus erythropolis*

Biochemical conversion of compounds was performed using *E. coli* KRX (Promega) cells transformed with the plasmid pJ423-SCH94-3944, thus, overexpressing the SCH94-3944 recombinant protein. The substrate was added to the cell culture to a final concentration of 12 g/L using an 2:1 substrate:Tween 80 emulsion. The bioconversion was performed as described in the experimental section. Negative controls were performed using cells transformed with a pJ423 expression plasmid without insert. Several substrates were tested: citral (a mixture composed of geranial and neral), citronelal (2,3-dihydrocitral) and (E)-2-dodecanal. The cells were incubated for 24 hours in the presence of the various compounds and the products of the conversion were analysed as described in the experimental section.

In the presence of the SCH94-3944 recombinant protein, geranial and neral were both converted to methylheptenone (FIG. 18) showing that this enzyme can cleave alpha-beta carbon-carbon double-bound of the acyclic monoterpene aldehydes as shown in the scheme below.

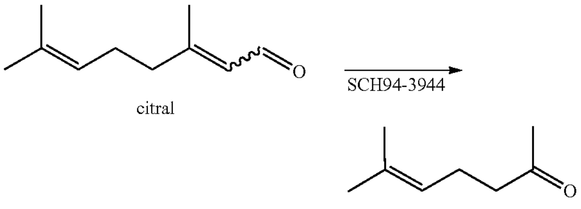

citral
methylheptenone

No conversion was obtained with citronelal of the formula

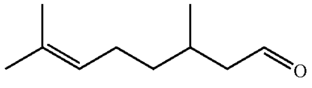
citronelal in the presence of the SCH94-3944 recombinant protein (FIG. 18), showing that the unsaturation of α,β-carbon bond is required for the catalysis.

Figure 18:
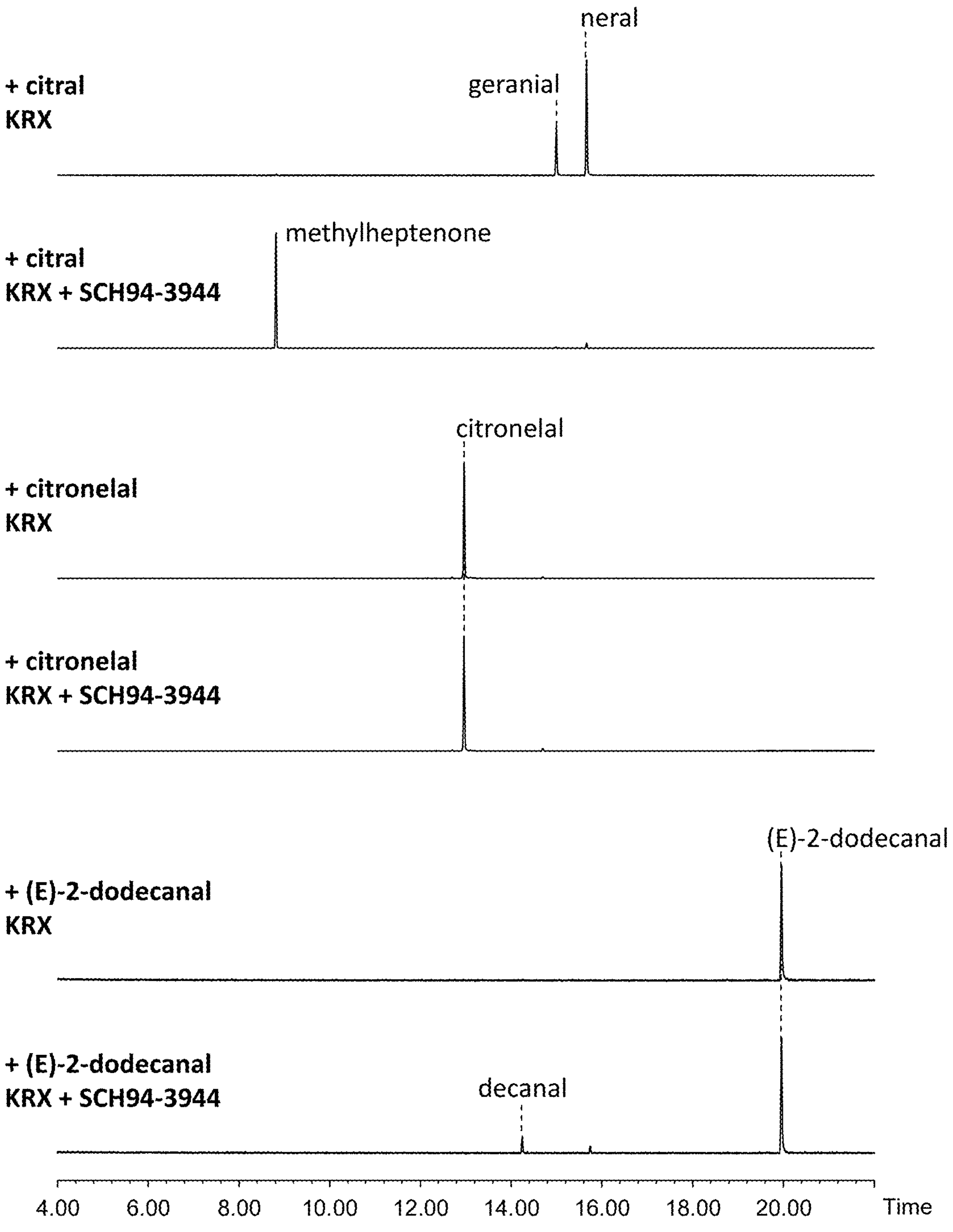
FIG. 18. GC-MS analysis of the products of the biotransformation of citral, citronelal and (E)-2-dodecanal by *E coli* cells expressing SCH94-3944. For each compounds the GC-MS analysis of the transformation using control *E. coli* cells and cells transformed to express the SCH94-3944 protein are show.

With (E)-2-dodecanal,

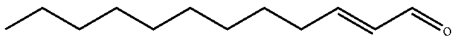
*(E)*-2-dodecanal conversion to decanal was observed. However, compared to citral, the conversion yield was significantly lower (FIG. 18). This observation suggests that the absence of the 3-methyl group has a negative effect on the enzymatic conversion by the SCH94-3944 protein.

Example 14: In Vivo Conversion of Copalal and Farnesal Using GXWXG and DUF4334 Domain Containing Proteins from Other Organisms The SCH94-3944 protein sequence contains a GXWXG protein family domain and a DUF4334 protein family domain. Proteins with similar domain architectures were searched in other organisms and tested to determine if the enzymatic activity associated with SCH94-3944 can also be associated with these homologous enzymes.

Figure 19:
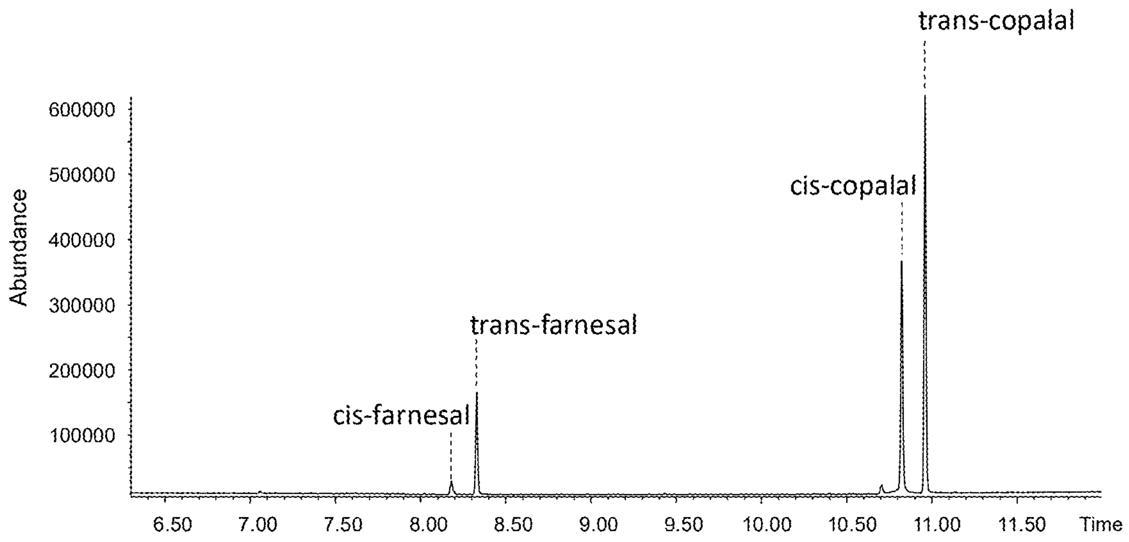
FIG. 19. GC-MS analysis of the sesquiterpenes and diterpenes produced using *E coli* cells expressing a CPP synthase, a phosphatase, an alcohol dehydrogenase. The chromatogram shows the GC-MS analysis of compounds produced by *E coli* cells transformed with the pJ401-CPAL-1 plasmid allowing the expression of the enzymes of a copalal biosynthetic pathway.

In this experiment, the plasmid pJ401-CPAL-1 (described above) was used to transform the DP1205 *E. coli* cells creating a background strain producing copalal (cis- and trans-isomer) as described in the previous section. In this strains a FPP synthase is expressed from the genomic integrated operons. Because the terpenyl phosphatase AspWeTPP can dephosphorylate FPP in addition to GGPP, and because AzeTolADH1 can also oxidize farnesol, a significant amount of trans farnesal was detected in addition to copalal when the pJ401-CPAL-1 was used to transform the DP1205 cells (FIG. 19).

This strain was then co-transformed with a second plasmid carrying a gene encoding for a protein containing a GXWXG protein family domain and a DUF4334 protein family domain. Several proteins were selected:

SCH80-05241 from *Rhodococcus rhodochrous* (® ATCC 12674™) (SEQ ID NO: 38),
Pdigit7033 from *Penicillium digitatum* (SEQ ID NO: 42),
PitalDUF3443-1 from *Penicillium italicum* (SEQ ID NO: 46),
AspWeDUF3443 from *Aspergillus wentii* (SEQ ID NO: 49),
RhoagDUF4334-2 from *Rhodococcus hoagii* strain PAM2288 (SEQ ID NO: 53),
RhoagDUF4334-3 from *Rhodococcus hoagii* strain N128 (SEQ ID NO: 56),
RhoagDUF4334-4 from *Rhodococcus hoagii* NBRC 10125 (SEQ ID NO: 59),
CnecaDUF4334 from *Cupriavidus necator* (SEQ ID NO: 62),
Rins-DUF4334 from *Ralstonia insidiosa* (SEQ ID NO: 69),
CgatDUF4334 from *Cryptococcus gattii* EJB2 (SEQ ID NO: 72),
GclavDUF4334 from *Grosmannia clavigera* kw1407 (SEQ ID NO: 75),
TcurvaDUF4334 from *Thermomonospora curvata* (SEQ ID NO: 81), and
PprotDUF4334 from *Pseudomonas protegens* (SEQ ID NO: 87).

Figure 20:
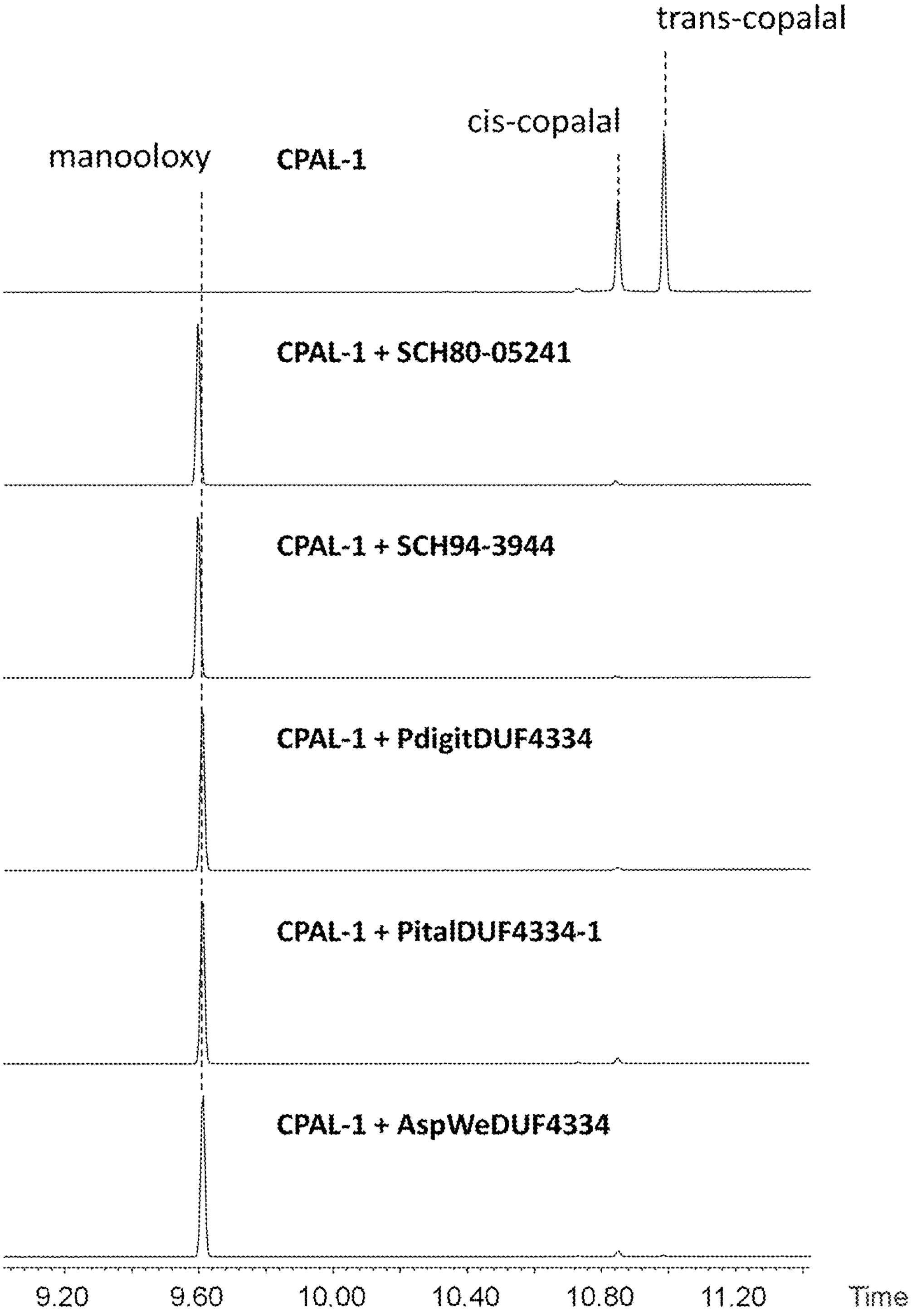
FIG. 20. GC-MS analysis of diterpenes and derivatives produced using *E coli* cells expressing a CPP synthase, a phosphatase, an alcohol dehydrogenase and SCH80-05241, SCH94-3944, PdigitDUF4334, PitalDUF4334-1 or AspWeDUF4334. The upper chromatogram shows the diterpene region in the GC-MS analysis of the compounds produced by *E coli* DP1205 cells transformed with the pJ401-CPAL-1 plasmid allowing the expression of the enzymes of a copalal biosynthetic pathway. The following chromatograms shows the GC-MS analysis of the compounds produced by the same *E coli* cells further transformed with a second plasmid expressing the SCH80-05241, SCH94-3944, PdigitDUF4334, PitalDUF4334-1 or AspWeDUF4334 recombinant proteins.
Figure 21:
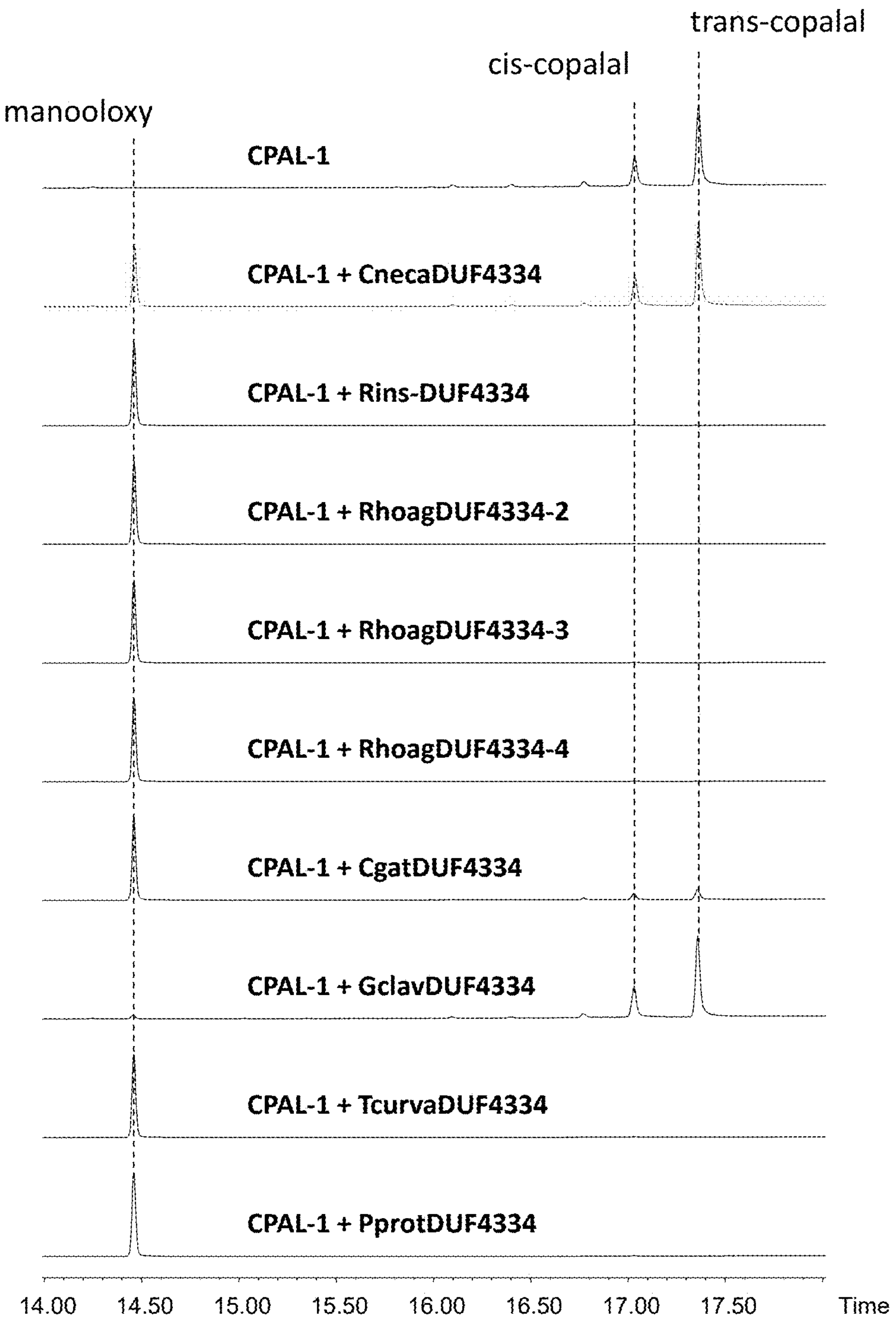
FIG. 21. GC-MS analysis of diterpenes and derivatives produced using *E coli* cells expressing a CPP synthase, a phosphatase, an alcohol dehydrogenase and CnecaDUF4334, Rins-DUF4334, RhoagDUF4334-2, RhoagDUF4334-3, RhoagDUF4334-4, CgatDUF4334, GclavDUF4334, TcurvaDUF4334 or PprotDUF4334. The upper chromatogram shows the diterpene region of a GC-MS analysis of the compounds produced by *E coli* DP1205 cells transformed with the pJ401-CPAL-1 plasmid allowing the expression of the enzymes of a copalal biosynthetic pathway. The following chromatograms shows the GC-MS analysis of the compounds produced by the same *E coli* cells further transformed with a second plasmid expressing the CnecaDUF4334, Rins-DUF4334, RhoagDUF4334-2, RhoagDUF4334-3, RhoagDUF4334-4, CgatDUF4334, GclavDUF4334, TcurvaDUF4334 or PprotDUF4334 recombinant proteins.
Figure 22:
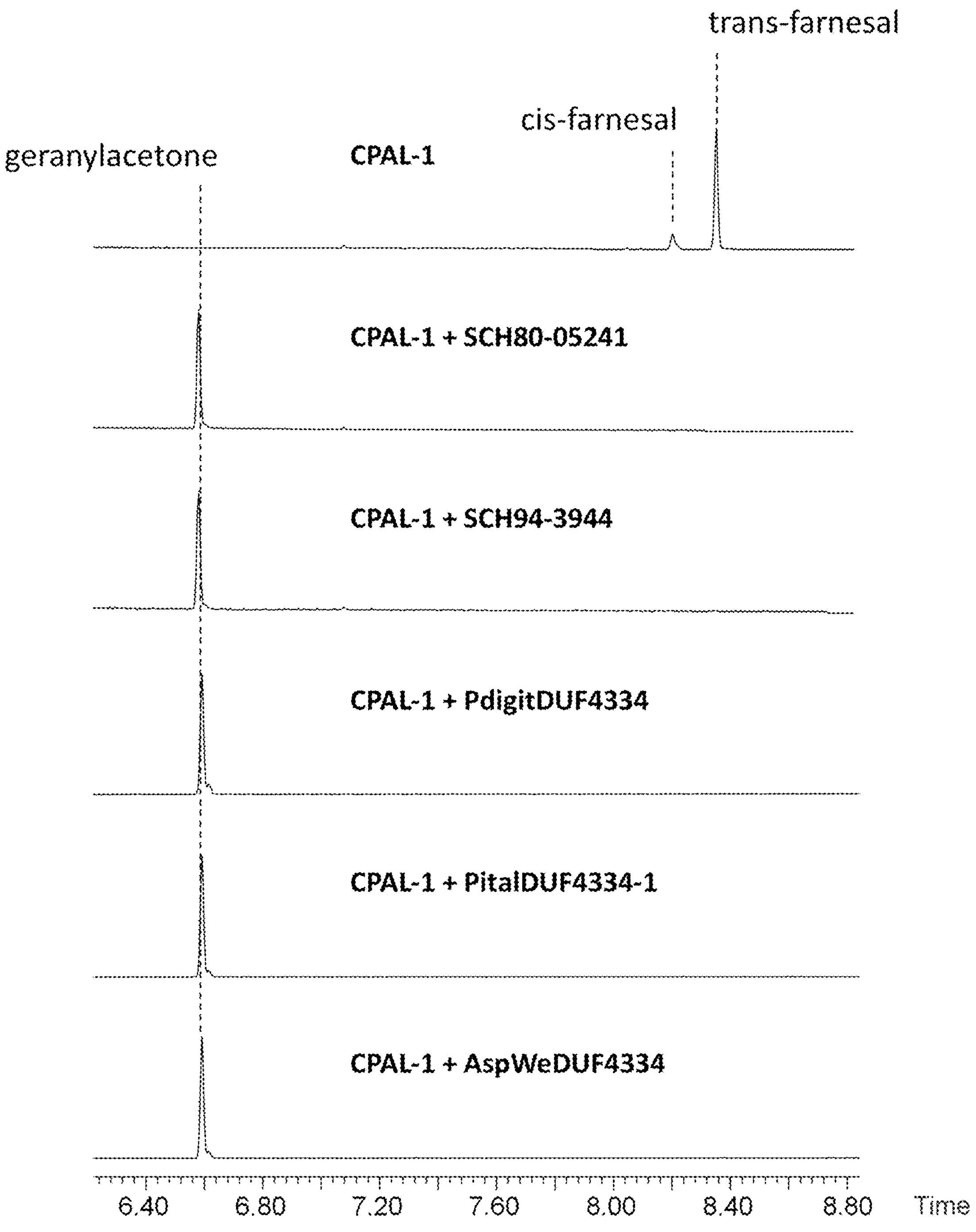
FIG. 22. GC-MS analysis of sesquiterpenes and derivatives produced using *E coli* cells expressing a phosphatase, an alcohol dehydrogenase and SCH80-05241, SCH94-3944, PdigitDUF4334, PitalDUF4334-1 or AspWeDUF4334. The upper chromatogram shows the sesquiterpene region in the GC-MS analysis of the compounds produced by *E coli* DP1205 cells transformed with the pJ401-CPAL-1 plasmid allowing the expression of the enzymes of a copalal biosynthetic pathway. The following chromatograms shows the GC-MS analysis of the compounds produced by the same *E. coli* cells further transformed with a second plasmid expressing the SCH80-05241, SCH94-3944, PdigitDUF4334, PitalDUF4334-1 or AspWeDUF4334 recombinant proteins.
Figure 23:
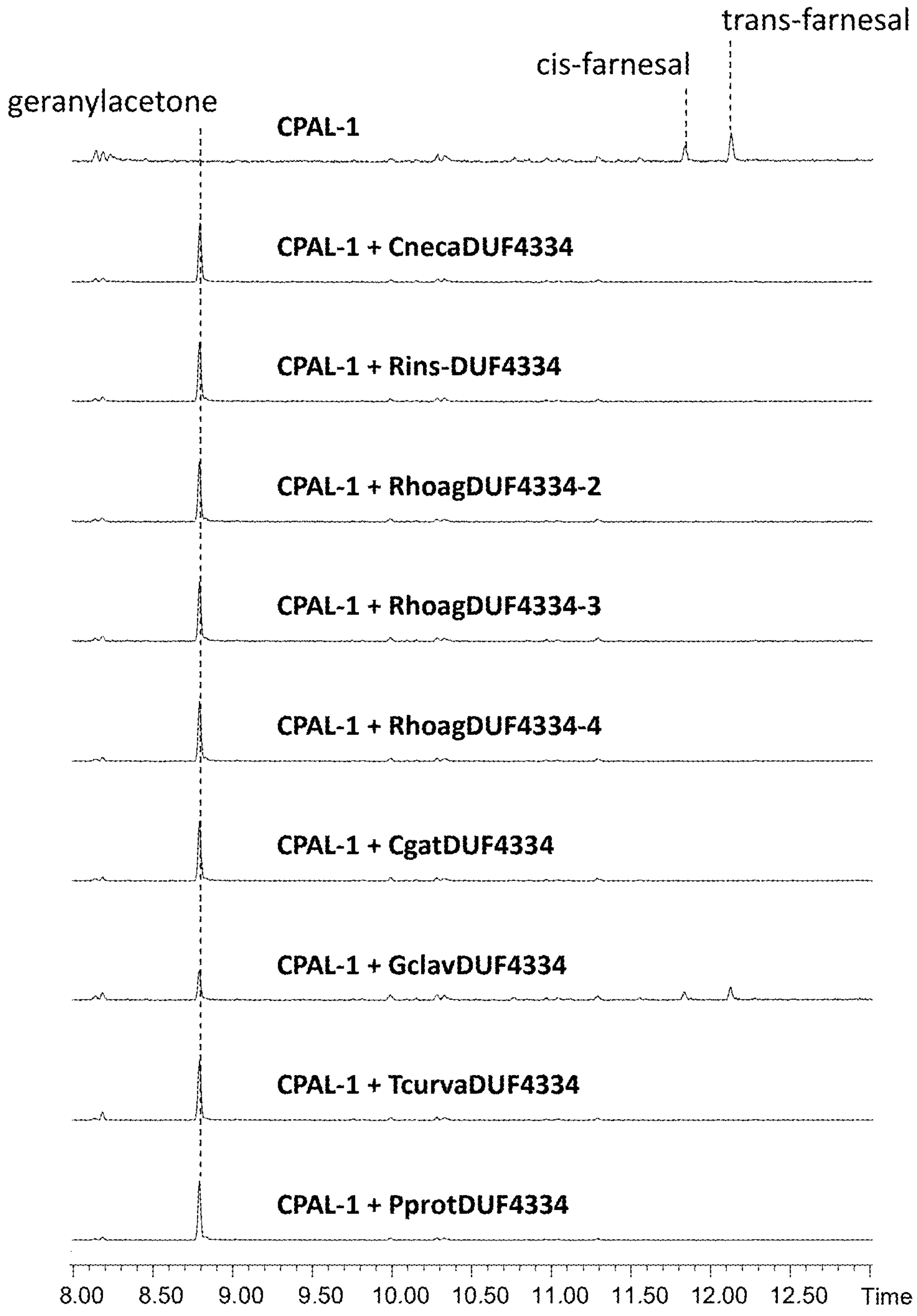
FIG. 23. GC-MS analysis of sesquiterpenes and derivatives produced using *E coli* cells expressing a phosphatase, an alcohol dehydrogenase and CnecaDUF4334, Rins-DUF4334, RhoagDUF4334-2, RhoagDUF4334-3, RhoagDUF4334-4, CgatDUF4334, GclavDUF4334, TcurvaDUF4334 or PprotDUF4334. The upper chromatogram shows the sesquiterpene region of the GC-MS analysis of the compounds produced by *E coli* cells transformed with the pJ401-CPAL-1 plasmid allowing the expression of the enzymes of a copalal biosynthetic pathway. The following chromatograms shows the GC-MS analysis of the compounds produced by the same *E coli* cells further transformed with a second plasmid expressing the CnecaDUF4334, Rins-DUF4334, RhoagDUF4334-2, RhoagDUF4334-3, RhoagDUF4334-4, CgatDUF4334, GclavDUF4334, TcurvaDUF4334 or PprotDUF4334 recombinant proteins.

Codon optimized cDNAs encoding for each of these proteins were designed and cloned in the pJ423 expression plasmids (ATUM, Newark, California). The DP1205 *E. coli* cells were co-transformed with one of these plasmids and with the plasmid pJ401-CPAL-1. FIGS. 20 and 21 show the conversion of cis-copalal and trans-copalal to manooloxy in the presence of each of the recombinant proteins containing a GXWXG and DUF4334 domain. Under the assay conditions the conversion of copalal was almost complete with each recombinant enzyme except for the GclavDUF4334 enzyme with which only a small conversion was observed. FIGS. 22 and 23 show the conversion of cis-farnesal and trans-farnesal to geranylacetone. The conversion of fanesal was also complete with each enzyme except for GclavDUF4334 with which only about 50% of the farnesal was converted.

This experiment shows that proteins containing a GXWXG protein family domain in the N-terminal region and a DUF4334 protein family domain in the C-terminal region can catalyse enal-cleaving activity on copalal and farnesal as shown in the schemes below.

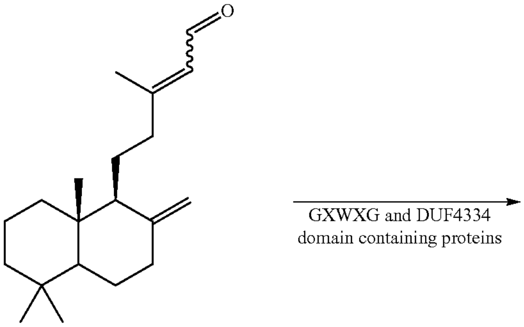

cis/trans-copalal

-continued

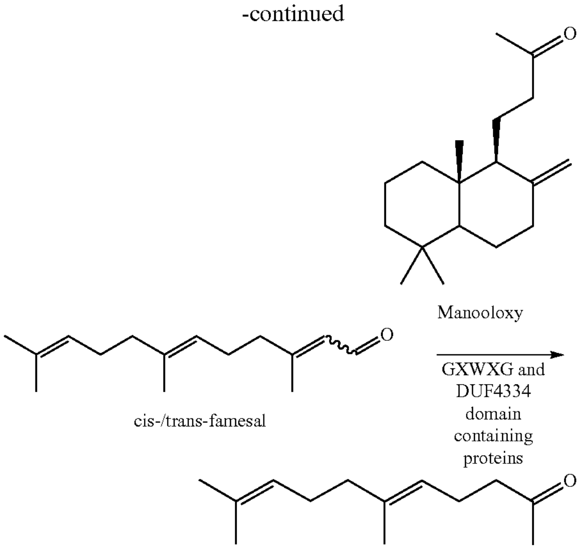

Manooloxy cis-/trans-farnesal geranylacetone

Example 15: Variants of SCH94-3944 with Single Amino Acid Modification

Figure 24:
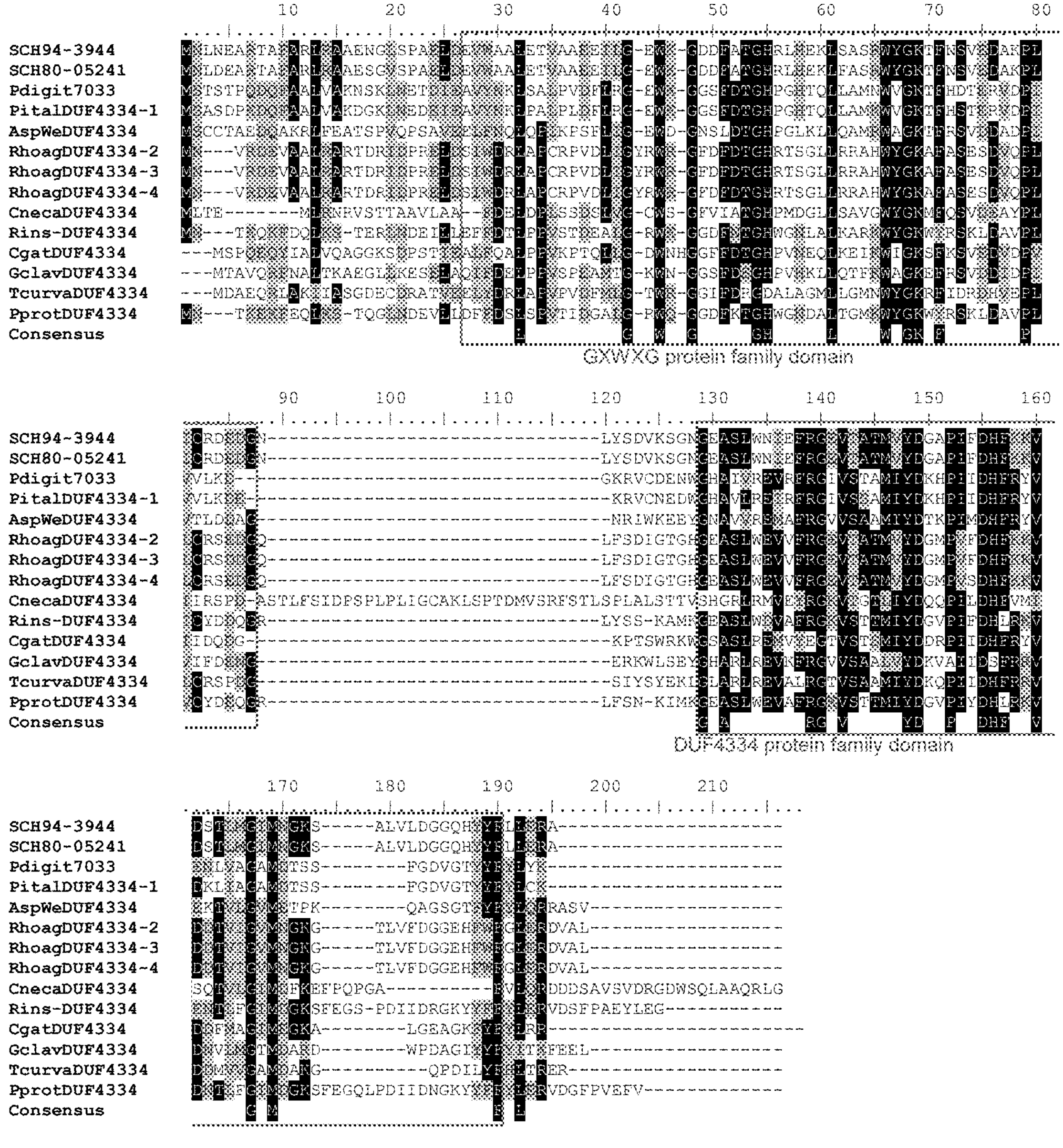
FIG. 24. Alignment and conserved amino acids of GXWXG and DUF4334 domain containing proteins catalazing the enzymatic enal-cleavage. The boxes show the predicted localization of the respective protein family domains. The depicted sequence listings correspond to the following: SCH94-3944 is set forth in SEQ ID NO:34, SCH80-05241 is set forth in SEQ ID NO:38, Pdigit7033 is set forth in SEQ ID NO: 42, PitalDUF4334-1 is set forth in SEQ ID NO: 46, AspWeDUF4334 is set forth in SEQ ID NO: 49, RhoagDUF4334-2 is set forth in SEQ ID NO: 53, RhoagDUF4334-3 is set forth in SEQ ID NO: 56, RhoagDUF4334-4 is set forth in SEQ ID NO: 59, CnecaDUF4334 is set forth in SEQ ID NO: 62, Rins-DUF4334 is set forth in SEQ ID NO: 69, CgatDUF4334 is set forth in SEQ ID NO: 72, GclavDUF4334 is set forth in SEQ ID NO: 75, TcurvaDUF4334 is set forth in SEQ ID NO:81, and PprotDUF4334 is set forth in SEQ ID NO: 87.

The alignment of the amino acid sequences of the GXWXG and DUF4334 domain containing proteins having enal-cleaving activities, showed conserved amino acids along the amino acid sequence and within said two protein domains (FIG. 24). Conserved residues in protein families are often important for the enzymatic activity.

To evaluate the participation of the conserved residues in the GXWXG and DUF4334 domain containing enzymes to the enzymatic activity, artificial mutants of the SCH94-3944 protein were design in which the conserved residues were individually replaced by an alanine residue. The following residue were mutated: W44, T51, H53, L59, W64, K67, S71, R106, Y115, D116, D122, M136, K139, F152, L154 and R156. The modified proteins were designated SCH94-3944-W44A, SCH94-3944-T51A, SCH94-3944-H53A, SCH94-3944-L59A, SCH94-3944-W64A, SCH94-3944-K67A, SCH94-3944-S71A, SCH94-3944-R106A, SCH94-3944-Y115A, SCH94-3944-D116A, SCH94-3944-D122A, SCH94-3944-M136A, SCH94-3944-K139A, SCH94-3944-F152A, SCH94-3944-L154A and SCH94-3944-R156A.

Figure 25:
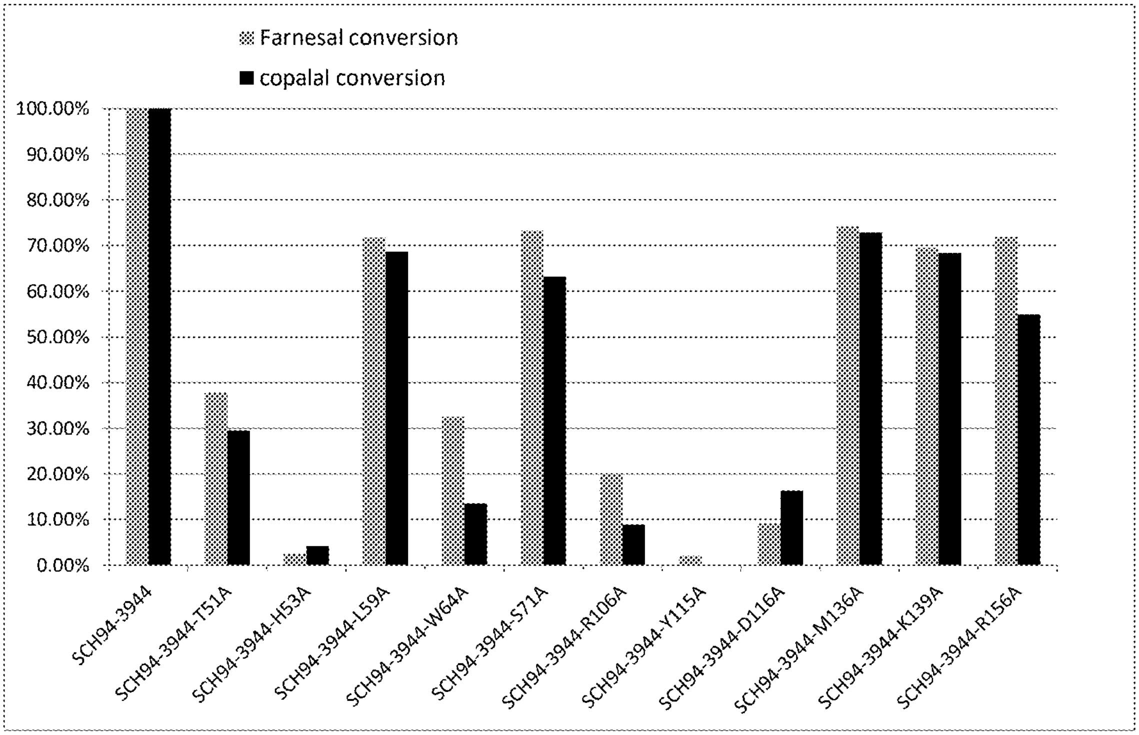
FIG. 25. Farnesal and copalal conversion activities by single amino acid variants of SCH94-3944. The activities are presented as the total amount of manooloxy and geranylacetone produced expressed in percentages relative to the wild type enzyme activities.

Codon optimized cDNAs encoding for each of these proteins were designed and cloned in the pJ423 expression plasmids (ATUM, Newark, California). The DP1205 *E. coli* cells were co-transformed with one of these plasmids and with plasmid pJ401-CPAL-1. In the presence of the SCH94-3944-W44A, SCH94-3944-K67A, SCH94-3944-D122A, SCH94-3944-F152A or SCH94-3944-L154A recombinant proteins, no conversion of copalal and farnesal was observed. In the presence of the SCH94-3944-T51A, SCH94-3944-H53A, SCH94-3944-L59A, SCH94-3944-W64A, SCH94-3944-S71, SCH94-3944-R106A, SCH94-3944-Y115A, SCH94-3944-D116A, SCH94-3944-M136A, SCH94-3944-K139A and SCH94-3944-R156A enzymes, conversion of copalal and farnesal was observed but with an efficiency lower than the wild type SCH94-3944 protein. FIG. 25 shows the activity of each single amino acid variants enzyme relative to the wild type SCH94-3944.

Example 16: In-Vivo Production of γ-Ambryl Acetate by Combining the Enal Cleaving Activity and the BVMO Activity in *E. coli* Cells In this experiment, the plasmid pJ401-CPAL-1 (described above) was used to transform the DP1205 *E. coli* cells creating a background strain producing copalal (cis- and trans-isomer) as described above.

This strain was then co-transformed with a second plasmid carrying a codon optimized nucleotide sequence encoding for either an enzyme with enal-cleaving activity or an enzyme with BVMO activity, or with a second vector carrying an operon composed of a codon optimize cDNA encoding for an enal-cleaving polypeptide and codon optimized cDNA encoding for a BVMO:

pJ423-AspWeBVMO, containing an optimized DNA sequence encoding for AspWeBVMO (SEQ ID NO: 17);

pJ423-SCH94-3944, containing an optimized DNA sequence encoding for SCH94-3944 (SEQ ID NO: 35);

pJ423-SCH94-3944-SCH23-BVMO, containing an optimized DNA sequence encoding for SCH94-3944 and SCH23-BVMO1 (SEQ ID NOs: 35 and 3);

pJ423-SCH94-3944-SCH24-BVMO, containing an optimized DNA sequence encoding for SCH94-3944 and SCH23-BVMO1 (SEQ ID NOs: 35 and 7);

pJ423-SCH94-3944-SCH46-BVMO, containing an optimized DNA sequence encoding for SCH94-3944 and SCH46-BVMO1 (SEQ ID NOs: 35 and 14).

The transformed cells were cultivated and the formation of terpene derivatives was analysed by GC-MS as described above.

When cells were transformed with the vector pJ401-CPAL-1 and with an empty pJ423 vector or pJ423-AspWeBVMO, formation of only cis-copalal and trans-copalal was observed. (FIG. 26).

Figure 26:
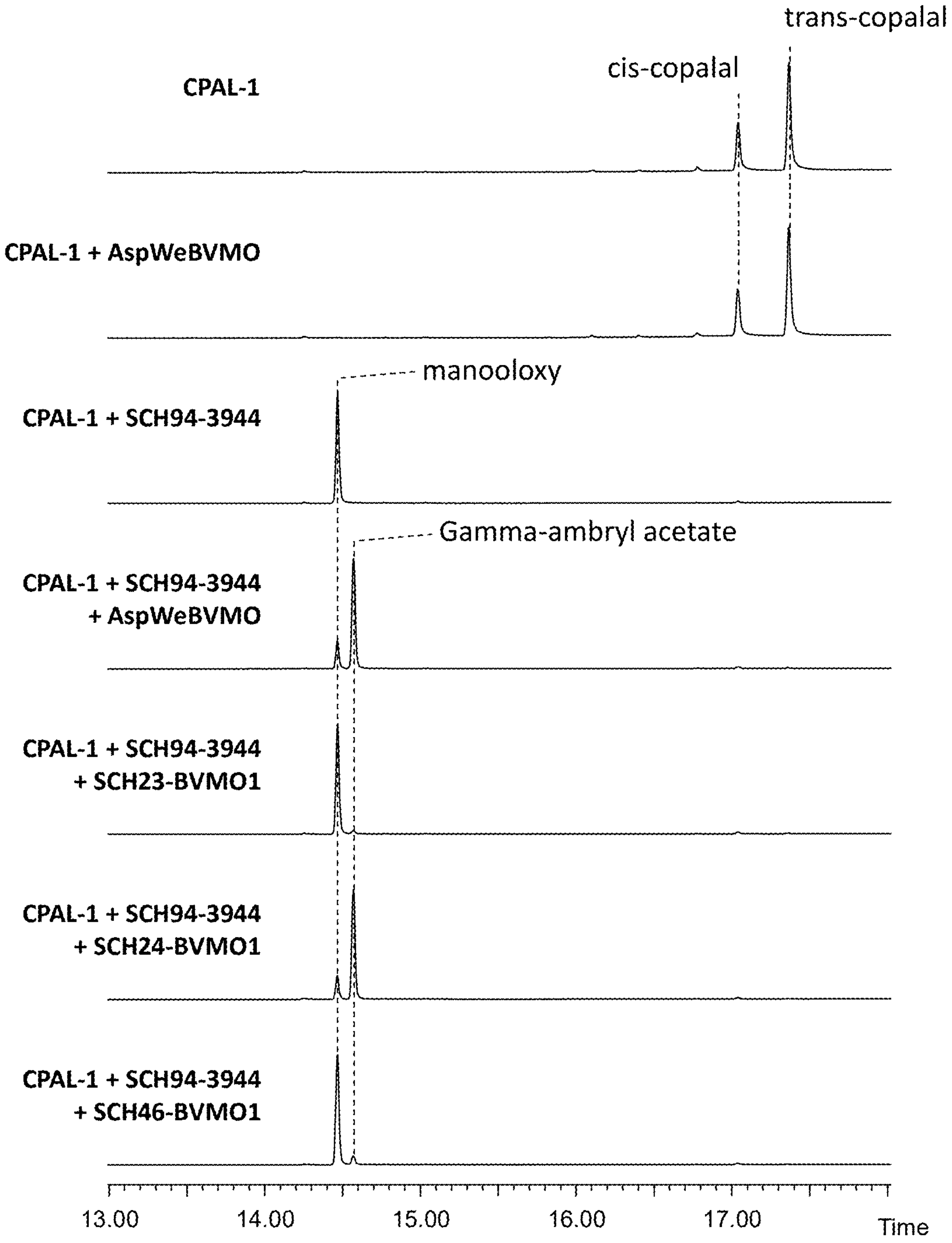
FIG. 26. GC-MS analysis of the biochemical production of manooloxy and gamma-ambryl acetate by *E. coli* cells expressing a CPP synthase, a phosphatase, an alcohol dehydrogenase, an enal cleaving enzyme and a BVMO. The upper chromatogram shows the diterpene region of the GC-MS analysis of the compounds produced by *E coli* DP1205 cells transformed with the pJ401-CPAL-1 plasmid allowing the expression of the enzymes of a copalal biosynthetic pathway. The following chromatograms shows the GC-MS analysis of the compounds produced by the same *E coli* cells further transformed with a second plasmid expressing the AspWeBVMO, SCH94-3944, SCH94-3944 together with AspWeBVMO, SCH94-3944 together with SCH23-BVMO1, SCH94-3944 together with SCH24-BVMO1, and SCH94-3944 together with SCH46-BVMO1.

When cells were transformed with the vector pJ401-CPAL-1 and with pJ423-SCH94-3944, formation of manooloxy was observed with complete conversion of copalal (FIG. 26).

When cells were transformed with the vector pJ401-CPAL-1 and with a pJ423 vector allowing the co-expression of a enal-cleaving polypeptide and a BVMO, formation of γ-ambryl acetate was observed in the addition of manooloxy. Variations in the ratio of manooloxy and gamma-ambryl acetate were observed depending on the BVMO enzyme.

This experiment shows that the following pathway can be introduced in a host cell to produce gamma-ambryl acetate.

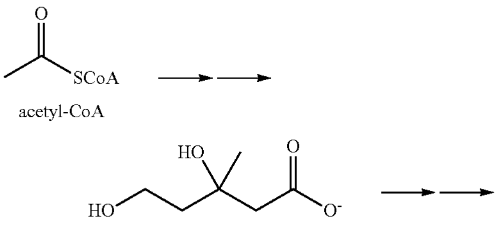

acetyl-CoA mevalonate

-continued

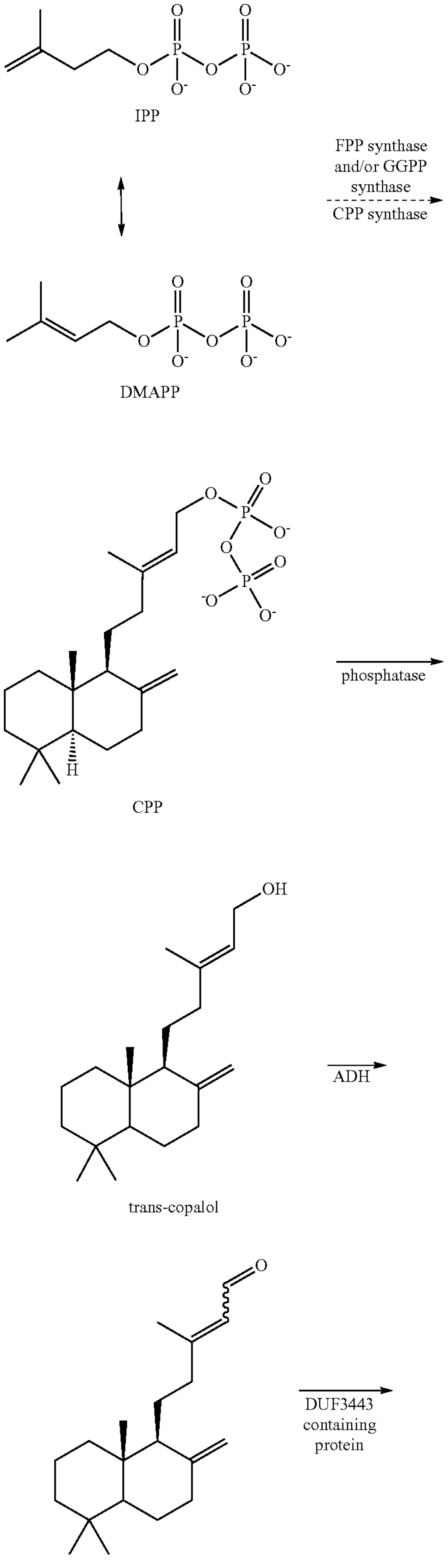

IPP

DMAPP

CPP trans-copalol cis-/trans-copalal

-continued

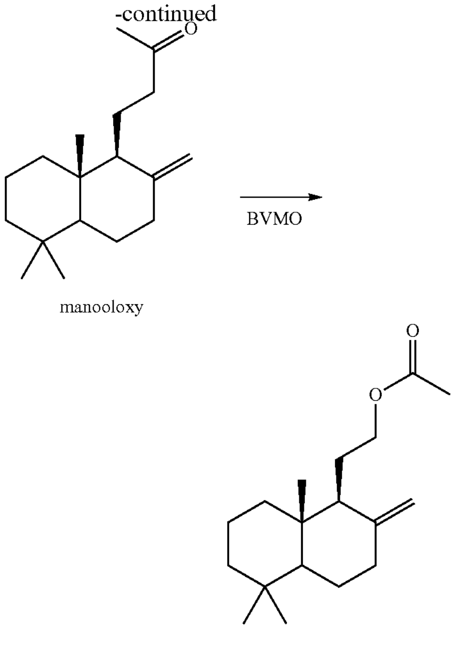

manooloxy gamma-ambrol acetate

Example 17: In Vivo Manooloxy Production in *Saccharomyces cerevisiae* Cells Using Sch23-ADH1 from *Hyphozyma roseonigra* and Different Enal Cleaving Polypeptides For the production of manooloxy, the genes encoding for the GGPP synthase carG (from *Blakeslea trispora*, NCBI accession JQ289995.1), the copalyl-pyrophosphate synthase SmCPS2 (from *Salvia miltiorrhiza*, NCBI accession ABV57835.1), the copalyl-pyrophosphate phosphatase TalVeTPP (from *Talaromyces verruculosus*, NCBI accession KUL89334.1), the alcohol dehydrogenase SCH23-ADH1 (from *Hyphozyma roseonigra*) and one of the tested enal-cleaving polypeptides were expressed in the engineered *Saccharomyces cerevisiae* strain YST075 as described in the general methods section.

Five enal-cleaving polypeptides were evaluated:

AspWeDUF4334 (from *Aspergillus wentii*; GenBank accession OJJ34591.1) (SEQ ID NO: 49).

CnecaDUF4334 (from *Cupriavidus necator*; GenBank accession WP_049800708.1) (SEQ ID NO: 62).

Pdigit7033 (from *Penicillium digitatum*) (SEQ ID NO: 42).

SCH94-3944 (from *Rhodococcus erytheropolis*) (SEQ ID NO: 34).

SCH80-05241 (from *Rhodococcus rhodochrous*).

All genes were codon optimized for their expression in *S. cerevisiae* (AspWeDUF4334, SEQ ID NO: 51; CnecaDUF4334, SEQ ID NO: 64; Pdigit7033, SEQ ID NO: 44; SCH94-03944, SEQ ID NO: 36; and SCH80-05241 SEQ ID NO: 40).

The constructed strains were termed YST184 (with AspWeDUF4334), YST185 (with CnecaDUF4334), YST186 (with Pdigit7033), YST187 (with SCH94-03944) and YST188 (with SCH80-05241). These strains were cultivated as described in the general methods section above; the production of manooloxy and other compounds was identified using GC-MS analysis.

Figure 27:
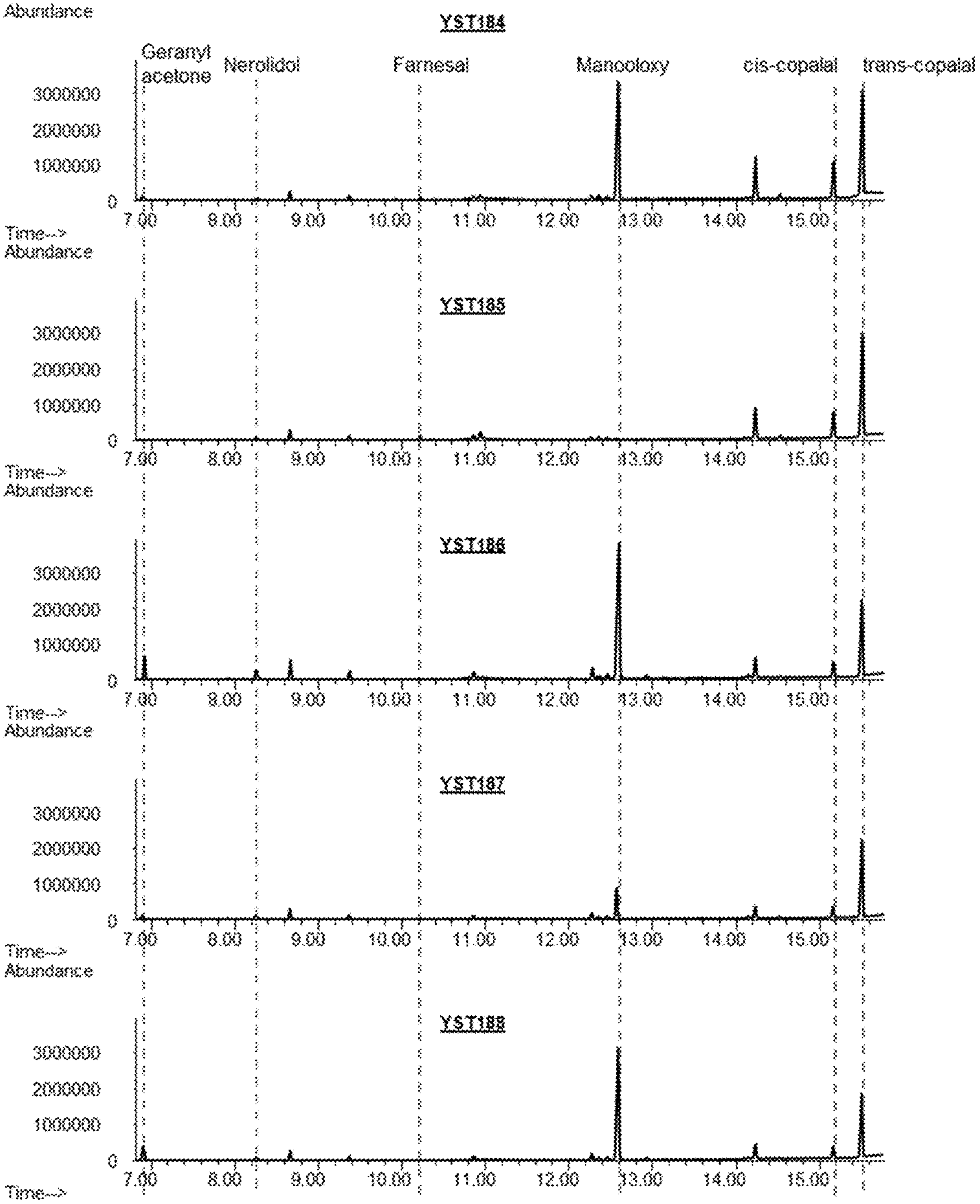
FIG. 27. GC-MS analysis of terpenes and derivatives produced using the modified *S. cerevisiae* strains expressing the GGPP synthase carG, the CPP synthase SmCPS2, the CPP phosphatase TalVeTPP, the alcohol dehydrogenase SCH23-ADH1 and either AspWeDUF4334 (YST184), CnecaDUF4334 (YST185), Pdigit7033 (YST186), SCH94-3944 (YST187) or SCH80-05241 (YST188).

Under the tested conditions, copalal, nerolidol, farnesal, geranyl acetone and manooloxy were identified in all cultures where the enal-cleaving polypeptides were expressed (FIG. 27). As expected, all tested enal-cleaving polypeptides were able to use farnesal or copalal as substrates to produce geranyl acetone and manooloxy, respectively. In the cultures ofYST184, YST185, YST186, YST187 andYST188, manooloxy represented 37%, 1%, 54%, 22% and 52%, respectively, of the sum of identified terpenes (FIG. 28A).

Figure 28:
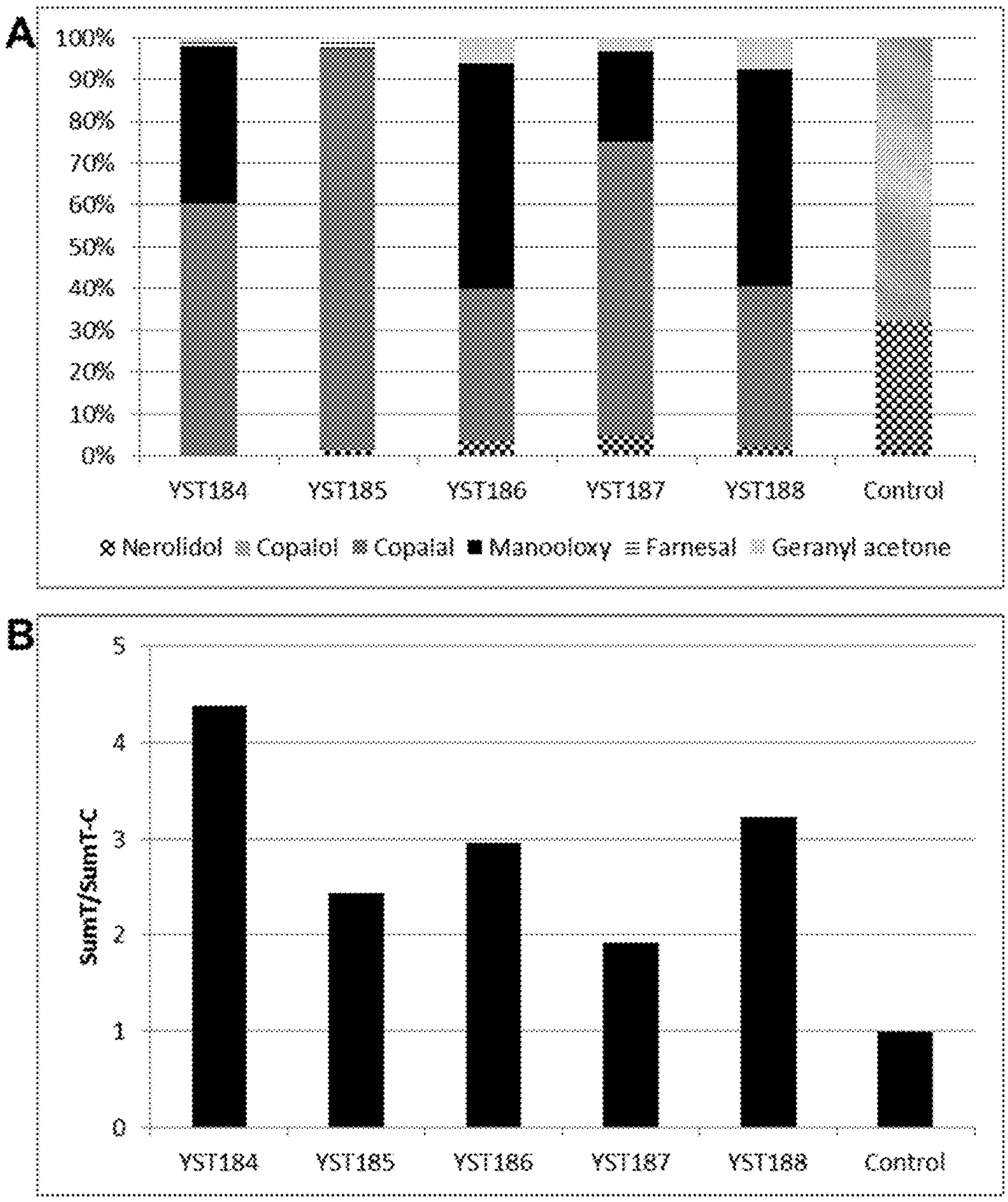
FIG. 28 A) Percentages of identified terpenes produced by YST184, YST185, YST186, YST187 and YST188. B) Total amount of identified terpenes (SumT) produced by YST184, YST185, YST186, YST187 and YST188 with respect to the amount of identified terpenes in control (SumT-C). The control strain was YST075 expressing the copalol biosynthetic pathway.

Interestingly, the total amount of identified terpenes in cultures from strains containing the alcohol dehydrogenase and the different enal-cleaving polypeptides were two- to four-folds higher than that of the control culture (FIG. 28B Example 18: In Vivo Gamma-Ambryl Acetate Production in *Saccharomyces cerevisiae* Cells Using SCH23-ADH1 from *Hyphozyma roseonigra*, AspWeDUF4334 from *Aspergillus wentii* and Different Baeyer-Villiger Monooxygenases (BVMOs)

For the production of gamma-ambryl acetate, the genes encoding for the GGPP synthase carG (from *Blakeslea trispora*, NCBI accession JQ289995.1), the copalyl-pyrophosphate synthase SmCPS2 (from *Salvia miltiorrhiza*, NCBI accession ABV57835.1), the copalyl-pyrophosphate phosphatase TalVeTPP (from *Talaromyces verruculosus*, NCBI accession KUL89334.1), the alcohol dehydrogenase SCH23-ADH1 (from *Hyphozyma roseonigra*), the enal-cleaving polypeptide AspWeDUF4334 (from *Aspergillus wentii*; GenBank accession OJJ34591.1) and one of the tested Baeyer-Villiger monooxygenases (BVMOs) were expressed in the engineered *Saccharomyces cerevisiae* strain YST075 as described in general methods.

Three BVMOs were evaluated:

SCH23-BVMO1 (from *Hyphozyma roseonigra*) (SEQ ID NO: 2).

SCH24-BVMO1 (from *Filobasidum magnum*) (SEQ ID NO: 6).

AspWeBVMO (from *Aspergillus wentii*; GenBank accession OJJ34587.1) (SEQ ID NO: 16).

All genes were codon optimized for their expression in *S. cerevisiae* (SCH23-BVMO1, SEQ ID NO: 4; SCH24-BVMO1, SEQ ID NO: 8; and AspWeBVMO, SEQ ID NO: 18).

The obtained strains were termed YST190 (with SCH23-BVMO1), YST191 (with SCH24-BVMO1) and YST192 (with AspWeBVMO). These strains were cultivated as described in the general methods section above; the production of manooloxy and other compounds was identified using GC-MS analysis.

Figure 29:
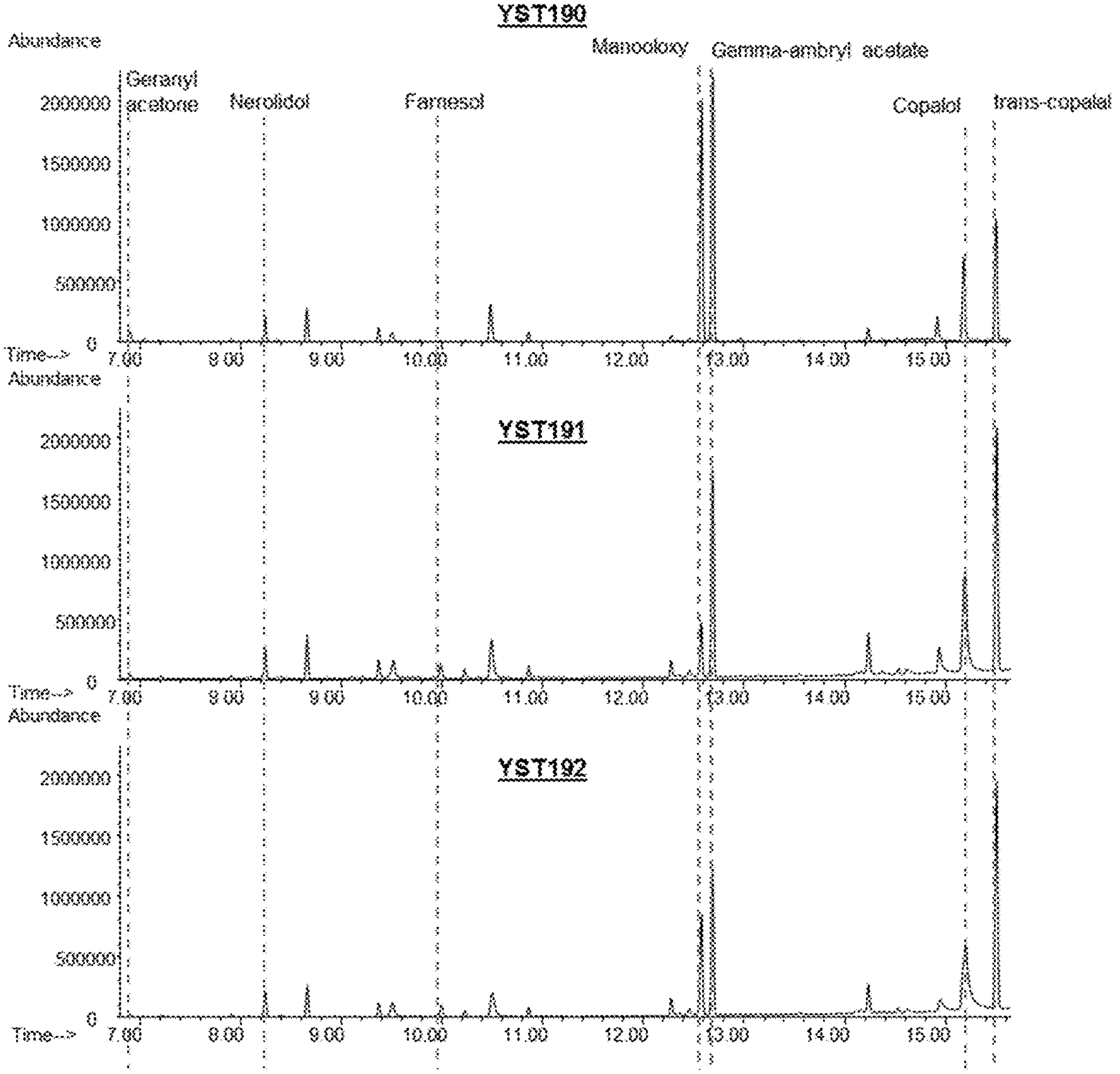
FIG. 29. GC-MS analysis of terpenes and derivatives produced using the modified *S. cerevisiae* strains expressing the GGPP synthase carG, the CPP synthase SmCPS2, the CPP phosphatase TalVeTPP, the alcohol dehydrogenase SCH23-ADH, the enal-cleaving polypeptide AspWeDUF4334 and either SCH23-BVMO1 (YST190), SCH24-BVMO1 (YST191) or AspWeBVMO (YST192).
Figure 30:
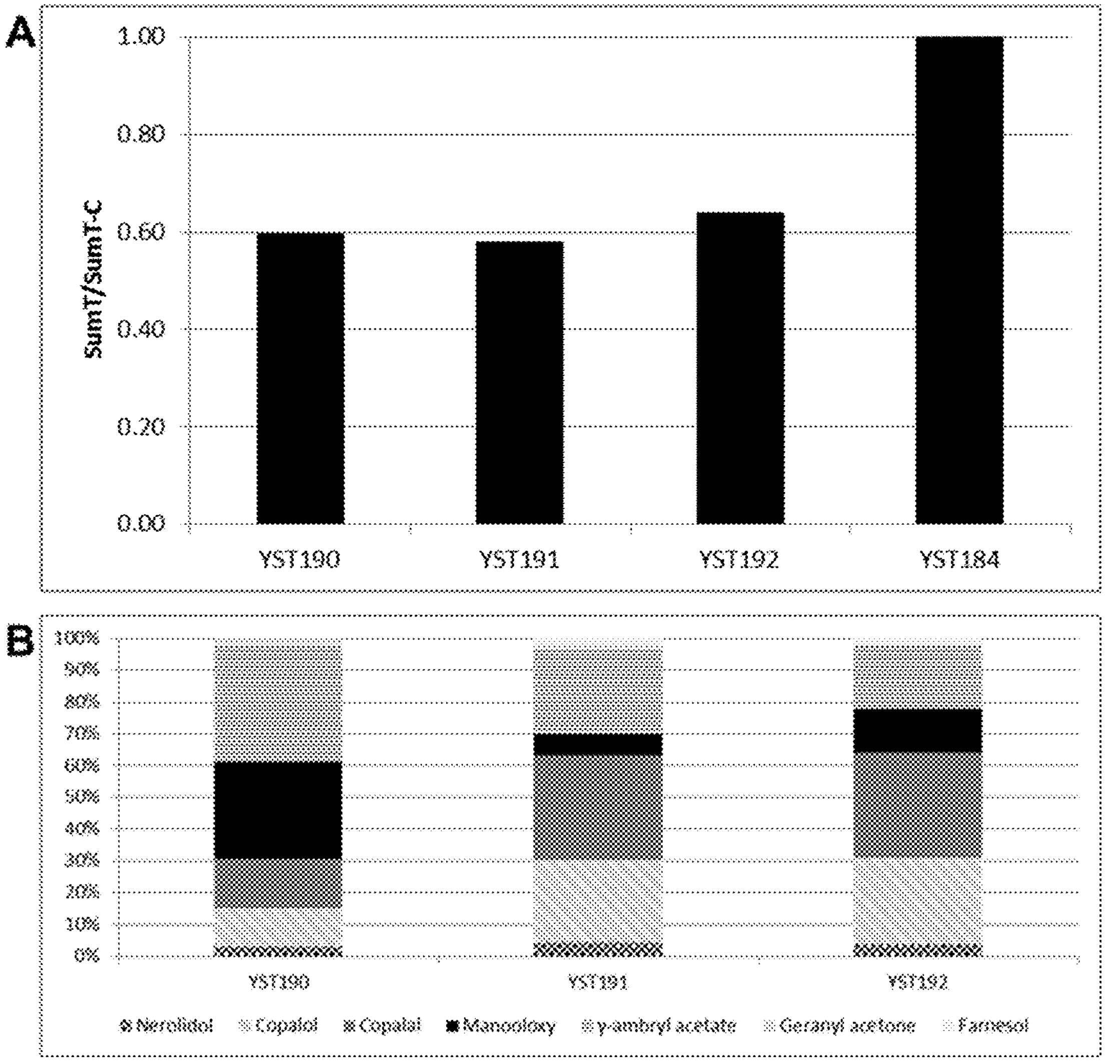
FIG. 30. A) Total amount of identified terpenes (SumT) produced by YST190, YST191 and YST192 with respect to the amount of identified terpenes in YST184 (SumT-C). B) Percentages of identified terpenes produced by YST190, YST191 and YST192.

Under the tested conditions, copalol, copalal, nerolidol, farnesol, geranyl acetone, manooloxy and gamma-ambryl acetate were identified in all cultures (FIG. 29). Interestingly, and different from previous experiments, the conversion of copalol to copalal was not complete. In addition, when compared with a strain not harboring BVMOs, the total amount of terpenes produced was lower (FIG. 30A). In the cultures of YST190, YST191 and YST192, gamma-ambryl acetate represented 37%, 27% and 20%, respectively, of the sum of identified terpenes (FIG. 30B).

Example 19: In-Vivo Production of Sclareol Oxide Using a Labdendiol Biosynthesis Pathway And a Carbon-Carbon Bound Enal-Cleaving Polypeptide In this experiment, the plasmid pJ401-LOH-2 (described above) was used to transform the DP1205 *E. coli* cells creating a background strain producing labdendiol ((13E)-13-Labdene-8,15-diol) as described above.

This strain was then co-transformed with a second plasmid carrying a codon optimized nucleotide sequence encoding for an alcohol dehydrogenase and an enzyme with enal-cleaving polypeptideenal-cleaving polypeptide activity:

pJ423-AzetolADH1, containing an optimized DNA sequence encoding for the alcohol dehydrogenase AzetolADH1; and pJ423-SCH94-3944-3945, containing optimized DNA sequences encoding for the alcohol dehydrogenase SCH94-3944 and the enal-cleaving polypeptide SCH94-3945.

The transformed cells were cultivated and the formation of terpene derivatives was analysed by GC-MS as described above.

Figure 31:
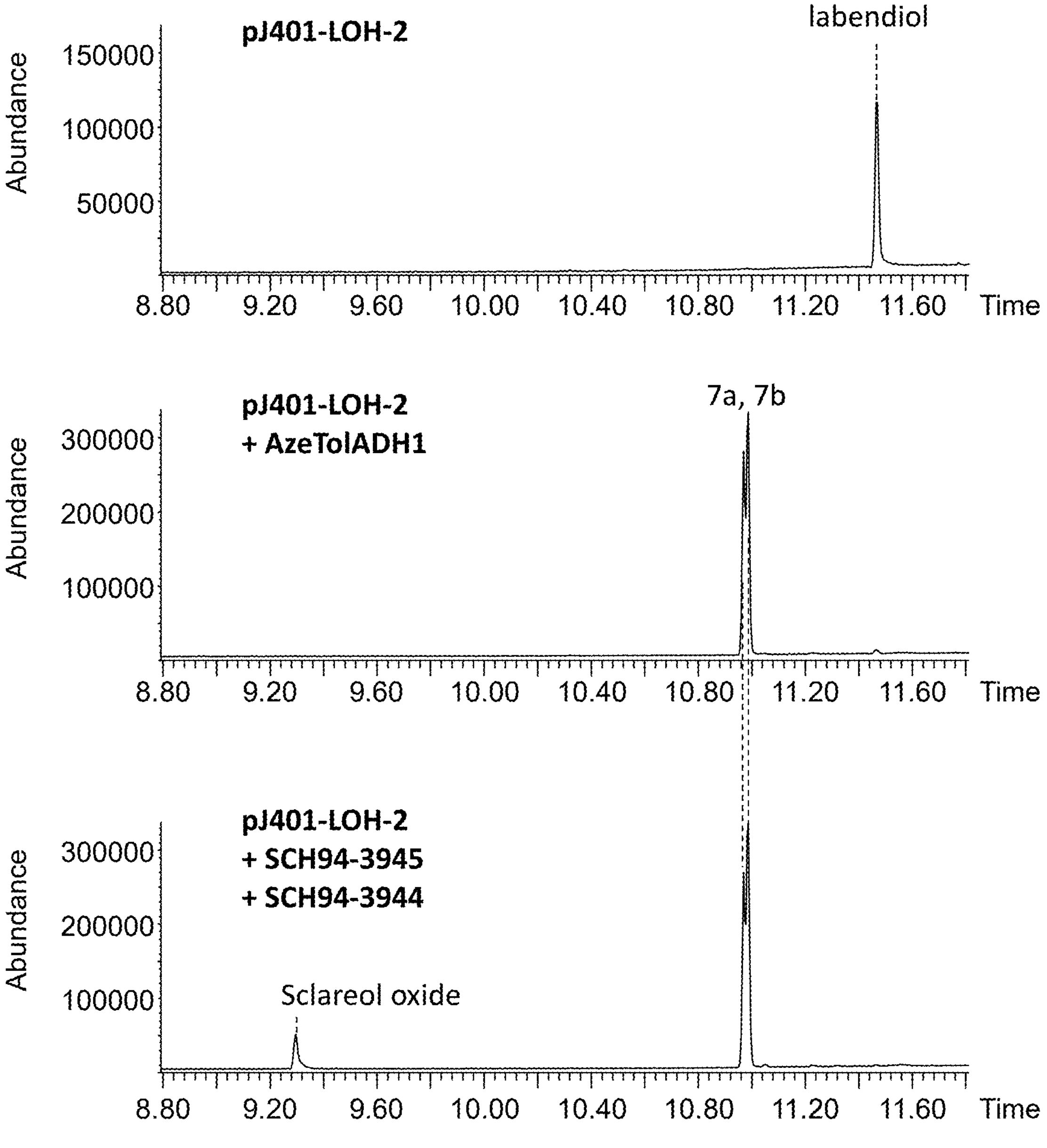
FIG. 31. GC-MS analysis of the diterpene and diterpene derivatives produce using *E. coli* cells expressing a LPP synthase, a phosphatase, an alcohol dehydrogenase and enal-cleaving polypeptide. The upper chromatogram shows the GC-MS analysis of the compounds produced by *E. coli* DP1205 cells transformed with the pJ401-LOH-2 vector allowing the expression of the enzymes of a labdendiol biosynthetic pathway. The following chromatograms shows the GC-MS analysis of the compounds produced by the same *E. coli* cells further transformed with a second plasmid expressing the AzeTolADH1 alcohol dehydrogenase or the SCH94-3945 alcohol dehydrogenase together with the SCH94-3944 enal-cleaving polypeptide.

When cells were transformed with the vector pJ401-LOH-2 and with an empty pJ423 vector formation of labdendiol was observed (FIG. 31).

When cells were transformed with the vector pJ401-LOH-2 and with pJ423-AzetolADH1 to co-express an alcohol dehydrogenase, formation of two new products were observed (FIG. 31). NMR analysis confirmed the two compounds as being two isomers of (+)-8,13-epoxy-labdan-15-al (compounds 7a and 7b) as shown in the scheme below. These two compounds result from the instability of 8-hydroxy-labd-13-en-15-al (6) produced by the oxidation of labdendiol. A postulated mechanism of dehydration and rearrangement of compound 6 to compound 7a and 7b is shown in the scheme below.

When cells were transformed with the vector pJ401-LOH-2 and with pJ423-SCH94-3944-3945 to co-express an alcohol dehydrogenase and a enal-cleaving polypeptide, formation of sclareol oxide was observed in addition to compounds 7a and 7b. The formation of sclareol oxide in the presence of a enal-cleaving polypeptide can be explained by the transformation steps shown in the scheme below. The SCH94-3944 enal-cleaving polypeptide catalyses the C=C double bond cleavage of compound 6 to the 8-Hydroxy-14,15-bisnorlabdan-13-one (8). Compound 8 is unstable and is converted under mild conditions to sclareol oxide (Barrero et al., Tetrahedron 49, (45) 1993, 10405-10412; Hua et al., Tetrahedron 67 (6) 2011, 1142-1144). The relative small final amounts of sclareol oxide relative to compounds 7a and 7b is due to the competition between the enzymatic activity of the SCH94-3944 and the chemical dehydration of compound 6.

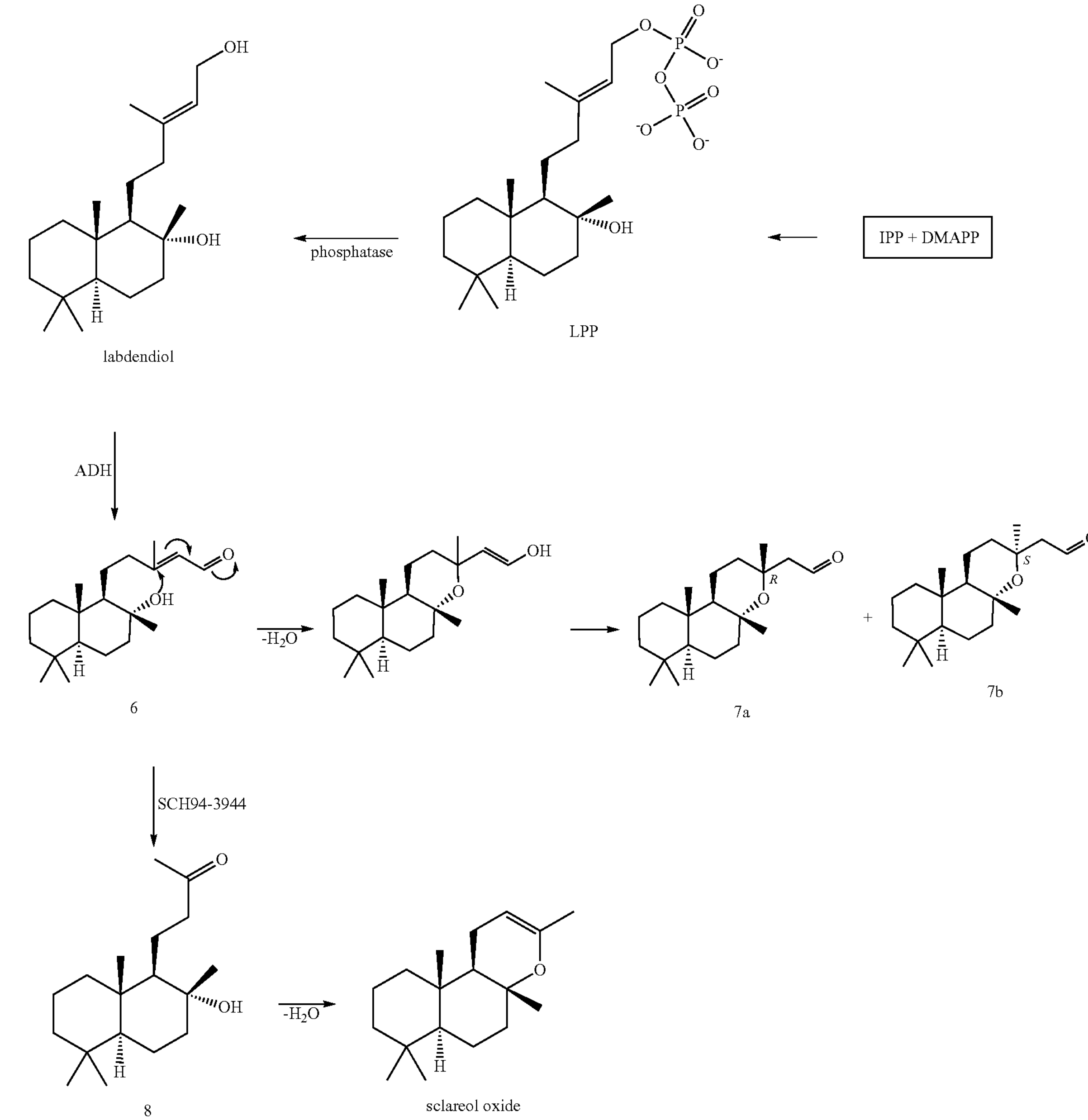

labdendiol

LPP

6

7a

7b

8 sclareol oxide

Example 20. In Vivo Gamma-Ambrol Production in *Saccharomyces cerevisiae* Cells Using Sch23-ADH1 from *Hyphozyma roseonigra*, AspWeDUF4334 from *Aspergillus wentii*, Sch23-BVMO1 from *Hyphozyma roseonigra* and Different Esterases For the production of gamma-ambrol, the genes encoding for the bifunctional enzyme PvCPS (from *Talaromyces verruculosus*), the copalyl-pyrophosphate phosphatase TalVeTPP (from *Talaromyces veruculosum*), the alcohol dehydrogenase SCH23-ADH1 (from *Hyphozyma roseonigra*), the enal-cleaving AspWeDUF4334 (from *Aspergillus wentii*), the BVMO SCH23-BVMO1 (from *Hyphozyma roseonigra*) and one of the tested esterases (EST) were expressed in the engineered *Saccharomyces cerevisiae* strain YST075 as described in general methods.

Two esterases were evaluated:

SCH23-EST1 (from *Hyphozyma roseonigra*).

SCH24-EST1 (from *Cryptococcus albidus*).

All genes were codon optimized for their expression in *S. cerevisiae* (SCH23-EST, SEQ ID NO: 22; SCH24-EST, SEQ ID NO: 26).

Figure 33:
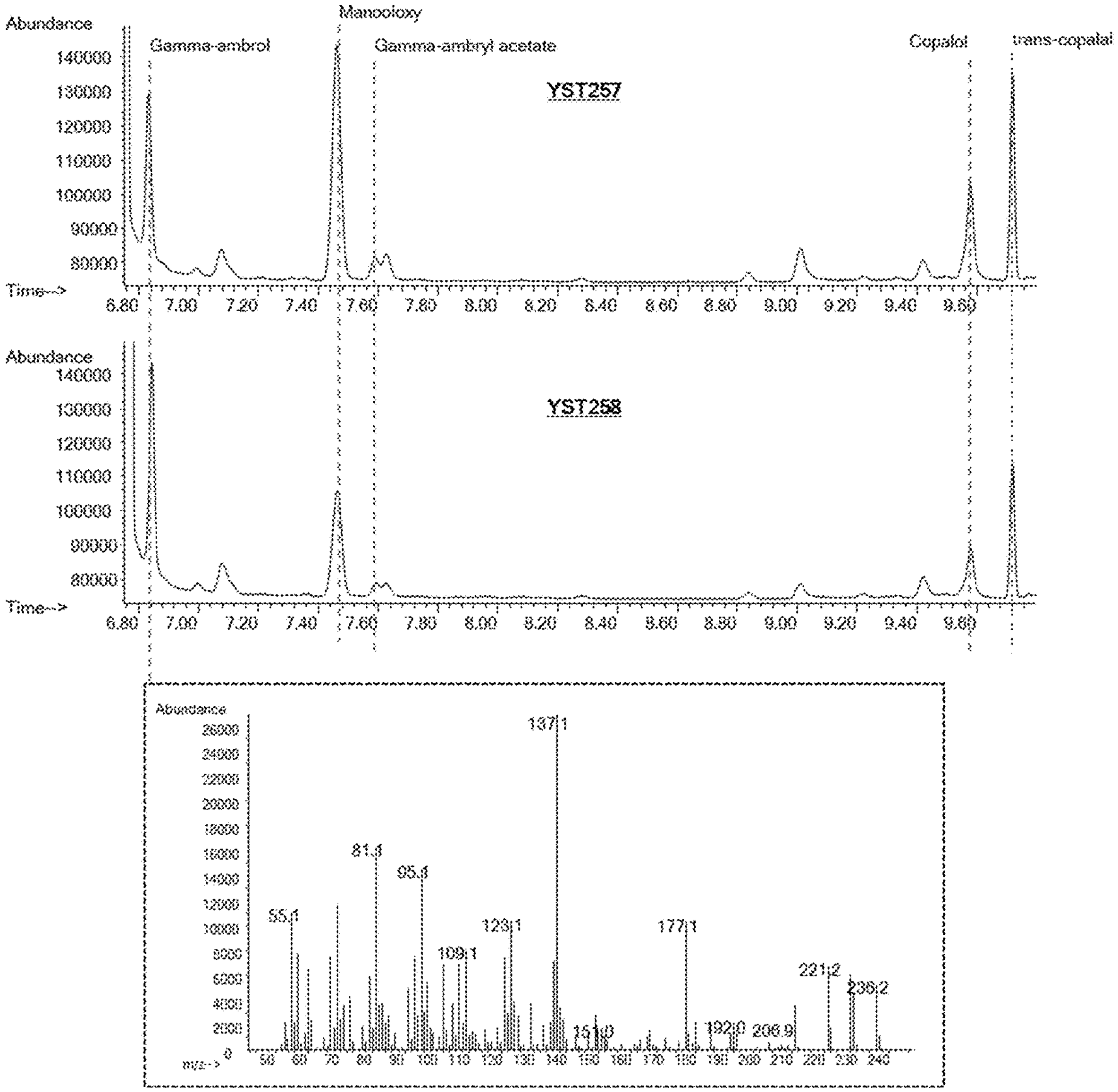
FIG. 33. GC-MS/FID analysis of terpenes and derivatives produced using the modified *S. cerevisiae* strains expressing the bifunctional PvCPS, the CPP phosphatase TalVeTPP, the alcohol dehydrogenase SCH23-ADH, the enal-cleaving polypeptide AspWeDUF4334, the Baeyer-Villiger monooxygenase SCH23-BVMO1 and either the esterase SCH23-EST (YST257) or the esterase SCH24-EST (YST258).

The obtained strains were termed YST257 (with SCH23-EST) and YST258 (with SCH24-EST). These strains were cultivated as described in general methods. Under the tested conditions, nerolidol, copalol, copalal, manooloxy, gamma-ambryl acetate and gamma-ambrol were identified in all cultures using GC-MS/FID analysis (FIG. 33). In the cultures of YST257 and YST258, gamma-ambrol represented 16% and 29%, respectively, of the sum of identified terpenes.

Example 21: In-Vivo Production of γ-Ambrol by Combining the Enal-Cleaving Activity, the BVMO Activity and the Esterase Activity in *E. coli* Cells A first vector was designed containing two operons each under the control of a T5 promoter. The first operon contains two cDNAs encoding for:

The AspWeTPP phosphatase from *Aspergillus wentii* (SEQ ID NO: 170) (GenBank accession OJJ34585.1); and PvCPS, a copalyl-diphosphate synthase from *Talaromyces verruculosus* (SED ID NO: 173) (GenBank accession BBF88128.1). PvCPS catalyzes the production of copalyl PP from IPP and DMAPP.

The cDNAs encoding for AspWeTPP and PvCPS were codon optimized (SEQ ID NOs: 171 and 174) and the operon was designed containing the two cDNAs and an RBS sequence (AAGGAGGTAAAAAA) (SEQ ID NO: 196) placed upstream of each the cDNAs.

The second operon contains two cDNAs encoding for:

SCH94-3944, an enal-cleaving polypeptide from *Rhodococcus* (SEQ ID NO: 34),

SCH94-3945, an alcohol dehydrogenase from *Rhodococcus* (SEQ ID NO: 161).

The cDNAs encoding for SCH94-3945 and SCH94-3944 were codon optimized (SEQ ID NOs: 162 and 35) and the operon was designed containing the two cDNAs and an RBS sequence (AAGGAGGTAAAAAA) (SEQ ID NO: 196) placed upstream of each the cDNAs.

The two operons were assembled in a single vector, providing pJ401-Mnoxy allowing to express all gene of the biosynthetic pathway from FPP to manooloxy.

Bacteria cells (DP1205) were co-transformed with the plasmid pJ401-Manoxy and with a second plasmid:

pJ423-SCH24-BVMO carrying a gene encoding for a BVMO, SCH24-BVMO (SEQ ID NO: 7) alone, pJ423-SCH24-BVMO-SCH24-EST, containing an operon composed of cDNA encoding for a BVMO, SCH24-BVMO1 (SEQ ID NO: 7), and a cDNA encoding for an esterase, SCH24-EST (SEQ ID NO: 25), or a control plasmid pJ423.

The transformed cells were cultivated and the production terpenes was analysed as described above under the conditions described in the experimental section.

When cells were transformed with the vector pJ401-Mnoxy and with an empty pJ423 vector, formation of only manooloxy was observed. (FIG. 34-A).

Figure 34:
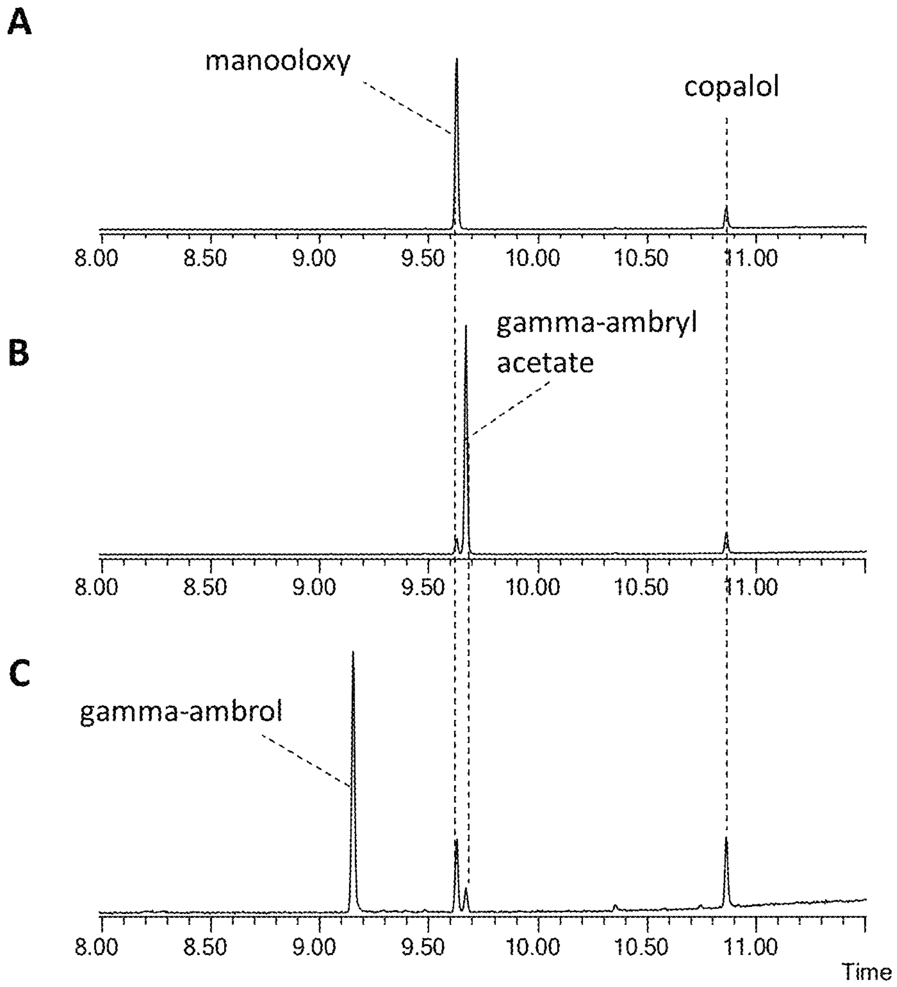
FIG. 34. GC-MS analysis of the biochemical production of gamma-ambrol by *E. coli* cells expressing a CPP synthase, a phosphatase, an alcohol dehydrogenase, an enal-cleaving enzyme, a BVMO and an esterase. A. GC-MS analysis of the compounds produced by *E coli* DP1205 cells transformed with the pJ401-Mnoxy plasmid allowing the expression of the enzymes of a manooloxy biosynthetic pathway. B. GC-MS analysis of the compounds produced by the same *E. coli* cells further expressing the a BVMO (SCH24-BVMO). C. GC-MS analysis of the compounds produced by the same *E. coli* cells further expressing the a BVMO (SCH24-BVMO) and an esterase (SCH24-EST).

When cells were transformed with the vector pJ401-Mnoxy and with pJ423-SCH24-BVMO, formation of γ-ambryl acetate was observed (FIG. 34-B).

When cells were transformed with the vector pJ401-Mnoxy and with pJ423-SCH24-BVMO-SCH24-EST, formation of γ-ambrol was observed (FIG. 34-B).

This experiment shows that the following pathway can be introduced in a host cell to produce gamma-ambrol.

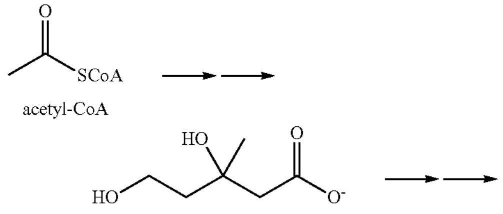
acetyl-CoA mevalonate

-continued

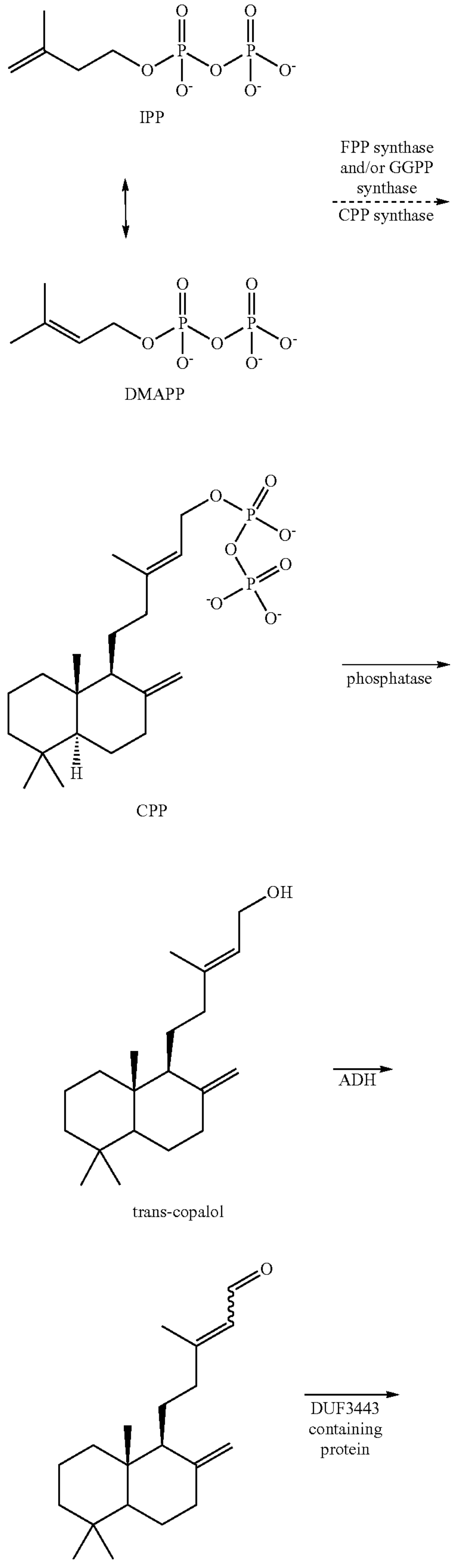

IPP

DMAPP

CPP trans-copalol cis-/trans-copalal

-continued

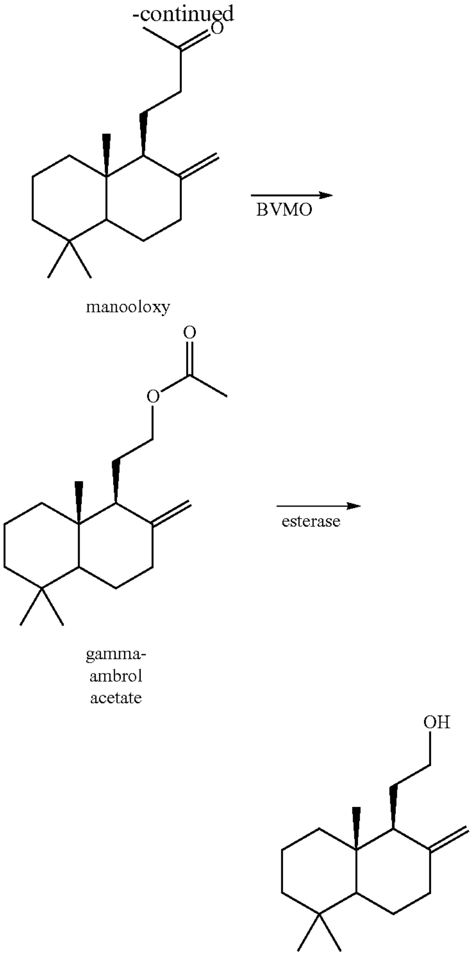

manooloxy gamma-ambrol acetate gamma-ambrol

The content of any document cross-referenced herein is incorporated by reference.

TABLE

Overview of Sequences

| SEQ ID | Description | Source | Type |
|---|---|---|---|
| | BVMOs | | |
| 1 | SCH23-BVMO1_wt | *Hyphozyma roseonigra* | NA |
| 2 | SCH23-BVMO1_wt | *Hyphozyma roseonigra* | AA |
| 3 | SCH23-BVMO1_ *E. coli* optimized | *Hyphozyma roseonigra* | NA |
| 4 | SCH23-BVMO1_ Yeast optimized | *Hyphozyma roseonigra* | NA |
| 5 | SCH24-BVMO1_wt | *Filobasidium magnum* | NA |
| 6 | SCH24-BVMO1_wt | *Filobasidium magnum* | AA |
| 7 | SCH24-BVMO1_ *E. coli* optimized | *Filobasidium magnum* | NA |
| 8 | SCH24-BVMO1_ Yeast optimized | *Filobasidium magnum* | NA |
| 9 | SCH25-BVMO1_wt | *Papiliotrema laurentii* | NA |
| 10 | SCH25-BVMO1_wt | *Papiliotrema laurentii* | AA |
| 11 | SCH25-BVMO1_ *E. coli* optimized | *Papiliotrema laurentii* | NA |
| 12 | SCH46-BVMO1_wt | *Bensingtonia ciliata* | NA |
| 13 | SCH46-BVMO1_wt | *Bensingtonia ciliata* | AA |
| 14 | SCH46-BVMO1_ *E. coli* optimized | *Bensingtonia ciliata* | NA |
| 15 | AspWeBVMO_wt | *Aspergillus wentii* | NA |
| 16 | AspWeBVMO_wt (OJJ34587.1) | *Aspergillus wentii* | AA |
| 17 | AspWeBVMO_ *E. coli* optimized | *Aspergillus wentii* | NA |
| 18 | AspWeBVMO_ Yeast optimized | *Aspergillus wentii* | NA |
| | Esterases | | |
| 19 | SCH23-EST_wt | *Hyphozyma roseonigra* | NA |
| 20 | SCH23-EST_wt | *Hyphozyma roseonigra* | AA |
| 21 | SCH23-EST_ *E. coli* optimized | *Hyphozyma roseonigra* | NA |
| 22 | SCH23-EST_ Yeast optimized | *Hyphozyma roseonigra* | NA |
| 23 | SCH24-EST_wt | *Filobasidium magnum* | NA |
| 24 | SCH24-EST_wt | *Filobasidium magnum* | AA |
| 25 | SCH24-EST_ *E. coli* optimized | *Filobasidium magnum* | NA |
| 26 | SCH24-EST_ Yeast optimized | *Filobasidium magnum* | NA |
| 27 | SCH25-EST_wt | *Papiliotrema laurentii* | NA |
| 28 | SCH25-EST_wt | *Papiliotrema laurentii* | AA |
| 29 | SCH25-EST_ *E. coli* optimized | *Papiliotrema laurentii* | NA |
| 30 | SCH46-EST_wt | *Bensingtonia ciliata* | NA |
| 31 | SCH46-EST_wt | *Bensingtonia ciliata* | AA |
| 32 | SCH46-EST_ *E. coli* optimized | *Bensingtonia ciliata* | NA |
| | Enal-cleaving polypeptides | | |
| 33 | SCH94-3944_wt | *Rhodococcus erythropolis* | NA |
| 34 | SCH94-3944_wt | *Rhodococcus erythropolis* | AA |
| 35 | SCH94-3944_ *E. coli* optimized | *Rhodococcus erythropolis* | NA |
| 36 | SCH94-3944_ Yeast optimized | *Rhodococcus erythropolis* | NA |
| 37 | SCH80-05241_wt | *Rhodococcus rhodochrous* | NA |
| 38 | SCH80-05241_wt | *Rhodococcus rhodochrous* | AA |
| 39 | SCH80-05241_ *E. coli* optimized | *Rhodococcus rhodochrous* | NA |
| 40 | SCH80-05241_ Yeast optimized | *Rhodococcus rhodochrous* | NA |
| 41 | Pdigit7033_wt | *Penicillium digitatum* | NA |
| 42 | Pdigit7033_wt | *Penicillium digitatum* | AA |
| 43 | Pdigit7033_ *E. coli* optimized | *Penicillium digitatum* | NA |
| 44 | Pdigit7033_ Yeast optimized | *Penicillium digitatum* | NA |
| 45 | PitalDUF4334-1_wt (JQGA01001114.1 71518-72084 (+)) | *Penicillium italicum* | NA |
| 46 | PitalDUF4334-1_wt (KGO69886.1) | *Penicillium italicum* | AA |
| 47 | PitalDUF4334-1_ *E. coli* optimized | *Penicillium italicum* | NA |
| 48 | AspWe DUF4334_wt (LISE01000065.1 (263404 to 263924)) | *Aspergillus wentii* | NA |
| 49 | AspWe DUF4334_wt (OJJ43591) | *Aspergillus wentii* | AA |
| 50 | AspWe DUF4334_ *E. coli* optimized | *Aspergillus wentii* | NA |
| 51 | AspWe DUF4334_ Yeast optimized | *Aspergillus wentii* | NA |
| 52 | RhoagDUF4334-2_wt (NZ_LWTW01000167.1 18658-19134 (−)) | *Rhodococcus hoagii* strain PAM2288 | NA |
| 53 | RhoagDUF4334-2_wt (WP_005516054) | *Rhodococcus hoagii* strain PAM2288 | AA |
| 54 | RhoagDUF4334-2_ *E. coli* optimized | *Rhodococcus hoagii* strain PAM2288 | NA |
| 55 | RhoagDUF4334-3_wt (NZ_LRQY01000021.1 163210-163686 (−)) | *Rhodococcus hoagii* strain N128 | NA |

TABLE-continued

Overview of Sequences

| SEQ ID | Description | Source | Type |
|---|---|---|---|
| 56 | RhoagDUF4334-3_wt (WP_013414658) | *Rhodococcus hoagii* strain N128 | AA |
| 57 | RhoagDUF4334-3_ *E. coli* optimized | *Rhodococcus hoagii* strain N128 | NA |
| 58 | RhoagDUF4334-4_wt (NZ_BCRL01000037.1 133790-134266 (+)) | *Rhodococcus hoagii* | NA |
| 59 | RhoagDUF4334-4_wt (WP_022593671) | *Rhodococcus hoagii* | AA |
| 60 | RhoagDUF4334-4_ *E. coli* optimized | | NA |
| 61 | CnecaDUF4334_wt (CP002879.1: 512553-513138) | *Cupriavidus necator* | NA |
| 62 | CnecaDUF4334_wt (WP_049800708.1) | *Cupriavidus necator* | AA |
| 63 | CnecaDUF4334_ *E. coli* optimized | *Cupriavidus necator* | NA |
| 64 | CnecaDUF4334_ Yeast optimized | *Cupriavidus necator* | NA |
| 65 | PitalDUF4334-2_wt (JQGA01000120.1 65652-66635 (+)) | *Penicillium italicum* | NA |
| 66 | PitalDUF4334-2_wt (KGO77618.1) | *Penicillium italicum* | AA |
| 67 | PitalDUF4334-2_ *E. coli* optimized | *Penicillium italicum* | NA |
| 68 | Rins-DUF4334_wt (NZ_PKPC01000002.1 18273-18773 (−)) | *Ralstonia insidiosa* | NA |
| 69 | Rins-DUF4334_wt (WP_104654734) | *Ralstonia insidiosa* | AA |
| 70 | Rins-DUF4334_ *E. coli* optimized | *Ralstonia insidiosa* | NA |
| 71 | CgatDUF4334_wt | *Cryptococcus gattii* EJ B2 | NA |
| 72 | CgatDUF4334_wt (KIR80015) | *Cryptococcus gattii* EJ B2 | AA |
| 73 | CgatDUF4334_ *E. coli* optimized | *Cryptococcus gattii* EJ B2 | NA |
| 74 | GclavDUF4334_wt (XM_014316402.1) | *Grosmannia clavigera* kw1407 | NA |
| 75 | GclavDUF4334_wt (XP_ 014171877.1) | *Grosmannia clavigera* kw1407 | AA |
| 76 | GclavDUF4334_ *E. coli* optimized | *Grosmannia clavigera* kw1407 | NA |
| 77 | OmaiusDUF4334_wt (KN832882.1 673187-675938 (−)) | *Oidiodendron maius* Zn | NA |
| 78 | OmaiusDUF4334_wt (KIM97275) | *Oidiodendron maius* Zn | AA |
| 79 | OmaiusDUF4334_ *E. coli* optimized | *Oidiodendron maius* Zn | NA |
| 80 | TcurvaDUF4334_wt (NC_013510.1) | *Thermomonospora curvata* | NA |
| 81 | Tcurva DUF4334_wt (WP_012851400.1) | *Thermomonospora curvata* | AA |
| 82 | TcurvaDUF4334_ *E. coli* optimized | *Thermomonospora curvata* | NA |
| 83 | DlitoDUF4334_wt (NZ_ LT629748.1 3096922-3097413 (+)) | *Pseudomonas litoralis* | NA |
| 84 | DlitoDUF4334_wt (WP_090274689) | *Pseudomonas litoralis* | AA |
| 85 | DlitoDUF4334_ *E. coli* optimized | *Pseudomonas litoralis* | NA |
| 86 | PprotDUF4334_wt (NC_021237.1 5528027-5528524 (−)) | *Pseudomonas protegens* | NA |
| 87 | PprotDUF4334_wt (WP_015636872.1) | *Pseudomonas protegens* | AA |
| 88 | PprotDUF4334_ *E. coli* optimized | *Pseudomonas protegens* | NA |
| 89 | SCH94-3944-W44A_variant | artificial | AA |

TABLE-continued

Overview of Sequences

| SEQ ID | Description | Source | Type |
|---|---|---|---|
| 90 | SCH94-3944-W44A_ *E. coli* optimized | artificial | NA |
| 91 | SCH94-3944-T51A_variant | artificial | AA |
| 92 | SCH94-3944-T51A _ *E. coli* optimized | artificial | NA |
| 93 | SCH94-3944-H53A_variant | artificial | AA |
| 94 | SCH94-3944-H53A_ *E. coli* optimized | artificial | NA |
| 95 | SCH94-3944-L59A_variant | artificial | AA |
| 96 | SCH94-3944-L59A_ *E. coli* optimized | artificial | NA |
| 97 | SCH94-3944-W64A_variant | artificial | AA |
| 98 | SCH94-3944-W64A_ *E. coli* optimized | artificial | NA |
| 99 | SCH94-3944-K67A_variant | artificial | AA |
| 100 | SCH94-3944-K67A_ *E. coli* optimized | artificial | NA |
| 101 | SCH94-3944-S71A_variant | artificial | AA |
| 102 | SCH94-3944-S71A_ *E. coli* optimized | artificial | NA |
| 103 | SCH94-3944-R106A_variant | artificial | AA |
| 104 | SCH94-3944-R106A_ *E. coli* optimized | artificial | NA |
| 105 | SCH94-3944-Y115A_variant | artificial | AA |
| 106 | SCH94-3944-Y115A_ *E. coli* optimized | artificial | NA |
| 107 | SCH94-3944-D116A_variant | artificial | AA |
| 108 | SCH94-3944-D116A_ *E. coli* optimized | artificial | NA |
| 109 | SCH94-3944-D122A_variant | artificial | AA |
| 110 | SCH94-3944-D122A_ *E. coli* optimized | artificial | NA |
| 111 | SCH94-3944-M136A_variant | artificial | AA |
| 112 | SCH94-3944-M136A_ *E. coli* optimized | artificial | NA |
| 113 | SCH94-3944-K139A_variant | artificial | AA |
| 114 | SCH94-3944-K139A *E. coli* optimized | artificial | NA |
| 115 | SCH94-3944-F152A_variant | artificial | AA |
| 116 | SCH94-3944-F152A_ *E. coli* optimized | artificial | NA |
| 117 | SCH94-3944-L154A_variant | artificial | AA |
| 118 | SCH94-3944-L154A_ *E. coli* optimized | artificial | NA |
| 119 | SCH94-3944-R156A_variant | artificial | AA |
| 120 | SCH94-3944-R156A_ *E. coli* optimized | artificial | NA |
| | Cassettes and primers | | |
| 121 | Integration cassette fragment 1 | artificial | NA |
| 122 | Integration cassette fragment 2 | artificial | NA |
| 123 | Integration cassette fragment 3 | artificial | NA |
| 124 | LEU2 yeast marker_primer 1 | artificial | NA |
| 125 | LEU2 yeast marker_primer 2 | artificial | NA |
| 126 | AmpR *E. coli* marker_primer 1 | artificial | NA |
| 127 | AmpR *E. coli* marker_primer 2 | artificial | NA |
| 128 | Yeast origin of replication_ primer 1 | artificial | NA |
| 129 | Yeast origin of replication_ primer 2 | artificial | NA |
| 130 | *E. coli* replication origin_ primer 1 | artificial | NA |
| 131 | *E. coli* replication origin_ primer 2 | artificial | NA |
| 132 | DNA fragment for *S. cerevisiae* co-transformation | artificial | NA |
| | ADHs | | |
| 133 | SCH23-ADH1_wt | *Hyphozyma roseonigra* | NA |
| 134 | SCH23-ADH1_wt | *Hyphozyma roseonigra* | AA |
| 135 | SCH23-ADH1_ Yeast optimized | *Hyphozyma roseonigra* | NA |
| 136 | SCH23-ADH2_wt | *Hyphozyma roseonigra* | NA |
| 137 | SCH23-ADH2_wt | *Hyphozyma roseonigra* | AA |
| 138 | SCH23-ADH2_ Yeast optimized | *Hyphozyma roseonigra* | NA |
| 139 | SCH24-ADH1_wt | *Filobasidium magnum* | NA |

TABLE-continued

| SEQ ID | Description | Source | Type |
|---|---|---|---|
| Overview of Sequences | | | |
| 140 | SCH24-ADH1_wt | *Filobasidium magnum* | AA |
| 141 | SCH24-ADH1_ Yeast optimized | *Filobasidium magnum* | NA |
| 142 | SCH24-ADH2_wt | *Filobasidium magnum* | NA |
| 143 | SCH24-ADH2_wt | *Filobasidium magnum* | AA |
| 144 | SCH24-ADH2_ Yeast optimized | *Filobasidium magnum* | NA |
| 145 | RrhSecADH_wt | *Rhodococcus* sp. | NA |
| 146 | RrhSecADH_wt (WP_ 043801412.1) | *Rhodococcus* sp. | AA |
| 147 | RrhSecADH_*E.coli* optimized | *Rhodococcus* sp. | NA |
| 148 | SCH80-00043_wt | *Rhodococcus rhodochrous* | NA |
| 149 | SCH80-00043_wt | *Rhodococcus rhodochrous* | AA |
| 150 | SCH80-00043_ *E. coli* optimized | *Rhodococcus rhodochrous* | NA |
| 151 | SCH80-04254_wt | *Rhodococcus rhodochrous* | NA |
| 152 | SCH80-04254_wt | *Rhodococcus rhodochrous* | AA |
| 153 | SCH80-04254_ *E. coli* optimized | *Rhodococcus rhodochrous* | NA |
| 154 | SCH80-06135_wt | *Rhodococcus rhodochrous* | NA |
| 155 | SCH80-06135_wt | *Rhodococcus rhodochrous* | AA |
| 156 | SCH80-06135_ *E. coli* optimized | *Rhodococcus rhodochrous* | NA |
| 157 | SCH80-06582_wt | *Rhodococcus rhodochrous* | NA |
| 158 | SCH80-06582_wt | *Rhodococcus rhodochrous* | AA |
| 159 | SCH80-06582_ *E. coli* optimized | *Rhodococcus rhodochrous* | NA |
| 160 | SCH94-03945_wt | *Rhodococcus erythropolis* | NA |
| 161 | SCH94-03945_wt | *Rhodococcus erythropolis* | AA |
| 162 | SCH94-03945_ *E. coli* optimized | *Rhodococcus erythropolis* | NA |
| 163 | SCH80-05240_wt | *Rhodococcus rhodochrous* | NA |
| 164 | SCH80-05240_wt | *Rhodococcus rhodochrous* | AA |
| 165 | SCH80-05240_ *E. coli* optimized | *Rhodococcus rhodochrous* | NA |
| 166 | AzeTolADH1_wt (NZ_ KB899498.1 215502-216629 (+)) | *Azoarcus toluclasticus* | NA |
| 167 | AzTolADH1_wt (WP_ 018990713.1) | *Azoarcus toluclasticus* | AA |
| 168 | AzTolADH1_*E. coli* optimized | *Azoarcus toluclasticus* | NA |
| Other sequences | | | |
| 169 | AspWeTPP_wt (OJJ34585.1) | *Aspergillus wentii* | NA |
| 170 | AspWeTPP_wt (KV878213.1:2482776-2483627) | *Aspergillus wentii* | AA |
| 171 | AspWeTPP_*E. coli* optimized | *Aspergillus wentii* | NA |
| 172 | PvCPS_wt (LC316181.1) | *Talaromyces verruculosus* | NA |
| 173 | PvCPS_wt (BBF88128.1) | *Talaromyces verruculosus* | AA |
| 174 | PvCPS_*E. coli* optimized | *Talaromyces verruculosus* | NA |
| 175 | TalCeTPP_wt (BBPS01001258.1 (16027-16959)) | *Talaromyces cellulolyticus* | NA |
| 176 | TalCeTPP_wt (GAM42000.1) | *Talaromyces cellulolyticus* | AA |
| 177 | TalCeTPP_*E. coli* optimized | *Talaromyces cellulolyticus* | NA |
| 178 | CdGeoA_wt | *Castellaniella defragrans* | NA |
| 179 | CdGeoA_wt (WP_043683915.1) | *Castellaniella defragrans* | AA |
| 180 | CdGeoA_*E. coli* optimized | *Castellaniella defragrans* | NA |
| 181 | GGPP synthase carG_wt (AFC92798.1) | *Blakeslea trispora* | NA |
| 182 | GGPP synthase carG_ wt (JQ289995.1) | *Blakeslea trispora* | AA |
| 183 | GGPP synthase carG_ Yeast optimized | *Blakeslea trispora* | NA |
| 184 | SmCPS2_wt (EU003997.1 73-2454 (+)) | *Salvia miltiorrhiza* | NA |
| 185 | SmCPS2_Yeast optimized | *Salvia miltiorrhiza* | AA |
| 186 | SmCPS2_Yeast optimized | *Salvia miltiorrhiza* | NA |
| 187 | SsLPS_wt (JN133923.1) | *Salvia sciarea* | NA |
| 188 | SsLPS_wt (AET21247.1) | *Salvia sciarea* | AA |
| 189 | SsLPS_*E. coli* optimized | *Salvia sciarea* | NA |
| 190 | CrtE_wt (M38424.1 40-963 (+)) | *Pantoea agglomerans* | NA |
| 191 | CrtE_wt (AAA24819.1) | *Pantoea agglomerans* | AA |
| 192 | CrtE_ Yeast optimized | *Pantoea agglomerans* | NA |
| 193 | TalVeTPP_wt (LHCL01000010.1 150095-151030 (+)) | *Talaromyces verruculosus* | NA |
| 194 | TalVeTPP_wt (KUL89334.1) | *Talaromyces verruculosus* | AA |
| 195 | TalVeTPP_Yeast optimized | *Talaromyces verruculosus* | NA |
| 196 | RBS sequence | artificial | AA |
| 197 | BVMO sequence motif 1 | artificial | AA |
| 198 | BVMO sequence motif 2 | artificial | AA |
| 199 | BVMO sequence motif 3 | artificial | AA |
| 200 | BVMO sequence motif 4 | artificial | AA |
| 201 | BVMO sequence motif 5 | artificial | AA |
| 202 | BVMO sequence motif 6 | artificial | AA |
| 203 | BVMO sequence motif 7 | artificial | AA |
| 204 | BVMO sequence motif 8 | artificial | AA |
| 205 | Enal-cleaving polypeptide sequence motif 1 | artificial | AA |
| 206 | Enal-cleaving polypeptide sequence motif 2 | artificial | AA |
| 207 | Enal-cleaving polypeptide sequence motif 3 | artificial | AA |
| 208 | Enal-cleaving polypeptide sequence motif 4 | artificial | AA |

SEQ ID NO 1: *Hyphozyma roseonigra* SCH23-BVMO1 wt

ATGCCTTCCGCAATCACCCCGCCGGTTGATCATCGCAGTCTTCCAGGTCTTTTCAAGCCACAGAGG

AAGCTCAAAGTGATATGTGTCGGAGCCGGCGCCTCGGGCTTACTTCTTTCCTACAAGATACAACGA

CACTTCGAGGATTTCGAGCTCCAAGTCTTTGAGAAGAATCCCGAGGTATCAGGAACCTGGTACGA

GAACAGGTATCCCGGCTGCGCTTGTGATGTTCCCTCGCATAATTATACATGGTCTTTTGAGCCCAA

AACCGACTGGTCCGCCAACTATGCATCATCGAAGGAGATTTTCAAATATTTCAAGGACTTCACGAG

GAAATATGGTCTAAGCAAGTACATCAAGCTGGAACATGAGGTCGTGGGAGCCACGTGGATGGAGG

CGGAGGCACAGTGGAAAGTTGACGTCAAGGACCTTCGAAGTGGAAACACGCAGAGCTCGTTTGCG

CATATACTGGTCAATGCAGGAGGCATTTTGAATGCTTGGCGATACCCGCCAATTCCAGGAATCAAG

GATTTCAAGGGTGATCTTGTTCACTCCGCAGCTTGGCCAGAACATCTTGATCTTAATGGGAAGGTT

GTCGGTCTCATCGGAAATGGATCCTCCGGCATTCAGATCCTTCCGGCCATCAAGAAGGATGTAAAG

CAACTCGTTACATTCATTCGGGAAGCAACTTGGGTGGCGCCTCCTTTAGGTCAAGCCTATCGTGCG

TTCTCGACTGATGAACAGGCTCAGTTTGCGCAAGATCCGCGCCATCACCTGGAGACACGGCGTGCA

-continued

ACTGAGGCTACCATGAATCAATCATTTGGTATCTTCCATTCGGGATCCGAGGAGCAGAAAGGGGTT

CGCCAATATATGCAGAATATCATGGAAACGAAGCTCAACAACAAACAGCTCGAGAGTGTGCTGAT

TCCTGAGTGGTCGGTCGGTTGTCGGCGTCTTACACCAGGTACTAATTATCTAGAATCCCTGTCAGA

CGACAATGTCAAGGTCGTCTATGGTGAGATCACACAAATTACCGAATCGGGTGTCATCTGCGATGA

TGGTAAAGGCGAATATCCCGTTGAAGTTCTTATTTGCGCCACCGGCTTCGACACCACCTTCAAACC

ACGATTCCCACTCATCGGTACAACCCAAGAGAAACTCAGTGATGTTTGGAAAGATGATCCGAGGG

GCTACTTTGGGATCGCAACCAACAACTATCCCAACTACTTCTTCACTCTTGGACCAAATTGTCCAAT

CGGTAATGGCCCCGTGCTGTGTGCCATTGAAGCTGAGGTTGAATATATAATCAACATGCTCTCGAA

GTTTCAGAAGGAGAACATTCGTTCTTTTGATATCAAGGCAGATGCTGTCGACGCCTTCAACGACTG

GAAGGATGACTTCATGAAAGATACCATCTGGGCAGAACAATGCCGGTCATGGTACAAGGCAGGAT

CCGCCACCGGTAAAATCCTTGCATTGTGGCCAGGCTCGACTTTGCACTACTTGGAAGCACTCAAGT

CGCCGCGGTGGGAGGACTGGGACTTCAAGTATCAGCCTGGTAGAAATCGTTTCCACTACTTTGGAA

ATGGTCATAGCTGTGCTGAGCAGGATGGCGATCTGAGCTGGTACATTCGCAACGAGGATGATTCTT

ATATTGATCCGGTACTCAAGCCGAAGCCGAAGGCAGCAGTTGAAAGCGAGGCACATATCGCCCTG

CCAGGAATCGGTCCGATGTTGATGGAAGACCCGCGTGATGTTGCTGTAGAGGCCTAG

SEQ ID NO 2: *Hyphozyma roseonigra* SCH23-BVMO1 wt
MPSAITPPVDHRSLPGLFKPQRKLKVICVGAGASGLLLSYKIQRHFEDFELQVFEKNPEVSGTWYENRY

PGCACDVPSHNYTWSFEPKTDWSANYASSKEIFKYFKDFTRKYGLSKYIKLEHEWGATWMEAEAQW

KVDVKDLRSGNTQSSFAHILVNAGGILNAWRYPPIPGIKDFKGDLVHSAAWPEHLDLNGKVVGLIGNG

SSGIQILPAIKKDVKQLVTFIREATWVAPPLGQAYRAFSTDEQAQFAQDPRHHLETRRATEATMNQSFG

IFHSGSEEQKGVRQYMQNIMETKLNNKQLESVLIPEWSVGCRRLTPGTNYLESLSDDNVKVVYGEITQI

TESGVICDDGKGEYPVEVLICATGFDTTFKPRFPLIGTTQEKLSDVWKDDPRGYFGIATNNYPNYFFTLG

PNCPIGNGPVLCAIEAEVEYIINMLSKFQKENIRSFDIKADAVDAFNDWKDDFMKDTIWAEQCRSWYK

AGSATGKILALWPGSTLHYLEALKSPRWEDWDFKYQPGRNRFHYFGNGHSCAEQDGDLSWYIRNEDD

SYIDPVLKPKPKAAVESEAHIALPGIGPMLMEDPRDVAVEA

SEQ ID NO 3: *Hyphozyma roseonigra* SCH23-BVMO1 *E. coli* optimized
ATGCCGTCTGCCATTACTCCACCTGTTGATCACCGTTCCCTGCCGGGCCTGTTTAAACCGCAGCGCA

AGCTGAAAGTGATTTGCGTGGGCGCGGGTGCGAGCGGCCTGCTGTTGAGCTACAAGATTCAGCGC

CACTTCGAAGATTTCGAGCTGCAAGTGTTTGAGAAGAACCCTGAAGTTAGCGGTACGTGGTACGA

GAACCGTTATCCGGGTTGTGCGTGCGATGTGCCGAGCCATAACTACACCTGGAGCTTTGAGCCGAA

AACGGATTGGTCCGCCAATTATGCGAGCAGCAAAGAGATTTTCAAATATTTCAAAGATTTTACGCG

TAAATATGGTCTGTCTAAATACATTAAATTGGAACATGAAGTGGTCGGCGCGACCTGGATGGAAG

CCGAGGCGCAGTGGAAAGTTGACGTTAAAGATCTGCGCAGCGGTAACACCCAGTCCAGCTTCGCG

CATATCCTGGTTAACGCCGGCGGCATTCTGAATGCCTGGCGTTATCCGCCGATTCCGGGCATCAAA

GATTTCAAGGGTGACCTGGTGCATAGCGCAGCATGGCCGGAGCATTTGGACCTGAATGGCAAAGT

CGTTGGTCTGATCGGCAACGGTAGCAGCGGTATCCAAATCCTGCCGGCAATTAAGAAAGACGTGA

AGCAACTGGTGACGTTTATCCGTGAAGCCACCTGGGTCGCACCGCCGCTGGGTCAAGCGTACCGTG

CGTTTTCCACCGACGAGCAAGCACAGTTTGCGCAGGACCCGCGCCACCACCTGGAAACCCGTCGT

GCGACCGAAGCCACCATGAATCAGAGCTTTGGTATTTTCCATAGCGGCAGCGAAGAACAGAAAGG

TGTCCGCCAGTACATGCAAAACATTATGGAAACCAAGCTGAATAATAAGCAACTGGAGAGCGTCC

TGATTCCGGAGTGGAGCGTCGGCTGTCGTCGTCTGACCCCGGGCACGAACTACCTGGAAAGCCTG

-continued

AGCGACGACAATGTCAAAGTTGTGTACGGTGAGATTACCCAAATCACCGAGAGCGGTGTCATCTG

CGATGACGGCAAGGGTGAGTATCCGGTTGAAGTCCTGATCTGCGCCACCGGTTTTGATACGACCTT

TAAACCGCGCTTCCCGCTGATCGGTACGACCCAGGAAAAGCTGAGCGACGTGTGGAAAGATGATC

CGCGCGGTTACTTCGGCATCGCGACGAATAATTATCCGAACTATTTCTTCACGCTGGGTCCGAACT

GCCCGATCGGTAATGGCCCGGTCCTGTGTGCGATCGAAGCCGAAGTTGAGTACATCATCAACATGC

TGAGCAAGTTTCAGAAAGAAAATATTCGCTCCTTCGACATTAAAGCCGACGCGGTGGACGCGTTTA

ATGATTGGAAAGACGATTTCATGAAAGATACCATCTGGGCAGAACAGTGCCGTAGCTGGTACAAG

GCCGGCAGCGCGACCGGCAAGATTCTGGCACTGTGGCCGGGCAGCACGCTGCACTACCTGGAAGC

GCTGAAAAGCCCGCGTTGGGAAGATTGGGACTTCAAGTATCAACCGGGCCGTAACCGTTTCCACT

ACTTTGGCAACGGTCACAGCTGTGCCGAGCAAGATGGCGACCTGTCCTGGTACATCCGTAATGAA

GATGACAGCTACATTGACCCGGTTCTGAAACCGAAGCCGAAAGCCGCGGTGGAGAGCGAGGCACA

CATCGCACTGCCGGGTATTGGCCCGATGCTGATGGAAGATCCGCGTGATGTCGCGGTTGAGGCGTA

A

SEQ ID NO 4: *Hyphozyma roseonigra* SCH23-BVMO1 Yeast optimized

ATGCCATCTGCTATCACTCCACCAGTTGACCACAGATCTTTGCCAGGTTTGTTCAAGCCACAAAGA

AAGTTGAAGGTTATCTGTGTTGGTGCTGGTGCTTCTGGTTTGTTGTTGTCTTACAAGATCCAAAGAC

ACTTCGAAGACTTCGAATTGCAAGTTTTCGAAAAGAACCCAGAAGTTTCTGGTACTTGGTACGAAA

ACAGATACCCAGGTTGTGCTTGTGACGTTCCATCTCACAACTACACTTGGTCTTTCGAACCAAAGA

CTGACTGGTCTGCTAACTACGCTTCTTCTAAGGAAATCTTCAAGTACTTCAAGGACTTCACTAGAA

AGTACGGTTTGTCTAAGTACATCAAGTTGGAACACGAAGTTGTTGGTGCTACTTGGATGGAAGCTG

AAGCTCAATGGAAGGTTGACGTTAAGGACTTGAGATCTGGTAACACTCAATCTTCTTTCGCTCACA

TCTTGGTTAACGCTGGTGGTATCTTGAACGCTTGGAGATACCCACCAATCCCAGGTATCAAGGACT

TCAAGGGTGACTTGGTTCACTCTGCTGCTTGGCCAGAACACTTGGACTTGAACGGTAAGGTTGTTG

GTTTGATCGGTAACGGTTCTTCTGGTATCCAAATCTTGCCAGCTATCAAGAAGGACGTTAAGCAAT

TGGTTACTTTCATCAGAGAAGCTACTTGGGTTGCTCCACCATTGGGTCAAGCTTACAGAGCTTTCTC

TACTGACGAACAAGCTCAATTCGCTCAAGACCCAAGACACCACTTGGAAACTAGAAGAGCTACTG

AAGCTACTATGAACCAATCTTTCGGTATCTTCCACTCTGGTTCTGAAGAACAAAAGGGTGTTAGAC

AATACATGCAAAACATCATGGAAACTAAGTTGAACAACAAGCAATTGGAATCTGTTTTGATCCCA

GAATGGTCTGTTGGTTGTAGAAGATTGACTCCAGGTACTAACTACTTGGAATCTTTGTCTGACGAC

AACGTTAAGGTTGTTTACGGTGAAATCACTCAAATCACTGAATCTGGTGTTATCTGTGACGACGGT

AAGGGTGAATACCCAGTTGAAGTTTTGATCTGTGCTACTGGTTTCGACACTACTTTCAAGCCAAGA

TTCCCATTGATCGGTACTACTCAAGAAAAGTTGTCTGACGTTTGGAAGGACGACCCAAGAGGTTAC

TTCGGTATCGCTACTAACAACTACCCAAACTACTTCTTCACTTTGGGTCCAAACTGTCCAATCGGTA

ACGGTCCAGTTTTGTGTGCTATCGAAGCTGAAGTTGAATACATCATCAACATGTTGTCTAAGTTCC

AAAAGGAAAACATCAGATCTTTCGACATCAAGGCTGACGCTGTTGACGCTTTCAACGACTGGAAG

GACGACTTCATGAAGGACACTATCTGGGCTGAACAATGTAGATCTTGGTACAAGGCTGGTTCTGCT

ACTGGTAAGATCTTGGCTTTGTGGCCAGGTTCTACTTTGCACTACTTGGAAGCTTTGAAGTCTCCAA

GATGGGAAGACTGGGACTTCAAGTACCAACCAGGTAGAAACAGATTCCACTACTTCGGTAACGGT

CACTCTTGTGCTGAACAAGACGGTGACTTGTCTTGGTACATCAGAAACGAAGACGACTCTTACATC

GACCCAGTTTTGAAGCCAAAGCCAAAGGCTGCTGTTGAATCTGAAGCTCACATCGCTTTGCCAGGT

ATCGGTCCAATGTTGATGGAAGACCCAAGAGACGTTGCTGTTGAAGCTTAA

-continued

SEQ ID NO 5: *Filobasidium magnum* SCH24-BVMO1 wt

ATGACTATCGATTTGCAGCAGCCCGACGCCGTGCCATTCACCTCTTCGACTTTTGTCGTGCCGGATC

CATCGAACCTGGCCTCTCAGGCACAGAATTCACAGCTCCAATCTGCTCAAGAAGGAGCAGAGTAC

CCTGTGAACGCACATGGGGTTCGAGGAGATGGAACGATTCATGAACGACCGATCAACGATCGCAG

GAAGATGCGCGTCATCTGCGTCGGTGCAGGCATCTCAGGTCTCTATATGGCCATCAAGCTCCCTCG

AAGTACGGAAAATGTAGAGCTCAAGATCTACGAGAAGAATCACGATCTCGGTGGGACCTGGCTGG

AGAATAGGTATCCAGGATGCGCTTGTGATGTACCAGCCCATGCCTACGCATACAGCTTCGAGAAC

AACCCCGAATTTCCTAGATTCTTTTCGAGCTCGGAAGACATCCACAAGTACTTGCTTCGCGTGGCT

GATAAATATGATTGCAAGAAATACATCGCATTCAACACCAAAGTAGTCGAGGCCATTTGGGACGA

AGAACAGGGCATCTATAACGTCAAGATTGAACGCTCGGATGGCACAGTATTCCAGGACACGTGCG

AAGTTCTATTGAACGCTTCTGGTATCCTTAACGCCTGGAGGTACCCTGGGATTCCTGGAATTAAGG

ACTACAAGGGCACGTTAATGCACTCGGCTACCTGGGACCGATCCGTGTCCCTGAAAGGCAAAAAG

GTTGCCCTCATCGGATCAGGATCATCAGGCATTCAGATCTTGCCCAACATCCTTGACGATTGCAAA

GAGGTCGTGACATACATCATTGATCCAGCCTGGATTGCCCCTGCGAATCTTGTCACGGCTGGAGTC

TCGGACGACGGTGAAGAGCCTAAGGAGCCGACGCCTGAAGAATTGGCGTCGAGTAGTGACTTCGC

CTACTCGCAAGAGCAAATCAATGGCTTCAAGAAGGACCCTAAGTCACTGATGGATCATCGAGCAA

CGCTCGAAAGGACGATGAATCAGTCTTTCCCCATCTTACTCAGAGGCTCACCGTCCAACCTTTATG

CCGCTTCTCTCTTTGAAGACCTGATGAGGAAACGCCTTGCCAAGAAGCCTGAGGTAGCGGATGCCA

TCATCCCCGAATGGTCAATCGGTTGCCGACGTCTCACTCCTGGACCACACTATCTTGAGGCCTTGT

GCAATCCCAAGGTCAAGATCTTGACCCAAGCTATCAAGTCCTTCTCCGATAAGGGAATGTACACTG

CCGATGGCGAACACGAAGACTTTGACGTGGTGATATGCGCGACTGGATTCGACGTATCGTTCCGAC

CCCGATTCAAATTTATCGGCAAGGACGGGTATGAGGTGCCCGAGAACTTTGGTCAGACTCCCAAA

GGTTACCTCGCTCTCGCTTACGCCGGTTTCCCTAATTCGTTCATCTTCATGGGGCCGAACGGACCTA

TCGCCAACGGATCTGTCGTGGTCTCCCTGGAGAAACAAGGCGACTACTTCATCAAGGCGATCAAC

AAGATCCAAAGGCAGAATATAAAAGGCATGACTGTCAGATTCGATGCGGTCGATGATTTCACCAA

CCACGTAGACAAATACATGGATAGGACCGTGCTCACCGATGACTGCATCAGCTGGTACAAGAACG

GGAAACGAGACGGACGAGTCAGTGCCGTCTGGCCTGGGAGCGCACTTCATTATATGGAGGCCATC

GCCGACCCTAGATGGGAGGATTACACCTACACTTATCGCGAACCCGGTCATTCTTTTTCGTTCTTGG

GAGATGGGACGTCCTGGGTCGAACACACCGGAGGAGACACGGCTTGGTACCTGAAAGAGACCCTC

TAA

SEQ ID NO 6: *Filobasidium magnum* SCH24-BVMO1 wt

MTIDLQQPDAVPFTSSTFVVPDPSNLASQAQNSQLQSAQEGAEYPVNAHGVRGDGTIHERPINDRRKM

RVICVGAGISGLYMAIKLPRSTENVELKIYEKNHDLGGTWLENRYPGCACDVPAHAYAYSFENNPEFP

RFFSSSEDIHKYLLRVADKYDCKKYIAFNTKVVEAIWDEEQGIYNVKIERSDGTVFQDTCEVLLNASGIL

NAWRYPGIPGIKDYKGTLMHSATWDRSVSLKGKKVALIGSGSSGIQILPNILDDCKEVVTYIIDPAWIAP

ANLVTAGVSDDGEEPKEPTPEELASSSDFAYSQEQINGFKKDPKSLMDHRATLERTMNQSFPILLRGSPS

NLYAASLFEDLMRKRLAKKPEVADAIIPEWSIGCRRLTPGPHYLEALCNPKVKILTQAIKSFSDKGMYT

ADGEHEDFDVVICATGFDVSFRPRFKFIGKDGYEVPENFGQTPKGYLALAYAGFPNSFIFMGPNGPIAN

GSVVVSLEKQGDYFIKAINKIQRQNIKGMTVRFDAVDDFTNHVDKYMDRTVLTDDCISWYKNGKRDG

RVSAVWPGSALHYMEAIADPRWEDYTYTYREPGHSFSFLGDGTSWVEHTGGDTAWYLKETL

-continued

SEQ ID NO 7: *Filobasidium magnum* SCH24-BVMO1 *E. coli* optimized
ATGACCATCGATTTGCAACAGCCAGACGCAGTCCCGTTTACGAGCAGCACTTTCGTCGTACCGGAC

CCGTCCAACCTGGCATCCCAGGCTCAAAACAGCCAACTGCAGAGCGCGCAAGAGGGCGCAGAGTA

CCCGGTGAATGCACACGGTGTCCGCGGTGACGGCACCATTCACGAGCGTCCGATCAATGACCGTC

GTAAAATGCGCGTCATCTGCGTTGGTGCGGGTATTAGCGGCCTGTATATGGCGATCAAACTGCCGC

GCAGCACCGAGAATGTTGAACTGAAGATCTACGAGAAAAACCATGACCTCGGCGGCACGTGGCTG

GAGAATCGCTACCCTGGCTGCGCGTGCGATGTTCCGGCGCATGCGTATGCATATTCTTTTGAGAAT

AATCCGGAATTTCCACGCTTTTTCAGCAGCAGCGAGGATATCCACAAGTACCTGTTGCGTGTTGCG

GACAAGTACGACTGTAAGAAATACATCGCCTTTAACACCAAAGTCGTTGAGGCTATCTGGGACGA

AGAACAGGGTATTTACAATGTGAAGATTGAGCGTAGCGACGGCACCGTGTTCCAGGACACCTGTG

AGGTGCTGCTGAACGCGAGCGGTATTCTGAATGCCTGGCGCTACCCGGGCATCCCTGGCATTAAGG

ATTACAAAGGTACGCTGATGCACAGCGCTACCTGGGACCGTAGCGTTTCTTTGAAAGGCAAAAAA

GTCGCACTGATTGGCAGCGGTAGCAGCGGTATCCAGATTCTGCCGAACATTCTGGACGACTGCAA

AGAAGTGGTCACGTACATTATCGACCCGGCGTGGATTGCTCCGGCTAACCTGGTGACCGCGGGTGT

CTCCGATGATGGTGAGGAACCGAAAGAGCCAACCCCTGAGGAACTGGCCTCATCCTCCGACTTCG

CTTATAGCCAGGAACAGATTAACGGCTTCAAGAAAGATCCGAAGTCGCTGATGGATCACCGCGCC

ACGCTGGAGCGTACCATGAATCAATCGTTTCCGATTCTGCTGCGTGGCTCTCCGAGCAACTTGTAT

GCCGCAAGCCTGTTCGAGGATTTGATGCGTAAGCGTCTGGCGAAGAAGCCGGAAGTTGCGGACGC

GATTATCCCGGAGTGGAGCATCGGTTGCAGACGCCTGACGCCGGGTCCGCATTACCTGGAAGCAC

TGTGTAACCCGAAAGTGAAGATCCTGACTCAGGCGATCAAGAGCTTTAGCGATAAGGGCATGTAT

ACTGCGGACGGTGAGCATGAAGATTTCGATGTTGTCATTTGTGCGACCGGTTTCGATGTGAGCTTT

CGTCCGCGCTTCAAGTTTATTGGTAAAGATGGCTATGAAGTCCCAGAGAATTTCGGCCAAACGCCG

AAAGGTTATCTGGCACTGGCGTACGCCGGCTTCCCGAACAGCTTCATCTTTATGGGTCCGAACGGT

CCGATTGCGAACGGTAGCGTTGTGGTGAGCCTGGAGAAGCAAGGTGACTACTTCATTAAAGCGAT

CAATAAGATCCAGCGTCAAAACATTAAGGGTATGACCGTTCGTTTCGACGCCGTGGATGATTTTAC

GAATCACAGTGGACAAATACATGGACCGTACGGTGCTGACCGACGATTGCATCAGCTGGTACAAG

AATGGTAAACGTGACGGTCGTGTTAGCGCAGTTTGGCCGGGTTCCGCGCTGCACTATATGGAAGCC

ATCGCAGACCCGCGTTGGGAAGATTACACCTACACCTATCGCGAACCGGGTCACTCTTTTAGCTTC

CTGGGTGATGGCACCAGCTGGGTTGAGCATACGGGTGGCGATACCGCCTGGTATTTGAAAGAAAC

CCTGTAA

SEQ ID NO 8: *Filobasidium magnum* SCH24-BVMO1 Yeast optimized
ATGACTATCGACTTGCAACAACCAGACGCTGTTCCATTCACTTCTTCTACTTTCGTTGTTCCAGACC

CATCTAACTTGGCTTCTCAAGCTCAAAACTCTCAATTGCAATCTGCTCAAGAAGGTGCTGAATACC

CAGTTAACGCTCACGGTGTTAGAGGTGACGGTACTATCCACGAAAGACCAATCAACGACAGAAGA

AAGATGAGAGTTATCTGTGTTGGTGCTGGTATCTCTGGTTTGTACATGGCTATCAAGTTGCCAAGA

TCTACTGAAAACGTTGAATTGAAGATCTACGAAAAGAACCACGACTTGGGTGGTACTTGGTTGGA

AAACAGATACCCAGGTTGTGCTTGTGACGTTCCAGCTCACGCTTACGCTTACTCTTTCGAAAACAA

CCCAGAATTCCCAAGATTCTTCTCTTCTTCTGAAGACATCCACAAGTACTTGTTGAGAGTTGCTGAC

AAGTACGACTGTAAGAAGTACATCGCTTTCAACACTAAGGTTGTTGAAGCTATCTGGGACGAAGA

ACAAGGTATCTACAACGTTAAGATCGAAAGATCTGACGGTACTGTTTTCCAAGACACTTGTGAAGT

TTTGTTGAACGCTTCTGGTATCTTGAACGCTTGGAGATACCCAGGTATCCCAGGTATCAAGGACTA

-continued

CAAGGGTACTTTGATGCACTCTGCTACTTGGGACAGATCTGTTTCTTTGAAGGGTAAGAAGGTTGC

TTTGATCGGTTCTGGTTCTTCTGGTATCCAAATCTTGCCAAACATCTTGGACGACTGTAAGGAAGTT

GTTACTTACATCATCGACCCAGCTTGGATCGCTCCAGCTAACTTGGTTACTGCTGGTGTTTCTGACG

ACGGTGAAGAACCAAAGGAACCAACTCCAGAAGAATTGGCTTCTTCTTCTGACTTCGCTTACTCTC

AAGAACAAATCAACGGTTTCAAGAAGGACCCAAAGTCTTTGATGGACCACAGAGCTACTTTGGAA

AGAACTATGAACCAATCTTTCCCAATCTTGTTGAGAGGTTCTCCATCTAACTTGTACGCTGCTTCTT

TGTTCGAAGACTTGATGAGAAAGAGATTGGCTAAGAAGCCAGAAGTTGCTGACGCTATCATCCCA

GAATGGTCTATCGGTTGTAGAAGATTGACTCCAGGTCCACACTACTTGGAAGCTTTGTGTAACCCA

AAGGTTAAGATCTTGACTCAAGCTATCAAGTCTTTCTCTGACAAGGGTATGTACACTGCTGACGGT

GAACACGAAGACTTCGACGTTGTTATCTGTGCTACTGGTTTCGACGTTTCTTTCAGACCAAGATTCA

AGTTCATCGGTAAGGACGGTTACGAAGTTCCAGAAAACTTCGGTCAAACTCCAAAGGGTTACTTG

GCTTTGGCTTACGCTGGTTTCCCAAACTCTTTCATCTTCATGGGTCCAAACGGTCCAATCGCTAACG

GTTCTGTTGTTGTTTCTTTGGAAAAGCAAGGTGACTACTTCATCAAGGCTATCAACAAGATCCAAA

GACAAAACATCAAGGGTATGACTGTTAGATTCGACGCTGTTGACGACTTCACTAACCACGTTGACA

AGTACATGGACAGAACTGTTTTGACTGACGACTGTATCTCTTGGTACAAGAACGGTAAGAGAGAC

GGTAGAGTTTCTGCTGTTTGGCCAGGTTCTGCTTTGCACTACATGGAAGCTATCGCTGACCCAAGA

TGGGAAGACTACACTTACACTTACAGAGAACCAGGTCACTCTTTCTCTTTCTTGGGTGACGGTACT

TCTTGGGTTGAACACACTGGTGGTGACACTGCTTGGTACTTGAAGGAAACTTTGTAA

SEQ ID NO 9: *Papiliotrema laurentii* SCH25-BVMO1 wt
ATGCCTTCCGCAATCACCCCGCCGGTTGATCATCGCAGTCTTCCAGGTCTTTTCAAGCCACAGAGG

AAGCTCAAAGTGATATGTGTCGGAGCCGGCGCCTCGGGCTTACTTCTTTCCTACAAGATACAACGA

CACTTCGAGGATTTCGAGCTCCAAGTCTTTGAGAAGAATCCTGAAGTATCAGGAACCTGGTACGAG

AACAGATATCCCGGCTGCGCTTGTGATGTTCCCTCGCATAATTATACATGGTCTTTTGAGCCCAAA

ACCGACTGGTCCGCCAACTATGCATCATCGAAGGAGATTTTCAAATATTTCAAGGACTTCACGAAG

AAGTATGGTCTTAGCAAGTACATCAAGCTGGAGCATGAGGTCGTGGGGGCCACGTGGATGGAGGC

GGAGGCACAGTGGAAAGTTGACGTCAAGGACCTTCGAAGTGGAAACACGCAGAGCTCGTTTGCGC

ATATACTGGTCAATGCAGGAGGCATTCTGAATGCTTGGCGATATCCGCCAATTCCAGGAATCAAGG

ATTTCAAGGGTGATCTTGTCCACTCCGCAGCTTGGCCAGAACATCTTGATCTTAATGGGAAGGTTG

TCGGTCTCATCGGAAATGGATCCTCCGGCATTCAGATCCTTCCGGCCATCAAGAAGGATGTAAAGC

AACTCGTTACATTCATTCGGGAAGCAACTTGGGTGGCGCCTCCTTTAGGTCAAGCCTATCGTGCGT

TCTCGACTGATGAACAGGCTCAGTTTGCGCAAGATCCGCGCCATCACCTGGAGACACGGCGTGCA

ATTGAGGCTACCATGAATCAATCATTTGGTATCTTCCATTCGGGATCCGAGGAGCAGAAAGGGGTT

CGCCAATATATGCAGAATATCATGGAAACGAAGCTCAACAACAAACAGCTCGAGAGTGTGCTGAT

TCCTGAGTGGTCGGTCGGTTGTCGGCGTCTTACACCAGGTACTAATTACCTAGAATCCCTGTCGGA

CGACAATGTCAAGGTCGTCTACGGTGAGATCACACAAATTACCGAATTGGGTGTCATCTGCGATGA

TGGCAAAGGCGAGTATCCCGTTGAAGTTCTTATTTGCGCCACTGGCTTCGACACCACCTTCAAACC

ACGATTCCCACTCATCGGTACAACCCAAGAGAAACTCAGTGATGTTTGGAAAGATGATCCGAGGG

GTTACTTCGGGATTGCAACCAACAACTATCCCAACTACTTCTTCACTCTTGGACCGAATTGTCCAAT

CGGTAATGGCCCCGTGCTGTGTGCCATCGAAGCTGAGGTTGATTATATAATCAACATGCTCTCAAA

GTTTCAAATGGAGAACATTCGTTCTTTTGATATCAAGGCAGATGCTGTCGACGCCTTCAACGACTG

GAAGGATGACTTCATGAAAGATACCATCTGGGCAGAACAATGCCGGTCATGGTACAAGGCAGGAT

-continued

CTGCCACCGGTAAAATCCTTGCATTGTGGCCAGGCTCGACTTTGCACTACTTGGAAGCACTCAAGT

CGCCGCGGTGGGAGGATTGGGACTTCAAGTATCAGCCTGGTAGAAATCGTTTCCACTACTTTGGAA

ATGGTCATAGCTGTGCTGAGCAGGATGGCGATCTGAGCTGGTACATTCGCAACGAGGATGATTCTT

ATATTGATCCGGTACTCAAGCCAAAGTCGAAGGCAGCAATTGAGAGCGAGGCACATATCGCCCTG

CCAGGAATCGGTCCGATGTTGATGGAAGACCCGCGTGATGTTGCTGTAGAGGCCTAG

SEQ ID NO 10: *Papiliotrema laurentii* SCH25-BVMO1 wt
MPSAITPPVDHRSLPGLFKPQRKLKVICVGAGASGLLLSYKIQRHFEDFELQVFEKNPEVSGTWYENRY

PGCACDVPSHNYTWSFEPKTDWSANYASSKEIFKYFKDFTKKYGLSKYIKLEHEVVGATWMEAEAQW

KVDVKDLRSGNTQSSFAHILVNAGGILNAWRYPPIPGIKDFKGDLVHSAAWPEHLDLNGKVVGLIGNG

SSGIQILPAIKKDVKQLVTFIREATWVAPPLGQAYRAFSTDEQAQFAQDPRHHLETRRAIEATMNQSFGI

FHSGSEEQKGVRQYMQNIMETKLNNKQLESVLIPEWSVGCRRLTPGTNYLESLSDDNVKVVYGEITQIT

ELGVICDDGKGEYPVEVLICATGFDTTFKPRFPLIGTTQEKLSDVWKDDPRGYFGIATNNYPNYFFTLGP

NCPIGNGPVLCAIEAEVDYIINMLSKFQMENIRSFDIKADAVDAFNDWKDDFMKDTIWAEQCRSWYKA

GSATGKILALWPGSTLHYLEALKSPRWEDWDFKYQPGRNRFHYFGNGHSCAEQDGDLSWYIRNEDDS

YIDPVLKPKSKAAIESEAHIALPGIGPMLMEDPRDVAVEA

SEQ ID NO 11: *Papiliotrema laurentii* SCH25-BVMO1 *E. coli* optimized
ATGCCATCTGCCATTACTCCACCTGTTGATCATCGTAGCCTGCCGGGTCTGTTCAAGCCGCAACGT

AAGTTGAAAGTGATCTGTGTTGGCGCGGGCGCGAGCGGCCTGTTGCTGAGCTACAAGATTCAGCG

TCACTTTGAGGACTTTGAGTTGCAAGTTTTTGAGAAAAACCCTGAAGTGAGCGGCACCTGGTACGA

GAATCGCTACCCGGGTTGCGCGTGCGATGTTCCGAGCCATAACTATACCTGGTCTTTTGAGCCGAA

AACGGATTGGTCCGCAAACTATGCCAGCAGCAAAGAAATTTTCAAGTACTTCAAAGATTTCACCA

AGAAATATGGTCTGTCTAAATACATTAAACTGGAACACGAAGTCGTGGGTGCGACGTGGATGGAA

GCGGAAGCTCAATGGAAAGTTGACGTCAAAGACTTGCGTAGCGGCAACACCCAGAGCTCCTTCGC

GCACATTCTGGTCAATGCCGGTGGCATTCTGAACGCTTGGCGTTACCCGCCGATTCCGGGTATCAA

AGATTTTAAGGGTGACCTGGTGCACTCGGCAGCGTGGCCGGAGCATCTGGATCTGAATGGTAAAG

TCGTTGGCCTGATTGGTAACGGTAGCAGCGGCATCCAAATTCTGCCGGCCATCAAAAAAGACGTG

AAACAACTGGTCACGTTTATCCGTGAGGCCACGTGGGTCGCCCCGCCGCTGGGCCAAGCGTACCG

CGCATTTAGCACCGACGAACAGGCGCAGTTTGCACAAGACCCGCGTCACCATCTGGAAACTCGTC

GCGCGATTGAAGCTACCATGAATCAGAGCTTCGGTATCTTCCACAGCGGTTCAGAGGAACAGAAA

GGTGTGCGTCAGTACATGCAGAATATCATGGAAACGAAATTGAATAACAAACAGCTGGAGAGCGT

GCTGATTCCGGAGTGGTCCGTGGGTTGTCGCCGTCTGACCCCGGGCACGAACTATCTGGAGAGCTT

GAGCGACGATAACGTGAAAGTTGTTTATGGCGAGATCACCCAGATCACCGAGCTGGGTGTGATTT

GCGATGATGGCAAGGGTGAGTACCCGGTCGAAGTGCTGATTTGCGCTACCGGTTTCGACACCACGT

TCAAACCGCGCTTCCCGTTGATTGGCACCACCCAGGAAAAGCTGAGCGACGTCTGGAAAGATGAC

CCTCGCGGTTATTTCGGTATCGCGACCAATAACTACCCGAACTACTTTTTCACCCTGGGTCCGAACT

GCCCGATCGGCAATGGTCCGGTCCTGTGTGCAATCGAAGCTGAAGTGGACTATATCATCAATATGC

TGAGCAAATTTCAGATGGAAAACATTCGCAGCTTCGACATTAAAGCCGACGCAGTTGATGCGTTTA

ACGACTGGAAAGATGACTTTATGAAAGACACCATCTGGGCAGAGCAGTGTCGTTCTTGGTACAAG

GCTGGTTCTGCGACGGGTAAGATTTTGGCACTGTGGCCGGGCAGCACGCTGCATTATCTGGAAGCC

CTGAAAAGCCCACGCTGGGAAGATTGGGACTTCAAGTATCAACCGGGTCGTAATCGCTTTCACTAC

-continued

TTCGGTAACGGCCACAGCTGCGCGGAGCAAGATGGTGATCTGTCCTGGTATATCCGTAATGAAGAT

GACAGCTACATTGACCCGGTACTGAAGCCGAAGTCCAAGGCAGCGATCGAGAGCGAAGCACACAT

CGCGCTGCCAGGCATTGGTCCGATGCTGATGGAGGACCCGCGTGACGTTGCGGTTGAGGCATAA

SEQ ID NO 12: *Bensinstonia ciliata* SCH46-BVMO1 wt
ATGCCTTCCGCAATCACCCCACCGGTTGATCATCGCAGTCTTCCAGGTCTTTTCAAGCCACAGAGG

AAGCTCAAAGTGATATGTGTCGGAGCCGGCGCCTCGGGCTTACTTCTTTCCTACAAGATACAACGA

CACTTCGAGGATTTCGAGCTCCAAGTCTTTGAGAAGAATCCTGAGGTATCAGGAACCTGGTACGAG

AACAGGTATCCCGGCTGTGCTTGTGATGTTCCCTCGCATAATTATACATGGTCTTTTGAGCCCAAA

ACCGACTGGTCCGCCAACTATGCATCATCGAAGGAGATTTTCAAATATTTCAAGGACTTCACGAAG

AAGTATGGTCTTAGCAAGTACATCAAGCTGGAGCATGAGGTCGTGGGGGCCACGTGGATGGAGGC

GGAGGCACAGTGGAAAGTTGACGTCAAGGACCTTCGAAGTGGAAACACGCAGAGCTCGTTTGCGC

ATATACTGGTCAATGCAGGAGGCATTCTGAATGCTTGGCGATATCCGCCAATTCCAGGAATCAAGG

ATTTCAAGGGTGATCTTGTCCACTCCGCAGCTTGGCCAGAACATCTTGATCTTAATGGGAAGGTTG

TCGGTCTAATCGGAAATGGATCCTCCGGCATTCAGATCCTTCCGGCCATCAAGAAGGATGTAAAGC

AACTCGTTACATTTATTCGGGAAGCAACTTGGGTGGCGCCTCCTTTAGGTCAAGCCTATCGTGCGT

TCTCGACTGATGAACAGGCTCAGTTTGCGCAAGATCCGCGCCATCACCTGGAAACACGTCGTGCAA

CTGAGGCTACCATGAATCAATCATTTGGTATCTTCCATTCGGGATCCGAGGAGCAGAAAGGAGTTC

GCCAATATATGCAGGATATCATGGAAACGAAGCTCAACAACAAACAGCTCGAGAGTGTGCTGATT

CCTGAGTGGTCGGTCGGTTGTCGGCGTCTTACACCAGGTACTAATTACCTAGAATCCCTATCGGAC

GACAATGTCAAGGTCGTCTACGGTGAAATCACACAAATTACCGAATCAGGTGTCATCTGCGATGAT

GGTAAAGGCGAATATCCCGTCGAAGTTCTTATTTGCGCCACCGGCTTCGACACCACCTTCAAACCA

CGATTTCCACTCATCGGCACTACGAAAGAGAAGCTCAGTGATGTTTGGAAAGATGATCCGAGGGG

CTACTTTGGGATCGCAACCAACAACTATCCCAACTACTTCTTCACTCTTGGACCGAATTGTCCAATC

GGTAATGGCCCCGTGCTGTGTGCCATTGAAGCTGAGGTTGAATATATAATCAACATGCTCTCGAAG

TTTCAGAAGGAGAACATTCGTTCTTTTGATATCAAGGCAGATGCTGTCGACGCCTTCAACGACTGG

AAGGATGACTTCATGAAAGATACCATCTGGGCAGAACAATGCCGGTCATGGTACAAGGCAGGATC

CGCCACTGGTAAAATCCTTGCATTGTGGCCAGGCTCGACTTTGCACTACTTGGAAGCACTCAAGTC

GCCGCGGTGGGAGGACTGGGACTTCAAGTATCAGCCTGGTAGAAATCGTTTCCATTACTTTGGAAA

TGGTCATAGCTGTGCTGAGCAGGATGGCGATCTGAGCTGGTACATCCGCAACGAGGATGATTCTTA

TATTGATCCGGTACTCAAGCCAAAGCCGAAGGCAGCAGTTGAGAGCGAGGCACATATCGCCCTGC

CAGGAATCGGTCCGATGTTGATGGAAGACCCGCGTGATGTTGCTGTAGAGGCCTAG

SEQ ID NO 13: *Bensinstonia ciliata* (ATCC 20919) SCH46-BVMO1 wt
MPSAITPPVDHRSLPGLFKPQRKLKVICVGAGASGLLLSYKIQRHFEDFELQVFEKNPEVSGTWYENRY

PGCACDVPSHNYTWSFEPKTDWSANYASSKEIFKYFKDFTKKYGLSKYIKLEHEVVGATWMEAEAQW

KVDVKDLRSGNTQSSFAHILVNAGGILNAWRYPPIPGIKDFKGDLVHSAAWPEHLDLNGKVVGLIGNG

SSGIQILPAIKKDVKQLVTFIREATWVAPPLGQAYRAFSTDEQAQFAQDPRHHLETRRATEATMNQSFG

IFHSGSEEQKGVRQYMQDIMETKLNNKQLESVLIPEWSVGCRRLTPGTNYLESLSDDNVKVVYGEITQI

TESGVICDDGKGEYPVEVLICATGFDTTFKPRFPLIGTTKEKLSDVWKDDPRGYFGIATNNYPNYFFTLG

PNCPIGNGPVLCAIEAEVEYIINMLSKFQKENIRSFDIKADAVDAFNDWKDDFMKDTIWAEQCRSWYK

AGSATGKILALWPGSTLHYLEALKSPRWEDWDFKYQPGRNRFHYFGNGHSCAEQDGDLSWYIRNEDD

SYIDPVLKPKPKAAVESEAHIALPGIGPMLMEDPRDVAVEA

-continued

SEQ ID NO 14: *Bensinstonia ciliata* SCH46-BVMO1 *E. coli* optimized
ATGCCATCTGCCATTACTCCACCTGTTGATCATCGTAGCCTGCCGGGTCTGTTCAAGCCGCAACGT

AAGTTGAAAGTGATCTGTGTTGGCGCGGGCGCGAGCGGCCTGTTGCTGAGCTACAAGATTCAGCG

TCACTTTGAGGACTTTGAGTTGCAAGTTTTTGAGAAAAACCCTGAAGTGAGCGGCACCTGGTACGA

GAATCGCTACCCGGGTTGCGCGTGCGATGTTCCGAGCCATAACTATACCTGGTCTTTTGAGCCGAA

AACGGATTGGTCCGCAAACTATGCCAGCAGCAAAGAAATTTTCAAGTACTTCAAAGATTTCACCA

AGAAATATGGTCTGTCTAAATACATTAAACTGGAACACGAAGTCGTGGGTGCGACGTGGATGGAA

GCGGAAGCTCAATGGAAAGTTGACGTCAAAGACTTGCGTAGCGGCAACACCCAGAGCTCCTTCGC

GCACATTCTGGTCAATGCCGGTGGCATTCTGAACGCTTGGCGTTACCCGCCGATTCCGGGTATCAA

AGATTTTAAGGGTGACCTGGTGCACTCGGCAGCGTGGCCGGAGCATCTGGATCTGAATGGTAAAG

TCGTTGGCCTGATTGGTAACGGTAGCAGCGGCATCCAAATTCTGCCGGCCATCAAAAAAGACGTG

AAACAACTGGTCACGTTTATCCGTGAGGCCACGTGGGTCGCCCCGCCGCTGGGCCAAGCGTACCG

CGCATTTAGCACCGACGAACAGGCGCAGTTTGCACAAGACCCGCGTCACCATCTGGAAACTCGTC

GCGCGACCGAAGCTACCATGAATCAGAGCTTCGGTATCTTCCACAGCGGTTCAGAGGAACAGAAA

GGTGTGCGTCAGTACATGCAGGATATCATGGAAACGAAATTGAATAACAAACAGCTGGAGAGCGT

GCTGATTCCGGAGTGGTCCGTGGGTTGTCGCCGTCTGACCCCGGGCACGAACTATCTGGAGAGCTT

GAGCGACGATAACGTGAAAGTTGTTTATGGCGAGATCACCCAGATCACCGAGTCCGGTGTGATTT

GCGATGATGGCAAGGGTGAGTACCCGGTCGAAGTGCTGATTTGCGCTACCGGTTTCGACACCACGT

TCAAACCGCGCTTCCCGTTGATTGGCACCACCAAAGAAAAGCTGAGCGACGTCTGGAAAGATGAC

CCTCGCGGTTATTTCGGTATCGCGACCAATAACTACCCGAACTACTTTTTCACCCTGGGTCCGAACT

GCCCGATCGGCAATGGTCCGGTCCTGTGTGCAATCGAAGCTGAAGTGGAGTATATCATCAATATGC

TGAGCAAATTTCAGAAAGAAAACATTCGCAGCTTCGACATTAAAGCCGACGCAGTTGATGCGTTT

AACGACTGGAAAGATGACTTTATGAAAGACACCATCTGGGCAGAGCAGTGTCGTTCTTGGTACAA

GGCTGGTTCTGCGACGGGTAAGATTTTGGCACTGTGGCCGGGCAGCACGCTGCATTATCTGGAAGC

CCTGAAAAGCCCACGCTGGGAAGATTGGGACTTCAAGTATCAACCGGGTCGTAATCGCTTTCACTA

CTTCGGTAACGGCCACAGCTGCGCGGAGCAAGATGGTGATCTGTCCTGGTATATCCGTAATGAAG

ATGACAGCTACATTGACCCGGTACTGAAGCCGAAGCCGAAGGCAGCGGTGGAGAGCGAAGCACA

CATCGCGCTGCCAGGCATTGGTCCGATGCTGATGGAGGACCCGCGTGACGTTGCGGTTGAGGCAT

AA

SEQ ID NO 15: *Aspergillus wentii* AspWeBVMO wt
ATGACCAAAGACAATACCACATCATTCCCCTCGCACGCCATCTACGAGCCACGCCGGACATTAAA

AGTGCTGGTCATAGGGGCTGGTGCGTCCGGTCTATTATTAGCATACAAACTACAGCGGCACTTTGA

TTGTGTGGAAATCACGGTGTTTGAGAAGAACCCCGCAGTGTCCGGCACTTGGTTTGAGAATCGATA

TCCGGGATGTGCCTGTGACGTTCCTTCGCATTGCTATACATGGTCCTTCGAGCCCAACCCCAACTG

GTCCGCCAACTACGCTGGAGCCGACGAGATTCGACAATACTTTGTCGATTTCTGCCATCGCCACGA

CTTGCAGAAATATATCCATCTGGAACATGAGGTGGTCCACGCAGCGTGGAAGTCGGAGACTGGCC

ACTGGGAGGTGCAAGTGCGCGATATACAACACAATTCTCACACACAGCATACTGCGCATATCTTG

ATTAATGCTACTGGAATACTGAATCAATGGAAGTGGCCATCCATTCCCGGATTACAGTCGTTCCAG

GGAGATCTTTTGCACAGTGCAGCATGGGACTCGTCAGTCAATCTAGAGGATAAAAACGGTCGCTGTC

ATTGGAAACGGATCATCCGGAATCCAGATTGTCCCAGCGATTCTACCCCAAGTGCGCAAACTCGTG

CACTTTACTCGTCAAGCGGCATGGGTCGCACCTCCAGTCAATGAAGAGTATCAGGAATACTCGCCC

GAACAGATCGAACGCTTTCGCTCAGACCCAACATACCTGCTTGGGGTTCGTCGACAGATTGAAGCA

-continued

CGGATGAACGGCTCATTTCTGAAATTCATCCAAGGCTCAGACATGCAACGTCGTGCACACGAGTAT

GTCATGCTGCACATGATGAAGAGACTGGACGGAGACGCCTCCCTGGCAGAGACCTTGGTACCAAC

CTTCCCATTTGGCTGTCGAAGACCGACGCCAGGAACCGGGTATCTCGAAGCACTGAAGGACTCGA

AAGTGGAAACAATTACCGGAGCCCGAATCGCGAATGTGACGGGTAACCAGGTGGTCCTCGAGAAT

GGCACGTCGTATACGGTGGATGCGATTGTGTGCGCCACGGGATTCGATACGTCTTACAAACCACGA

TTCCCACTGGTCGGCAGAGACAGCACCACTCTCAGCGAGGCCTGGAAGGACGAAGTGTCTGCATA

TCTGGGGCTTACAGTTCCTGGATTTCCCAACTATTTTTCCATCTTGGGACCGAACTGTCCGGTGGGT

AACGGGCCGGTGTTGATCAGTATCGAAAAACAGGTCGAATATATTGTTCAGGTACTGGGGAAAAT

GCAGAAGGAGAATCTACAGTCATTTGAAGTCCGGCGGACGGCAACAGACTCGTTTAACCAATGGA

AGGATGCATTCATGCAAAACACGGTGTGGACGAGTGGTTGTCGCAGCTGGTATCAGAATGGCTCG

AAAGGGAACCAGATCGTGGCTCTCTGGCCTGGATCCACGTTGCACTATTTGGAGGCGATTCAGCAT

CCACGATACGAGGACTACATCTGGACCAGTCCACCTGGTGTCAATCCATGGGCCTTTCTAGGCAAC

GGGCAGAGTACGGCCGAAACCCGTCCCGGAGGCGACACGAGTTGGTATCTGCGTTCGAAAGATGA

TTCATTTATAGATCCATGTCTGAGACAGCTTTAG

SEQ ID NO 16: *Aspersillus wentii* AspWeBVMO wt (OJJ34587.1)
MTKDNTTSFPSHAIYEPRRTLKVLVIGAGASGLLLAYKLQRHFDCVEITVFEKNPAVSGTWFENRYPGC

ACDVPSHCYTWSFEPNPNWSANYAGADEIRQYFVDFCHRHDLQKYIHLEHEVVHAAWKSETGHWEV

QVRDIQHNSHTQHTAHILINATGILNQWKWPSIPGLQSFQGDLLHSAAWDSSVNLEDKTVAVIGNGSSG

IQIVPAILPQVRKLVHFTRQAAWVAPPVNEEYQEYSPEQIERFRSDPTYLLGVRRQIEARMNGSFLKFIQ

GSDMQRRAHEYVMLHMMKRLDGDASLAETLVPTFPFGCRRPTPGTGYLEALKDSKVETITGARIANV

TGNQVVLENGTSYTVDAIVCATGFDTSYKPRFPLVGRDSTTLSEAWKDEVSAYLGLTVPGFPNYFSILG

PNCPVGNGPVLISIEKQVEYIVQVLGKMQKENLQSFEVRRTATDSFNQWKDAFMQNTVWTSGCRSWY

QNGSKGNQIVALWPGSTLHYLEAIQHPRYEDYIWTSPPGVNPWAFLGNGQSTAETRPGGDTSWYLRSK

DDSFIDPCLRQL*

SEQ ID NO 17: *Aspersillus wentii* AspWeBVMO *E. coli* optimized
ATGACCAAAGATAACACCACGTCCTTTCCGAGCCACGCCATTTACGAGCCGCGCCGTACCCTGAAA

GTCCTGGTGATCGGTGCTGGCGCGAGCGGTTTGTTGCTGGCATATAAGCTGCAGCGCCACTTCGAT

TGCGTTGAGATTACCGTATTCGAGAAGAATCCGGCAGTCAGCGGCACCTGGTTTGAGAATCGTTAC

CCTGGTTGTGCATGTGACGTGCCGAGCCATTGCTACACCTGGTCGTTCGAGCCAAACCCGAATTGG

AGCGCAAACTACGCGGGTGCGGATGAAATTCGCCAGTATTTCGTTGATTTCTGTCACCGTCATGAT

CTGCAGAAGTACATCCATCTGGAGCACGAAGTCGTTCATGCGGCATGGAAATCGGAGACTGGTCA

CTGGGAAGTGCAAGTCCGTGACATCCAGCACAACAGCCATACCCAGCACACGGCGCACATTTTGA

TCAACGCAACGGGTATCCTGAATCAATGGAAATGGCCGAGCATTCCGGGCCTGCAGAGCTTTCAG

GGTGATCTGCTGCATAGCGCAGCGTGGGACAGCTCCGTCAACTTAGAGGATAAGACCGTCGCGGT

GATCGGTAATGGCAGCAGCGGTATCCAGATTGTGCCGGCCATCCTGCCGCAAGTGCGCAAACTGG

TTCACTTTACGCGTCAAGCGGCATGGGTGGCACCGCCGGTGAACGAAGAGTACCAAGAGTACAGC

CCGGAGCAAATTGAGCGTTTCCGTAGCGACCCGACCTACCTGTTGGGCGTCCGCCGTCAAATTGAA

GCCCGTATGAACGGCAGCTTTCTGAAGTTTATTCAGGGCAGCGACATGCAGCGCAGAGCGCACGA

ATACGTTATGCTGCACATGATGAAGCGTCTGGACGGTGATGCGAGCCTTGCTGAGACTCTGGTGCC

GACGTTTCCGTTCGGCTGCCGTCGTCCGACCCCGGGCACCGGTTATCTGGAAGCGCTGAAAGACTC

TAAAGTTGAAACGATCACGGGTGCCCGTATCGCAAATGTTACGGGCAACCAAGTTGTCCTGGAGA

-continued

ACGGTACTAGCTATACGGTCGATGCTATTGTCTGTGCTACCGGTTTCGACACCAGCTATAAGCCGC

GTTTCCCGCTGGTTGGCCGCGACTCTACCACCCTGAGCGAAGCCTGGAAAGACGAAGTGTCTGCGT

ACCTGGGTCTGACCGTTCCGGGTTTTCCGAACTATTTCAGCATCCTGGGTCCTAATTGCCCGGTCGG

TAATGGTCCGGTTTTGATCAGCATCGAGAAACAAGTGGAGTATATCGTGCAAGTTCTGGGTAAGAT

GCAGAAAGAAAACTTGCAGTCCTTCGAAGTTCGCCGTACCGCCACCGACAGCTTCAATCAGTGGA

AAGATGCGTTCATGCAAAACACGGTGTGGACCTCAGGTTGCCGTTCTTGGTATCAGAATGGCAGCA

AGGGCAACCAAATTGTCGCGCTGTGGCCGGGTTCCACGCTGCACTACCTGGAAGCGATTCAACATC

CTCGCTACGAAGATTATATCTGGACGAGCCCACCGGGTGTTAATCCGTGGGCGTTTCTGGGCAATG

GCCAGAGCACCGCGGAAACCCGTCCGGGTGGCGACACTTCCTGGTATCTCCGCTCCAAAGATGAC

AGCTTTATTGACCCATGCCTGCGTCAGCTGTAA

SEQ ID NO 18: *Aspergillus wentii* AspWeBVMO Yeast optimized
ATGACTAAGGACAACACTACTTCTTTCCCATCTCACGCTATCTACGAACCAAGAAGAACTTTGAAG

GTTTTGGTTATCGGTGCTGGTGCTTCTGGTTTGTTGTTGGCTTACAAGTTGCAAAGACACTTCGACT

GTGTTGAAATCACTGTTTTCGAAAAGAACCCAGCTGTTTCTGGTACTTGGTTCGAAAACAGATACC

CAGGTTGTGCTTGTGACGTTCCATCTCACTGTTACACTTGGTCTTTCGAACCAAACCCAAACTGGTC

TGCTAACTACGCTGGTGCTGACGAAATCAGACAATACTTCGTTGACTTCTGTCACAGACACGACTT

GCAAAAGTACATCCACTTGGAACACGAAGTTGTTCACGCTGCTTGGAAGTCTGAAACTGGTCACTG

GGAAGTTCAAGTTAGAGACATCCAACACAACTCTCACACTCAACACACTGCTCACATCTTGATCAA

CGCTACTGGTATCTTGAACCAATGGAAGTGGCCATCTATCCCAGGTTTGCAATCTTTCCAAGGTGA

CTTGTTGCACTCTGCTGCTTGGGACTCTTCTGTTAACTTGGAAGACAAGACTGTTGCTGTTATCGGT

AACGGTTCTTCTGGTATCCAAATCGTTCCAGCTATCTTGCCACAAGTTAGAAAGTTGGTTCACTTCA

CTAGACAAGCTGCTTGGGTTGCTCCACCAGTTAACGAAGAATACCAAGAATACTCTCCAGAACAA

ATCGAAAGATTCAGATCTGACCCAACTTACTTGTTGGGTGTTAGAAGACAAATCGAAGCTAGAAT

GAACGGTTCTTTCTTGAAGTTCATCCAAGGTTCTGACATGCAAAGAAGAGCTCACGAATACGTTAT

GTTGCACATGATGAAGAGATTGGACGGTGACGCTTCTTTGGCTGAAACTTTGGTTCCAACTTTCCC

ATTCGGTTGTAGAAGACCAACTCCAGGTACTGGTTACTTGGAAGCTTTGAAGGACTCTAAGGTTGA

AACTATCACTGGTGCTAGAATCGCTAACGTTACTGGTAACCAAGTTGTTTTGGAAAACGGTACTTC

TTACACTGTTGACGCTATCGTTTGTGCTACTGGTTTCGACACTTCTTACAAGCCAAGATTCCCATTG

GTTGGTAGAGACTCTACTACTTTGTCTGAAGCTTGGAAGGACGAAGTTTCTGCTTACTTGGGTTTG

ACTGTTCCAGGTTTCCCAAACTACTTCTCTATCTTGGGTCCAAACTGTCCAGTTGGTAACGGTCCAG

TTTTGATCTCTATCGAAAAGCAAGTTGAATACATCGTTCAAGTTTTGGGTAAGATGCAAAAGGAAA

ACTTGCAATCTTTCGAAGTTAGAAGAACTGCTACTGACTCTTTCAACCAATGGAAGGACGCTTTCA

TGCAAAACACTGTTTGGACTTCTGGTTGTAGATCTTGGTACCAAAACGGTTCTAAGGGTAACCAAA

TCGTTGCTTTGTGGCCAGGTTCTACTTTGCACTACTTGGAAGCTATCCAACACCCAAGATACGAAG

ACTACATCTGGACTTCTCCACCAGGTGTTAACCCATGGGCTTTCTTGGGTAACGGTCAATCTACTGC

TGAAACTAGACCAGGTGGTGACACTTCTTGGTACTTGAGATCTAAGGACGACTCTTTCATCGACCC

ATGTTTGAGACAATTGTAA

SEQ ID NO 19: *Hyphozyma roseoniera* SCH23-EST wt
ATGCCTTCCGATCTTCCCCGACCAGCATATGACCCGGAAATAGAGCCCTTCCTCTCTATGGTCCCAT

TACCACCAACAATCAATGCGGATATCATGAAAGAATTGCGTAAAGCACCTCTGCTCAGTCAAGCG

CCTGACCTCGACGCATTACTTTCCGACAAGCCAATAACTCACCGCGAAGTCAGCATTCCAGGTCTC

AATTCCCAAGATCCACAAATCACGTTGTCAATATTCTCCAGTACATTGGAGGGTGGCCCGAAACCA

-continued

TGTATCTATTTCGTTCATGGTGGCGGTATGATCATCGGATGTCGATTCGTGGGTATTGAGGATTATC

TTCAATACGTCGAGCAGAACGACGCTGTCGTCGTGGCTGTAGAGTATCGTCTCGCTCCGGAACACC

CGGACCCAGCGCCTGTCAATGATTGTTACGCTGGACTTTTATGGACGGCAGCAAATGCTGCAGAGC

TAGGCATCGATCTGGAGAGACTGTTGATCTGTGGCGCTTCTGCTGGTGGTGGTCTTTCTGCTGGAG

TGGCATTGATGGCACGAGACAAGAAAGGTCCAAAATTGGTAGGACAATTGTTATGCTATCCAATG

CTCGACGATAGGAATGATTCACTCTCAAGTCAGCAGTACGTGGATGAAGGTGTTTGGAGTCGTGGT

AGCAATGCATTTGGCTGGAAGCAATTGCTTGGAGACAGGGCGGGCAAAGAGGGAGTCAGTATTTA

TGCTGCGCCGGCAAGAGCAACTGATTTGAGCGGACTGCCGAACACTTTCATCGACGTTGGCAGCG

CTGAAGTCTTCAGGGATGAGGACATCGCTTATGCCTCGAGGTTATGGGCTGTTGGTGTCCAAGCGG

AACTTCATGTGTGGCCGGGTGGATATCATGCTGCGGAGAACATGGCACCTGGGACTGATTACTCTA

AGAAGGTGAAAGCGACTCGCTTGGCATGGATGAAGAGAGTCTTCATGAAAGCCCCAAAGTCGACG

ACAGAGTCGTTGCCTGCTCCAACAGTGGATGAAGCTGTTGGCACAATATGA

SEQ ID NO 20: *Hyphozyma roseoniera* SCH23-EST wt
MPSDLPRPAYDPEIEPFLSMVPLPPTINADIMKELRKAPLLSQAPDLDALLSDKPITHREVSIPGLNSQDP

QITLSIFSSTLEGGPKPCIYFVHGGGMIIGCRFVGIEDYLQYVEQNDAVVVAVEYRLAPEHPDPAPVNDC

YAGLLWTAANAAELGIDLERLLICGASAGGGLSAGVALMARDKKGPKLVGQLLCYPMLDDRNDSLSS

QQYVDEGVWSRGSNAFGWKQLLGDRAGKEGVSIYAAPARATDLSGLPNTFIDVGSAEVFRDEDIAYA

SRLWAVGVQAELHVWPGGYHAAENMAPGTDYSKKVKATRLAWMKRVFMKAPKSTTESLPAPTVDE

AVGTI

SEQ ID NO 21: *Hyphozyma roseonisra* SCH23-EST *E. coli* optimized
ATGCCATCGGATCTGCCGCGCCCAGCCTACGACCCTGAAATCGAACCGTTCTTGAGCATGGTTCCG

CTGCCTCCGACCATTAACGCGGACATTATGAAAGAACTGCGTAAGGCCCCACTGCTGAGCCAGGC

TCCGGATCTGGATGCCCTGCTGAGCGACAAGCCGATTACTCACCGTGAGGTGTCCATCCCGGGTCT

GAACAGCCAGGACCCGCAGATTACCCTGAGCATCTTTAGCTCTACCCTGGAGGGTGGCCCGAAGC

CGTGTATCTACTTCGTGCACGGTGGCGGCATGATTATTGGCTGTCGCTTCGTCGGTATTGAGGACT

ACTTGCAATACGTGGAACAGAATGACGCGGTCGTTGTGGCCGTTGAGTATCGTCTGGCACCGGAA

CATCCGGACCCGGCACCGGTGAATGACTGCTACGCGGGTCTGCTGTGGACCGCTGCGAACGCGGC

AGAACTGGGCATCGATTTGGAGCGTCTGCTGATCTGCGGCGCTTCTGCGGGTGGCGGTCTGTCAGC

GGGTGTGGCGCTGATGGCACGCGACAAAAAGGGTCCGAAACTGGTCGGTCAGCTGCTGTGCTATC

CGATGCTCGACGATCGTAACGATAGCTTGAGCAGCCAGCAATACGTAGATGAGGGTGTTTGGAGC

CGTGGTAGCAATGCGTTTGGTTGGAAGCAACTGCTGGGTGATCGTGCCGGCAAAGAGGGCGTGTC

CATTTACGCGGCACCGGCTCGCGCAACCGACCTGTCTGGCTTGCCTAACACGTTTATCGACGTTGG

TTCCGCCGAGGTTTTCCGTGATGAAGATATCGCGTATGCGAGCCGCTTATGGGCAGTCGGTGTTCA

AGCGGAGCTGCATGTCTGGCCGGGTGGTTATCACGCTGCGGAGAATATGGCACCGGGCACCGATT

ATAGCAAAAAAGTCAAGGCGACGCGTCTGGCATGGATGAAACGCGTCTTTATGAAGGCCCCGAAA

AGCACCACGGAGAGCCTGCCGGCACCGACGGTTGACGAAGCGGTGGGCACGATCTAA

SEQ ID NO 22: *Hyphozyma roseonisra* SCH23-EST Yeast optimized
ATGCCATCTGACTTGCCAAGACCAGCTTACGACCCAGAAATCGAACCATTCTTGTCTATGGTTCCA

TTGCCACCAACTATCAACGCTGACATCATGAAGGAATTGAGAAAGGCTCCATTGTTGTCTCAAGCT

CCAGACTTGGACGCTTTGTTGTCTGACAAGCCAATCACTCACAGAGAAGTTTCTATCCCAGGTTTG

AACTCTCAAGACCCACAAATCACTTTGTCTATCTTCTCTTCTACTTTGGAAGGTGGTCCAAAGCCAT

GTATCTACTTCGTTCACGGTGGTGGTATGATCATCGGTTGTAGATTCGTTGGTATCGAAGACTACTT

-continued

GCAATACGTTGAACAAAACGACGCTGTTGTTGTTGCTGTTGAATACAGATTGGCTCCAGAACACCC

AGACCCAGCTCCAGTTAACGACTGTTACGCTGGTTTGTTGTGGACTGCTGCTAACGCTGCTGAATT

GGGTATCGACTTGGAAAGATTGTTGATCTGTGGTGCTTCTGCTGGTGGTGGTTTGTCTGCTGGTGTT

GCTTTGATGGCTAGAGACAAGAAGGGTCCAAAGTTGGTTGGTCAATTGTTGTGTTACCCAATGTTG

GACGACAGAAACGACTCTTTGTCTTCTCAACAATACGTTGACGAAGGTGTTTGGTCTAGAGGTTCT

AACGCTTTCGGTTGGAAGCAATTGTTGGGTGACAGAGCTGGTAAGGAAGGTGTTTCTATCTACGCT

GCTCCAGCTAGAGCTACTGACTTGTCTGGTTTGCCAAACACTTTCATCGACGTTGGTTCTGCTGAAG

TTTTCAGAGACGAAGACATCGCTTACGCTTCTAGATTGTGGGCTGTTGGTGTTCAAGCTGAATTGC

ACGTTTGGCCAGGTGGTTACCACGCTGCTGAAAACATGGCTCCAGGTACTGACTACTCTAAGAAGG

TTAAGGCTACTAGATTGGCTTGGATGAAGAGAGTTTTCATGAAGGCTCCAAAGTCTACTACTGAAT

CTTTGCCAGCTCCAACTGTTGACGAAGCTGTTGGTACTATCTAA

SEQ ID NO 23: *Filobasidium magnum* SCH24-EST wt
ATGACTCATAGCCCTCCACTCGATGCCGAACTTTCGCTACTCCGATATGCTCCTGCTGTTCCCGTGG

GATGGCAGTTGGGACGAAAACTCTTGCGGATGAACACACTCATGACGCGCCCTATGGAGGGTGTC

ATGCGAGATGATGTGGTCATACCAAATCTTGATGGTACTGCCAACATCAGACTGTTCATTTGTCGC

CCTCAAGACCCTACTGAGACTATGCCGGTGATACTTTGGTTACACGGAGGCGGTATGGTCGCAGGT

CATTACAAACAAGACTCCGGGTTCATGGACATCTGGGCCAAGCGCCTAGGAGCCTTTGTGGTTTCG

GTCGATTATCGTCTGGCTCCCGAGGCCAAGGCTCCAGCCGCTCTAGACGATTGCATCGCTGCTTGG

CAATGGATCACCACGCAGACCGCTCGAGGCATCGACACTACCCGCATGGCGGTGGGTGGTGCGAG

CGCAGGAGGAGGCCTGGCGGCCAGTACCGTTCAGCGACTTGTCGATCTCGGAGGAGTGAAACCTG

TCTTTCAATTGCTCATCTATCCCATGTTGGACGACAGGACGGTGGTCAGATTTGATCCCGACCGAA

GATATTACATGTGGACACCGGATTGTAATCGATATGGCTGGACCTCGTACCTCGGAGTCCCTCCAG

GGAGCGCTGAGGTGCCTCCCTATGCGTCGGCGGCACGTCGACCGGATCTATCAGGTCTACCTCCCA

CCTGGATCGGTGTTGGGTCACTGGATCTCTTTCACGACGAGGACATGGATTATGCGCGCAGGTTAC

GTGAGAGCGGAGTTCCGGTTGAGGAATATGTCGCTGTCGGAGCGCCTCATGCCTTCGACACGATAT

ATGGAAAGGCGAAGGTCACCTTGGATTTCTGGGACTCGCATTTCAACGCCCTTCGAAGGGCTTTGT

GTCTCGACTGA

SEQ ID NO 24: *Filobasidium magnum* SCH24-EST wt
MTHSPPLDAELSLLRYAPAVPVGWQLGRKLLRMNTLMTRPMEGVMRDDVVIPNLDGTANIRLFICRPQ

DPTETMPVILWLHGGGMVAGHYKQDSGFMDIWAKRLGAFVVSVDYRLAPEAKAPAALDDCIAAWQ

WITTQTARGIDTTRMAVGGASAGGGLAASTVQRLVDLGGVKPVFQLLIYPMLDDRTVVRFDPDRRYY

MWTPDCNRYGWTSYLGVPPGSAEVPPYASAARRPDLSGLPPTWIGVGSLDLFHDEDMDYARRLRESG

VPVEEYVAVGAPHAFDTIYGKAKVTLDFWDSHFNALRRALCLD

SEQ ID NO 25: *Filobasidium magnum* SCH24-EST *E. coli* optimized
ATGACCCACTCGCCGCCACTGGATGCCGAACTGAGCTTGCTGCGCTACGCCCCTGCCGTTCCGGTG

GGTTGGCAGCTGGGTCGCAAACTGCTGCGTATGAACACCTTGATGACCCGTCCGATGGAAGGTGTC

ATGCGCGACGATGTGGTTATTCCGAATCTGGACGGCACGGCTAACATCCGTCTGTTTATCTGTCGT

CCGCAAGACCCGACCGAGACTATGCCGGTTATCCTGTGGCTGCACGGTGGCGGCATGGTCGCAGG

CCACTACAAACAAGACAGCGGTTTCATGGACATTTGGGCGAAGCGCCTGGGTGCGTTTGTTGTTAG

CGTTGATTATCGCCTGGCGCCTGAGGCTAAGGCACCGGCAGCGCTCGATGACTGCATCGCGGCGTG

GCAGTGGATTACCACCCAGACCGCGCGTGGTATTGACACCACTCGTATGGCAGTGGGTGGTGCGA

GCGCGGGTGGCGGTCTGGCGGCAAGCACGGTTCAGCGTCTTGTCGATCTGGGCGGTGTGAAACCG

-continued

GTCTTTCAACTGCTGATCTATCCGATGCTGGACGATCGTACCGTGGTGCGCTTCGACCCGGATCGT

CGTTATTACATGTGGACGCCGGACTGCAACAGATACGGCTGGACCAGCTACCTGGGCGTGCCACC

GGGTAGCGCAGAGGTCCCGCCGTATGCCTCCGCGGCTCGTCGTCCGGATCTGTCCGGCCTGCCGCC

GACGTGGATCGGTGTCGGCTCTCTGGATCTGTTCCATGACGAAGATATGGATTACGCACGTCGTTT

GCGCGAGAGCGGTGTGCCGGTCGAAGAGTATGTTGCTGTGGGTGCCCCGCATGCGTTCGACACGA

TTTACGGCAAGGCCAAAGTTACGCTGGACTTTTGGGATAGCCACTTCAATGCGCTGCGCCGTGCGT

TGTGTTTAGACTAA

SEQ ID NO 26: *Filobasidium magnum* SCH24-EST Yeast optimized
ATGACTCACTCTCCACCATTGGACGCTGAATTGTCTTTGTTGAGATACGCTCCAGCTGTTCCAGTTG

GTTGGCAATTGGGTAGAAAGTTGTTGAGAATGAACACTTTGATGACTAGACCAATGGAAGGTGTT

ATGAGAGACGACGTTGTTATCCCAAACTTGGACGGTACTGCTAACATCAGATTGTTCATCTGTAGA

CCACAAGACCCAACTGAAACTATGCCAGTTATCTTGTGGTTGCACGGTGGTGGTATGGTTGCTGGT

CACTACAAGCAAGACTCTGGTTTCATGGACATCTGGGCTAAGAGATTGGGTGCTTTCGTTGTTTCT

GTTGACTACAGATTGGCTCCAGAAGCTAAGGCTCCAGCTGCTTTGGACGACTGTATCGCTGCTTGG

CAATGGATCACTACTCAAACTGCTAGAGGTATCGACACTACTAGAATGGCTGTTGGTGGTGCTTCT

GCTGGTGGTGGTTTGGCTGCTTCTACTGTTCAAAGATTGGTTGACTTGGGTGGTGTTAAGCCAGTTT

TCCAATTGTTGATCTACCCAATGTTGGACGACAGAACTGTTGTTAGATTCGACCCAGACAGAAGAT

ACTACATGTGGACTCCAGACTGTAACAGATACGGTTGGACTTCTTACTTGGGTGTTCCACCAGGTT

CTGCTGAAGTTCCACCATACGCTTCTGCTGCTAGAAGACCAGACTTGTCTGGTTTGCCACCAACTT

GGATCGGTGTTGGTTCTTTGGACTTGTTCCACGACGAAGACATGGACTACGCTAGAAGATTGAGAG

AATCTGGTGTTCCAGTTGAAGAATACGTTGCTGTTGGTGCTCCACACGCTTTCGACACTATCTACG

GTAAGGCTAAGGTTACTTTGGACTTCTGGGACTCTCACTTCAACGCTTTGAGAAGAGCTTTGTGTTT

GGACTAA

SEQ ID NO 27: *Papiliotrema laurentii* SCH25-EST wt
ATGCCTTCCAATCTCCCCCGACCAGCATATGACCCGGAAATAGAGCCATTCCTCTCTATGGTCCCA

TTACCACCAACAATCAATGCGGATATCATGAGAGAACTGCGTAAAGCGCCTCTACTCAGTCAAGC

GCCTGACCTCGACGCATTACTTTCCGGCAAACCAATAACTCACCGCGAAGTCAGCATTCCAGGTCT

CAATTCTTCAGATCCACAAATCACGTTGTCGATATTCTCCAGTACATTGACGAGCGGTCCAAAACC

ATGTATTTATTTCGTTCATGGTGGCGGTATGATCATCGGATGTCGATTCGTGGGTATTGAGGATTAT

CTTCAGTACGTCGAGCAGAATGACGCTGTCGTCGTGGCTGTGGAATATCGTCTTGCGCCGGAAAAT

CCAGATCCAGCGCCTGTCAATGATTGTTACGCTGGACTTCTATGGACCGCAGCAAATGCTGCAGAA

CTGGGCATTGATCTGGAGAGACTGTTGATCTGTGGCGCTTCTGCCGGTGGTGGTCTTTCTGCTGGA

GTGGCTTTGATGGCGCGAGACAAGAAAGGTCCGAAACTGGTAGGACAATTGTTATGTTATCCGAT

GCTCGACGATAGGAATGATTCCCTTTCAAGTCAGCAGTACGTCGATGAAGGTGTTTGGAGTCGTGG

TAGCAATGCATTCGGGTGGAAGCAATTGCTTGGAGACAGGGCAGGCAAAGAAGGTGTCAGCATCT

ATGCTGCACCGGCGAGGGCAACTGATTTGAGCGGACTGCCGAACACTTTCATCGACGTTGGCAGC

GCTGAAGTCTTCAGGGATGAGGACATCGCTTATGCCTCGAGGTTATGGGCTGTCGGTGTCCAAGCA

GAACTTCATGTGTGGCCGGGTGGATATCATGCTGCGGAAAACATGGCACCGGGGACTGACTACTC

TAACAAGGTGAAAGCTGCCCGCTTGGCATGGATGAAGAGAGTCTTCATGAAAGCCCCAAAGTCGA

CGACAGAGTCGTTACCTGCTCCAACAGTGGATGAAGCTGTTGGCACAATATGA

-continued

SEQ ID NO 28: *Papiliotrema laurentii* SCH25-EST wt
MPSNLPRPAYDPEIEPFLSMVPLPPTINADIMRELRKAPLLSQAPDLDALLSGKPITHREVSIPGLNSSDPQ

ITLSIFSSTLTSGPKPCIYFVHGGGMIIGCRFVGIEDYLQYVEQNDAVVVAVEYRLAPENPDPAPVNDCY

AGLLWTAANAAELGIDLERLLICGASAGGGLSAGVALMARDKKGPKLVGQLLCYPMLDDRNDSLSSQ

QYVDEGVWSRGSNAFGWKQLLGDRAGKEGVSIYAAPARATDLSGLPNTFIDVGSAEVFRDEDIAYAS

RLWAVGVQAELHVWPGGYHAAENMAPGTDYSNKVKAARLAWMKRVFMKAPKSTTESLPAPTVDEA

VGTI

SEQ ID NO 29: *Papiliotrema laurentii* SCH25-EST *E. coli* optimized
ATGCCAAGCAACTTGCCGCGCCCAGCCTACGATCCGGAAATTGAGCCTTTTCTGTCTATGGTCCCG

CTGCCGCCGACCATCAACGCGGACATTATGCGTGAGCTGCGTAAAGCCCCGCTGCTGAGCCAGGC

ACCGGACCTCGACGCACTGCTGAGCGGCAAGCCGATCACTCACCGTGAAGTCAGCATTCCGGGTC

TGAACAGCAGCGACCCGCAAATCACCCTGAGCATTTTCTCCAGCACGTTGACCAGCGGTCCGAAA

CCGTGCATCTATTTTGTGCACGGTGGCGGTATGATTATTGGTTGTCGCTTCGTCGGCATTGAAGATT

ATCTGCAATATGTTGAGCAAAATGACGCGGTGGTTGTGGCGGTTGAGTATCGTCTGGCCCCTGAAA

ATCCGGACCCGGCACCGGTTAATGATTGCTACGCGGGTCTGCTGTGGACCGCAGCGAACGCAGCG

GAGCTGGGTATCGATTTGGAACGCCTGCTGATCTGTGGCGCGAGCGCTGGCGGTGGTCTGAGCGC

GGGTGTGGCGCTGATGGCTCGCGACAAAAAGGGTCCAAAACTGGTCGGTCAGCTGTTGTGCTACC

CGATGCTGGACGATCGTAACGACAGCTTGAGCTCTCAACAGTACGTCGATGAGGGTGTTTGGAGC

CGTGGCAGCAATGCTTTCGGCTGGAAACAGCTGCTGGGCGATCGTGCGGGTAAGGAAGGCGTGTC

GATCTATGCCGCTCCGGCACGCGCAACCGATCTGTCTGGCCTGCCGAACACGTTCATCGATGTCGG

TAGCGCTGAGGTGTTTCGTGACGAAGATATCGCGTACGCCTCACGTCTGTGGGCCGTCGGTGTGCA

GGCCGAGCTGCATGTTTGGCCGGGTGGCTACCATGCAGCCGAGAATATGGCGCCTGGCACCGACT

ACTCCAATAAAGTGAAGGCAGCGCGCCTGGCGTGGATGAAGCGTGTGTTTATGAAAGCGCCGAAG

TCCACGACCGAGAGCCTGCCGGCACCGACCGTTGACGAAGCGGTTGGTACGATTTAA

SEQ ID NO 30: *Bensingtonia ciliata* SCH46-EST wt
ATGCCTTCCAATCTCCCTCGACCAGCATATGACCCGGAAATAGAGCCATTCCTCTCTATGGTCCCA

TTACCACCAACAATCAATGCGGATATCATGAGAGAACTGCGTAAAGCACCTCTACTCAGTCAAGC

GCCTGACCTCGACGCATTACTTTCCGGCAGACCGATAACTCACCGCGAAGTCAGCATTCCAGGTCT

CAATTCCCAGGATCCACAAATCACGTTGTCAATATTCTCCAGTACATTGACGAGCGGTCCAAAACC

ATGTATTTATTTCGTTCATGGTGGCGGTATGATCATCGGATGTCGATTCGTGGGTATTGAGGATTAT

CTTCAATACGTCGAGCAGAACGACGCTGTCGTTGTGGCTGTGGAATATCGTCTTGCTCCGGAAAAC

CCGGACCCAGCGCCTGTTAATGATTGTTACGCCGGACTTTTATGGACCGCAGCGAATGCTGCAGAG

CTAGGCATCGATCTGGAGAGACTGTTGATCTGTGGCGCTTCTGCCGGTGGTGGTCTTTCTGCTGGA

GTGGCATTGATGGCACGAGACAAGAAAGGTCCAAAATTGGTAGGACAATTGTTATGCTATCCAAT

GCTCGACGATAGGAATGATTCACTCTCAAGTCAGCAGTACGTGGATGAAGGTGTTTGGAGTCGTG

GTAGCAATGCATTTGGCTGGAAGCAATTGCTTGGAGACAGGGCGGGCAAAGAGGGAGTCAGTATT

TATGCTGCGCCGGCAAGAGCAACTGATTTGAGCGGACTGCCGAACACTTTCATCGACGTTGGCAGC

GCTGAGGTCTTCAGGGATGAGGACATCGCTTATGCCTCGAGGTTATGGGCTGTCGGTGTCCAAGCA

GAACTTCATGTGTGGCCCGGTGGATATCATGCTGCGGAGAACATGGCACCGGGGACTGACTACTCT

AAGAAGGTGAAAGCTGCGCGCTTGGCATGGATGAAGAGAGTCTTCCTGAAAGCCCCAAAGCCGAC

GACTGAGTCGTTGCCTGCTCCAACAGTGGATGAAGCTGTTGGCACAATATGA

-continued

SEQ ID NO 31: *Bensingtonia ciliata* SCH46-EST wt
MPSNLPRPAYDPEIEPFLSMVPLPPTINADIMRELRKAPLLSQAPDLDALLSGRPITHREVSIPGLNSQDP

QITLSIFSSTLTSGPKPCIYFVHGGGMIIGCRFVGIEDYLQYVEQNDAVVVAVEYRLAPENPDPAPVNDC

YAGLLWTAANAAELGIDLERLLICGASAGGGLSAGVALMARDKKGPKLVGQLLCYPMLDDRNDSLSS

QQYVDEGVWSRGSNAFGWKQLLGDRAGKEGVSIYAAPARATDLSGLPNTFIDVGSAEVFRDEDIAYA

SRLWAVGVQAELHVWPGGYHAAENMAPGTDYSKKVKAARLAWMKRVFLKAPKPTTESLPAPTVDE

AVGTI

SEQ ID NO 32: *Bensingtonia ciliata* SCH46-EST *E. coli* optimized
ATGCCATCGAATCTGCCGCGTCCAGCCTACGACCCTGAAATTGAACCTTTCTTGAGCATGGTGCCG

CTGCCGCCGACGATTAACGCTGATATCATGCGTGAGCTGCGCAAGGCACCGCTGCTGAGCCAAGC

GCCGGACCTGGATGCGCTGTTGAGCGGTCGCCCGATCACCCACCGCGAAGTCAGCATCCCGGGTCT

GAACTCTCAGGACCCGCAGATCACCTTGTCAATCTTTAGCAGCACCTTGACTTCCGGTCCGAAGCC

GTGCATTTATTTTGTCCACGGTGGTGGCATGATTATCGGCTGTCGTTTCGTTGGTATTGAAGATTAC

TTACAATATGTGGAACAAAATGATGCAGTGGTTGTGGCAGTGGAGTACCGCCTGGCGCCTGAGAA

CCCGGACCCAGCGCCGGTGAACGACTGCTACGCGGGTCTGTTGTGGACGGCAGCTAACGCAGCAG

AGCTGGGTATCGATCTGGAGCGCCTGCTGATCTGCGGTGCGAGCGCGGGTGGCGGCCTGTCCGCTG

GCGTTGCGCTGATGGCCCGTGACAAAAAGGGTCCGAAACTGGTTGGCCAGCTGCTGTGTTATCCGA

TGCTGGACGACCGTAATGACAGCCTGAGCAGCCAGCAATACGTGGATGAGGGCGTCTGGAGCCGT

GGTAGCAATGCGTTCGGTTGGAAGCAACTGCTGGGCGATCGTGCCGGCAAAGAGGGCGTTAGCAT

CTATGCGGCACCGGCGCGTGCCACGGATCTGTCTGGTCTGCCGAACACCTTCATTGACGTTGGTAG

CGCTGAAGTTTTTCGCGATGAAGATATTGCGTACGCGAGCCGTCTGTGGGCAGTCGGCGTCCAGGC

AGAGCTCCATGTCTGGCCGGGTGGCTATCATGCGGCCGAGAATATGGCACCGGGTACGGACTACA

GCAAAAAAGTTAAAGCTGCGCGTCTGGCCTGGATGAAGCGTGTTTTCCTGAAAGCGCCGAAGCCG

ACCACCGAGTCCCTGCCGGCACCGACCGTGGATGAAGCCGTGGGCACCATTTAA

SEQ ID NO 33: *Rhodococcus erythropolis* SCH94-3944 wt
ATGAATCTCAACGAAGCCCGAACTGCTTTCGCCCGGCTCCGTGCAGCGGAAAATGGTTTATCACCA

GCAGAACTCGACGAAGTGTGGGCCGCGCTGGAAACCGTCGCCGCTGAAGAAATCCTCGGTGAGTG

GAAAGGTGACGACTTCGCCACCGGTCATCGTCTGCACGAAAAGCTGTCCGCGAGCCGCTGGTACG

GCAAGACTTTCAATTCCGTCGAGGATGCCAAGCCGTTGATCTGCCGAGACGAAGACGGAAATCTC

TATTCCGACGTCAAGAGCGGCAATGGCGAGGCAAGTCTGTGGAACATCGAGTTTCGTGGTGAAGT

GACCGCGACCATGGTCTACGACGGCGCGCCGATTTTCGACCACTTCAAGAAAGTCGACGATTCGA

CGCTCATGGGCATCATGAACGGAAAGTCGGCGTTGGTCCTCGACGGCGGGCAGCACTACTACTTCC

TGCTCGAGCGAGCGTGA

SEQ ID NO 34: *Rhodococcus erythropolis* SCH94-3944 wt (WP_042451379)
MNTNEARTAFARIRAAENGTSPARIDEVWAATRTVAABETTGEWKGDDFATGHRIHEKISASRWYG

KTFNSVEDAKPLICRDEDGNLYSDVKSGNGEASLWNIEFRGEVTATMVYDGAPIFDHFKKVDDSTLMG

IMNGKSALVLDGGQHYYFLLERA

SEQ ID NO 35: *Rhodococcus erythropolis* SCH94-3944 *E. coli* optimized
ATGAACTTAAATGAAGCGCGTACCGCATTTGCACGTCTGAGAGCTGCCGAGAACGGTCTGAGCCC

GGCTGAGCTGGATGAAGTGTGGGCAGCGCTGGAGACTGTGGCGGCTGAAGAAATCCTGGGTGAGT

GGAAGGGTGACGATTTTGCGACGGGTCACCGTCTGCACGAGAAACTGTCGGCGAGCCGCTGGTAT

GGTAAGACCTTCAACTCTGTTGAAGATGCAAAGCCGCTGATTTGCCGTGACGAAGATGGCAATCTG

TACTCCGATGTCAAGAGCGGTAACGGTGAGGCCAGCCTGTGGAATATCGAGTTTCGCGGCGAAGT

-continued

CACCGCGACGATGGTTTACGATGGTGCCCCGATCTTCGACCATTTCAAAAAGTTGACGACAGCAC

CCTGATGGGCATTATGAATGGCAAAAGCGCGTTGGTGTTGGACGGTGGCCAGCATTACTATTTCCT

GCTGGAGCGTGCGTAA

SEQ ID NO 36: *Rhodococcus erythropolis* SCH94-3944 Yeast optimized
ATGAACTTGGACGAAGCTAGAACTGCTTTCGCTAGATTGAGAGCTGCTGAATCTGGTGTTTCTCCA

GCTGAATTGGACGAAGTTTGGGCTGCTTTGGAAACTGTTGCTGCTGAAGAAATCTTGGGTGAATGG

AAGGGTGACGACTTCGCTACTGGTCACAGATTGCACGAAAAGTTGTTCGCTTCTAGATGGTACGGT

AAGACTTTCAACTCTGTTGAAGACGCTAAGCCATTGATCTGTAGAGACGAAGACGGTAACTTGTAC

TCTGACGTTAAGTCTGGTAACGGTGAAGCTTCTTTGTGGAACATCGAATTCAGAGGTGAAGTTACT

GCTACTATGGTTTACGACGGTGCTCCAATCTTCGACCACTTCAAGAAGGTTGACGACTCTACTTTG

ATGGGTATCATGAACGGTAAGTCTGCTTTGGTTTTGGACGGTGGTCAACACTACTACTTCTTGTTGG

AAAGAGCTTAA

SEQ ID NO 37: *Rhodococcus rhodochrous* SCH80-05241 wt
ATGAATCTCGACGAAGCCCGAACTGCTTTCGCCCGGCTCCGTGCTGCGGAAAGTGGTGTATCACCA

GCAGAACTCGACGAAGTGTGGGCCGCGCTGGAAACCGTCGCCGCCGAAGAAATCCTCGGCGAGTG

GAAGGGTGACGACTTCGCCACCGGTCACCGTCTTCACGAAAAGCTGTTCGCGAGCCGTTGGTACG

GCAAGACCTTCAACTCGGTCGAGGACGCCAAGCCGTTGATCTGCCGAGACGAAGACGGCAACCTC

TACTCCGACGTCAAGAGCGGCAATGGCGAGGCAAGTCTGTGGAACATCGAGTTTCGTGGCGAAGT

CACGGCGACGATGGTCTACGACGGCGCGCCGATCTTCGACCACTTCAAGAAGGTCGACGATTCGA

CGCTCATGGGCATCATGAACGGAAAATCGGCGTTGGTTCTCGACGGCGGACAGCACTACTACTTCC

TGCTCGAGCGAGCGTGA

SEQ ID NO 38: *Rhodococcus rhodochrous* SCH80-05241 wt
MNLDEARTAFARLRAAESGVSPAELDEVWAALETVAAEEILGEWKGDDFATGHRLHEKLFASRWYG

KTFNSVEDAKPLICRDEDGNLYSDVKSGNGEASLWNIEFRGEVTATMVYDGAPIFDHFKKVDDSTLMG

IMNGKSALVLDGGQHYYFLLERA*

SEQ ID NO 39: *Rhodococcus rhodochrous* SCH80-05241 *E. coli* optimized
ATGAATCTGGACGAAGCCCGTACTGCTTTCGCCCGTCTGCGCGCTGCTGAATCTGGTGTTAGCCCG

GCAGAGCTGGACGAAGTGTGGGCAGCGCTGGAAACCGTTGCGGCGGAAGAAATTCTGGGTGAGTG

GAAGGGCGATGACTTCGCAACGGGCCATCGCTTGCACGAGAAATTGTTCGCGAGCCGCTGGTATG

GTAAGACCTTTAACAGCGTCGAAGATGCGAAACCGCTGATCTGCCGTGATGAAGATGGCAACCTG

TACAGCGACGTCAAGAGCGGTAATGGTGAGGCCAGCCTGTGGAATATCGAGTTTCGTGGCGAAGT

GACCGCGACGATGGTGTACGACGGTGCACCGATTTTTGATCATTTCAAAAAAGTCGATGACAGCA

CCCTGATGGGCATCATGAACGGTAAGTCCGCGCTGGTTCTGGACGGTGGCCAGCACTATTACTTTC

TGCTGGAGCGTGCGTAA

SEQ ID NO 40: *Rhodococcus rhodochrous* SCH80-05241 Yeast optimized
ATGAACTTGAACGAAGCTAGAACTGCTTTCGCTAGATTGAGAGCTGCTGAAAACGGTTTGTCTCCA

GCTGAATTGGACGAAGTTTGGGCTGCTTTGGAAACTGTTGCTGCTGAAGAAATCTTGGGTGAATGG

AAGGGTGACGACTTCGCTACTGGTCACAGATTGCACGAAAAGTTGTCTGCTTCTAGATGGTACGGT

AAGACTTTCAACTCTGTTGAAGACGCTAAGCCATTGATCTGTAGAGACGAAGACGGTAACTTGTAC

TCTGACGTTAAGTCTGGTAACGGTGAAGCTTCTTTGTGGAACATCGAATTCAGAGGTGAAGTTACT

GCTACTATGGTTTACGACGGTGCTCCAATCTTCGACCACTTCAAGAAGGTTGACGACTCTACTTTG

ATGGGTATCATGAACGGTAAGTCTGCTTTGGTTTTGGACGGTGGTCAACACTACTACTTCTTGTTGG

AAAGAGCTTAA

-continued

SEQ ID NO 41: *Penicillium disitatum* Pdigit7033 wt
ATGTCCACAAGCACCCCACAGGATCAGTTTGCTGCCCTAGTTGCAAAAAACAGCAAGTTGAATGA

AACCGACATCGAGGCTGTTTATAACAAGCTTTCAGCTCTTCCCGTCGATTTCCTCCGTGGAGAATG

GAAGGGTGGAAGCTTCGACACCGGCCACCCAGGCCACACCCAGCTTTTGGCTATGAACTGGGTTG

GAAAGACGTTCCACGATACCGAGCGCGTCGACCCTATTGTTGTGTTAAAGGATGGAAAGCGTGTA

TGCGATGAGAACTGGGGCCATGCTATCGTCCGTGAGGTTCGTTTCCGTGGTATTGTGTCAACCGCT

ATGATCTATGACAAGCACCCTATCATTGATCACTTCCGCTATGTTAATGAGAACCTCGTTGCTGGC

GCCATGGACACTAGCTCCTTCGGTGACGTTGGTACCTACTACTTCTACCTATACAAATAG

SEQ ID NO 42: *Penicillium disitatum* Pdigit7033 wt
MSTSTPQDQFAALVAKNSKLNETDIEAVYNKLSALPVDFLRGEWKGGSFDTGHPGHTQLLAMNWVG

KTFHDTERVDPIVVLKDGKRVCDENWGHAIVREVRFRGIVSTAMIYDKHPIIDHFRYVNENLVAGAMD

TSSFGDVGTYYFYLYK*

SEQ ID NO 43: *Penicillium disitatum* Pdigit7033 *E. coli* optimized
ATGTCCACTAGCACCCCACAAGATCAATTTGCCGCACTGGTTGCCAAAAACTCTAAACTGAATGAA

ACCGACATTGAAGCTGTCTATAACAAGTTGAGCGCGTTGCCGGTGGATTTCCTGCGTGGCGAGTGG

AAGGGCGGCAGCTTCGACACCGGTCACCCGGGTCACACGCAGCTGCTGGCAATGAATTGGGTCGG

TAAGACCTTTCATGATACCGAGCGTGTGGACCCGATCGTCGTTCTGAAGGACGGTAAACGTGTGTG

CGACGAGAATTGGGGTCACGCGATCGTTCGCGAAGTTCGCTTCCGTGGTATCGTGAGCACCGCGAT

GATCTATGATAAACACCCGATTATTGATCATTTCCGCTATGTTAACGAAAACCTGGTCGCGGGTGC

GATGGATACGTCGAGCTTTGGCGACGTGGGCACGTACTACTTTTACCTGTACAAATAA

SEQ ID NO 44: *Penicillium digitatum* Pdigit7033 Yeast optimized
ATGTCTACTTCTACTCCACAAGACCAATTCGCTGCTTTGGTTGCTAAGAACTCTAAGTTGAACGAA

ACTGACATCGAAGCTGTTTACAACAAGTTGTCTGCTTTGCCAGTTGACTTCTTGAGAGGTGAATGG

AAGGGTGGTTCTTTCGACACTGGTCACCCAGGTCACACTCAATTGTTGGCTATGAACTGGGTTGGT

AAGACTTTCCACGACACTGAAAGAGTTGACCCAATCGTTGTTTTGAAGGACGGTAAGAGAGTTTGT

GACGAAAACTGGGGTCACGCTATCGTTAGAGAAGTTAGATTCAGAGGTATCGTTTCTACTGCTATG

ATCTACGACAAGCACCCAATCATCGACCACTTCAGATACGTTAACGAAAACTTGGTTGCTGGTGCT

ATGGACACTTCTTCTTTCGGTGACGTTGGTACTTACTACTTCTACTTGTACAAGTAA

SEQ ID NO 45: *Penicillium italicum* PitalDUF4334-1 wt (JQGA01001114.1
71518-72084 (+))
ATGTCGGCCAGTGACCCCAAGGACCAGTTTGCTGCCCTAGTTGCCAAGGACGGCAAGTTGAATGA

AGACGAAATCGAGGCTGTTTACAACAAGCTTCCTGCTCTTCCCCTCGATTTCCTCCGTGGAGAATG

GAAGGGTGGAAGCTTCGACACCGGTCACCCTGGTCACACCCAACTCTTGGCAATGAAATGGGTTG

GGAAGACATTCCATTCCACCGAACGGGTTGACCCTATTGTTGTGTTAAAGGATGAAAAGCGTGTAT

GCAATGAGGACTGGGGCCATGCAGTCCTCCGTGAGATTCGTTTCCGTGGTATTGTGTCATCTGCTA

TGATCTATGACAAGCACCCTATCATCGACCACTTCCGCTATGTCAACGACAAGCTCATTGCTGGCG

CCATGGACACTAGCAGCTTCGGTGACGTTGGCACCTACTACTTCTACCTGTGCAAATAG

SEQ ID NO 46: *Penicillium italicum* PitalDUF4334-1 wt (KGO69886.1)
MSASDPKDQFAALVAKDGKLNEDEIEAVYNKLPALPLDFLRGEWKGGSFDTGHPGHTQLLAMKWVG

KTFHSTERVDPIVVLKDEKRVCNEDWGHAVLREIRFRGIVSSAMIYDKHPIIDHFRYVNDKLIAGAMDT

SSFGDVGTYYFYLCK*

SEQ ID NO 47: *Penicillium italicum* PitalDUF4334-1 *E. coli* optimized
ATGAGCGCTTCGGACCCAAAAGATCAATTCGCAGCATTGGTGGCAAAGGACGGTAAACTGAACGA

AGATGAAATCGAAGCCGTCTATAACAAGCTGCCTGCGCTGCCGCTGGACTTCTTGCGTGGTGAGTG

-continued

GAAGGGCGGCAGCTTTGATACCGGTCATCCGGGCCACACTCAGCTGCTGGCGATGAAATGGGTGG

GTAAAACCTTTCACAGCACCGAGCGCGTGGACCCGATCGTCGTTCTGAAAGATGAGAAGCGTGTC

TGTAATGAAGATTGGGGTCACGCCGTGCTGCGCGAGATTCGTTTTCGCGGTATCGTTTCTAGCGCG

ATGATTTATGACAAGCATCCGATTATTGACCACTTCCGTTACGTTAATGACAAGCTGATCGCGGGT

GCGATGGATACGTCCAGCTTTGGCGACGTTGGCACGTACTATTTCTACCTGTGCAAATAA

SEQ ID NO 48: *Aspergillus wentii* AspWe DUF4334 wt (LJSE01000065.1 (263404 to 263924))
ATGAGCTGTTGCACCGCCGAGGACCAGGCCAAACGGCTCTTCGAAGCGACCAGCCCCGTCCAACC

ATCAGCAGTCGAAGAACTCTTCAACCAACTCCAACCGATAAAGCCCTCATTCCTGATTGGCGAATG

GGACGGAAATAGCCTGGACACCGGCCATCCCGGTCTCAAGCTGCTCCAGGCGATGCGGTGGGCGG

GTAAGACATTTCGATCCGTGGATGACGCCGATCCGATTGTGACGCTGGACGATGCTGGCAATCGCA

TCTGGAAAGAGGAGTACGGTAATGCTGTGGTACGAGAAATGGCGTTTCGCGGAGTCGTTTCGGCG

GCGATGATCTACGACACCAAGCCCATCATGGACCATTTTCGATACGTGGACGAAAAGACAGTGCT

GGGTGTGATGGAAACCCCCAAGCAGGCTGGAAGCGGAACCTTTTATTTCTATCTGCAGCGTCGTGC

TTCTGTCTAA

SEQ ID NO 49: *Aspergillus wentii* AspWe DUF4334 wt (OJJ43591)
MSCCTAEDQAKRLFEATSPVQPSAVEELFNQLQPIKPSFLIGEWDGNSLDTGHPGLKLLQAMRWAGKT

FRSVDDADPIVTLDDAGNRIWKEEYGNAVVREMAFRGVVSAAMIYDTKPIMDHFRYVDEKTVLGVM

ETPKQAGSGTFYFYLQRRASV

SEQ ID NO 50: *Aspergillus wentii* AspWe DUF4334 *E. coli* optimized
ATGTCGTGTTGCACCGCCGAAGATCAAGCCAAACGTCTGTTCGAAGCCACTAGCCCGGTTCAACCG

AGCGCGGTCGAAGAACTGTTCAATCAGCTGCAACCGATTAAGCCTTCCTTCCTGATCGGTGAGTGG

GATGGCAACAGCCTGGATACCGGTCATCCGGGCTTGAAGCTGCTGCAGGCAATGCGCTGGGCGGG

TAAGACCTTTCGTTCTGTGGATGACGCTGACCCAATTGTTACCCTGGACGACGCGGGTAATCGTAT

TTGGAAAGAGGAATACGGTAACGCAGTGGTTCGCGAGATGGCGTTTCGTGGTGTGGTCAGCGCGG

CAATGATCTATGACACGAAGCCGATCATGGATCACTTTCGCTATGTTGACGAGAAAACGGTCCTGG

GCGTGATGGAAACGCCGAAACAGGCTGGTAGCGGCACCTTCTACTTTTACTTGCAGCGTCGTGCGA

GCGTCTAA

SEQ ID NO 51: *Aspergillus wentii* AspWe DUF4334 Yeast optimized
ATGTCTTGTTGTACTGCTGAAGACCAAGCTAAGAGATTGTTCGAAGCTACTTCTCCAGTTCAACCA

TCTGCTGTTGAAGAATTGTTCAACCAATTGCAACCAATCAAGCCATCTTTCTTGATCGGTGAATGG

GACGGTAACTCTTTGGACACTGGTCACCCAGGTTTGAAGTTGTTGCAAGCTATGAGATGGGCTGGT

AAGACTTTCAGATCTGTTGACGACGCTGACCCAATCGTTACTTTGGACGACGCTGGTAACAGAATC

TGGAAGGAAGAATACGGTAACGCTGTTGTTAGAGAAATGGCTTTCAGAGGTGTTGTTTCTGCTGCT

ATGATCTACGACACTAAGCCAATCATGGACCACTTCAGATACGTTGACGAAAAGACTGTTTTGGGT

GTTATGGAAACTCCAAAGCAAGCTGGTTCTGGTACTTTCTACTTCTACTTGCAAAGAAGAGCTTCT

GTTTAA

SEQ ID NO 52: *Rhodococcus hoagii* strain PAM2288 RhoagDUF4334-2 wt (NZ LWTW01000167.1 18658-19134 (-))
ATGAACGTACGAGACGAGGTCGCCGCGCTGCGGGCGCGCACCGACCGGATCGATCCGCGGGAACT

CGATTCGATCTGGGACCGCTTGGCCCCGTGTCGGCCCGTGGATCTGATCGGGTACCGCTGGAGGGG

TTTCGACTTCGACACCGGACATCGCACGAGTGGGCTCCTCCGTCGAGCTCATTGGTACGGCAAGGC

ATTCGCCAGCGAGTCCGACGTGCAGCCTCTGCTGTGCCGCAGCGAGGACGGACAGCTGTTCTCCGA

CATCGGAACCGGGCACGGCGAGGCCAGCCTGTGGGAGGTCGTGTTCCGCGGGGAGGTGACCGCGA

-continued

CGATGGTCTACGACGGCATGCCGGTGTTCGACCACTTCAAGAAGGTCGACGACGACACCGTCATC

GGCGTCATGAACGGCAAGGGCACGTTGGTGTTCGACGGCGGCGAACACTTCTGGTTCGGGCTGGA

GCGAGACGTCGCACTCTGA

SEQ ID NO 53: *Rhodococcus hoagii* strain PAM2288 RhoagDUF4334-2 wt (WP_005516054)

MNVRDEVAALRARTDRIDPRELDSIWDRLAPCRPVDLIGYRWRGFDFDTGHRTSGLLRRAHWYGKAF

ASESDVQPLLCRSEDGQLFSDIGTGHGEASLWEVVFRGEVTATMVYDGMPVFDHFKKVDDDTVIGVM

NGKGTLVFDGGEHFWFGLERDVAL*

SEQ ID NO 54: *Rhodococcus hoagii* strain PAM2288 RhoagDUF4334-2 *E. coli* optimized

ATGAATGTTCGTGATGAAGTTGCAGCTCTGCGTGCCCGTACTGATAGAATCGACCCGCGTGAGCTG

GATAGCATTTGGGACCGTCTGGCACCATGTCGTCCGGTGGACCTGATCGGTTACCGTTGGCGCGGT

TTCGATTTCGACACCGGTCACCGTACCTCCGGTCTGTTGCGTCGCGCGCATTGGTATGGTAAGGCC

TTTGCGAGCGAGAGCGACGTGCAACCGTTGCTGTGCCGCTCTGAGGACGGCCAGCTGTTTAGCGAT

ATTGGCACCGGTCACGGTGAGGCGAGCCTGTGGGAAGTTGTCTTTCGCGGCGAAGTGACCGCGAC

GATGGTTTACGACGGTATGCCGGTGTTCGACCACTTCAAAAAAGTTGATGACGACACGGTGATCG

GTGTCATGAACGGCAAGGGCACGCTGGTCTTTGATGGTGGCGAGCATTTCTGGTTTGGCCTGGAAC

GCGATGTCGCGCTGTAA

SEQ ID NO 55: *Rhodococcus hoagii* strain N128 RhoagDUF4334-3 wt (NZ LRQY01000021.1 163210-163686 (-))

ATGAACGTACGAGACGAGGTCGCCGCGCTGCGGGCGCGCACCGACCGGATCGATCCGCGGGAACT

CGATTCGATCTGGGACCGCTTGGCCCCGTGTCGGCCCGTGGATCTGATCGGGTACCGCTGGAGGGG

TTTCGACTTCGACACCGGACATCGCACGAGTGGGCTCCTCCGTCGAGCTCATTGGTACGGCAAGGC

ATTCGCCAGCGAGTCCGACGTGCAGCCTCTGCTGTGCCGCAGCGACGACGGACAGCTGTTCTCCGA

CATCGGAACCGGGCACGGCGAGGCCAGCCTGTGGGAGGTCGTGTTCCGCGGGGAGGTGACCGCGA

CGATGGTCTACGACGGCATGCCGGTGTTCGACCACTTCAAGAAGGTCGACGACGACACCGTCATC

GGCGTCATGAACGGCAAGGGCACGTTGGTGTTCGACGGCGGCGAACACTTCTGGTTCGGGCTGGA

GCGAGACGTCGCACTCTGA

SEQ ID NO 56: *Rhodococcus hoagii* strain N128 RhoagDUF4334-3 wt (WP_013414658)

MNVRDEVAALRARTDRIDPRELDSIWDRLAPCRPVDLIGYRWRGFDFDTGHRTSGLLRRAHWYGKAF

ASESDVQPLLCRSDDGQLFSDIGTGHGEASLWEVVFRGEVTATMVYDGMPVFDHFKKVDDDTVIGVM

NGKGTLVFDGGEHFWFGLERDVAL*

SEQ ID NO 57: *Rhodococcus hoagii* strain N128 RhoagDUF4334-3 *E. coli* optimized

ATGAATGTTCGTGATGAAGTTGCAGCTCTGCGTGCCCGTACTGATAGAATCGACCCGCGTGAGCTG

GATAGCATTTGGGACCGTCTGGCACCATGTCGTCCGGTGGACCTGATCGGTTACCGTTGGCGCGGT

TTCGATTTCGACACCGGTCACCGTACCTCCGGTCTGTTGCGTCGCGCGCATTGGTATGGTAAGGCC

TTTGCGAGCGAGAGCGACGTGCAACCGTTGCTGTGCCGCTCTGATGACGGCCAGCTGTTTAGCGAT

ATTGGCACCGGTCACGGTGAGGCGAGCCTGTGGGAAGTTGTCTTTCGCGGCGAAGTGACCGCGAC

GATGGTTTACGACGGTATGCCGGTGTTCGACCACTTCAAAAAAGTTGATGACGACACGGTGATCG

GTGTCATGAACGGCAAGGGCACGCTGGTCTTTGATGGTGGCGAGCATTTCTGGTTTGGCCTGGAAC

GCGATGTCGCGCTGTAA

SEQ ID NO 58: *Rhodococcus hoagii* RhoagDUF4334-4 wt (NZ BCRL01000037.1 133790-134266 (+))

ATGAACGTACGAGACGAGGTCGCCGCGCTGCGGGCGCGCACCGACCGGATCGATCCGCGGGAACT

CGATTCGATCTGGGACCGCTTGGCCCCGTGTCGGCCCGTGGATCTGATCGGGTACCGCTGGCGGGG

-continued

TTTCGACTTCGACACCGGACATCGCACGAGTGGGCTCCTCCGTCGAGCGCATTGGTACGGCAAGGC

ATTCGCCAGCGAGTCCGACGTGCAGCCTCTGCTGTGCCGCAGCGAGGACGGACAGCTGTTCTCCGA

CATCGGAACCGGGCACGGCGAGGCCAGCCTGTGGGAGGTCGTGTTCCGCGGGGAGGTGACCGCGA

CGATGGTCTACGACGGCATGCCGGTGTCCGACCACTTCAAGAAGGTCGACGACGACACCGTCATC

GGCGTCATGAACGGCAAGGGCACGTTGGTGTTCGACGGCGGCGAACACTTCTGGTTCGGGCTGGA

GCGAGACGTCGCACTCTGA

SEQ ID NO 59: *Rhodococcus hoagii* RhoagDUF4334-4 wt (WP_022593671)
MNVRDEVAALRARTDRIDPRELDSIWDRLAPCRPVDLIGYRWRGFDFDTGHRTSGLLRRAHWYGKAF

ASESDVQPLLCRSEDGQLFSDIGTGHGEASLWEVVFRGEVTATMVYDGMPVSDHFKKVDDDTVIGVM

NGKGTLVFDGGEHFWFGLERDVAL*

SEQ ID NO 60: *Rhodococcus hoagii* RhoagDUF4334-4 *E. coli* optimized
ATGAATGTTCGTGATGAAGTTGCAGCTCTGCGTGCCCGTACTGATAGAATCGACCCGCGTGAGCTG

GATAGCATTTGGGACCGTCTGGCACCATGTCGTCCGGTGGACCTGATCGGTTACCGTTGGCGCGGT

TTCGATTTCGACACCGGTCACCGTACCTCCGGTCTGTTGCGTCGCGCGCATTGGTATGGTAAGGCC

TTTGCGAGCGAGAGCGACGTGCAACCGTTGCTGTGCCGCTCTGAGGACGGCCAGCTGTTTAGCGAT

ATTGGCACCGGTCACGGTGAGGCGAGCCTGTGGGAAGTTGTCTTTCGCGGCGAAGTGACCGCGAC

GATGGTTTACGACGGTATGCCGGTGAGCGACCACTTCAAAAAAGTTGATGACGACACGGTGATCG

GTGTCATGAACGGCAAGGGCACGCTGGTCTTTGATGGTGGCGAGCATTTCTGGTTTGGCCTGGAAC

GCGATGTCGCGCTGTAA

SEQ ID NO 61: *Cupriavidus necator* CnecaDUF4334 wt (CP002879.1: 512553-513138)
ATGCTGACAGAAATGCTGCGGAATCGAGTCTCTACAACTGCGGCGGTACTGGCCGCTTTCGATGAA

CTTGATCCATTATCGAGCGATTCGCTAGTTGGCTGCTGGAGTGGTTTTGTGATCGCTACCGGGCAC

CCCATGGACGGTCTTCTGAGCGCTGTCGGCTGGTACGGGAAAATGTTCCAAAGCGTGGATGAGGC

ATATCCGCTGATCATCCGGTCCCCGGACGCCAGTACGCTTTTTTCGATCGATCCCAGCCCTTTGCCA

CTTATAGGCTGCGCGAAGTTATCTCCCACGGATATGGTGTCGCGTTTTTCAACACTTTCCCCGTTGG

CCCTGAGCACAACCGTCTCTCACGGTCGGCTGCGTATGGTCGAGTATCGCGGAAAGGTCACAGGA

ACTCTGATCTACGACCAGCAGCCGATACTCGATCATTTCGTGATGATTGATTCGCAAACGGTACTT

GGAATTATGGATTTTAAAGAGTTCCCGCAGCCAGGCGCGTTTGTGCTGCAGCGCGATGACGACAGT

GCCGTCAGCGTTGATCGCGGCGACTGGTCCCAACTGGCGGCGCAACGGCTCGGGTGA

SEQ ID NO 62: *Cupriavidus necator* CnecaDUF4334 wt (WP_049800708)
MLTEMLRNRVSTTAAVLAAFDELDPLSSDSLVGCWSGFVIATGHPMDGLLSAVGWYGKMFQSVDEA

YPLIIRSPDASTLFSIDPSPLPLIGCAKLSPTDMVSRFSTLSPLALSTTVSHGRLRMVEYRGKVTGTLIYDQ

QPILDHFVMIDSQTVLGIMDFKEFPQPGAFVLQRDDDSAVSVDRGDWSQLAAQRLG*

SEQ ID NO 63: *Cupriavidus necator* CnecaDUF4334 *E. coli* optimized
ATGTTGACTGAAATGCTGCGTAACCGTGTGTCTACCACTGCCGCTGTCCTGGCCGCTTTTGACGAG

CTGGACCCGCTGTCATCCGACAGCCTGGTTGGCTGCTGGAGCGGTTTCGTTATCGCGACGGGTCAC

CCTATGGATGGTCTGCTGAGCGCGGTGGGCTGGTACGGTAAAATGTTCCAGAGCGTTGATGAAGC

ATACCCGCTGATCATCCGCTCCCCGGACGCGAGCACGCTGTTTAGCATTGATCCGTCCCCGCTGCC

GCTGATTGGTTGTGCGAAGCTGTCGCCAACCGATATGGTGAGCCGCTTCAGCACCTTAAGCCCGCT

GGCGCTGAGCACCACCGTATCTCACGGTCGTCTGCGTATGGTTGAGTATCGTGGTAAGGTTACCGG

CACGCTCATCTATGACCAACAGCCGATTTTGGATCATTTCGTCATGATTGACAGCCAAACGGTGCT

-continued

GGGCATCATGGATTTCAAAGAATTTCCGCAGCCGGGTGCGTTTGTCTTGCAGCGTGACGACGATAG

CGCAGTCAGCGTGGATCGCGGCGACTGGAGCCAACTGGCAGCCCAACGCCTGGGCTAA

SEQ ID NO 64: *Cupriavidus necator* CnecaDUF4334 Yeast optimized
ATGTTGACTGAAATGTTGAGAAACAGAGTTTCTACTACTGCTGCTGTTTTGGCTGCTTTCGACGAAT

TGGACCCATTGTCTTCTGACTCTTTGGTTGGTTGTTGGTCTGGTTTCGTTATCGCTACTGGTCACCCA

ATGGACGGTTTGTTGTCTGCTGTTGGTTGGTACGGTAAGATGTTCCAATCTGTTGACGAAGCTTACC

CATTGATCATCAGATCTCCAGACGCTTCTACTTTGTTCTCTATCGACCCATCTCCATTGCCATTGAT

CGGTTGTGCTAAGTTGTCTCCAACTGACATGGTTTCTAGATTCTCTACTTTGTCTCCATTGGCTTTGT

CTACTACTGTTTCTCACGGTAGATTGAGAATGGTTGAATACAGAGGTAAGGTTACTGGTACTTTGA

TCTACGACCAACAACCAATCTTGGACCACTTCGTTATGATCGACTCTCAAACTGTTTTGGGTATCAT

GGACTTCAAGGAATTCCCACAACCAGGTGCTTTCGTTTTGCAAAGAGACGACGACTCTGCTGTTTC

TGTTGACAGAGGTGACTGGTCTCAATTGGCTGCTCAAAGATTGGGTTAA

SEQ ID NO 65: *Penicillium italicum* PitalDUF4334-2 wt (JQGA01000120.1 65652-66635 (+))
ATGACAATCCAATTCCCAATCATGTCATTCGACTGTTTCCAGCCAAGCCCAGCCAAGAAATTCGTC

TCTCTCACCAAACACCCTCGGGTGACTGGTGGGAAAATCAACACCGTCTTTCCTGAGCTCAAGCCT

CTTCAGCCAGACGACCTAATCGGCGAATGGGACGGATATATTCTTGTCACGGGCCACCCCTTTGAA

GAAGAACTGGACACGCTGAATTGGTTCGGAAATACATTTTATTCCACCGACGACGTGGCACCGCTG

ACTGTTGCGCGGAACGGGGTGCGGGTGCCCTTCGAGGATTGGGGGCGTGCATCTCTACGTGAAAT

CAAATATCAAGGAGTCGTCTCTGCGGCTTTGGTCTATGATAAACGACCAATGATGGTCTATTATCG

AGCCGTGAAACATAACATGGTGGCTGGGGGTATTGAGAGTAAAGAGTGGTAG

SEQ ID NO 66: *Penicillium italicum* PitalDUF4334-2 wt (KGO77618.1)
MTIQFPIMSFDCFQPSPAKKFVSLTKHPRVTGGKINTVFPELKPLQPDDLIGEWDGYILVTGHPFEEELDT

LNWFGNTFYSTDDVAPLTVARNGVRVPFEDWGRASLREIKYQGVVSAALVYDKRPMMVYYRAVKH

NMVAGGIESKEW*

SEQ ID NO 67: *Penicillium italicum* PitalDUF4334-2 *E. coli* optimized
ATGACCATTCAATTTCCTATCATGTCTTTTGATTGTTTTCAGCCGAGCCCAGCGAAGAAATTCGTGA

GCTTGACGAAACATCCGCGTGTTACCGGTGGCAAGATCAATACGGTTTTCCCGGAACTGAAACCGC

TGCAACCGGACGACCTGATCGGTGAGTGGGACGGTTACATTCTGGTGACGGGCCACCCGTTCGAA

GAAGAACTGGATACCTTGAACTGGTTCGGCAATACTTTCTATAGCACCGACGATGTCGCTCCGCTG

ACCGTCGCCCGCAACGGTGTGCGTGTTCCGTTTGAGGATTGGGGTCGTGCGTCCCTGCGTGAGATC

AAGTACCAGGGTGTGGTTAGCGCAGCGCTGGTCTACGACAAACGCCCGATGATGGTGTATTATCG

CGCAGTTAAGCACAACATGGTCGCGGGTGGCATTGAGAGCAAAGAGTGGTAA

SEQ ID NO 68: *Ralstonia insidiosa* Rins-DUF4334 wt (NZ PKPC01000002.1 18273-18773 (-))
ATGAACACGAAGCAGAAATTCGATCAACTCAAGAGCACGGAACGCCTGAATGACGAAATCCTGTT

GGAGTTCTTCGACACCCTTCCCCCCGTTTCTACGGACGAAGCGCTGGGTCGCTGGAAAGGCGGTGA

CTTCAATACGGGGCATTGGGGCAACCTCGCTCTGAAAGCAAGGAAGTGGTACGGAAAGTGGTATC

GCAGCAAGCTGGATGCGGTACCGCTTATCTGTTACGACGACCAAGGCCGCCTATATTCCAGCAAG

GCCATGAAGGGCGAAGCGTCGCTTTGGGATGTGGCGTTCCGCGGAAAGGTCTCGACCACCATGAT

CTACGACGGCGTGCCGATCTTCGATCATTTGCGCAAGGTCGACGAGAACACGCTGTTCGGCATCAT

GGATGGCAAATCGTTTGAGGGGTCCCCCGACATCATCGACCGCGGCAAGTACTACTTTTTCTACCT

CGAGAGGGTAGACAGCTTCCCGGCCGAATATCTGGAAGGCTGA

-continued

SEQ ID NO 69: *Ralstonia insidiosa* Rins-DUF4334 wt (WP_104654734)
MNTKQKFDQLKSTERLNDEILLEFFDTLPPVSTDEALGRWKGGDFNTGHWGNLALKARKWYGKWYR

SKLDAVPLICYDDQGRLYSSKAMKGEASLWDVAFRGKVSTTMIYDGVPIFDHLRKVDENTLFGIMDG

KSFEGSPDIIDRGKYYFFYLERVDSFPAEYLEG*

SEQ ID NO 70: *Ralstonia insidiosa* Rins-DUF4334 *E. coli* optimized
ATGAACACCAAGCAAAAGTTTGACCAGCTGAAGTCCACCGAGCGCCTGAATGATGAAATCCTGTT

GGAATTTTTCGATACCCTGCCTCCGGTGAGCACCGATGAAGCGCTGGGCCGTTGGAAGGGTGGCG

ACTTCAATACGGGTCATTGGGGTAACCTGGCCCTGAAAGCGCGTAAATGGTACGGCAAATGGTAT

CGCAGCAAACTGGACGCAGTTCCACTGATTTGCTATGACGATCAGGGCCGTCTGTACTCTAGCAAG

GCTATGAAAGGTGAGGCGAGCCTGTGGGATGTTGCGTTTCGTGGTAAAGTGAGCACGACTATGAT

CTACGACGGTGTCCCGATTTTCGACCACTTGCGTAAAGTCGATGAGAACACGCTGTTTGGTATCAT

GGATGGTAAGTCGTTCGAGGGTAGCCCGGACATTATCGACCGTGGCAAGTACTATTTCTTTTATCT

GGAGCGCGTTGACAGCTTCCCGGCAGAGTACCTGGAAGGCTAA

SEQ ID NO 71: *Cryptococcus gattii* EJB2 CgatDUF4334 wt (KN848661.1 262486-263032 (-))
ATGTCCCCTCAGGAACAGTATATTGCTCTCGTCCAGGCCGGCGGCAAGTCGGACCCATCCACCATT

GAAGCTCTTTTCCAAGCGCTTCCGCCGGTCAAGCCCACTCAGCTGCTAGGCGACTGGAATCACGGC

GGATTTTTCGACACAGGCCATCCGGTTAACGAGCAACTCAAAGAGATTAAATGGATTGGAAAGTC

ATTTAAGTCCGTCGAAGATGTTGATCCTGTGATTATTGACCAGGATGGTAAGCCAACTAGCTGGAG

GAAGTGGGGGTCAGCCAGCCTGCGAGAGATGGTGTATGAAGGCACTGTATCAACGTCGATGATAT

ATGATGACCGACCAATCATCGATCACTTCCGCTACGTAGATGACGACTTTATGGCGGGGATAATGG

AAGGGAAGGCTCTGGGGGAGGCGGGGAAGTTTTATTTCTATTTGAGAAGATAG

SEQ ID NO 72: *Cryptococcus gattii* EJB2 CgatDUF4334 wt (KIR80015)
MSPQEQYIALVQAGGKSDPSTIEALFQALPPVKPTQLLGDWNHGGFFDTGHPVNEQLKEIKWIGKSFKS

VEDVDPVIIDQDGKPTSWRKWGSASLREMVYEGTVSTSMIYDDRPIIDHFRYVDDDFMAGIMEGKALG

EAGKFYFYLRR*

SEQ ID NO 73: *Cryptococcus gattii* EJB2 CgatDUF4334 *E. coli* optimized
ATGAGCCCACAAGAACAATACATTGCATTAGTCCAGGCCGGTGGTAAGAGCGATCCTAGCACGAT

CGAAGCGCTGTTTCAGGCATTGCCGCCGGTTAAACCGACCCAGCTGCTGGGCGATTGGAATCACG

GTGGCTTCTTTGACACGGGCCATCCGGTGAACGAACAACTGAAAGAAATCAAGTGGATTGGCAAA

TCCTTCAAATCGGTCGAAGATGTTGATCCGGTGATCATCGACCAGGACGGTAAGCCGACTAGCTGG

CGTAAGTGGGGTTCTGCGAGCCTGCGTGAGATGGTTTATGAGGGCACCGTGAGCACCAGCATGAT

TTATGACGACCGCCCGATCATTGATCACTTTCGTTACGTCGATGACGACTTCATGGCTGGTATTATG

GAAGGCAAGGCACTGGGTGAGGCCGGTAAATTCTACTTTTATCTGCGCCGTTAA

SEQ ID NO 74: *Grosmannia clavigera* kw1407 GclavDUF4334 wt (XM_014316402.1)
ATGACAGCTGTACAGCGATTTAACGCACTCACCAAAGCAGAAGGGCTTCTCAAGGAGTCTGAGCT

TGCACAAATTTTCGACGAGCTCCCTCCTGTTTCTCCAGAAGCTATGACAGGCAAGTGGAATGGAGG

CAGCTTTGACAGTGGCCATCCTGTCCACAAGCTGCTTCAAACTTTTAAATGGGCAGGGAAAGAATT

CCGCTCCGTTGACGATATCGACCCGATTGTGATCTTCGACGAAAATGGGGAGCGAAAGTGGCTATC

CGAGTATGGACATGCAAGACTGCGTGAAGTTAAGTTTCGGGGAGTTGTATCTGCCGCCTTGGTATA

CGACAAAGTTGCCATTATCGACTCGTTTCGTCGGGTTTCGGACAACGTGCTGATGGGAACTATGGA

CGCCAGGGACTGGCCGGATGCTGGCATCTACTACTTTTACATCACCAAGTTTGAAGAATTGTGA

-continued

SEQ ID NO 75: *Grosmannia clavigera* kw1407 GclavDUF4334 wt (XP_014171877.1)
MTAVQRFNALTKAEGLLKESELAQIFDELPPVSPEAMTGKWNGGSFDSGHPVHKLLQTFKWAGKEFR

SVDDIDPIVIFDENGERKWLSEYGHARLREVKFRGVVSAALVYDKVAIIDSFRRVSDNVLMGTMDARD

WPDAGIYYFYITKFEEL*

SEQ ID NO 76: *Grosmannia clavigera* kw1407 GclavDUF4334 *E. coli* optimized
ATGACTGCTGTTCAACGTTTTAACGCATTGACCAAAGCCGAGGGTTTGCTGAAAGAATCTGAGCTG

GCACAGATTTTCGACGAACTGCCGCCGGTTAGCCCAGAGGCCATGACCGGTAAGTGGAATGGTGG

CAGCTTTGATTCCGGCCATCCGGTGCACAAGCTGCTGCAGACGTTCAAATGGGCGGGTAAAGAATT

TCGTAGCGTTGACGACATTGACCCGATCGTGATCTTTGATGAGAATGGCGAGCGCAAGTGGCTGA

GCGAGTATGGTCACGCACGCCTGCGTGAAGTGAAGTTCCGTGGTGTCGTCAGCGCGGCTCTGGTCT

ATGACAAAGTCGCGATCATTGACAGCTTCCGCCGTGTTAGCGATAACGTGCTGATGGGTACGATGG

ATGCGCGTGATTGGCCGGATGCGGGCATTTACTACTTCTACATCACCAAGTTTGAAGAACTGTAA

SEQ ID NO 77: *Oidiodendron maius* Zn OmaiusDUF4334 wt (KN832882.1 673187-675938 (-))
ATGGCTTCTACTTTATATGAAGCTAGAGTTATTTTGGCACTTAAAGCTATTCAAAACAGCAACAAT

CTTAGCTTACGAGCTGCAGCAAAGCTGTATGATGTACAGCCAACAACCCTATATTACCGACAAGCT

GGCCGACCTGCACGACATGATATTCCACCTAACTCTCGCAAGCTTACGGATCTAGAAGAGGAGAC

GATTGTTCGCCCGACGGAACAGTTTATTGCCCTAGCTCAGGCCCAGGGCCGGCTTGATGCCACATT

GATTGACGCGGTGTTTAACAAGTTTGGCCCAGTCAAGCCAGAGCTGATGCTAGGCAAGTGGAGTG

GTGGGATTTTAGACACCGGCCATCCTATGGGAGATACACTGAAGGAGATACGATGGGTGGGCAAG

AATTTCACCTCCACTGAACACGTGGACCCGGTTATTATCGACAAGAACGGCCAAAGGGCCAGCTG

GGGGAAGTGGGGCCTTGCTACCCTACGTGAGGTCTTGTATCGAGATGTTGTCTCGACGGCGATGAT

CTACGATGACCGCCCGGTCTTTGACTATTTCCGTTTCGCTAATGATGATATGGTTGCTGGTATCATG

GAAGGGAAGGAGTTGGGAGGGAGACTTTTCTATTTCTACCTGAAGAGATAG

SEQ ID NO 78: *Oidiodendron maius* Zn OmaiusDUF4334 wt (KIM97275)
MASTLYEARVILALKAIQNSNNLSLRAAAKLYDVQPTTLYYRQAGRPARHDIPPNSRKLTDLEEETIVR

PTEQFIALAQAQGRLDATLIDAVFNKFGPVKPELMLGKWSGGILDTGHPMGDTLKEIRWVGKNFTSTE

HVDPVIIDKNGQRASWGKWGLATLREVLYRDVVSTAMIYDDRPVFDYFRFANDDMVAGIMEGKELG

GRLFYFYLKR*

SEQ ID NO 79: *Oidiodendron maius* Zn OmaiusDUF4334 *E. coli* optimized
ATGGCAAGCACTTTGTATGAAGCTCGCGTGATTCTGGCGCTGAAAGCGATTCAAAATAGCAACAA

TCTGAGCTTGCGTGCAGCCGCGAAGCTCTATGATGTCCAGCCGACCACGCTGTACTATCGTCAGGC

CGGTCGTCCAGCTCGCCACGACATCCCGCCGAACTCCCGTAAGCTGACCGATCTGGAAGAGGAAA

CGATCGTTCGCCCGACCGAGCAATTCATCGCGTTAGCACAAGCACAGGGCCGTCTGGATGCGACC

CTGATTGATGCAGTTTTCAATAAGTTTGGTCCGGTGAAGCCTGAGCTGATGCTGGGTAAGTGGAGC

GGTGGCATTCTGGACACGGGTCACCCGATGGGCGATACCCTGAAAGAAATCCGTTGGGTGGGTAA

AAATTTCACCAGCACCGAACATGTTGATCCGGTCATCATTGACAAAAACGGTCAGCGCGCTTCTTG

GGGCAAGTGGGGTCTGGCCACCTTGCGTGAAGTTCTGTACCGCGACGTCGTCAGCACGGCGATGA

TTTACGATGACCGTCCGGTGTTTGACTATTTTCGTTTCGCGAACGACGACATGGTTGCGGGTATCAT

GGAAGGCAAAGAACTGGGTGGCCGTCTGTTTTACTTCTACCTGAAACGCTAA

SEQ ID NO 80: *Thermomonospora curvata* TcurvaDUF4334 wt (NC_013510.1)
ATGGATGCGGAACAGCGCCTTGCCAAGATCATCGCGTCCGGCGACGAGTGCGACCGGGCCACCGT

GGAGGAACTGTACGACCGGCTGGCCCCCGTGCCGGTGGACTTCATGCTCGGCACCTGGCGGGGCG

-continued

GCATCTTCGACCGGGGCGACGCGCTGGCGGGGATGCTGCTGGGGATGAACTGGTACGGCAAGCGG

TTCATCGACCGCGACCACGTCGAGCCGCTGCTGTGCCGCTCCCCCGACGGCTCGATCTACTCCTAC

GAGAAGCTCGGGCTGGCCCGGCTGCGCGAGGTCGCCCTGCGCGGCACGGTCTCGGCGGCCATGAT

CTACGACAAGCAGCCCATCATCGACCACTTCCGGCGGGTCAACGACGACATGGTGGTCGGCGCCA

TGGACGCCAAGGGCCAGCCCGACATCCTCTACTTCCACCTCACCCGGGAACGCTGA

SEQ ID NO 81: *Thermomonospora curvata* TcurvaDUF4334 wt (WP_012851400.1)
MDAEQRLAKIIASGDECDRATVEELYDRLAPVPVDFMLGTWRGGIFDRGDALAGMLLGMNWYGKRFI

DRDHVEPLLCRSPDGSIYSYEKLGLARLREVALRGTVSAAMIYDKQPIIDHFRRVNDDMVVGAMDAK

GQPDILYFHLTRER*

SEQ ID NO 82: *Thermomonospora curvata* TcurvaDUF4334 *E. coli* optimized
ATGGATGCGGAACAAAGACTGGCTAAAATTATTGCATCTGGTGATGAGTGTGATCGTGCAACCGT

GGAAGAACTGTATGACCGTTTGGCCCCTGTCCCGGTTGACTTCATGCTGGGTACGTGGCGTGGTGG

CATCTTCGATCGTGGTGATGCGCTGGCGGGTATGCTGCTGGGTATGAATTGGTATGGCAAGCGCTT

TATCGACCGCGACCACGTCGAGCCACTGCTGTGCCGTAGCCCGGATGGCTCCATCTACAGCTACGA

GAAACTGGGTCTGGCCCGTTTGCGCGAAGTGGCACTGCGTGGCACCGTTAGCGCGGCTATGATTTA

TGACAAACAGCCGATTATCGACCATTTCCGTCGCGTGAACGACGACATGGTTGTCGGCGCGATGG

ATGCGAAGGGTCAGCCGGACATCCTGTACTTTCACCTGACCCGCGAGCGTTAA

SEQ ID NO 83: *Pseudomonas litoralis* DlitoDUF4334 wt (NZ LT629748.1 3096922-3097413 (+))
ATGACTGCAACACTGGCCGCCCTCAGCCTGACCACCCTGCTTGCCGGGCCCAGTCTGGCCGCAGAT

ACGGAACAGCAATGGCTGGAGATGATCGCCAGCGGTGAAGCCTATTCGGCGGACACCCTGGTGCC

TCTGTTCAAACAACTCGAACCGGTGGATACCGACTTCATGGTCGGCACATGGAAGGGCGGCAAGT

TCGACGGCGGCGCCGAGCCGGACCCGATCAACTGGTACGGCAAACGTTTCACCTCGACCACCGAT

GTCGAGCCGTTATTGGTAAACGATGCCGAGGGCGAGGTGATCACCCACGACCGGCTCGGCGCCGC

ACAGATGCGCCAGGTGGTGTTCGATGGGAAGGTATCGGCCGCGTTGATCTACGACAGCCAGCCGA

TCATGGATTACCTCCGCAAGGTCAACGAGGATGTGGTCATCGGCCTGGGCGACATCAAGGGCAAG

CCTACCGATTTCTTTTTCTATCTGGTACGCGATTAA

SEQ ID NO 84: *Pseudomonas litoralis* DlitoDUF4334 wt (WP_090274689)
MTATLAALSLTTLLAGPSLAADTEQQWLEMIASGEAYSADTLVPLFKQLEPVDTDFMVGTWKGGKFD

GGAEPDPINWYGKRFTSTTDVEPLLVNDAEGEVITHDRLGAAQMRQVVFDGKVSAALIYDSQPIMDYL

RKVNEDVVIGLGDIKGKPTDFFFYLVRD*

SEQ ID NO 85: *Pseudomonas litoralis* DlitoDUF4334 *E. coli* optimized
ATGACTGCGACTTTGGCTGCTCTGAGCTTGACGACCCTGTTGGCTGGCCCATCTTTGGCTGCGGAC

ACCGAGCAGCAATGGCTGGAAATGATTGCAAGCGGCGAGGCGTATAGCGCGGACACCCTGGTGCC

GCTGTTCAAGCAACTGGAGCCTGTCGATACGGACTTCATGGTCGGCACGTGGAAGGGCGGCAAAT

TTGATGGTGGTGCCGAACCGGACCCGATTAACTGGTACGGTAAGCGTTTTACCAGCACGACCGATG

TGGAGCCGCTGCTGGTGAATGACGCCGAGGGTGAAGTTATCACCCACGATCGTCTGGGTGCGGCA

CAGATGCGCCAAGTTGTTTTTGATGGCAAAGTCTCCGCAGCGCTGATCTACGACAGCCAGCCGATT

ATGGACTATCTGCGCAAAGTGAACGAAGATGTTGTCATCGGTCTGGGTGACATCAAGGGTAAACC

GACCGACTTTTTCTTCTACCTGGTTCGTGATTAA

SEQ ID NO 86: *Pseudomonas protegens* PprotDUF4334 wt (NC_021237.1 5528027-5528524 (-))
ATGAATACGAAAGAAAAGTTTGAACAGCTTAAGAGCACGCAAGGTCTTAATGATGAAGTACTGTT

GGACTTCTTTGACTCGCTTTCTCCAGTCACAATCGATGGCGCGTTGGGCCGTTGGCAAGGTGGTGA

-continued

CTTCAAGACAGGACACTGGGGCAATGACGCACTTACCGGAATGAAGTGGTACGGAAAGTGGTACC

GGAGCAAGTTGGATGCCGTTCCCCTAGTCTGCTACGACGAACAGGGCCGACTATTTTCCAACAAGA

TCATGAAAGGTGAGGCCTCTCTCTGGGAGGTGGCGTTTCGTGGCAAGGTTTCGACTACGATGATCT

ACGATGGCGTTCCGATTTATGATCACTTGCGCAAGGTCGATGACAACACCCTTTTCGGGATCATGG

ATGGTAAGTCCTTTGAGGGGCAGCTCCCCGACATCATCGACAATGGCAAGTACTACTTCTTCTACC

TCGAAAGGGTCGATGGCTTCCCTGTCGAGTTCGTCTAG

SEQ ID NO 87: *Pseudomonas protegens* PprotDUF4334 wt (WP_015636872.1)
MNTKEKFEQLKSTQGLNDEVLLDFFDSLSPVTIDGALGRWQGGDFKTGHWGNDALTGMKWYGKWY

RSKLDAVPLVCYDEQGRLFSNKIMKGEASLWEVAFRGKVSTTMIYDGVPIYDHLRKVDDNTLFGIMD

GKSFEGQLPDIIDNGKYYFFYLERVDGFPVEFV*

SEQ ID NO 88: *Pseudomonas protegens* PprotDUF4334 *E. coli* optimized
ATGAACACGAAAGAAAAGTTTGAACAGTTGAAAAGCACCCAAGGTCTGAACGATGAAGTTTTGCT

GGATTTCTTCGATAGCCTGAGCCCAGTGACCATTGACGGTGCACTGGGCCGTTGGCAGGGTGGCGA

CTTCAAGACCGGTCACTGGGGCAACGACGCGCTGACTGGCATGAAATGGTACGGTAAATGGTATC

GCAGCAAACTGGATGCTGTGCCGCTGGTGTGCTACGACGAACAGGGTCGTCTGTTTTCCAATAAGA

TCATGAAAGGTGAGGCCAGCCTGTGGGAAGTCGCGTTCCGCGGTAAGGTTAGCACGACGATGATT

TATGATGGTGTGCCGATCTATGACCATCTGCGTAAAGTTGATGACAATACCCTGTTTGGCATCATG

GATGGCAAGTCTTTTGAGGGTCAACTGCCGGACATCATTGACAATGGCAAGTACTACTTCTTCTAC

CTGGAGCGTGTTGACGGTTTTCCGGTCGAGTTCGTCTAA

SEQ ID NO 89: Artificial SCH91-3944-W44A variant
MNLNEARTAFARLRAAENGLSPAELDEVWAALETVAAEEILGEAKGDDFATGHRLHEKLSASRWYGK

TFNSVEDAKPLICRDEDGNLYSDVKSGNGEASLWNIEFRGEVTATMVYDGAPIFDHFKKVDDSTLMGI

MNGKSALVLDGGQHYYFLLERA

SEQ ID NO 90: Artificial SCH91-3944-W44A *E. coli* optimized
ATGAACTTAAATGAAGCGCGTACCGCATTTGCACGTCTGAGAGCTGCCGAGAACGGTCTGAGCCC

GGCTGAGCTGGATGAAGTGTGGGCAGCGCTGGAGACTGTGGCGGCTGAAGAAATCCTGGGTGAGG

CAAAGGGTGACGATTTTGCGACGGGTCACCGTCTGCACGAGAAACTGTCGGCGAGCCGCTGGTAT

GGTAAGACCTTCAACTCTGTTGAAGATGCAAAGCCGCTGATTTGCCGTGACGAAGATGGCAATCTG

TACTCCGATGTCAAGAGCGGTAACGGTGAGGCCAGCCTGTGGAATATCGAGTTTCGCGGCGAAGT

CACCGCGACGATGGTTTACGATGGTGCCCCGATCTTCGACCATTTCAAAAAAGTTGACGACAGCAC

CCTGATGGGCATTATGAATGGCAAAAGCGCGTTGGTGTTGGACGGTGGCCAGCATTACTATTTCCT

GCTGGAGCGTGCGTAA

SEQ ID NO 91: Artificial SCH91-3944-T51A variant
MNLNEARTAFARLRAAENGLSPAELDEVWAALETVAAEEILGEWKGDDFAAGHRLHEKLSASRWYG

KTFNSVEDAKPLICRDEDGNLYSDVKSGNGEASLWNIEFRGEVTATMVYDGAPIFDHFKKVDDSTLMG

IMNGKSALVLDGGQHYYFLLERA

SEQ ID NO 92: Artificial SCH91-3944-T51A *E. coli* optimized

ATGAACTTAAATGAAGCGCGTACCGCATTTGCACGTCTGAGAGCTGCCGAGAACGGTCTGAGCCC

GGCTGAGCTGGATGAAGTGTGGGCAGCGCTGGAGACTGTGGCGGCTGAAGAAATCCTGGGTGAGT

GGAAGGGTGACGATTTTGCGGCCGGTCACCGTCTGCACGAGAAACTGTCGGCGAGCCGCTGGTAT

GGTAAGACCTTCAACTCTGTTGAAGATGCAAAGCCGCTGATTTGCCGTGACGAAGATGGCAATCTG

TACTCCGATGTCAAGAGCGGTAACGGTGAGGCCAGCCTGTGGAATATCGAGTTTCGCGGCGAAGT

CACCGCGACGATGGTTTACGATGGTGCCCCGATCTTCGACCATTTCAAAAAAGTTGACGACAGCAC

-continued

CCTGATGGGCATTATGAATGGCAAAAGCGCGTTGGTGTTGGACGGTGGCCAGCATTACTATTTCCT

GCTGGAGCGTGCGTAA

SEQ ID NO 93: Artificial SCH91-3944-H53A variant
MNLNEARTAFARLRAAENGLSPAELDEVWAALETVAAEEILGEWKGDDFATGARLHEKLSASRWYG

KTFNSVEDAKPLICRDEDGNLYSDVKSGNGEASLWNIEFRGEVTATMVYDGAPIFDHFKKVDDSTLMG

IMNGKSALVLDGGQHYYFLLERA

SEQ ID NO 94: Artificial SCH91-3944-H53A *E. coli* optimized
ATGAACTTAAATGAAGCGCGTACCGCATTTGCACGTCTGAGAGCTGCCGAGAACGGTCTGAGCCC

GGCTGAGCTGGATGAAGTGTGGGCAGCGCTGGAGACTGTGGCGGCTGAAGAAATCCTGGGTGAGT

GGAAGGGTGACGATTTTGCGACGGGTGCACGTCTGCACGAGAAACTGTCGGCGAGCCGCTGGTAT

GGTAAGACCTTCAACTCTGTTGAAGATGCAAAGCCGCTGATTTGCCGTGACGAAGATGGCAATCTG

TACTCCGATGTCAAGAGCGGTAACGGTGAGGCCAGCCTGTGGAATATCGAGTTTCGCGGCGAAGT

CACCGCGACGATGGTTTACGATGGTGCCCCGATCTTCGACCATTTCAAAAAAGTTGACGACAGCAC

CCTGATGGGCATTATGAATGGCAAAAGCGCGTTGGTGTTGGACGGTGGCCAGCATTACTATTTCCT

GCTGGAGCGTGCGTAA

SEQ ID NO 95: Artificial SCH91-3944-L59A variant
MNLNEARTAFARLRAAENGLSPAELDEVWAALETVAAEEILGEWKGDDFATGHRLHEKASASRWYG

KTFNSVEDAKPLICRDEDGNLYSDVKSGNGEASLWNIEFRGEVTATMVYDGAPIFDHFKKVDDSTLMG

IMNGKSALVLDGGQHYYFLLERA

SEQ ID NO 96: Artificial SCH91-3944-L59A *E. coli* optimized
ATGAACTTAAATGAAGCGCGTACCGCATTTGCACGTCTGAGAGCTGCCGAGAACGGTCTGAGCCC

GGCTGAGCTGGATGAAGTGTGGGCAGCGCTGGAGACTGTGGCGGCTGAAGAAATCCTGGGTGAGT

GGAAGGGTGACGATTTTGCGACGGGTCACCGTCTGCACGAGAAAGCATCGGCGAGCCGCTGGTAT

GGTAAGACCTTCAACTCTGTTGAAGATGCAAAGCCGCTGATTTGCCGTGACGAAGATGGCAATCTG

TACTCCGATGTCAAGAGCGGTAACGGTGAGGCCAGCCTGTGGAATATCGAGTTTCGCGGCGAAGT

CACCGCGACGATGGTTTACGATGGTGCCCCGATCTTCGACCATTTCAAAAAAGTTGACGACAGCAC

CCTGATGGGCATTATGAATGGCAAAAGCGCGTTGGTGTTGGACGGTGGCCAGCATTACTATTTCCT

GCTGGAGCGTGCGTAA

SEQ ID NO 97: Artificial SCH91-3944-W64A variant
MNLNEARTAFARLRAAENGLSPAELDEVWAALETVAAEEILGEWKGDDFATGHRLHEKLSASRAYGK

TFNSVEDAKPLICRDEDGNLYSDVKSGNGEASLWNIEFRGEVTATMVYDGAPIFDHFKKVDDSTLMGI

MNGKSALVLDGGQHYYFLLERA

SEQ ID NO 98: Artificial SCH91-3944-W64A *E. coli* optimized

ATGAACTTAAATGAAGCGCGTACCGCATTTGCACGTCTGAGAGCTGCCGAGAACGGTCTGAGCCC

GGCTGAGCTGGATGAAGTGTGGGCAGCGCTGGAGACTGTGGCGGCTGAAGAAATCCTGGGTGAGT

GGAAGGGTGACGATTTTGCGACGGGTCACCGTCTGCACGAGAAACTGTCGGCGAGCCGCGCCTAT

GGTAAGACCTTCAACTCTGTTGAAGATGCAAAGCCGCTGATTTGCCGTGACGAAGATGGCAATCTG

TACTCCGATGTCAAGAGCGGTAACGGTGAGGCCAGCCTGTGGAATATCGAGTTTCGCGGCGAAGT

CACCGCGACGATGGTTTACGATGGTGCCCCGATCTTCGACCATTTCAAAAAAGTTGACGACAGCAC

CCTGATGGGCATTATGAATGGCAAAAGCGCGTTGGTGTTGGACGGTGGCCAGCATTACTATTTCCT

GCTGGAGCGTGCGTAA

-continued

SEQ ID NO 99: Artificial SCH91-3944-K67A variant
MNLNEARTAFARLRAAENGLSPAELDEVWAALETVAAEEILGEWKGDDFATGHRLHEKLSASRWYG

ATFNSVEDAKPLICRDEDGNLYSDVKSGNGEASLWNIEFRGEVTATMVYDGAPIFDHFKKVDDSTLMG

IMNGKSALVLDGGQHYYFLLERA

SEQ ID NO 100: Artificial SCH91-3944-K67A *E. coli* optimized
ATGAACTTAAATGAAGCGCGTACCGCATTTGCACGTCTGAGAGCTGCCGAGAACGGTCTGAGCCC

GGCTGAGCTGGATGAAGTGTGGGCAGCGCTGGAGACTGTGGCGGCTGAAGAAATCCTGGGTGAGT

GGAAGGGTGACGATTTTGCGACGGGTCACCGTCTGCACGAGAAACTGTCGGCGAGCCGCTGGTAT

GGTGCAACCTTCAACTCTGTTGAAGATGCAAAGCCGCTGATTTGCCGTGACGAAGATGGCAATCTG

TACTCCGATGTCAAGAGCGGTAACGGTGAGGCCAGCCTGTGGAATATCGAGTTTCGCGGCGAAGT

CACCGCGACGATGGTTTACGATGGTGCCCCGATCTTCGACCATTTCAAAAAAGTTGACGACAGCAC

CCTGATGGGCATTATGAATGGCAAAAGCGCGTTGGTGTTGGACGGTGGCCAGCATTACTATTTCCT

GCTGGAGCGTGCGTAA

SEQ ID NO 101: Artificial SCH91-3944-S71A variant
MNLNEARTAFARLRAAENGLSPAELDEVWAALETVAAEEILGEWKGDDFATGHRLHEKLSASRWYG

KTFNAVEDAKPLICRDEDGNLYSDVKSGNGEASLWNIEFRGEVTATMVYDGAPIFDHFKKVDDSTLM

GIMNGKSALVLDGGQHYYFLLERA

SEQ ID NO 102: Artificial SCH91-3944-S71A *E. coli* optimized
ATGAACTTAAATGAAGCGCGTACCGCATTTGCACGTCTGAGAGCTGCCGAGAACGGTCTGAGCCC

GGCTGAGCTGGATGAAGTGTGGGCAGCGCTGGAGACTGTGGCGGCTGAAGAAATCCTGGGTGAGT

GGAAGGGTGACGATTTTGCGACGGGTCACCGTCTGCACGAGAAACTGTCGGCGAGCCGCTGGTAT

GGTAAGACCTTCAACGCAGTTGAAGATGCAAAGCCGCTGATTTGCCGTGACGAAGATGGCAATCT

GTACTCCGATGTCAAGAGCGGTAACGGTGAGGCCAGCCTGTGGAATATCGAGTTTCGCGGCGAAG

TCACCGCGACGATGGTTTACGATGGTGCCCCGATCTTCGACCATTTCAAAAAAGTTGACGACAGCA

CCCTGATGGGCATTATGAATGGCAAAAGCGCGTTGGTGTTGGACGGTGGCCAGCATTACTATTTCC

TGCTGGAGCGTGCGTAA

SEQ ID NO 103: Artificial SCH91-3944-R106A variant
MNLNEARTAFARLRAAENGLSPAELDEVWAALETVAAEEILGEWKGDDFATGHRLHEKLSASRWYG

KTFNSVEDAKPLICRDEDGNLYSDVKSGNGEASLWNIEFAGEVTATMVYDGAPIFDHFKKVDDSTLMG

IMNGKSALVLDGGQHYYFLLERA

SEQ ID NO 104: Artificial SCH91-3944-R106A *E. coli* optimized
ATGAACTTAAATGAAGCGCGTACCGCATTTGCACGTCTGAGAGCTGCCGAGAACGGTCTGAGCCC

GGCTGAGCTGGATGAAGTGTGGGCAGCGCTGGAGACTGTGGCGGCTGAAGAAATCCTGGGTGAGT

GGAAGGGTGACGATTTTGCGACGGGTCACCGTCTGCACGAGAAACTGTCGGCGAGCCGCTGGTAT

GGTAAGACCTTCAACTCTGTTGAAGATGCAAAGCCGCTGATTTGCCGTGACGAAGATGGCAATCTG

TACTCCGATGTCAAGAGCGGTAACGGTGAGGCCAGCCTGTGGAATATCGAGTTTGCAGGCGAAGT

CACCGCGACGATGGTTTACGATGGTGCCCCGATCTTCGACCATTTCAAAAAAGTTGACGACAGCAC

CCTGATGGGCATTATGAATGGCAAAAGCGCGTTGGTGTTGGACGGTGGCCAGCATTACTATTTCCT

GCTGGAGCGTGCGTAA

SEQ ID NO 105: Artificial SCH91-3944-Y115A variant
MNLNEARTAFARLRAAENGLSPAELDEVWAALETVAAEEILGEWKGDDFATGHRLHEKLSASRWYG

KTFNSVEDAKPLICRDEDGNLYSDVKSGNGEASLWNIEFRGEVTATMVADGAPIFDHFKKVDDSTLMG

IMNGKSALVLDGGQHYYFLLERA

-continued

SEQ ID NO 106: Artificial SCH91-3944-Y115A *E. coli* optimized
ATGAACTTAAATGAAGCGCGTACCGCATTTGCACGTCTGAGAGCTGCCGAGAACGGTCTGAGCCC

GGCTGAGCTGGATGAAGTGTGGGCAGCGCTGGAGACTGTGGCGGCTGAAGAAATCCTGGGTGAGT

GGAAGGGTGACGATTTTGCGACGGGTCACCGTCTGCACGAGAAACTGTCGGCGAGCCGCTGGTAT

GGTAAGACCTTCAACTCTGTTGAAGATGCAAAGCCGCTGATTTGCCGTGACGAAGATGGCAATCTG

TACTCCGATGTCAAGAGCGGTAACGGTGAGGCCAGCCTGTGGAATATCGAGTTTCGCGGCGAAGT

CACCGCGACGATGGTTGCCGATGGTGCCCCGATCTTCGACCATTTCAAAAAAGTTGACGACAGCAC

CCTGATGGGCATTATGAATGGCAAAAGCGCGTTGGTGTTGGACGGTGGCCAGCATTACTATTTCCT

GCTGGAGCGTGCGTAA

SEQ ID NO 107: Artificial SCH91-3944-D116A variant
MNLNEARTAFARLRAAENGLSPAELDEVWAALETVAAEEILGEWKGDDFATGHRLHEKLSASRWYG

KTFNSVEDAKPLICRDEDGNLYSDVKSGNGEASLWNIEFRGEVTATMVYAGAPIFDHFKKVDDSTLMG

IMNGKSALVLDGGQHYYFLLERA

SEQ ID NO 108: Artificial SCH91-3944-D116A *E. coli* optimized
ATGAACTTAAATGAAGCGCGTACCGCATTTGCACGTCTGAGAGCTGCCGAGAACGGTCTGAGCCC

GGCTGAGCTGGATGAAGTGTGGGCAGCGCTGGAGACTGTGGCGGCTGAAGAAATCCTGGGTGAGT

GGAAGGGTGACGATTTTGCGACGGGTCACCGTCTGCACGAGAAACTGTCGGCGAGCCGCTGGTAT

GGTAAGACCTTCAACTCTGTTGAAGATGCAAAGCCGCTGATTTGCCGTGACGAAGATGGCAATCTG

TACTCCGATGTCAAGAGCGGTAACGGTGAGGCCAGCCTGTGGAATATCGAGTTTCGCGGCGAAGT

CACCGCGACGATGGTTTACGCCGGTGCCCCGATCTTCGACCATTTCAAAAAAGTTGACGACAGCAC

CCTGATGGGCATTATGAATGGCAAAAGCGCGTTGGTGTTGGACGGTGGCCAGCATTACTATTTCCT

GCTGGAGCGTGCGTAA

SEQ ID NO 109: Artificial SCH91-3944-D122A variant
MNLNEARTAFARLRAAENGLSPAELDEVWAALETVAAEEILGEWKGDDFATGHRLHEKLSASRWYG

KTFNSVEDAKPLICRDEDGNLYSDVKSGNGEASLWNIEFRGEVTATMVYDGAPIFAHFKKVDDSTLMG

IMNGKSALVLDGGQHYYFLLERA

SEQ ID NO 110: Artificial SCH91-3944-D122A *E. coli* optimized
ATGAACTTAAATGAAGCGCGTACCGCATTTGCACGTCTGAGAGCTGCCGAGAACGGTCTGAGCCC

GGCTGAGCTGGATGAAGTGTGGGCAGCGCTGGAGACTGTGGCGGCTGAAGAAATCCTGGGTGAGT

GGAAGGGTGACGATTTTGCGACGGGTCACCGTCTGCACGAGAAACTGTCGGCGAGCCGCTGGTAT

GGTAAGACCTTCAACTCTGTTGAAGATGCAAAGCCGCTGATTTGCCGTGACGAAGATGGCAATCTG

TACTCCGATGTCAAGAGCGGTAACGGTGAGGCCAGCCTGTGGAATATCGAGTTTCGCGGCGAAGT

CACCGCGACGATGGTTTACGATGGTGCCCCGATCTTCGCACATTTCAAAAAAGTTGACGACAGCAC

CCTGATGGGCATTATGAATGGCAAAAGCGCGTTGGTGTTGGACGGTGGCCAGCATTACTATTTCCT

GCTGGAGCGTGCGTAA

SEQ ID NO 111: Artificial SCH91-3944-M136A variant
MNLNEARTAFARLRAAENGLSPAELDEVWAALETVAAEEILGEWKGDDFATGHRLHEKLSASRWYG

KTFNSVEDAKPLICRDEDGNLYSDVKSGNGEASLWNIEFRGEVTATMVYDGAPIFDHFKKVDDSTLMG

IANGKSALVLDGGQHYYFLLERA

SEQ ID NO 112: Artificial SCH91-3944-M136A *E. coli* optimized
ATGAACTTAAATGAAGCGCGTACCGCATTTGCACGTCTGAGAGCTGCCGAGAACGGTCTGAGCCC

GGCTGAGCTGGATGAAGTGTGGGCAGCGCTGGAGACTGTGGCGGCTGAAGAAATCCTGGGTGAGT

GGAAGGGTGACGATTTTGCGACGGGTCACCGTCTGCACGAGAAACTGTCGGCGAGCCGCTGGTAT

GGTAAGACCTTCAACTCTGTTGAAGATGCAAAGCCGCTGATTTGCCGTGACGAAGATGGCAATCTG

-continued

TACTCCGATGTCAAGAGCGGTAACGGTGAGGCCAGCCTGTGGAATATCGAGTTTCGCGGCGAAGT

CACCGCGACGATGGTTTACGATGGTGCCCCGATCTTCGACCATTTCAAAAAAGTTGACGACAGCAC

CCTGATGGGCATTGCAAATGGCAAAAGCGCGTTGGTGTTGGACGGTGGCCAGCATTACTATTTCCT

GCTGGAGCGTGCGTAA

SEQ ID NO 113: Artificial SCH91-3944-K139A variant
MNTNEARTAFARIRAAENGTSPARIDEVWAATRTVAAEETTGEWKGDDFATGHRIHEKISASRWYG

KTFNSVEDAKPLICRDEDGNLYSDVKSGNGEASLWNIEFRGEVTATMVYDGAPIFDHFKKVDDSTLMG

IMNGASALVLDGGQHYYFLLERA

SEQ ID NO 114: Artificial SCH91-3944-K139A *E. coli* optimized
ATGAACTTAAATGAAGCGCGTACCGCATTTGCACGTCTGAGAGCTGCCGAGAACGGTCTGAGCCC

GGCTGAGCTGGATGAAGTGTGGGCAGCGCTGGAGACTGTGGCGGCTGAAGAAATCCTGGGTGAGT

GGAAGGGTGACGATTTTGCGACGGGTCACCGTCTGCACGAGAAACTGTCGGCGAGCCGCTGGTAT

GGTAAGACCTTCAACTCTGTTGAAGATGCAAAGCCGCTGATTTGCCGTGACGAAGATGGCAATCTG

TACTCCGATGTCAAGAGCGGTAACGGTGAGGCCAGCCTGTGGAATATCGAGTTTCGCGGCGAAGT

CACCGCGACGATGGTTTACGATGGTGCCCCGATCTTCGACCATTTCAAAAAAGTTGACGACAGCAC

CCTGATGGGCATTATGAATGGCGCAAGCGCGTTGGTGTTGGACGGTGGCCAGCATTACTATTTCCT

GCTGGAGCGTGCGTAA

SEQ ID NO 115: Artificial SCH91-3944-F152A variant
MNLNEARTAFARLRAAENGLSPAELDEVWAALETVAAEEILGEWKGDDFATGHRLHEKLSASRWYG

KTFNSVEDAKPLICRDEDGNLYSDVKSGNGEASLWNIEFRGEVTATMVYDGAPIFDHFKKVDDSTLMG

IMNGKSALVLDGGQHYYALLERA

SEQ ID NO 116: Artificial SCH91-3944-F152A *E. coli* optimized
ATGAACTTAAATGAAGCGCGTACCGCATTTGCACGTCTGAGAGCTGCCGAGAACGGTCTGAGCCC

GGCTGAGCTGGATGAAGTGTGGGCAGCGCTGGAGACTGTGGCGGCTGAAGAAATCCTGGGTGAGT

GGAAGGGTGACGATTTTGCGACGGGTCACCGTCTGCACGAGAAACTGTCGGCGAGCCGCTGGTAT

GGTAAGACCTTCAACTCTGTTGAAGATGCAAAGCCGCTGATTTGCCGTGACGAAGATGGCAATCTG

TACTCCGATGTCAAGAGCGGTAACGGTGAGGCCAGCCTGTGGAATATCGAGTTTCGCGGCGAAGT

CACCGCGACGATGGTTTACGATGGTGCCCCGATCTTCGACCATTTCAAAAAAGTTGACGACAGCAC

CCTGATGGGCATTATGAATGGCAAAAGCGCGTTGGTGTTGGACGGTGGCCAGCATTACTATGCACT

GCTGGAGCGTGCGTAA

SEQ ID NO 117: Artificial SCH91-3944-L154A variant
MNLNEARTAFARLRAAENGLSPAELDEVWAALETVAAEEILGEWKGDDFATGHRLHEKLSASRWYG

KTFNSVEDAKPLICRDEDGNLYSDVKSGNGEASLWNIEFRGEVTATMVYDGAPIFDHFKKVDDSTLMG

IMNGKSALVLDGGQHYYFLAERA

SEQ ID NO 118: Artificial SCH91-3944-L154A *E. coli* optimized
ATGAACTTAAATGAAGCGCGTACCGCATTTGCACGTCTGAGAGCTGCCGAGAACGGTCTGAGCCC

GGCTGAGCTGGATGAAGTGTGGGCAGCGCTGGAGACTGTGGCGGCTGAAGAAATCCTGGGTGAGT

GGAAGGGTGACGATTTTGCGACGGGTCACCGTCTGCACGAGAAACTGTCGGCGAGCCGCTGGTAT

GGTAAGACCTTCAACTCTGTTGAAGATGCAAAGCCGCTGATTTGCCGTGACGAAGATGGCAATCTG

TACTCCGATGTCAAGAGCGGTAACGGTGAGGCCAGCCTGTGGAATATCGAGTTTCGCGGCGAAGT

CACCGCGACGATGGTTTACGATGGTGCCCCGATCTTCGACCATTTCAAAAAAGTTGACGACAGCAC

CCTGATGGGCATTATGAATGGCAAAAGCGCGTTGGTGTTGGACGGTGGCCAGCATTACTATTTCCT

GGCCGAGCGTGCGTAA

-continued

SEQ ID NO 119: Artificial SCH91-3944-R156A variant
MNTNEARTAFARIRAAENGTSPARIDEVWAATRTVAAEETTGEWKGDDFATGHRIHEKISASRWYG

KTFNSVEDAKPLICRDEDGNLYSDVKSGNGEASLWNIEFRGEVTATMVYDGAPIFDHFKKVDDSTLMG

IMNGKSALVLDGGQHYYFLLEAA

SEQ ID NO 120: Artificial SCH91-3944-R156A *E. coli* optimized
ATGAACTTAAATGAAGCGCGTACCGCATTTGCACGTCTGAGAGCTGCCGAGAACGGTCTGAGCCC

GGCTGAGCTGGATGAAGTGTGGGCAGCGCTGGAGACTGTGGCGGCTGAAGAAATCCTGGGTGAGT

GGAAGGGTGACGATTTTGCGACGGGTCACCGTCTGCACGAGAAACTGTCGGCGAGCCGCTGGTAT

GGTAAGACCTTCAACTCTGTTGAAGATGCAAAGCCGCTGATTTGCCGTGACGAAGATGGCAATCTG

TACTCCGATGTCAAGAGCGGTAACGGTGAGGCCAGCCTGTGGAATATCGAGTTTCGCGGCGAAGT

CACCGCGACGATGGTTTACGATGGTGCCCCGATCTTCGACCATTTCAAAAAAGTTGACGACAGCAC

CCTGATGGGCATTATGAATGGCAAAAGCGCGTTGGTGTTGGACGGTGGCCAGCATTACTATTTCCT

GCTGGAGGCAGCGTAA

SEQ ID NO 121: Integration cassette fragment 1
GCAGGCAGCTCCATTTCATGTAGGTGATTTATCCCTCCGGGCGGTATTTGAGACTCTCGG SEQ ID NO 122: Integration cassette fragment 2
ACTGCTGGGTACTGTTCAGGCACGATAGGAAATGCGTCCAGCGCATACACCAGTCTTAGC SEQ ID NO 123: Integration cassette fragment 3
AGTCGACCTTACAGCGCCTGGGACTCTACATAAACATGCAGCGAACATGCTTTCCAACGC SEQ ID NO 124: LEU2 yeast marker primer 1
AGGTGCAGTTCGCGTGCAATTATAACGTCGTGGCAACTGTTATCAGTCGTACCGCGCCATTCGACT

ACGTCGTAAGGCC

SEQ ID NO 125: LEU2 yeast marker primer 2
TCGTGGTCAAGGCGTGCAATTCTCAACACGAGAGTGATTCTTCGGCGTTGTTGCTGACCATCGACG

GTCGAGGAGAACTT

SEQ ID NO 126: AmpR *E. coli* marker primer 1
TGGTCAGCAACAACGCCGAAGAATCACTCTCGTGTTGAGAATTGCACGCCTTGACCACGACACGTT

AAGGGATTTTGGTCATGAG

SEQ ID NO 127: AmpR *E. coli* marker primer 2
AACGCGTACCCTAAGTACGGCACCACAGTGACTATGCAGTCCGCACTTTGCCAATGCCAAAAATGT

GCGCGGAACCCCTA

SEQ ID NO 128: Yeast origin of replication primer 1
TTGGCATTGGCAAAGTGCGGACTGCATAGTCACTGTGGTGCCGTACTTAGGGTACGCGTTCCTGAA

CGAAGCATCTGTGCTTCA

SEQ ID NO 129: Yeast origin of replication primer 2
CCGAGATGCCAAAGGATAGGTGCTATGTTGATGACTACGACACAGAACTGCGGGTGACATAATGA

TAGCATTGAAGGATGAGACT

SEQ ID NO 130: *E. coli* replication origin primer 1
ATGTCACCCGCAGTTCTGTGTCGTAGTCATCAACATAGCACCTATCCTTTGGCATCTCGGTGAGCA

AAAGGCCAGCAAAAGG

SEQ ID NO 131: *E. coli* replication origin primer 2
CTCAGATGTACGGTGATCGCCACCATGTGACGGAAGCTATCCTGACAGTGTAGCAAGTGCTGAGC

GTCAGACCCCGTAGAA

SEQ ID NO 132: DNA fragment for *S. cerevisiae* co-transformation
ATTCCTAGTGACGGCCTTGGGAACTCGATACACGATGTTCAGTAGACCGCTCACACATGG SEQ ID NO 133: *Hyphozyma roseoniera* SCH23-ADH1 wt
ATGCAATTCAGCATCGGAGATGTACTCGCCATTGTAGATAAAACAATCCTCAACCCACTCGTCGTC

AGCGCAGGACTTCTGTCTCTGCACTTTCTCACCAATGACAAATACGCAATCACTGCGAATGACGGT

-continued

CTATTCCCTTATCAAATTAGCACTCCAGACTCGCATCGAAAAGCCCTTTTTGCACTTGGCTTTGGTC

TACTTCTCAGAGCCAATCGCTACATGAGCAGAAAAGCTCTGAACAACAACACCGCCGCACAATTC

GACTGGAATCGTGAGATCATCGTTGTTACTGGTGGATCTGGTGGTATCGGTGCTCAGGCCGCGCAG

AAATTGGCAGAAAGAGGATCGAAAGTGATTGTTATTGATGTGCTACCACTTACCTTTGACAAGCCC

AAGAATTTGTACCACTATAAATGTGATCTCACAAACTACAAAGAGCTCCAAGAAGTTGCGGCTAA

GATCGAAAGAGAAGTTGGCACTCCGACTTGTGTAGTTGCGAATGCAGGAATATGTCGTGGAAAGA

ACATATTCGATGCTACAGAACGAGATGTTCAGCTTACCTTTGGAGTCAACAATCTGGGACTTCTAT

GGACAGCCAAAACCTTTCTCCCATCAATGGCCAAAGCAAATCATGGCCATTTCTTGATCATCGCCT

CTCAAACCGGCCATCTAGCGACCGCAGGAGTAGTCGACTATGCAGCGACCAAAGCAGCAGCAATC

GCCATATATGAAGGTCTACAAACAGAGATGAAGCACTTTTATAAAGCGCCTGCTGTACGCGTATCT

TGTATCTCCCCATCCGCGGTCAAGACGAAGATGTTTGCAGGCATCAAGACTGGAGGCAATTTCTTC

ATGCCAATGTTGACGCCTGATGATCTTGGAGACCTGATTGCAAAGACTTTGTGGGACGGTGTGGCA

GTCAATATTTTGAGCCCTGCGGCGGCATATATCAGCCCGCCCACGAGAGCTTTGCCAGATTGGATG

AGGGTTGGCATGCAGGATGCTGGTGCTGAGATCATGACGGAATTGACTCCTCATAAGCCGTTGGA

GTAG

SEQ ID NO 134: *Hyphozyma roseonigra* SCH23-ADH1 wt
MQFSIGDVLAIVDKTILNPLVVSAGLLSLHFLTNDKYAITANDGLFPYQISTPDSHRKALFALGFGLLLR

ANRYMSRKALNNNTAAQFDWNREIIVVTGGSGGIGAQAAQKLAERGSKVIVIDVLPLTFDKPKNLYHY

KCDLTNYKELQEVAAKIEREVGTPTCVVANAGICRGKNIFDATERDVQLTFGVNNLGLLWTAKTFLPS

MAKANHGHFLIIASQTGHLATAGVVDYAATKAAAIAIYEGLQTEMKHFYKAPAVRVSCISPSAVKTKM

FAGIKTGGNFFMPMLTPDDLGDLIAKTLWDGVAVNILSPAAAYISPPTRALPDWMRVGMQDAGAEIM

TELTPHKPLE

SEQ ID NO 135: *Hyphozyma roseonigra* SCH23-ADH1 Yeast optimized
ATGCAATTCTCTATCGGTGACGTTTTGGCTATCGTTGACAAGACTATCTTGAACCCATTGGTTGTTT

CTGCTGGTTTGTTGTCTTTGCACTTCTTGACTAACGACAAGTACGCTATCACTGCTAACGACGGTTT

GTTCCCATACCAAATCTCTACTCCAGACTCTCACAGAAAGGCTTTGTTCGCTTTGGGTTTCGGTTTG

TTGTTGAGAGCTAACAGATACATGTCTAGAAAGGCTTTGAACAACAACACTGCTGCTCAATTCGAC

TGGAACAGAGAAATCATCGTTGTTACTGGTGGTTCTGGTGGTATCGGTGCTCAAGCTGCTCAAAAG

TTGGCTGAAAGAGGTTCTAAGGTTATCGTTATCGACGTTTTGCCATTGACTTTCGACAAGCCAAAG

AACTTGTACCACTACAAGTGTGACTTGACTAACTACAAGGAATTGCAAGAAGTTGCTGCTAAGATC

GAAAGAGAAGTTGGTACTCCAACTTGTGTTGTTGCTAACGCTGGTATCTGTAGAGGTAAGAACATC

TTCGACGCTACTGAAAGAGACGTTCAATTGACTTTCGGTGTTAACAACTTGGGTTTGTTGTGGACT

GCTAAGACTTTCTTGCCATCTATGGCTAAGGCTAACCACGGTCACTTCTTGATCATCGCTTCTCAAA

CTGGTCACTTGGCTACTGCTGGTGTTGTTGACTACGCTGCTACTAAGGCTGCTGCTATCGCTATCTA

CGAAGGTTTGCAAACTGAAATGAAGCACTTCTACAAGGCTCCAGCTGTTAGAGTTTCTTGTATCTC

TCCATCTGCTGTTAAGACTAAGATGTTCGCTGGTATCAAGACTGGTGGTAACTTCTTCATGCCAAT

GTTGACTCCAGACGACTTGGGTGACTTGATCGCTAAGACTTTGTGGGACGGTGTTGCTGTTAACAT

CTTGTCTCCAGCTGCTGCTTACATCTCTCCACCAACTAGAGCTTTGCCAGACTGGATGAGAGTTGGT

ATGCAAGACGCTGGTGCTGAAATCATGACTGAATTGACTCCACACAAGCCATTGGAATAA

SEQ ID NO 136: *Hyphozyma roseonigra* SCH23-ADH2 wt
ATGGCGACGATACCGACCACAATGACCGCAGCGACAATCGTTGAATTCAACAAGCCCATCGTGCT

AAAGAACGACATACCAGTTCCAGACCTACCAGAGAACAAGATTCTTGTTAGGATAGCTGCAACAT

-continued

CATTATGCTCAAGCGACTTGATGGCGTACAAAGGTTACATGGATTTCATGACCAAGACGCCTTACT

GCGGAGGACACGAGCCCGTGGGAACGGTGGTGAAAGTCGGTTCTTCGGTAAAAGGCTACTCGGTT

GGAGATCGCGTTGGCATATTGATGTTCTTCGATACCTGTGGAACATGCAATGACTGCTTCTCGGGT

GAACATCGCTTTTGCAGCACAAAGAAAATCCTAGGCTTCGCGGAAAGCTGGGGAGGATTTTCAGA

ATACGCACTTGCTGATCCCATCTCGACCATCAAGCTCCCGGAAGGGTTGAGTTTCGATGTAGCAGC

GCCTTTGTTCTGCGCTGGGATCACAGCCTACAGCGCGCTGTTGAAGGTGAAGAGTCATGCCGGTCA

ACTCATCAATATCATCGGCTGTGGAGGCGTAGGACATATGGCTATATTGTATGCGAGAGCTATGGG

ATATCGAGTTCATGTTTACGATATATCCGATTCCAAGGTCGAATTTGCACTCTTTCTCGGCGCAGAT

GCAGCCTTCAACACTCTGACCTATACCGGTCCAATAGAATCAGCATCTTCTACGTTAGTCGTAAGT

GGAGCAAATGCAGCATACCAGAGCGCTCTAGGCATGACGAGTAATCATGGAGTCGTCCTGGGTAT

TGGACTACCAGCGGGAGGTGTGGTCATTGATGTGCCAGCTTGGGGTACGAAAGGCGTTACATTCGT

CCCATGCAACACAGGCTCGAAACAGGAACTAGAAGAAGCGCTAGAATTGGCTGTGAGAAAGGAT

ATCAAACCATTACTTGACATCCGCCATATCGACACAATTAATGAGGCATATCAAGATTTGGCGGAG

GGAAAGATCAATGGGAGGATTGTTTTCCACTTCGAGTGA

SEQ ID NO 137: *Hyphozyma roseonigra* SCH23-ADH2 wt
MATIPTTMTAATIVEFNKPIVLKNDIPVPDLPENKILVRIAATSLCSSDLMAYKGYMDFMTKTPYCGGH

EPVGTVVKVGSSVKGYSVGDRVGILMFFDTCGTCNDCFSGEHRFCSTKKILGFAESWGGFSEYALADPI

STIKLPEGLSFDVAAPLFCAGITAYSALLKVKSHAGQLINIIGCGGVGHMAILYARAMGYRVHVYDISD

SKVEFALFLGADAAFNTLTYTGPIESASSTLVVSGANAAYQSALGMTSNHGVVLGIGLPAGGVVIDVPA

WGTKGVTFVPCNTGSKQELEEALELAVRKDIKPLLDIRHIDTINEAYQDLAEGKINGRIVFHFE

SEQ ID NO 138: *Hyphozyma roseonigra* SCH23-ADH2 Yeast optimized
ATGGCTACTATCCCAACTACTATGACTGCTGCTACTATCGTTGAATTCAACAAGCCAATCGTTTTGA

AGAACGACATCCCAGTTCCAGACTTGCCAGAAAACAAGATCTTGGTTAGAATCGCTGCTACTTCTT

TGTGTTCTTCTGACTTGATGGCTTACAAGGGTTACATGGACTTCATGACTAAGACTCCATACTGTGG

TGGTCACGAACCAGTTGGTACTGTTGTTAAGGTTGGTTCTTCTGTTAAGGGTTACTCTGTTGGTGAC

AGAGTTGGTATCTTGATGTTCTTCGACACTTGTGGTACTTGTAACGACTGTTTCTCTGGTGAACACA

GATTCTGTTCTACTAAGAAGATCTTGGGTTTCGCTGAATCTTGGGGTGGTTTCTCTGAATACGCTTT

GGCTGACCCAATCTCTACTATCAAGTTGCCAGAAGGTTTGTCTTTCGACGTTGCTGCTCCATTGTTC

TGTGCTGGTATCACTGCTTACTCTGCTTTGTTGAAGGTTAAGTCTCACGCTGGTCAATTGATCAACA

TCATCGGTTGTGGTGGTGTTGGTCACATGGCTATCTTGTACGCTAGAGCTATGGGTTACAGAGTTC

ACGTTTACGACATCTCTGACTCTAAGGTTGAATTCGCTTTGTTCTTGGGTGCTGACGCTGCTTTCAA

CACTTTGACTTACACTGGTCCAATCGAATCTGCTTCTTCTACTTTGGTTGTTTCTGGTGCTAACGCT

GCTTACCAATCTGCTTTGGGTATGACTTCTAACCACGGTGTTGTTTTGGGTATCGGTTTGCCAGCTG

GTGGTGTTGTTATCGACGTTCCAGCTTGGGGTACTAAGGGTGTTACTTTCGTTCCATGTAACACTGG

TTCTAAGCAAGAATTGGAAGAAGCTTTGGAATTGGCTGTTAGAAAGGACATCAAGCCATTGTTGG

ACATCAGACACATCGACACTATCAACGAAGCTTACCAAGACTTGGCTGAAGGTAAGATCAACGGT

AGAATCGTTTTCCACTTCGAATAA

SEQ ID NO 139: *Filobasidium magnum* SCH24-ADH1 wt
ATGCCAACCCCTATCTTTGGCGCCCGAGAGGGTTTCACTATCGACTCCGTACTGAGCATCCTGGAT

GCGACCGTACTTAACCCCTGGTTTACCGGCGTGTGCCTAATAGCCGTCTGCGCCCGAGATCGCACC

ATTACGTACCCGGACTGGCCGGCGGCTCTGGACCAGGTGCTCCCCTTCTTGTCGCAGATGTGGAGG

GAAACTGTCAGACCGACCTTTGGCGACCGCAACGTCCTTCATCTGTTGACCACTGTGTGTGTCGGC

-continued

CTTGCCATCCGAACCAACAGACGGATGAGTCGGGGAGCGAGGAACAATTGGGTGTGGGATACTAG

TTATGACTGGAAGAAGGAGATCGTAGTGGTTACGGGAGGAGCTGCCGGGTTTGGTGCAGACATCG

TACAACAGCTAGACACGCGTGGAATCCAGGTCGTCGTCTTGGATGTGGGATCCCTCACCTATAGGC

CTTCGAGCAGAGTTCATTATTACAAGTGCGACGTGTCGAACCCACAAGACGTCGCCAGCGTGGCTA

AAGCTATCGTATCCAACGTCGGGCACCCGACCATATTGGTCAACAACGCTGGCGTATTCAGGGGTG

CGACTATTCTCTCCACGACACCGCGCGACCTCGACATGACCTACGACATCAACGTCAAAGCGCACT

ATCATCTCACGAAGGCGTTCCTCCCGAACATGATCTCCAAGAACCATGGACATATTGTGACTGTGT

CAAGCGCGACCGCATACGCTCAAGCTTGTTCTGGCGTGTCATACTGTTCCTCAAAGGCCGCCATCT

TGTCATTTCACGAAGGACTGAGCGAAGAGATTTTGTGGATCTATAAGGCGCCCAAAGTCCGGACCT

CGGTCATCTGCCCCGGACACGTCAATACGGCCATGTTTACAGGCATTGGAGCCGCCGCTCCCTCGT

TCATGGCACCTGCACTTCATCCCTCGACAGTCGCCGAGACAATCGTCGATGTATTGCTCTCATGCG

AGTCTCAACACGTCCTGATGCCCGCCGCCATGCACATGTCAGTCGCCGGACGAGCGCTGCCCACCT

GGTTCTTCCGGGGGTTGTTGGCATCGGGCAAGGATACCATGGGTAGCGTTGTCCGCCGATGA

SEQ ID NO 140: *Filobasidium magnum* SCH24-ADH1 wt

MPTPIFGAREGFTIDSVLSILDATVLNPWFTGVCLIAVCARDRTITYPDWPAALDQVLPFLSQMWRETV

RPTFGDRNVLHLLTTVCVGLAIRTNRRMSRGARNNWVWDTSYDWKKEIVVVTGGAAGFGADIVQQL

DTRGIQVVVLDVGSLTYRPSSRVHYYKCDVSNPQDVASVAKAIVSNVGHPTILVNNAGVFRGATILSTT

PRDLDMTYDINVKAHYHLTKAFLPNMISKNHGHIVTVSSATAYAQACSGVSYCSSKAAILSFHEGLSEE

ILWIYKAPKVRTSVICPGHVNTAMFTGIGAAAPSFMAPALHPSTVAETIVDVLLSCESQHVLMPAAMH

MSVAGRALPTWFFRGLLASGKDTMGSVVRR*

SEQ ID NO 141: *Filobasidium magnum* SCH24-ADH1 Yeast optimized
ATGCCAACTCCAATCTTCGGTGCTAGAGAAGGTTTCACTATCGACTCTGTTTTGTCTATCTTGGACG

CTACTGTTTTGAACCCATGGTTCACTGGTGTTTGTTTGATCGCTGTTTGTGCTAGAGACAGAACTAT

CACTTACCCAGACTGGCCAGCTGCTTTGGACCAAGTTTTGCCATTCTTGTCTCAAATGTGGAGAGA

AACTGTTAGACCAACTTTCGGTGACAGAAACGTTTTGCACTTGTTGACTACTGTTTGTGTTGGTTTG

GCTATCAGAACTAACAGAAGAATGTCTAGAGGTGCTAGAAACAACTGGGTTTGGGACACTTCTTA

CGACTGGAAGAAGGAAATCGTTGTTGTTACTGGTGGTGCTGCTGGTTTCGGTGCTGACATCGTTCA

ACAATTGGACACTAGAGGTATCCAAGTTGTTGTTTTGGACGTTGGTTCTTTGACTTACAGACCATCT

TCTAGAGTTCACTACTACAAGTGTGACGTTTCTAACCCACAAGACGTTGCTTCTGTTGCTAAGGCT

ATCGTTTCTAACGTTGGTCACCCAACTATCTTGGTTAACAACGCTGGTGTTTTCAGAGGTGCTACTA

TCTTGTCTACTACTCCAAGAGACTTGGACATGACTTACGACATCAACGTTAAGGCTCACTACCACT

TGACTAAGGCTTTCTTGCCAAACATGATCTCTAAGAACCACGGTCACATCGTTACTGTTTCTTCTGC

TACTGCTTACGCTCAAGCTTGTTCTGGTGTTTCTTACTGTTCTTCTAAGGCTGCTATCTTGTCTTTCC

ACGAAGGTTTGTCTGAAGAAATCTTGTGGATCTACAAGGCTCCAAAGGTTAGAACTTCTGTTATCT

GTCCAGGTCACGTTAACACTGCTATGTTCACTGGTATCGGTGCTGCTGCTCCATCTTTCATGGCTCC

AGCTTTGCACCCATCTACTGTTGCTGAAACTATCGTTGACGTTTTGTTGTCTTGTGAATCTCAACAC

GTTTTGATGCCAGCTGCTATGCACATGTCTGTTGCTGGTAGAGCTTTGCCAACTTGGTTCTTCAGAG

GTTTGTTGGCTTCTGGTAAGGACACTATGGGTTCTGTTGTTAGAAGATAA

SEQ ID NO 142: *Filobasidium magnum* SCH24-ADH2 wt
ATGGAGCCACCCCAGACTATGAAGGCCGCCTTGGTCACCGCATACAACGAGCCCCTGATTGTGAA

AGACGTTGCTACACCCGAGCCGGGCCCTGGACAGATTCTCGTTCGGGTCAAAGCTAGTTCGCTTTG

CATGTCAGATATCGGAGGCTATGTCGGAGCGATGGGGGAATTTATCACGCTCCCCTATTGTCCAGG

-continued

TCATGAACCCGCCGGAGAGATCGTCGCCCTTGGCGACAACGTGTCCGGCTTCTCCGTTGGGGATCG

GGTTACTTATATGGCCGCTCTAGATCCTTGTATGGGCTGCCGAGACTGTCTCCGAGGTGCCATTCG

ATTCTGCTCCAAACGCTCGAATCTCGGCTTCAGCCACCAGTACGGCGGGTTCTCCGAGTACTCTCT

CGCCAGCCCATACTCGATGGCCAAGGTGCCGGACGAACTGTCCCTCGAGGAAGCTGCGAGCATGT

CCTGTGCCGGGGTGACCGCTTTCGGTGCTCTCAAGCTATTGAGCAAGTATCAGGCTCCGGGAGGCA

TCATCAATGTCTTGGGCTGCGGCGGCGTTGGTCATCTGGTCATCAAGTTTGCCGTCGCGCTCGGCT

ACACCGTGCACGCTTTCGACATTAACGATGGCAAACTCAAACTGGCCGAGGAGTGCGGGGCATCT

AAAGCCTTCCTTTCAAAGGGAGATCCCACCCAGGCGATGATGGCAGAGAGTACGATAGTCATCTC

GGGTGTCAACGCGGCCTATGATTTCGCTATTAAAGCTACTCTGGCCGGTGGACGTATCATTGCGAT

TGGGCACCCACATTCGGCGACTCCGATGCCTCTCGGCTCGATGATCATCAACGACATCTCGTTGAT

CGTGAGCAATCAAGGTACAAGGGTGGATCTACAAGAAGCCTTGGATTTCGCCGCTCGATCCGGTG

TCAGACCGAACATTACAATCAACGAAGGTCTGGACGGCATCAATCAGGGCTATAAATCGGTCATG

ACAGGCGCTGTAGAAGGCAGATTGGTCTACAAATTCTAG

SEQ ID NO 143: *Filobasidium magnum* SCH24-ADH2 wt
MEPPQTMKAALVTAYNEPLIVKDVATPEPGPGQILVRVKASSLCMSDIGGYVGAMGEFITLPYCPGHEP

AGEIVALGDNVSGFSVGDRVTYMAALDPCMGCRDCLRGAIRFCSKRSNLGFSHQYGGFSEYSLASPYS

MAKVPDELSLEEAASMSCAGVTAFGALKLLSKYQAPGGIINVLGCGGVGHLVIKFAVALGYTVHAFDI

NDGKLKLAEECGASKAFLSKGDPTQAMMAESTIVISGVNAAYDFAIKATLAGGRIIAIGHPHSATPMPL

GSMIINDISLIVSNQGTRVDLQEALDFAARSGVRPNITINEGLDGINQGYKSVMTGAVEGRLVYKF

SEQ ID NO 144: *Filobasidium magnum* SCH24-ADH2 Yeast optimized
ATGGAACCACCACAAACTATGAAGGCTGCTTTGGTTACTGCTTACAACGAACCATTGATCGTTAAG

GACGTTGCTACTCCAGAACCAGGTCCAGGTCAAATCTTGGTTAGAGTTAAGGCTTCTTCTTTGTGT

ATGTCTGACATCGGTGGTTACGTTGGTGCTATGGGTGAATTCATCACTTTGCCATACTGTCCAGGTC

ACGAACCAGCTGGTGAAATCGTTGCTTTGGGTGACAACGTTTCTGGTTTCTCTGTTGGTGACAGAG

TTACTTACATGGCTGCTTTGGACCCATGTATGGGTTGTAGAGACTGTTTGAGAGGTGCTATCAGAT

TCTGTTCTAAGAGATCTAACTTGGGTTTCTCTCACCAATACGGTGGTTTCTCTGAATACTCTTTGGC

TTCTCCATACTCTATGGCTAAGGTTCCAGACGAATTGTCTTTGGAAGAAGCTGCTTCTATGTCTTGT

GCTGGTGTTACTGCTTTCGGTGCTTTGAAGTTGTTGTCTAAGTACCAAGCTCCAGGTGGTATCATCA

ACGTTTTGGGTTGTGGTGGTGTTGGTCACTTGGTTATCAAGTTCGCTGTTGCTTTGGGTTACACTGT

TCACGCTTTCGACATCAACGACGGTAAGTTGAAGTTGGCTGAAGAATGTGGTGCTTCTAAGGCTTT

CTTGTCTAAGGGTGACCCAACTCAAGCTATGATGGCTGAATCTACTATCGTTATCTCTGGTGTTAAC

GCTGCTTACGACTTCGCTATCAAGGCTACTTTGGCTGGTGGTAGAATCATCGCTATCGGTCACCCA

CACTCTGCTACTCCAATGCCATTGGGTTCTATGATCATCAACGACATCTCTTTGATCGTTTCTAACC

AAGGTACTAGAGTTGACTTGCAAGAAGCTTTGGACTTCGCTGCTAGATCTGGTGTTAGACCAAACA

TCACTATCAACGAAGGTTTGGACGGTATCAACCAAGGTTACAAGTCTGTTATGACTGGTGCTGTTG

AAGGTAGATTGGTTTACAAGTTCTAA

SEQ ID NO 145: *Rhodococcus* sp. RrhSecADH wt (NZ AZHI01000124.1 6627-7664 (+))
ATGAAAGCCGTCCAGTACACCGAGATCGGCTCCGAGCCGGTCGTTGTCGACATCCCCACCCCGAC

GCCCGGGCCGGGTGAGATCCTGCTGAAGGTCACCGCGGCCGGGCTGTGCCACTCGGACATCTTCGT

GATGGACATGCCGGCGGCGCAGTACGCCTACGGCCTGCCGCTCACCCTCGGCCACGAGGGTGTCG

GCACCGTCGCCGAACTCGGCGAGGGCGTCACGGGATTCGGGGTGGGGGACGCCGTCGCCGTGTAC

-continued

GGGCCGTGGGGCTGCGGTGCGTGCCACGCCTGCGCGCGCGGCCGGGAGAACTACTGCACCCGCGC

CGCCGACCTGGGCATCACGCCACCCGGTCTCGGCTCGCCCGGATCGATGGCCGAGTACATGATCGT

CGATTCGGCGCGCCACCTCGTCCCGATCGGAGACCTCGACCCGGTCGCCGCGGCGCCGCTCACCGA

CGCCGGTCTGACGCCGTACCACGCGATCTCCCGGGTCCTGCCGCTGCTGGGGCCGGGCTCGACGGC

CGTCGTCATCGGTGTCGGCGGGCTCGGCCACGTCGGCATCCAGATCCTGCGCGCCGTCAGCGCGGC

CCGTGTGATCGCCGTCGACCTCGACGACGACCGTCTCGCCCTCGCCCGCGAGGTCGGCGCCGACGC

GGCGGTGAAGTCGGGCGCCGGTGCGGCGGACGCGATCCGGGAACTGACCGGCGGCCAGGGCGCG

ACGGCGGTGTTCGACTTCGTCGGCGCCCAGTCGACGATCGACACGGCGCAGCAGGTGGTCGCGGT

CGACGGGCACATCTCGGTCGTGGGCATCCACGCCGGCGCACACGCCAAGGTCGGGTTCTTCATGAT

CCCGTTCGGCGCCTCCGTCGTGACCCCGTACTGGGGCACCCGGTCGGAACTGATGGAGGTCGTCGC

GCTGGCCCGCGCCGGCCGGCTGGACATCCACACCGAGACGTTCACCCTCGACGAGGGGCCGGCGG

CGTACCGGCGGCTGCGCGAGGGCAGCATCCGCGGCCGCGGCGTGGTGGTTCCCTGA

SEQ ID NO 146: *Rhodococcus* sp. RrhSecADH wt (WP_043801412.1)
MKAVQYTEIGSEPVVVDIPTPTPGPGEILLKVTAAGLCHSDIFVMDMPAAQYAYGLPLTLGHEGVGTV

AELGEGVTGFGVGDAVAVYGPWGCGACHACARGRENYCTRAADLGITPPGLGSPGSMAEYMIVDSA

RHLVPIGDLDPVAAAPLTDAGLTPYHAISRVLPLLGPGSTAVVIGVGGLGHVGIQILRAVSAARVIAVDL

DDDRLALAREVGADAAVKSGAGAADAIRELTGGQGATAVFDFVGAQSTIDTAQQVVAVDGHISVVGI

HAGAHAKVGFFMIPFGASVVTPYWGTRSELMEVVALARAGRLDIHTETFTLDEGPAAYRRLREGSIRG

RGVVVP*

SEQ ID NO 147: *Rhodococcus* sp. RrhSecADH *E. coli* optimized
ATGAAAGCAGTGCAATATACGGAAATTGGCTCGGAACCTGTTGTGGTGGACATCCCGACCCCGAC

CCCGGGTCCTGGTGAAATCCTGCTGAAAGTTACCGCTGCCGGCCTGTGCCACAGCGACATCTTCGT

GATGGACATGCCGGCTGCCCAGTACGCTTACGGTCTGCCACTGACGCTGGGTCACGAAGGCGTGG

GTACGGTCGCCGAACTGGGCGAGGGTGTCACCGGTTTCGGTGTCGGTGATGCCGTGGCAGTGTAC

GGTCCGTGGGGTTGCGGTGCGTGCCACGCGTGTGCGCGCGGCCGCGAGAATTACTGTACGCGTGC

AGCGGACCTGGGTATTACCCCGCCGGGCCTGGGCAGCCCGGGTAGCATGGCAGAGTACATGATCG

TTGATAGCGCACGTCATCTGGTGCCGATTGGCGATTTGGACCCGGTCGCGGCAGCCCCGCTGACTG

ACGCGGGCTTGACCCCGTATCATGCAATCTCCCGTGTACTGCCACTGCTCGGTCCGGGCAGCACCG

CTGTGGTTATCGGCGTCGGTGGCCTGGGTCATGTTGGCATCCAGATTCTGCGTGCAGTCAGCGCGG

CACGCGTGATCGCGGTTGATCTGGACGACGATCGCCTGGCCCTGGCGCGTGAGGTCGGTGCGGAT

GCTGCGGTTAAGTCTGGTGCCGGTGCAGCGGATGCGATTCGTGAGCTGACGGGTGGCCAGGGTGC

GACCGCCGTGTTTGATTTCGTTGGCGCGCAGAGCACCATTGATACGGCGCAACAAGTCGTTGCGGT

CGATGGTCACATTTCCGTTGTGGGTATCCACGCGGGTGCACATGCCAAGGTCGGCTTTTTCATGAT

CCCGTTTGGTGCTAGCGTTGTTACCCCGTATTGGGGCACGCGCAGCGAGCTGATGGAAGTCGTGGC

TTTGGCGCGTGCGGGTCGTCTGGACATTCACACCGAGACTTTCACCTTGGACGAAGGCCCGGCAGC

GTATCGTCGTCTGCGCGAGGGTAGCATTCGTGGCCGTGGTGTTGTTGTCCCGTAA

SEQ ID NO 148: *Rhodococcus rhodochrous* SCH80-00043 wt
ATGAAGACCAAAGCTGCTGTACTGCTCGAGCCCGGAAAGCCTTTCGAGATCATGGAACTCGACCT

CGACGGCCCGGGTGTGGGTGAGGTACTGATCAAGTACACCGCTGCCGGACTGTGCCATTCGGATCT

GCACCTGACCGACGGTGATCTCCCGCCGCGTTACCCGATCGTCGGCGGACACGAAGGCTCGGGCA

TCATCGAAGAGGTCGGCCCAGGCGTCACGAAGGTCAAGCCGGGCGACCATGTCGTGTGTAGCTTC

ATCCCCAACTGCGGCACCTGTCGCTACTGCTCGACCGGTCGCCAGAACCTCTGCGACATGGGTGCC

-continued

ACCATCCTCGAAGGCTCGATGCCCGACGGTTCCTTCCGTTTCCACGGCAACGGAATGGATTTCGGC

GGAATGTGCATGTTGGGAACGTTCTCCGAGCGCGCCACCATTTCTCAGCACTCGGTAGTCAAGATC

GACGACTGGCTTCCCTTGGAGACAGCGGTGGTCGTCGGCTGCGGCGTGCCTTCGGGTTGGGGAAC

GGCAGTAAATGCCGGTAACCTTCGCGCCGGTGACACCGCTGTGATCTACGGCATCGGTGGTCTCGG

CATCAACGCCGTCCAGGGCGCCGTTTCGGCCGGCTGCAAGTACGTCGTTGTGGTCGATCCGGTTGC

TCTCAAGCGTGAGACCGCACTGAAGTTCGGTGCAACCCATGCCTTTGCAGACGCCGAGAGCGCTG

CTGCCAAGGTCAACGAGCTGACGTGGGGACAGGGTGCCGACGCTGCGCTCATCCTTGTCGGCACC

GTCGACGAGGACGTGGTCAGTGCAGCGACGGCAGTGATCGGCAAGGGTGGCACCGTGGTGATCAC

GGGACTCGCCGACCCCGCCAAGCTGACCGTTCACGTGTCGGGTACCGACCTGACGCTGAATCAGA

AGACGATCAAGGGCACGTTGTTCGGGTCCATGAATCCGCAGTACGACATCGTGCGACTGCTGCGTC

TCTACGATGCCGGTCAGCTCAAGCTCGACGAACTGATCACCAACACCTACAGCCTCGAAGACGTC

AACAAGGGCTACCAGGATCTACGTGACGGCAAGAACATCCGTGGCGTGATCATTCACGACAAGTA

A

SEQ ID NO 149: *Rhodococcus rhodochrous* SCH80-00043 wt
MKTKAAVLLEPGKPFEIMELDLDGPGVGEVLIKYTAAGLCHSDLHLTDGDLPPRYPIVGGHEGSGIIEE

VGPGVTKVKPGDHVVCSFIPNCGTCRYCSTGRQNLCDMGATILEGSMPDGSFRFHGNGMDFGGMCML

GTFSERATISQHSVVKIDDWLPLETAVVVGCGVPSGWGTAVNAGNLRAGDTAVIYGIGGLGINAVQGA

VSAGCKYVVVVDPVALKRETALKFGATHAFADAESAAAKVNELTWGQGADAALILVGTVDEDVVSA

ATAVIGKGGTVVITGLADPAKLTVHVSGTDLTLNQKTIKGTLFGSMNPQYDIVRLLRLYDAGQLKLDE

LITNTYSLEDVNKGYQDLRDGKNIRGVIIHDK*

SEQ ID NO 150: *Rhodococcus rhodochrous* SCH80-00043 *E. coli* optimized
ATGAAAACGAAAGCCGCAGTGTTGTTGGAGCCGGGCAAACCATTTGAGATCATGGAACTGGATCT

GGACGGTCCGGGTGTCGGTGAAGTGCTGATCAAGTACACCGCAGCGGGCTTGTGCCACTCTGATCT

GCACCTGACCGACGGCGACTTGCCGCCACGTTACCCGATTGTGGGTGGCCATGAGGGTAGCGGTA

TCATTGAAGAGGTTGGTCCGGGCGTTACCAAGGTCAAACCGGGTGATCACGTCGTGTGCTCTTTCA

TCCCGAATTGTGGTACGTGCCGCTATTGTAGCACGGGTCGTCAGAACCTGTGCGACATGGGTGCCA

CCATTTTAGAGGGCTCCATGCCTGATGGCTCCTTCCGTTTTCACGGCAACGGTATGGACTTTGGTGG

CATGTGCATGCTGGGTACGTTCAGCGAACGCGCGACCATCAGCCAACATAGCGTCGTTAAGATCG

ATGACTGGCTCCCGCTGGAAACCGCAGTTGTTGTTGGTTGTGGTGTTCCGAGCGGTTGGGGTACTG

CGGTCAATGCCGGTAATCTGCGTGCTGGTGACACCGCGGTCATTTATGGTATTGGCGGCCTGGGTA

TCAACGCTGTGCAGGGCGCAGTTAGCGCGGGCTGCAAATACGTCGTTGTGGTTGACCCGGTTGCGC

TGAAACGTGAGACTGCGCTGAAATTTGGCGCAACCCACGCGTTCGCAGACGCGGAGAGCGCAGCT

GCGAAAGTGAACGAACTGACCTGGGGTCAGGGTGCGGATGCGGCACTGATCTTGGTCGGCACCGT

GGACGAAGATGTCGTGAGCGCGGCGACTGCTGTTATCGGTAAGGGTGGCACCGTTGTGATCACCG

GTCTGGCCGATCCGGCAAAGCTGACCGTTCATGTCAGCGGTACGGACCTGACCCTGAATCAGAAA

ACCATTAAGGGCACGCTGTTCGGTTCGATGAACCCGCAGTACGACATTGTGCGCCTGCTGCGTCTG

TACGATGCGGGTCAACTGAAACTGGACGAACTTATTACGAATACGTATAGCCTGGAAGATGTGAA

CAAAGGCTACCAAGATCTGCGTGATGGTAAGAATATTCGTGGTGTCATTATCCACGACAAGTGA

SEQ ID NO 151: *Rhodococcus rhodochrous* SCH80-04254 wt
ATGAAGGCAGCCCAGCTCATGGGGCCCGGGCTCCTGGAAATCAACGACGTGCCGGTCCCGGAGAT

CGGCCCGTCGGAACTACTGATTCGGGTGGGCGCAGCGGGAATCTGCCACTCCGATCTCCATCTCCT

GCACTTTCCGTACAAGATGCGCGAAGAACCGCTGACAATCGGCCACGAAATTGCCGGAACGATCG

-continued

AAGCCGTCGGGAGTGGCGTCGACGGCCGTTCCGTCGGAGAGCGTGGCGTCGTCTACCTCTGTTGGT

CATGTGGACAGTGCCGAGAATGCATGAGCGGCAACGAGAATATGTGCCTCGCCGCTGGACGCACC

GCGATGCCGCCCTGCCCCGGACTCGGCCCTGAGGGCGGGATGGCCGAGTACGTCAAGATCCCGGC

TCGCTCATTCGTACCCATCGGAGACCTCGACTTCCTGCAGGCCGCACCTCTCGCCGATGCGGCACT

GACGAGCTACCACGCCATTCGCGGTGCCCGCGAACATCTCCAGCCCGGTGCCACCGCCGTCGTGAT

CGGCGTCGGCGGACTCGGTCACGTTGCAGTACAGATACTTCGCGCGATCAGTGCCGTGCGCATCAT

CGCCGTCGATGTCGGACAGGATCAACTCGATCTCGCCAAACGTTGCGGCGCCGACATCACGCTCG

AATCGGGACCGGACACCGCGCAGCACATCCTCGACCTCACATCGGCCAGAGGCGCAGAAGTCATC

TTCGACTTCGTCGGTATCGACGCAACTGCACAGATGTCTGTTCAAGCGGTTGCGCCGAACGGCGCG

TATCGCATGGTAGGTCTCGGAGGCGGAAACCCCGGAATCACTGCCGAAGCTGCCGGCGGACCAGG

CTGGCCATGGGGCGCATCGATCCGGAAGTCCTACGGCGGCACCAGAAACGACCTCGTCGATTCCA

TCGCCCTGGCACAGGCCGGTCTGGTAACGGTAGAAGTAGCCCGCTTCGACCTCGCTGATGCCCGCG

ACGCACTCGACCGTCTCGAACACGGCAAGGTCACCGGACGCGCAGTGCTCGTACCCTGA

SEQ ID NO 152: *Rhodococcus rhodochrous* SCH80-04254 wt
MKAAQLMGPGLLEINDVPVPEIGPSELLIRVGAAGICHSDLHLLHFPYKMREEPLTIGHEIAGTIEAVGS

GVDGRSVGERGVVYLCWSCGQCRECMSGNENMCLAAGRTAMPPCPGLGPEGGMAEYVKIPARSFVPI

GDLDFLQAAPLADAALTSYHAIRGAREHLQPGATAVVIGVGGLGHVAVQILRAISAVRIIAVDVGQDQ

LDLAKRCGADITLESGPDTAQHILDLTSARGAEVIFDFVGIDATAQMSVQAVAPNGAYRMVGLGGGNP

GITAEAAGGPGWPWGASIRKSYGGTRNDLVDSIALAQAGLVTVEVARFDLADARDALDRLEHGKVTG

RAVLVP*

SEQ ID NO 153: *Rhodococcus rhodochrous* SCH80-04254 *E. coli* optimized
ATGAAAGCTGCACAACTGATGGGTCCGGGTCTGTTGGAAATTAATGATGTTCCAGTCCCAGAAATT

GGTCCGAGCGAGCTGCTGATCCGTGTTGGCGCTGCCGGCATTTGCCACAGCGATCTGCATCTGCTG

CACTTCCCGTACAAGATGCGTGAGGAACCGTTAACCATTGGTCACGAAATCGCGGGCACGATCGA

AGCCGTTGGTAGCGGTGTGGATGGCCGCAGCGTTGGTGAGCGTGGCGTGGTTTACCTGTGCTGGTC

CTGTGGTCAGTGCCGCGAGTGCATGTCCGGCAATGAAAACATGTGTCTGGCGGCTGGTCGTACCGC

AATGCCGCCATGTCCGGGTTTGGGTCCTGAGGGTGGCATGGCCGAATATGTCAAGATCCCGGCGC

GTAGCTTCGTGCCGATTGGCGATCTGGACTTTCTGCAGGCAGCGCCTTTGGCGGACGCAGCACTGA

CCAGCTACCACGCGATCCGTGGTGCCCGCGAACACTTGCAGCCGGGTGCAACCGCAGTGGTCATT

GGTGTCGGCGGCTTGGGTCATGTGGCAGTGCAAATCCTGCGCGCGATTTCTGCGGTCCGTATCATT

GCGGTTGATGTGGGCCAGGACCAACTGGACCTGGCGAAGCGTTGTGGCGCGGACATCACCCTGGA

GAGCGGTCCTGACACCGCGCAACATATCCTGGACCTGACCTCCGCTCGTGGTGCCGAAGTGATTTT

TGACTTCGTCGGTATCGATGCGACGGCACAGATGAGCGTCCAAGCGGTAGCCCCGAATGGCGCAT

ACCGTATGGTTGGTCTGGGTGGTGGCAACCCGGGCATTACTGCAGAGGCAGCGGGTGGTCCTGGTT

GGCCGTGGGGTGCTTCGATCCGCAAAAGCTATGGCGGCACGCGTAACGACCTGGTTGATTCTATTG

CGTTGGCCCAGGCTGGTCTTGTTACCGTTGAAGTGGCGCGCTTTGACCTGGCAGACGCCCGTGATG

CGCTGGACCGTCTGGAGCATGGTAAAGTGACGGGTCGCGCTGTGCTGGTGCCGTAA

SEQ ID NO 154: *Rhodococcus rhodochrous* SCH80-06135 wt
ATGAAGGCAATCCAGTACACGAGAATCGGCGCAGAACCCGAACTCACGGAGATTCCCAAACCCGA

GCCCGGTCCAGGTGAAGTGCTCCTGGAAGTCACCGCTGCCGGCGTCTGCCACTCGGACGACTTCAT

CATGAGCCTGCCCGAAGAGCAGTACACCTACGGCCTTCCTCTCACGCTCGGCCACGAAGGCGCCG

GCCGGGTCGCCGCCGTCGGCGAGGGCGTCGAAGGACTCGACATCGGAACCAATGTCGTCGTCTAC

-continued

GGACCCTGGGGCTGTGGCAGCTGTTGGCACTGCTCGCAAGGACTCGAAAACTACTGTTCTCGGGCA

AAAGAACTCGGCATCAATCCTCCTGGTCTCGGTGCACCCGGCGCGTTGGCCGAATTCATGATCGTC

GATTCACCTCGCCACCTCGTCCCGATCGGCGACCTCGATCCGGTCAAGACGGTGCCGCTGACCGAC

GCCGGTCTGACTCCGTATCACGCGATCAAGCGTTCACTGCCGAAACTTCGCGGTGGCGCGTACGCC

GTCGTCATCGGTACCGGCGGTCTCGGCCATGTCGCCATCCAACTCCTCCGCCACCTCTCGGCAGCA

ACCGTCATCGCACTCGACGTGAGCGCGGACAAGCTCGAACTGGCAACCAAGGTAGGCGCTCACGA

AGTGGTCCTGTCCGACAAGGACGCGGCCGAGAACGTCCGCAGGATCACCGGAAGTCAGGGCGCCG

CACTGGTTCTCGACTTCGTCGGCTATCAGCCCACCATCGACACCGCGATGGCTGTCGCCGGCGTCG

GATCGGACGTCACGATCGTCGGGATCGGCGACGGGCAGGCCCATGCCAAAGTCGGGTTCTTCCAA

AGTCCTTACGAGGCTTCTGTGACAGTTCCGTACTGGGGTGCCCGCAACGAGCTGATCGAATTGATC

GACCTGGCGCACGCCGGCATCTTCGACATCGCGGTGGAGACCTTCAGTCTCGACAACGGCGCCGA

AGCGTATCGACGACTGGCCGCCGGAACGCTCAGCGGCCGCGCGGTTGTGGTCCCTGGTCTGTGA

SEQ ID NO 155: *Rhodococcus rhodochrous* SCH80-06135 wt
MKAIQYTRIGAEPELTEIPKPEPGPGEVLLEVTAAGVCHSDDFIMSLPEEQYTYGLPLTLGHEGAGRVA

AVGEGVEGLDIGTNVVVYGPWGCGSCWHCSQGLENYCSRAKELGINPPGLGAPGALAEFMIVDSPRH

LVPIGDLDPVKTVPLTDAGLTPYHAIKRSLPKLRGGAYAVVIGTGGLGHVAIQLLRHLSAATVIALDVS

ADKLELATKVGAHEVVLSDKDAAENVRRITGSQGAALVLDFVGYQPTIDTAMAVAGVGSDVTIVGIG

DGQAHAKVGFFQSPYEASVTVPYWGARNELIELIDLAHAGIFDIAVETFSLDNGAEAYRRLAAGTLSGR

AVVVPGL*

SEQ ID NO 156: *Rhodococcus rhodochrous* SCH80-06135 *E. coli* optimized
ATGAAAGCAATCCAATATACCCGCATTGGTGCAGAGCCTGAGTTGACCGAGATCCCGAAACCGGA

ACCGGGTCCTGGCGAAGTTCTGCTCGAAGTTACCGCTGCGGGTGTGTGCCACAGCGATGACTTTAT

CATGTCGCTGCCAGAGGAACAATACACGTACGGCTTACCGCTGACGCTGGGTCATGAGGGCGCTG

GTCGTGTTGCAGCGGTGGGTGAGGGTGTCGAGGGCCTGGACATTGGCACCAACGTTGTCGTGTAC

GGTCCGTGGGGTTGCGGCTCTTGTTGGCATTGCTCCCAGGGCCTGGAGAATTACTGTTCCCGCGCG

AAAGAACTGGGTATCAATCCGCCTGGTCTGGGTGCTCCAGGTGCGCTGGCTGAGTTCATGATTGTC

GATAGCCCGCGTCACTTGGTTCCGATCGGTGACCTGGACCCGGTGAAAACCGTCCCGCTGACCGAT

GCGGGCTTGACGCCGTATCACGCGATTAAGCGCAGCCTGCCGAAACTGCGTGGTGGCGCGTATGC

AGTCGTCATCGGTACTGGTGGCTTGGGCCATGTTGCGATTCAGCTGCTGCGTCATCTGTCTGCCGC

GACGGTTATCGCGCTGGACGTGAGCGCCGATAAGCTCGAACTGGCCACTAAGGTTGGCGCGCACG

AAGTCGTTCTGAGCGATAAAGACGCAGCCGAAAATGTGCGTCGTATTACCGGTAGCCAGGGTGCA

GCATTGGTTCTGGACTTCGTTGGTTATCAGCCGACGATCGACACCGCGATGGCCGTTGCGGGCGTT

GGTAGCGATGTCACCATTGTGGGTATTGGCGATGGTCAAGCCCACGCCAAGGTTGGTTTCTTTCAA

AGCCCGTATGAAGCGAGCGTCACGGTGCCGTACTGGGGTGCGCGCAACGAACTGATCGAGCTGAT

CGATCTGGCTCACGCGGGTATTTTCGACATCGCAGTCGAAACCTTTAGCCTGGATAACGGCGCAGA

GGCATACCGTCGTCTGGCGGCTGGCACTCTGAGCGGTCGCGCAGTGGTAGTGCCGGGTCTGTAA

SEQ ID NO 157: *Rhodococcus rhodochrous* SCH80-06582 wt
ATGTTGGCAGTCCAGCTGACGGCGTGGGGTCAGCCTCCGCAGGTGCGTGAGATCCCCGTACCCGA

GCCCGCTGAGGGGCAACTGTTGATCAAAGTCGGCGCCGCTGGTCTGTGCCGCTCGGATCTGCACGT

CATGGATTCGCCCGCCGGACGTTTCGATTACCCGTTGCCGCTCACACTCGGCCATGAGGTTGCCGG

TACCGTCGTCGGTGCGGGACCGCTGGCCGATCACGCGTGGATCGGTGAAAATGTTGTCATTCATGG

TGTTTGGCCATGTGGCCGGTGCCGCAATTGCCGGCGCGAGCGCGAGAACTACTGCTTGGAGAAAG

-continued

TCCCGCGTGGGGACGGCCGACTCAGCCCGATCGGAAACGGGTTGGGCCATCCGGGCGGGCTGGCA

GAATACCTGCTGGTGCCCTCGGAAGCTGTTCTCGTTCGCGTCGGTTCGCTGAGCCCCCAGCAGGCC

GCTCCGCTCGCCGACGCCGGCCTGACCGCATATCATGCGATCCGGACCAACAGCGACGTCATCGA

CTCGGACACTGTGGCTTTGGTGATAGGAATCGGCGGTCTCGGCCATCTGGCGGTGCAGATCCTGCG

CTCTTTCGGCGTCACAGACATCATCGCCGTCGAGACAAGAACCCAGACACACGCTCTCGCGCTCGA

ATCGGGAGCACACGCGTGTTTTGCGACGCTCGCGGAAGCGACAGAGGCTGTGGCGAGCCTCGGCG

GTGCCGACGTGGTCTTCGACTTTGTCGGGGCTCAGGCGACGGTCGAACCCGCTCCGGCGCTTCTCG

CTCCCGGCGGCCGAGTTGTCGTCGTGGGAAGTGCGGGCGGGCAACTGACCGTCGGCAAAAGCCTT

GGTTTGGTCAACGGCTGGCAAGTTCGGGCGCCGTTCTGGGGCACCATCGAGGACCTGCGTCAGGT

GGTCGAACTCGCCAGTGCAGGAAAGCTGCATGCCGAGGTGACCACGTTCACGTTCGACAGCGCAC

TGGAGGCATACGATCGCCTGCGTTCAGGCGATCTGTCCGGCCGCGCCGTACTGGTTCCCACAGCCC

CTTCATCGCTGTGA

SEQ ID NO 158: *Rhodococcus rhodochrous* SCH80-06582 wt
MLAVQLTAWGQPPQVREIPVPEPAEGQLLIKVGAAGLCRSDLHVMDSPAGRFDYPLPLTLGHEVAGTV

VGAGPLADHAWIGENVVIHGVWPCGRCRNCRRERENYCLEKVPRGDGRLSPIGNGLGHPGGLAEYLL

VPSEAVLVRVGSLSPQQAAPLADAGLTAYHAIRTNSDVIDSDTVALVIGIGGLGHLAVQILRSFGVTDII

AVETRTQTHALALESGAHACFATLAEATEAVASLGGADVVFDFVGAQATVEPAPALLAPGGRVVVVG

SAGGQLTVGKSLGLVNGWQVRAPFWGTIEDLRQVVELASAGKLHAEVTTFTFDSALEAYDRLRSGDL

SGRAVLVPTAPSSL*

SEQ ID NO 159: *Rhodococcus rhodochrous* SCH80-06582 *E. coli* optimized
ATGTTAGCTGTTCAACTCACCGCATGGGGCCAACCACCACAAGTTCGCGAAATCCCGGTTCCGGAA

CCAGCCGAGGGCCAACTGCTGATTAAGGTTGGCGCAGCCGGTCTGTGCCGTAGCGACCTTCACGTT

ATGGACAGCCCTGCTGGTCGTTTTGATTACCCGTTGCCGCTGACGCTGGGTCACGAAGTGGCCGGC

ACGGTTGTCGGTGCCGGTCCGTTGGCAGACCACGCGTGGATTGGTGAGAACGTCGTGATTCACGGT

GTGTGGCCGTGTGGCCGTTGTCGTAATTGCCGTCGCGAGCGTGAGAACTACTGTTTGGAAAAAGTG

CCGCGTGGTGACGGTCGTCTGTCCCCGATCGGCAATGGTCTGGGTCATCCGGGTGGTCTGGCAGAG

TATCTGCTGGTGCCGAGCGAAGCCGTCCTGGTGCGTGTCGGCTCTCTGAGCCCGCAACAGGCAGCA

CCGCTGGCAGATGCGGGTCTGACCGCGTATCACGCGATTCGCACGAATAGCGACGTTATCGACTCT

GATACCGTGGCGCTGGTCATCGGTATTGGTGGCCTGGGTCACCTGGCCGTTCAGATTCTGCGTTCC

TTCGGCGTGACGGACATCATTGCAGTCGAGACTCGTACCCAGACGCATGCGTTGGCCCTGGAGAG

CGGTGCGCATGCGTGCTTTGCGACCCTGGCGGAAGCAACCGAAGCGGTTGCGAGCTTGGGCGGTG

CAGATGTTGTCTTTGACTTCGTTGGTGCGCAGGCGACTGTTGAGCCGGCACCAGCTCTGCTGGCAC

CTGGTGGCCGTGTTGTCGTGGTGGGTTCTGCGGGTGGCCAACTGACCGTCGGCAAATCCCTGGGTC

TGGTGAATGGCTGGCAAGTGCGTGCGCCGTTTTGGGGCACCATTGAAGATTTGCGTCAAGTCGTGG

AACTGGCGTCTGCAGGCAAGTTGCACGCCGAAGTTACCACGTTCACGTTCGATAGCGCGCTGGAA

GCGTACGACCGCCTGCGTAGCGGTGATCTGAGCGGTCGCGCTGTACTGGTTCCGACCGCCCCTAGC

AGCCTGTAA

SEQ ID NO 160: *Rhodococcus erythropolis* SCH94-03945 wt
ATGATTCGCGCCGAACAGAATTCGAGATCCTCCATGCAGATGACAGCGGCGCTCTCACACGGCCC

GCACTCCCCCTTCACGCTCGACACCGTCGAGATCGACGACCCCCGCGCAGACGAGATCCTGGTTCG

CATCGTCGCGACCGGCCTGTGCCACACAGATCTGTTCACGAAGTCGGCGCTACCGGAAAGACTCG

GCCCCTGCGTGTTCGGGCACGAAGGGGCGGGGGTGGTCGAGGCCGTCGGCTCGTCGATCGACAGC

-continued

ATTGCGCCCGGTGATCACGTGTTGCTGAGCTACCGCAGTTGCGGTGTGTGCAGGCAGTGTCTCAGC

GGCCATCGGGCGTACTGCGAAAGCTCACACGGGCTCAACAGCTCTGGCGCACGCACCGACGGCTC

GACGCCGATCCGGCGAGACGGAACCCCGCTACGGTCCGCCTTCTTCGGCCAGTCCAGCTTCGCGGA

ATACGTCATCGCCTCTGCCGACAACACCGTCGTCGTCGATCCTGCGGTGGACCTGACCGTCGCAGC

TCCGCTCGGCTGCGGGTTTCAAACCGGCGCCGGCGCGGTACTGAATCTGCTTCGCCCCGAGCCCGA

CTCGACGTTTGTCGTTTTCGGGGCAGGCAGCGTCGGACTCGCAGCGCTGCTGGCGGCGAGGGCTGC

CGGCGTTTCCACCCTGGTCGCCGTGGACCCCGTTGCGCAGCGGCGCGCACTCGCCGAGGAATTCGG

CGCCGTCACTGTCGATCCCTCGAATGAAGATGTGATCGACGCGGTCCACGCCGCCACCGACGGAG

GTTCGACGCATTCCCTCGACACCACCGGAATCGGCTCCGTGATCAATCAAGCCGTCACATCACTTC

GAGCACGGGGAACACTGGCGGTAGTCGGACTCGGAGCATCCACGGTCGAGGTGAACATGGCCGAC

ATCATGCTGAGCGGAAAGACAATTCGAGGATGCATCGAAGGAGAGTCGGAAGTCTCGACGTTCAT

CCCCGAACTCGTCGAACTCTTCACTGGTGGCCGGTTTCCGATCGACCGCTTGGTGACGCGCTACGC

ATTCGCCGACATCAACAAAGCCGTCGAAGATCAAGCGTCGGGGCGCGTCATCAAACCCGTTCTCG

TGTGGTGA

SEQ ID NO 161: *Rhodococcus erythropolis* SCH94-03945 wt
MIRAEQNSRSSMQMTAALSHGPHSPFTLDTVEIDDPRADEILVRIVATGLCHTDLFTKSALPERLGPCVF

GHEGAGVVEAVGSSIDSIAPGDHVLLSYRSCGVCRQCLSGHRAYCESSHGLNSSGARTDGSTPIRRDGT

PLRSAFFGQSSFAEYVIASADNTVVVDPAVDLTVAAPLGCGFQTGAGAVLNLLRPEPDSTFVVFGAGSV

GLAALLAARAAGVSTLVAVDPVAQRRALAEEFGAVTVDPSNEDVIDAVHAATDGGSTHSLDTTGIGS

VINQAVTSLRARGTLAVVGLGASTVEVNMADIMLSGKTIRGCIEGESEVSTFIPELVELFTGGRFPIDRL

VTRYAFADINKAVEDQASGRVIKPVLVW*

SEQ ID NO 162: *Rhodococcus erythropolis* SCH94-03945 *E. coli* optimized
ATGATTAGAGCAGAACAGAACAGCCGCAGCTCCATGCAAATGACCGCGGCACTGTCACATGGTCC

GCACAGCCCGTTTACGCTGGATACGGTTGAGATTGACGATCCACGCGCCGACGAAATTCTGGTACG

CATCGTTGCGACTGGTCTGTGTCATACGGACTTGTTTACCAAGAGCGCGCTGCCGGAGCGCCTGGG

TCCGTGCGTGTTCGGCCACGAGGGTGCGGGCGTGGTTGAGGCAGTTGGCTCTAGCATTGACAGCAT

CGCTCCGGGTGATCACGTCCTGTTGTCCTACCGTAGCTGCGGCGTCTGCCGTCAGTGCCTGAGCGG

CCACCGTGCTTACTGTGAGAGCTCCCACGGCCTGAATAGCTCCGGTGCTCGTACCGACGGTAGCAC

CCCGATCCGTCGTGATGGTACGCCGCTTCGTAGCGCGTTCTTCGGTCAATCCAGCTTCGCGGAATA

TGTTATCGCAAGCGCAGACAACACCGTTGTGGTCGATCCGGCCGTGGACTTGACCGTTGCAGCACC

GCTGGGTTGTGGCTTTCAGACCGGCGCCGGCGCGGTGCTGAATCTGCTGCGCCCTGAGCCGGACAG

CACTTTCGTCGTCTTTGGTGCCGGCAGCGTCGGTTTGGCGGCACTGCTGGCGGCGCGTGCGGCGGG

TGTTTCGACCCTGGTCGCAGTTGATCCGGTCGCGCAGCGCCGTGCGTTGGCCGAAGAATTTGGTGC

CGTTACCGTCGATCCGAGCAACGAAGATGTTATTGACGCTGTGCACGCGGCGACCGACGGTGGCA

GCACGCATTCTCTGGATACCACGGGCATCGGTTCTGTGATTAACCAAGCCGTGACCTCTCTGCGTG

CGCGTGGTACTCTGGCTGTGGTTGGCCTGGGTGCTAGCACGGTCGAGGTGAATATGGCAGACATTA

TGCTGAGCGGTAAAACGATCCGTGGTTGCATCGAGGGCGAGAGCGAAGTTTCGACGTTTATCCCG

GAACTGGTCGAGCTGTTCACCGGTGGCCGTTTCCCGATTGACCGCCTGGTTACCCGTTATGCATTC

GCCGATATCAACAAAGCTGTGGAAGATCAAGCGTCCGGTCGCGTCATCAAGCCAGTGCTGGTGTG

GTAA

-continued

SEQ ID NO 163: *Rhodococcus rhodochrous* SCH80-05240 wt
ATGATTCGCGCCGAACAGAATTCGACGTCCGCCATGCAGATGACAGCGGCGCTCTCACACGGCCC

GCACTCCCCCTTCACACTCGACACCGTCGAGATCGACGAACCCCGCGCAGACGAGATCCTGGTTCG

CATCGTCGCGACCGGCCTGTGCCACACAGATCTGTTCACGAAGTCGGTGCTACCGGAACGACTCGG

CCCCTGCGTGTTCGGGCACGAAGGGGCGGGGGTGGTCGAGGCCGTCGGCTCGGCGATCGACAAGG

TCGTGCCCGGCGATCACGTGTTGTTGAGCTACCGCAGTTGCGGTGTGTGCAGGCAGTGTCTCAGCG

GCCATCGGGCGTACTGCGAAAGCTCACACGGGCTCAACAGCTCTGGCGCACGCACCGACGGCTCG

ACGCCGGTCCGGCGAAGCGGAACTCCGATACGGTCCGCCTTCTTCGGCCAGTCCAGCTTCGCGGAA

TACGTCATCGCCACTGCCGACAACACCGTCGTCGTCGATCCTGCAGTGGACCTGACCGTCGCGGCT

CCCCTCGGCTGCGGATTTCAAACCGGCGCGGGTGCCGTGCTGAATCTACTTCGCCCCGAGCCCGAC

TCGACGTTTGTCGTCTTCGGAGCCGGCAGCGTCGGACTCGCAGCGCTACTGGCAGCGAGGGCTGCC

GGCGTTTCCACCCTGGTCGCCGTGGACCCCGTTGCGCAGCGGCGCGCACTCGCCGAGGAATTCGGC

GCCGTCACTGTCGATCCGACCACCGAGGACGCGGTCGAAGCAGTACGCGCCGCCACCGACGGAGG

TTCGACACATTCCCTCGACACCACCGGAATCGGCTCCGTGATCAATCAAGCCGTCACATCACTTCG

AGCACGGGGAACACTGGCGGTAGTCGGACTCGGAGCGTCCACGGTCGAGATGAACATGGCCGACA

TCATGCTGAGCGGAAAGACAATTCGAGGATGCATCGAAGGAGAGTCGGAAGTCTCGACGTTCATC

CCCGAACTCGTCGAACTCTTCACTGGTGGCCGGTTTCCGATCGACCGCTTGGTGACGCGCTACGCC

TTCTCCGACATCAACAAAGCCGTCGAAGATCAAGCGTCGGGGCGCGTCATCAAACCCGTTCTCGTG

TGGTGA

SEQ ID NO 164: *Rhodococcus rhodochrous* SCH80-05240 wt
MIRAEQNSTSAMQMTAALSHGPHSPFTLDTVEIDEPRADEILVRIVATGLCHTDLFTKSVLPERLGPCVF

GHEGAGVVEAVGSAIDKVVPGDHVLLSYRSCGVCRQCLSGHRAYCESSHGLNSSGARTDGSTPVRRS

GTPIRSAFFGQSSFAEYVIATADNTVVVDPAVDLTVAAPLGCGFQTGAGAVLNLLRPEPDSTFVVFGAG

SVGLAALLAARAAGVSTLVAVDPVAQRRALAEEFGAVTVDPTTEDAVEAVRAATDGGSTHSLDTTGI

GSVINQAVTSLRARGTLAVVGLGASTVEMNMADIMLSGKTIRGCIEGESEVSTFIPELVELFTGGRFPID

RLVTRYAFSDINKAVEDQASGRVIKPVLVW*

SEQ ID NO 165: *Rhodococcus rhodochrous* SCH80-05240 *E. coli* optimized
ATGATTAGAGCAGAACAGAACAGCACCAGCGCGATGCAAATGACCGCGGCACTGTCACATGGTCC

GCACAGCCCGTTTACGCTGGATACGGTTGAGATTGACGAGCCACGCGCCGACGAAATTCTGGTAC

GCATCGTTGCGACTGGTCTGTGTCATACGGACTTGTTTACCAAGAGCGTCCTGCCGGAGCGCCTGG

GTCCGTGCGTGTTCGGCCACGAGGGTGCGGGCGTGGTTGAGGCAGTTGGCTCTGCCATTGACAAA

GTTGTTCCGGGTGATCACGTCCTGTTGTCCTACCGTAGCTGCGGCGTCTGCCGTCAGTGCCTGAGC

GGCCACCGTGCTTACTGTGAGAGCTCCCACGGCCTGAATAGCTCCGGTGCTCGTACCGACGGTAGC

ACCCCGGTGCGTCGTAGCGGTACGCCGATTCGTAGCGCGTTCTTCGGTCAATCCAGCTTCGCGGAA

TATGTTATCGCAACCGCAGACAACACCGTTGTGGTCGATCCGGCCGTGGACTTGACCGTTGCAGCA

CCGCTGGGTTGTGGCTTTCAGACCGGCGCCGGCGCGGTGCTGAATCTGCTGCGCCCTGAGCCGGAC

AGCACTTTCGTCGTCTTTGGTGCCGGCAGCGTCGGTTTGGCGGCACTGCTGGCGGCGCGTGCGGCG

GGTGTTTCGACCCTGGTCGCAGTTGATCCGGTCGCGCAGCGCCGTGCGTTGGCCGAAGAATTTGGT

GCCGTTACCGTCGATCCGACGACCGAAGATGCCGTTGAAGCTGTGCGCGCGGCGACCGACGGTGG

CAGCACGCATTCTCTGGATACCACGGGCATCGGTTCTGTGATTAACCAAGCCGTGACCTCTCTGCG

TGCGCGTGGTACTCTGGCTGTGGTTGGCCTGGGTGCTAGCACGGTCGAGATGAATATGGCAGACAT

TATGCTGAGCGGTAAAACGATCCGTGGTTGCATCGAGGGCGAGAGCGAAGTTTCGACGTTTATCCC

-continued

GGAACTGGTCGAGCTGTTCACCGGTGGCCGTTTCCCGATTGACCGCCTGGTTACCCGTTATGCATT

CAGCGATATCAACAAAGCTGTGGAAGATCAAGCGTCCGGTCGCGTCATCAAGCCAGTGCTGGTGT

GGTAA

SEQ ID NO 166: *Azoarcus toluclasticus* AzTolADHI wt(NZ KB899498.1: 215502-216629 (+))
ATGGGAAGCATCCAGGATTCGCTGTTCATTCGGGCACGCGCTGCCGTGCTGCGTACGGTGGGCGG

GCCGCTCGAGATCGAGAACGTGCGCATCAGCCCCCCCAAGGGCGATGAAGTGCTGGTGCGCATGG

TCGGAGTCGGCGTATGCCATACCGACGTGGTGTGCCGCGACGGTTTTCCCGTGCCGCTGCCGATTG

TGCTCGGGCACGAAGGCTCCGGCATCGTCGAGGCCGTCGGCGAGCGCGTGACGAAAGTGAAGCCG

GGCCAGCGTGTCGTGCTGTCGTTCAACTCCTGCGGGCACTGCGCGAGCTGCTGCGAGGATCACCCG

GCGACCTGCCACCAGATGCTGCCGCTCAACTTCGGCGCGGCGCAGCGCGTCGATGGGGGCACGGT

GATCGATGCGTCCGGCGAAGCGGTGCAGAGCCTCTTCTTCGGTCAGTCCTCGTTTGGCACCTACGC

GCTCGCGCGCGAAGTGAATACGGTCCCGGTTCCGGACGCCGTGCCGCTCGAAATCCTCGGCCCGCT

CGGTTGCGGGATCCAGACCGGGGCGGGTGCGGCGATCAATTCGCTCGCGCTGAAACCGGGCCAAT

CGCTCGCGATCTTCGGCGGGGGCAGCGTCGGCCTGAGCGCGCTGCTCGGCGCGCTCGCGGTCGGT

GCCGGCCCGGTGGTCGTGATTGAGCCCAACGAACGGCGTCGCGCGCTGGCGCTCGATCTGGGTGC

AAGCCACGCCTTCGATCCCTTCAACACCGAGGATCTCGTCGCGAGCATCAAGGCTGCGACCGGCG

GAGGCGTCACGCACTCGCTCGATTCGACGGGCCTCCCCCCCGTCATCGCCAACGCGATCAACTGCA

CCCTCCCGGGCGGCACCGTCGGCCTGCTGGGGGTGCCGTCACCCGAAGCCGCGGTGCCTGTGACCC

TGCTGGACCTGCTCGTGAAAAGCGTCACCCTGCGCCCGATCACCGAAGGCGACGCGAACCCGCAG

GAATTCATCCCGCGCATGGTCCAACTCTACCGCGACGGCAAGTTCCCCTTCGACAAGCTGATCACC

ACCTATCGCTTCGACGACATTAATCAAGCCTTCAAGGCGACCGAGACCGGAGAGGCGATCAAGCC

GGTGCTGGTGTTCTGA

SEQ ID NO 167: *Azoarcus toluclasticus* AzTolADH1 wt (WP_018990713.1)
MGSIQDSLFIRARAAVLRTVGGPLEIENVRISPPKGDEVLVRMVGVGVCHTDVVCRDGFPVPLPIVLGH

EGSGIVEAVGERVTKVKPGQRVVLSFNSCGHCASCCEDHPATCHQMLPLNFGAAQRVDGGTVIDASG

EAVQSLFFGQSSFGTYALAREVNTVPVPDAVPLEILGPLGCGIQTGAGAAINSLALKPGQSLAIFGGGSV

GLSALLGALAVGAGPVVVIEPNERRRALALDLGASHAFDPFNTEDLVASIKAATGGGVTHSLDSTGLPP

VIANAINCTLPGGTVGLLGVPSPEAAVPVTLLDLLVKSVTLRPITEGDANPQEFIPRMVQLYRDGKFPFD

KLITTYRFDDINQAFKATETGEAIKPVLVF*

SEQ ID NO 168: *Azoarcus toluclasticus* AzTolADH1 *E. coli* optimized
ATGGGTTCTATTCAAGATTCTCTGTTCATCCGTGCACGCGCCGCTGTTCTGCGTACTGTCGGTGGCC

CGCTGGAAATTGAAAACGTCCGCATTAGCCCTCCGAAGGGTGACGAAGTGCTCGTGCGTATGGTT

GGTGTTGGTGTGTGCCATACCGACGTTGTGTGTCGCGATGGCTTCCCGGTTCCGCTGCCGATTGTGC

TGGGTCACGAGGGCAGCGGTATTGTCGAGGCAGTGGGCGAGCGTGTGACCAAGGTTAAACCGGGT

CAGCGTGTCGTTTTATCCTTCAATAGCTGTGGTCATTGCGCGTCCTGCTGCGAGGACCACCCGGCC

ACCTGTCACCAGATGCTGCCACTGAACTTTGGTGCGGCGCAGCGCGTGGATGGTGGCACCGTTATC

GACGCGAGCGGCGAGGCAGTGCAGAGCCTGTTTTTTGGTCAAAGCTCTTTCGGTACGTATGCATTG

GCGCGTGAAGTCAATACCGTACCGGTGCCGGATGCAGTTCCGTTGGAAATCCTGGGCCCGTTGGGT

TGCGGCATCCAGACGGGTGCGGGTGCGGCTATCAACAGCCTGGCGCTGAAACCTGGTCAATCGCT

GGCAATCTTCGGTGGCGGCAGCGTCGGTCTGTCCGCCCTGCTGGGCGCGCTGGCCGTGGGCGCGG

GCCCGGTCGTTGTCATTGAGCCGAACGAACGTCGTCGTGCGTTGGCGCTGGACCTGGGTGCGAGCC

-continued

ATGCATTTGATCCGTTCAACACTGAAGATTTGGTTGCGAGCATCAAAGCCGCTACGGGTGGCGGCG

TTACCCACAGCCTGGACAGCACGGGTCTGCCGCCGGTCATCGCGAATGCAATCAACTGTACCTTGC

CGGGCGGCACGGTCGGTCTGCTGGGCGTCCCGAGCCCAGAGGCTGCCGTTCCGGTGACGCTGCTG

GATCTGCTGGTTAAATCAGTTACCCTGCGTCCGATTACCGAGGGTGACGCCAATCCGCAAGAATTT

ATTCCGCGTATGGTCCAGCTGTACCGCGACGGTAAATTTCCGTTTGATAAGCTGATTACGACCTAC

CGCTTCGACGACATCAATCAAGCGTTCAAGGCAACCGAAACCGGTGAAGCGATTAAGCCAGTGCT

GGTGTTTTAA

SEQ ID NO 169: *Aspersillus wentii* AspWeTPP wt (KV878213.1: 2482776-2483627)
ATGGCATCTGTACCAGCTCCCCCATTTGTCCACGTCGAAGGAATGAGCAATTTCCGATCGATAGGA

GGATATCCCCTTGAGACAGCATCGACAAACAATCACCGCTCCACGAGGCAAGGATTCGCATTTCG

CAGTGCCGATCCAACCTACGTCACCCAGAAAGGCCTGGAAACCATCCTTTCGCTCGACATCACTCG

AGCCTTTGACCTCCGCTCACTGGAAGAAGCAAAGGCACAGCGCGCAAAACTCCAGGCCGCCTCAG

GATGTCTCGACTGCAGCATCAGCCAGCACATGATCCACCAGCCCACACCCCTATTTCCAGATGGGG

ACTGGAGTCCAGAGGCCGCAGGGGAGCGGTATCTGCAGTACGCCCAGGCTGAGGGAGATGGGAT

ATCGGGCTACGTGGAGGTCTACGGAAACATGCTCGAGGAAGGTTGGATGGCGATTCGCGAGATTC

TGCTTCATGTCCGGGACCGGCCTACAGAGGCGTTTCTATGCCATTGTAGTGCAGGGAAAGATCGTA

CGGGGATTGTCATTGCGGTTTTGTTGAAGGTTGCAGGGTGCTCGGATGATCTTGTGTGCAGAGAGT

ATGAGTTGACCGAGATCGGGTTGGCTCGACGGAGGGAGTTTATCGTGCAGCATCTGCTTAAGAAG

CCGGAAATGAATGGATCGAGGGAACTGGCCGAAAGAGTGGCGGGGGCCAGGTATGAGAATATGA

AGGAAACGCTGGAGATGGTGCAAACTAGATATAGAGGGATGAGGGGCTATTGCAAGGAGATTTGC

GGCTTGACCGACGAAGATCTATCTATTATCCAGGGGAACTTGACTAGTCCGGAGAGTCCTATCTTC

TAA

SEQ ID NO 170: *Aspersillus wentii* AspWeTPP wt (OJJ34585.1)
MASVPAPPFVHVEGMSNFRSIGGYPLETASTNNHRSTRQGFAFRSADPTYVTQKGLETILSLDITRAFDL

RSLEEAKAQRAKLQAASGCLDCSISQHMIHQPTPLFPDGDWSPEAAGERYLQYAQAEGDGISGYVEVY

GNMLEEGWMAIREILLHVRDRPTEAFLCHCSAGKDRTGIVIAVLLKVAGCSDDLVCREYELTEIGLARR

REFIVQHLLKKPEMNGSRELAERVAGARYENMKETLEMVQTRYRGMRGYCKEICGLTDEDLSIIQGNL

TSPESPIF

SEQ ID NO 171: *Aspergillus wentii* AspWeTPP *E. coli* optimized
ATGGCGTCTGTCCCTGCTCCACCGTTTGTTCATGTTGAAGGTATGTCTAATTTTCGTAGCATCGGTG

GCTACCCGCTGGAGACTGCCTCCACGAATAACCATCGCTCGACCCGTCAAGGCTTCGCGTTTCGTA

GCGCGGACCCGACGTATGTGACGCAGAAAGGCCTGGAAACCATTCTGTCCCTGGATATTACCCGC

GCATTTGACTTGCGTAGCTTGGAAGAAGCAAAGGCACAACGTGCGAAGTTGCAGGCCGCGAGCGG

TTGTCTGGATTGCAGCATTAGCCAACACATGATCCACCAACCGACCCCGCTGTTCCCGGATGGTGA

CTGGTCCCCGGAAGCGGCGGGTGAGCGCTACTTGCAGTACGCACAAGCTGAGGGTGATGGTATCA

GCGGTTATGTCGAAGTTTATGGTAATATGCTGGAAGAGGGCTGGATGGCGATCCGTGAGATTCTGC

TGCACGTCCGTGACCGCCCGACCGAAGCATTCCTGTGCCACTGTTCCGCCGGTAAAGATCGTACGG

GTATCGTGATTGCTGTTCTGCTCAAAGTCGCGGGTTGCAGCGACGACCTGGTGTGTCGTGAGTACG

AACTGACCGAGATTGGCCTGGCGCGCCGTAGAGAGTTCATCGTTCAGCATCTGCTGAAGAAACCG

GAAATGAACGGCAGCCGTGAGCTGGCGGAGCGCGTCGCAGGCGCCCGTTACGAGAACATGAAAG

-continued

AAACCCTGGAAATGGTGCAGACCCGTTACCGCGGCATGCGCGGCTATTGCAAAGAAATCTGCGGT

CTGACCGACGAAGATCTGAGCATTATCCAGGGTAACCTGACGAGCCCGGAGAGCCCGATTTTCTA

A

SEQ ID NO 172: *Talaromyces verruculosus* PvCPS (LC316181.1)
ATGAGCCCAATGGATTTACAAGAATCAGCGGCAGCTTTGGTGCGGCAGTTGGGGGAGAGAGTCGA

AGATCGCCGTGGTTTTGGATTCATGAGCCCTGCCATCTATGATACCGCATGGGTCTCTATGATTAG

CAAGACAATCGATGACCAAAAAACATGGTTGTTTGCAGAATGTTTCCAGTACATTCTTTCTCATCA

GCTCGAAGACGGTGGTTGGGCAATGTATGCATCTGAAATCGACGCCATCCTAAACACTTCGGCCTC

ATTACTATCATTAAAGAGACATCTTTCAAATCCCTATCAAATTACATCTATCACACAAGAGGATCT

GTCCGCCCGCATTAACAGGGCTCAGAATGCTTTACAGAAGCTTCTCAATGAGTGGAATGTCGACAG

CACGCTCCACGTGGGATTCGAGATCCTAGTTCCGGCCCTACTCAGGTATCTCGAAGATGAGGGCAT

CGCTTTTGCTTTTTCTGGTAGAGAGCGCCTGCTTGAGATTGAGAAACAGAAATTATCAAAGTTCAA

AGCACAGTATCTATACCTTCCAATCAAAGTGACAGCTTTGCATTCTCTGGAAGCGTTCATAGGCGC

CATTGAGTTTGATAAAGTCAGTCACCACAAAGTCAGCGGTGCGTTCATGGCATCTCCATCATCCAC

AGCAGCTTACATGATGCATGCGACACAATGGGATGATGAATGCGAGGATTACCTACGCCACGTCA

TTGCTCATGCATCTGGGAAAGGATCCGGAGGTGTTCCAAGCGCTTTTCCTTCCACCATCTTTGAAA

GCGTTTGGCCTCTATCAACTCTGCTAAAGGTGGGATATGATCTCAACTCGGCACCTTTTATCGAAA

AAATCAGATCATACTTGCATGATGCATATATTGCTGAAAAGGGAATTCTCGGCTTCACTCCTTTTGT

TGGCGCTGATGCAGATGATACCGCTACCACCATATTGGTGCTCAATCTTTTGAACCAACCAGTCTC

AGTCGACGCGATGTTGAAGGAATTTGAAGAAGAACATCACTTCAAAACCTACTCTCAGGAGCGCA

ATCCTAGTTTCTCGGCCAATTGTAACGTTCTTCTTGCCTTACTATACAGTCAAGAGCCATCGCTTTA

TAGCGCGCAGATCGAAAAAGCTATAAGGTTCCTCTATAAGCAATTCACAGATTCAGAAATGGACG

TTCGAGACAAATGGAATCTATCACCATACTATTCTTGGATGCTCATGACACAAGCCATCACGCGGT

TGACGACTCTTCAGAAGACTTCGAAACTTTCAACATTGAGAGATGATTCTATCAGCAAAGGCTTGA

TTAGTCTGCTGTTTAGGATAGCTTCTACCGTGGTTAAAGACCAAAAGCCAGGAGGTTCTTGGGGCA

CTCGAGCTTCGAAAGAAGAGACTGCCTACGCAGTGTTGATTCTCACATATGCTTTCTACCTCGATG

AGGTTACGGAGTCGTTGCGGCATGATATCAAGATCGCCATTGAGAATGGTTGCTCATTCCTATCTG

AAAGAACCATGCAGTCCGATTCGGAGTGGCTTTGGGTTGAGAAAGTCACATATAAATCAGAGGTT

CTTTCGGAAGCATATATCTTGGCCGCTCTTAAACGGGCAGCTGACTTACCCGACGAAAATGCAGAA

GCAGCCCCCGTCATAAATGGAATTTCTACAAATGGATTTGAGCATACCGATAGAATTAACGGCAA

GCTTAAAGTCAATGGTACCAACGGTACAAATGGCAGTCATGAGACAAACGGTATCAACGGTACGC

ATGAAATTGAACAGATCAATGGCGTCAACGGCACGAATGGTCACTCTGATGTGCCTCACGATACA

AATGGCTGGGTAGAAGAGCCGACCGCCATCAATGAGACAAATGGCCACTACGTGAATGGCACGAA

TCACGAGACTCCCCTTACCAACGGCATTTCCAATGGAGATTCTGTTTCCGTTCATACAGACCACTC

GGACAGTTACTATCAGCGCAGTGATTGGACAGCCGACGAAGAACAAATTCTTCTCGGTCCATTTGA

CTACCTGGAGAGCCTGCCAGGCAAGAATATGCGCTCACAACTGATTCAATCATTCAACACATGGCT

CAAAGTCCCAACTGAGAGCTTGGATGTTATTATTAAGGTGATTTCAATGTTGCATACGGCCTCTCT

CTTGATCGATGATATTCAGGATCAATCAATACTCCGCCGCGGGCAACCTGTAGCGCACAGCATCTT

TGGCACAGCGCAAGCAATGAACTCAGGGAATTATGTCTACTTTCTAGCCCTTAGGGAGGTTCAGAA

ACTACAAAACCCGAAAGCCATCAGTATTTATGTTGACTCTTTGATTGATCTTCACCGTGGCCAAGG

CATGGAGCTTTTCTGGCGGGATTCTCTCATGTGCCCAACCGAAGAGCAGTACCTTGACATGGTCGC

-continued

AAACAAAACTGGCGGCCTGTTTTGCCTTGCTATCCAATTGATGCAAGCTGAAGCCACTATCCAAGT

CGACTTCATACCACTTGTCCGACTACTCGGCATCATCTTCCAGATTTGTGATGATTACTTGAATCTG

AAGTCTACGGCCTATACAGACAACAAAGGGTTGTGTGAGGATTTGACAGAGGGCAAATTCTCTTTT

CCTATCATCCATAGCATTCGATCCAACCCTGGCAACCGACAGCTAATCAACATCTTGAAGCAAAAG

CCACGTGAAGACGACATCAAACGCTATGCTCTATCCTATATGGAAAGCACCAACTCATTTGAGTAT

ACTCGGGGTGTCGTTAGAAAACTGAAGACCGAGGCAATCGATACTATTCAAGGCTTGGAGAAGCA

CGGCCTGGAAGAGAATATTGGCATTCGAAAGATACTAGCTCGCATGTCCCTTGAGCTATGA

SEQ ID NO 173: *Talaromyces verruculosus* PvCPS (BBF88128.1)
MSPMDLQESAAALVRQLGERVEDRRGFGFMSPAIYDTAWVSMISKTIDDQKTWLFAECFQYILSHQLE

DGGWAMYASEIDAILNTSASLLSLKRHLSNPYQITSITQEDLSARINRAQNALQKLLNEWNVDSTLHVG

FEILVPALLRYLEDEGIAFAFSGRERLLEIEKQKLSKFKAQYLYLPIKVTALHSLEAFIGAIEFDKVSHHK

VSGAFMASPSSTAAYMMHATQWDDECEDYLRHVIAHASGKGSGGVPSAFPSTIFESVWPLSTLLKVGY

DLNSAPFIEKIRSYLHDAYIAEKGILGFTPFVGADADDTATTILVLNLLNQPVSVDAMLKEFEEEHHFKT

YSQERNPSFSANCNVLLALLYSQEPSLYSAQIEKAIRFLYKQFTDSEMDVRDKWNLSPYYSWMLMTQA

ITRLTTLQKTSKLSTLRDDSISKGLISLLFRIASTVVKDQKPGGSWGTRASKEETAYAVLILTYAFYLDEV

TESLRHDIKIAIENGCSFLSERTMQSDSEWLWVEKVTYKSEVLSEAYILAALKRAADLPDENAEAAPVI

NGISTNGFEHTDRINGKLKVNGTNGTNGSHETNGINGTHEIEQINGVNGTNGHSDVPHDTNGWVEEPT

AINETNGHYVNGTNHETPLTNGISNGDSVSVHTDHSDSYYQRSDWTADEEQILLGPFDYLESLPGKNM

RSQLIQSFNTWLKVPTESLDVIIKVISMLHTASLLIDDIQDQSILRRGQPVAHSIFGTAQAMNSGNYVYFL

ALREVQKLQNPKAISIYVDSLIDLHRGQGMELFWRDSLMCPTEEQYLDMVANKTGGLFCLAIQLMQAE

ATIQVDFIPLVRLLGIIFQICDDYLNLKSTAYTDNKGLCEDLTEGKFSFPIIHSIRSNPGNRQLINILKQKPR

EDDIKRYALSYMESTNSFEYTRGVVRKLKTEAIDTIQGLEKHGLEENIGIRKILARMSLEL

SEQ ID NO 174: *Talaromyces verruculosus* PvCPS *E. coli* optimized
ATGAGCCCTATGGATTTGCAAGAAAGCGCCGCAGCCCTGGTCCGTCAATTGGGTGAACGCGTTGA

GGATCGCCGCGGTTTTGGTTTCATGAGCCCGGCCATTTATGACACGGCCTGGGTTAGCATGATTAG

CAAGACCATCGACGACCAAAAAACTTGGCTGTTTGCGGAGTGCTTCCAGTACATTCTGTCTCACCA

ACTGGAAGATGGTGGCTGGGCGATGTACGCATCCGAAATCGATGCCATCTTGAATACTTCCGCGTC

ACTGCTGTCCCTGAAACGCCACCTGTCCAACCCTTACCAGATCACCAGCATCACTCAGGAAGATCT

GAGCGCTCGCATCAACCGCGCTCAAAACGCCCTGCAGAAATTGCTGAACGAGTGGAACGTTGACT

CCACGCTGCACGTCGGTTTCGAGATTCTGGTTCCGGCGCTGCTGCGCTATCTGGAAGATGAAGGCA

TCGCGTTTGCGTTCTCGGGTCGTGAGCGTTTGTTAGAGATTGAGAAACAAAAACTGTCCAAGTTTA

AAGCGCAGTATTTGTACTTACCGATTAAGGTCACCGCACTGCATAGCCTGGAAGCCTTCATCGGCG

CTATTGAGTTCGACAAAGTCAGCCATCACAAAGTATCCGGTGCTTTCATGGCGTCGCCGTCTAGCA

CCGCAGCATACATGATGCATGCGACGCAATGGGATGACGAATGTGAGGATTACTTGCGTCACGTG

ATCGCGCATGCGTCAGGTAAGGGTTCTGGCGGCGTGCCGAGCGCCTTTCCGAGCACCATCTTCGAG

AGCGTTTGGCCGCTGTCTACTCTGCTGAAAGTTGGCTATGATCTGAATAGCGCTCCGTTCATCGAG

AAAATTCGTAGCTACTTGCACGATGCCTATATCGCAGAGAAAGGTATTCTCGGTTTCACCCCGTTC

GTTGGCGCTGACGCGGACGACACCGCTACCACGATTCTGGTGTTGAATCTGCTGAACCAACCGGTG

AGCGTGGACGCGATGTTGAAAGAATTTGAAGAGGAACATCACTTCAAGACCTACAGCCAAGAGCG

TAATCCGAGCTTTTCCGCAAACTGTAATGTTCTGCTGGCGCTGCTGTACAGCCAGGAACCGAGCCT

GTACAGCGCGCAAATCGAAAAAGCGATCCGTTTTCTGTATAAGCAATTCACCGACTCTGAGATGG

-continued

ATGTGCGCGATAAATGGAACCTGTCCCCGTATTATAGCTGGATGCTGATGACCCAGGCCATCACCC

GTCTGACGACCCTGCAAAAGACCAGCAAGCTGAGCACGCTGCGTGATGACAGCATTAGCAAGGGC

CTGATTTCTCTGCTGTTCCGCATTGCATCCACCGTGGTTAAAGATCAAAAACCGGGTGGCAGCTGG

GGCACGCGTGCGAGCAAAGAAGAAACGGCATACGCCGTGCTGATTCTGACCTACGCGTTTTATCT

GGACGAGGTGACCGAGTCTCTGCGCCACGATATCAAAATTGCAATCGAGAATGGTTGCTCGTTCCT

GAGCGAGCGCACCATGCAAAGCGACAGCGAGTGGCTGTGGGTCGAAAAGGTTACCTACAAGAGC

GAAGTGCTGAGCGAAGCATACATCCTGGCAGCTCTGAAACGTGCGGCAGACTTGCCGGATGAGAA

CGCTGAGGCAGCCCCAGTGATCAACGGTATCTCTACCAATGGCTTTGAGCACACCGACCGCATTAA

TGGTAAACTCAAGGTCAATGGTACGAATGGCACCAACGGTTCCCACGAAACGAACGGTATCAATG

GCACCCATGAGATTGAGCAAATTAATGGTGTCAACGGCACGAATGGCCATAGCGACGTGCCACAT

GACACGAATGGTTGGGTCGAGGAACCGACGGCGATTAATGAAACGAACGGTCACTACGTTAACGG

CACCAACCATGAGACTCCGCTGACCAATGGTATTAGCAATGGTGACTCCGTGAGCGTTCACACCGA

CCATAGCGACAGCTACTATCAGCGTAGCGACTGGACCGCGGATGAAGAACAGATCCTGCTGGGTC

CATTCGATTACCTGGAATCCCTGCCTGGTAAAAATATGCGCAGCCAGCTGATCCAGTCTTTCAATA

CGTGGCTGAAGGTCCCGACCGAGAGCTTGGACGTGATTATTAAGGTCATTAGCATGCTGCACACTG

CTAGCCTGCTGATCGACGATATTCAGGACCAAAGCATCCTGCGTCGTGGTCAGCCTGTGGCGCACT

CGATCTTCGGCACCGCGCAAGCGATGAACTCTGGTAACTATGTTTACTTCCTGGCATTGCGTGAAG

TTCAGAAATTGCAAAACCCGAAGGCTATCAGCATTTATGTGGACAGCTTGATCGATCTTCATCGCG

GCCAGGGCATGGAACTGTTCTGGCGTGATTCTCTGATGTGCCCGACTGAAGAACAGTATCTGGACA

TGGTGGCGAACAAGACCGGTGGCCTGTTTTGTCTGGCGATTCAGCTGATGCAGGCAGAAGCGACC

ATTCAGGTTGATTTTATTCCGCTGGTGCGTCTGCTGGGTATCATTTTCCAGATTTGCGACGACTACC

TGAACTTGAAAAGCACTGCGTATACCGACAACAAAGGTCTGTGTGAAGATCTTACCGAGGGTAAA

TTCTCCTTCCCGATCATTCACAGCATCCGTAGCAATCCGGGCAATCGTCAGCTGATCAATATTCTGA

AGCAAAAACCGCGCGAAGATGACATCAAGCGTTACGCACTGTCCTATATGGAGAGCACGAATAGC

TTCGAGTACACCCGTGGCGTCGTCCGTAAATTGAAAACCGAAGCAATTGACACGATTCAAGGTCTG

GAGAAGCATGGCCTGGAAGAAAACATTGGTATTCGTAAGATTCTGGCGCGTATGAGCCTGGAACT

GTAA

SEQ ID NO 175: *Talaromyces cellulolyticus* TalCeTPP wt

ATGTCTAATGACACCACTAGCACGGCTTCTGCCGGAACAGCAACTTCTTCGCGGTTTCTTTCTGTGG

GCGGAGTTGTGAATTTCCGTGAACTGGGCGGTTATCCATGTGATTCTGTCCCTCCTGCTCCTGCCTC

AAACGGCTCACCGGACAACGCATCTGAAGCGATCCTTTGGGTTGGCCACTCGTCCATTCGGCCTAG

GTTTCTCTTTCGATCGGCACAGCCGTCTCAGATTACCCCGGCCGGTATTGAGACATTGATCCGCCA

GCTTGGCATCCAGGCAATTTTTGACTTTCGTTCACGGACGGAAATTCAGCTTGTCGCCACTCGCTAT

CCTGATTCGCTACTCGAGATACCTGGTACGACTCGCTATTCCGTGCCCGTCTTCACGGAGGGCGAC

TATTCCCCGGCGTCATTAGTCAAGAGGTACGGAGTGTCCTCCGATACTGCAACTGATTCCACTTCC

TCCAAATGTGCCAAGCCTACAGGATTCGTCCACGCATATGAGGCTATCGCACGCAGCGCAGCAGA

AAACGGCAGTTTTCGTAAAATAACGGACCACATAATACAACATCCGGACCGGCCTATCCTGTTTCA

CTGTACATTGGGAAAAGACCGAACCGGTGTATTTGCAGCATTGTTATTGAGTCTTTGCGGGGTACC

AAACGACACGATAGTTGAAGACTATGCTATGACTACCGAGGGATTTGGGGTCTGGCGAGAACATC

TAATTCAACGCCTGTTACAAAGAAAGGATGCAGCTACGCGTGAGGATGCAGAATTCATTATTGCC

AGCCACCCGGAGAGTATGAAGGCTTTTCTAGAAGATGTGGTAGCAACCAAGTTCGGGGATGCTCG

-continued

AAATTACTTTATCCAGCACTGTGGATTGACGGAAGCGGAGGTTGATAAGCTAATTCGGACACTGGT

CATTGCGAATTGA

SEQ ID NO 176: *Talaromyces cellulolyticus* TalCeTPP wt (GAM42000.1)
MSNDTTSTASAGTATSSRFLSVGGVVNFRELGGYPCDSVPPAPASNGSPDNASEAILWVGHSSIRPRFLF

RSAQPSQITPAGIETLIRQLGIQAIFDFRSRTEIQLVATRYPDSLLEIPGTTRYSVPVFTEGDYSPASLVKRY

GVSSDTATDSTSSKCAKPTGFVHAYEAIARSAAENGSFRKITDHIIQHPDRPILFHCTLGKDRTGVFAAL

LLSLCGVPNDTIVEDYAMTTEGFGVWREHLIQRLLQRKDAATREDAEFIIASHPESMKAFLEDVVATKF

GDARNYFIQHCGLTEAEVDKLIRTLVIAN

SEQ ID NO 177: Talaromyces *cellulolyticus* TalCeTPP *E. coli* optimized
ATGAGCAACGACACGACCAGCACCGCATCCGCAGGCACCGCAACTTCTTCGCGCTTTCTGAGCGTC

GGTGGCGTGGTTAACTTCCGTGAGTTGGGTGGCTACCCGTGCGACAGCGTTCCTCCTGCACCAGCA

AGCAATGGTAGCCCGGACAATGCGAGCGAAGCGATTCTGTGGGTTGGTCACAGCAGCATTCGTCC

GCGCTTCTTGTTTCGTAGCGCACAGCCGTCCCAGATCACCCCGGCCGGTATTGAAACGCTGATTCG

CCAACTCGGTATTCAAGCGATCTTTGACTTTCGTTCCCGTACCGAGATCCAACTGGTGGCAACCCG

CTACCCAGATAGCCTGCTGGAAATTCCGGGCACGACTCGTTACTCTGTTCCGGTCTTTACCGAGGG

CGACTACAGCCCGGCTTCTCTGGTTAAGCGTTATGGTGTCTCTAGCGACACGGCAACGGATAGCAC

CAGCTCAAAGTGCGCGAAACCGACCGGCTTTGTGCATGCTTATGAAGCGATTGCTCGTTCTGCCGC

GGAGAACGGTAGCTTCCGCAAGATCACCGACCACATTATCCAACATCCGGATCGCCCGATCCTGTT

TCACTGCACGCTGGGCAAAGACCGTACCGGTGTTTTCGCAGCGCTGCTGCTGAGCTTGTGTGGTGT

CCCGAATGACACCATCGTGGAAGATTATGCGATGACGACCGAAGGCTTCGGTGTGTGGCGTGAGC

ACTTGATTCAGCGTCTGCTGCAGCGCAAAGATGCGGCTACGCGTGAAGATGCCGAGTTCATTATCG

CGAGCCATCCGGAGAGCATGAAAGCGTTCCTGGAAGATGTCGTTGCGACCAAATTCGGTGACGCC

CGCAACTACTTTATCCAGCACTGTGGTCTGACCGAAGCCGAAGTGGATAAGCTGATCCGTACGCTG

GTGATCGCGAATTAA

SEQ ID NO 178: *Castellaniella defrasrans* CdGeoA wt (NZ HG916765.1 3061533-3062654 (+))
ATGAACGACACCCAGGATTTCATTTCCGCGCAGGCCGCCGTGCTGCGCCAGGTCGGCGGGCCGCTC

GCGGTCGAGCCCGTGCGCATCAGCATGCCCAAAGGCGACGAGGTCTTGATCCGCATCGCCGGCGT

GGGCGTCTGCCACACCGACCTGGTGTGCCGCGACGGATTTCCCGTGCCGCTGCCGATCGTGCTCGG

CCACGAAGGCTCCGGCACCGTCGAGGCGGTGGGCGAGCAGGTGCGCACGCTCAAGCCCGGCGACC

GGGTCGTGCTGTCCTTCAATTCCTGCGGGCATTGCGGCAATTGCCACGACGGCCATCCGTCGAACT

GCCTGCAGATGCTGCCCCTGAACTTCGGCGGCGCGCAGCGCGTGGACGGCGGCCAGGTGCTGGAC

GGCGCCGGCCATCCCGTGCAGAGCATGTTCTTCGGCCAGTCCTCGTTCGGCACGCATGCCGTGGCG

CGCGAAATCAATGCGGTCAAGGTCGGCGACGACCTGCCGCTGGAACTGCTGGGCCCGCTGGGCTG

CGGCATCCAGACCGGCGCGGGCGCGGCGATCAATTCGCTGGGGATCGGCCCGGGCCAGTCCCTGG

CCATCTTCGGCGGTGGCGGCGTCGGCCTGAGCGCGCTGCTGGGCGCGCGCGCCGTCGGGGCGGAC

CGGGTCGTGGTGATCGAGCCCAATGCCGCGCGCGCCGGGCCCTGGCCCTGGAACTGGGCGCCAGCCA

TGCCCTCGACCCGCACGCCGAAGGCGACCTGGTGGCCGCGATCAAGGCGGCCACCGGCGGCGGCG

CGACCCACTCGCTGGACACGACGGGCCTGCCCCCGGTCATCGGCAGCGCGATCGCCTGCACCCTGC

CGGGCGGCACCGTGGGCATGGTCGGACTGCCGGCGCCCGATGCCCCGGTGCCGGCGACCCTGCTC

GATCTGCTGAGCAAAAGCGTCACCCTGCGCCCGATCACCGAGGGCGACGCGGACCCGCAGCGCTT

CATCCCGCGCATGCTGGATTTCCATCGCGCGGGCAAATTCCCGTTCGACCGGCTGATCACCCGCTA

-continued

CCGTTTCGACCAGATCAACGAGGCCCTGCACGCCACCGAGAAGGGCGAGGCGATCAAGCCGGTGC

TGGTGTTCTGA

SEQ ID NO 179: *Castellaniella defrasrans* CdGeoA wt (WP_043683915.1)
MNDTQDFISAQAAVLRQVGGPLAVEPVRISMPKGDEVLIRIAGVGVCHTDLVCRDGFPVPLPIVLGHEG

SGTVEAVGEQVRTLKPGDRVVLSFNSCGHCGNCHDGHPSNCLQMLPLNFGGAQRVDGGQVLDGAGH

PVQSMFFGQSSFGTHAVAREINAVKVGDDLPLELLGPLGCGIQTGAGAAINSLGIGPGQSLAIFGGGGV

GLSALLGARAVGADRVVVIEPNAARRALALELGASHALDPHAEGDLVAAIKAATGGGATHSLDTTGL

PPVIGSAIACTLPGGTVGMVGLPAPDAPVPATLLDLLSKSVTLRPITEGDADPQRFIPRMLDFHRAGKFP

FDRLITRYRFDQINEALHATEKGEAIKPVLVF

SEQ ID NO 180: *Castellaniella defrasrans* CdGeoA *E. coli* optimized
ATGAACGATACGCAGGATTTTATTAGCGCCCAAGCCGCAGTGTTACGTCAGGTCGGTGGCCCGCTG

GCCGTTGAGCCTGTTCGTATCAGCATGCCGAAGGGTGACGAAGTCCTGATTCGTATCGCGGGTGTT

GGTGTGTGCCACACCGACTTGGTGTGCCGTGATGGCTTCCCGGTGCCGCTGCCAATTGTGCTGGGT

CACGAGGGTAGCGGTACTGTCGAAGCCGTCGGTGAACAAGTCCGTACCCTGAAACCGGGCGATCG

CGTCGTGCTGAGCTTTAACAGCTGCGGTCATTGCGGTAACTGTCACGACGGTCACCCGAGCAATTG

CCTGCAGATGCTGCCGCTGAACTTCGGTGGCGCGCAACGCGTGGACGGTGGCCAAGTTTTGGACG

GTGCGGGTCATCCGGTTCAGTCCATGTTTTTCGGCCAGTCCAGCTTTGGCACCCACGCAGTAGCGC

GCGAGATCAACGCAGTCAAGGTCGGCGATGATCTGCCACTGGAACTGCTGGGTCCGTTGGGTTGT

GGCATTCAAACCGGTGCGGGTGCAGCTATCAATTCTCTGGGCATTGGTCCGGGTCAGTCTCTGGCT

ATCTTCGGCGGCGGCGGCGTGGGTCTGAGCGCACTGCTGGGCGCCCGTGCGGTGGGTGCCGACCG

TGTTGTTGTCATTGAGCCGAATGCAGCGCGCCGTGCGCTGGCATTGGAACTGGGTGCCAGCCACGC

ACTGGACCCGCATGCCGAGGGCGACCTTGTTGCGGCGATTAAAGCTGCGACGGGTGGCGGCGCTA

CGCATAGCTTGGATACGACCGGCCTGCCGCCAGTCATTGGCTCCGCGATCGCGTGTACTCTGCCGG

GTGGCACCGTTGGTATGGTTGGTCTGCCGGCGCCGGACGCACCGGTCCCTGCGACGCTGTTGGATC

TGCTGAGCAAATCGGTTACCCTGCGTCCGATTACCGAGGGTGACGCTGACCCGCAACGCTTCATCC

CGCGTATGCTGGATTTCCATCGTGCGGGCAAGTTTCCGTTCGACCGCCTGATCACCCGTTACCGCTT

TGATCAGATCAATGAAGCGCTGCACGCGACCGAGAAAGGTGAAGCAATCAAACCGGTTCTGGTGT

TTTAA

SEQ ID NO 181: *Blakeslea trispora* GGPP synthase carG wt (JQ289995.1)
ATGTTGACCTCTAGCAAATCAATTGAATCCTTCCCCAAGAATGTTCAACCTTATGGCAAGCATTAT

CAAAATGGCTTGGAACCTGTTGGAAAAAGCCAAGAAGATATTCTCTTGGAGCCATTCCACTATCTC

TGTTCGAATCCTGGTAAAGATGTCCGAACCAAGATGATTGAAGCGTTCAATGCTTGGCTGAAAGTA

CCCAAGGACGATTTGATCGTCATCACACGTGTGATTGAAATGCTTCATAGTGCTAGTTTGTTAATT

GATGATGTGGAAGATGATTCCGTGTTGCGTCGTGGTGTTCCTGCAGCTCATCATATATATGGTACT

CCTCAAACTATCAATTGTGCTAATTACGTGTACTTTCTTGCACTGAAAGAAATTGCCAAGTTGAAC

AAGCCCAACATGATTACTATCTATACCGATGAATTGATCAATTTGCACAGAGGGCAAGGAATGGA

ATTGTTTTGGCGTGACACCTTAACTTGTCCTACAGAGAAAGAATTTCTTGACATGGTAAACGACAA

AACTGGTGGCCTCTTGAGATTAGCTGTGAAACTTATGCAAGAAGCTAGTCAATCGGGAACTGATTA

TACGGGACTCGTAAGTAAGATTGGTATCCATTTCCAAGTACGCGACGATTATATGAATTTGCAGTC

AAAAAACTATGCTGACAACAAAGGATTCTGCGAAGACTTGACAGAAGGAAAATTCTCTTTCCCTA

TTATACATTCAATCCGCTCTGACCCAAGCAATCGCCAGCTTTTGAACATTTTAAAACAGCGCAGTA

GCTCTATCGAACTCAAGCAATTTGCCTTGCAGCTACTGGAAAACACAAACACTTTCCAATACTGTC

-continued

GTGATTTCTTACGTGTCTTGGAAAAGGAAGCTAGAGAAGAAATTAAGCTTTTAGGGGGTAACATC

ATGTTGGAGAAAATTATGGATGTCTTGAGTGTCAATGAATAA

SEQ ID NO 182: *Blakeslea trispora* GGPP synthase carG wt (AFC92798.1)
MLTSSKSIESFPKNVQPYGKHYQNGLEPVGKSQEDILLEPFHYLCSNPGKDVRTKMIEAFNAWLKVPK

DDLIVITRVIEMLHSASLLIDDVEDDSVLRRGVPAAHHIYGTPQTINCANYVYFLALKEIAKLNKPNMITI

YTDELINLHRGQGMELFWRDTLTCPTEKEFLDMVNDKTGGLLRLAVKLMQEASQSGTDYTGLVSKIGI

HFQVRDDYMNLQSKNYADNKGFCEDLTEGKFSFPIIHSIRSDPSNRQLLNILKQRSSSIELKQFALQLLE

NTNTFQYCRDFLRVLEKEAREEIKLLGGNIMLEKIMDVLSVNE*

SEQ ID NO 183: *Blakeslea trispora* GGPP synthase carG Yeast optimized
ATGTTGACATCTTCTAAGTCCATCGAATCTTTCCCAAAGAACGTTCAACCATACGGTAAACACTAT

CAAAACGGTTTAGAACCAGTCGGTAAGTCTCAAGAAGACATCTTGTTGGAACCTTTCCACTACTTA

TGTTCTAATCCAGGTAAGGATGTTAGAACCAAGATGATTGAAGCTTTCAACGCCTGGTTGAAAGTC

CCAAAGGACGATTTGATTGTTATCACCAGAGTCATTGAAATGTTGCACTCCGCTTCTTTGTTGATTG

ATGACGTCGAGGACGATTCTGTCTTGAGAAGAGGTGTCCCAGCCGCCCACCATATCTACGGTACCC

CTCAAACCATCAACTGCGCTAACTACGTTTATTTCTTGGCCTTGAAAGAAATCGCCAAGTTGAACA

AGCCAAATATGATTACTATTTATACCGATGAATTGATCAACTTGCACAGAGGTCAAGGTATGGAAT

TGTTCTGGCGTGATACCTTGACCTGCCCAACTGAGAAAGAGTTTTTGGATATGGTTAACGATAAGA

CTGGTGGTTTGTTGAGATTGGCCGTCAAGTTGATGCAAGAGGCTTCTCAATCTGGTACCGACTATA

CTGGTTTGGTTTCTAAGATCGGTATCCATTTTCAAGTTAGAGATGACTACATGAACTTGCAATCCA

AAAACTACGCCGATAATAAGGGTTTCTGTGAAGATTTGACCGAAGGTAAGTTCTCCTTTCCAATTA

TTCACTCTATCAGATCTGACCCATCCAACAGACAATTATTGAATATTTTGAAGCAAAGATCTTCTTC

TATTGAATTGAAACAATTCGCTTTACAATTGTTAGAAAACACTAACACTTTTCAATACTGTAGAGA

TTTCTTGAGAGTTTTGGAAAAGGAAGCCAGAGAAGAGATCAAATTATTGGGTGGTAACATCATGTT

GGAAAAGATTATGGACGTCTTGTCTGTTAATGAATAA

SEQ ID NO 184: *Salvia miltiorrhiza* SmCPS2 wt (EU003997.1 73-2454 (+))
ATGGCCTCCTTATCCTCTACAATCCTCAGCCGCTCTCCGGCGGCCCGCCGCAGAATTACGCCGGCG

TCGGCTAAGCTTCACCGGCCGGAATGTTTCGCCACCAGTGCATGGATGGGCAGCAGCAGTAAAAA

CCTTTCTCTCAGCTACCAACTTAATCACAAGAAAATATCAGTTGCCACAGTAGATGCGCCGCAGGT

GCATGACCACGACGGCACTACCGTTCATCAAGGCCATGATGCGGTGAAGAATATTGAGGATCCCA

TTGAATACATCAGGACGTTGTTGAGGACGACGGGGGACGGGAGAATAAGCGTGTCGCCGTACGAC

ACGGCGTGGGTGGCGATGATCAAGGACGTGGAGGGGGCGGGACGGCCCCCAGTTCCCCTCCAGCCT

CGAGTGGATCGTGCAGAATCAACTCGAGGATGGATCGTGGGGCGATCAGAAGCTTTTCTGCGTCT

ACGATCGCCTCGTCAATACCATCGCGTGCGTGGTAGCCTTGAGATCGTGGAATGTTCATGCTCACA

AGGTCAAAAGAGGAGTGACGTACATCAAGGAAAATGTGGATAAACTTATGGAGGGAAATGAGGA

GCACATGACTTGTGGGTTCGAAGTGGTGTTTCCGGCGCTTCTACAAAAAGCGAAAAGCTTAGGCAT

CGAAGATCTTCCTTACGATTCTCCGGCGGTGCAGGAGGTTTATCATGTCAGGGAACAAAAGTTGAA

AAGGATTCCACTGGAGATTATGCACAAAATACCGACATCATTATTATTTAGTTTGGAAGGGCTCGA

AAATTTGGATTGGGACAAACTTTTGAAACTGCAGTCAGCCGACGGTTCCTTCCTCACCTCTCCCTCC

TCCACCGCCTTCGCGTTCATGCAAACCAAGGATGAAAAATGCTACCAATTCATCAAGAACACGAT

AGACACTTTCAACGGAGGAGCGCCACACACTTATCCCGTCGACGTGTTTGGAAGGCTCTGGGCGAT

CGACCGGCTGCAGCGCCTCGGAATTTCCCGCTTTTTTGAGCCGGAGATTGCTGATTGCTTAAGCCA

CATCCACAAATTTTGGACGGATAAGGGAGTTTTCAGTGGGAGAGAATCGGAGTTTTGCGACATTG

-continued

ACGATACATCCATGGGAATGAGGCTTATGAGGATGCATGGATATGATGTTGATCCAAATGTGCTG

AGGAATTTCAAGCAGAAAGATGGTAAATTCTCTTGCTACGGCGGGCAGATGATCGAGTCGCCTTCT

CCGATATACAATCTTTACAGAGCTTCTCAGCTCCGATTTCCCGGCGAGGAAATCCTCGAAGATGCG

AAGAGATTCGCCTACGATTTCTTGAAAGAAAAACTAGCCAACAATCAGATTCTGGATAAATGGGT

TATTTCTAAGCACTTGCCTGATGAGATCAAGCTCGGGCTAGAGATGCCGTGGCTCGCCACCCTACC

CCGCGTCGAGGCGAAGTACTACATCCAGTACTACGCCGGCTCCGGCGACGTGTGGATCGGAAAGA

CGCTGTACAGGATGCCGGAGATCAGCAACGACACGTACCACGACCTAGCCAAGACGGATTTCAAG

AGATGCCAAGCGAAGCATCAGTTCGAGTGGCTCTACATGCAAGAATGGTACGAGAGCTGCGGCAT

CGAGGAATTCGGGATAAGCAGAAAGGACCTTCTGCTTTCCTATTTCTTGGCGACCGCGAGCATCTT

CGAGCTCGAGAGGACCAACGAGCGAATCGCGTGGGCCAAATCGCAGATCATCGCTAAGATGATCA

CTTCTTTCTTCAACAAGGAAACTACGTCGGAGGAGGACAAGCGAGCTCTTTTGAACGAGCTCGGA

AACATTAATGGCCTCAACGACACAAACGGCGCAGGGAGAGAAGGTGGGGCCGGTAGCATTGCGCT

AGCGACCCTCACTCAGTTCCTCGAGGGATTCGACAGATACACCAGACACCAGCTGAAAAATGCTT

GGAGCGTATGGCTGACGCAGCTGCAACATGGCGAAGCAGACGACGCGGAGCTCCTAACCAACACG

TTGAACATCTGCGCCGGCCACATCGCCTTCAGGGAAGAAATACTGGCGCACAACGAGTACAAAGC

TCTCTCCAACCTAACCAGCAAAATCTGTCGACAGCTTTCTTTCATTCAAAGCGAAAAGGAGATGGG

AGTAGAGGGCGAGATCGCAGCGAAATCGAGCATAAAAAACAAGGAACTCGAAGAAGACATGCAA

ATGTTGGTGAAGTTGGTGCTTGAGAAATATGGGGGCATAGATAGAAATATAAAGAAAGCGTTTTT

AGCAGTTGCGAAGACTTATTATTACAGAGCGTATCATGCCGCCGACACCATAGACACACACATGTT

TAAAGTGCTTTTCGAGCCAGTCGCGTGA

SEQ ID NO 185: *Salvia miltiorrhiza* SmCPS2
MATVDAPQVHDHDGTTVHQGHDAVKNIEDPIEYIRTLLRTTGDGRISVSPYDTAWVAMIKDVEGRDG

PQFPSSLEWIVQNQLEDGSWGDQKLFCVYDRLVNTIACVVALRSWNVHAHKVKRGVTYIKENVDKL

MEGNEEHMTCGFEVVFPALLQKAKSLGIEDLPYDSPAVQEVYHVREQKLKRIPLEIMHKIPTSLLFSLEG

LENLDWDKLLKLQSADGSFLTSPSSTAFAFMQTKDEKCYQFIKNTIDTFNGGAPHTYPVDVFGRLWAI

DRLQRLGISRFFEPEIADCLSHIHKFWTDKGVFSGRESEFCDIDDTSMGMRLMRMHGYDVDPNVLRNF

KQKDGKFSCYGGQMIESPSPIYNLYRASQLRFPGEEILEDAKRFAYDFLKEKLANNQILDKWVISKHLP

DEIKLGLEMPWLATLPRVEAKYYIQYYAGSGDVWIGKTLYRMPEISNDTYHDLAKTDFKRCQAKHQF

EWLYMQEWYESCGIEEFGISRKDLLLSYFLATASIFELERTNERIAWAKSQIIAKMITSFFNKETTSEEDK

RALLNELGNINGLNDTNGAGREGGAGSIALATLTQFLEGFDRYTRHQLKNAWSVWLTQLQHGEADDA

ELLTNTLNICAGHIAFREEILAHNEYKALSNLTSKICRQLSFIQSEKEMGVEGEIAAKSSIKNKELEEDMQ

MLVKLVLEKYGGIDRNIKKAFLAVAKTYYYRAYHAADTIDTHMFKVLFEPVA*

SEQ ID NO 186: *Salvia miltiorrhiza* SmCPS2 Yeast optimized
ATGGCTACTGTTGACGCTCCACAAGTTCACGACCACGACGGTACTACTGTTCACCAAGGTCACGAC

GCTGTTAAGAACATCGAAGACCCAATCGAATACATCAGAACTTTGTTGAGAACTACTGGTGACGG

TAGAATCTCTGTTTCTCCATACGACACTGCTTGGGTTGCTATGATCAAGGACGTTGAAGGTAGAGA

CGGTCCACAATTCCCATCTTCTTTGGAATGGATCGTTCAAAACCAATTGGAAGACGGTTCTTGGGG

TGACCAAAAGTTGTTCTGTGTTTACGACAGATTGGTTAACACTATCGCTTGTGTTGTTGCTTTGAGA

TCTTGGAACGTTCACGCTCACAAGGTTAAGAGAGGTGTTACTTACATCAAGGAAAACGTTGACAA

GTTGATGGAAGGTAACGAAGAACACATGACTTGTGGTTTCGAAGTTGTTTTCCCAGCTTTGTTGCA

AAAGGCTAAGTCTTTGGGTATCGAAGACTTGCCATACGACTCTCCAGCTGTTCAAGAAGTTTACCA

-continued

CGTTAGAGAACAAAAGTTGAAGAGAATCCCATTGGAAATCATGCACAAGATCCCAACTTCTTTGTT

GTTCTCTTTGGAAGGTTTGGAAAACTTGGACTGGGACAAGTTGTTGAAGTTGCAATCTGCTGACGG

TTCTTTCTTGACTTCTCCATCTTCTACTGCTTTCGCTTTCATGCAAACTAAGGACGAAAAGTGTTAC

CAATTCATCAAGAACACTATCGACACTTTCAACGGTGGTGCTCCACACACTTACCCAGTTGACGTT

TTCGGTAGATTGTGGCTATCGACAGATTGCAAAGATTGGGTATCTCTAGATTCTTCGAACCAGAA

ATCGCTGACTGTTTGTCTCACATCCACAAGTTCTGGACTGACAAGGGTGTTTTCTCTGGTAGAGAA

TCTGAATTCTGTGACATCGACGACACTTCTATGGGTATGAGATTGATGAGAATGCACGGTTACGAC

GTTGACCCAAACGTTTTGAGAAACTTCAAGCAAAAGGACGGTAAGTTCTCTTGTTACGGTGGTCAA

ATGATCGAATCTCCATCTCCAATCTACAACTTGTACAGAGCTTCTCAATTGAGATTCCCAGGTGAA

GAAATCTTGGAAGACGCTAAGAGATTCGCTTACGACTTCTTGAAGGAAAAGTTGGCTAACAACCA

AATCTTGGACAAGTGGGTTATCTCTAAGCACTTGCCAGACGAAATCAAGTTGGGTTTGGAAATGCC

ATGGTTGGCTACTTTGCCAAGAGTTGAAGCTAAGTACTACATCCAATACTACGCTGGTTCTGGTGA

CGTTTGGATCGGTAAGACTTTGTACAGAATGCCAGAAATCTCTAACGACACTTACCACGACTTGGC

TAAGACTGACTTCAAGAGATGTCAAGCTAAGCACCAATTCGAATGGTTGTACATGCAAGAATGGT

ACGAATCTTGTGGTATCGAAGAATTCGGTATCTCTAGAAAGGACTTGTTGTTGTCTTACTTCTTGGC

TACTGCTTCTATCTTCGAATTGGAAAGAACTAACGAAAGAATCGCTTGGGCTAAGTCTCAAATCAT

CGCTAAGATGATCACTTCTTTCTTCAACAAGGAAACTACTTCTGAAGAAGACAAGAGAGCTTTGTT

GAACGAATTGGGTAACATCAACGGTTTGAACGACACTAACGGTGCTGGTAGAGAAGGTGGTGCTG

GTTCTATCGCTTTGGCTACTTTGACTCAATTCTTGGAAGGTTTCGACAGATACACTAGACACCAATT

GAAGAACGCTTGGTCTGTTTGGTTGACTCAATTGCAACACGGTGAAGCTGACGACGCTGAATTGTT

GACTAACACTTTGAACATCTGTGCTGGTCACATCGCTTTCAGAGAAGAAATCTTGGCTCACAACGA

ATACAAGGCTTTGTCTAACTTGACTTCTAAGATCTGTAGACAATTGTCTTTCATCCAATCTGAAAAG

GAAATGGGTGTTGAAGGTGAAATCGCTGCTAAGTCTTCTATCAAGAACAAGGAATTGGAAGAAGA

CATGCAAATGTTGGTTAAGTTGGTTTTGGAAAAGTACGGTGGTATCGACAGAAACATCAAGAAGG

CTTTCTTGGCTGTTGCTAAGACTTACTACTACAGAGCTTACCACGCTGCTGACACTATCGACACTCA

CATGTTCAAGGTTTTGTTCGAACCAGTTGCTTAA

SEQ ID NO 187: *Salvia sclarea* SsLPS wt (JN133923.1)
ATGACTTCTGTAAATTTGAGCAGAGCACCAGCAGCGATTACCCGGCGCAGGCTGCAGCTACAGCC

GGAATTTCATGCCGAGTGTTCATGGCTGAAAAGCAGCAGCAAACACGCGCCCTTGACCTTGAGTTG

CCAAATCCGTCCTAAGCAACTCTCCCAAATAGCTGAATTGAGAGTAACAAGCCTGGATGCGTCGC

AAGCGAGTGAAAAAGACATTTCCCTTGTTCAAACTCCGCATAAGGTTGAGGTTAATGAAAAGATC

GAGGAGTCAATCGAGTACGTCCAAAATCTGTTGATGACGTCGGGCGACGGGCGAATAAGCGTGTC

ACCCTATGACACGGCAGTGATCGCCCTGATCAAGGACTTGAAAGGGCGCGACGCCCCGCAGTTTC

CGTCATGTCTCGAGTGGATCGCGCACCACCAACTGGCTGATGGCTCATGGGGCGACGAATTCTTCT

GTATTTATGATCGGATTCTAAATACATTGGCATGTGTCGTAGCCTTGAAATCATGGAACCTTCACTC

TGATATTATTGAAAAAGGAGTGACGTACATCAAGGAGAATGTGCATAAACTTAAAGGTGCAAATG

TTGAGCACAGGACAGCGGGGTTCGAACTTGTGGTTCCTACTTTTATGCAAATGGCCACAGATTTGG

GCATCCAAGATCTGCCCTATGATCATCCCCTCATCAAGGAGATTGCTGACACAAAACAACAAAGA

TTGAAAGAGATACCCAAGGATTTGGTTTACCAAATGCCAACGAATTTACTGTACAGTTTAGAAGGG

TTAGGAGATTTGGAGTGGGAAAGGCTACTGAAACTGCAGTCGGGCAATGGCTCCTTCCTCACTTCG

CCGTCGTCCACCGCCGCCGTCTTGATGCATACCAAAGATGAAAAATGTTTGAAATACATCGAAAAC

-continued

GCCCTCAAGAATTGCGACGGAGGAGCACCACATACTTATCCAGTCGATATCTTCTCAAGACTTTGG

GCAATCGATAGGCTACAACGCCTAGGAATTTCTCGTTTCTTCCAGCACGAGATCAAGTATTTCTTA

GATCACATCGAAAGCGTTTGGGAGGAGACCGGAGTTTTCAGTGGAAGATATACGAAATTTAGCGA

TATTGATGACACGTCCATGGGCGTTAGGCTTCTCAAAATGCACGGATACGACGTCGATCCAAATGT

ACTAAAACATTTCAAGCAACAAGATGGTAAATTTTCCTGCTACATTGGTCAATCGGTCGAGTCTGC

ATCTCCAATGTACAATCTTTATAGGGCTGCTCAACTAAGATTTCCAGGAGAAGAAGTTCTTGAAGA

AGCCACTAAATTTGCCTTTAACTTCTTGCAAGAAATGCTAGTCAAAGATCGACTTCAAGAAAGATG

GGTGATATCCGACCACTTATTTGATGAGATAAAGCTGGGGTTGAAGATGCCATGGTACGCCACTCT

ACCCCGAGTCGAGGCTGCATATTATCTAGACCATTATGCTGGTTCTGGTGATGTATGGATTGGCAA

GAGTTTCTACAGGATGCCAGAAATCAGCAATGATACATACAAGGAGCTTGCGATATTGGATTTCA

ACAGATGCCAAACACAACATCAGTTGGAGTGGATCCACATGCAGGAATGGTACGACAGATGCAGC

CTTAGCGAATTCGGGATAAGCAAAAGAGAGTTGCTTCGCTCTTACTTTCTGGCCGCAGCAACCATA

TTCGAACCGGAGAGAACTCAAGAGAGGCTTCTGTGGGCCAAAACCAGAATTCTTTCTAAGATGAT

CACTTCATTTGTCAACATTAGTGGAACAACACTATCTTTGGACTACAATTTCAATGGCCTCGATGA

AATAATTAGTAGTGCCAATGAAGATCAAGGACTGGCTGGGACTCTGCTGGCAACCTTCCATCAACT

TCTAGACGGATTCGATATATACACTCTCCATCAACTCAAACATGTTTGGAGCCAATGGTTCATGAA

AGTGCAGCAAGGAGAGGGAAGCGGCGGGGAAGACGCGGTGCTCCTAGCGAACACGCTCAACATC

TGCGCCGGCCTCAACGAAGACGTGTTGTCCAACAATGAATACACGGCTCTGTCCACCCTCACAAAT

AAAATCTGCAATCGCCTCGCCCAAATTCAAGACAATAAGATTCTCCAAGTTGTGGATGGGAGCAT

AAAGGATAAGGAGCTAGAACAGGATATGCAGGCGTTGGTGAAGTTAGTGCTTCAAGAAAATGGCG

GCGCCGTAGACAGAAACATCAGACACACGTTTTTGTCGGTTTCCAAGACTTTCTACTACGATGCCT

ACCACGACGATGAGACGACCGATCTTCATATCTTCAAAGTACTCTTTCGACCGGTTGTATGA

SEQ ID NO 188: *Salvia sclarea* SsLPS *E. coli* optimized
MASQASEKDISLVQTPHKVEVNEKIEESIEYVQNLLMTSGDGRISVSPYDTAVIALIKDLKGRDAPQFPS

CLEWIAHHQLADGSWGDEFFCIYDRILNTLACVVALKSWNLHSDIIEKGVTYIKENVHKLKGANVEHR

TAGFELVVPTFMQMATDLGIQDLPYDHPLIKEIADTKQQRLKEIPKDLVYQMPTNLLYSLEGLGDLEW

ERLLKLQSGNGSFLTSPSSTAAVLMHTKDEKCLKYIENALKNCDGGAPHTYPVDIFSRLWAIDRLQRLG

ISRFFQHEIKYFLDHIESVWEETGVFSGRYTKFSDIDDTSMGVRLLKMHGYDVDPNVLKHFKQQDGKFS

CYIGQSVESASPMYNLYRAAQLRFPGEEVLEEATKFAFNFLQEMLVKDRLQERWVISDHLFDEIKLGLK

MPWYATLPRVEAAYYLDHYAGSGDVWIGKSFYRMPEISNDTYKELAILDFNRCQTQHQLEWIHMQE

WYDRCSLSEFGISKRELLRSYFLAAATIFEPERTQERLLWAKTRILSKMITSFVNISGTTLSLDYNFNGLD

EIISSANEDQGLAGTLLATFHQLLDGFDIYTLHQLKHVWSQWFMKVQQGEGSGGEDAVLLANTLNICA

GLNEDVLSNNEYTALSTLTNKICNRLAQIQDNKILQVVDGSIKDKELEQDMQALVKLVLQENGGAVDR

NIRHTFLSVSKTFYYDAYHDDETTDLHIFKVLFRPVV*

SEQ ID NO 189: *Salvia sclarea* SsLPS *E. coli* optimized
ATGGCATCCCAAGCGTCCGAGAAAGATATTAGCCTGGTTCAAACCCCGCATAAGGTCGAGGTCAA

CGAAAAGATCGAAGAGAGCATCGAGTACGTCCAAAATCTGCTGATGACGAGCGGTGACGGTCGTA

TCTCCGTGTCTCCGTACGATACCGCGGTCATCGCTCTGATTAAAGATCTGAAGGGTCGCGACGCAC

CGCAGTTCCCGAGCTGTCTGGAGTGGATTGCGCACCACCAGTTAGCGGATGGTAGCTGGGGCGAC

GAGTTCTTTTGTATCTATGACCGCATTTTGAATACCCTGGCGTGCGTCGTCGCACTGAAATCTTGGA

ATCTGCACAGCGACATTATTGAAAAAGGCGTGACCTACATTAAGGAAAACGTCCATAAGCTGAAA

GGCGCGAATGTTGAGCATAGAACCGCCGGTTTTGAGCTGGTTGTTCCGACCTTCATGCAGATGGCG

-continued

ACTGACCTGGGTATTCAGGATCTGCCGTACGATCATCCTCTTATCAAAGAAATCGCTGATACGAAG

CAACAGCGCCTGAAAGAAATTCCGAAAGATTTGGTTTATCAGATGCCGACCAATCTGCTGTATAGC

CTGGAAGGCCTGGGCGATTTAGAGTGGGAGCGTTTGCTGAAGCTGCAGTCTGGTAATGGTAGCTTC

CTGACGAGCCCAAGCAGCACGGCGGCAGTTCTGATGCATACCAAAGACGAGAAGTGTTTGAAATA

CATTGAGAATGCGCTGAAGAACTGCGACGGTGGCGCTCCTCATACGTATCCGGTTGACATCTTTAG

CCGCTTGTGGGCGATCGACCGTTTGCAACGTCTGGGCATTAGCCGTTTCTTCCAACACGAGATCAA

ATACTTTCTGGACCACATCGAGTCAGTCTGGGAAGAAACCGGCGTGTTTAGCGGTCGTTACACGAA

GTTTAGCGACATCGATGACACGAGCATGGGTGTCCGCCTGCTGAAAATGCACGGTTACGACGTAG

ACCCAAACGTGTTGAAACACTTTAAGCAGCAAGACGGCAAATTCAGCTGCTACATCGGCCAGAGC

GTCGAGAGCGCGAGCCCGATGTATAATCTGTACCGTGCCGCCCAGCTGCGTTTCCCGGGTGAAGA

AGTGCTTGAAGAAGCAACTAAATTCGCGTTTAACTTCCTGCAAGAGATGCTGGTGAAGGATCGCTT

GCAAGAGCGTTGGGTTATTAGCGATCACCTGTTTGACGAGATTAAGCTCGGTCTGAAGATGCCGTG

GTATGCTACCCTGCCGCGTGTTGAGGCCGCTTATTACCTGGATCACTATGCGGGTAGCGGTGATGT

GTGGATTGGTAAGTCTTTTTACCGCATGCCGGAGATTAGCAATGACACCTACAAAGAATTGGCCAT

CCTGGACTTTAACCGTTGTCAGACTCAGCATCAGCTGGAGTGGATTCACATGCAAGAGTGGTATGA

CCGCTGCTCTCTGTCCGAGTTTGGTATTAGCAAGCGTGAGCTGCTGCGTAGCTACTTCCTGGCTGCC

GCAACCATTTTCGAACCGGAACGCACCCAAGAGCGTCTGCTCTGGGCAAAGACCCGCATCCTGAG

CAAGATGATTACCAGCTTCGTCAACATCTCCGGTACGACCCTGAGCCTGGATTACAACTTCAACGG

TTTGGATGAGATCATTTCCAGCGCGAATGAAGATCAGGGTCTGGCGGGTACGCTGTTGGCCACGTT

CCATCAACTGCTGGATGGTTTCGACATTTACACCCTGCACCAACTGAAACACGTCTGGTCGCAATG

GTTTATGAAAGTTCAGCAAGGCGAGGGCTCCGGCGGCGAAGATGCGGTCCTGCTGGCAAATACTC

TGAATATCTGCGCGGGTCTGAATGAAGATGTGCTGTCGAACAACGAGTATACCGCGCTGAGCACG

CTGACGAACAAGATCTGCAACCGTCTGGCCCAGATCCAGGACAACAAGATTCTGCAAGTGGTGGA

CGGCAGCATCAAAGACAAAGAACTGGAACAGGATATGCAGGCATTGGTTAAACTGGTGCTGCAGG

AAAACGGTGGCGCAGTGGACCGTAACATCCGTCACACGTTTCTGAGCGTTAGCAAGACCTTCTACT

ATGACGCGTATCACGACGATGAAACCACCGATCTGCATATCTTTAAAGTCCTGTTCCGTCCGGTTG

TTTAA

SEQ ID NO 190: *Pantoea asslomerans* CrtE wt (M38424.1 40-963 (+))
ATGGTGAGTGGCAGTAAAGCGGGCGTTTCGCCTCATCGCGAAATAGAAGTAATGAGACAATCCAT

TGACGATCACCTGGCTGGCCTGTTACCTGAAACCGACAGCCAGGATATCGTCAGCCTTGCGATGCG

TGAAGGCGTCATGGCACCCGGTAAACGGATCCGTCCGCTGCTGATGCTGCTGGCCGCCCGCGACCT

CCGCTACCAGGGCAGTATGCCTACGCTGCTCGATCTCGCCTGCGCCGTTGAACTGACCCATACCGC

GTCGCTGATGCTCGACGACATGCCCTGCATGGACAACGCCGAGCTGCGCCGCGGTCAGCCCACTA

CCCACAAAAAATTTGGTGAGAGCGTGGCGATCCTTGCCTCCGTTGGGCTGCTCTCTAAAGCCTTTG

GTCTGATCGCCGCCACCGGCGATCTGCCGGGGGAGAGGCGTGCCCAGGCGGTCAACGAGCTCTCT

ACCGCCGTGGGCGTGCAGGGCCTGGTACTGGGGCAGTTTCGCGATCTTAACGATGCCGCCCTCGAC

CGTACCCCTGACGCTATCCTCAGCACCAACCACCTCAAGACCGGCATTCTGTTCAGCGCGATGCTG

CAGATCGTCGCCATTGCTTCCGCCTCGTCGCCGAGCACGCGAGAGACGCTGCACGCCTTCGCCCTC

GACTTCGGCCAGGCGTTTCAACTGCTGGACGATCTGCGTGACGATCACCCGGAAACCGGTAAAGA

TCGCAATAAGGACGCGGGAAAATCGACGCTGGTCAACCGGCTGGGCGCAGACGCGGCCCGGCAA

AAGCTGCGCGAGCATATTGATTCCGCCGACAAACACCTCACTTTTGCCTGTCCGCAGGGCGGCGCC

-continued

ATCCGACAGTTTATGCATCTGTGGTTTGGCCATCACCTTGCCGACTGGTCACCGGTCATGAAAATC

GCCTGA

SEQ ID NO 191: *Pantoea agglomerans* CrtE wt (AAA24819.1)
MVSGSKAGVSPHREIEVMRQSIDDHLAGLLPETDSQDIVSLAMREGVMAPGKRIRPLLMLLAARDLRY

QGSMPTLLDLACAVELTHTASLMLDDMPCMDNAELRRGQPTTHKKFGESVAILASVGLLSKAFGLIAA

TGDLPGERRAQAVNELSTAVGVQGLVLGQFRDLNDAALDRTPDAILSTNHLKTGILFSAMLQIVAIASA

SSPSTRETLHAFALDFGQAFQLLDDLRDDHPETGKDRNKDAGKSTLVNRLGADAARQKLREHIDSADK

HLTFACPQGGAIRQFMHLWFGHHLADWSPVMKIA*

SEQ ID NO 192: *Pantoea asslomerans* CrtE Yeast optimized
ATGGTTTCTGGTTCGAAAGCAGGAGTATCACCTCATAGGGAAATCGAAGTCATGAGACAGTCCATT

GATGACCACTTAGCAGGATTGTTGCCAGAAACAGATTCCCAGGATATCGTTAGCCTTGCTATGAGA

GAAGGTGTTATGGCACCTGGTAAACGTATCAGACCTTTGCTGATGTTACTTGCTGCAAGAGACCTG

AGATATCAGGGTTCTATGCCTACACTACTGGATCTAGCTTGTGCTGTTGAACTGACACATACTGCTT

CCTTGATGCTGGATGACATGCCTTGTATGGACAATGCGGAACTTAGAAGAGGTCAACCAACAACC

CACAAGAAATTCGGAGAATCTGTTGCCATTTTGGCTTCTGTAGGTCTGTTGTCGAAAGCATTTGGC

TTGATTGCTGCAACTGGTGATCTTCCAGGTGAAAGGAGAGCACAAGCTGTAAACGAGCTATCTACT

GCAGTTGGTGTTCAAGGTCTAGTCTTAGGACAGTTCAGAGATTTGAATGACGCAGCTTTGGACAGA

ACTCCTGATGCTATCCTGTCTACGAACCATCTGAAGACTGGCATCTTGTTCTCAGCTATGTTGCAAA

TCGTAGCCATTGCTTCTGCTTCTTCACCATCTACTAGGGAAACGTTACACGCATTCGCATTGGACTT

TGGTCAAGCCTTTCAACTGCTAGACGATTTGAGGGATGATCATCCAGAGACAGGTAAAGACCGTA

ACAAAGACGCTGGTAAAAGCACTCTAGTCAACAGATTGGGTGCTGATGCAGCTAGACAGAAACTG

AGAGAGCACATTGACTCTGCTGACAAACACCTGACATTTGCATGTCCACAAGGAGGTGCTATAAG

GCAGTTTATGCACCTATGGTTTGGACACCATCTTGCTGATTGGTCTCCAGTGATGAAGATCGCCTA

A

SEQ ID NO 193: *Talaromyces verruculosus* TalVeTPP wt (LHCL01000010.1
150095-151030 (+))
ATGTCTAATGACACCACTACCACGGCTTCTGCCGGAACAGCAACTTCTTCGCGGTTTCTTTCCGTGG

GGGGAGTTGTGAACTTCCGTGAACTGGGCGGTTACCCATGTGATTCTGTCCCTCCTGCTCCTGCCTC

AAACGGCTCACCGGACAATGCATCTGAAGCGACCCTTTGGGTTGGCCACTCGTCCATTCGGCCTGG

ATTTCTGTTTCGATCGGCACAGCCGTCTCAGATTACCCCGGCCGGTATTGAGACATTGATCCGCCA

GCTTGGCATCCAGACAATTTTTGACTTTCGTTCAAGGACGGAAATTGAGCTTGTTGCCACTCGCTAT

CCTGATTCGCTACTTGAGATACCTGGCACGACTCGCTATTCCGTGCCCGTCTTCTCGGAAGGCGAC

TATTCCCCAGCGTCATTAGTCAAGAGGTACGGAGTGTCCTCCGATACTGCAACCGATTCCACTTCC

TCCAAAAGTGCTAAGCCTACAGGATTCGTCCACGCATATGAGGCTATCGCACGCAGTGCAGCAGA

AAACGGCAGTTTTCGTAAGATAACGGACCACATAATACAACATCCGGACCGGCCTATTCTGTTTCA

CTGTACACTGGGGAAAGACCGAACCGGTGTGTTTGCAGCATTGTTATTGAGTCTTTGCGGGGTACC

AGACGAGACGATAGTTGAAGACTATGCTATGACTACCGAGGGATTTGGAGCCTGGCGGGAACATC

TAATTCAACGCTTGCTACAAAGGAAGGATGCAGCTACGCGCGAGGATGCAGAATCCATTATTGCC

AGCCCCCCGGAGACTATGAAGGCTTTTCTAGAAGATGTGGTAGCAGCCAAGTTCGGGGGTGCTCG

AAATTACTTTATCCAGCACTGTGGATTTACGGAAGCTGAGGTTGATAAGTTAAGCCATACACTGGC

CATTACGAATTGA

-continued

SEQ ID NO 194: *Talaromyces verruculosus* TalVeTPP wt (KUL89334.1)
MSNDTTTTASAGTATSSRFLSVGGVVNFRELGGYPCDSVPPAPASNGSPDNASEATLWVGHSSIRPGFL

FRSAQPSQITPAGIETLIRQLGIQTIFDFRSRTEIELVATRYPDSLLEIPGTTRYSVPVFSEGDYSPASLVKR

YGVSSDTATDSTSSKSAKPTGFVHAYEAIARSAAENGSFRKITDHIIQHPDRPILFHCTLGKDRTGVFAA

LLLSLCGVPDETIVEDYAMTTEGFGAWREHLIQRLLQRKDAATREDAESIIASPPETMKAFLEDVVAAK

FGGARNYFIQHCGFTEAEVDKLSHTLAITN

SEQ ID NO 195: *Talaromyces verruculosus* TalVeTPP Yeast optimized
ATGTCTAACGACACTACTACTACTGCTTCTGCTGGTACTGCTACTTCTTCTAGATTCTTGTCTGTTG

GTGGTGTTGTTAACTTCAGAGAATTGGGTGGTTACCCATGTGACTCTGTTCCACCAGCTCCAGCTTC

TAACGGTTCTCCAGACAACGCTTCTGAAGCTACTTTGTGGGTTGGTCACTCTTCTATCAGACCAGGT

TTCTTGTTCAGATCTGCTCAACCATCTCAAATCACTCCAGCTGGTATCGAAACTTTGATCAGACAAT

TGGGTATCCAAACTATCTTCGACTTCAGATCTAGAACTGAAATCGAATTGGTTGCTACTAGATACC

CAGACTCTTTGTTGGAAATCCCAGGTACTACTAGATACTCTGTTCCAGTTTTCTCTGAAGGTGACTA

CTCTCCAGCTTCTTTGGTTAAGAGATACGGTGTTTCTTCTGACACTGCTACTGACTCTACTTCTTCTA

AGTCTGCTAAGCCAACTGGTTTCGTTCACGCTTACGAAGCTATCGCTAGATCTGCTGCTGAAAACG

GTTCTTTCAGAAAGATCACTGACCACATCATCCAACACCCAGACAGACCAATCTTGTTCCACTGTA

CTTTGGGTAAGGACAGAACTGGTGTTTTCGCTGCTTTGTTGTTGTCTTTGTGTGGTGTTCCAGACGA

AACTATCGTTGAAGACTACGCTATGACTACTGAAGGTTTCGGTGCTTGGAGAGAACACTTGATCCA

AAGATTGTTGCAAAGAAAGGACGCTGCTACTAGAGAAGACGCTGAATCTATCATCGCTTCTCCACC

AGAAACTATGAAGGCTTTCTTGGAAGACGTTGTTGCTGCTAAGTTCGGTGGTGCTAGAAACTACTT

CATCCAACACTGTGGTTTCACTGAAGCTGAAGTTGACAAGTTGTCTCACACTTTGGCTATCACTAA

CTAA

SEQ ID NO 196: Artificial RBS sequence
AAGGAGGTAAAAAA

SEQ ID NO 197: Artificial BYMO sequence motif 8
GAGxSGL $X_4$ can be any naturally occurring amino acid, particularly A or I The numbering of X corresponds to its position in the sequence.

SEQ ID NO 198:
Artificial BYMO sequence motif 1
EKNxxxxGTWxENRYPGCACDVPxHxYxxSFE $X_4$ can be any naturally occurring amino acid, particularly H or P.

$X_5$ can be any naturally occurring amino acid, particularly A, D, or E.

$X_6$ can be any naturally occurring amino acid, particularly L or V.

$X_7$ can be any naturally occurring amino acid, particularly G or S.

$X_{11}$ can be any naturally occurring amino acid, particularly F, L, or Y.

$X_{24}$ can be any naturally occurring amino acid, particularly A or S.

$X_{26}$ can be any naturally occurring amino acid, particularly A, C, or N.

$X_{28}$ can be any naturally occurring amino acid, particularly A or T.

$X_{29}$ can be any naturally occurring amino acid, particularly W or Y.

The numbering of X corresponds to its position in the sequence.

SEQ ID NO 199:
Artificial BVMO sequence motif 2
LxNAxGILNxWxxPxIPG $X_2$ can be any naturally occurring amino acid, particularly I, L, or V.

$X_5$ can be any naturally occurring amino acid, particularly G, S, or T.

$X_{10}$ can be any naturally occurring amino acid, particularly A or Q.

$X_{12}$ can be any naturally occurring amino acid, particularly K or R.

$X_{13}$ can be any naturally occurring amino acid, particularly W or Y.

$X_{15}$ can be any naturally occurring amino acid, particularly G, P, or S.

The numbering of X corresponds to its position in the sequence.

SEQ ID NO 200:
Artificial BVMO sequence motif 3
LxxKxVxxIGxGSSGIQIxPxI $X_2$ can be any naturally occurring amino acid, particularly E, K, or N.

$X_3$ can be any naturally occurring amino acid, particularly D or G.

$X_5$ can be any naturally occurring amino acid, particularly K, T, or V.

$X_7$ can be any naturally occurring amino acid, particularly A or G.

$X_8$ can be any naturally occurring amino acid, particularly L or V.

$X_{11}$ can be any naturally occurring amino acid, particularly N or S.

$X_{19}$ can be any naturally occurring amino acid, particularly L or V.

$X_{21}$ can be any naturally occurring amino acid, particularly A or N.

The numbering of X corresponds to its position in the sequence.

```
SEQ ID NO 201:
Artificial BVMO sequence motif 4
GCRRxTPGxxYLExL
```

$X_5$ can be any naturally occurring amino acid, particularly L or P.

$X_9$ can be any naturally occurring amino acid, particularly P or T.

$X_{10}$ can be any naturally occurring amino acid, particularly G, H, or N.

$X_{14}$ can be any naturally occurring amino acid, particularly A or S.

The numbering of X corresponds to its position in the sequence.

```
SEQ ID NO 202:
Artificial BVMO sequence motif 5
CATGFDxxxxPRFxxxG
```

$X_7$ can be any naturally occurring amino acid, particularly T or V.

$X_8$ can be any naturally occurring amino acid, particularly S or T.

$X_9$ can be any naturally occurring amino acid, particularly F or Y.

$X_{10}$ can be any naturally occurring amino acid, particularly K or R.

$X_{14}$ can be any naturally occurring amino acid, particularly K or P.

$X_{15}$ can be any naturally occurring amino acid, particularly F or L.

$X_{16}$ can be any naturally occurring amino acid, particularly I or V.

The numbering of X corresponds to its position in the sequence.

```
SEQ ID NO 203:
Artificial BVMO sequence motif 6
PNxFxxxGPNxPxxNGxV
```

$X_3$ can be any naturally occurring amino acid, particularly S or Y.

$X_5$ can be any naturally occurring amino acid, particularly F, I, or S.

$X_6$ can be any naturally occurring amino acid, particularly F, I, or T.

$X_7$ can be any naturally occurring amino acid, particularly L or M.

$X_{11}$ can be any naturally occurring amino acid, particularly C or G.

$X_{13}$ can be any naturally occurring amino acid, particularly I or V.

$X_{14}$ can be any naturally occurring amino acid, particularly A or G.

$X_{17}$ can be any naturally occurring amino acid, particularly P or S.

The numbering of X corresponds to its position in the sequence.

```
SEQ ID NO 204:
Artificial BVMO sequence motif 7
AxWPGSxLHYxEAxxxPRxED
```

$X_2$ can be any naturally occurring amino acid, particularly L or V.

$X_7$ can be any naturally occurring amino acid, particularly A or T.

$X_{11}$ can be any naturally occurring amino acid, particularly L or M.

$X_{14}$ can be any naturally occurring amino acid, particularly I or L.

$X_{15}$ can be any naturally occurring amino acid, particularly A, K, or Q.

$X_{16}$ can be any naturally occurring amino acid, particularly D, H, or S.

$X_{19}$ can be any naturally occurring amino acid, particularly W or Y.

The numbering of X corresponds to its position in the sequence.

```
SEQ ID NO 205:
Artificial enal-cleaving polypeptide
sequence motif 1
G-[Y or-]-x-W-x-G-x-x-[F, L or I]-

x-[T, S or R]-G-[H or D]

GxxWxGxxxxxGx
```

$X_2$ can be Y or can be deleted.

$X_3$ can be any naturally occurring amino acid.

$X_5$ can be any naturally occurring amino acid.

$X_7$ can be any naturally occurring amino acid.

$X_8$ can be any naturally occurring amino acid.

$X_9$ can be F, L, or I.

$X_{10}$ can be any naturally occurring amino acid.

$X_{11}$ can be R, S, or T.

$X_{13}$ can be H or D.

The numbering of X corresponds to its position in the sequence.

```
SEQ ID NO 206:
Artificial enal-cleaving polypeptide
sequence motif 2
W-[Y, A or V]-G-K-x-[F or Y]-x-[S or D]

WxGKxxxx
```

$X_2$ can be A, V, or Y.

$X_5$ can be any naturally occurring amino acid.

$X_6$ can be F or Y.

$X_7$ can be any naturally occurring amino acid.

$X_8$ can be D or S.

The numbering of X corresponds to its position in the sequence.

```
SEQ ID NO 207: Artificial enal-
cleaving polypeptide sequence motif 3
[G or S]-x-[A or G]-x-[L or V]-x-x-x-x-

[F, Y or L]-R-G-x-VxxxxxxxxxxRGxV
```

$X_1$ can be G or S.
$X_2$ can be any naturally occurring amino acid.
$X_3$ can be A or G.
$X_4$ can be any naturally occurring amino acid.
$X_5$ can be L or V.
$X_6$ can be any naturally occurring amino acid.
$X_7$ can be any naturally occurring amino acid.
$X_8$ can be any naturally occurring amino acid.
$X_9$ can be any naturally occurring amino acid.
$X_{10}$ can be F, L, or Y.
$X_{13}$ can be any naturally occurring amino acid.

The numbering of X corresponds to its position in the sequence.

```
SEQ ID NO 208: Artificial enal-cleaving
polypeptide sequence motif 4
[M or L]-[V or I]-Y-D-x-x-P-[I or V]-

x-D-[H or S]-[F or L]xxYDxxPxxDxx
```

$X_1$ can be L or M.
$X_2$ can be I or V.
$X_5$ can be any naturally occurring amino acid.
$X_6$ can be any naturally occurring amino acid.
$X_8$ can be I or V.
$X_9$ can be any naturally occurring amino acid.
$X_{11}$ can be H or S.
$X_{12}$ can be F or L.

The numbering of X corresponds to its position in the sequence.

---

The invention claimed is:

1. A biocatalytic method of preparing a compound of formula IV

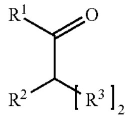

(IV)

wherein $R^1$ represents H or lower alkyl;

$R^2$ represents H, a linear or branched, saturated or unsaturated, optionally substituted hydrocarbyl residue, or a residue Cyc-A- wherein

Cyc represents an optionally substituted, saturated or unsaturated, mono- or polycyclic hydrocarbyl residue, and A represents a chemical bond or an optionally substituted, straight chain or branched alkylene bridge;

and $R^3$ represent independently of each other H or lower alkyl; comprising the steps of (1) contacting a compound of formula V

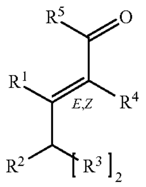

(V)

wherein $R^1$, $R^2$ and $R^3$ are as defined above; and $R^4$ represents H or lower alkyl, $R^5$ represents H or lower alkyl, and wherein said compound of formula V is present in stereoisomerically essentially pure form or as a mixture of stereoisomers, with a polypeptide having enal-cleaving activity, and optionally (2) isolating the compound of formula IV as obtained in step (1), wherein said compound of formula IV is provided in stereoisomerically pure form, or as a mixture of stereoisomers;

wherein said polypeptide having enal-cleaving activity is a polypeptide comprising an amino acid sequence selected from the group consisting of:

a) SCH94-3944 set forth in SEQ ID NO: 34;
b) SCH80-05241 set forth in SEQ ID NO: 38;
c) Pdigit7033 set forth in SEQ ID NO: 42;
d) PitalDUF4334-1 set forth in SEQ ID NO: 46;
e) AspWeDUF4334 set forth in SEQ ID NO: 49;
f) RhoagDUF4334-2 set forth in SEQ ID NO: 53;
g) RhoagDUF4334-3 set forth in SEQ ID NO: 56;
h) RhoagDUF4334-4 set forth in SEQ ID NO: 59;
i) CnecaDUF4334 set forth in SEQ ID NO: 62;
j) Rins-DUF4334 set forth in SEQ ID NO: 69;
k) CgatDUF4334 set forth in SEQ ID NO: 72;
l) GclavDUF4334 set forth in SEQ ID NO: 75;
m) TcurvaDUF4334 set forth in SEQ ID NO:81;
n) PprotDUF4334 set forth in SEQ ID NO: 87; and
o) polypeptides comprising an amino acid sequence that has at least 90% sequence identity to any one of the amino acid sequences of a) to n) and retaining said enzymatic activity of degrading a terpene precursor of formula (V).

2. The method of claim 1, wherein the compound of formula V is a terpene, wherein $R^1$ represents H or methyl, $R^2$ represents H or a non-cyclic, linear or branched, saturated or unsaturated, hydrocarbyl residue having 1 to 20, carbon atoms; or a cyclic group Cyc-A-, wherein A represents a straight chain or branched $C_1$-$C_4$-alkylene bridge; and Cyc represents a mono- or polycyclic, saturated or unsaturated hydrocarbyl residue, optionally substituted with 1-10 substituents which are independently selected from $C_1$-$C_4$-alkyl, $C_1$-$C_4$-alkylidene, $C_2$-$C_4$-alkenyl, oxo, hydroxy, or amino;

each $R^3$ represents H, $R^4$ represents H or methyl, and $R^5$ represents H or methyl.

3. The method of claim 1, wherein the compound of formula IV possesses a labdane-type structure, and/or wherein Cyc-A represents a residue of one of the formulae IIIa, IIIb or IIIc (IIIa)

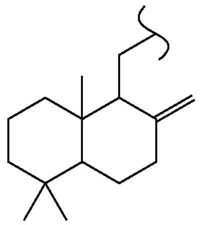

(IIIb)

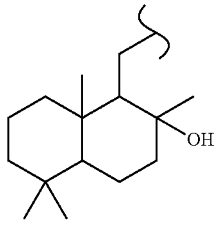

(IIIc)

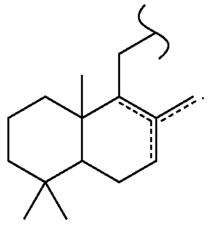

4. The method of claim 1, further comprising as step (3) the processing of the compound of formula IV formed in step (1) or isolated in step (2) to obtain a derivative thereof using chemical or biocatalytic synthesis or a combination of both, and as step (4) optionally isolating the derivative of step (3).

5. The method of claim 4, wherein step (3) comprises the processing of the compound of formula IV formed in step (1) or isolated in step (2) with a polypeptide having Baeyer-Villiger monooxygenase (BVMO) activity so as to form the respective carbonyl ester (EC.1.13.14.-), and optionally further comprises the hydrolysis of the carbonyl ester compound with an esterase (EC 3.1.1) to the corresponding de-esterified product;

and optionally isolating the derivative of step (3);

wherein the polypeptide having Baeyer-Villiger monooxygenase (BVMO) activity is selected from the group consisting of (1) the group of polypeptides containing a flavin-containing monooxygenase (FMO) protein family domain having the Pfam ID number PF00743 within their amino acid sequence or a domain retaining at least 90% sequence identity to PF00743;

(2) the group of polypeptides that comprise at least one sequence motif/domain selected from the group consisting of GAGxSGL set forth in SEQ ID NO:197;

EKNxxxxGTWxENRYPGCACDVPxHxYXXSFE set forth in SEQ ID NO:198;

LxNAxGILNxWxxPxIPG set forth in SEQ ID NO:199;

LxxKxVxxIGxGSSGIQIxPxI set forth in SEQ ID NO:200;

GCRRxTPGxxYLExL set forth in SEQ ID NO:201;

CATGFDxxxxPRFxxxG set forth in SEQ ID NO:202;

PNxFxxxGPNxPxxNGxV set forth in SEQ ID NO:203;

AxWPGSxLHYxEAxxxPRxED set forth in SEQ ID NO:204;

wherein residues x represent independently of each other any natural amino acid residue; and (3) the group of polypeptides selected from the group consisting of (a) polypeptides comprising the amino acid sequence of SCH23-BVMO1 set forth in SEQ ID NO:2;

(b) polypeptides comprising the amino acid sequence of SCH24-BVMO1 set forth in SEQ ID NO:6;

(c) polypeptides comprising the amino acid sequence of SCH25-BVMO1 set forth in SEQ ID NO:10;

(d) polypeptides comprising the amino acid sequence of SCH46-BVMO1 set forth in SEQ ID NO:13;

(e) polypeptides comprising the amino acid sequence of AspWeBVMO set forth in SEQ ID NO:16; and (f) polypeptides comprising an amino acid sequence that has at least 70%, identity to any one of the amino acid sequences of a) to e).

6. An in vivo method for preparing labdane-type terpenes which method comprises providing a recombinant host expressing a set of polypeptides having enzymatic activities required for catalyzing the following sequence of reaction steps:

(1) optionally converting a labdane alcohol to the respective labdane aldehyde through the enzymatic action of an ADH polypeptide, (2) converting said ladbane aldehyde of step (1) to the respective dinorlabdane carbonyl compound through the action of a method comprising the steps of contacting the corresponding non-degraded precursor of the general formula V (V)

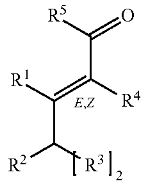

wherein $R^1$, $R^2$ and $R^3$ are as defined above; and $R^4$ represents H or lower alkyl, $R^5$ represents H or lower alkyl, and wherein said compound of formula V may be present in stereoisomerically essentially pure form or as a mixture of stereoisomers, with a polypeptide having enal-cleaving activity, and optionally isolating the degraded product of formula IV as obtained in step (1), wherein said compound of formula IV is provided in stereoisomerically pure form, or as a mixture of stereoisomers;

(3) optionally converting said dinorlabdane carbonyl compound of step (2) to the respective tetranorlabdanyl acetate through the action of the method of claim 4;

(4) optionally converting said tetranorlabdanyl acetate of step (3) to the respective tetranorlabdane alcohol through the action a polypeptide having esterase activity; and optionally (5) isolating the product of step (2), (3) or (4), wherein said polypeptide having enal-cleaving activity is a polypeptide comprising an amino acid sequence selected from the group consisting of:

a) SCH94-3944 set forth in SEQ ID NO: 34;
b) SCH80-05241 set forth in SEQ ID NO: 38;
c) Pdigit7033 set forth in SEQ ID NO: 42;
d) PitalDUF4334-1 set forth in SEQ ID NO: 46;
e) AspWeDUF4334 set forth in SEQ ID NO: 49;
f) RhoagDUF4334-2 set forth in SEQ ID NO: 53;
g) RhoagDUF4334-3 set forth in SEQ ID NO: 56;
h) RhoagDUF4334-4 set forth in SEQ ID NO: 59;
i) CnecaDUF4334 set forth in SEQ ID NO: 62;
i) Rins-DUF4334 set forth in SEQ ID NO: 69;
k) CgatDUF4334 set forth in SEQ ID NO: 72;
l) GclavDUF4334 set forth in SEQ ID NO: 75;
m) TcurvaDUF4334 set forth in SEQ ID NO:81;
n) PprotDUF4334 set forth in SEQ ID NO: 87; and
o) polypeptides comprising an amino acid sequence that has at least 90% sequence identity to any one of the amino acid sequences of a) to n) and retaining said enzymatic activity of degrading a terpene precursor of formula (V).

7. A method of preparing an epoxy-tetranorlabdane compound, which method comprises (1) providing a tetranorlabdane alcohol or a tetranorlabdane acetate, or a dinorlabdane carbonyl compound, by applying a biocatalytic method comprising the method steps of claim 1, and optionally isolating said product; and (2) converting said product of step (1) to epoxy-tetranorlabdane by applying one or more chemical and/or biochemical conversion steps.

8. A method of preparing a diepoxy-dinorlabdane, which method comprises (1) providing a dinorlabdane carbonyl compound, by applying a method which comprising the method steps of claim 1, and optionally isolating said dinorlabdane carbonyl compound; and (2) converting said dinorlabdane carbonyl compound to said diepoxy-dinorlabdane by applying one or more chemical and/or biochemical conversion steps.

9. The method of claim 4, wherein said derivative is selected from the group consisting of a hydrocarbon, alcohol, diol, triol, acetal, ketal, aldehyde, acid, ether, amide, ketone, lactone, epoxide, acetate, glycoside and an ester.

10. The method of claim 5, further comprising processing the carbonyl ester and/or corresponding de-esterified product to obtain a derivative thereof using chemical or biocatalytic synthesis or a combination of both, and as step (4) optionally isolating the derivative of step (3).

11. The method of claim 10, wherein said derivative is selected from the group consisting of a hydrocarbon, alcohol, diol, triol, acetal, ketal, aldehyde, acid, ether, amide, ketone, lactone, epoxide, acetate, glycoside and an ester.

12. A method of preparing an epoxy-tetranorlabdane compound, which method comprises (1) providing a tetranorlabdane alcohol or a tetranorlabdane acetate or a dinorlabdane carbonyl compound, by applying a biocatalytic method comprising the method steps of claim 1, optionally isolating said product; and (2) converting said product of step (1) to epoxy-tetranorlabdane by applying one or more chemical and/or biochemical conversion steps.

13. A method of preparing a diepoxy-dinorlabdane, which method comprises:

(1) providing a dinorlabdane carbonyl compound by applying a method which results in the formation of said dinorlabdane carbonyl compound and which comprises the method steps of claim 1, optionally isolating said dinorlabdane carbonyl compound; and (2) converting said dinorlabdane carbonyl compound to said diepoxy-dinorlabdabe by applying one or more chemical and/or biochemical conversion steps.

14. The method of claim 12, wherein the epoxy-tetranorlabdane compound is ambrox.

15. The method of claim 12, wherein the tetranorlabdane alcohol is gamma-ambrol.

16. The method of claim 12, wherein the tetranorlabdane acetate is gamma-ambryl acetate.

17. The method of claim 12, wherein the dinorlabdane carbonyl compound is manooloxy.

18. The method of claim 12, wherein the diepoxy-dinorlabdane is Z11.

19. The method of claim 12, wherein the dinorlabdane carbonyl compound is manooloxy.

20. The method of claim 1, wherein said polypeptide having enal-cleaving activity is a polypeptide comprising an amino acid sequence selected from the group consisting of:

a) SCH94-3944 set forth in SEQ ID NO: 34;
b) SCH80-05241 set forth in SEQ ID NO: 38;
c) Pdigit7033 set forth in SEQ ID NO: 42;
d) PitalDUF4334-1 set forth in SEQ ID NO: 46;
e) AspWeDUF4334 set forth in SEQ ID NO: 49;
f) RhoagDUF4334-2 set forth in SEQ ID NO: 53;
g) RhoagDUF4334-3 set forth in SEQ ID NO: 56;

h) RhoagDUF4334-4 set forth in SEQ ID NO: 59;
i) CnecaDUF4334 set forth in SEQ ID NO: 62;
j) Rins-DUF4334 set forth in SEQ ID NO: 69;
k) CgatDUF4334 set forth in SEQ ID NO: 72;
l) GclavDUF4334 set forth in SEQ ID NO: 75;
m) TcurvaDUF4334 set forth in SEQ ID NO:81; and
n) PprotDUF4334 set forth in SEQ ID NO: 87.

* * * * *